US011596646B2

(12) United States Patent
Zhang et al.

(10) Patent No.: US 11,596,646 B2
(45) Date of Patent: Mar. 7, 2023

(54) OLIGONUCLEOTIDE COMPOSITIONS AND METHODS THEREOF

(71) Applicant: WAVE LIFE SCIENCES LTD., Singapore (SG)

(72) Inventors: Jason Jingxin Zhang, Walpole, MA (US); Chikdu Shakti Shivalila, Somerville, MA (US); Chandra Vargeese, Schwenksville, PA (US); Naoki Iwamoto, Brighton, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 88 days.

(21) Appl. No.: 16/755,544

(22) PCT Filed: Oct. 12, 2018

(86) PCT No.: PCT/US2018/055653
§ 371 (c)(1),
(2) Date: Apr. 10, 2020

(87) PCT Pub. No.: WO2019/075357
PCT Pub. Date: Apr. 18, 2019

(65) Prior Publication Data
US 2021/0228615 A1 Jul. 29, 2021

Related U.S. Application Data

(60) Provisional application No. 62/701,078, filed on Jul. 20, 2018, provisional application No. 62/571,686, filed on Oct. 12, 2017.

(51) Int. Cl.
*C07H 21/04* (2006.01)
*A61K 31/7125* (2006.01)
*C12N 15/113* (2010.01)

(52) U.S. Cl.
CPC ........ *A61K 31/7125* (2013.01); *C12N 15/113* (2013.01); *C12N 2310/31* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 7,101,993 B1 | 9/2006 | Cook et al. | |
| 8,470,987 B2 | 6/2013 | Wada et al. | |
| 8,729,036 B2 | 5/2014 | Zamore et al. | |
| 8,822,671 B2 | 9/2014 | Shimizu et al. | |
| 8,859,755 B2 | 10/2014 | Wada et al. | |
| 9,394,333 B2 | 7/2016 | Wada et al. | |
| 9,476,044 B2 | 10/2016 | Tuschl et al. | |
| 9,598,458 B2 | 3/2017 | Shimizu et al. | |
| 9,605,019 B2 | 3/2017 | Verdine et al. | |
| 9,617,547 B2 | 4/2017 | Gemba | |
| 9,695,211 B2 | 7/2017 | Wada et al. | |
| 9,744,183 B2 | 8/2017 | Verdine et al. | |
| 9,982,257 B2 | 5/2018 | Butler et al. | |
| 10,059,941 B2 * | 8/2018 | Krieg | C12N 15/113 |
| 10,144,933 B2 | 12/2018 | Gemba et al. | |
| 10,149,905 B2 | 12/2018 | Gemba et al. | |
| 10,160,969 B2 | 12/2018 | Meena et al. | |
| 10,167,309 B2 | 1/2019 | Shimizu et al. | |
| 10,280,192 B2 | 5/2019 | Verdine et al. | |
| 10,307,434 B2 | 6/2019 | Verdine et al. | |
| 10,322,173 B2 | 6/2019 | Gemba et al. | |
| 10,329,318 B2 | 6/2019 | Wada et al. | |
| 10,428,019 B2 | 10/2019 | Wada et al. | |
| 10,450,568 B2 | 10/2019 | Butler et al. | |
| 10,479,995 B2 | 11/2019 | Vargeese et al. | |
| 10,590,413 B2 | 3/2020 | Butler et al. | |
| 10,696,711 B2 | 6/2020 | Shimizu et al. | |
| 10,724,035 B2 | 7/2020 | Vargeese et al. | |
| 10,815,482 B2 | 10/2020 | Meena et al. | |

(Continued)

FOREIGN PATENT DOCUMENTS

WO WO-2004/007718 A2 1/2004
WO WO-2005/014609 A2 2/2005

(Continued)

OTHER PUBLICATIONS

U.S. Appl. No. 16/624,896, filed Dec. 19, 2019, Butler et al.
U.S. Appl. No. 16/869,126, filed May 7, 2020, Vargeese et al.
U.S. Appl. No. 17/046,752, filed Oct. 9, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
U.S. Appl. No. 17/439,755, filed Sep. 15, 2021, Kandasamy et al.
U.S. Appl. No. 17/465,238, filed Feb. 9, 2021, Shimizu et al.

(Continued)

*Primary Examiner* — Kimberly Chong
(74) *Attorney, Agent, or Firm* — Choate, Hall & Stewart LLP; Xiaodong Li; Dustin K. Goncharoff

(57) ABSTRACT

Among other things, the present disclosure provides technologies for altering splicing, particularly for increasing inclusion of exons in splicing products. In some embodiments, the present disclosure provides SMN2 oligonucleotides, compositions, and methods thereof. In some embodiments, the present disclosure provides chirally controlled SMN2 oligonucleotide compositions. In some embodiments, provided oligonucleotides and compositions can increase level of an exon 7-containing SMN2 splicing product and/or a gene product thereof. In some embodiments, the present disclosure provides methods for treatment of splicing-related conditions, disorders and diseases. In some embodiments, the present disclosure provides methods for treating SMN2-related conditions, disorders and diseases such as SMA (spinal muscular atrophy) and ALS (amyotrophic lateral sclerosis).

14 Claims, 7 Drawing Sheets
Specification includes a Sequence Listing.

(56) References Cited

U.S. PATENT DOCUMENTS

| | | | |
|---|---|---|---|
| 11,013,757 | B2 | 5/2021 | Zhang et al. |
| 11,136,346 | B2 | 10/2021 | Shimizu et al. |
| 2007/0292408 | A1 | 12/2007 | Singh et al. |
| 2018/0028554 | A1* | 2/2018 | Van Deutekom ....... A61P 21/00 |
| 2019/0077817 | A1 | 3/2019 | Butler et al. |
| 2019/0127733 | A1 | 5/2019 | Butler et al. |
| 2019/0249173 | A1 | 8/2019 | Vargeese et al. |
| 2019/0264267 | A1 | 8/2019 | Yang et al. |
| 2019/0375774 | A1 | 12/2019 | Butler et al. |
| 2020/0157545 | A1 | 5/2020 | Vargeese et al. |
| 2020/0190515 | A1 | 6/2020 | Vargeese et al. |
| 2020/0231620 | A1 | 7/2020 | Bowman et al. |
| 2020/0299692 | A1 | 9/2020 | Frank-Kamenetsky et al. |
| 2020/0362337 | A1 | 11/2020 | Dodart et al. |
| 2021/0032620 | A1 | 2/2021 | Vargeese et al. |
| 2021/0115444 | A1 | 4/2021 | Meena et al. |
| 2021/0130821 | A1 | 5/2021 | Butler et al. |
| 2021/0198305 | A1 | 7/2021 | Vargeese et al. |
| 2021/0254062 | A1 | 8/2021 | Zhang et al. |

FOREIGN PATENT DOCUMENTS

| | | | |
|---|---|---|---|
| WO | WO-2005/023828 | A1 | 3/2005 |
| WO | WO-2005/028494 | A1 | 3/2005 |
| WO | WO-2005/070859 | A1 | 8/2005 |
| WO | WO-2005/085272 | A1 | 9/2005 |
| WO | WO-2005/092909 | A1 | 10/2005 |
| WO | WO-2007/002390 | A2 | 1/2007 |
| WO | WO-2010/064146 | A2 | 6/2010 |
| WO | WO-2010/120820 | A1 | 10/2010 |
| WO | WO-2010/148249 | A1 | 12/2010 |
| WO | WO-2011/005761 | A1 | 1/2011 |
| WO | WO-2011/034072 | A1 | 3/2011 |
| WO | WO-2011/108682 | A1 | 9/2011 |
| WO | WO-2012/039448 | A1 | 3/2012 |
| WO | WO-2012/073857 | A1 | 6/2012 |
| WO | WO-2013/012758 | A1 | 1/2013 |
| WO | WO-2014/010250 | A1 | 1/2014 |
| WO | WO-2014/010718 | A1 | 1/2014 |
| WO | WO-2014/012081 | A2 | 1/2014 |
| WO | WO-2014/076195 | A1 | 5/2014 |
| WO | WO-2014/110291 | A1 | 7/2014 |
| WO | WO-2015/108046 | A1 | 7/2015 |
| WO | WO-2015/108047 | A1 | 7/2015 |
| WO | WO-2015/108048 | A1 | 7/2015 |
| WO | WO-2015/168618 | A2 | 11/2015 |
| WO | WO-2017/015555 | A1 | 1/2017 |
| WO | WO-2017/015575 | A1 | 1/2017 |
| WO | WO-2017/062862 | A2 | 4/2017 |
| WO | WO-2017/160741 | A1 | 9/2017 |
| WO | WO-2017/192664 | A1 | 11/2017 |
| WO | WO-2017/192679 | A1 | 11/2017 |
| WO | WO-2017/210647 | A1 | 12/2017 |
| WO | WO-2018/022473 | A1 | 2/2018 |
| WO | WO-2018/067973 | A1 | 4/2018 |
| WO | WO-2018/098264 | A1 | 5/2018 |
| WO | WO-2018/223056 | A1 | 12/2018 |
| WO | WO-2018/223073 | A1 | 12/2018 |
| WO | WO-2018/223081 | A1 | 12/2018 |
| WO | WO-2018/237194 | A1 | 12/2018 |
| WO | WO-2019/002237 | A1 | 1/2019 |
| WO | WO-2019/032607 | A1 | 2/2019 |
| WO | WO-2019/032612 | A1 | 2/2019 |
| WO | WO-2019/055951 | A1 | 3/2019 |
| WO | WO-2019/075357 | A1 | 4/2019 |
| WO | WO-2019/200185 | A1 | 10/2019 |
| WO | WO-2019/217784 | A1 | 11/2019 |
| WO | WO-2020/118246 | A1 | 6/2020 |
| WO | WO-2020/160336 | A1 | 8/2020 |
| WO | WO-2020/191252 | A1 | 9/2020 |
| WO | WO-2020/196662 | A1 | 10/2020 |
| WO | WO-2020/219981 | A2 | 10/2020 |
| WO | WO-2020/219983 | A2 | 10/2020 |
| WO | WO-2020/227691 | A2 | 11/2020 |
| WO | WO-2021/071788 | A2 | 4/2021 |
| WO | WO-2021/071858 | A1 | 4/2021 |
| WO | WO-2021/178237 | A2 | 9/2021 |
| WO | WO-2021/237223 | A1 | 11/2021 |

OTHER PUBLICATIONS

U.S. Appl. No. 17/605,997, filed Oct. 22, 2021, Byrne et al.
U.S. Appl. No. 17/605,998, filed Oct. 22, 2021, Byrne et al.
U.S. Appl. No. 17/609,330, filed Nov. 5, 2021, Liu et al.
Burghes, A.H. et al., Antisense Oligonucleotides and Spinal Muscular Atrophy: Skipping Along, Genes and Development, 24(15): 1574-1579 (2010).
International Search Report for PCT/US2018/055653, 4 pages (dated Jan. 18, 2019).
Koch, T., LNA Therapeutics—update, Navigate the phosphorothioate diastereoisomer space, Roche pRED RNA Therapeutics Research, EuroTIDES, PostillionConventionCenter, Amsterdam, Netherlands (Nov. 6-9, 2018).
Shen, W. et al., Acute hepatotoxicity of 2' fluoro-modified 5-10-5 gapmer phosphorothioate oligonucleotides in mice correlates with intracellular protein binding and the loss of DBHS proteins, Nucl. Acids Res., 46(5):2204-2217 (2018).
Written Opinion for PCT/US2018/055653, 15 pages (dated Jan. 18, 2019).

\* cited by examiner

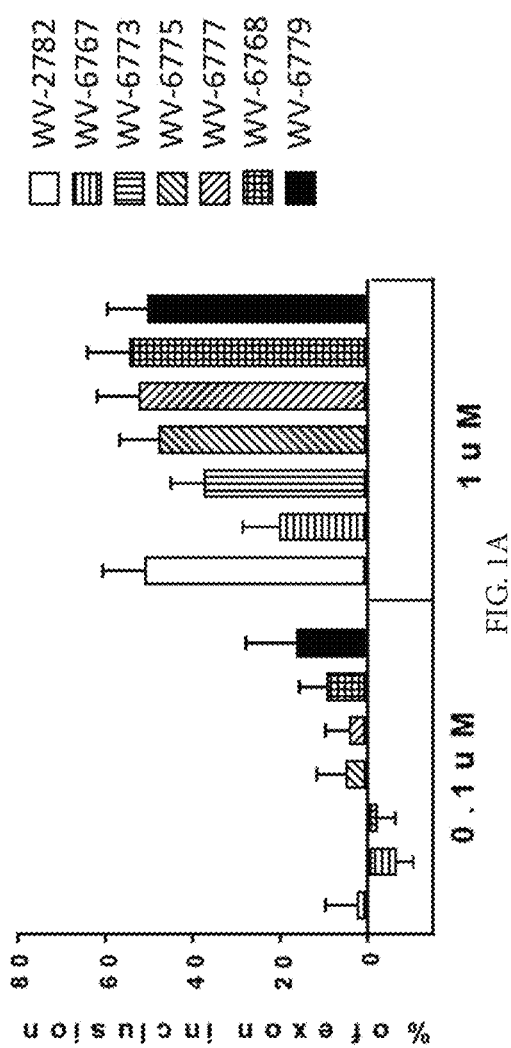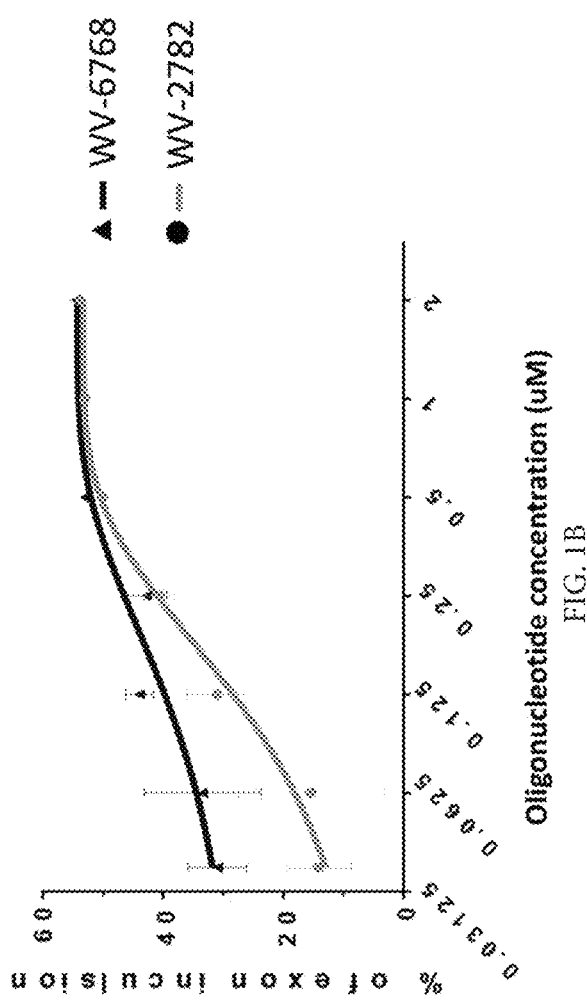
FIG. 1A
FIG. 1B

OLIGONUCLEOTIDE COMPOSITIONS AND METHODS THEREOF

CROSS-REFERENCE TO RELATED APPLICATIONS

This application is a National Stage Entry of PCT Application No. PCT/US2018/055653, filed Oct. 12, 2018 and published Apr. 18, 2019 as WO 2019/075357, which claims priority to United States Provisional Application Nos. 62/571,686 filed Oct. 12, 2017, and 62/701,078, filed Jul. 20, 2018, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Nov. 14, 2018, is named Sequence_Listing.txt and is 120,641 bytes in size.

BACKGROUND

It is reported that improved, in some cases corrected, RNA splicing may be beneficial to patients having or suffering from certain conditions, disorders, and/or diseases, e.g., SMA (spinal muscular atrophy), ALS (amyotrophic lateral sclerosis), etc.

SUMMARY

Among other things, the present disclosure provides technologies (e.g., compositions, methods, etc.) for altering splicing of nucleic acids, particularly splicing of transcripts. In some embodiments, the present disclosure provides oligonucleotide compositions and methods thereof that can promote inclusion of a certain nucleic acid sequence, e.g., an exon or a portion thereof, in splicing products compared to an appropriate reference condition (e.g., absence of the oligonucleotide compositions, presence of an appropriate reference oligonucleotide composition, etc.). Particularly, the present disclosure encompasses the recognition that stereochemistry (e.g., of chiral linkage phosphorus atoms), optionally combined with chemical modifications, e.g., sugar modifications, base modifications, internucleotidic linkage modifications, etc., can provide oligonucleotides and compositions thereof with improved properties and/or activities. As recognized and demonstrated in the present disclosure, oligonucleotide stereoisomers, such as those contained in stereorandom oligonucleotide compositions (e.g., those comprising a plurality of oligonucleotides sharing the same constitution (as appreciated by those skilled in the art, identity and connectivity (and corresponding bond multiplicities) of atoms in a molecular entity (omitting any distinction arising from their spatial arrangement)) but different stereochemical configurations at their linkage phosphorus atoms) can have dramatically different properties and/or activities, e.g., activity for promoting inclusion of certain exons in splicing products; thus, stereorandom oligonucleotide compositions are random mixtures of oligonucleotides having different properties and/or activities, including oligonucleotides that have no desired activities and/or even negative effects. Among other things, the present disclosure demonstrates that chirally controlled oligonucleotide compositions (e.g., a chirally controlled oligonucleotide composition comprising a non-random (pre-determined) level of a plurality of identical oligonucleotides) can provide more uniform and/or improved properties and/or activities, e.g., more effective inclusion of desired nucleic acid sequences in splicing products (e.g., more effective inclusion of desired exons in mRNA products), compared to an appropriate reference oligonucleotide composition (e.g., an otherwise identical but non-chirally controlled oligonucleotide composition).

In some embodiments, provided technologies are particularly useful for promoting inclusion of a target exon into a splicing product compared to an appropriate reference technology. In some embodiments, a target exon is an exon that is absent from one or more splicing products but are present in one or more other splicing products. In some embodiments, one or more splicing products that contain a target exon is not associated, or is associated to a lesser extent, with a condition, disorder or disease compared to one or more splicing products that do not contain the target exon. In some embodiments, provided technologies provide an increased level of inclusion of a nucleic acid sequence, e.g., a target exon, into one or more splicing products compared to a reference technology. In some embodiments, an increase is about at least 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, or 1,000% of a reference level (e.g., level of a reference technology).

In some embodiments, the present disclosure provides a composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
which composition is chirally controlled in that it is enriched, relative to a substantially racemic preparation of oligonucleotides having the same base sequence, for oligonucleotides of the particular oligonucleotide type, wherein:
the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

Among other things, the present disclosure demonstrates that oligonucleotides comprising additional chemical moieties (e.g., carbohydrate moieties), particularly chemical moieties that bind to the asialoglycoprotein receptor (ASGR or ASPGR), can provide unexpectedly high activities (e.g., see FIG. 3). In some embodiments, an oligonucleotide, an oligonucleotide composition, a plurality of oligonucleotides, and/or a particular oligonucleotide type is further characterized or defined by chemical modifications including but not limited to: sugar modifications or patterns thereof, and/or additional chemical moieties. In some embodiments, an oligonucleotide, an oligonucleotide composition, a plurality of oligonucleotides, and/or a particular oligonucleotide type is further characterized or defined by chemical modifications including but not limited to: sugar modifications or patterns thereof, and/or an additional chemical moiety capable of binding to the asialoglycoprotein receptor (ASGR or ASPGR). In some embodiments, an oligonucleotide comprising one or more additional chemical moieties, e.g., ASGR ligands (e.g., GalNAc moieties or a variant or derivative thereof), is an SMN2 oligonucleotide. In some embodiments, an oligonucleotide comprising one or more additional chemical moieties, e.g., ASGR ligands (e.g., GalNAc moieties or a variant or derivative thereof), is a stereorandom SMN2 oligonucleotide (e.g., an oligonucleotide comprising the oligonucleotide chain of Nusinersen and one or more additional chemical moieties (e.g., Mod001 connected to 5'-end of Nusinersen optionally through a linker as certain oligonucleotides in Table 1A)). In some embodiments, a provided oligonucleotide composition is a stereorandom oligonucleotide composition comprising a stereorandom SMN2 oligonucleotide that comprises one or more additional chemical moieties, e.g., ASGR ligands (e.g., GalNAc moieties or a variant or derivative thereof). In some embodiments, an oligonucleotide comprising one or more additional chemical moieties, e.g., ASGR ligands (e.g., GalNAc moieties or a variant or derivative thereof), is a chirally controlled SMN2 oligonucleotide. In some embodiments, a provided oligonucleotide composition is a chirally controlled oligonucleotide composition comprising a plurality of SMN2 oligonucleotides each of which comprises one or more additional chemical moieties, e.g., ASGR ligands (e.g., GalNAc moieties or a variant or derivative thereof), wherein the SMN2 oligonucleotides comprise one or more chirally controlled internucleotidic linkages as described in the present disclosure. In some embodiments, SMN2 oligonucleotides of the plurality are structurally identical.

Various chemical moieties that can bind to ASGR and many technologies for designing, developing, preparing, and/or assessing ASGR ligand are known in the art and can be utilized in accordance with the present disclosure. In some embodiments, an additional chemical moiety is, comprises, or is a derivative of an ASGR ligand. In some embodiments, an additional chemical moiety is a carbohydrate moiety (e.g., monocyclic, bicyclic, polycyclic sugar moieties). In some embodiments, an additional chemical moiety is galactose or a derivative thereof. In some embodiments, an additional chemical moiety is GalNAc or a variant or derivative thereof. In some embodiments, an oligonucleotide comprises two or more additional chemical moieties, which can be the same or different. In some embodiments, an oligonucleotide comprises two or more ASGR ligand moieties, for example, in some embodiments, an oligonucleotide comprises two or more GalNAc moieties or a variant or derivative thereof. In some embodiments, as demonstrated herein, GalNAc or a variant or derivative thereof can be incorporated as mono-antennary, bi-antennary, tri-antennary, or multi-antennary (e.g., comprising four or more branches or antennae) structures (e.g., as in Mod001).

In some embodiments, an SMN2 oligonucleotide, an SMN2 oligonucleotide composition, a plurality of SMN2 oligonucleotides, and/or a particular SMN2 oligonucleotide type comprises an additional chemical moiety capable of binding to the asialoglycoprotein receptor (ASGR or ASPGR), wherein the additional chemical moiety is GalNAc or a variant or derivative thereof.

In some embodiments, provided oligonucleotides and/or compositions, e.g., an SMN2 oligonucleotide, an SMN2 oligonucleotide composition, a plurality of SMN2 oligonucleotides, and/or a particular SMN2 oligonucleotide type, etc., comprise one or more (e.g., 1, 2, 3, 4, 5, 6, 7, 8, 9, 10, 11, 12, 13, 14, 15, 16, 17, 18, 19, 20, or more) chirally controlled internucleotidic linkages and one or more additional chemical moieties capable of binding to the asialoglycoprotein receptor (ASGR or ASPGR). In some embodiments, an additional chemical moiety is GalNAc or a variant or derivative thereof.

In some embodiments, provided oligonucleotides and/or compositions, e.g., an SMN2 oligonucleotide, an SMN2 oligonucleotide composition, a plurality of SMN2 oligonucleotides, and/or a particular SMN2 oligonucleotide type, do not comprise a chirally controlled internucleotidic linkage (stereorandom or not chirally controlled) but comprise an additional chemical moiety capable of binding to the asialoglycoprotein receptor (ASGR or ASPGR). In some embodiments, an additional chemical moiety is GalNAc or a variant or derivative thereof.

In some embodiments, a negative control reference composition is a composition in whose presence inclusion of an exon occurs at a level lower or no more than a target threshold of interest. In some embodiments, a target threshold of interest is a level of exon inclusion of an oligonucleotide composition which is not chirally controlled and/or does not further comprise an additional chemical moiety capable of binding to the asialoglycoprotein receptor, e.g., Nusinersen for SMN2 exon 7 inclusion. In some embodiments, a target threshold is 1, 1.1, 1.2, 1.3, 1.4, 1.5, 1.6, 1.7, 1.8, 1.9, 2, 2.5, 3, 3.5, 4, 4.5, 5, 6, 7, 8, 9, or 10 fold of a level of exon inclusion observed in the absence of any oligonucleotides or other treatment in an otherwise identical or comparable condition. In some embodiments, a target threshold is 1, 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, or 20, or more standard deviation above a level of exon inclusion observed in the absence of any oligonucleotides or other treatment in an otherwise identical or comparable condition.

In some embodiments, the present disclosure provides a method for altering splicing of a nucleic acid, comprising administering an oligonucleotide composition comprising a plurality of oligonucleotides of a particular oligonucleotide type defined by:
 1) base sequence;
 2) pattern of backbone linkages;
 3) pattern of backbone chiral centers; and
 4) pattern of backbone phosphorus modifications,
which composition is chirally controlled in that it is enriched, relative to a substantially racemic preparation of oligonucleotides having the same base sequence, for oligonucleotides of the particular oligonucleotide type, wherein:
 the oligonucleotide composition is characterized in that, when it is contacted with a nucleic acid in a nucleic acid splicing system, splicing of the nucleic acid is altered in that level of inclusion of a target nucleic acid sequence is increased relative to that observed under a reference condition selected from the group consisting of absence of the composition, presence of a reference composition, and combinations thereof.

In some embodiments, the present disclosure provides a method for altering splicing of a target transcript, comprising administering an oligonucleotide composition comprising a plurality of oligonucleotides of a particular oligonucleotide type defined by:
 1) base sequence;
 2) pattern of backbone linkages;
 3) pattern of backbone chiral centers; and
 4) pattern of backbone phosphorus modifications,
which composition is chirally controlled in that it is enriched, relative to a substantially racemic preparation of oligonucleotides having the same base sequence, for oligonucleotides of the particular oligonucleotide type, wherein:
 the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a reference composition, and combinations thereof.

In some embodiments, the present disclosure provides, in a method for altering splicing of a nucleic acid by contacting the nucleic acid with an oligonucleotide composition comprising oligonucleotides sharing a common base sequence, the improvement that comprises using as the oligonucleotide composition a chirally controlled oligonucleotide composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications, which composition is chirally controlled in that it is enriched, relative to a substantially racemic preparation of oligonucleotides having the same common base sequence, for oligonucleotides of the particular oligonucleotide type, wherein:

the chirally controlled oligonucleotide composition is characterized in that, when it is contacted with a nucleic acid in a nucleic acid splicing system, splicing of the nucleic acid is altered in that level of inclusion of a target nucleic acid sequence is increased relative to that observed when using an otherwise comparable oligonucleotide composition, comprising oligonucleotides of the same common base sequence, that is not chirally controlled.

In some embodiments, the present disclosure provides, in a method for altering transcript splicing of a target transcript by contacting the transcript with an oligonucleotide composition comprising oligonucleotides sharing a common base sequence, the improvement that comprises using as the oligonucleotide composition a chirally controlled oligonucleotide composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications, which composition is chirally controlled in that it is enriched, relative to a substantially racemic preparation of oligonucleotides having the same common base sequence, for oligonucleotides of the particular oligonucleotide type, wherein:

the chirally controlled oligonucleotide composition is characterized in that, when it is contacted with a transcript in a transcript splicing system, splicing of the transcript is altered in that level of inclusion of a nucleic acid sequence is increased relative to that observed when using an otherwise comparable oligonucleotide composition, comprising oligonucleotides of the same common base sequence, that is not chirally controlled.

In some embodiments, oligonucleotides of the same oligonucleotide type have the same base and/or sugar modifications, and/or additional chemical moieties. In some embodiments, oligonucleotides of the same type are structurally identical.

In some embodiments, in provided methods the oligonucleotides of the particular oligonucleotide type further comprise an additional chemical moiety capable of binding to the asialoglycoprotein receptor (ASGR or ASPGR). In some embodiments, the additional chemical moiety is GalNAc or a variant or derivative thereof.

In some embodiments, provided methods are performed in the central nervous system and/or liver and/or other tissue that typically express the asialoglycoprotein receptor.

Among other things, the present disclosure demonstrates that the incorporation of a chemical moiety capable of binding to the asialoglycoprotein receptor improves the efficacy of oligonucleotides in treating and/or preventing SMA as shown in a SMA equivalent in test animals. Without wishing to be bound by any particular theory, the improvement may be related to increased delivery to, and/or increased production of functional transcripts (e.g., full-length SMN in SMA) and/or products thereof, in the central nervous system and/or liver and/or other tissues that express the asialoglycoprotein receptor.

In some embodiments, a base sequence of provided oligonucleotides is or comprises a base sequence that is at least 60%, 65%, 70%, 75%, 80%, 85%, 90%, or 95%, or 100%, complementary to, or identical with, a portion of a nucleic acid sequence. In some embodiments, a base sequence is at least 60%, 65%, 70%, 75%, 80%, 85%, 90%, or 95%, or 100%, complementary to a portion of a transcript. In some embodiments, a base sequence is at least 60%, 65%, 70%, 75%, 80%, 85%, 90%, or 95%, or 100%, identical with a portion of a transcript. In some embodiments, a base sequence is at least 60%, 65%, 70%, 75%, 80%, 85%, 90%, or 95%, or 100%, complementary to a portion of a pre-mRNA. In some embodiments, a base sequence is at least 60%, 65%, 70%, 75%, 80%, 85%, 90%, or 95%, or 100%, identical with a portion of a pre-mRNA. In some embodiments, a base sequence is at least 60%, 65%, 70%, 75%, 80%, 85%, 90%, or 95%, or 100%, complementary to a portion of an intron sequence. In some embodiments, a base sequence is at least 60%, 65%, 70%, 75%, 80%, 85%, 90%, or 95%, or 100%, identical with a portion of an intron sequence. In some embodiments, a base sequence is at least 60%, 65%, 70%, 75%, 80%, 85%, 90%, or 95%, or 100%, complementary to a portion of a mRNA. In some embodiments, a base sequence is at least 60%, 65%, 70%, 75%, 80%, 85%, 90%, or 95%, or 100%, identical with a portion of a mRNA. In some embodiments, a percentage is at least 80%. In some embodiments, a percentage is at least 85%. In some embodiments, a percentage is at least 90%. In some embodiments, a percentage is at least 95%. In some embodiments, a percentage is 100%. In some embodiments, a portion is at least 10, 11, 12, 13, 14, 15, 16, 17, 18, 19, 20, 21, 22, 23, 24 or 25 nucleobases in length. In some embodiments, a portion is unique to a nucleic acid in that no other genomic sequences or transcripts therefrom contain an identical sequence to the portion. In some embodiments, an oligonucleotide targeting a nucleic acid, wherein a base sequence of the oligonucleotide is or comprises a base sequence that is at least 60%, 65%, 70%, 75%, 80%, 85%, 90%, or 95%, or 100% complementary to a portion of the nucleic acid sequence as described in the present disclosure. In some embodiments, an oligonucleotide targeting a nucleic acid, wherein a base sequence of the oligonucleotide is or comprises a base sequence that is at least 60%, 65%, 70%, 75%, 80%, 85%, 90%, or 95%, or 100% identical to a portion of the nucleic acid sequence as described in the present disclosure.

In some embodiments, a base sequence of provided oligonucleotides is or comprises a base sequence which is at least 60%, 65%, 70%, 75%, 80%, 85%, 90%, or 95%, or 100%, complementary to, or identical with, a portion of a SMN2 sequence ("SMN2 oligonucleotides"). In some embodiments, a base sequence is at least 60%, 65%, 70%, 75%, 80%, 85%, 90%, or 95%, or 100%, complementary to a portion of a SMN2 sequence. In some embodiments, a base sequence is at least 60%, 65%, 70%, 75%, 80%, 85%, 90%, or 95%, or 100%, identical with a portion of a SMN2 sequence. In some embodiments, a base sequence is at least 60%, 65%, 70%, 75%, 80%, 85%, 90%, or 95%, or 100%, complementary to a portion of a SMN2 transcript. In some embodiments, a base sequence is at least 60%, 65%, 70%, 75%, 80%, 85%, 90%, or 95%, or 100%, identical with a portion of a SMN2 transcript. In some embodiments, a base sequence is at least 60%, 65%, 70%, 75%, 80%, 85%, 90%, or 95%, or 100%, complementary to a portion of a SMN2 pre-mRNA. In some embodiments, a base sequence is at least 60%, 65%, 70%, 75%, 80%, 85%, 90%, or 95%, or 100%, identical with a portion of a SMN2 pre-mRNA. In some embodiments, a base sequence is at least 60%, 65%, 70%, 75%, 80%, 85%, 90%, or 95%, or 100%, complementary to a portion of a SMN2 intron sequence. In some embodiments, a base sequence is at least 60%, 65%, 70%, 75%, 80%, 85%, 90%, or 95%, or 100%, identical with a portion of a SMN2 intron sequence. In some embodiments, a base sequence is at least 60%, 65%, 70%, 75%, 80%, 85%, 90%, or 95%, or 100%, complementary to a portion of a SMN2 mRNA. In some embodiments, a base sequence is at least 60%, 65%, 70%, 75%, 80%, 85%, 90%, or 95%, or 100%, identical with a portion of a SMN2 mRNA. In some embodiments, a percentage is at least 80%. In some embodiments, a percentage is at least 85%. In some embodiments, a percentage is at least 90%. In some embodiments, a percentage is at least 95%. In some embodiments, a percentage is 100%. In some embodiments, the percentage is 100% and the portion is at least 10, 11, 12, 13, 14, 15, 16, 17, 18, 19, 20, 21, 22, 23, 24 or 25 nucleobases in length. In some embodiments, the present disclosure provides oligonucleotide compositions targeting SMN2 which are useful in various applications, e.g., therapeutic, diagnostic, and/or research applications, including but not limited to treatment of various SMN2-related conditions, disorders, and/or diseases, e.g., SMA (spinal muscular atrophy), ALS (amyotrophic lateral sclerosis), etc. In some embodiments, provided oligonucleotide compositions are chirally controlled oligonucleotide compositions. In some embodiments, an oligonucleotide targeting SMN2 is a SMN2 oligonucleotide. In some embodiments, the sequence of a portion is or comprises TCACTTTCATAATGCTGG (SEQ ID NO: 1).

In some embodiments, the present disclosure pertains to an oligonucleotide composition which targets SMN2 and is capable of enhancing the level, activity, and/or expression of an exon 7-containing SMN2 mRNA. In some embodiments, the present disclosure pertains to an oligonucleotide composition which targets SMN2 and is capable of enhancing the level, activity, and/or expression of an exon 7-containing SMN2 mRNA. In some embodiments, the present disclosure pertains to an oligonucleotide composition which targets SMN2 ISS-N1 and is capable of enhancing the level, activity, and/or expression of an exon 7-containing SMN2 mRNA. In some embodiments, the present disclosure pertains to an oligonucleotide composition which is capable of enhancing the level, activity, and/or expression of an exon 7-containing SMN2 mRNA, wherein the base sequence of the oligonucleotides is TCACTTTCATAATGCTGG (SEQ ID NO: 1). In some embodiments, such oligonucleotide compositions are chirally controlled. In some embodiments, such oligonucleotide compositions comprise oligonucleotides comprising at least one chirally controlled internucleotidic linkage. In some embodiments, such oligonucleotide compositions comprise oligonucleotides comprising at least one chirally controlled phosphorothioate internucleotidic linkage. In some embodiments, such oligonucleotide compositions comprise oligonucleotides which comprise a chirally controlled internucleotidic linkage, and/or an additional chemical moiety capable of binding to the asialoglycoprotein receptor (including but not limited to GalNAc or a variant or derivative thereof).

Among other things, the present disclosure encompasses the recognition that structural elements of oligonucleotides (e.g., SMN2 oligonucleotides), such as base sequence, chemical modifications (e.g., modifications of sugar, base, and/or internucleotidic linkages, and patterns thereof), and/or stereochemistry [e.g., stereochemistry of backbone linkage phosphorus chiral centers (of chiral internucleotidic linkages), and/or patterns thereof], can have a significant impact on activities and/or properties, e.g., stability, toxicity, delivery, etc. In some embodiments, the present disclosure provides oligonucleotides and compositions comprising oligonucleotides that have a particular base sequence, and/or pattern of sugar modifications (e.g., 2'-OMe, 2'-F, 2'-MOE, LNA, cEt, tc-DNA, morpholino, thiomorpholino, etc.), and/or pattern or base modifications (e.g., 5-methylcytosine), and/or pattern of backbone modifications (e.g., natural phosphate linkages, modified internucleotidic linkages, etc.), and/or pattern of backbone chiral centers (e.g., Rp or Sp configuration of backbone linkage phosphorus atoms). In some embodiments, a pattern (e.g., of sugar, base and/or internucleotidic linkage) modifications can be an absence of modifications (e.g., the presence only of natural sugars, bases and/or internucleotidic linkages). For example, if an oligonucleotide comprises only natural nucleobases and no modified bases, its pattern of base modifications consists only of natural bases (no modifications). In some embodiments, provided oligonucleotides can increase levels, expression, and/or activity of beneficial mRNAs and/or products (e.g., proteins) encoded thereby; for example, in some embodiments, the present disclosure provides SMN2 oligonucleotides that can increase level, expression and/or activity of a beneficial SMN2 mRNA and/or its gene product, e.g., an exon 7-containing SMN2 mRNA and/or a full-length SMN protein encoded thereby.

In some embodiments, modifications of internucleotidic linkages can convert linkage phosphorus atoms in modified internucleotidic linkages into chiral centers. For example, in a phosphorothioate diester internucleotidic linkage (phosphorothioate or PS, —O—P(O)(SH)—O—, which can exist as a salt form), one of the non-bridging oxygen (O) atoms bonded to a linkage phosphorus (P) atom is replaced with a sulfur (S) atom. Using a chiral modified internucleotidic linkage, e.g., a PS internucleotidic linkage, in oligonucleotides creates a chiral center at a linkage phosphorus atom, which can have either an "Rp" or "Sp" configuration. Thus, a conventional stereorandom composition of oligonucleotides having n chiral linkage phosphorus atoms (e.g., linkage phosphorus atoms of PS linkages) without control of linkage phosphorus stereochemistry is a random mixture of stereoisomers and can randomly contain over $2^n$ stereoisomers: if n is 10, over 1,000 ($2^{10}$) stereoisomers; if n is 15, over 32,000 ($2^{15}$) stereoisomers; if n is 20, over 1,000,000 ($2^{20}$) stereoisomers.

In a stereorandom mixture, all the oligonucleotides can have the same base sequence, pattern of base modifications, pattern of chemical modifications, pattern of internucleotidic linkages, and additional chemical moieties (if any), but the oligonucleotides differ in stereochemistry of their backbone chiral centers. In some embodiments, a plurality of oligonucleotides in a stereorandom composition have the same constitution but differ in linkage phosphorus stereochemistry and are stereoisomers (often diastereomers). As demonstrated in the present disclosure, various stereoisomers can differ, often dramatically, in their activities and properties; a stereorandom oligonucleotide composition therefore is a random mixture of oligonucleotide stereoisomers of various properties and/or activities. In some embodiments, in contrast to stereorandom compositions, a chirally controlled oligonucleotide composition is chirally controlled in that it comprises a plurality of oligonucleotides which have a) a common base sequence; and b) a common pattern of backbone linkages, which comprises at least one chiral internucleotidic linkage comprising a chiral linkage phosphorus; wherein one or more of the chiral internucleotidic linkages are independently stereochemically pure within the composition (chirally controlled internucleotidic linkages, wherein their chiral linkage phosphorus atoms are not randomly Rp and Sp as in stereorandom compositions). In some embodiments, a plurality of oligonucleotides in a chirally controlled oligonucleotide composition have 1) a common base sequence; 2) a common pattern of backbone linkages; 3) a common pattern of backbone chiral centers; and 4) a pattern of backbone phosphorus modifications, wherein at least one internucleotidic linkage is a chirally controlled internucleotidic linkage. In some embodiments, a plurality of oligonucleotides of a chirally controlled oligonucleotide composition have the same constitution. In some embodiments, a plurality of oligonucleotides of a chirally controlled oligonucleotide composition are of a particular oligonucleotide type defined by 1) base sequence; 2) pattern of backbone linkages; 3) pattern of backbone chiral centers; and 4) pattern of backbone phosphorus modifications. In some embodiments, a chirally controlled oligonucleotide composition is chirally controlled in that it is enriched, relative to a substantially racemic preparation of oligonucleotides having the same common base sequence, for oligonucleotides of the particular oligonucleotide type. In some embodiments, a substantially racemic preparation of oligonucleotides is a composition prepared using traditional phosphoramidite chemistry. In some embodiments, a composition is completely chirally controlled in that each chiral internucleotidic linkage of the plurality of oligonucleotides is independently a chirally controlled internucleotidic linkage. In some embodiments, a chirally controlled oligonucleotide composition is an enriched (compared to a racemic or stereorandom composition) or substantially pure preparation of a single oligonucleotide in that a non-random level of the oligonucleotides have a common base sequence, common pattern of chemical modifications (e.g., base modification, sugar modification, internucleotidic linkage modifications, additional chemical moieties, etc.), a common pattern of backbone linkages, and a common pattern of backbone chiral centers.

In some embodiments, control of stereochemistry enables precise control and ability to optimize critical constructs into one defined and consistent profile. In some embodiments, control of stereochemistry has the potential for safer, more effective, targeted medicines that can address difficult-to-treat diseases. In some embodiments, a chirally controlled (or stereopure) oligonucleotide composition has improved activity relative to a corresponding stereorandom oligonucleotide composition. In some embodiments, a chirally controlled (or stereopure) oligonucleotide composition has increased reliable therapeutic effects and/or decreased unintended off-target effects relative to a corresponding stereorandom oligonucleotide composition.

Among other things, the present disclosure encompasses the recognition that stereorandom oligonucleotide preparations contain a plurality of distinct chemical entities that differ from one another, e.g., in the stereochemical structure (or stereochemistry) of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence, base modifications, and/or chemical modifications, they are different chemical entities at least due to their different backbone stereochemistry, and they can have, as demonstrated herein, different properties, e.g., sensitivity to nucleases, activities, distribution, etc. In some embodiments, a particular stereoisomer may be defined, for example, by its base sequence, its length, its pattern of backbone linkages, and its pattern of backbone chiral centers.

In some embodiments, the present disclosure provides a SMN2 oligonucleotide composition, wherein a SMN2 oligonucleotide is an oligonucleotide which targets a SMN2 transcript. In some embodiments, the present disclosure provides a chirally controlled SMN2 oligonucleotide composition. In some embodiments, a SMN2 oligonucleotide targets an intron sequence of SMN2. In some embodiments, a SMN2 oligonucleotide targets intron 7 of SMN2. In some embodiments, a SMN2 oligonucleotide targets ISS-N1 (intronic splicing silencer) of SMN2. As demonstrated herein, chirally controlled oligonucleotide compositions of oligonucleotides of particular oligonucleotide types demonstrated higher activity (e.g., promoting inclusion of exon 7 of SMN2) than the corresponding stereorandom oligonucleotide compositions, especially at low concentrations.

In some embodiments, the present disclosure provides oligonucleotide compositions comprising an additional chemical moiety capable of binding to the asialoglycoprotein receptor (including but not limited to GalNAc or a variant or derivative thereof), wherein the oligonucleotides target an intron sequence of SMN2. In some embodiments, provided oligonucleotide compositions target intron 7 of SMN2. In some embodiments, provided oligonucleotide compositions target ISS-N1 (intronic splicing silencer) of SMN2. As demonstrated herein, in some embodiments, compositions of oligonucleotides comprising such additional chemical moieties demonstrated higher activity (e.g., prevention or treatment of SMA or an equivalent disorder) than the corresponding oligonucleotide composition which lacks the additional moiety. In some embodiments, provided oligonucleotide compositions are chirally controlled. In some embodiments, provided compositions oligonucleotide are not chirally controlled.

In some embodiments, the present disclosure provides methods for treating conditions, disorders and/or diseases associated with splicing, particularly splicing that excludes one or more exons and leads to mRNA and/or proteins of lower activities compared to those produced when said one or more exons are included. In some embodiments, the present disclosure pertains to a method of treating a SMN2-related condition, disorder, or disease (e.g., SMA, ALS, etc.) in a subject, comprising administering a therapeutically effective amount of a chirally controlled SMN2 oligonucleotide composition to a subject suffering therefrom or susceptible thereto.

In some embodiments, base sequence of a provided oligonucleotide (e.g. an oligonucleotide in a composition, e.g., a provided chirally controlled oligonucleotide composition, an oligonucleotide comprising an additional chemical moiety capable of binding to the asialoglycoprotein receptor and/or a chirally controlled internucleotidic linkage, etc.) is or comprises, or is complementary to (e.g., can completely hybridize to) a sequence that is or comprises a target sequence. In some embodiments, base sequence of a provided oligonucleotide is, or is complementary to (e.g., can completely hybridize to) a target sequence. In some embodiments, base sequence of a provided oligonucleotide is a target sequence. In some embodiments, a target sequence is a sequence to which an SMN2 oligonucleotide binds. In some embodiments, a base sequence or a target sequence of a provided oligonucleotide is TCACTTTCATAATGCTGG (SEQ ID NO: 479) or CUUUCNNNNNGCUGG (SEQ ID NO: 2), or a portion thereof comprising 13 contiguous bases of TCACTTTCATAATGCTGG (SEQ ID NO: 479) or CUUUCNNNNNGCUGG (SEQ ID NO: 2), wherein each T can be independently substituted with U and vice versa. In some embodiments, a base sequence or a target sequence of a provided oligonucleotide is TCACTTTCATAATGCTGG (SEQ ID NO: 479) or CUUUCNNNNNGCUGG (SEQ ID NO: 2), or a portion thereof comprising 15 contiguous bases, or a sequence comprising 15 contiguous bases (with 0-3 mismatches) of TCACTTTCATAATGCTGG (SEQ ID NO: 479) or CUUUCNNNNNGCUGG (SEQ ID NO: 2), wherein each T can be independently substituted with U and vice versa. In some embodiments, an oligonucleotide having a base sequence described herein further comprise an additional chemical moiety capable of binding to the asialoglycoprotein receptor (ASGR or ASPGR). In some embodiments, the additional chemical moiety is GalNAc or a variant or derivative thereof. In some embodiments, a base sequence or a target sequence of a SMN2 oligonucleotide is TCACTTTCATAATGCTGG (SEQ ID NO: 479) or CUUUCNNNNNGCUGG (SEQ ID NO: 2), or a portion thereof comprising 13 contiguous bases of TCACTTTCATAATGCTGG (SEQ ID NO: 479) or CUUUCNNNNNGCUGG (SEQ ID NO: 2), wherein each T can be independently substituted with U and vice versa, and wherein the SMN2 oligonucleotide comprises an additional chemical moiety capable of binding to the asialoglycoprotein receptor (ASGR or ASPGR). In some embodiments, compositions of such SMN2 oligonucleotides are chirally controlled. In some embodiments, compositions of such SMN2 oligonucleotides are stereorandom. In some embodiments, a base sequence or a target sequence of a SMN2 oligonucleotide is TCACTTTCATAATGCTGG (SEQ ID NO: 479) or CUUUCNNNNNGCUGG (SEQ ID NO: 2), or a portion thereof comprising 13 contiguous bases of TCACTTTCATAATGCTGG (SEQ ID NO: 479) or CUUUCNNNNNGCUGG (SEQ ID NO: 2), wherein each T can be independently substituted with U and vice versa, and wherein the SMN2 oligonucleotide is stereorandom and the oligonucleotide comprises an additional chemical moiety capable of binding to the asialoglycoprotein receptor (ASGR or ASPGR). In some embodiments, a base sequence or a target sequence of a SMN2 oligonucleotide is TCACTTTCATAATGCTGG (SEQ ID NO: 479) or CUUUCNNNNNGCUGG (SEQ ID NO: 2), or a portion thereof comprising 13 contiguous bases of TCACTTTCATAATGCTGG (SEQ ID NO: 479) or CUUUCNNNNNGCUGG (SEQ ID NO: 2), wherein each T can be independently substituted with U and vice versa, and wherein the SMN2 oligonucleotide is chirally controlled and the oligonucleotide comprises an additional chemical moiety capable of binding to the asialoglycoprotein receptor (ASGR or ASPGR). In some embodiments, the additional chemical moiety is GalNAc or a variant or derivative thereof. In many embodiments, a target sequence is identical to, or is an exact complement of, a sequence of a provided oligonucleotide, or of consecutive residues therein (e.g., a provided chirally controlled SMN2 oligonucleotide composition comprises a plurality of oligonucleotides whose common base sequence includes a target-binding sequence that is identical to, or an exact complement of, a target sequence). In some embodiments, a target binding sequence is an exact complement of a target sequence of a transcript (e.g., pre-mRNA, mRNA, etc.). A target-binding sequence/target sequence can be of various lengths to provide oligonucleotides with desired activities and/or properties. In some embodiments, a target binding sequence/target sequence comprises 5-50 (e.g., 10-40, 15-30, 15-25, 16-25, 17-25, 18-25, 19-25, 20-25, 10, 11, 12, 13, 14, 15, 16, 17, 18, 19, 20, 21, 22, 23, 24, 25, or more) bases. In some embodiments, a small number of differences/mismatches is tolerated between (a relevant portion of) an oligonucleotide and its target sequence, including but not limited to the 5' and/or 3'-end regions of the target and/or oligonucleotide sequence. In many embodiments, a target sequence is present within a target gene. In many embodiments, a target sequence is present within a transcript (e.g., an mRNA and/or a pre-mRNA) produced from a target gene. In some embodiments, a target sequence is an intron sequence. In some embodiments, a target sequence is an exon sequence. In some embodiments, a sequence is any sequence disclosed herein. In some embodiments, a target sequence is in intron 7 of SMN2. In some embodiments, a target sequence is or comprises ISS-N1. In some embodiments, a target sequence is or comprises a sequence complementary to ISS-N1. In some embodiments, a target sequence is ISS-N1. In some embodiments, a target sequence is complementary to ISS-N1. In some embodiments, a target sequence is or comprises a sequence that is about 60-100%, e.g., 60%, 65%, 70%, 75%, 80%, 85%, 90%, 95%, or 100%, identical to ISS-N1. In some embodiments, a target sequence is or comprises a sequence that is about 60-100%, e.g., 60%, 65%, 70%, 75%, 80%, 85%, 90%, 95%, or 100%, complementary to ISS-N1.

In some embodiments, the present disclosure provides oligonucleotides having a base sequence which consists of, comprises, or comprises a portion (e.g., a span of 10, 11, 12, 13, 14, 15, 16, 17, 18, 19 or more contiguous bases) of a base sequence disclosed herein (wherein each U can be independently substituted by T and vice versa) and which comprise at least one sugar, base or internucleotidic linkage or modification thereof described herein or known in the art, including but not limited to, sugars, bases, and internucleotidic linkages of natural RNA and DNA, 2'-modifications such as 2'-MOE, 2'-OMe, and 2'-F, nucleobase modifications such as 5'-methyl, 5'-E-vinyl phosphonate (5'-E-VP) or 5'-vinyl, modifications as in LNA, cEt, cyclo-DNA, and morpholino, phosphodiester linkage (natural phosphate linkage, —O—P(O)OH—O—, and salt forms thereof), phosphorothioate diester linkage (phosphorothioate linkage, —O—P(O)SH—O—, and salt forms thereof, optionally and independently as stereochemical pure Rp or Sp forms thereof) etc. In some embodiments, a base, sugar or internucleotidic linkage is alkylated or halogenated.

Unless otherwise noted, all sequences presented herein (e.g., base sequences, patterns of chemistry, modification, and/or stereochemistry, etc.) are presented in 5' to 3' order.

In some embodiments, the present disclosure encompasses the recognition that various optional additional chemical moieties, such as carbohydrate moieties, sugar moieties, targeting moieties, etc., when incorporated into oligonucleotides, can improve one or more properties and/or activities. In some embodiments, an additional chemical moiety is a lipid moiety. In some embodiments, an additional moiety is a carbohydrate moiety. In some embodiments, an additional chemical moiety is a targeting moiety. In some embodiments, an additional chemical moiety is selected from a lipid, GalNac, glucose, GluNAc (N-acetyl amine glucosamine) and anisamide moieties, including mono-, di- and triantennary forms thereof, and moieties having the structures of:

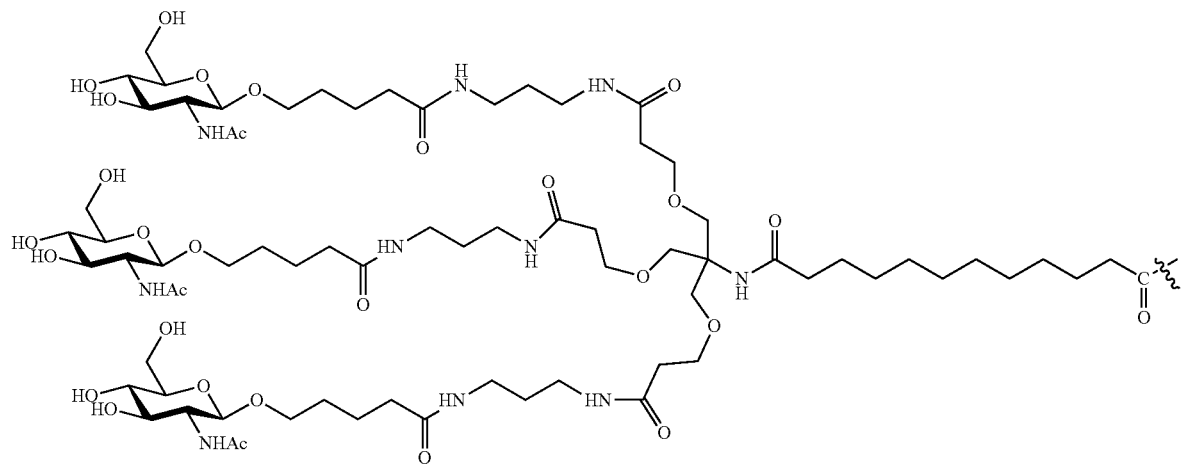
,
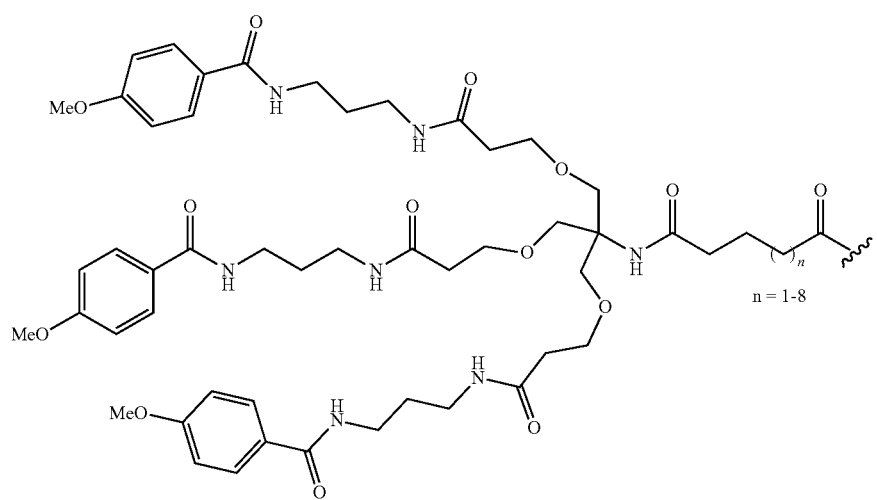
n = 1-8
,
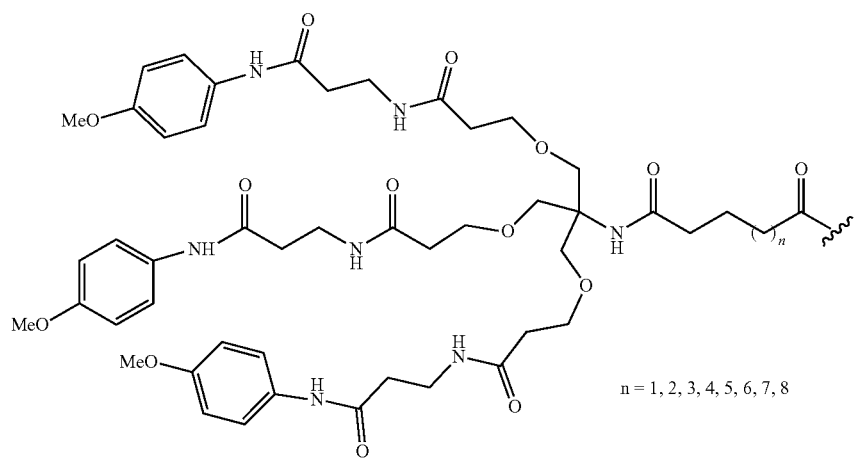
n = 1, 2, 3, 4, 5, 6, 7, 8
,

-continued

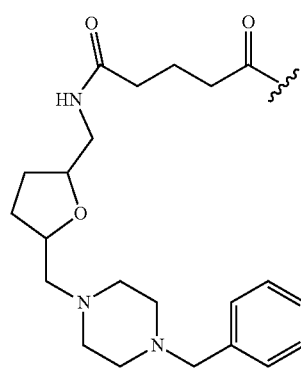

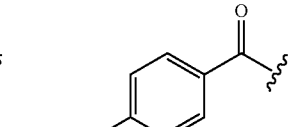

$R^s$ = F, OMe, OH, NHAc, MHCOCF$_3$

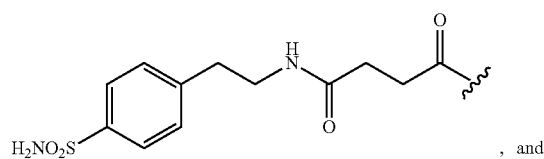

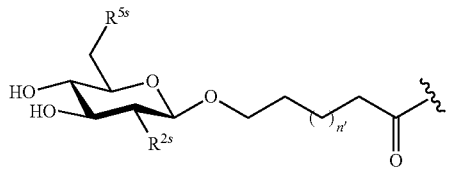

n' = 0, 1

$R^{2s}$ = NHAc, $R^{5s}$ = OH;
$R^{2s}$ = NHCOC6H4OMe(p-anisoyl), $R^{5s}$ = OH;
$R^{2s}$ = NHAc, $R^{5c}$ = NHCOC6H4OMe(p-anisoyl); or
$R^{2s}$ = OH, $R^{5s}$ = NHCOC6H4OMe(p-anisoyl)

In some embodiments, an oligonucleotide can comprise two or more additional chemical moieties, wherein the additional chemical moieties are identical or different, or are of the same category (e.g., carbohydrate moiety, sugar moiety, targeting moiety, etc.) or not of the same category. In some embodiments, certain additional chemical moieties facilitate delivery of oligonucleotides to desired cells, tissues and/or organs, including but not limited to particular cells, parts or portions of the central nervous system. In some embodiments, certain additional chemical moieties facilitate internalization of oligonucleotides. In some embodiments, certain additional chemical moieties increase oligonucleotide stability. In some embodiments, the present disclosure provides technologies for incorporating various additional chemical moieties into oligonucleotides. In some embodiments, the present disclosure provides, for example, reagents and methods, for introducing additional chemical moieties through internucleotidic linkages, sugars and/or nucleobases (e.g., by covalent linkage, optionally via a linker, to a site on a sugar, a nucleobase, or an internucleotidic linkage).

In some embodiments, the present disclosure provides preferential increase of level and/or activity of a transcript of a nucleic acid sequence (e.g., an exon 7-containing mRNA), which transcript comprises a target exon that is absent from a disease-associated, reference transcript of the nucleic acid sequence (e.g., exon 7-deleted SMN2 mRNA), wherein the transcript is less or not disease-associated compared to the reference transcript, and/or whose encoded product (e.g., full length SMN protein or FL-SMN) is less or not disease-associated compared to the encoded product of the reference transcript, and/or can alleviate and/or treat a condition, disorder and/or disease associated with an encoded product of the reference transcript (e.g., a truncated SMN protein from exon 7-deleted SMN2 mRNA, which protein is generally readily degraded). In some embodiments, provided technologies increase the level of a target-exon containing mRNA, e.g., an exon 7-containing SMN2 mRNA, or a product encoded thereby, by at least 10, 20, 30, 40, 50, 60, 70, 80, 90, 100, 150, 200, 300, 400, 500 percent or more, relative to a control or reference condition. In some embodiments, a control or reference condition can be absence of a treatment/SMN2 oligonucleotide composition which is chirally controlled and/or further comprises an additional chemical moiety capable of binding to the asialoglycoprotein receptor. In some embodiments, a control or reference condition can be administration of a stereorandom oligonucleotide composition, such as a stereorandom SMN2 oligonucleotide composition (e.g., a Nusinersen composition). Nusinersen is reportedly prepared as a stereorandom SMN2 oligonucleotide composition, wherein the oligonucleotides have the base sequence of TCACTTTCAT-AATGCTGG (SEQ ID NO: 1) and each sugar moiety is a 2'-MOE and each internucleotidic linkage is a phosphorothioate internucleotidic linkage, but the composition is non-chirally controlled (stereorandom) in that a mixture of stereoisomers with different backbone stereochemistry patterns exist in the composition at random levels.

In some embodiments, a SMN2 oligonucleotide comprises a non-negatively charged internucleotidic linkage. In some embodiments, a SMN2 oligonucleotide has a base sequence which is any base sequence described herein (e.g., a base sequence of an oligonucleotide in Table 1A) and comprises a non-negatively charged internucleotidic linkage. In some embodiments, a SMN2 oligonucleotide has a base sequence which is any base sequence described herein and comprises a non-negatively charged internucleotidic linkage, and further comprises an additional chemical moiety capable of binding to the asialoglycoprotein receptor. In some embodiments, provided compositions of such SMN2 oligonucleotides are chirally controlled. In some embodiments, provided compositions of such SMN2 oligonucleotides are not chirally controlled.

In some embodiments, a reference and/or negative control composition is a stereorandom (non-chirally controlled) SMN2 oligonucleotide composition comprising oligonucleotides that share the same constitution as oligonucleotides of a chirally controlled oligonucleotide composition. In some embodiments, a reference and/or negative control composition is a SMN2 oligonucleotide composition whose SMN2 oligonucleotides do not contain any additional chemical moieties capable of binding to the asialoglycoprotein receptor.

In some embodiments, a reference and/or control composition is a Nusinersen composition, which is stereorandom and lacks an additional chemical moiety capable of binding to the asialoglycoprotein receptor. In some embodiments, in some experiments described herein, Nusinersen is represented by WV-2782. In some embodiments, as demonstrated herein, SMN2 oligonucleotide compositions which are chirally controlled and/or comprise additional chemical moieties capable of binding to the asialoglycoprotein receptor have unexpectedly high activities, improved delivery, and/or decreased immune response relative to a Nusinersen composition.

In some embodiments, administration of a provided composition, e.g., a chirally controlled oligonucleotide composition, is associated with longer duration of activity, higher activity at low concentrations, and/or fewer and/or less severe adverse effects than administration of an equivalent amount of a corresponding stereorandom oligonucleotide composition.

In some embodiments, administration of a SMN2 oligonucleotide composition whose oligonucleotides comprise additional chemical moieties capable of binding to the asialoglycoprotein receptor (including but not limited to GalNAc or a variant or derivative thereof) is associated with longer duration of activity and/or other beneficial characteristics than administration of an equivalent amount of a corresponding oligonucleotide composition whose oligonucleotides do not contain such additional chemical moieties. In some embodiments, a SMN2 oligonucleotide composition is chirally controlled. In some embodiments, a SMN2 oligonucleotide composition is stereorandom.

In some embodiments, administration of a stereorandom SMN2 oligonucleotide composition whose oligonucleotides comprise additional chemical moieties capable of binding to the asialoglycoprotein receptor (including but not limited to GalNAc or a variant or derivative thereof) is associated with longer duration of activity and/or other beneficial characteristics than administration of an equivalent amount of a corresponding oligonucleotide composition whose oligonucleotides do not contain such additional chemical moieties.

In clinical trials, people treated with Nusinersen reportedly had an increased risk of upper and lower respiratory infections and congestion, ear infections, constipation, pulmonary aspiration, teething, and scoliosis. One infant in a clinical trial reportedly had severe lowering of salt levels and several had rashes. There is a reported risk that growth of infants and children might be stunted. In older clinical trial subjects, the most common adverse events were reportedly headache, back pain, and adverse effects from the spinal injection.

In some embodiments, administration of provided oligonucleotide compositions, e.g., a chirally controlled oligonucleotide composition, a SMN2 oligonucleotide composition, etc. is associated with fewer and/or less severe adverse effects than administration of an equivalent or comparable amount of a corresponding stereorandom oligonucleotide composition, e.g., a Nusinersen composition.

In some embodiments, the present disclosure demonstrates that certain provided structural elements, technologies and/or features are particularly useful for oligonucleotides that enhance the level, expression and/or activity of exon 7-containing SMN2 mRNA or its gene product relative to a SMN2 mRNA that does not contain exon 7 in a cell extract, cell, tissue, organ and/or organism. Regardless, however, the teachings of the present disclosure are not limited to oligonucleotides that participate in or operate via any particular mechanism. In some embodiments, the present disclosure provides oligonucleotides that modulate mRNA splicing. In some embodiments, the present disclosure provides oligonucleotides that modulate SMN2 mRNA splicing. In some embodiments, the present disclosure provides oligonucleotides that modulate SMN2 mRNA splicing in that they decrease skipping of exon 7 of the SMN2 gene. In some embodiments, the present disclosure provides oligonucleotides having a base sequence which consists of, comprises, or comprises a portion (e.g., a span of 10, 11, 12, 13, 14, 15, 16, 17, 18, 19 or more contiguous bases) of a base sequence disclosed herein (wherein each U can be optionally and independently substituted by T and vice versa). In some embodiments, provided oligonucleotides may alternatively or additionally function as single-stranded RNA interference agents, double-stranded RNA interference agents, or antisense oligonucleotides (e.g., which operate via a RNAse H-mediated mechanism or steric hindrance of translation), wherein the oligonucleotides comprise at least one non-naturally-occurring modification of a base, sugar or internucleotidic linkage. In some embodiments, a SMN2 oligonucleotide is an antisense oligonucleotide which is antisense to a target nucleic acid or sequence (e.g., a SMN2 oligonucleotide antisense to a SMN2 mRNA). In some embodiments, a provided oligonucleotide mediates skipping modulation (increasing beneficial skipping that produces a desired product, and/or decreasing deleterious skipping that produces an undesired product, e.g., increasing levels of an exon 7-containing SMN2 mRNA, and/or decreasing levels of an exon 7-deleted SMN2 mRNA). In some embodiments, an antisense oligonucleotide directs RNase H-mediated cleavage of a target nucleic acid. In some embodiments, an antisense oligonucleotide is not capable of directing RNase H-mediated cleavage of a target nucleic acid (or significant levels of this activity).

In some embodiments, the present disclosure pertains to any SMN2 oligonucleotide which operates through any mechanism, and which comprises any sequence, structure or format (or portion thereof) described herein, wherein the oligonucleotide comprises at least one non-naturally-occurring modification of a base, sugar or internucleotidic linkage. In some embodiments, the present disclosure pertains to any SMN2 oligonucleotide which comprises at least one stereocontrolled (chirally controlled) internucleotidic linkage (including but not limited to a phosphorothioate linkage in the Sp or Rp configuration) and/or comprises an additional chemical moiety capable of binding to the asialoglycoprotein receptor (including but not limited to GalNAc or a variant or derivative thereof). In some embodiments, a SMN2 oligonucleotide comprises a non-negatively charged internucleotidic linkage.

In some embodiments, an oligonucleotide comprises one or more nucleotides. In some embodiments, a sugar, base and/or internucleotidic linkage is a natural sugar, base and/or internucleotidic linkage. In some embodiments, a nucleotide is a natural nucleotide. In some embodiments, a nucleotide is a modified nucleotide. In some embodiments, a nucleotide is a nucleotide analog. In some embodiments, a base is a modified base. In some embodiments, a base is a protected nucleobase, such as a protected nucleobase used in oligonucleotide synthesis. In some embodiments, a base is a base analog. In some embodiments, a sugar is a modified sugar. In some embodiments, a sugar is a sugar analog. In some embodiments, an internucleotidic linkage is a modified internucleotidic linkage. In some embodiments, a nucleotide comprises a base, a sugar, and an internucleotidic linkage, wherein each of the base, the sugar, and the internucleotidic linkage is independently and optionally naturally-occurring or non-naturally occurring. In some embodiments, a nucleoside comprises a base and a sugar, wherein each of the base and the sugar is independently and optionally naturally-occurring or non-naturally occurring. Non-limiting examples of nucleotides include natural DNA and RNA nucleotides; and those which comprise one or more modifications at the bases, sugars and/or internucleotidic linkages. Non-limiting examples of sugars include ribose and deoxyribose; and ribose and deoxyribose with 2'-modifications, including but not limited to 2'-F, LNA, alpha-L-LNA, 2'-OMe, 2'-MOE, cEt, cyclo-DNA, GNA, and Morpholino modifications. In some embodiments, an oligonucleotide comprises a tricyclo-DNA (tc-DNA or tcDNA). In some embodiments, an internucleotidic linkage is a phosphorothioate or phosphodiester. In some embodiments, an internucleotidic linkage is a chirally controlled phosphorothioate (e.g., in the Sp or Rp configuration) or phosphodiester. In some embodiments, an internucleotidic linkage can have the structure of any internucleotidic linkage known in the art. In some embodiments, an internucleotidic linkage can have the structure of any internucleotidic linkage described in, as a non-limiting example, WO 2017/015555 or WO 2017/062862. In some embodiments an internucleotidic linkage is a non-negatively charged internucleotidic linkage. In some embodiments, an internucleotidic linkage is a moiety which does not comprise a phosphorus but serves to link two natural or non-natural sugars.

In some embodiments, the present disclosure provides compositions comprising multimers of oligonucleotides, wherein at least one oligonucleotide is a provided chirally controlled oligonucleotide, e.g., a provided chirally controlled SMN2 oligonucleotide, and/or comprises an additional chemical moiety capable of binding to the asialoglycoprotein receptor (including but not limited to GalNAc or a variant or derivative thereof). In some embodiments, both or all the monomer oligonucleotides of a multimer are the same. In some embodiments, in a multimer, at least one monomer oligonucleotide is different than another monomer oligonucleotide. In some embodiments, monomer oligonucleotides of a multimer target the same nucleic acid (e.g., a gene) or products thereof. In some embodiments, monomer oligonucleotides of a multimer target different nucleic acid (e.g., a gene) or products thereof. In some embodiments, a composition comprises a multimer of two or more of any: oligonucleotides of a first plurality and/or oligonucleotides of a second plurality, wherein the oligonucleotides of the first and second plurality can independently enhance the level, expression and/or activity of exon 7-containing SMN2 mRNA or its gene product relative to exon 7-deleted SMN2 mRNA, or increase inclusion of exon 7 of a SMN2 mRNA, in a cell extract, cell, tissue, organ and/or organism. In some embodiments, a target is intron 7 of SMN2. In some embodiments, the different targets are all in SMN2.

In some embodiments, the present disclosure provides an oligonucleotide composition comprising a first plurality of oligonucleotides which share:

1) a common base sequence;
2) a common pattern of backbone linkages;
3) a common pattern of backbone chiral centers; and which composition is a substantially pure preparation of a single oligonucleotide in that a non-random or controlled level of the oligonucleotides in the composition have the common base sequence and length, the common pattern of backbone linkages, and the common pattern of backbone chiral centers.

In some embodiments, provided oligonucleotides, e.g., oligonucleotides of a plurality in a provided chirally controlled oligonucleotide composition or SMN2 oligonucleotide composition, etc., are SMN2 oligonucleotides. In some embodiments, provided oligonucleotides, e.g., oligonucleotides of a plurality in a provided chirally controlled oligonucleotide composition (e.g., chirally controlled oligonucleotide composition of a plurality of oligonucleotides which can target SMN2, e.g., intron 7 of SMN2), SMN2 oligonucleotides, etc., comprises one or more blocks. In some embodiments, a block comprises one or more consecutive nucleosides, and/or nucleotides, and/or sugars, or bases, and/or internucleotidic linkages. In some embodiments, a provided oligonucleotide composition, e.g., a chirally controlled oligonucleotide composition, a SMN2 oligonucleotide composition, etc., comprises a plurality of oligonucleotides which comprise three or more blocks, wherein the blocks on either end are not identical and the oligonucleotide is thus asymmetric. In some embodiments, provided oligonucleotides comprise or are of the structure of first block-second block-third block.

In some embodiments, each sugar moiety of a first and a third blocks independently comprises a 2'-modification as described in the present disclosure, and each internucleotidic linkage of a first and a third block is independently a chirally controlled internucleotidic linkage as described in the present disclosure comprising a linkage phosphorus having Sp configuration. In some embodiments, each sugar moiety of a second moiety independently comprises a 2'-modification as described in the present disclosure, and each internucleotidic linkage of a second moiety is independently a natural phosphate linkage, a chirally controlled internucleotidic linkage comprising a linkage phosphorus having Sp configuration, or a chirally controlled internucleotidic linkage comprising a linkage phosphorus having Rp configuration. In some embodiments, a second block comprises one or more chirally controlled internucleotidic linkages each independently comprising a linkage phosphorus having Rp configuration. In some embodiments, a second block comprises one or more chirally controlled internucleotidic linkages each independently comprising a linkage phosphorus having Sp configuration. In some embodiments, a second block comprises one or more natural phosphate linkages. In some embodiments, a second block comprises one or more natural phosphate linkages and one or more chirally controlled internucleotidic linkages each independently comprising a linkage phosphorus having Rp configuration. In some embodiments, a 2'-modification is 2'-MOE. In some embodiments, a chirally controlled internucleotidic linkage is a phosphorothioate internucleotidic linkage. In some embodiments, a first and third block are 2'-MOE and phosphorothioate in the Sp configuration; and a second block is 2'-MOE and phosphorothioate in the Rp configuration. In some embodiments, a first and third block are 2'-MOE and phosphorothioate in the Sp configuration; and a second block is 2'-MOE and any combination of phosphorothioate in the Rp and Sp figurations. In some embodiments, a first and third block are 2'-MOE and phosphorothioate in the Sp configuration; and a second block is 2'-MOE and any combination of phosphodiesters and/or phosphorothioate in the Rp and/or Sp figurations. In some embodiments, a first and third block are 2'-MOE and phosphorothioate in the Sp configuration; and a second block is 2'-F and phosphorothioate in the Sp configuration. In some embodiments, a first and third block are 2'-MOE and phosphorothioate in the Sp configuration; and a second block is 2'-F and any combination of phosphorothioate in the Rp and Sp figurations. In some embodiments, a first and third block are 2'-MOE and phosphorothioate in the Sp configuration; and a second block is 2'-F and any combination of phosphodiesters and/or phosphorothioate in the Rp and/or Sp figurations. In some embodiments, a first and third block are 2'-MOE and any combination of phosphodiester and phosphorothioate in the Sp configuration; and a second block is 2'-F and any combination of phosphorothioate in the Rp and Sp figurations. In some embodiments, a first and third block are 2'-MOE and phosphorothioate in the Sp configuration; and a second block is 2'-F and any combination of phosphodiesters and phosphorothioate in the Sp figurations. In some embodiments, a first and third block are 2'-MOE and phosphorothioate in the Sp configuration; and a second block is 2'-OMe. In some embodiments, a first and third block are 2'-OMe and phosphorothioate in the Rp configuration; and a second block is 2'-MOE and phosphorothioate in the Sp configuration. In some embodiments, a first and third block are 2'-OMe and a combination of phosphodiester and phosphorothioate in the Rp configuration; and a second block is 2'-MOE and phosphorothioate in the Sp configuration. In some embodiments, a first block is a 5'-wing. In some embodiments, a second block is a core. In some embodiments, a third block is a 3'-wing.

In some embodiments, provided oligonucleotides comprise one or more sugar modifications. In some embodiments, an oligonucleotide comprises one, two, three, four, five, six, seven, eight, nine, ten, or more sugar moieties each independently comprising a sugar modification. In some embodiments, an oligonucleotide comprises two, three, four, five, six, seven, eight, nine, ten, or more consecutive sugar moieties each independently comprising a sugar modification. In some embodiments, a sugar modification is at the 2'-position. In some embodiments, a sugar modification is selected from: 2'-F, 2'-OMe, 2'-MOE (2'-O-(2-methoxyethyl)), LNA, alpha-L-LNA, GNA, cEt and cyclo-DNA. In some embodiments, all sugar moieties of provided oligonucleotides independently comprise a 2'-MOE modification. In some embodiments, all sugar moieties of provided oligonucleotides independently comprise a 2'-OMe modification. In some embodiments, an oligonucleotide comprises one, two, three, four, five, six, seven, eight, nine, ten, or more 2'-MOE. In some embodiments, an oligonucleotide comprises two, three, four, five, six, seven, eight, nine, ten, or more consecutive sugar moieties comprising 2'-OMe. In some embodiments, an oligonucleotide comprises one, two, three, four, five, six, seven, eight, nine, ten, or more 2'-F. In some embodiments, an oligonucleotide comprises one, two, three, four, five, six, seven, eight, nine, ten, or more LNA. In some embodiments, an oligonucleotide comprises one, two, three, four, five, six, seven, eight, nine, ten, or more alpha-L-LNA. In some embodiments, an oligonucleotide comprises one, two, three, four, five, six, seven, eight, nine, ten, or more GNA. In some embodiments, an oligonucleotide comprises one, two, three, four, five, six, seven, eight, nine, ten, or more cEt. In some embodiments, an oligonucleotide comprises one, two, three, four, five, six, seven, eight, nine, ten, or more tricyclo-DNA.

In some embodiments, a provided SMN2 oligonucleotide comprises one or more block, wherein a block comprises one or more consecutive sugars, bases, internucleotidic linkages, nucleosides and/or nucleotides, wherein the sugars, bases, internucleotidic linkages, nucleosides and/or nucleotides of one block differ from the sugars, bases, internucleotidic linkages, nucleosides and/or nucleotides of an adjacent block.

In some embodiments, provided oligonucleotides comprise sugars with a particular sugar modification which alternate with sugars with no modification or a different modification. In some embodiments, sugars with a particular modification appear in one or more blocks.

In some embodiments, provided oligonucleotides comprise one or more blocks comprising sugars with a particular 2' modification which alternate with sugars which independently have no modification or have a different modification. In some embodiments, provided oligonucleotides comprise one or more blocks comprising sugars with a 2'-F modification which alternate with sugars which independently have no modification or have a different modification. In some embodiments, provided oligonucleotides comprise one or more blocks comprising sugars with a 2'-OMe modification which alternate with sugars which independently have no modification or a different modification. In some embodiments, provided oligonucleotides comprise one or more blocks comprising sugars with a 2'-OMe modification which alternate with sugars with a 2'-F modification.

In some embodiments, provided oligonucleotides comprise alternating blocks comprising modified sugar moieties and unmodified sugar moieties. In some embodiments, modified sugar moieties comprise 2'-modifications. In some embodiments, provided oligonucleotides comprise alternating 2'-OMe modified sugar moieties and unmodified sugar moieties.

In some embodiments, a block is a stereochemistry block. In some embodiments, a block is an Rp block in that each linkage phosphorus of the block is Rp. In some embodiments, a block is an Sp block in that each linkage phosphorus of the block is Sp. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage of the block is a natural phosphate linkage.

In some embodiments, a pattern of sugar modifications of is or comprises $(Ms-M_H-Ms)_{4-10}-Ms$, $(Ms-M_H-M_H)_{4-10}-Ms$, or $(Ms)_{4-10}-(M_H)_{4-12}-(Ms)_{4-10}$, wherein each Ms is independently a 2' modification of a sugar, e.g, each independently selected from 2'-F, 2'-MOE, 2'-OMe, LNA, cEt, and tricyclo sugar modifications; and $M_H$ is no substitution at 2'-position (two —H at 2'-position).

In some embodiments, a provided oligonucleotide, e.g., at least one block, is modified (e.g., sugar modifications, base modifications, internucleotidic linkage modifications, etc.) to increase stability (e.g., resistance to nuclease degradation), cellular uptake, binding affinity to a target nucleic acid sequence, and/or other activities/properties.

In some embodiments, some combinations of bases, sugar modifications and/or internucleotidic linkages are particularly stable.

In some embodiments, provided oligonucleotides, e.g., provided oligonucleotides of a plurality in provided chirally controlled oligonucleotide compositions, or a portion thereof, e.g., a block, a wing, a core, etc., have a pattern of backbone chiral centers. A pattern of backbone chiral centers comprises at least one Rp or Sp. In some embodiments, a pattern of backbone chiral centers is or comprises (Sp)t[(Op)n(Sp)m]y, (Rp)t(Np)n(Rp)m, (Rp)t(Sp)n(Rp)m, (Rp)t[(Np/Op)n]y(Rp)m, (Rp)t[(Sp/Np)n]y(Rp)m, (Rp)t[(Sp/Op)n]y(Rp)m, (Np/Op)t(Np)n(Np/Op)m, (Np/Op)t(Sp)n(Np/Op)m, (Np/Op)t[(Np/Op)n]y(Np/Op)m, (Np/Op)t[(Sp/Op)n]y(Np/Op)m, (Np/Op)t[(Sp/Op)n]y(Np/Op)m, (Rp/Op)t(Np)n(Rp/Op)m, (Rp/Op)t(Sp)n(Rp/Op)m, (Rp/Op)t[(Np/Op)n]y(Rp/Op)m, (Rp/Op)t[(Sp/Op)n]y(Rp/Op)m, or (Rp/Op)t[(Sp/Op)n]y(Rp/Op)m (unless otherwise specified, description of patterns of modifications and stereochemistry are from 5' to 3' as typically used in the art), wherein Sp indicates S configuration of a chiral linkage phosphorus of a chiral modified internucleotidic linkage, Rp indicates R configuration of a chiral linkage phosphorus of a chiral modified internucleotidic linkage, Op indicates an achiral linkage phosphorus of a natural phosphate linkage, each Np is independently Rp, or Sp, and each of m, n, t and y is independently 1-50 as described in the present disclosure. In some embodiments, a pattern of backbone chiral centers is or comprises (Rp)t(Sp)n(Rp)m. In some embodiments, y, t, n and m each are independently 1-20. In some embodiments, y is 1. In some embodiments, y is at least 2, 3, 4, 5, 6, 7, 8, 9, 10, 11, 12, 13, 14, or 15. In some embodiments, y is 2, 3, 4, 5, 6, 7, 8, 9, 10, 11, 12, 13, 14, or 15. In some embodiments, n is 1. In some embodiments, n is at least 2, 3, 4, 5, 6, 7, 8, 9, 10, 11, 12, 13, 14, or 15. In some embodiments, n is 2, 3, 4, 5, 6, 7, 8, 9, 10, 11, 12, 13, 14, or 15. In some embodiments, m is 1. In some embodiments, m is at least 2, 3, 4, 5, 6, 7, 8, 9, 10, 11, 12, 13, 14, or 15. In some embodiments, m is 2, 3, 4, 5, 6, 7, 8, 9, 10, 11, 12, 13, 14, or 15. In some embodiments, tis 1. In some embodiments, t is at least 2, 3, 4, 5, 6, 7, 8, 9, 10, 11, 12, 13, 14, or 15. In some embodiments, t is 2, 3, 4, 5, 6, 7, 8, 9, 10, 11, 12, 13, 14, or 15. In some embodiments, each oft and m is independently at least 2, 3, 4, 5, 6, 7, 8, 9, 10, 11, 12, 13, 14, or 15. In some embodiments, each oft and m is independently at least 3. In some embodiments, each oft and m is independently at least 4. In some embodiments, each oft and m is independently at least 5. In some embodiments, each oft and m is independently at least 6. In some embodiments, each oft and m is independently at least 7. In some embodiments, each of t and m is independently at least 8. In some embodiments, each oft and m is independently at least 9. In some embodiments, each oft and m is independently at least 10. In some embodiments, provided oligonucleotides comprises a block, e.g., a first block, a 5'-wing, etc., that has a pattern of backbone chiral centers of or comprising a t-section, e.g., (Sp)t, (Rp)t, (Np/Op)t, (Rp/Op)t, etc., a block, e.g., a second block, a core, etc., that has a pattern of backbone chiral centers of or comprising a y- or n-section, e.g., (Np)n, (Sp)n, [(Np/Op)n]y, [(Rp/Op)n]y, [(Sp/Op)n]y, etc., and a block, e.g., a third block, a 3'-wing, etc., that has a pattern of backbone chiral centers of or comprising a m-section, e.g., (Sp)m, (Rp)m, (Np/Op)m, (Rp/Op)m, etc. In some embodiments, a t-, y-, n-, or m-section that comprises Np or Rp independently comprises at least 10%, 20%, 30%, 40%, 50%, 60%, 70%, 75%, 80%, 85%, 90%, or 95%, or 100% Rp. In some embodiments, a t- or m-section that comprises Np or Rp independently comprises at least 10%, 20%, 30%, 40%, 50%, 60%, 70%, 75%, 80%, 85%, 90%, or 95%, or 100% Rp. In some embodiments, provided oligonucleotides comprise at least 10%, 20%, 30%, 40%, 50%, 60%, 70%, 75%, 80%, 85%, 90%, or 95%, or 100% Rp. In some embodiments, a percentage is at least 10%. In some embodiments, a percentage is at least 20%. In some embodiments, a percentage is at least 30%. In some embodiments, a percentage is at least 40%. In some embodiments, a percentage is at least 50%. In some embodiments, a percentage is at least 60%. In some embodiments, a percentage is at least 70%. In some embodiments, a percentage is at least 75%. In some embodiments, a percentage is at least 80%. In some embodiments, a percentage is at least 85%. In some embodiments, a percentage is at least 90%. In some embodiments, a percentage is at least 95%. In some embodiments, a percentage is 100%.

In some embodiments, each sugar moiety bonded to a Rp or Op linkage phosphorus at 3' independently comprises a modification. In some embodiments, each sugar moiety bonded to a Rp or Op linkage phosphorus at 5' independently comprises a modification. In some embodiments, each sugar moiety bonded to a Rp linkage phosphorus at 3' independently comprises a modification. In some embodiments, each sugar moiety bonded to a Rp linkage phosphorus at 5' independently comprises a modification. In some embodiments, each sugar moiety bonded to an Op linkage phosphorus at 3' independently comprises a modification. In some embodiments, each sugar moiety bonded to an Op linkage phosphorus at 5' independently comprises a modification. In some embodiments, each sugar moiety bonded to a Sp linkage phosphorus at 3' independently comprises a modification. In some embodiments, each sugar moiety bonded to a Sp linkage phosphorus at 5' independently comprises a modification. In some embodiments, each sugar moiety independently comprises a modification. In some embodiments, a modification is a 2'-modification. In some embodiments, a modification is 2'-OR, wherein R is not hydrogen. In some embodiments, a modification is 2'-OR, wherein R is optionally substituted $C_{1-6}$ alkyl. In some embodiments, a modification is 2'-OR, wherein R is substituted $C_{1-6}$ alkyl. In some embodiments, a modification is 2'-OR, wherein R is optionally substituted $C_{2-6}$ alkyl. In some embodiments, a modification is 2'-OR, wherein R is substituted $C_{2-6}$ alkyl. In some embodiments, R is —CH$_2$CH$_2$OMe. In some embodiments, a modification is or comprises -L-connecting two sugar carbons, e.g., those found in LNA. In some embodiments, a modification is -L-connecting $C_2$ and C4 of a sugar moiety. In some embodiments, L is —CH$_2$—CH(R)—, wherein R is as described in the present disclosure. In some embodiments, L is —CH$_2$—CH(R)—, wherein R is as described in the present disclosure and is not hydrogen. In some embodiments, L is —CH$_2$—(R)—CH(R)—, wherein R is as described in the present disclosure and is not hydrogen. In some embodiments, L is —CH$_2$—(S)—CH(R)—, wherein R is as described in the present disclosure and is not hydrogen.

In some embodiments, a provided pattern of backbone chiral centers is or comprises (Rp/Sp)-(All Rp or All Sp)-(Rp/Sp), wherein each Rp/Sp is independently Rp or Sp. In some embodiments, a provided pattern of backbone chiral centers is or comprises (Rp)-(All Sp)-(Rp). In some embodiments, a provided pattern of backbone chiral centers is or comprises (Sp)-(All Sp)-(Sp). In some embodiments, a provided pattern of backbone chiral centers is or comprises (Sp)-(All Rp)-(Sp). In some embodiments, a provided pattern of backbone chiral centers is or comprises (Rp/Sp)-(repeating (Sp)m(Rp)n)-(Rp/Sp). In some embodiments, a provided pattern of backbone chiral centers is or comprises (Rp/Sp)-(repeating SpSpRp)-(Rp/Sp).

Provided oligonucleotides can be of various lengths, e.g., of 10-200, 15-100, 15-50, 15-40, 15-30, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 55, 60, 70, 80, 90, or 100 nucleobases, wherein each nucleobases is independently an optionally substituted nucleobase selected from A, T, C, G, U, and tautomers thereof. In some embodiments, a length is about 15 to about 49, about 17 to about 49, about 19 to about 29, about 19 to about 25, or about 19 to about 23 nucleobases. In some embodiments, a length is no more than 25 nucleobases. In some embodiments, a length is no more than 30 nucleobases. n some embodiments, a length is no more than 35 nucleobases. In some embodiments, a length is no more than 40 nucleobases. In some embodiments, a length is no more than 45 nucleobases. In some embodiments, a length is no more than 50 nucleobases. In some embodiments, a length is no more than 55 nucleobases. In some embodiments, a length is no more than 60 nucleobases.

In some embodiments, a provided oligonucleotide has any of the Formats illustrated in FIG. 2A, 2B, 2C or 2D, or any structural element illustrated in any of the Formats illustrated in FIG. 2A, 2B, 2C or 2D, wherein the oligonucleotide can target SMN2.

In some embodiments, provided technologies (e.g., oligonucleotides, oligonucleotide compositions, methods, etc.) are useful for treating conditions, diseases and/or disorders associated with splicing. In some embodiments, the present disclosure provides technologies that can provide non-disease-associated products (e.g., transcripts, proteins, etc., presence and/or activity of which are not associated (e.g., correlated), or are associated to a less extent (e.g., show less significant, or statistically insignificant correlation, etc.), with presence, incidence, and/or severity of one or more disorders, diseases and/or conditions), optionally preferentially, compared to disease-associated products (e.g., transcripts, proteins, etc., presence and/or activity of which are associated (e.g., correlated) with presence, incidence, and/or severity of one or more disorders, diseases and/or conditions). Particularly, in some embodiments, the present disclosure provides technologies that can promote inclusion of one or more exons whose absence in one or more splicing products are associated with one or more conditions, diseases and/or disorders to provide non-disease-associated products. In some embodiments, the present disclosure provides technologies that can promote inclusion of one or more exons in splicing products, e.g., mRNA, which encode proteins that can alleviate and/or treat one or more conditions, diseases and/or disorders that are associated with exclusion of the one or more exons in splicing products. In some embodiments, provided oligonucleotide compositions are chirally controlled oligonucleotide compositions. In some embodiments, provided oligonucleotides are SMN2 oligonucleotides. In some embodiments, provided SMN2 oligonucleotide compositions are chirally controlled and/or comprise an additional chemical moiety capable of binding to the asialoglycoprotein receptor (including but not limited to GalNAc or a variant or derivative thereof). In some embodiments, provided SMN2 oligonucleotides and/or compositions thereof, e.g., provided SMN2 oligonucleotide compositions, can be used to treat or used to manufacture a medicament for treatment of a SMN2-related condition, disorder and/or disease. In some embodiments, the present disclosure provides methods of using oligonucleotides disclosed herein to treat and/or to manufacture a treatment for, a SMN2-related disorder, e.g., SMA, ALS, etc.

In some embodiments, the base sequence of oligonucleotides of a provided SMN2 oligonucleotide composition, e.g., a chirally controlled SMN2 oligonucleotide composition, consists of the base sequence of an oligonucleotide disclosed herein. In some embodiments, the base sequence of a provided SMN2 oligonucleotide, e.g., a chirally controlled SMN2 oligonucleotide, comprises the base sequence of an oligonucleotide disclosed herein. In some embodiments, the base sequence of a provided SMN2 oligonucleotide, e.g., a chirally controlled SMN2 oligonucleotide, comprises a sequence comprising the sequence of 13 contiguous bases of the base sequence of an oligonucleotide disclosed herein. In some embodiments, the base sequence of a provided SMN2 oligonucleotide, e.g., a chirally controlled SMN2 oligonucleotide, comprises a sequence comprising the sequence of 15 contiguous bases of the base sequence of an oligonucleotide disclosed herein. In some embodiments, the base sequence of a provided SMN2 oligonucleotide, e.g., a chirally controlled SMN2 oligonucleotide, comprises a sequence comprising the sequence of 20 contiguous bases, with up to 5 mismatches, of the base sequence of an oligonucleotide disclosed herein. In some embodiments, a provided SMN2 oligonucleotide, e.g., a chirally controlled SMN2 oligonucleotide, can enhance/increase the level, expression and/or activity of exon 7-containing SMN2 mRNA or its gene product relative to exon 7-deleted SMN2 mRNA. In some embodiments, a provided SMN2 oligonucleotide, e.g., a chirally controlled SMN2 oligonucleotide, increases inclusion of exon 7 of a SMN2 mRNA.

In some embodiments, the base sequence of a provided oligonucleotide, e.g., a chirally controlled oligonucleotide, a SMN2 oligonucleotide, etc., is or comprises: a 15-base portion of any base sequence disclosed herein; or a base sequence which has 0-3 mismatches from a 15-base portion of any base sequence disclosed herein. In some embodiments, a mismatch is a difference between the base sequences when two sequences are maximally aligned and compared. As a non-limiting example, a mismatch is counted if a difference exists between the base at a particular location in one sequence and the base at the corresponding position in another sequence. In some embodiments, a mismatch is counted, for example, if a position in one sequence has a particular base (e.g., A), and the corresponding position on the other sequence has a different base (e.g., G, C or U). In some embodiments, a mismatch is also counted, e.g., if a position in one sequence has a base (e.g., A), and the corresponding position on the other sequence has no base (e.g., that position is an abasic nucleotide which comprises a phosphate-sugar backbone but no base) or that position is skipped. In some embodiments, the base sequence of an oligonucleotide comprises a 15-base portion of a base sequence disclosed herein, except that one or more positions is abasic (e.g., a base is absent at one or more positions but the sequence otherwise comprises a complete 15-base portion). In some embodiments, a single-stranded nick in either sequence (or in the sense or antisense strand) may not be counted as mismatch, for example, in some embodiments, no mismatch would be counted if one sequence comprises the sequence 5'-AG-3', but the other sequence comprises the sequence 5'-AG-3' with a single-stranded nick between the A and the G. A base modification is generally not considered a mismatch, for example, if one sequence comprises a C, and the other sequence comprises a modified C (e.g., 5 mC) at the same position, no mismatch may be counted. In some embodiments, for purposes of counting mismatches, substitution of a T for U or vice versa is not considered a mismatch.

In some embodiments, an oligonucleotide is complementary, in some embodiments, totally or 100% complementary to (e.g., can completely hybridize to), a target sequence (e.g., a SMN2 target or RNA, such as a pre-mRNA or a portion thereof, such as intron 7 or ISS-N1). In some embodiments, an oligonucleotide is totally (100%) complementary to a target sequence meaning that the base sequence of the oligonucleotide has no mismatches with a sequence which is fully complementary (e.g., base-pairs via Watson-Crick basepairing) to the target sequence. In addition, a provided oligonucleotide, e.g., a SMN2 oligonucleotide, can have a small number of internal mismatches and still increase/enhance the level, expression and/or activity of exon 7-containing SMN2 mRNA or its gene product relative to exon 7-deleted SMN2 mRNA, or increase inclusion of exon 7 of a SMN2 mRNA, in a cell extract, cell, tissue, organ and/or organism. If a first base sequence of an oligonucleotide has a small number of mismatches from a reference base sequence which is 100% complementary to a target sequence, then the first base sequence is substantially (e.g., at least 70%, 75%, 80%, 85%, 90%, 91%, 92%, 93%, 94%, 95%, 96%, 97%, 98%, or 99%) complementary to the target sequence.

In some embodiments, provided oligonucleotides have a common pattern of backbone linkages. In some embodiments, a common pattern of backbone linkages comprises at least 10 modified internucleotidic linkages. In some embodiments, a modified internucleotidic linkage is a phosphorothioate linkage. In some embodiments, a common pattern of backbone linkages comprises at least 10 phosphorothioate linkages.

In some embodiments, provided oligonucleotides have a common pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, oligonucleotides of a particular type are chemically identical in that, among other things, they have the same base sequence (including length), the same pattern of chemical modifications to sugar and base moieties, the same additional chemical moieties (if any), the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications.

Among other things, the present disclosure provides technologies for optimizing properties and/or activities of oligonucleotides. In some embodiments, the present disclosure provides oligonucleotides and compositions thereof with improved properties and/or activities, e.g., ability to mediate enhanced exon-inclusion in splicing, e.g., production of increased level of exon 7-containing SMN2 mRNA relative to exon 7-deleted SMN2 mRNA, in a cell extract, cell, tissue, organ and/or organism, etc. In some embodiments, the present disclosure provides methods for lowering immune response associated with administration of oligonucleotides and compositions thereof (e.g., for administering oligonucleotide compositions so that undesirable immune responses to oligonucleotides in the compositions are reduced, for example relative to those observed with a reference (e.g., non-chirally controlled) composition of nucleotides of comparable or identical nucleotide sequence, or of the same constitution). In some embodiments, the present disclosure provides methods for increasing binding to certain proteins by oligonucleotides and compositions thereof. In some embodiments, the present disclosure provides methods for increasing binding to certain proteins by chirally controlled oligonucleotides and compositions thereof. In some embodiments, the present disclosure provides methods for enhancing delivery of oligonucleotides and compositions thereof. Among other things, the present disclosure encompasses the recognition that optimal delivery of oligonucleotides to their targets, in some embodiments, involves balance of oligonucleotides binding to certain proteins so that oligonucleotides can be transported to the desired locations, and oligonucleotide release so that oligonucleotides can be properly released from certain proteins to perform their desired functions, for example, hybridization with their targets, cleavage of their targets, inhibition of translation, modulation of transcript processing, etc. Among other things, the present disclosure demonstrates that improvement of oligonucleotide properties and/or activities can be achieved through chemical modifications and/or stereochemistry.

In some embodiments, the sequence of provided oligonucleotides comprises a sequence selected from Table 1A. In some embodiments, the sequence of provided oligonucleotides is a sequence selected from Table 1A. In some embodiments, a pattern of sugar modifications comprises or is one selected from those described in Table 1A. In some embodiments, a pattern of internucleotidic linkages comprises or is one selected from those described in Table 1A. In some embodiments, a pattern of backbone chiral centers comprises or is one selected from those described in Table 1A. In some embodiments, an additional chemical moiety, if any, is selected from those described in Table 1A.

In some embodiments, the present disclosure provides a SMN2 oligonucleotide which is selected from any of the Tables, e.g., Table 1A, or otherwise disclosed herein. In some embodiments, the present disclosure provides a SMN2 oligonucleotide selected from any of the Tables, including but not limited to Table 1A, or otherwise disclosed herein, wherein the oligonucleotide is conjugated to a an additional chemical moiety.

In some embodiments, the present disclosure provides a compound, e.g., an oligonucleotide, having the structure of formula O-I:

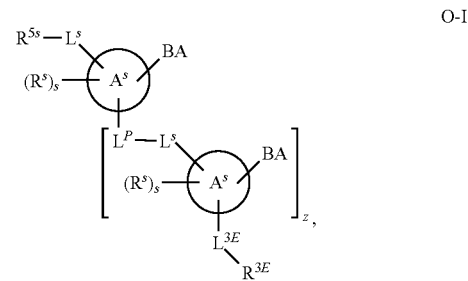

O-I or a salt thereof, wherein:

$R^{5s}$ is independently R' or —OR';

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_{1-6}$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Ring $A^s$ is independently an optionally substituted 3-20 membered monocyclic, bicyclic or polycyclic ring having 0-10 heteroatoms independently selected from oxygen, nitrogen, sulfur, phosphorus and silicon;

each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$;

each s is independently 0-20;

each BA is independently an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;

each $L^P$ is independently an internucleotidic linkage;

z is 1-1000;

$L^{3E}$ is -L$^s$- or -L$^s$-L$^s$-;

$R^{3E}$ is —R', -L$^s$-R', —OR', or a support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, at least one $L^P$ is a chirally controlled internucleotidic linkage. In some embodiments, each $L^P$ is independently a chirally controlled internucleotidic linkage. In some embodiments, each $L^P$ comprising a chiral linkage phosphorus is independently a chirally controlled internucleotidic linkage. In some embodiments, each $L^P$ independently has a structure of formula I or a salt form thereof. In some embodiments, each $L^P$ is independently selected from natural phosphate linkage and phosphorothioate internucleotidic linkages. In some embodiments, at least one $L^P$ is non-negatively charged internucleotidic linkage.

In some embodiments, a compound of formula O-I or a salt thereof is a chirally controlled oligonucleotide. In some embodiments, the present disclosure provides a chirally controlled oligonucleotide composition comprising a plurality of oligonucleotides of a particularly oligonucleotide type, wherein each oligonucleotide of the plurality is independently a compound of formula O-I or a salt thereof, wherein at least one $L^P$ is a chirally controlled internucleotidic linkage. In some embodiments, the present disclosure provides a chirally controlled oligonucleotide composition comprising a plurality of oligonucleotides of a particularly oligonucleotide type, wherein each oligonucleotide of the plurality is independently a compound of formula O-I or a salt thereof, wherein each $L^P$ is independently a chirally controlled internucleotidic linkage or an internucleotidic linkage comprising an achiral phosphorus linkage. In some embodiments, the present disclosure provides a chirally controlled oligonucleotide composition comprising a plurality of oligonucleotides of a particularly oligonucleotide type, wherein each oligonucleotide of the plurality is independently a compound of formula O-I or a salt thereof, wherein each $L^P$ is independently a chirally controlled internucleotidic linkage or a natural phosphate linkage.

In some embodiments, the present disclosure provides a compound of structure:

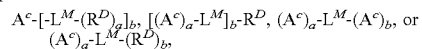

or a salt thereof, wherein each variable is independently as described in the present disclosure.

In some embodiments, each $A^c$ is independently an oligonucleotide moiety of an oligonucleotide of formula O-I or a salt thereof (e.g., H-$A^c$, [H]$_a$-$A^c$ or [H]$_b$-$A^c$ is an oligonucleotide of formula O-I or a salt thereof). In some embodiments, the present disclosure provides an oligonucleotide having the structure of $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, or a salt thereof. In some embodiments, the present disclosure provides oligonucleotide compositions comprising oligonucleotides having the structure of $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, or a salt thereof. In some embodiments, the present disclosure provides oligonucleotide compositions comprising non-random or controlled levels (as described in the present disclosure) of oligonucleotides having the structure of $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, or a salt thereof. In some embodiments, the present disclosure provides chirally controlled SMN2 oligonucleotide compositions comprising oligonucleotides having the structure of $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, or a salt thereof. In some embodiments, oligonucleotides of a plurality (e.g., a first plurality), or oligonucleotides of an oligonucleotide type, are oligonucleotides having the structure of $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, or a salt thereof. In some embodiments, oligonucleotides in provided compositions, e.g., provided chirally controlled SMN2 oligonucleotide compositions, have the structure of $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, or a salt thereof. In some embodiments, the structure is $A^c$-[-$L^M$-($R^D$)$_a$]$_b$ or a salt thereof. In some embodiments, the structure is [($A^c$)$_a$-$L^M$]$_b$-$R^D$ or a salt thereof. In some embodiments, the structure is ($A^c$)$_a$-$L^M$-($A^c$)$_b$ or a salt thereof. In some embodiments, the structure is $A^c$-[-$L^M$-($R^D$)$_a$]$_b$ or a salt thereof.

In some embodiments, $L^M$ is $L^{LD}$. In some embodiments, $L^M$ is multivalent so that more than one groups of $R^D$ are connected through one $L^M$. In some embodiments, a is two or more. In some embodiments, a is 2, 3, 4, 5, 6, 7, 8, 9, or 10 or more. In some embodiments, a is 2. In some embodiments, a is 3. In some embodiments, a is 4. In some embodiments, a is 5.

In some embodiments, $R^D$ is an additional chemical moiety. In some embodiments, $R^D$ is a targeting moiety. In some embodiments, $R^D$ is a lipid moiety. In some embodiments, $R^D$ is a carbohydrate moiety. In some embodiments, $R^D$ is a ligand moiety of a cell receptor, for example, a sigma receptor, as described in the present disclosure.

In some embodiments, the present disclosure provides an oligonucleotide composition comprising a plurality of oligonucleotides having the structure of:

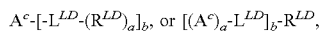

wherein:
each $A^c$ is independently an oligonucleotide moiety (e.g., H-$A^c$, [H]$_a$-$A^c$ or [H]$_b$-$A^c$ is an oligonucleotide);
a is 1-1000;
b is 1-1000;
each $L^{LD}$ is independently a linker moiety; and
each $R^{LD}$ is independently a targeting moiety.

As appreciated by those having ordinary skill in the art, activities and/or properties of oligonucleotide compositions as described herein can be assessed using various appropriate assays in accordance with the present disclosure, for example, those described in US 20150211006, US 20150211006, WO 2017015555, WO 2017015575, WO 2017062862, WO 2017160741, those utilized to assess Nusinersen, etc. Those skilled in the art are aware of and/or are able to develop appropriate assays for assessing particular oligonucleotides and/or compositions thereof in accordance with the present disclosure.

BRIEF DESCRIPTION OF THE DRAWINGS

FIGS. 1A, 1B and 1C. FIGS. 1A, 1B and 1C show percentage (%) of SMN2 exon 7 inclusion in SMA patient-derived fibroblasts following treatment with various SMN2 oligonucleotides. Oligonucleotides include: WV-2782, WV-6767, WV-6773, WV-6775, WV-6777, WV-6779 and WV-6768 (FIG. 1A); WV-2782 and WV-6768 (FIG. 1B); and WV-6780, WV-6781, WV-6782, WV-6783, WV-6784, WV-6785, WV-6786, WV-6787, WV-6767, and WV-2782 (FIG. 1C). Oligonucleotides were delivered by electroporation at 0.1 or 1.0 µM (FIG. 1A); 0.03125 to 2 µM (FIG. 1B); or 1.0, 0.25 or 0.0625 µM (FIG. 1C). Percentage of SMN2 exon 7 inclusion was determined by RT-qPCR from samples collected four days after electroporation, and experiments were done in replicates.

Figure 2B:
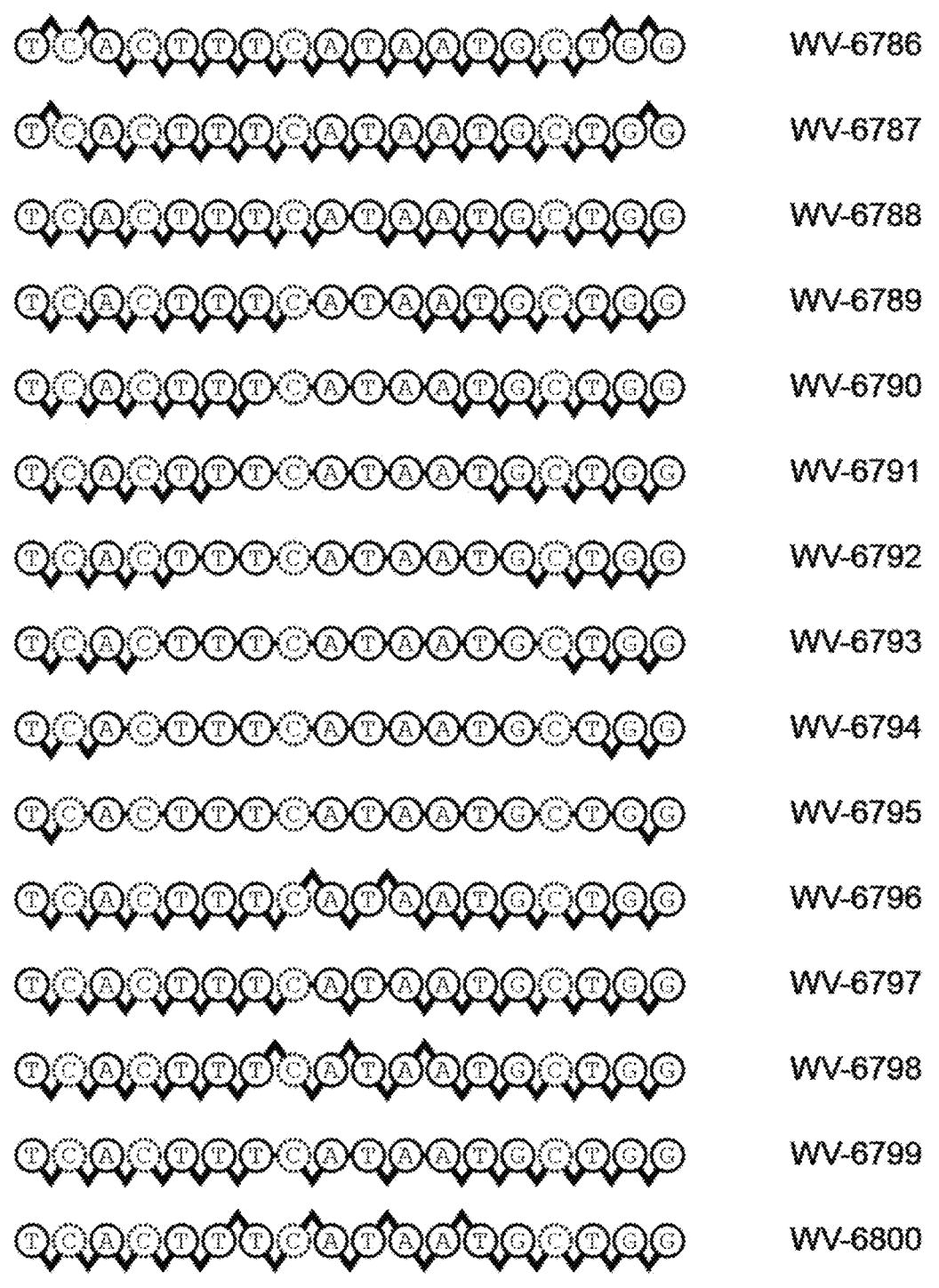

FIGS. 2A, 2B, 2C and 2D (SEQ ID NOS 200, 206, 208, 210, 212, 201, 213-248, 199, and 249-255). FIGS. 2A to 2D illustrate certain provided SMN2 oligonucleotides as examples. Symbols for FIGS. 2A to 2D are illustrated at the bottom of FIG. 2D. Chemical structures for the triantennary anisamide, triantennary GalNac and L001 linker (C6 amine linker) are provided e.g., after Table 1A.

DETAILED DESCRIPTION OF CERTAIN EMBODIMENTS

Definitions

Figure 1C:
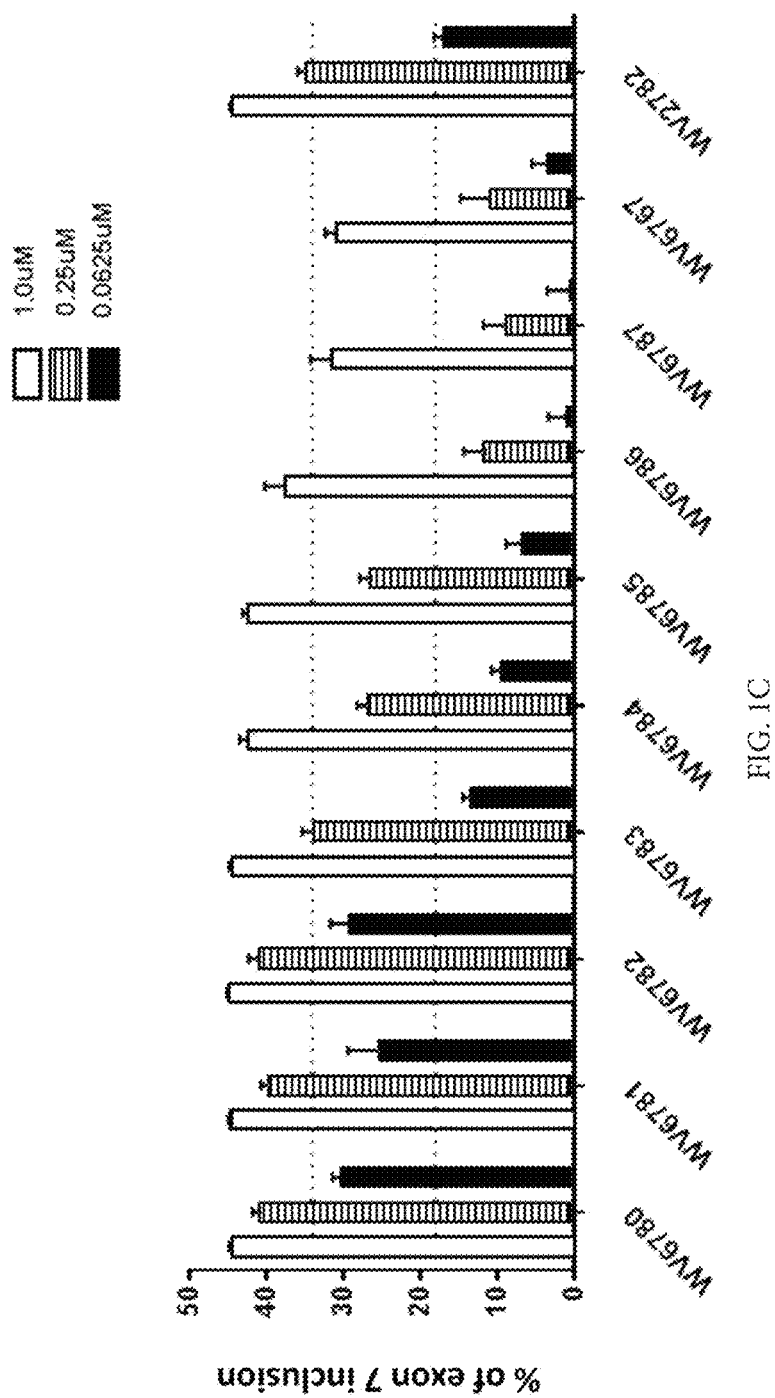
Figure 2A:
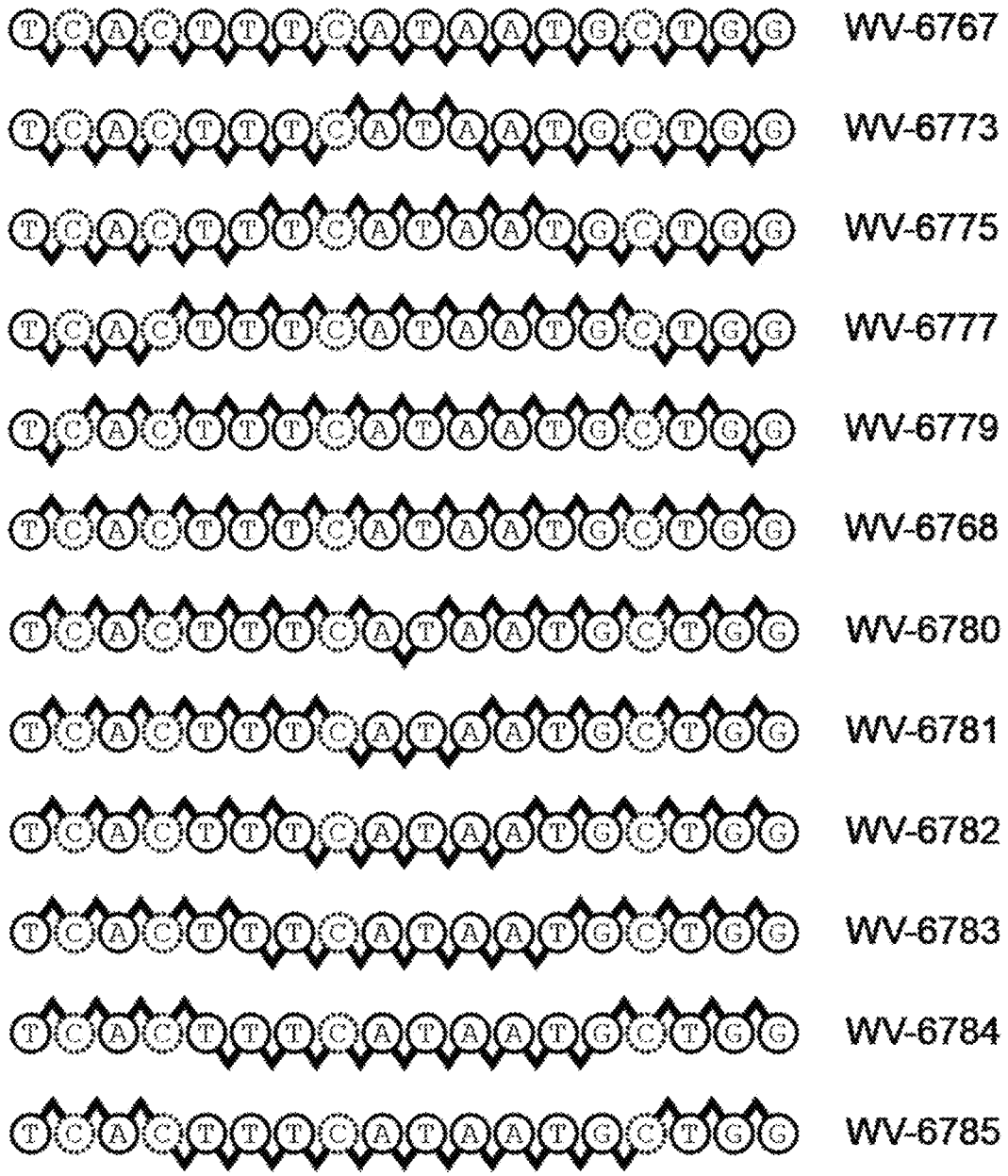
Figure 2C:
Figure 2D:
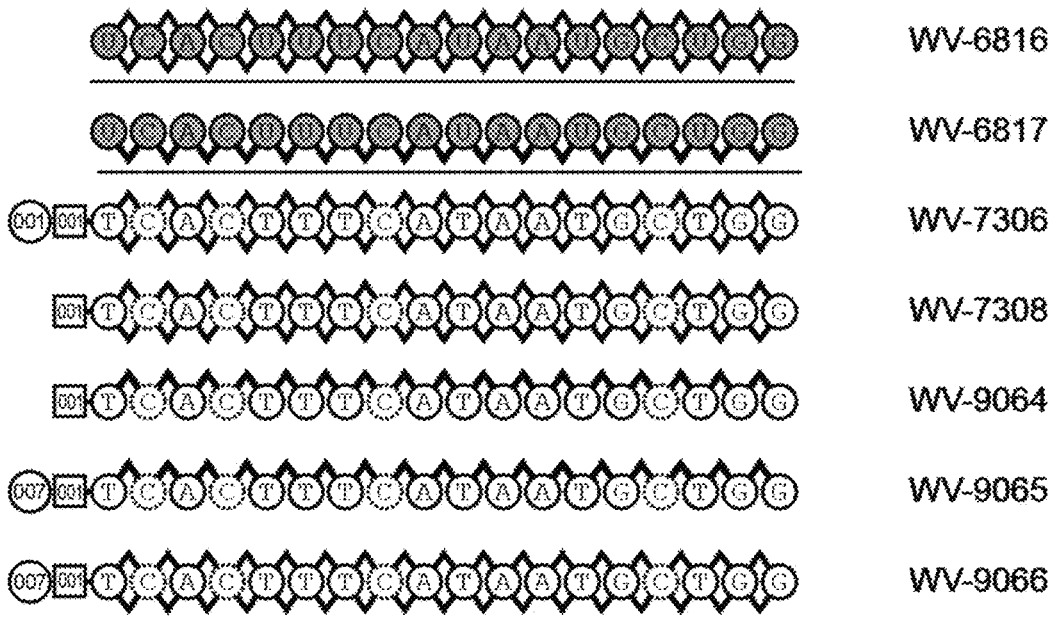
Figure 2D:
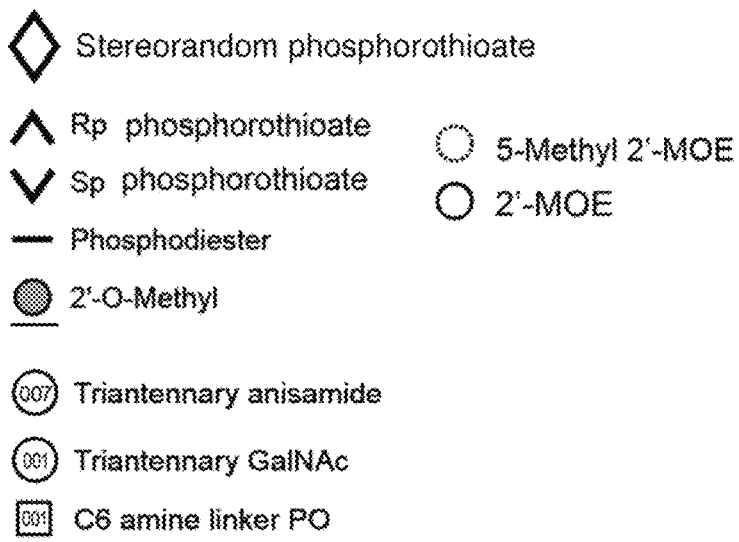

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkenyl: As used herein, the term "alkenyl" refers to an aliphatic group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, an alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an aliphatic group, as defined herein, having one or more triple bonds.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate and/or a pig). In some embodiments, animals include, but are not limited to, mammals, birds, reptiles, amphibians, fish and/or worms. In some embodiments, an animal may be a transgenic animal, a genetically-engineered animal and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Equivalent agents: Those of ordinary skill in the art, reading the present disclosure, will appreciate that the scope of useful agents in the context of the present disclosure is not limited to those specifically mentioned or exemplified herein. In particular, those skilled in the art will recognize that active agents typically have a structure that consists of a core and attached pendant moieties, and furthermore will appreciate that simple variations of such core and/or pendant moieties may not significantly alter activity of the agent. For example, in some embodiments, substitution of one or more pendant moieties with groups of comparable three-dimensional structure and/or chemical reactivity characteristics may generate a substituted compound or portion equivalent to a parent reference compound or portion. In some embodiments, addition or removal of one or more pendant moieties may generate a substituted compound equivalent to a parent reference compound. In some embodiments, alteration of core structure, for example by addition or removal of a small number of bonds (typically not more than 5, 4, 3, 2, or 1 bonds, and often only a single bond) may generate a substituted compound equivalent to a parent reference compound. In many embodiments, equivalent compounds may be prepared by methods illustrated in general reaction schemes as, for example, described below, or by modifications thereof, using readily available starting materials, reagents and conventional or provided synthesis procedures. In these reactions, it is also possible to make use of variants, which are in themselves known, but are not mentioned here.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted form thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocycle: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+NR$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

In vitro: As used herein, the term "in vitro" refers to events that occur in an artificial environment, e.g., in a test tube or reaction vessel, in cell culture, etc., rather than within an organism (e.g., animal, plant and/or microbe).

In vivo: As used herein, the term "in vivo" refers to events that occur within an organism (e.g., animal, plant and/or microbe).

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)N(R^\circ)_2$; $-N(R^\circ)C(S)N(R^\circ)_2$; $-(CH_2)_{0-4}N(R^\circ)C(O)OR^\circ$; $-N(R^\circ)N(R^\circ)C(O)R^\circ$; $-N(R^\circ)N(R^\circ)C(O)N(R^\circ)_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSi(R^\circ)_3$; $-(CH_2)_{0-4}OC(O)R^\circ$; $C(O)(CH_2)_{0-4}SR^\circ$, $-SC(S)SR^\circ$; $-(CH_2)_{0-4}SC(O)R^\circ$; $-(CH_2)_{0-4}C(O)N(R^\circ)_2$; $-C(S)N(R^\circ)_2$; $-C(S)SR^\circ$; $-SC(S)SR^\circ$, $-(CH_2)_{0-4}OC(O)N(R^\circ)_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2N(R^\circ)_2$; $-(CH_2)_{0-4}S(O)R^\circ$; $-N(R^\circ)S(O)_2N(R^\circ)_2$; $-N(R^\circ)S(O)_2R^\circ$; $-N(OR^\circ)R^\circ$; $-C(NH)N(R^\circ)_2$; $-Si(R^\circ)_3$; $-OSi(R^\circ)_3$; $-P(R^\circ)_2$; $-P(OR^\circ)_2$; $-P(R^\circ)(OR^\circ$; $-OP(R^\circ)_2$; $-OP(OR^\circ)_2$; $-OP(R^\circ)(OR^\circ$; $-P[N(R^\circ)_2]_2$ $-P(R^\circ)[N(R^\circ)_2]$; $-P(OR^\circ)[N(R^\circ)_2]$; $-OP)[N(R^\circ)_2]_2$; $-OP(R^\circ)[N(R^\circ)_2]$; $-OP(OR^\circ)[N(R^\circ)_2]$; $-N(R^\circ)P(R^\circ)_2$; $-N(R^\circ)P(OR^\circ)_2$; $-N(R^\circ)P(R^\circ)(OR^\circ$; $-N(R^\circ)P[N(R^\circ)_2]_2$; $-N(R^\circ)P(R^\circ)[N(R^\circ)_2]$; $-N(R^\circ)P(OR^\circ)[N(R^\circ)_2]$; $-B(R^\circ)_2$; $-B(R^\circ)(OR^\circ)$; $-B)(OR^\circ)_2$; $-OB(R^\circ)_2$; $-OB(R^\circ)(OR^\circ$; $-OB(OR^\circ)_2$; $-P(O)(R^\circ)_2$; $-P(O)(R^\circ)(OR^\circ$; $-P(O)(R^\circ)(SR^\circ)$; $-P(O)(R^\circ)[N(R^\circ)_2]$; $-P(O)(OR^\circ)_2$; $-P(O)(SR^\circ)_2$; $-P(O)(OR^\circ)[N(R^\circ)_2]$; $-P(O)(SR^\circ)[N(R^\circ)_2]$; $-P(O)(OR^\circ)(SR^\circ$; $-P(O)[N(R^\circ)_2]_2$; $-OP(O)(R^\circ)_2$; $-OP(O)

(R°)(OR°; —OP(O)(R°)(SR°; —OP(O)(R°)[N(R°)$_2$]; —OP(O)(OR°)$_2$; —OP(O)(SR°)$_2$; —OP(O)(OR°)[N(R°)$_2$]; —OP(O)(SR°)[N(R°)$_2$]; —OP(O)(OR°)(SR°; —OP(O)[N(R°)$_2$]$_2$; —SP(O)(R°)$_2$; —SP(O)(R°)(OR°; —SP(O)(R°)(SR°; —SP(O)(R°)[N(R°)$_2$]; —SP(O)(OR°)$_2$; —SP(O)(SR°)$_2$; —SP(O)(OR°)[N(R°)$_2$]; —SP(O)(SR°)[N(R°)$_2$]; —SP(O)(OR°)(SR°; —SP(O)[N(R°)$_2$]$_2$; —N(R°)P(O)(R°)$_2$; —N(R°)P(O)(R°)(OR°; —N(R°)P(O)(R°)(SR°; —N(R°)P(O)(R°)[N(R°)$_2$]; —N(R°)P(O)(OR°)$_2$; —N(R°)P(O)(SR°)$_2$; —N(R°)P(O)(OR°)[N(R°)$_2$]; —N(R°)P(O)(SR°)[N(R°)$_2$]; —N(R°)P(O)(OR°)(SR°; —N(R°)P(O)[N(R°)$_2$]$_2$; —P(R°)$_2$[B(R°)$_3$]; —P(OR°)$_2$[B(R°)$_3$]; —P(NR°)$_2$[B(R°)$_3$]; —P(R°)(OR°)[B(R°)$_3$]; —P(R°)[N(R°)$_2$][B(R°)$_3$]; —P(OR°)[N(R°)$_2$][B(R°)$_3$]; —OP(R°)$_2$[B(R°)$_3$]; —OP(OR°)$_2$[B(R°)$_3$]; —OP(NR°)$_2$[B(R°)$_3$]; —OP(R°)(OR°)[B(R°)$_3$]; —OP(R°)[N(R°)$_2$][B(R°)$_3$]; —OP(OR°)[N(R°)$_2$][B(R°)$_3$]; —N(R°)P(R°)$_2$[B(R°)$_3$]; —N(R°)P(OR°)$_2$[B(R°)$_3$]; —N(R°)P(NR°)$_2$[B(R°)$_3$]; —N(R°)P(R°)(OR°)[B(R°)$_3$]; —N(R°)P(R°)[N(R°)$_2$][B(R°)$_3$]; —N(R°)P(OR°)[N(R°)$_2$][B(R°)$_3$]; —P(OR')[B(R')$_3$]—; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-20}$ aliphatic, C$_{1-20}$ heteroaliphatic having 1-5 heteroatoms independently selected from nitrogen, oxygen, sulfur, silicon and phosphorus, —CH$_2$—(C$_{6-14}$ aryl), —O(CH$_2$)$_{0-1}$(C$_{6-14}$ aryl), —CH$_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of R°, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$R$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, and a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents, e.g., on a suitable carbon atom, are independently the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur.

Suitable substituents on the aliphatic group of R* are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. In some embodiments, suitable substituents on a substitutable nitrogen are —R$^\dagger$, —NR$^\dagger$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, a provided compound comprises one or more acidic groups, e.g., an oligonucleotide, and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, a provided oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen in the acidic groups are replaced with cations. In some embodiments, a pharmaceutically acceptable salt is a sodium salt of a provided oligonucleotide. In some embodiments, a pharmaceutically acceptable salt is a sodium salt of a provided oligonucleotide, wherein each acidic phosphate group exists as a salt form (all sodium salt).

Protecting group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (e.g., Protecting Groups in Organic Synthesis, T. W. Greene and P. G. M. Wuts, $3^{rd}$ edition, John Wiley & Sons, 1999; Current Protocols in Nucleic Acid Chemistry, edited by Serge L. Beaucage et al. 06/2012; etc.). Example protecting groups (and associated protected moieties) are described in detail below. Protected hydroxyl groups are well known in the art and include those described in detail in Protecting Groups in Organic Synthesis, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenyl sulfonyl)

ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Sample: A "sample" as used herein is a specific organism or material obtained therefrom. In some embodiments, a sample is a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchoalveolar lavages; aspirates; scrapings; bone marrow specimens; tissue biopsy specimens; surgical specimens; feces, other body fluids, secretions and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, a sample is an organism. In some embodiments, a sample is a plant. In some embodiments, a sample is an animal. In some embodiments, a sample is a human. In some embodiments, a sample is an organism other than a human.

Subject: As used herein, the term "subject" or "test subject" refers to any organism to which a provided compound or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. A base sequence which is substantially complementary to a second sequence is not identical to the second sequence, but is mostly or nearly identical to the second sequence. In addition, one of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder and/or condition has been diagnosed with and/or displays one or more symptoms of a disease, disorder and/or condition.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition is predisposed to have that disease, disorder and/or condition. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound (e.g., a SMN2 oligonucleotide) employed; specific composition employed; age, body weight, general health, sex and diet of the subject; time of administration, and rate of excretion of the specific active compound (e.g., a SMN2 oligonucleotide) employed; duration of the treatment; drugs and/or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

Nucleic acid: The term "nucleic acid", as used herein, includes any nucleotides and polymers thereof. The term "polynucleotide", as used herein, refers to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from modified nucleotides and/or modified polynucleotides, such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified internucleotidic linkages. The term encompasses nucleic acids containing any combinations of nucleobases, modified nucleobases, sugars, modified sugars, phosphate bridges or modified internucleotidic linkages. Examples include, and are not limited to, nucleic acids containing ribose moieties, nucleic acids containing deoxy-ribose moieties, nucleic acids containing both ribose and deoxyribose moieties, nucleic acids containing ribose and modified ribose moieties. Unless otherwise specified, the prefix poly- refers to a nucleic acid containing 2 to about 10,000 nucleotide monomer units and wherein the prefix oligo- refers to a nucleic acid containing 2 to about 200 nucleotide monomer units.

Nucleotide: The term "nucleotide" as used herein refers to a monomeric unit of a polynucleotide that consists of a nucleobase, a sugar, and one or more internucleotidic linkages. The naturally occurring bases (guanine, (G), adenine, (A), cytosine, (C), thymine, (T), and uracil (U)) are derivatives of purine or pyrimidine, though naturally and non-naturally occurring base analogs are also included. The naturally occurring sugar is the pentose (five-carbon sugar) deoxyribose (which forms DNA) or ribose (which forms RNA), though naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, phosphorodithioates, H-phosphonates, phosphoramidates, boranophosphates, methylphosphonates, alkylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Nucleoside: The term "nucleoside" refers to a moiety wherein a nucleobase or a modified nucleobase is covalently bound to a sugar or a modified sugar.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars. In some embodiments, a sugar is D-2-deoxyribose. In some embodiments, a sugar is beta-D-deoxyribofuranose. In some embodiments, a sugar moiety is a beta-D-deoxyribofuranose moiety. In some embodiments, a sugar is D-ribose. In some embodiments, a sugar is beta-D-ribofuranose. In some embodiments, a sugar moiety is a beta-D-ribofuranose moiety. In some embodiments, a sugar is optionally substituted beta-D-deoxyribofuranose or beta-D-ribofuranose. In some embodiments, a sugar moiety is an optionally substituted beta-D-deoxyribofuranose or beta-D-ribofuranose moiety. In some embodiments, a sugar moiety/unit in an oligonucleotide, nucleic acid, etc. is a sugar which comprises one or more carbon atoms each independently connected to an internucleotidic linkage, e.g., optionally substituted beta-D-deoxyribofuranose or beta-D-ribofuranose whose 5'-C and/or 3'-C are each independently connected to an internucleotidic linkage (e.g., a natural phosphate linkage, a modified internucleotidic linkage, a chirally controlled internucleotidic linkage, etc.).

Modified sugar: The term "modified sugar" refers to a moiety that can replace a sugar. A modified sugar mimics the spatial arrangement, electronic properties, or some other physicochemical property of a sugar. In some embodiments, a modified sugar is substituted beta-D-deoxyribofuranose or beta-D-ribofuranose. In some embodiments, a modified sugar comprises a 2'-modification. In some embodiments, a modified sugar comprises a linker (e.g., optionally substituted bivalent heteroaliphatic) connecting two sugar carbon atoms (e.g., C2 and C4), e.g., as found in LNA. In some embodiments, a linker is —O—CH(R)—, wherein R is as described in the present disclosure. In some embodiments, a linker is —O—CH(R)—, wherein O is connected to C2, and —CH(R)— is connected to C4 of a sugar, and R is as described in the present disclosure. In some embodiments, R is methyl. In some embodiments, R is —H. In some embodiments, —CH(R)— is of S configuration. In some embodiments, —CH(R)— is of R configuration.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, a modified nucleobase is a substituted nucleobase which nucleobase is selected from A, T, C, G, U, and tautomers thereof. In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs. In some embodiments, a nucleobase is an optionally substituted A, T, C, G, or U, or a substituted nucleobase which nucleobase is selected from A, T, C, G, U, and tautomers thereof.

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases. In some embodiments, a modified nucleobase is a substituted nucleobase which nucleobase is selected from A, T, C, G, U, and tautomers thereof.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule. In some embodiments, a moiety of a compound is a monovalent, bivalent, or polyvalent group formed from the compound by removing one or more —H and/or equivalents thereof from a compound.

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

Internucleotidic linkage: As used herein, the phrase "internucleotidic linkage" refers generally to a linkage linking nucleoside units of an oligonucleotide or a nucleic acid. In some embodiments, an internucleotidic linkage is a phosphodiester linkage, as found in naturally occurring DNA and RNA molecules (a natural phosphate linkage). In some embodiments, an internucleotidic linkage includes a modified internucleotidic linkage. In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described in the present disclosure. In some embodiments, an internucleotidic linkage is a phosphotriester linkage, phosphorothioate diester linkage (

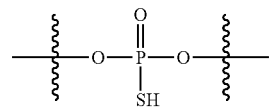

), or modified phosphorothioate triester linkage. In some embodiments, an internucleotidic linkage has the structure of formula I or a salt form thereof. In some embodiments, an internucleotidic linkage is one of, e.g., PNA (peptide nucleic acid) or PMO (phosphorodiamidate Morpholino oligomer) linkage. It is understood by a person of ordinary skill in the art that an internucleotidic linkage may exist as an anion or cation at a given pH due to the existence of acid or base moieties in the linkage, for example, natural phosphate linkages and phosphorothioate diester linkages may exist as salt forms. In some embodiments, an internucleotidic linkage comprises a chiral linkage phosphorus. In some embodiments, an internucleotidic linkage is a chirally controlled internucleotidic linkage.

Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications. In some embodiments, oligonucleotides of a common designated "type" are structurally identical to one another.

One of skill in the art appreciates that synthetic methods of the present disclosure can provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide is designed and/or selected in advance to have a particular combination of stereocenters at the linkage phosphorus. In some embodiments, an oligonucleotide is designed and/or determined to have a particular combination of modifications at the linkage phosphorus. In some embodiments, an oligonucleotide is designed and/or selected to have a particular combination of modifications at the bases. In some embodiments, an oligonucleotide is designed and/or selected to have a particular combination of modifications at the sugars. In some embodiments, an oligonucleotide is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in pre-determined relative amounts.

Chiral control: As used herein, "chiral control" refers to control of the stereochemical designation of a chiral linkage phosphorus in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled (stereocontrolled) oligonucleotide composition", "chirally controlled (stereocontrolled) nucleic acid composition", and the like, as used herein, refers to a composition that comprises a plurality of oligonucleotides (or nucleic acids, chirally controlled oligonucleotides or chirally controlled nucleic acids) which share 1) a common base sequence, 2) a common pattern of backbone linkages, and 3) a common pattern of backbone phosphorus modifications, wherein the plurality of oligonucleotides (or nucleic acids) share the same stereochemistry at one or more chiral internucleotidic linkages (chirally controlled internucleotidic linkages, whose chiral linkage phosphorus is Rp or Sp in the composition, not a random Rp and Sp mixture as non-chirally controlled internucleotidic linkages). Level of the plurality of oligonucleotides (or nucleic acids) in a chirally controlled oligonucleotide composition is non-random (pre-determined, controlled), e.g., through chirally controlled oligonucleotide preparation to stereoselectively form one or more chiral internucleotidic linkages (e.g., using chiral auxiliaries as exemplified in the present disclosure, compared to non-chirally controlled (stereorandom, non-stereoselective, racemic) oligonucleotide synthesis such as traditional phosphoramidite-based oligonucleotide synthesis using no chiral auxiliaries or chiral catalysts to purposefully control stereoselectivity). In some embodiments, a chirally controlled oligonucleotide composition is enriched, relative to a substantially racemic preparation of oligonucleotides having the common base sequence, the common pattern of backbone linkages, and the common pattern of backbone phosphorus modifications, for oligonucleotides of the plurality. In some embodiments, a chirally controlled oligonucleotide composition comprises a plurality of oligonucleotides of a particular oligonucleotide type defined by: 1) base sequence; 2) pattern of backbone linkages; 3) pattern of backbone chiral centers; and 4) pattern of backbone phosphorus modifications, wherein it is enriched, relative to a substantially racemic preparation of oligonucleotides having the same base sequence, for oligonucleotides of the particular oligonucleotide type.

In some embodiments, the plurality of oligonucleotides in a chirally controlled oligonucleotide composition share the same base sequence, the same, if any, nucleobase, sugar, and internucleotidic linkage modifications, and the same stereochemistry (Rp or Sp) independently at linkage phosphorus chiral centers of one or more chirally controlled internucleotidic linkages, though stereochemistry of certain linkage phosphorus chiral centers may differ. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a predetermined level is about 0.1%-100%, (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotides, or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications, or of all oligonucleotides in a composition that share a common base sequence and the same constitution. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 0.1%-100% (e.g., about 1%-100%, 5%-100%, 10%-100%, 20%-100%, 30%-100%, 40%-100%, 50%-100%, 60%-100%, 70%-100%, 80%-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide or nucleic acids types. For instance, in some embodiments a chirally controlled oligonucleotide composition comprises one oligonucleotide type at a predetermined level. In some embodiments, a chirally controlled oligonucleotide composition comprises more than one oligonucleotide type, each independently at a predetermined level. In some embodiments, a chirally controlled oligonucleotide composition comprises multiple oligonucleotide types, each independently at a predetermined level. In some embodiments, a chirally controlled oligonucleotide composition is a composition of oligonucleotides of an oligonucleotide type, which composition comprises a predetermined level of a plurality of oligonucleotides of the oligonucleotide type.

Chirally pure: as used herein, the phrase "chirally pure" is used to describe an oligonucleotide or compositions thereof, in which all are nearly all (the rest are impurities) of the oligonucleotide molecules exist in a single diastereomeric form with respect to the linkage phosphorus atoms.

Predetermined: By predetermined (or pre-determined) is meant deliberately selected or non-random or controlled, for example as opposed to randomly occurring, random, or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that are not controlled to intentionally generate the particular chemistry and/or stereochemistry features are not "predetermined" compositions. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is chiral. In some embodiments, a linkage phosphorus atom is achiral.

For purposes of this disclosure, the chemical elements are identified in accordance with the Periodic Table of the Elements, CAS version, Handbook of Chemistry and Physics, 67th Ed., 1986-87, inside cover.

Unless otherwise specified, salts, such as pharmaceutically acceptable acid or base addition salts, stereoisomeric forms, and tautomeric forms, of provided compounds (e.g., oligonucleotides, agents, etc.) are included. Unless otherwise specified, singular forms "a", "an", and "the" include the plural reference unless the context clearly indicates otherwise. Thus, for example, a reference to "a compound" may include a plurality of such compounds.

DESCRIPTION OF CERTAIN EMBODIMENTS

Most transcripts, e.g., pre-mRNAs, undergo splicing processes. Splicing of pre-mRNA to provide mature mRNA is an essential step for expression of most genes in higher eukaryotes. Many conditions, disorders and diseases are associated with aberrant splicing, for example, those described in WO 2017062862; Scotti and Swanson, Nature Reviews Genetics 17, 19-32 (2016); Havens et al., Wiley Interdiscip. Rev. RNA. 2013 May; 4(3): 247-266; Tazi et al., Biochimica et Biophysica Acta 1792 (2009) 14-26; Douglas and Wood, etc. In some embodiments, a condition, disorder, and/or disease is characterized by exclusion of an exon during splicing, and patients suffering from such a condition, disorder and/or disease may benefit from inclusion of the exon during splicing, e.g., SMA or ALS. Among other things, the present disclosure provides technologies for promoting inclusion of an exon to increase the level of non-disease-associated splicing products, optionally preferably over disease-associated products, e.g., SMN2 mRNA containing exon 7 over SMN2 mRNA not containing exon 7.

Proximal spinal muscular atrophy (SMA) is reportedly the second most common autosomal recessive disorder, and is characterized by the loss of motor neurons in the brainstem and anterior horn of the spinal cord (Pearn, Lancet 8174, 919-922). SMA is reportedly the most common cause of genetically determined neonatal death. In general, the earlier the symptoms appear, the shorter the expected life-span. Once symptoms appear, the motor neuron cells reportedly quickly deteriorate. All forms of SMA reportedly have in common weakness caused by denervation, that is, the muscle atrophies because it has lost the signal to contract due to loss of the innervating nerve. Spinal muscular atrophy reportedly only affects motor nerves. Heritable disorders that cause both weakness due to motor denervation along with sensory impairment due to sensory denervation are reportedly known by the inclusive label Charcot-Marie-Tooth or Hereditary Motor Sensory Neuropathy. The course of SMA is reportedly directly related to the severity of weakness. Infants with the severe form of SMA frequently succumb to respiratory disease due to weakness of the muscles that support breathing. Children with milder forms of SMA reportedly naturally live much longer although they may need extensive medical support, especially those at the more severe end of the spectrum. Type I SMA, also known as severe infantile SMA or Werdnig-Hoffmann disease, is reportedly the most severe, and manifests in the first year of life. This type reportedly generally onsets quickly and unexpectedly after birth; babies diagnosed with Type I SMA do not generally live past one year of age. Pneumonia is reportedly considered the ultimate cause of death due to deterioration of survival motor neurons; motor neuron death causes insufficient functioning of the major bodily organ systems, particularly respiratory (e.g., breathing and ridding of pooled secretions inside lungs). Type II SMA, or intermediate SMA, reportedly describes those children who are never able to stand and walk, but who are able to maintain a sitting position at least some time in their life. The onset of weakness is reportedly usually recognized some time between 6 and 18 months. Weakness slowly and gradually increases over the life of the individual. Type III SMA patients reportedly are able to walk at some time.

It was reported that linkage mapping identified the Survival of Motor Neuron (SMN) gene as the genetic locus of SMA (Lefebvre et al., Cell 80, 1-5), and that deletions or other mutations within both chromosomal copies of SMN1 cause proximal SMA (Lefebvre et al., Cell 80, 1-5). SMN1 encodes a ubiquitously expressed 38 kDa SMN protein that is necessary for snRNP assembly, an essential process for cell survival (Wan et al. 2005. Mol. Cell. Biol. 25:5543-5551).

A nearly identical copy of the gene, SMN2, exists in the centromere of chromosome 5q13 and encodes the same SMN protein. However, SMN2 generally fails to fully compensate for the loss of SMN1, because approximately 80% of SMN2 transcripts are improperly spliced, resulting in skipping of exon 7, which produces an unstable truncated protein, SMNΔ7 (Lorson, C. L., et al. 1998. Nat. Genet. 19:63-66). The small amounts of stable, full-length SMN produced from SMN2 are only capable of ameliorating the disease temporarily; most patients with congenital SMA do not survive past two years.

It is reported that SMN1 and SMN2 differ by a critical C to T substitution at position 6 of exon 7 (C6U in transcript of SMN2) (Lorson, C. L., et al. 1999. Proc. Natl. Acad. Sci. USA 96:6307-6311; Monani, U. R., et al. 1999. Hum. Mol. Genet. 8:1177-1183). C6U does not change the coding sequence, but is sufficient to cause exon 7 skipping in many transcripts.

Exon 7 of SMN2 is reported to have a weak 3' ss (splice site) (Lim, S. R., and K. J. Hertel. 2001. J. Biol. Chem. 276:45476-45483), likely due to its suboptimal polypyrimidine tract. An improved polypyrimidine tract reportedly promoted inclusion of exon 7 in SMN2 (Lorson, C. L., and E. J. Androphy. 2000. Hum. Mol. Genet. 9:259-265), indicating that the negative interactions at C6U and the positive interactions at the polypyrimidine tract were mutually exclusive. Several splicing factors have been implicated in modulation of SMN exon 7 splicing. Most studied among them has reportedly been the SR-like protein, Tra2-beta 1, that binds to a purine-rich ESE in the middle of exon 7 (Hofmann, Y., et al. 2000. Proc. Natl. Acad. Sci. USA 97:9618-23). Elevated expression of Tra2-beta 1 (ibid.) or its associated proteins, hnRNP G (Hofmann, Y., and B. Wirth. 2002. Hum. Mol. Genet. 11:2037-2049) and Srp30c (Young, P. J., et al. 2002. Hum. Mol. Genet. 11:577-587), has been reported to promote exon 7 inclusion in SMN2. A recent report in which increased expression of STAR (signal transduction and activation of RNA) family of proteins promoted exclusion of exon 7 reportedly indicated that tissue-specific regulation might occur (Stoss, O., et al. 2004. Mol. Cell. Neurosci. 27:8-21). Proteins interacting with intronic sequences reportedly could also affect regulation of exon 7 splicing. Consistently, cis-elements present in intron 6 and intron 7 have been reported to modulate exon 7 splicing (Miyajima, H., et al. 2002. J. Biol. Chem. 277:23271-23277; Miyaso, H., et al. 2003. J. Biol. Chem. 278:15825-15831). These results have reported the complexity of pre-mRNA splicing, in which exon 7 is defined by a network of interactions involving several proteins.

SMN function reportedly correlates with its ability to self-associate (Lorson et al., Nat. Genet. 19, 63-66). It is reported that SMN also performs a housekeeping role by helping regenerate the spliceosome through a multi-component SMN complex (Meister et al., Trends Cell Biol. 12, 472-478; Gubitz et al., Exp. Cell. Res. 296, 51-56). Many recent reviews highlight the functional role of SMN with direct implications to SMA (Ogino and Wilson, Expert. Rev. Mol. Diagn. 4, 15-29; Iannaccone et al., Curr. Neurol. Neurosci. Rep. 4, 74-80). In some embodiments, defects caused by the lack of SMN1 can be partially compensated by high copy number of SMN2, which produces low levels of the full-length protein (Monani et al., Hum. Mol. Genet. 9, 2451-2457; Stoilov et al., DNA Cell Biol. 21, 803-818). Most SMA patients reportedly have an SMN2 gene, thus, therapies that improve the levels of exon 7 inclusion in SMN2 can be effective.

SMN1 and SMN2 are further described in, for example, Pellizzoni et al. 2007 EMBO Rep. 8: 340-5; Awano et al. 2014 Neurother. 11: 786-795; Burglen et al. 1996 Genom. 32: 479-482; Clark, F., and T. A. Thanaraj. 2002. Hum. Mol. Genet. 11:451-64; Miriami, E., et al. 2003. Nucleic Acids Res. 31:1974-1983; Zhang, X. H., and L. A. Chasin. 2004. Genes Dev. 18:1241-1250; Zhang, X. H., et al. 2005. Genome Res. 15:768-779; Lorson et al. 2010 Human Mol.

Genet. 19: R111-R118; Singh et al. 2013 Nucl. Acids Res. 41: 8144-8165; Liu et al. 1996 EMBO J. 15: 3555-3565; Lorson et al. 1999 Proc. Natl. Acad. Sci. US 96: 6307-6311; Peeters et al. 2014 Brain 137: 2879-2896; Sarachan et al. 2012 Biochem. J. 445: 361-370; Singh et al. 2006 Mol. Cell. Biol. 26: 1333-1346; and Tisdale et al. 2015 J. Neurosci. 35: 8691-8700.

In some embodiments, SMA is caused by loss of the SMN1 gene from both chromosomes. In some embodiments, a patient's chromosomes comprise more than one copy of SMN2, and an increasing number of SMN2 copies are reportedly related to less severe disease. SMA has reportedly been divided into various types. In some embodiments, SMA includes SMA 1, SMA 2, and SMA 3. In some embodiments, the severity of SMA, ranging from SMA 1 to SMA 3, is reportedly partially related to how well the remaining SMN 2 gene copy or copies can make up for the loss of SMN 1. In some embodiments, SMA includes Type I SMA, Type II SMA, and Type III SMA. In some embodiments, SMA includes Type 0, Type 1, Type 2, Type 3, and Type 4 SMA. In some embodiments, Type 0 to 4 are described as follows: Type 0: Onset: prenatal; function: respiratory failure at birth; median survival: weeks; Type 1: Onset: 0-6 months; function: never sit; median survival: <1 year; Type 2: Onset: <18 months; function: ability to sit; median survival: >25 years; Type 3: Onset: >18 months; function: ability to stand or be ambulatory; median survival: Adult; Type 4: Onset: 30 years; function: ability to be ambulatory; median survival: Adult. See, for example, Arnold et al. 2015 Muscle Nerve 51: 157-167. In some embodiments, Type I SMA is also designated Werdnig-Hoffman disease. In some embodiments, Type II SMA is also designated Dubowitz disease. In some embodiments, Type III SMA is also designated Kugelberg-Welander disease. See also: Butchbach et al. 216 Front. Mol. Biosci. Vol. 3, Article 7; Edens et al. 2015 Biochim. Biophys. Acta 1852: 685-692.

In some embodiments, the present disclosure provides compositions for blocking inhibitory effects of the SMN2 intronic splice silencing domain, ISS-N1. In particular, the disclosure among other things provides compositions comprising oligonucleotide compositions that block splice inhibitory effects of the ISS-N1 domain. Among other things, certain provided oligonucleotides can modulate splicing of the SMN2 pre-mRNA to include exon 7 (or to prevent the exclusion of exon 7) in processed forms of the transcript. Agents capable of blocking the splicing effect of ISS-N1 have high value as SMA therapeutics. Such agents can also be used in treatment of amyotrophic lateral sclerosis (ALS), another neurological disease characterized by low levels of SMN protein (Veldink, J. H., et al. 2005 Neurology 65(6):820-5). Among other things, the present disclosure provides agents capable of blocking splicing inhibitory effects of the SMN2 ISS-N1 domain, including but not limited to, e.g., agents that disrupt the interaction of an ISS-N1-interacting protein with the ISS-N1 sequence, agents that sequester an ISS-N1 interacting protein, agents that disrupt the structure of the ISS-N1 domain and/or surrounding regions (including, e.g., the U1 snRNP binding site within the SMN2 pre-mRNA that lies proximal to the ISS-N1 sequence domain).

Nusinersen, marketed as SPINRAZA™, is a stereorandom SMN2 oligonucleotide composition, which has been approved in the U.S. for intrathecal use in the treatment of spinal muscular atrophy (SMA) in pediatric and adult patients. SPINRAZA™ was reportedly shown to increase exon 7 inclusion in SMN2 messenger ribonucleic acid (mRNA) transcripts and production of full-length SMN protein. SPINRAZA™ is also reported to elicit various adverse effects in some patients receiving it, e.g., as described elsewhere herein.

In some embodiments, as demonstrated herein, the present disclosure provides various oligonucleotide compositions, e.g., chirally controlled oligonucleotide compositions, that have significantly improved properties and/or activities compared to stereorandom compositions such as Nusinersen, e.g., greatly improved efficiency for exon-inclusion particularly at low concentrations. Example results include those presented in FIGS. 1A, 1B and 1C, and Table 2A, Table 2B and Table 2C. For example, as described herein, several chirally controlled SMN2 oligonucleotides showed higher activity, especially at low concentrations, than the corresponding stereorandom SMN2 oligonucleotide WV-2782 (which is equivalent to Nusinersen). For example, several chirally controlled oligonucleotides showed higher activities than Nusinersen (stereorandom WV-2782) at 0.1 μM, e.g., chirally controlled oligonucleotide compositions of WV-6779 (which was significantly more active than WV-2782) and WV-6768 (which was significantly more active than WV-2782) in FIG. 1A. In FIG. 1B, stereorandom WV-2782 and chirally controlled WV-6768 were tested over several concentrations from 0.03125 to 2 μM and the chirally controlled oligonucleotide composition of WV-6768 demonstrated higher activity at lower concentrations. FIG. 1C showed that several chirally controlled oligonucleotides, including WV-6780, WV-6781 and WV-6782, had higher activity than the stereorandom WV-2782, at lower concentrations e.g., 0.0625 μM.

In addition, as shown in Table 2C and elsewhere herein, a provided oligonucleotide comprising an additional chemical moiety capable of binding to the asialoglycoprotein receptor provided a longer duration of efficacy in vivo than Nusinersen (which does not comprise an additional chemical moiety capable of binding to the asialoglycoprotein receptor), wherein duration of efficacy was measured by the percentage of surviving animals having a disease model for SMA.

In some embodiments, the present disclosure pertains to a SMN2 oligonucleotide composition, wherein the oligonucleotide has: A) the base sequence; B) pattern of base modification; C) pattern of sugar modification; D) pattern of backbone linkages; E) pattern of backbone chiral centers; and F) additional chemical moieties (if any), of any SMN2 oligonucleotide described herein.

In some embodiments, the present disclosure pertains to a chirally controlled SMN2 oligonucleotide composition, wherein the oligonucleotide has: A) the base sequence; B) pattern of base modification; C) pattern of sugar modification; D) pattern of backbone linkages; E) pattern of backbone chiral centers; and F) additional chemical moieties (if any), of: WV-6779, WV-6768, WV-6780, WV-6781, or WV-6782.

In some embodiments, the present disclosure pertains to a chirally controlled SMN2 oligonucleotide composition, wherein the oligonucleotide is WV-6779, WV-6768, WV-6780, WV-6781, or WV-6782.

In some embodiments, the present disclosure pertains to a chirally controlled SMN2 oligonucleotide composition, wherein the base sequence of oligonucleotide is the base sequence of WV-6779, WV-6768, WV-6780, WV-6781, WV-6782, or WV-7306.

In some embodiments, the present disclosure pertains to a chirally controlled SMN2 oligonucleotide composition, wherein the base sequence and pattern of sugar modifications of oligonucleotide are the base sequence and pattern of sugar modifications of WV-6779, WV-6768, WV-6780, WV-6781, or WV-6782.

In some embodiments, the present disclosure pertains to a chirally controlled SMN2 oligonucleotide composition, wherein the base sequence and pattern of backbone linkages of oligonucleotide are the base sequence and pattern of backbone linkages of WV-6779, WV-6768, WV-6780, WV-6781, or WV-6782.

In some embodiments, the present disclosure pertains to a chirally controlled SMN2 oligonucleotide composition, wherein the base sequence, pattern of sugar modifications and pattern of backbone linkages of oligonucleotide are the base sequence, pattern of sugar modifications and pattern of backbone linkages of WV-6779, WV-6768, WV-6780, WV-6781, or WV-6782.

In some embodiments, base sequence of provided oligonucleotides comprises or is, or comprises or is a sequence complementary to, the intronic splicing silencer-N1 or ISS-N1 (5'-CCAGCAUUAUGAAAG-3' (SEQ ID NO: 3)), or a partial sequence or variant thereof capable of inhibiting the exclusion of exon 7 during splicing of a SMN2 pre-mRNA. In some embodiments, one such partial sequence is the complement of 5'-CCAGCAUU-3'. In some embodiments, critical residues that mediate the splice site inhibitory activity of the ISS-N1 sequence can also be represented by the sequence 5'-CCAGCNNNNNGAAAG-3' (SEQ ID NO: 4). In some embodiments, base sequence of provided oligonucleotides comprises or is, or comprises or is a sequence complementary to, 5'-CCAGCNNNNNGAAAG-3' (SEQ ID NO: 4), wherein N is A, T, C, G or U.

In some embodiments, base sequence of provided oligonucleotides comprises or is the complement of the intronic splicing silencer-N1 or ISS-N1 (5'-CCAGCAUUAUGAAAG-3' (SEQ ID NO: 3)), or base sequence of provided oligonucleotides comprises or is a partial sequence or variant thereof capable of inhibiting the exclusion of exon 7 during splicing of a SMN2 pre-mRNA. In some embodiments, one such effective sequence thereof is the complement of 5'-CCAGCAUU-3'. In some embodiments, critical residues that mediate the splice site inhibitory activity of the ISS-N1 sequence can also be represented by the sequence 5'-CCAGCNNNNNGAAAG-3' (SEQ ID NO: 4). In some embodiments, base sequence of provided oligonucleotides comprises or is the complement of 5'-CCAGCNNNNNGAAAG-3' (SEQ ID NO: 4), wherein N is A, T, C, G or U.

In some embodiments, an oligonucleotide composition targets a SMN2 transcript in that it comprises a plurality of oligonucleotides as described in the present disclosure, wherein oligonucleotides of the plurality are SMN2 oligonucleotides. In some embodiments, an oligonucleotide composition targets intron 7 of SMN2. In some embodiments, an oligonucleotide composition targets ISS-N1 of SMN2. In some embodiments, the present disclosure provides an oligonucleotide composition, wherein the base sequence of oligonucleotides of the oligonucleotide composition comprises 13 contiguous bases of any SMN2 sequence disclosed herein. In some embodiments, the present disclosure provides an oligonucleotide composition, wherein the base sequence of oligonucleotides (e.g., oligonucleotides of a plurality) of the oligonucleotide composition comprises 15 contiguous bases of any SMN2 sequence disclosed herein.

In some embodiments, a SMN2 oligonucleotide composition is chirally controlled or stereodefined in that at least one internucleotidic linkage comprises a chiral center which is chirally controlled or stereodefined within the composition. In some embodiments, a chirally controlled oligonucleotide composition targets a SMN2 transcript in that it comprises a plurality of oligonucleotides of a particular oligonucleotide type as described in the present disclosure, wherein oligonucleotides of the plurality are SMN2 oligonucleotides. In some embodiments, a chirally controlled oligonucleotide composition targets intron 7 of SMN2. In some embodiments, a chirally controlled oligonucleotide composition targets ISS-N1 of SMN2. In some embodiments, the present disclosure provides a chirally controlled oligonucleotide composition, wherein the base sequence of oligonucleotides of the chirally controlled oligonucleotide composition comprises 13 contiguous bases of any SMN2 sequence disclosed herein. In some embodiments, the present disclosure provides a chirally controlled oligonucleotide composition, wherein the base sequence of oligonucleotides (e.g., oligonucleotides of a plurality) of the chirally controlled oligonucleotide composition comprises 15 contiguous bases of any SMN2 sequence disclosed herein.

In some embodiments, the present disclosure provides an oligonucleotide composition, wherein the base sequence of oligonucleotides of the oligonucleotide composition is any SMN2 sequence disclosed herein, and wherein the oligonucleotide composition is chirally controlled and/or the oligonucleotides of composition comprise an additional chemical moiety capable of binding to the asialoglycoprotein receptor. In some embodiments, the present disclosure provides an oligonucleotide composition, wherein the base sequence of oligonucleotides of the oligonucleotide composition is any SMN2 sequence disclosed herein. In some embodiments, the present disclosure provides a SMN2 oligonucleotide composition, wherein the base sequence of oligonucleotides of the oligonucleotide composition is TCACTTTCATAATGCTGG (SEQ ID NO: 1). In some embodiments, the present disclosure provides a SMN2 oligonucleotide composition, wherein the base sequence of oligonucleotides of the oligonucleotide composition is TCACTTTCATAATGCTGG (SEQ ID NO: 479) or CUUUCNNNNNGCUGG (SEQ ID NO: 2), wherein each T can be independently substituted by U or vice versa. In some embodiments, the present disclosure provides a SMN2 oligonucleotide composition, wherein the base sequence of oligonucleotides of the oligonucleotide composition comprises 15 contiguous bases of TCACTTTCATAATGCTGG (SEQ ID NO: 479) or CUUUCNNNNNGCUGG (SEQ ID NO: 2), wherein each T can be independently substituted by U or vice versa. In some embodiments, the present disclosure provides a SMN2 oligonucleotide composition, wherein the base sequence of oligonucleotides of the oligonucleotide composition comprises a sequence of 15 contiguous bases with 0-3 mismatches of TCACTTTCATAATGCTGG (SEQ ID NO: 479) or CUUUCNNNNNGCUGG (SEQ ID NO: 2), wherein each T can be independently substituted by U or vice versa. In some embodiments, the oligonucleotide composition is chirally controlled and/or oligonucleotides of the composition further comprise an additional chemical moiety capable of binding to the asialoglycoprotein receptor.

In some embodiments, the present disclosure pertains to an oligonucleotide composition (e.g., a chirally controlled oligonucleotide composition, a SMN2 oligonucleotide composition, etc.), which oligonucleotide composition comprises oligonucleotides of a base sequence which is at least 80% complementary to intron 7 of the SMN2 gene over the entire length of the oligonucleotide composition and at least 85% identical to the sequence of TAATGCTGG, ATAATGCTGG (SEQ ID NO: 5), CATAATGCTGG (SEQ ID NO: 6), TCATAATGCTGG (SEQ ID NO: 7), TTCATAATGCTGG (SEQ ID NO: 8), TTTCATAATGCTGG (SEQ ID NO: 9), CTTTCATAATGCTGG (SEQ ID NO: 10), ACTTTCATAATGCTGG (SEQ ID NO: 11), CACTTTCATAATGCTGG (SEQ ID NO: 12), TCACTTTCATAATGCTGG (SEQ ID NO: 479), TTCACTTTCATAATGCTGG (SEQ ID NO: 13), ATTCACTTTCATAATGCTGG (SEQ ID NO: 14), or CUUUCNNNNNGCUGG (SEQ ID NO: 2), wherein each T can be independently replaced by U and vice versa, wherein the oligonucleotide composition is capable of mediating an increase in the level, expression and/or activity of exon 7-containing SMN2 mRNA or its gene product in a cell or organism. In some embodiments, the oligonucleotide composition is chirally controlled and/or further comprises an additional chemical moiety capable of binding to the asialoglycoprotein receptor.

In some embodiments, the present disclosure pertains to a composition comprising an oligonucleotide composition, wherein the base sequence of oligonucleotides of the oligonucleotide composition is or comprises TCACTTTCATAATGCTGG (SEQ ID NO: 479) or a 15-base portion thereof, wherein each T can be optionally and independently substituted with U. In some embodiments, the oligonucleotide composition is chirally controlled and/or further comprises an additional chemical moiety capable of binding to the asialoglycoprotein receptor.

In some embodiments, the present disclosure pertains to a composition comprising an oligonucleotide composition, wherein the base sequence of oligonucleotides of the oligonucleotide composition is or comprises TCACTTTCATAATGCTGG (SEQ ID NO: 479), or a 15-base portion thereof, wherein each T can be optionally and independently substituted with U, wherein the oligonucleotide composition is capable of mediating an increase in the level, expression and/or activity of exon 7-containing SMN2 mRNA or its gene product in a cell or organism. In some embodiments, the oligonucleotide composition is chirally controlled and/or further comprises an additional chemical moiety capable of binding to the asialoglycoprotein receptor.

In some embodiments, the composition comprises a pharmaceutically acceptable carrier. In some embodiments, the present disclosure pertains to a salt of an oligonucleotide. In some embodiments, the present disclosure pertains to a sodium salt of an oligonucleotide.

In some embodiments, the present disclosure pertains to a method of increasing the level, expression and/or activity of exon 7-containing SMN2 mRNA or its gene product in a cell or organism comprising contacting the cell with or administering to the organism an oligonucleotide composition, which oligonucleotide composition comprises oligonucleotides of a base sequence which is at least 80% complementary to intron 7 of the SMN2 gene over the entire length of the oligonucleotide composition and at least 85% complementary to the sequence of CCAGCAUU, CCAGCAUUAUGAAAG (SEQ ID NO: 481), CCAGCAUUAUGAAAGUGA (SEQ ID NO: 15), CCAGCAUUAUGAAAGUGAAU (SEQ ID NO: 16), or CCAGCNNNNNGAAAG (SEQ ID NO: 482), wherein each T can be independently replaced by U and vice versa, such that the level, expression and/or activity of exon 7-containing SMN2 mRNA or its gene production the cell is increased. In some embodiments, the oligonucleotide composition is chirally controlled and/or further comprises an additional chemical moiety capable of binding to the asialoglycoprotein receptor.

In some embodiments, the present disclosure pertains to a method of increasing the level, expression and/or activity of exon 7-containing SMN2 mRNA or its gene product in a cell or organism comprising contacting the cell with or administering to the organism an oligonucleotide composition, which oligonucleotide composition comprises a base sequence which is at least 80% complementary to intron 7 of the SMN2 gene over the entire length of the oligonucleotide composition and at least 85% identical to the sequence of TAATGCTGG, ATAATGCTGG (SEQ ID NO: 5), CATAATGCTGG (SEQ ID NO: 6), TCATAATGCTGG (SEQ ID NO: 7), TTCATAATGCTGG (SEQ ID NO: 8), TTTCATAATGCTGG (SEQ ID NO: 9), CTTTCATAATGCTGG (SEQ ID NO: 10), ACTTTCATAATGCTGG (SEQ ID NO: 11), CACTTTCATAATGCTGG (SEQ ID NO: 12), TCACTTTCATAATGCTGG (SEQ ID NO: 479), TTCACTTTCATAATGCTGG (SEQ ID NO: 13), ATTCACTTTCATAATGCTGG (SEQ ID NO: 14), or CUUUCNNNNNGCUGG (SEQ ID NO: 2), wherein each T can be independently replaced by U and vice versa. In some embodiments, the oligonucleotide composition is chirally controlled and/or further comprises an additional chemical moiety capable of binding to the asialoglycoprotein receptor.

In some embodiments, the level, expression and/or activity of exon 7-containing SMN2 mRNA or its gene product in the cell or organism is increased relative to exon-deleted SMN2 mRNA.

In some embodiments, an organism is a mammal. In some embodiments, an organism is a human. In some embodiments, a human has spinal muscular atrophy (SMA).

In some embodiments, the present disclosure pertains to a method of treating spinal muscular atrophy (SMA) in a subject, comprising administering to the subject an oligonucleotide composition, wherein oligonucleotides of the composition comprises a sequence: at least 80% complementary to intron 7 of the SMN2 gene over the entire length of the oligonucleotide composition and at least 85% complementary to the sequence of CCAGCAUU, CCAGCAUUAUGAAAG (SEQ ID NO: 481), CCAGCAUUAUGAAAGUGA (SEQ ID NO: 15), CCAGCAUUAUGAAAGUGAAU (SEQ ID NO: 16), or CCAGCNNNNNGAAAG (SEQ ID NO: 482), wherein each T can be independently replaced by U and vice versa. In some embodiments, provided methods comprise a dose effective to increase the level, expression and/or activity of exon 7-containing SMN2 mRNA or its gene product in a cell of the subject, such that SMA in the patient is treated. In some embodiments, the oligonucleotide composition is chirally controlled and/or further comprises an additional chemical moiety capable of binding to the asialoglycoprotein receptor.

In some embodiments, the present disclosure pertains to a method of treating spinal muscular atrophy (SMA) in a subject, comprising administering to the subject an oligonucleotide composition, which oligonucleotide composition comprises oligonucleotides of a sequence: at least 80% complementary to intron 7 of the SMN2 gene over the entire length of the oligonucleotide and at least 85% identical to the sequence of TAATGCTGG, ATAATGCTGG (SEQ ID NO: 5), CATAATGCTGG (SEQ ID NO: 6), TCATAATGCTGG (SEQ ID NO: 7), TTCATAATGCTGG (SEQ ID NO: 8), TTTCATAATGCTGG (SEQ ID NO: 9), CTTTCATAATGCTGG (SEQ ID NO: 10), ACTTTCATAATGCTGG (SEQ ID NO: 11), CACTTTCATAATGCTGG (SEQ ID NO: 12), TCACTTTCATAATGCTGG (SEQ ID NO: 479), TTCACTTTCATAATGCTGG (SEQ ID NO: 13), ATT- CACTTTCATAATGCTGG (SEQ ID NO: 14), or CUUUCNNNNNGCUGG (SEQ ID NO: 2), wherein each T can be independently replaced by U and vice versa. In some embodiments, the oligonucleotide composition is chirally controlled and/or further comprises an additional chemical moiety capable of binding to the asialoglycoprotein receptor.

In some embodiments, the present disclosure pertains to a method for inhibiting an SMN2 pre-mRNA intronic splicing silencer site in a cell or organism comprising contacting the cell with or administering to the organism an oligonucleotide composition 100% complementary to the sequence of CCAGCAUU, such that the SMN2 intronic splicing silencer site is inhibited. In some embodiments, the oligonucleotide composition is chirally controlled and/or further comprises an additional chemical moiety capable of binding to the asialoglycoprotein receptor.

In some embodiments, the present disclosure pertains to a method of administering an oligonucleotide composition to a subject comprising administering to a subject an oligonucleotide composition, which oligonucleotide composition comprises a sequence: at least 80% complementary to intron 7 of the SMN2 gene over the entire length of the oligonucleotide and at least 85% complementary to the sequence of CCAGCAUU, CCAGCAUUAUGAAAG (SEQ ID NO: 3), CCAGCAUUAUGAAAGUGA (SEQ ID NO: 485), or CCAGCAUUAUGAAAGUGAAU (SEQ ID NO: 486); wherein the oligonucleotide composition is administered at an amount effective to increase the level, expression and/or activity of exon 7-containing SMN2 mRNA or its gene product in a cell of the subject. In some embodiments, the oligonucleotide composition is chirally controlled and/or further comprises an additional chemical moiety capable of binding to the asialoglycoprotein receptor.

In some embodiments, the present disclosure pertains to the use of a SMN2 oligonucleotide in treatment of a SMN2-related disorder. In some embodiments, the present disclosure pertains to the use of a SMN2 oligonucleotide composition in treatment of a SMN2-related disorder. In some embodiments, a SMN2-related disorder is SMA or ALS. In some embodiments, the oligonucleotide composition is chirally controlled and/or further comprises an additional chemical moiety capable of binding to the asialoglycoprotein receptor.

In some embodiments, a SMN2 oligonucleotide can be used to treat ALS (amyotrophic lateral sclerosis). In some embodiments, the present disclosure pertains to methods of treatment for ALS comprising administering a therapeutically effective amount of an SMN2 oligonucleotide, in some embodiments, as a chirally controlled oligonucleotide composition. In some embodiments, ALS is MIM: 612069. Amyotrophic lateral sclerosis (ALS) is a reportedly a fatal neurodegenerative disease characterized clinically by progressive paralysis leading to death, often from respiratory failure, typically within two to three years of symptom onset (Rowland and Shneider, N. Engl. J. Med., 2001, 344, 1688-1700). ALS reportedly is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). Clinical, genetic, and epidemiological data reportedly support the hypothesis that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133). A number of genes have been discovered as potentially causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Linkage analysis of kindreds involving multiple cases of ALS, FTD, and ALS-FTD had reportedly suggested that there was an important locus for the disease on the short arm of chromosome 9, identified as C9orf72 (Boxer et al., J. Neurol. Neurosurg. Psychiatry, 2011, 82, 196-203; Morita et al., Neurology, 2006, 66, 839-844; Pearson et al. J. Neurol., 2011, 258, 647-655; Vance et al., Brain, 2006, 129, 868-876). This mutation had been found to be the most common genetic cause of ALS and FTD. In some embodiments, ALS-FTD causing mutation is a large hexanucleotide (e.g., GGGGCC or G4C2) repeat expansion in the first intron of the C9orf72 gene on chromosome 9 (Renton et al., Neuron, 2011, 72, 257-268; DeJesus-Hernandez et al., Neuron, 2011, 72, 245-256). The incidence of ALS is reportedly 1:50,000. Familial ALS reportedly represents 5-10% of all ALS cases; C9orf72 mutations reportedly can be the most common cause of ALS (40-50%). ALS is reportedly associated with degeneration of both upper and lower motor neurons in the motor cortex of the brain, the brain stem, and the spinal cord. Symptoms of ALS reportedly include: muscle weakness and/or muscle atrophy, trouble swallowing or breathing, cramping, stiffness. Respiratory failure is reportedly the main cause of death. The relationship of SMN to amyotrophic lateral sclerosis is reported in, for example, Crawford et al. 2002 Ann. Neurol. 52: 857-8, with an author reply 858-61. In addition, an abnormal SMN1 gene copy number is reportedly a susceptibility factor for amyotrophic lateral sclerosis. Corcia et al. 2002 Ann. Neurol. 51: 243-6. In addition, SMN genotypes producing less SMN protein reportedly increase susceptibility to and severity of sporadic ALS. Veldink et al. 2005 Neurol. 65: 820-825.

Base Sequence

As described herein, a base sequence of provided oligonucleotides (e.g., oligonucleotide of a plurality in chirally controlled oligonucleotide compositions, SMN2 oligonucleotide compositions, etc.) can target (identical to or complementary to) an exon sequence, an intron sequence, or a sequence comprising both an exon and an intron sequence, of a transcript (target sequence). In some embodiments, base sequence of provided oligonucleotides is identical to a target sequence. In some embodiments, a base sequence is complementary to a target sequence. In some embodiments, a base sequence is at least 50%, 55%, 60%, 65%, 70%, 75%, 80%, 85%, 90%, 95%, 96%, 97%, 98%, 99%, or 100%, identical or complementary to a target sequence. In some embodiments, a percentage is at least 60%. In some embodiments, a percentage is at least 70%. In some embodiments, a percentage is at least 80%. In some embodiments, a percentage is at least 85%. In some embodiments, a percentage is at least 90%. In some embodiments, a percentage is at least 85%. In some embodiments, a base sequence is 100% identical to a target sequence. In some embodiments, a base sequence is 100% complementary to a target sequence.

In some embodiments, a target sequence comprises or is an ISS-N1 sequence. In some embodiments, a base sequence of a SMN2 oligonucleotide is complementary to an ISS-N1 sequence. In some embodiments, a target sequence is an intron sequence of SMN2. In some embodiments, a base sequence of a SMN2 oligonucleotide is or comprises a sequence that is at least 85%, 90%, 95%, or 100%, identical to the sequence of TAATGCTGG (SEQ ID NO: 5), ATAATGCTGG (SEQ ID NO: 5), CATAATGCTGG (SEQ ID NO: 6), TCATAATGCTGG (SEQ ID NO: 7), TTCATAATGCTGG (SEQ ID NO: 8), TTTCATAATGCTGG (SEQ ID NO: 9), CTTTCATAATGCTGG (SEQ ID NO: 10), ACTTTCATAATGCTGG (SEQ ID NO: 11), CACTTTCATAATGCTGG (SEQ ID NO: 12), TCACTTTCATAATGCTGG (SEQ ID NO: 479), TTCACTTTCATAATGCTGG (SEQ ID NO: 13), ATTCACTTTCATAATGCTGG (SEQ ID NO: 14), or CUUUCNNNNNGCUGG (SEQ ID NO: 2), wherein each T can be independently replaced by U and vice versa. In some embodiments, a base sequence is or comprises a sequence that is TAATGCTGG, ATAATGCTGG (SEQ ID NO: 5), CATAATGCTGG (SEQ ID NO: 6), TCATAATGCTGG (SEQ ID NO: 7), TTCATAATGCTGG (SEQ ID NO: 8), TTTCATAATGCTGG (SEQ ID NO: 9), CTTTCATAATGCTGG (SEQ ID NO: 10), ACTTTCATAATGCTGG (SEQ ID NO: 11), CACTTTCATAATGCTGG (SEQ ID NO: 12), TCACTTTCATAATGCTGG (SEQ ID NO: 479), TTCACTTTCATAATGCTGG (SEQ ID NO: 13), ATTCACTTTCATAATGCTGG (SEQ ID NO: 14), or CUUUCNNNNNGCUGG (SEQ ID NO: 2), wherein each T can be independently replaced by U and vice versa. In some embodiments, the oligonucleotide composition is chirally controlled and/or further comprises an additional chemical moiety capable of binding to the asialoglycoprotein receptor.

Length

As described in the present disclosure, provided oligonucleotides can be of various lengths, e.g., 2-200, 10-15, 10-25, 15-20, 15-25, 15-40, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 60, 70, 80, 90, 100, 150, nucleobases in length, wherein each nucleobase is independently optionally substituted A, T, C, G, or U, or an optionally substituted tautomer of A, T, C, G, or U. In some embodiments, provided oligonucleotides, e.g., oligonucleotide of a plurality in chirally controlled oligonucleotide compositions, SMN2 oligonucleotide compositions, etc., are 15 nucleobases in length. In some embodiments, provided oligonucleotides are 16 nucleobases in length. In some embodiments, provided oligonucleotides are 17 nucleobases in length. In some embodiments, provided oligonucleotides are 18 nucleobases in length. In some embodiments, provided oligonucleotides are 19 nucleobases in length. In some embodiments, provided oligonucleotides are 20 nucleobases in length. In some embodiments, provided oligonucleotides are 21 nucleobases in length. In some embodiments, provided oligonucleotides are 22 nucleobases in length. In some embodiments, provided oligonucleotides are 23 nucleobases in length. In some embodiments, provided oligonucleotides are 24 nucleobases in length. In some embodiments, provided oligonucleotides are 25 nucleobases in length. In some embodiments, each nucleobase is independently an optionally substituted nucleobase selected from A, T, C, G and U or a tautomer thereof.

As described in the present disclosure, provided oligonucleotides, oligonucleotides of a plurality in an oligonucleotide compositions (e.g., chirally controlled oligonucleotide compositions, SMN2 oligonucleotide compositions, etc.), may comprise various modifications, e.g., base modifications, sugar modifications, internucleotidic linkage modifications, etc. In some embodiments, the oligonucleotide composition comprises at least one modified nucleotide, at least one modified sugar moiety, at least one morpholino moiety, at least one 2'-deoxy ribonucleotide, at least one locked nucleotide, and/or at least one bicyclic nucleotide.

Nucleobases

In some embodiments, a nucleobase, e.g., BA, in provided oligonucleotides is a natural nucleobase (e.g., adenine, cytosine, guanosine, thymine, or uracil) or a modified nucleobase derived from a natural nucleobase, e.g., optionally substituted adenine, cytosine, guanosine, thymine, or uracil, or tautomeric forms thereof. Examples include, but are not limited to, uracil, thymine, adenine, cytosine, and guanine, and tautomeric forms thereof, having their respective amino groups protected by protecting groups, e.g., one or more of —R, —C(O)R, etc. Example protecting groups are widely known in the art and can be utilized in accordance with the present disclosure. In some embodiments, a protected nucleobase and/or derivative is selected from nucleobases with one or more acyl protecting groups, 2-fluorouracil, 2-fluorocytosine, 5-bromoura-cil, 5-iodouracil, 2,6-diaminopurine, azacytosine, pyrimidine analogs such as pseudoisocytosine and pseudouracil and other modified nucleobases such as 8-substituted purines, xanthine, or hy-poxanthine (the latter two being the natural degradation products). Example modified nucleobases are also disclosed in Chiu and Rana, *RNA,* 2003, 9, 1034-1048, Limbach et al. *Nucleic Acids Re- search,* 1994, 22, 2183-2196 and Revankar and Rao, *Comprehensive Natural Products Chemistry*, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a modified base is optionally substituted adenine, cytosine, guanine, thymine, or uracil. In some embodiments, a modified nucleobase is independently adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen or sulfur;

(3) one or more double bonds in a nucleobase are independently hydrogenated; or (4) one or more optionally substituted aryl or heteroaryl rings are independently inserted into a nucleobase.

In some embodiments, other nucleosides can also be used in technologies disclosed in the present disclosure and may include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formyl cytosine; 5-carboxyl cytosine; $N^6$-methyl adenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

Representative U.S. patents that teach preparation of certain of noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, modified nucleobases, sugars, and internucleotidic linkages of each of which are incorporated by reference.

In some embodiments, a base, e.g., BA, is optionally substituted A, T, C, G or U, or an optionally substituted tautomer thereof, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-R' are optionally taken together with their intervening atoms to form a 3-30 membered bicyclic or polycyclic ring having 0-10 heteroatom atoms. In some embodiments, a modified base is optionally substituted A, T, C, G or U, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-$R^1$ are optionally taken together with their intervening atoms to form a 3-30 membered bicyclic or polycyclic ring having 0-10 heteroatom atoms, wherein the modified base is different than the natural A, T, C, G and U. In some embodiments, a base is optionally substituted A, T, C, G or U, or an optionally substituted tautomer of A, T, C, G or U. In some embodiments, a modified base is substituted A, T, C, G or U, wherein the modified base is different than the natural A, T, C, G and U. In some embodiments, each nucleobase independently comprises a nitrogen atom. In some embodiments, each nucleobase independently comprises a heteroaryl ring. In some embodiments, each nucleobase independently comprises a heteroaryl ring having at least one nitrogen atom.

Example nucleobases include those described in US 20110294124, US 20120316224, US 20140194610, US 20150211006, US 20150197540, and WO 2015107425, nucleobases of each of which are incorporated herein by reference.

Sugars

In some embodiments, provided compounds, e.g., oligonucleotides, comprise one or more modified sugar moieties. In some embodiments, a sugar moiety is

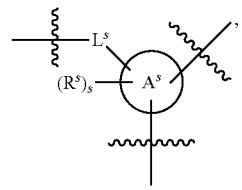

wherein each variable is independently as described in the present disclosure. In some embodiments, a sugar moiety is

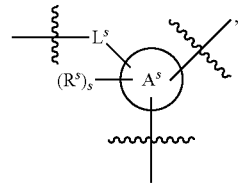

wherein $L^s$ is —$C(R^{5s})_2$—, wherein each $R^{5s}$ is independently as described in the present disclosure. In some embodiments, a sugar moiety has the structure of

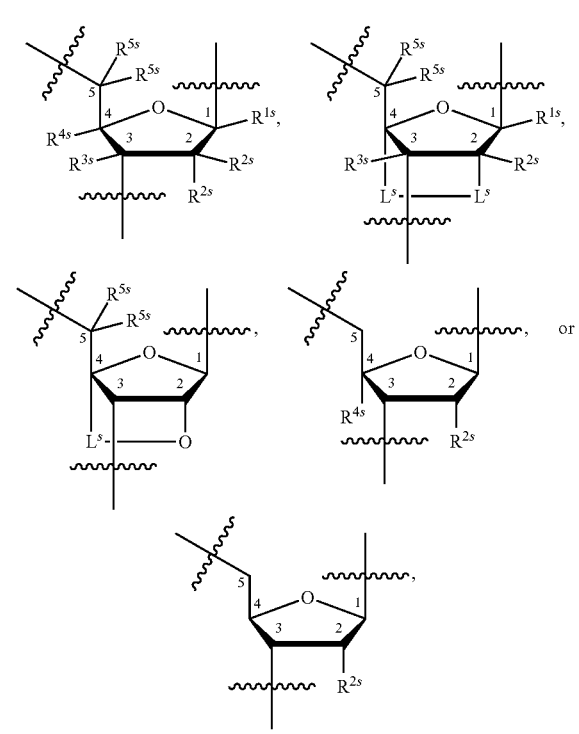

wherein each variable is independently as described in the present disclosure. In some embodiments, a sugar moiety has the structure of

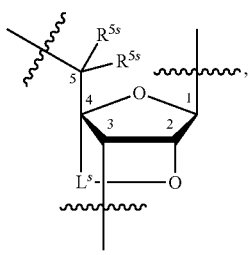

wherein each variable is independently as described in the present disclosure. In some embodiments, L^s is —CH(R)—, wherein R is as described in the present disclosure. In some embodiments, R is —H. In some embodiments, R is not —H, and L^s is —(R)—CH(R)—. In some embodiments, R is not —H, and L^s is —(S)—CH(R)—. In some embodiments, R, as described in the present disclosure, is optionally substituted $C_{1-6}$ alkyl. In some embodiments, R is methyl.

Various types of sugar modifications are known and can be utilized in accordance with the present disclosure. In some embodiments, a sugar modification is a 2'-modification. In some embodiments, a 2'-modification is 2'-F. In some embodiments, a 2'-modification is 2'-OR, wherein R is not hydrogen. In some embodiments, a 2'-modification is 2'-OR, wherein R is optionally substituted $C_{1-6}$ aliphatic. In some embodiments, a 2'-modification is 2'-OR, wherein R is optionally substituted $C_{1-6}$ alkyl. In some embodiments, a 2'-modification is 2'-OMe. In some embodiments, a 2'-modification is 2'-MOE. In some embodiments, a 2'-modification is a LNA sugar modification (C2-O—$CH_2$—C4). In some embodiments, a 2'-modification is (C2-O—$C(R)_2$—C4), wherein each R is independently as described in the present disclosure. In some embodiments, a 2'-modification is (C2-O—CHR—C4), wherein R is as described in the present disclosure. In some embodiments, a 2'-modification is (C2-O—(R)—CHR—C4), wherein R is as described in the present disclosure and is not hydrogen. In some embodiments, a 2'-modification is (C2-O—(S)—CHR—C4), wherein R is as described in the present disclosure and is not hydrogen. In some embodiments, R is optionally substituted $C_{1-6}$ aliphatic. In some embodiments, R is optionally substituted $C_{1-6}$ alkyl. In some embodiments, R is unsubstituted $C_{1-6}$ alkyl. In some embodiments, R is methyl. In some embodiments, R is ethyl. In some embodiments, a 2'-modification is (C2-O—CHR—C4), wherein R is optionally substituted $C_{1-6}$ aliphatic. In some embodiments, a 2'-modification is (C2-O—CHR—C4), wherein R is optionally substituted $C_{1-6}$ alkyl. In some embodiments, a 2'-modification is (C2-O—CHR—C4), wherein R is methyl. In some embodiments, a 2'-modification is (C2-O—CHR—C4), wherein R is ethyl. In some embodiments, a 2'-modification is (C2-O—(R)—CHR—C4), wherein R is optionally substituted $C_{1-6}$ aliphatic. In some embodiments, a 2'-modification is (C2-O—(R)—CHR—C4), wherein R is optionally substituted $C_{1-6}$ alkyl. In some embodiments, a 2'-modification is (C2-O—(R)—CHR—C4), wherein R is methyl. In some embodiments, a 2'-modification is (C2-O—(R)—CHR—C4), wherein R is ethyl. In some embodiments, a 2'-modification is (C2-O—(S)—CHR—C4), wherein R is optionally substituted $C_{1-6}$ aliphatic. In some embodiments, a 2'-modification is (C2-O—(S)—CHR—C4), wherein R is optionally substituted $C_{1-6}$ alkyl. In some embodiments, a 2'-modification is (C2-O—(S)—CHR—C4), wherein R is methyl. In some embodiments, a 2'-modification is (C2-O—(S)—CHR—C4), wherein R is ethyl. In some embodiments, a 2'-modification is C2-O—(R)—CH($CH_2CH_3$)—C4. In some embodiments, a 2'-modification is C2-O—(S)—CH($CH_2CH_3$)—C4. In some embodiments, a sugar moiety is a natural DNA sugar moiety. In some embodiments, a sugar moiety is a natural DNA sugar moiety modified at 2' (2'-modification). In some embodiments, a sugar moiety is an optionally substituted natural DNA sugar moiety. In some embodiments, a sugar moiety is an 2'-substituted natural DNA sugar moiety.

In some embodiments, linkage phosphorus in nucleotides can be linked to various positions of a sugar or modified sugar. For example, in some embodiments, linkage phosphorus can be linked to the 2', 3', 4' or 5' hydroxyl moiety of a sugar or modified sugar. In some embodiments, nucleotides or modified nucleotides comprising an unprotected —OH moiety are used in accordance with the present disclosure.

In some embodiments, a sugar has the structure of

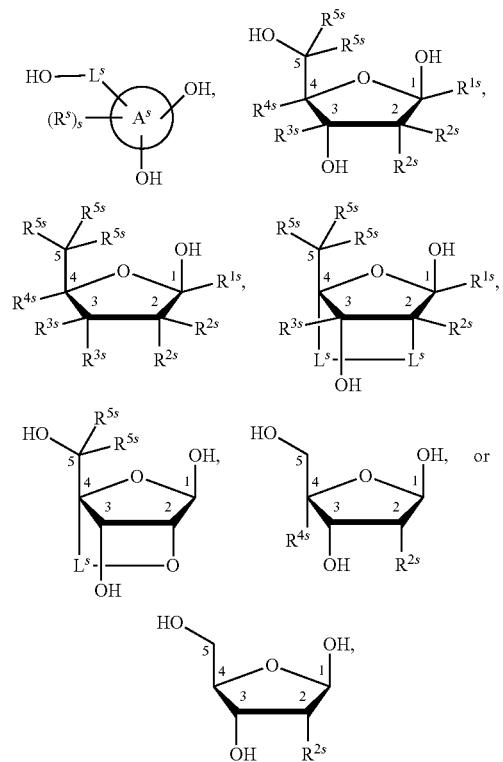

wherein each variable is independently as described in the present disclosure. In some embodiments, a nucleoside has the structure of

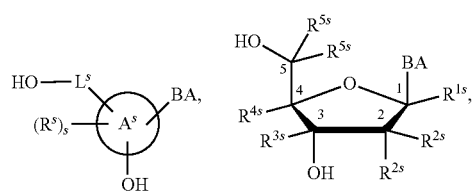

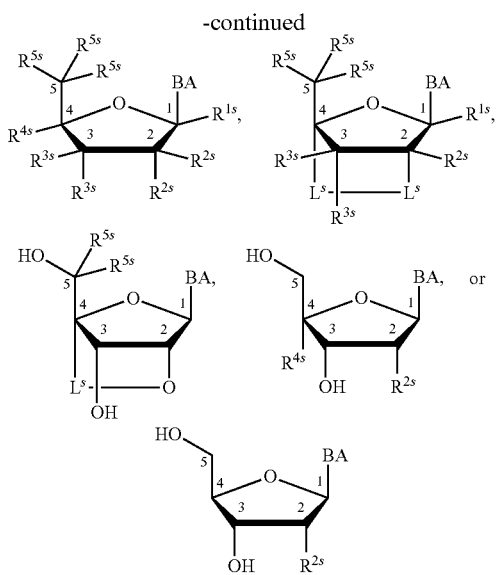

wherein each variable is independently as described in the present disclosure. In some embodiments, a nucleoside moiety has the structure of

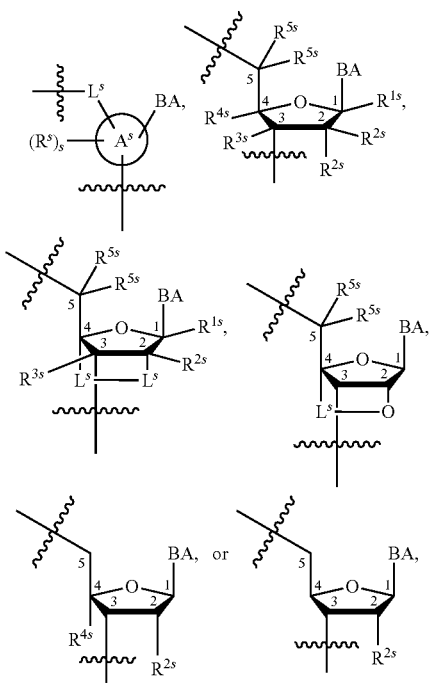

wherein each variable is independently as described in the present disclosure.

As described in the present disclosure, various types of modified sugars can be utilized in accordance with the present disclosure. In some embodiments, a modified sugar contains one or more substituents at the 2' position selected from (e.g., a 2'-modification): —F; —CF$_3$; —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ al-kyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted, and each independently contain or are of, e.g., 1-30, 1-20, 1-10, 1-9, 1-8, 1-7, 1-6, 1-5, 1-4, 1-3, 1-2, or 1, carbon. In some embodiments, examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. In some embodiments, a modified sugar is selected from those described in WO 2001/088198; and Martin et al., *Helv. Chim. Acta*, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmaco-dynamic properties of a nucleic acid, or other substituents having similar properties. In some embodiments, modifications are made at one or more of 2', 3', 4', 5', and/or 6'-positions (if any) of sugar or modified sugar moieties, including 3'-positions of a sugar moiety on a 3'-terminal nucleotide and/or 5' positions of a 5'-terminal nucleotide. In some embodiments, a RNA comprises a sugar which has, at the 2' position, a 2'-OH, or 2'-OR, wherein R is optionally substituted C$_{1-6}$ alkyl. In some embodiments, a 2'-modification is 2'-OMe. In some embodiments, a 2'-modification is 2'-OCH$_2$CH$_2$OMe. In some embodiments, a 2'-modification is 2'-F.

In some embodiments, the 2'-OH of a ribose is replaced with a substituent selected from: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ al-kylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted, and each independently contain or are of, e.g., 1-30, 1-20, 1-10, 1-9, 1-8, 1-7, 1-6, 1-5, 1-4, 1-3, 1-2, or 1, carbon. In some embodiments, a 2'-OH is replaced with —H (deoxyribose). In some embodiments, a 2'-OH is replaced with —F. In some embodiments, a 2'-OH is replaced with —OR', wherein R' is as described in the present disclosure and is not hydrogen. In some embodiments, a 2'-OH is replaced with —OMe. In some embodiments, a 2'-OH is replaced with —OCH$_2$CH$_2$OMe.

Modified sugars also include sugars of locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L$^s$-as defined herein. In some embodiments, -L$^s$-is —O—C(R)$_2$—, wherein each R is independently as described in the present disclosure. In some embodiments, -L$^s$- is —O—CHR—, wherein R is as described in the present disclosure. In some embodiments, -L$^s$- is —O—(R)—CHR—, wherein R is as described in the present disclosure. In some embodiments, -L$^s$- is —O—(S)—CHR—, wherein R is as described in the present disclosure. In some embodiments, -L$^s$- is —O—CH$_2$—, wherein —CH$_2$— is optionally substituted. In some embodiments, -L$^s$- is —O—CH$_2$—. In some embodiments, -L$^s$- is —O—CH(Et)-. In some embodiments, -L$^s$- is —O—(R)—CH(Et)-. In some embodiments, -L$^s$- is —O—(S)—CH(Et)-. In some embodiments, -L$^s$- is —O—CH(Me)-. In some embodiments, -L$^s$- is —O—(R)—CH (Me)-. In some embodiments, -L$^s$- is —O—(S)—CH(Me)-. In some embodiments, -L$^s$- is between C2 and C4 of a sugar moiety.

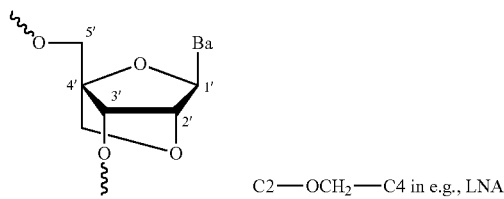

C2—OCH$_2$—C4 in e.g., LNA

In some embodiments, a modified sugar is a sugar of ENA or modified ENA (such as those described in, e.g., Seth et al., J Am Chem Soc. 2010 Oct. 27; 132(42): 14942-14950). In some embodiments, a modified sugar is any of those found in an XNA (xenonucleic acid), for instance, arabinose, anhydrohexitol, threose, 2'fluoroarabinose, or cyclohexene.

In some embodiments, modified sugars are sugar mimetics such as cyclobutyl or cyclopentyl moieties in place of pentofuranosyl. Representative United States patents that teach preparation of such modified sugar structures include, but are not limited to, U.S. Pat. Nos. 4,981,957; 5,118,800; 5,319,080; and 5,359,044. In some embodiments, modified sugars are sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

Non-limiting examples of modified sugars include glycerol, which form glycerol nucleic acid (GNA) analogues. In some embodiments, an GNA analogue is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603. In some embodiments, another example of a GNA derived analogue, flexible nucleic acid (FNA) based on the mixed acetal aminal of formyl glycerol, is described in Joyce G F et al., PNAS, 1987, 84, 4398-4402 and Heuberger B D and Switzer C, J. Am. Chem. Soc., 2008, 130, 412-413.

Additional non-limiting examples of modified sugars include hexopyranosyl (6' to 4'), pentopyranosyl (4' to 2'), pentopyranosyl (4' to 3'), or tetrofuranosyl (3' to 2') sugars. as defined herein.

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a provided oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, a sugar is D-2-deoxyribose. In some embodiments, a sugar is beta-D-deoxyribofuranose. In some embodiments, a sugar moiety is a beta-D-deoxyribofuranose moiety. In some embodiments, a sugar is D-ribose. In some embodiments, a sugar is beta-D-ribofuranose. In some embodiments, a sugar moiety is a beta-D-ribofuranose moiety. In some embodiments, a sugar is optionally substituted beta-D-deoxyribofuranose or beta-D-ribofuranose. In some embodiments, a sugar moiety is an optionally substituted beta-D-deoxyribofuranose or beta-D-ribofuranose moiety. In some embodiments, a sugar moiety/unit in an oligonucleotide, nucleic acid, etc. is a sugar which comprises one or more carbon atoms each independently connected to an internucleotidic linkage, e.g., optionally substituted beta-D-deoxyribofuranose or beta-D-ribofuranose whose 5'-C and/or 3'-C are each independently connected to an internucleotidic linkage (e.g., a natural phosphate linkage, a modified internucleotidic linkage, a chirally controlled internucleotidic linkage, etc.). In some embodiments, unless otherwise specified, each sugar moiety in a provided oligonucleotide is a 2-deoxyribose moiety as in natural DNA

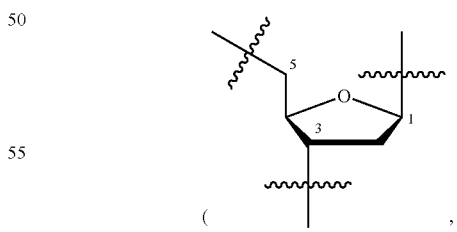

( , wherein, as appreciated by those skilled in the art, C1 is typically connected to a nucleobase, and C3 and C5 are typically and independently connected to —OH, internucleotidic linkages, —O-protecting group, support (optionally via a linker), etc.).

In some embodiments, each nucleoside of a provided oligonucleotide comprises a 2'-O-methoxyethyl sugar modification.

In some embodiments, the oligonucleotide composition comprises at least one locked nucleic acid (LNA) nucleotide.

In some embodiments, the oligonucleotide composition comprises at least one modified nucleotide comprising a modified sugar moiety which is modified at the 2'-position.

In some embodiments, the oligonucleotide composition comprises modified sugar moiety which comprises a 2'-substituent selected from the group consisting of: H, OR, R, halo, SH, SR, NH$_2$, NHR, NR$_2$, and ON, where R is a C$_1$-C$_6$ alkyl, alkenyl, or alkynyl and halo is F, Cl, Br or I.

In some embodiments, the oligonucleotide composition comprises at least one modified nucleotide selected from the group consisting of 2'-fluoro-cytidine, 2'-fluoro-uridine, 2'-fluoro-adenosine, 2'-fluoro-guanosine, 2'-amino-cytidine, 2'-amino-adenosine, 2'-amino-guanosine and 2'-amino-butyryl-pyrene-uridine.

In some embodiments, the oligonucleotide composition comprises at least one modified nucleotide selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine.

Example internucleotidic linkages include those described in US 20110294124, US 20120316224, US 20140194610, US 20150211006, US 20150197540, and WO 2015107425, internucleotidic linkages of each of which are incorporated herein by reference.

Internucleotidic Linkages

Various internucleotidic linkages can utilized in accordance with the present disclosure, in some embodiments, with high stereopurity (chirally controlled internucleotidic linkage), for example, those of US20150211006, US20170037399, WO2017/015555, WO2017/015575, and WO2017/062862. In some embodiments, an internucleotidic linkage is a natural phosphate linkage (acid form is —O—P(O)(OH)—(O)—; can exist as various salt forms). In some embodiments, an internucleotidic linkage is a phosphorothioate linkage (acid form is —O—P(O)(SH)—(O)—; can exist as various salt forms).

In some embodiments, provided oligonucleotides comprise one or more chiral internucleotidic linkages. In some embodiments, provided oligonucleotides comprise one or more modified chiral internucleotidic linkages (each independently comprising a chiral linkage phosphorus). In some embodiments, provided oligonucleotides comprise one or more natural phosphate linkages and one or more modified chiral internucleotidic linkages. In some embodiments, provided oligonucleotides comprise one or more natural phosphate linkages and one or more phosphorothioate internucleotidic linkages. In some embodiments, provided oligonucleotides comprise one or more natural phosphate linkages and one or more phosphorothioate internucleotidic linkages. In some embodiments, one or more modified internucleotidic linkages are chiral and are each independently chirally controlled. In some embodiments, each modified internucleotidic linkages is chiral and is each independently chirally controlled. In some embodiments, each chiral modified internucleotidic linkages is each independently chirally controlled.

In some embodiments, provided oligonucleotides comprise one or more chirally controlled internucleotidic linkages. In some embodiments, provided oligonucleotides comprise 1-30, e.g., 1, 2, 3, 4, 5, 6, 7, 8, 9, 10, 11, 12, 13, 14, 15, 16, 17, 18, 19, 20, 21, 22, 23, 24, or 25, chirally controlled internucleotidic linkages. In some embodiments, provided oligonucleotides comprise at least 1, 2, 3, 4, 5, 6, 7, 8, 9, 10, 11, 12, 13, 14, 15, 16, 17, 18, 19, 20, 21, 22, 23, 24, or 25, chirally controlled internucleotidic linkages.

In some embodiments, a modified internucleotidic linkage is a phosphorothioate linkage.

In some embodiments, an internucleotidic linkage has the structure of formula I:

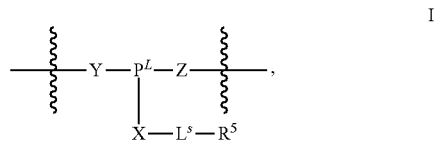

or a salt form thereof, wherein:
P$^L$ is P(=W), P, or P→B(R')$_3$;
W is O, S or Se;
each of R$^1$ and R$^5$ is independently —H, -L$^s$-R, halogen, —CN, —NO$_2$, -L$^s$-Si(R)$_3$, —OR, —SR, or —N(R)$_2$;
each of X, Y and Z is independently —O—, —S—, —N(-L$^s$-R$^1$)—, or L$^s$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a C$_3$-20 cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, an internucleotidic linkage of formula I is a chiral internucleotidic linkage. In some embodiments, P in $P^L$ is a chiral linkage phosphorus. In some embodiments, a chiral linkage phosphorus is Rp. In some embodiments, a chiral linkage phosphorus is Sp. In some embodiments, $P^L$ is P(=W). In some embodiments, $P^L$ is P. In some embodiments, $P^L$ is P→B(R')$_3$.

In some embodiments, an internucleotidic linkage of formula I having the structure of formula I-a-1:

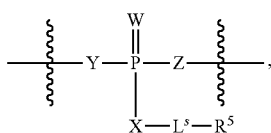

I-a-1 or a salt form thereof, wherein each other variable is independently as described in the present disclosure.

In some embodiments, an internucleotidic linkage of formula I or I-a-1 having the structure of formula I-a-2:

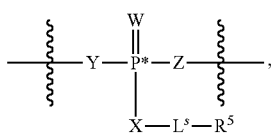

I-a-2 or a salt form thereof, wherein P* is an asymmetric phosphorus atom, and each other variable is independently as described in the present disclosure.

In some embodiments, an internucleotidic linkage has the structure of formula I-b:

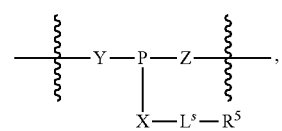

I-b or a salt form thereof, wherein each variable is independently as described in the present disclosure. In some embodiments, an internucleotidic linkage of formula I has the structure of formula I-b.

In some embodiments, an internucleotidic linkage of formula I having the structure of formula I-c:

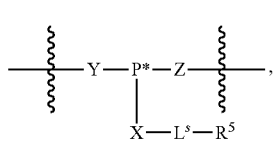

I-c or a salt form thereof, wherein P* is an asymmetric phosphorus atom, and each other variable is independently as described in the present disclosure.

In some embodiments, an internucleotidic linkage has the structure of formula I-d:

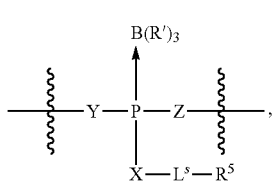

I-d or a salt form thereof, wherein each variable is independently as described in the present disclosure.

In some embodiments, an internucleotidic linkage of formula I-e having the structure of:

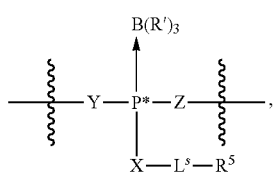

I-e or a salt form thereof, wherein P* is an asymmetric phosphorus atom, and each other variable is independently as described in the present disclosure.

In some embodiments, the present disclosure provides oligonucleotides comprising one or more internucleotidic linkages having the structure of formula I, I-a-1, I-a-2, I-b, I-c, I-d, or I-e, or a salt form thereof. In some embodiments, provided oligonucleotides comprise 1-100, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70 80, 90, 100 or more internucleotidic linkages having the structure of formula I, I-a-1, I-a-2, I-b, I-c, I-d, or I-e, or a salt form thereof. In some embodiments, provided oligonucleotides comprise one or more such internucleotidic linkages. In some embodiments, provided oligonucleotides comprise two or more such internucleotidic linkages. In some embodiments, provided oligonucleotides comprise three or more such internucleotidic linkages. In some embodiments, provided oligonucleotides comprise four or more such internucleotidic linkages. In some embodiments, provided oligonucleotides comprise five or more such internucleotidic linkages. In some embodiments, provided oligonucleotides comprise six or more such internucleotidic linkages. In some embodiments, provided oligonucleotides comprise seven or more such internucleotidic linkages. In some embodiments, provided oligonucleotides comprise eight or more such internucleotidic linkages. In some embodiments, provided oligonucleotides comprise nine or more such internucleotidic linkages. In some embodiments, provided oligonucleotides comprise ten or more such internucleotidic linkages. In some embodiments, provided oligonucleotides comprise 11 or more such internucleotidic linkages. In some embodiments, provided oligonucleotides comprise 12 or more such internucleotidic linkages. In some embodiments, provided oligonucleotides comprise 13 or more such internucleotidic linkages. In some embodiments, provided oligonucleotides comprise 14 or more such internucleotidic linkages. In some embodiments, provided oligonucleotides comprise 15 or more such internucleotidic linkages. In some embodiments, provided oligonucleotides comprise 16 or more such internucleotidic linkages. In some embodiments, provided oligonucleotides comprise 17 or more such internucleotidic linkages. In some embodiments, provided oligonucleotides comprise 18 or more such internucleotidic linkages. In some embodiments, provided oligonucleotides comprise 19 or more such internucleotidic linkages. In some embodiments, provided oligonucleotides comprise 20 or more such internucleotidic linkages. In some embodiments, provided oligonucleotides comprise 21 or more such internucleotidic linkages. In some embodiments, provided oligonucleotides comprise 25 or more such internucleotidic linkages. In some embodiments, such an internucleotidic linkage is chiral. In some embodiments, each such an chiral internucleotidic linkage and independently chirally controlled In some embodiments, a provided oligonucleotide comprises at least two types of internucleotidic linkages, each independently having the structure of formula I, I-a-1, I-a-2, I-b, I-c, I-d, or I-e, or a salt form thereof. In some embodiments, a provided oligonucleotide comprise at least two types of chiral internucleotidic linkages, each independently having the structure of formula I, I-a-1, I-a-2, I-b, I-c, I-d, or I-e, or a salt form thereof. In some embodiments, the two types may have the same or different phosphorus configuration (Rp or Sp), or one or both can be stereorandom (e.g., formed not through chirally controlled synthesis). In some embodiments, a stereorandom linkage has diastereomeric purity less than 85%, 80%, 75%, 70%, 65%, 60%, or 55%. In some embodiments, P* is not stereorandom, and is either Rp or Sp. In some embodiments, in one type W is S and in the other type W is O. In some embodiments, one type is a natural phosphate linkage (—O—P(O)(OH)—O—, which may exist as —O—P(O)(O⁻)—O—, for example, at certain pH and/or when provided as a salt), and the other is a phosphorothioate linkage (—O—P(O)(SH)—O—, which may exist as —O—P(O)(S⁻)—O—, for example, at certain pH and/or when provided as a salt).

In some embodiments, each $L^P$ independently has the structure of I, I-a-1, I-a-2, I-b, I-c, I-d, or I-e, or a salt form thereof.

In some embodiments, at least one $L^P$ comprises W, wherein W is S. In some embodiments, at least 2, 3, 4, 5, 6, 7, 8, 9, 10, 11, 12, 13, 14, 15, 16, 17, 18, 19, 20 $L^P$ comprises W, wherein W is S. In some embodiments, at least one $L^P$ comprises W, wherein W is O. In some embodiments, at least 2, 3, 4, 5, 6, 7, 8, 9, 10, 11, 12, 13, 14, 15, 16, 17, 18, 19, 20 $L^P$ comprises W, wherein W is O.

In some embodiments, each internucleotidic linkage in provided oligonucleotides is independently selected from a natural phosphate linkage and a phosphorothioate linkage, which may independently exist as a salt form (e.g., sodium salt).

In some embodiments, the oligonucleotide composition comprises at least one modified linkage. In some embodiments, the oligonucleotide composition comprises at least one phosphorothioate linkage. In some embodiments, the oligonucleotide composition comprises at least one phosphorothioate linkage which is chirally controlled.

Example internucleotidic linkages include those described in US 20110294124, US 20120316224, US 20140194610, US 20150211006, US 20150197540, and WO 2015107425, internucleotidic linkages of each of which are incorporated herein by reference.

In some embodiments, an internucleotidic linkage, e.g., $L^P$, is a non-negatively charged internucleotidic linkage. In some embodiments, a modified internucleotidic linkage is a neutral internucleotidic linkage. In some embodiments, provided oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, a modified internucleotidic linkage (e.g., a non-negatively charged internucleotidic linkage) comprises optionally substituted triazolyl. In some embodiments, a modified internucleotidic linkage (e.g., a non-negatively charged internucleotidic linkage) comprises optionally substituted alkynyl. In some embodiments, a modified internucleotidic linkage comprises a triazole or alkyne moiety. In some embodiments, a triazole moiety, e.g., a triazolyl group, is optionally substituted. In some embodiments, a triazole moiety, e.g., a triazolyl group) is substituted. In some embodiments, a triazole moiety is unsubstituted. In some embodiments, a modified internucleotidic linkage comprises an optionally substituted cyclic guanidine moiety. In some embodiments, a modified internucleotidic linkage comprises an optionally substituted cyclic guanidine moiety and has the structure of:

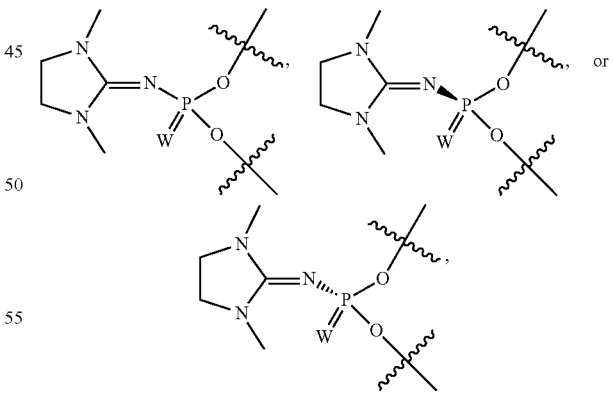

wherein W is O or S. In some embodiments, W is O. In some embodiments, W is S. In some embodiments, a non-negatively charged internucleotidic linkage is stereochemically controlled.

In some embodiments, an internucleotidic linkage comprising a triazole moiety (e.g., an optionally substituted triazolyl group) in a provided oligonucleotide, e.g., a SMN2 oligonucleotide, has the structure of:

In some embodiments, an internucleotidic linkage comprising a triazole moiety has the formula of

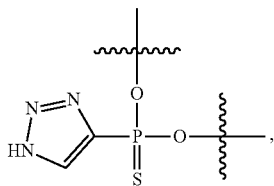

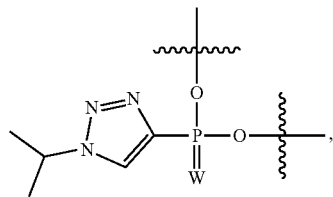

where W is O or S. In some embodiments, an internucleotidic linkage comprising an alkyne moiety (e.g., an optionally substituted alkynyl group) has the formula of:

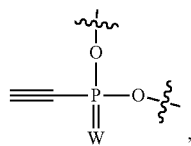

wherein W is O or S. In some embodiments, an internucleotidic linkage comprises a cyclic guanidine moiety. In some embodiments, an internucleotidic linkage comprising a cyclic guanidine moiety has the structure of:

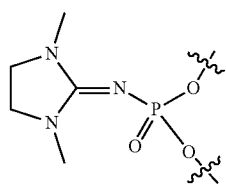

In some embodiments, a neutral internucleotidic linkage or internucleotidic linkage comprising a cyclic guanidine moiety is stereochemically controlled.

In some embodiments, a SMN2 oligonucleotide comprises a lipid moiety In some embodiments, an internucleotidic linkage comprises a Tmg group

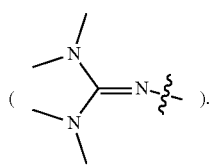

In some embodiments, an internucleotidic linkage comprises a Tmg group and has the structure of

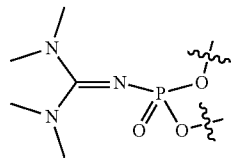

(the "Tmg internucleotidic linkage"). In some embodiments, neutral internucleotidic linkages include internucleotidic linkages of PNA and PMO, and an Tmg internucleotidic linkage.

In some embodiments, a non-negatively charged internucleotidic linkage has the structure of formula I, I-a, I-b, I-c, I-n-1, I-n-2, I-n-3, II, II-a-1, II-a-2, II-b-1, II-b-2, II-c-1, II-c-2, II-d-1, or II-d-2, etc., or a salt form thereof. In some embodiments, each $L^P$ is independently a non-negatively charged internucleotidic linkage that has the structure of formula I, I-a, I-b, I-c, I-n-1, I-n-2, I-n-3, II, II-a-1, II-a-2, II-b-1, II-b-2, II-c-1, II-c-2, II-d-1, or II-d-2, etc., or a salt form thereof. In some embodiments, a non-negatively charged internucleotidic linkage comprises an optionally substituted 3-20 membered heterocyclyl or heteroaryl group having 1-10 heteroatoms. In some embodiments, a non-negatively charged internucleotidic linkage comprises an optionally substituted 3-20 membered heterocyclyl or heteroaryl group having 1-10 heteroatoms, wherein at least one heteroatom is nitrogen. In some embodiments, such a heterocyclyl or heteroaryl group is of a 5-membered ring. In some embodiments, such a heterocyclyl or heteroaryl group is of a 6-membered ring.

In some embodiments, a non-negatively charged internucleotidic linkage comprises an optionally substituted 5-20 membered heteroaryl group having 1-10 heteroatoms. In some embodiments, a non-negatively charged internucleotidic linkage comprises an optionally substituted 5-20 membered heteroaryl group having 1-10 heteroatoms, wherein at least one heteroatom is nitrogen. In some embodiments, a non-negatively charged internucleotidic linkage comprises an optionally substituted 5-6 membered heteroaryl group having 1-4 heteroatoms, wherein at least one heteroatom is nitrogen. In some embodiments, a non-negatively charged internucleotidic linkage comprises an optionally substituted 5-membered heteroaryl group having 1-4 heteroatoms, wherein at least one heteroatom is nitrogen. In some embodiments, a heteroaryl group is directly bonded to a linkage phosphorus. In some embodiments, a non-negatively charged internucleotidic linkage comprises an optionally substituted triazolyl group. In some embodiments, a non-negatively charged internucleotidic linkage comprises an unsubstituted triazolyl group, e.g.,

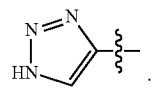

In some embodiments, a non-negatively charged internucleotidic linkage comprises a substituted triazolyl group, e.g.,

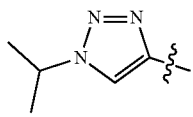

In some embodiments, a non-negatively charged internucleotidic linkage comprises an optionally substituted 5-20 membered heterocyclyl group having 1-10 heteroatoms. In some embodiments, a non-negatively charged internucleotidic linkage comprises an optionally substituted 5-20 membered heterocyclyl group having 1-10 heteroatoms, wherein at least one heteroatom is nitrogen. In some embodiments, a non-negatively charged internucleotidic linkage comprises an optionally substituted 5-6 membered heterocyclyl group having 1-4 heteroatoms, wherein at least one heteroatom is nitrogen. In some embodiments, a non-negatively charged internucleotidic linkage comprises an optionally substituted 5-membered heterocyclyl group having 1-4 heteroatoms, wherein at least one heteroatom is nitrogen. In some embodiments, at least two heteroatoms are nitrogen. In some embodiments, a heterocyclyl group is directly bonded to a linkage phosphorus. In some embodiments, a heterocyclyl group is bonded to a linkage phosphorus through a linker, e.g., =N— when the heterocyclyl group is part of a guanidine moiety who directed bonded to a linkage phosphorus through its =N—. In some embodiments, a non-negatively charged internucleotidic linkage comprises an optionally substituted

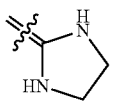

group. In some embodiments, a non-negatively charged internucleotidic linkage comprises an substituted

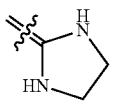

group. In some embodiments, a non-negatively charged internucleotidic linkage comprises a

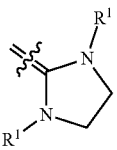

group. In some embodiments, each $R^1$ is independently optionally substituted $C_{1-6}$ alkyl. In some embodiments, each $R^1$ is independently methyl.

In some embodiments, a modified internucleotidic linkage, e.g., a non-negatively charged internucleotidic linkage, comprises a triazole or alkyne moiety, each of which is optionally substituted. In some embodiments, a modified internucleotidic linkage comprises a triazole moiety. In some embodiments, a modified internucleotidic linkage comprises a unsubstituted triazole moiety. In some embodiments, a modified internucleotidic linkage comprises a substituted triazole moiety. In some embodiments, a modified internucleotidic linkage comprises an alkyl moiety. In some embodiments, a modified internucleotidic linkage comprises an optionally substituted alkynyl group. In some embodiments, a modified internucleotidic linkage comprises an unsubstituted alkynyl group. In some embodiments, a modified internucleotidic linkage comprises a substituted alkynyl group. In some embodiments, an alkynyl group is directly bonded to a linkage phosphorus.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage. In some embodiments, an oligonucleotide comprises at least one phosphorothioate internucleotidic linkage and at least one non-negatively charged internucleotidic linkage. In some embodiments, an oligonucleotide comprises at least one phosphorothioate internucleotidic linkage, at least one natural phosphate linkage, and at least one non-negatively charged internucleotidic linkage. In some embodiments, oligonucleotides comprise one or more, e.g., 1, 2, 3, 4, 5, 6, 7, 8, 9, 10, 11, 12, 13, 14, 15, 16, 17, 18, 19, 20 or more non-negatively charged internucleotidic linkages. In some embodiments, a non-negatively charged internucleotidic linkage is not negatively charged in that at a given pH in an aqueous solution less than 50%, 40%, 40%, 30%, 20%, 10%, 5%, or 1% of the internucleotidic linkage exists in a negatively charged salt form. In some embodiments, a pH is about pH 7.4. In some embodiments, a pH is about 4-9. In some embodiments, the percentage is less than 10%. In some embodiments, the percentage is less than 5%. In some embodiments, the percentage is less than 1%. In some embodiments, an internucleotidic linkage is a non-negatively charged internucleotidic linkage in that the neutral form of the internucleotidic linkage has no pKa that is no more than about 1, 2, 3, 4, 5, 6, or 7 in water. In some embodiments, no pKa is 7 or less. In some embodiments, no pKa is 6 or less. In some embodiments, no pKa is 5 or less. In some embodiments, no pKa is 4 or less. In some embodiments, no pKa is 3 or less. In some embodiments, no pKa is 2 or less. In some embodiments, no pKa is 1 or less. In some embodiments, pKa of the neutral form of an internucleotidic linkage can be represented by pKa of the neutral form of a compound having the structure of $CH_3$—the internucleotidic linkage—$CH_3$. For example, pKa of the neutral form of an internucleotidic linkage having the structure of formula I may be represented by the pKa of the neutral form of a compound having the structure of

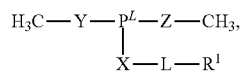

pKa of

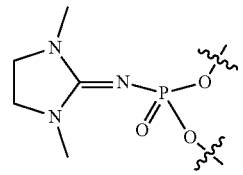

can be represented by pKa

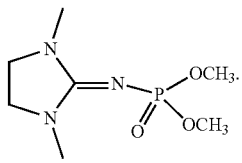

In some embodiments, a non-negatively charged internucleotidic linkage is a neutral internucleotidic linkage. In some embodiments, a non-negatively charged internucleotidic linkage is a positively-charged internucleotidic linkage. In some embodiments, a non-negatively charged internucleotidic linkage comprises a guanidine moiety. In some embodiments, a non-negatively charged internucleotidic linkage comprises a heteroaryl base moiety. In some embodiments, a non-negatively charged internucleotidic linkage comprises a triazole moiety. In some embodiments, a non-negatively charged internucleotidic linkage comprises an alkynyl moiety.

In some embodiments, a non-negatively charged internucleotidic linkage has the structure of formula I, I-a, I-b, I-c, I-n-1, I-n-2, I-n-3, II, II-a-1, II-a-2, II-b-1, II-b-2, II-c-1, II-c-2, II-d-1, or II-d-2, or a salt form thereof (not negatively charged). In some embodiments, an internucleotidic linkage, e.g., a non-negatively charged internucleotidic linkage, has the structure of formula I-n-1 or a salt form thereof:

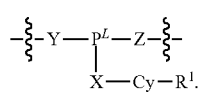

I-n-1

In some embodiments, X is a covalent bond and —X-Cy-$R^1$ is -Cy-$R^1$. In some embodiments, -Cy- is an optionally substituted bivalent group selected from a 5-20 membered heteroaryl ring having 1-10 heteroatoms, and a 3-20 membered heterocyclyl ring having 1-10 heteroatoms. In some embodiments, -Cy- is an optionally substituted bivalent 5-20 membered heteroaryl ring having 1-10 heteroatoms. In some embodiments, -Cy-$R^1$ is optionally substituted 5-20 membered heteroaryl ring having 1-10 heteroatoms, wherein at least one heteroatom is nitrogen. In some embodiments, -Cy-$R^1$ is optionally substituted 5-membered heteroaryl ring having 1-4 heteroatoms, wherein at least one heteroatom is nitrogen. In some embodiments, -Cy-$R^1$ is optionally substituted 6-membered heteroaryl ring having 1-4 heteroatoms, wherein at least one heteroatom is nitrogen. In some embodiments, -Cy-$R^1$ is optionally substituted triazolyl.

In some embodiments, an internucleotidic linkage, e.g., a non-negatively charged internucleotidic linkage, has the structure of formula I-n-2 or a salt form thereof:

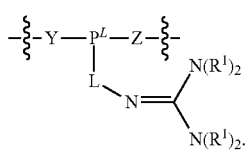

I-n-2

In some embodiments, $R^1$ is R'. In some embodiments, L is a covalent bond. In some embodiments, an internucleotidic linkage, e.g., a non-negatively charged internucleotidic linkage, has the structure of formula I-n-3 or a salt form thereof:

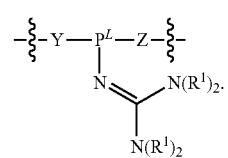

I-n-3

In some embodiments, two R' on different nitrogen atoms are taken together to form a ring as described. In some embodiments, a formed ring is 5-membered. In some embodiments, a formed ring is 6-membered. In some embodiments, a formed ring is substituted. In some embodiments, the two R' group that are not taken together to form a ring are each independently R. In some embodiments, the two R' group that are not taken together to form a ring are each independently hydrogen or an optionally substituted $C_{1-6}$ aliphatic. In some embodiments, the two R' group that are not taken together to form a ring are each independently hydrogen or an optionally substituted $C_{1-6}$ alkyl. In some embodiments, the two R' group that are not taken together to form a ring are the same. In some embodiments, the two R' group that are not taken together to form a ring are different. In some embodiments, both of them are —$CH_3$.

In some embodiments, a internucleotidic linkage, e.g., a non-negatively charged internucleotidic linkage, has the structure of formula II or a salt form thereof:

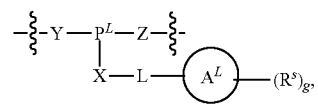

II or a salt form thereof, wherein:
$P^L$ is P(=W), P, or P→B(R')$_3$;
W is O, N(-L-$R^5$), S or Se;
each of X, Y and Z is independently —O—, —S—, —N(-L-$R^5$)—, or L;
Ring $A^L$ is an optionally substituted 3-20 membered monocyclic, bicyclic or polycyclic ring having 0-10 heteroatoms;
each $R^s$ is independently —H, halogen, —CN, —$N_3$, —NO, —$NO_2$, -L-R', -L-Si(R)$_3$, -L-OR', -L-SR', -L-N(R')$_2$, —O-L-R', —O-L-Si(R)$_3$, —O-L-OR', —O-L-SR', or —O-L-N(R')$_2$;
g is 0-20;
each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N (R')—, —N(R')C(O)O—, —S(O)—, —S(O)$_2$—, —S(O)$_2$N (R')—, —C(O)S—, —C(O)O—, —P(O)(OR')—, —P(O) (SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more CH or carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted trivalent or tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or, two or more R groups on the same atom are optionally and independently taken together with the atom to form an optionally substituted, 3-30 membered, monocyclic, bicyclic or polycyclic ring having, in addition to the atom, 0-10 heteroatoms, or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, a internucleotidic linkage, e.g., a non-negatively charged internucleotidic linkage of formula II, has the structure of formula II-a-1 or a salt form thereof:

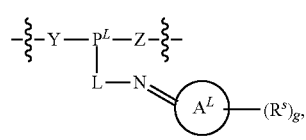

II-a-1 or a salt form thereof.

In some embodiments, a internucleotidic linkage, e.g., a non-negatively charged internucleotidic linkage of formula II, has the structure of formula II-a-2 or a salt form thereof:

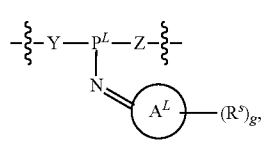

II-a-2 or a salt form thereof.

In some embodiments, A$^L$ is bonded to —N═ or L through a carbon atom. In some embodiments, an internucleotidic linkage, e.g., a non-negatively charged internucleotidic linkage of formula II or II-a-1, II-a-2, has the structure of formula II-b-1 or a salt form thereof:

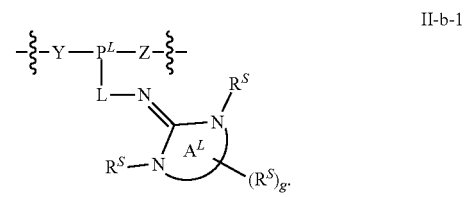

II-b-1

In some embodiments, a structure of formula II-a-1 or II-a-2 may be referred to a structure of formula II-a. In some embodiments, a structure of formula II-b-1 or II-b-2 may be referred to a structure of formula II-b. In some embodiments, a structure of formula II-c-1 or II-c-2 may be referred to a structure of formula II-c. In some embodiments, a structure of formula II-d-1 or II-d-2 may be referred to a structure of formula II-d.

In some embodiments, A$^L$ is bonded to —N═ or L through a carbon atom. In some embodiments, an internucleotidic linkage, e.g., a non-negatively charged internucleotidic linkage of formula II or II-a-1, II-a-2, has the structure of formula II-b-2 or a salt form thereof:

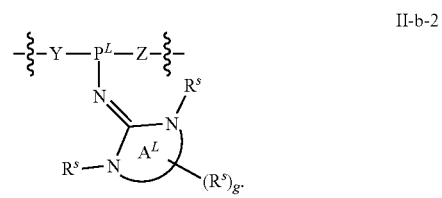

II-b-2

In some embodiments, Ring A$^L$ is an optionally substituted 3-20 membered monocyclic ring having 0-10 heteroatoms (in addition to the two nitrogen atoms for formula II-b). In some embodiments, Ring A$^L$ is an optionally substituted 5-membered monocyclic saturated ring.

In some embodiments, an internucleotidic linkage, e.g., a non-negatively charged internucleotidic linkage of formula II, II-a, or II-b, has the structure of formula II-c-1 or a salt form thereof:

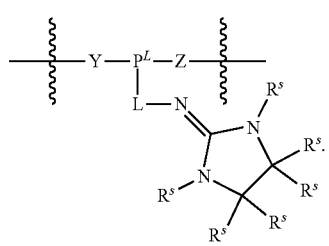

II-c-1

In some embodiments, an internucleotidic linkage, e.g., a non-negatively charged internucleotidic linkage of formula II, II-a, or II-b, has the structure of formula II-c-2 or a salt form thereof:

II-c-2

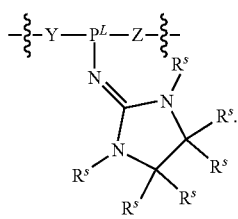

In some embodiments, an internucleotidic linkage, e.g., a non-negatively charged internucleotidic linkage of formula II, II-a, II-b, or II-c has the structure of formula II-d-1 or a salt form thereof:

II-d-1

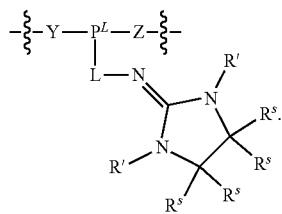

In some embodiments, an internucleotidic linkage, e.g., a non-negatively charged internucleotidic linkage of formula II, II-a, II-b, or II-c has the structure of formula II-d-2 or a salt form thereof:

II-d-2

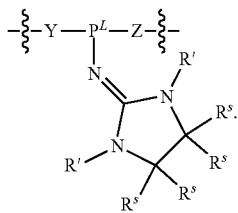

In some embodiments, each R' is independently optionally substituted $C_{1-6}$ aliphatic. In some embodiments, each R' is independently optionally substituted $C_{1-6}$ alkyl. In some embodiments, each R' is independently —$CH_3$. In some embodiments, each $R^s$ is —H.

In some embodiments, a non-negatively charged internucleotidic linkage has the structure of

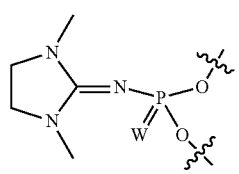

In some embodiments, a non-negatively charged internucleotidic linkage has the structure of In some embodiments, a non-negatively charged internucleotidic linkage has the structure of

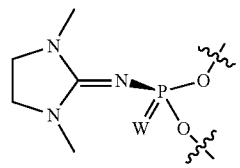

In some embodiments, a non-negatively charged internucleotidic linkage has the structure of

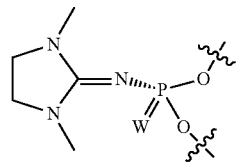

In some embodiments, a non-negatively charged internucleotidic linkage has the structure of

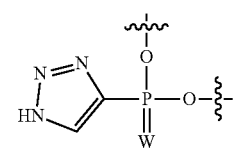

In some embodiments, a non-negatively charged internucleotidic linkage has the structure of

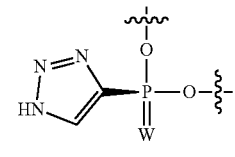

In some embodiments, a non-negatively charged internucleotidic linkage has the structure of

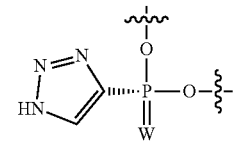

In some embodiments, a non-negatively charged internucleotidic linkage has the structure of

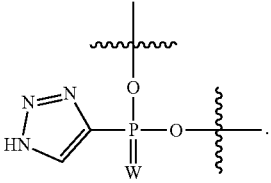

In some embodiments, a non-negatively charged internucleotidic linkage has the structure of In some embodiments, a non-negatively charged internucleotidic linkage has the structure of

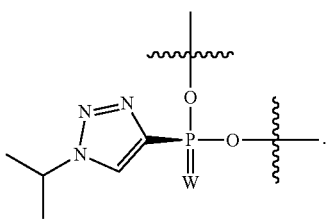

In some embodiments, a non-negatively charged internucleotidic linkage has the structure of

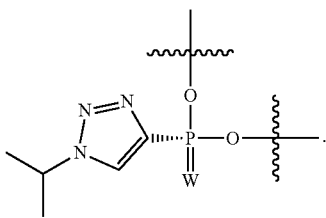

In some embodiments, a non-negatively charged internucleotidic linkage has the structure of

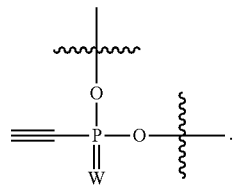

In some embodiments, a non-negatively charged internucleotidic linkage has the structure of

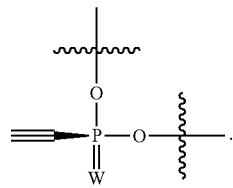

In some embodiments, a non-negatively charged internucleotidic linkage has the structure of

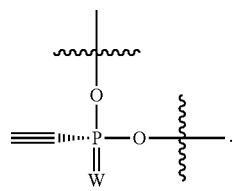

In some embodiments, W is O. In some embodiments, W is S.

In some embodiments, each $L^P$ independently has the structure of formula I, I-a-1, I-a-2, I-b, I-c, I-d, I-e, I-n-1, I-n-2, I-n-3, II, II-a-1, II-a-2, II-b-1, II-b-2, II-c-1, II-c-2, II-d-1, or II-d-2, or a salt form thereof.

In some embodiments, the present disclosure provides oligonucleotides comprising one or more non-negatively charged internucleotidic linkages. In some embodiments, a non-negatively charged internucleotidic linkage is a neutral internucleotidic linkage. In some embodiments, the present disclosure provides oligonucleotides comprising one or more neutral internucleotidic linkages. In some embodiments, a non-negatively charged internucleotidic linkage has the structure of formula I-n-1, I-n-2, I-n-3, II, II-a-1, II-a-2, II-b-1, II-b-2, II-c-1, II-c-2, II-d-1, or II-d-2, or a salt form thereof.

In some embodiments, a non-negatively charged internucleotidic linkage comprises a triazole moiety. In some embodiments, a non-negatively charged internucleotidic linkage comprises an optionally substituted triazolyl group. In some embodiments, a non-negatively charged internucleotidic linkage has the structure of

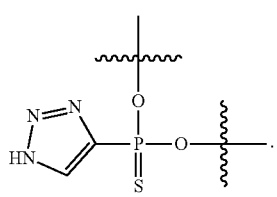 [SMILES: *OP(=S)(O*)c1c[nH]nn1]

In some embodiments, a non-negatively charged internucleotidic linkage has the structure of

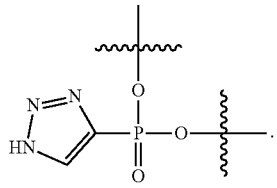

In some embodiments, a non-negatively charged internucleotidic linkage comprises a substituted triazolyl group. In some embodiments, a non-negatively charged internucleotidic linkage has the structure of

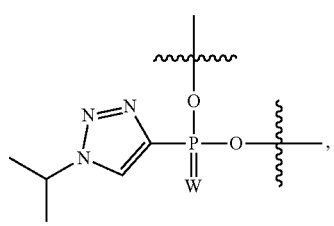

wherein W is O or S. In some embodiments, a non-negatively charged internucleotidic linkage comprises an optionally substituted alkynyl group. In some embodiments, a non-negatively charged internucleotidic linkage has the structure of

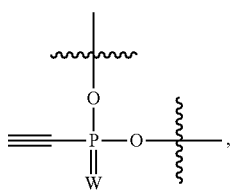

wherein W is O or S.

In some embodiments, the present disclosure provides oligonucleotides comprising an internucleotidic linkage, e.g., a non-negatively charged internucleotidic linkage, which comprises a cyclic guanidine moiety. In some embodiments, an internucleotidic linkage comprises a cyclic guanidine and has the structure of:

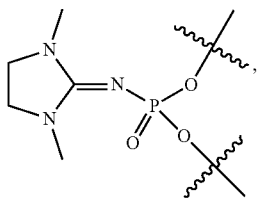 [SMILES: *OP(=O)(N=C1N(C)CCN1C)O*]

In some embodiments, an internucleotidic linkage, e.g., a non-negatively charged internucleotidic linkage, comprising a cyclic guanidine is stereochemically controlled.

In some embodiments, a non-negatively charged internucleotidic linkage, or a neutral internucleotidic linkage, is or comprising a structure selected from

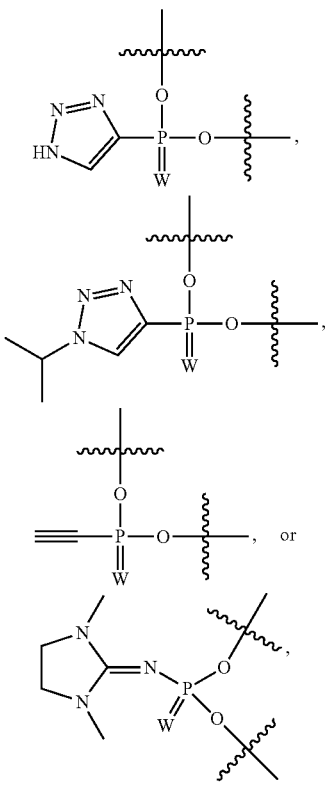

wherein W is O or S. In some embodiments, a non-negatively charged internucleotidic linkage is a chirally controlled internucleotidic linkage. In some embodiments, a neutral internucleotidic linkage is a chirally controlled internucleotidic linkage. In some embodiments, a nucleic acid or an oligonucleotide comprising a modified internucleotidic linkage comprising a cyclic guanidine moiety is a siRNA, double-straned siRNA, single-stranded siRNA, gapmer, skipmer, blockmer, antisense oligonucleotide, antagomir, microRNA, pre-microRNAs, antimir, supermir, ribozyme, U1 adaptor, RNA activator, RNAi agent, decoy oligonucleotide, triplex forming oligonucleotide, aptamer or adjuvant.

In some embodiments, an oligonucleotide comprises a neutral internucleotidic linkage and a chirally controlled internucleotidic linkage. In some embodiments, an oligonucleotide comprises a neutral internucleotidic linkage and a chirally controlled internucleotidic linkage which is a phosphorothioate in the Rp or Sp configuration. In some embodiments, the present disclosure provides an oligonucleotide comprising one or more non-negatively charged internucleotidic linkages and one or more phosphorothioate internucleotidic linkage, wherein each phosphorothioate internucleotidic linkage in the oligonucleotide is independently a chirally controlled internucleotidic linkage. In some embodiments, the present disclosure provides an oligonucleotide comprising one or more neutral internucleotidic linkages and one or more phosphorothioate internucleotidic linkage, wherein each phosphorothioate internucleotidic linkage in the oligonucleotide is independently a chirally controlled internucleotidic linkage. In some embodiments, a provided oligonucleotide comprises at least 5, 6, 7, 8, 9, 10, 11, 12, 13, 14, 15, 16, 17, 18, 19, 20 or more chirally controlled phosphorothioate internucleotidic linkages.

Without wishing to be bound by any particular theory, the present disclosure notes that a neutral internucleotidic linkage can be more hydrophobic than a phosphorothioate internucleotidic linkage (PS), which is more hydrophobic than a phosphodiester linkage (natural phosphate linkage, PO). Typically, unlike a PS or PO, a neutral internucleotidic linkage bears less charge. Without wishing to be bound by any particular theory, the present disclosure notes that incorporation of one or more neutral internucleotidic linkages into an oligonucleotide may increase oligonucleotides' ability to be taken up by a cell and/or to escape from endosomes. Without wishing to be bound by any particular theory, the present disclosure notes that incorporation of one or more neutral internucleotidic linkages can be utilized to modulate melting temperature between an oligonucleotide and its target nucleic acid.

Without wishing to be bound by any particular theory, the present disclosure notes that incorporation of one or more non-negatively charged internucleotidic linkages, e.g., neutral internucleotidic linkages, into an oligonucleotide may be able to increase the oligonucleotide's ability to mediate a function such as exon skipping or gene knockdown. In some embodiments, an oligonucleotide capable of mediating knockdown of level of a nucleic acid or a product encoded thereby comprises one or more non-negatively charged internucleotidic linkages. In some embodiments, an oligonucleotide capable of mediating knockdown of expression of a target gene comprises one or more non-negatively charged internucleotidic linkages. In some embodiments, an oligonucleotide capable of mediating knockdown of expression of a target gene comprises one or more neutral internucleotidic linkages.

In some embodiments, a non-negatively charged internucleotidic linkage is not chirally controlled. In some embodiments, a non-negatively charged internucleotidic linkage is chirally controlled. In some embodiments, a non-negatively charged internucleotidic linkage is chirally controlled and its linkage phosphorus is Rp. In some embodiments, a non-negatively charged internucleotidic linkage is chirally controlled and its linkage phosphorus is Sp.

In some embodiments, a provided oligonucleotide comprises 1, 2, 3, 4, 5, 6, 7, 8, 9, 10, or more non-negatively charged internucleotidic linkages. In some embodiments, a provided oligonucleotide comprises 1, 2, 3, 4, 5, 6, 7, 8, 9, 10, or more neutral internucleotidic linkages. In some embodiments, each of non-negatively charged internucleotidic linkage and/or neutral internucleotidic linkages is optionally and independently chirally controlled. In some embodiments, each non-negatively charged internucleotidic linkage in an oligonucleotide is independently a chirally controlled internucleotidic linkage. In some embodiments, each neutral internucleotidic linkage in an oligonucleotide is independently a chirally controlled internucleotidic linkage. In some embodiments, at least one non-negatively charged internucleotidic linkage/neutral internucleotidic linkage has the structure of

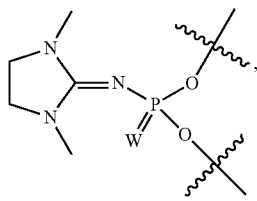

wherein W is O or S. In some embodiments, at least one non-negatively charged internucleotidic linkage/neutral internucleotidic linkage has the structure of

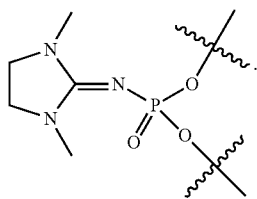

In some embodiments, at least one non-negatively charged internucleotidic linkage/neutral internucleotidic linkage has the structure of

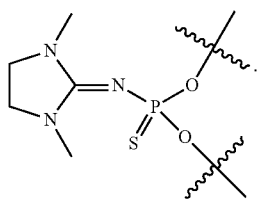

In some embodiments, at least one non-negatively charged internucleotidic linkage/neutral internucleotidic linkage has the structure of

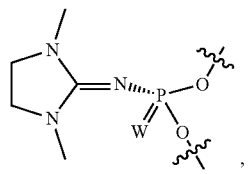

wherein W is O or S. In some embodiments, at least one non-negatively charged internucleotidic linkage/neutral internucleotidic linkage has the structure of

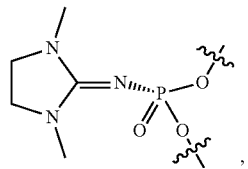

In some embodiments, at least one non-negatively charged internucleotidic linkage/neutral internucleotidic linkage has the structure of

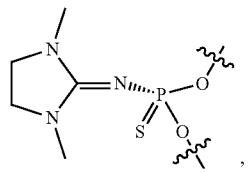

In some embodiments, at least one non-negatively charged internucleotidic linkage/neutral internucleotidic linkage has the structure of

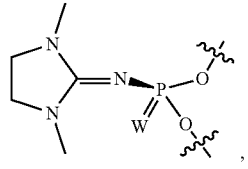

wherein W is O or S. In some embodiments, at least one non-negatively charged internucleotidic linkage/neutral internucleotidic linkage has the structure of

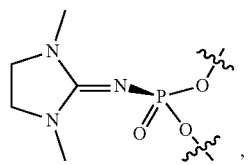

In some embodiments, at least one non-negatively charged internucleotidic linkage/neutral internucleotidic linkage has the structure of

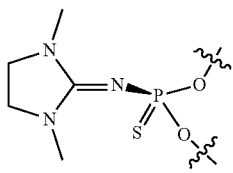

In some embodiments, a provided oligonucleotide comprises at least one non-negatively charged internucleotidic linkage wherein its linkage phosphorus is in Rp configuration, and at least one non-negatively charged internucleotidic linkage wherein its linkage phosphorus is in Sp configuration.

In some embodiments, various oligonucleotides are described herein, which comprise an internucleotidic linkage designated as nX:

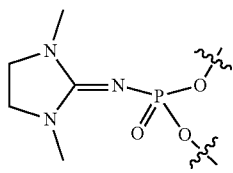

(also known as n001), which is stereorandom (not chirally controlled).

Non-limiting examples of oligonucleotides comprising a non-negatively charged internucleotidic linkage include WV-14512, WV-14513, WV-14514, WV-14515, WV-14516, WV-14517, WV-14518, WV-14519, WV-14520, and WV-14521.

In some embodiments, the present disclosure provides an oligonucleotide, e.g., a SMN2 oligonucleotide, consisting of or comprising a region of consecutive nucleotidic units:

$(Nu^M)t[(Nu^O)n(Nu^M)m]y$ wherein:
each $Nu^M$ is independently a nucleotidic unit comprising a modified internucleotidic linkage;
each $Nu^O$ is independently a nucleotidic unit comprising a natural phosphate linkage;
each of t, n, and m is independently 1-20; and
y is 1-10.
wherein the oligonucleotide may not contain an internucleotidic linkage at its 5'-end and/or 3'-end.

In some embodiments, each $Nu^M$ is a nucleotidic unit comprising a stereocontrolled phosphorothioate, and each $Nu^O$ is independently a nucleotidic unit comprising a natural phosphate linkage.

In some embodiments, as demonstrated in the present disclosure, such oligonucleotides provide improved properties, e.g., improved stability, and/or activities.

As defined herein, each $Nu^M$ independently comprises a modified internucleotidic linkage. In some embodiments, a modified internucleotidic linkage is a chiral internucleotidic linkage. In some embodiments, a modified internucleotidic linkage is a phosphorothioate diester linkage. In some embodiments, a modified internucleotidic linkage is chiral and is chirally controlled. In some embodiments, each modified internucleotidic linkage is chirally controlled. In some embodiments, internucleotidic linkage of $Nu^M$ is a chirally controlled phosphorothioate diester linkage. In some embodiments, $Nu^M$ of a provided chirally controlled oligonucleotide compositions comprises different types of modified internucleotidic linkages. In some embodiments, $Nu^M$ of a provided chirally controlled oligonucleotide compositions comprises chiral internucleotidic linkages having linkage phosphorus atoms of different configuration. In some embodiments, $Nu^M$ of a provided chirally controlled oligonucleotide compositions comprises different types of modified internucleotidic linkages. In some embodiments, $Nu^M$ of a provided chirally controlled oligonucleotide compositions comprises chiral internucleotidic linkages having linkage phosphorus atoms of different configuration. In some embodiments, at least one chiral internucleotidic linkage of $Nu^M$ is Sp at its linkage phosphorus. In some embodiments, at least 2, 3, 4, 5, 6, 7, 8, 9, or 10 $Nu^M$ each independently comprise a chiral internucleotidic linkage of Sp at its linkage phosphorus. In some embodiments, each chiral internucleotidic linkage of $Nu^M$ is Sp at its linkage phosphorus. In some embodiments, at least one chiral internucleotidic linkage of $Nu^M$ is Rp at its linkage phosphorus. In some embodiments, at least one chiral internucleotidic linkage of $Nu^M$ is Rp at its linkage phosphorus, and at least one chiral internucleotidic linkage of $Nu^M$ is Sp at its linkage phosphorus. Additional nucleotidic unit comprising modified internucleotidic linkages suitable for $Nu^M$ are known in the art and/or described in the present disclosure and can be utilized in accordance with the present disclosure.

As defined herein, each $Nu^O$ is independently a nucleotidic unit comprising a natural phosphate linkage. In some embodiments, at least one $Nu^O$ is a nucleotidic unit comprising a natural phosphate linkage, wherein the natural phosphate linkage is bonded to a 5'-nucleotidic unit and a carbon atom of the sugar unit of the nucleotidic unit, wherein the carbon atom is bonded to less than two hydrogen atoms. In some embodiments, each $Nu^O$ is independently a nucleotidic unit comprising a natural phosphate linkage, wherein the natural phosphate linkage is bonded to a 5'-nucleotidic unit and a carbon atom of the sugar unit of the nucleotidic unit, wherein the carbon atom is bonded to less than two hydrogen atoms. In some embodiments, at least one $Nu^O$ comprises a structure of $-C(R^{5s})_2-$, which structure is directly boned to the natural phosphate linkage of $Nu^O$ and a ring moiety of the sugar unit of $Nu^O$. In some embodiments, each $Nu^O$ independently comprises a structure of $-C(R^{5s})_2-$, which structure is directly boned to the natural phosphate linkage of $Nu^O$ and a ring moiety of the sugar unit of $Nu^O$.

In some embodiments, each $Nu^O$ independently has the structure of formula N-I:

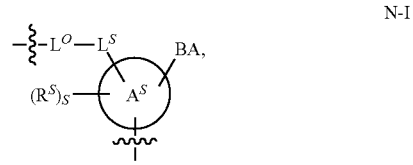

or a salt form thereof, wherein $L^O$ is a natural phosphate linkage, and each of other variables is independently as described in the present disclosure.

In some embodiments,

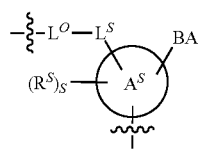

has the structure of

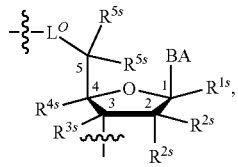

wherein each of $R^{1s}$, $R^{2s}$, $R^{3s}$, and $R^{4s}$ is independently $R^s$ and as described in the present disclosure. In some embodiments,

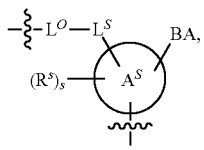

has the structure of

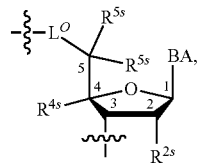

wherein each of $R^{1s}$, $R^{2s}$, $R^{3s}$, and $R^{4s}$ is independently as described in the present disclosure. In some embodiments,

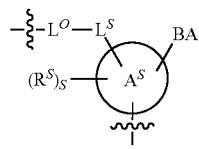

has the structure of

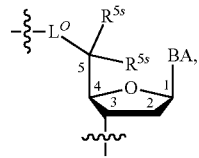

wherein each of $R^{1s}$, $R^{2s}$, $R^{3s}$, and $R^{4s}$ is independently as described in the present disclosure.

In some embodiments, each $Nu^M$ independently has the structure of formula N-II:

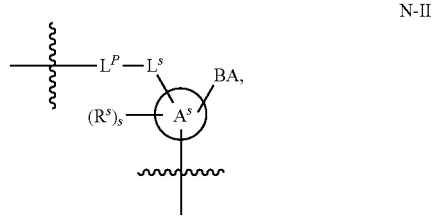

N-II or a salt form thereof, wherein $L^P$ is a modified internucleotidic linkage, and each of other variables is independently as described in the present disclosure. In some embodiments, $L^P$ is a modified internucleotidic linkage having the structure of formula I.

In some embodiments,

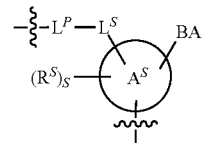

has the structure of

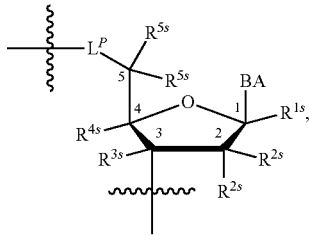

wherein each of $R^{1s}$, $R^{2s}$, $R^{3s}$, and $R^{4s}$ is independently $R^s$ and as described in the present disclosure. In some embodiments,

has the structure of

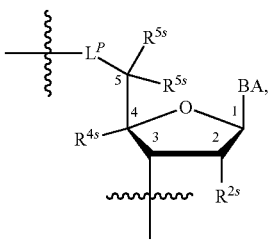

wherein each of $R^{1s}$, $R^{2s}$, $R^{3s}$, and $R^{4s}$ is independently as described in the present disclosure. In some embodiments,

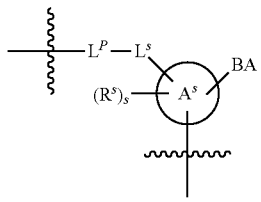

has the structure of

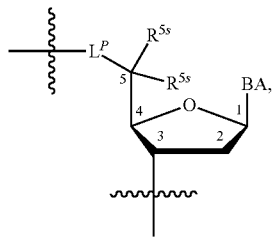

wherein each of $R^{1s}$, $R^{2s}$, $R^{3s}$, and $R^{4s}$ is independently as described in the present disclosure.

In some embodiments, $L^s$ is —$C(R^{5s})_2$—. In some embodiments, one $R^{5s}$ is —H and $L^s$ is —$CHR^{5s}$—. In some embodiments, each $R^{5s}$ is independently R. In some embodiments, In some embodiments, —$C(R^{5s})_2$— is —$C(R)_2$—. In some embodiments, one $R^{5s}$ is —H and —$C(R^{5s})_2$— is —CHR—. In some embodiments, R is not hydrogen. In some embodiments, R is optionally substituted $C_{1-6}$ aliphatic. In some embodiments, R is optionally substituted $C_{1-6}$ alkyl. In some embodiments, R is substituted. In some embodiments, R is unsubstituted. In some embodiments, R is methyl. Additional example R groups are widely described in the present disclosure. In some embodiments, the C of —$C(R^{5s})_2$— is chiral and is R. In some embodiments, the C of —$C(R^{5s})_2$— is chiral and is S. In some embodiments, —$C(R^{5s})_2$— is —(R)—CHMe-. In some embodiments, —$C(R^{5s})_2$— is —(S)—CHMe-.

Stereochemistry

Among other things, the present disclosure provides oligonucleotides comprising one or more chirally controlled internucleotidic linkages. In some embodiments, the present disclosure provides chirally controlled oligonucleotide compositions. In some embodiments, each chiral linkage phosphorus of provided oligonucleotides is independently chirally controlled (stereocontrolled) (e.g., each independently having a stereopurity (diastereopurity) of at least 80%, 85%, 90%, 95%, 96%, 97%, 98%, or 99% (e.g., as typically assessed using an appropriate dimer comprising an internucleotidic linkage containing the linkage phosphorus, and the two nucleoside units being linked by the internucleotidic linkage)). In some embodiments, a stereopurity is at least 90%. In some embodiments, a stereopurity is at least 95%. In some embodiments, a stereopurity is at least 96%. In some embodiments, a stereopurity is at least 97%. In some embodiments, a stereopurity is at least 98%. In some embodiments, a stereopurity is at least 99%. With the capability to fully control stereochemistry and other modifications (e.g., base modifications, sugar modifications, internucleotidic linkage modifications, etc.), the present disclosure provides technologies of improved properties and/or activities compared to corresponding non-chirally controlled technologies.

In some embodiments, provided oligonucleotides, e.g., provided oligonucleotides of a plurality in provided chirally controlled oligonucleotide compositions, or a portion thereof, e.g., a block, a wing, a core, etc., have a pattern of backbone chiral centers (linkage phosphorus chiral centers) that is or comprises (Sp)t[(Op)n(Sp)m]y, (Rp)t(Np)n(Rp)m, (Rp)t(Sp)n(Rp)m, (Rp)t[(Np/Op)n]y(Rp)m, (Rp)t[(Sp/Np)n]y(Rp)m, (Rp)t[(Sp/Op)n]y(Rp)m, (Np/Op)t(Np)n(Np/Op)m, (Np/Op)t(Sp)n(Np/Op)m, (Np/Op)t[(Np/Op)n]y(Np/Op)m, (Np/Op)t[(Sp/Op)n]y(Np/Op)m, (Np/Op)t[(Sp/Op)n]y(Np/Op)m, (Rp/Op)t(Np)n(Rp/Op)m, (Rp/Op)t(Sp)n(Rp/Op)m, (Rp/Op)t[(Np/Op)n]y(Rp/Op)m, (Rp/Op)t[(Sp/Op)n]y(Rp/Op)m, or (Rp/Op)t[(Sp/Op)n]y(Rp/Op)m (unless otherwise specified, description of patterns of modifications and stereochemistry are from 5' to 3' as typically used in the art), wherein Sp indicates S configuration of a chiral linkage phosphorus of a chiral modified internucleotidic linkage, Rp indicates R configuration of a chiral linkage phosphorus of a chiral modified internucleotidic linkage, Op indicates an achiral linkage phosphorus of a natural phosphate linkage, each Np is independently Rp, or Sp, and each of m, n, t and y is independently 1-50 as described in the present disclosure.

In some embodiments, a pattern of backbone chiral centers is or comprises (Sp)t[(Op)n(Sp)m]y. In some embodiments, a pattern of backbone chiral centers is or comprises (Rp)t(Np)n(Rp)m. In some embodiments, a pattern of backbone chiral centers is or comprises (Rp)t(Sp)n(Rp)m. In some embodiments, a pattern of backbone chiral centers is or comprises (Rp)t[(Np/Op)n]y(Rp)m. In some embodiments, a pattern of backbone chiral centers is or comprises (Rp)t[(Sp/Np)n]y(Rp)m. In some embodiments, a pattern of backbone chiral centers is or comprises (Rp)t[(Sp/Op)n]y(Rp)m. In some embodiments, a pattern of backbone chiral centers is or comprises (Np/Op)t(Np)n(Np/Op)m. In some embodiments, a pattern of backbone chiral centers is or comprises (Np/Op)t(Sp)n(Np/Op)m. In some embodiments, a pattern of backbone chiral centers is or comprises (Np/Op)t[(Np/Op)n]y(Np/Op)m. In some embodiments, a pattern of backbone chiral centers is or comprises (Np/Op)t[(Sp/Op)n]y(Np/Op)m. In some embodiments, a pattern of backbone chiral centers is or comprises (Np/Op)t[(Sp/Op)n]y(Np/Op)m. In some embodiments, a pattern of backbone chiral centers is or comprises (Rp/Op)t(Np)n(Rp/Op)m. In some embodiments, a pattern of backbone chiral centers is or comprises (Rp/Op)t(Sp)n(Rp/Op)m. In some embodiments, a pattern of backbone chiral centers is or comprises (Rp/Op)t[(Np/Op)n]y(Rp/Op)m. In some embodiments, a pattern of backbone chiral centers is or comprises (Rp/Op)t[(Sp/Op)n]y(Rp/Op)m. In some embodiments, a pattern of backbone chiral centers is or comprises (Rp)(Rp/Op)t[(Sp/Op)n]y(Rp/Op)m(Rp).

In some embodiments, the present disclosure provides a chirally controlled oligonucleotide composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
wherein:
oligonucleotides of the plurality comprise at least 1, 2, 3, 4, 5, 6, 7, 8, 9, or 10 chirally controlled internucleotidic linkages; and the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

In some embodiments, the present disclosure provides a chirally controlled oligonucleotide composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
wherein:
oligonucleotides of the plurality comprise at least 1, 2, 3, 4, 5, 6, 7, 8, 9, or 10 chirally controlled internucleotidic linkages; and
the pattern of backbone chiral centers is or comprises (Rp/Op)t[(Np/Op)n]y(Rp/Op)m.

In some embodiments, the present disclosure provides chirally controlled oligonucleotide composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
wherein:
oligonucleotides of the plurality comprise at least 1, 2, 3, 4, 5, 6, 7, 8, 9, or 10 chirally controlled internucleotidic linkages; and
the pattern of backbone chiral centers is or comprises (Rp)(Rp/Op)t[(Np/Op)n]y(Rp/Op)m(Rp).

In some embodiments, the present disclosure provides a chirally controlled oligonucleotide composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
wherein:
oligonucleotides of the plurality comprise at least 1, 2, 3, 4, 5, 6, 7, 8, 9, or 10 chirally controlled internucleotidic linkages; and
the pattern of backbone chiral centers is or comprises (Rp)t[(Np/Op)n]y(Rp)m.

In some embodiments, each of (Rp/Op)t and (Rp/Op)m independently comprises at least 1, 2, 3, 4, 5, 6, 7, 8, 9, or 10 Rp. In some embodiments, each of (Rp/Op)t and (Rp/Op)m independently comprises at least 2, 3, 4, 5, 6, 7, 8, 9, or 10 Rp. In some embodiments, each of (Rp/Op)t and (Rp/Op)m independently comprises at least 3 Rp. In some embodiments, each of (Rp/Op)t and (Rp/Op)m independently comprises at least 4 Rp. In some embodiments, each of (Rp/Op)t and (Rp/Op)m independently comprises at least 5 Rp. In some embodiments, y, t, n and m each are independently 1-20 as described in the present disclosure. In some embodiments, y is 1. In some embodiments, y is at least 2, 3, 4, 5, 6, 7, 8, 9, 10, 11, 12, 13, 14, or 15. In some embodiments, y is 2, 3, 4, 5, 6, 7, 8, 9, 10, 11, 12, 13, 14, or 15. In some embodiments, y is 1, 2, 3, 4, 5, 6, 7, 8, 9, or 10. In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10. In some embodiments, each (Np/Op) is Np. In some embodiments, each (Np/Op) is Sp.

In some embodiments, n is 1. In some embodiments, n is at least 2, 3, 4, 5, 6, 7, 8, 9, 10, 11, 12, 13, 14, or 15. In some embodiments, n is 2, 3, 4, 5, 6, 7, 8, 9, 10, 11, 12, 13, 14, or 15. In some embodiments, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, m is 0-50. In some embodiments, m is 1-50. In some embodiments, m is 1. In some embodiments, m is 2-50. In some embodiments, m is at least 2, 3, 4, 5, 6, 7, 8, 9, 10, 11, 12, 13, 14, or 15. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is at least 2. In some embodiments, m is at least 3. In some embodiments, m is at least 4. In some embodiments, m is at least 5. In some embodiments, m is at least 6. In some embodiments, m is at least 7. In some embodiments, m is at least 8. In some embodiments, m is at least 9. In some embodiments, m is at least 10. In some embodiments, m is at least 11. In some embodiments, m is at least 12. In some embodiments, m is at least 13. In some embodiments, m is at least 14. In some embodiments, m is at least 15. In some embodiments, m is at least 16. In some embodiments, m is at least 17. In some embodiments, m is at least 18. In some embodiments, m is at least 19. In some embodiments, m is at least 20. In some embodiments, m is at least 21. In some embodiments, m is at least 22. In some embodiments, m is at least 23. In some embodiments, m is at least 24. In some embodiments, m is at least 25. In some embodiments, m is at least greater than 25.

In some embodiments, t is 1-20. In some embodiments, t is 1. In some embodiments, t is at least 2, 3, 4, 5, 6, 7, 8, 9, 10, 11, 12, 13, 14, or 15. In some embodiments, t is 2, 3, 4, 5, 6, 7, 8, 9, 10, 11, 12, 13, 14, or 15. In some embodiments, t is 1-5. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20.

In some embodiments, each of t and m is independently at least 2, 3, 4, 5, 6, 7, 8, 9, 10, 11, 12, 13, 14, or 15. In some embodiments, each of t and m is independently at least 3. In some embodiments, each of t and m is independently at least 4. In some embodiments, each of t and m is independently at least 5. In some embodiments, each of t and m is independently at least 6. In some embodiments, each of t and m is independently at least 7. In some embodiments, each of t and m is independently at least 8. In some embodiments, each of t and m is independently at least 9. In some embodiments, each of t and m is independently at least 10.

In some embodiments, provided oligonucleotides comprises a block, e.g., a first block, a 5'-wing, etc., that has a pattern of backbone chiral centers of or comprising a t-section, e.g., (Sp)t, (Rp)t, (Np/Op)t, (Rp/Op)t, etc., a block, e.g., a second block, a core, etc., that has a pattern of backbone chiral centers of or comprising a y- or n-section, e.g., (Np)n, (Sp)n, [(Np/Op)n]y, [(Rp/Op)n]y, [(Sp/Op)n]y, etc., and a block, e.g., a third block, a 3'-wing, etc., that has a pattern of backbone chiral centers of or comprising a m-section, e.g., (Sp)m, (Rp)m, (Np/Op)m, (Rp/Op)m, etc.

In some embodiments, a t-, y-, n-, or m-section that comprises Np or Rp, e.g., (Rp)t, (Np/Op)t, (Rp/Op)t, (Np)n, [(Np/Op)n]y, [(Rp/Op)n]y, (Rp)m, (Np/Op)m, (Rp/Op)m, etc. independently comprises at least 10%, 20%, 30%, 40%, 50%, 60%, 70%, 75%, 80%, 85%, 90%, or 95%, or 100% Rp. In some embodiments, a t- or m-section that comprises Np or Rp independently comprises at least 10%, 20%, 30%, 40%, 50%, 60%, 70%, 75%, 80%, 85%, 90%, or 95%, or 100% Rp. In some embodiments, provided oligonucleotides comprise at least 10%, 20%, 30%, 40%, 50%, 60%, 70%, 75%, 80%, 85%, 90%, or 95%, or 100% Rp. In some embodiments, at least 10%, 20%, 30%, 40%, 50%, 60%, 70%, 75%, 80%, 85%, 90%, or 95%, or 100% of all linkage phosphorus of provided oligonucleotides are chirally controlled and Rp. In some embodiments, at least 10%, 20%, 30%, 40%, 50%, 60%, 70%, 75%, 80%, 85%, 90%, or 95%, or 100% of all chirally internucleotidic linkages (either chirally controlled or not) of provided oligonucleotides are Rp. In some embodiments, at least 10%, 20%, 30%, 40%, 50%, 60%, 70%, 75%, 80%, 85%, 90%, or 95%, or 100% of all phosphorothioate internucleotidic linkages of provided oligonucleotides are Rp. In some embodiments, at least 10%, 20%, 30%, 40%, 50%, 60%, 70%, 75%, 80%, 85%, 90%, or 95%, or 100% of all chirally controlled internucleotidic linkages of provided oligonucleotides are Rp. In some embodiments, at least 10%, 20%, 30%, 40%, 50%, 60%, 70%, 75%, 80%, 85%, 90%, or 95%, or 100% of chirally controlled phosphorothioate internucleotidic linkages of provided oligonucleotides are Rp. In some embodiments, a percentage is at least 10%. In some embodiments, a percentage is at least 20%. In some embodiments, a percentage is at least 30%. In some embodiments, a percentage is at least 40%. In some embodiments, a percentage is at least 50%. In some embodiments, a percentage is at least 60%. In some embodiments, a percentage is at least 70%. In some embodiments, a percentage is at least 75%. In some embodiments, a percentage is at least 80%. In some embodiments, a percentage is at least 85%. In some embodiments, a percentage is at least 90%. In some embodiments, a percentage is at least 95%. In some embodiments, a percentage is 100%.

In some embodiments, each sugar moiety bonded to a Rp or Op linkage phosphorus at 3' independently comprises a modification. In some embodiments, each sugar moiety bonded to a Rp or Op linkage phosphorus at 5' independently comprises a modification. In some embodiments, each sugar moiety bonded to a Rp linkage phosphorus at 3' independently comprises a modification. In some embodiments, each sugar moiety bonded to a Rp linkage phosphorus at 5' independently comprises a modification. In some embodiments, each sugar moiety bonded to an Op linkage phosphorus at 3' independently comprises a modification. In some embodiments, each sugar moiety bonded to an Op linkage phosphorus at 5' independently comprises a modification. In some embodiments, each sugar moiety bonded to a Sp linkage phosphorus at 3' independently comprises a modification. In some embodiments, each sugar moiety bonded to a Sp linkage phosphorus at 5' independently comprises a modification. In some embodiments, each sugar moiety independently comprises a modification. In some embodiments, a modification is a 2'-modification. In some embodiments, a modification is 2'-OR, wherein R is not hydrogen. In some embodiments, a modification is 2'-OR, wherein R is optionally substituted $C_{1-6}$ alkyl. In some embodiments, a modification is 2'-OR, wherein R is substituted $C_{1-6}$ alkyl. In some embodiments, a modification is 2'-OR, wherein R is optionally substituted $C_{2-6}$ alkyl. In some embodiments, a modification is 2'-OR, wherein R is substituted $C_{2-6}$ alkyl. In some embodiments, R is —CH$_2$CH$_2$OMe. In some embodiments, a modification is or comprises -L-connecting two sugar carbons, e.g., those found in LNA. In some embodiments, a modification is -L- connecting $C_2$ and $C_4$ of a sugar moiety. In some embodiments, L is —CH$_2$—CH(R)—, wherein R is as described in the present disclosure. In some embodiments, L is —CH$_2$—CH(R)—, wherein R is as described in the present disclosure and is not hydrogen. In some embodiments, L is —CH$_2$—(R)—CH(R)—, wherein R is as described in the present disclosure and is not hydrogen. In some embodiments, L is —CH$_2$—(S)—CH(R)—, wherein R is as described in the present disclosure and is not hydrogen. In some embodiments, a block, a wing, a core, or an oligonucleotide has sugar modifications as described in the present disclosure.

In some embodiments, a provided pattern of backbone chiral centers is or comprises (Rp/Sp)-(All Rp or All Sp)-(Rp/Sp), wherein each Rp/Sp is independently Rp or Sp. In some embodiments, a provided pattern of backbone chiral centers is or comprises (Rp)-(All Sp)-(Rp). In some embodiments, a provided pattern of backbone chiral centers is or comprises (Sp)-(All Sp)-(Sp). In some embodiments, a provided pattern of backbone chiral centers is or comprises (Sp)-(All Rp)-(Sp). In some embodiments, a provided pattern of backbone chiral centers is or comprises (Rp/Sp)-(repeating (Sp)m(Rp)n)-(Rp/Sp). In some embodiments, a provided pattern of backbone chiral centers is or comprises (Rp/Sp)-(repeating SpSpRp)-(Rp/Sp).

In some embodiments, a SMN2 oligonucleotide comprises an internucleotidic linkage which is not chirally controlled. In some embodiments, a SMN2 oligonucleotide composition comprises one or more phosphorothioates which are not chirally controlled. In some embodiments, a SMN2 oligonucleotide composition comprises one or more phosphorothioates, none of which are chirally controlled. In some embodiments, in a SMN2 oligonucleotide composition, each internucleotidic linkage is a phosphorothioate, and none of which are chirally controlled. In some embodiments, a SMN2 oligonucleotide composition comprising an internucleotidic linkage which is not chirally controlled further comprises an additional chemical moiety capable of binding to the asialoglycoprotein receptor. In some embodiments, a moiety is GalNAc or a variant or derivative thereof. In some embodiments, a SMN2 oligonucleotide comprises an internucleotidic linkage which is chirally controlled.

Blocks

In some embodiments, provided oligonucleotides comprise one or more blocks, characterized by base modifications, sugar modifications, types of internucleotidic linkages, stereochemistry of linkage phosphorus, etc. In some embodiments, provided oligonucleotides comprises or are of a 5'-first block-second block-third block structure. In some embodiments, a first block is a 5'-wing. In some embodiments, a second block is a core. In some embodiments, a third block a 3'-wing. In some embodiments, provided oligonucleotides comprises or are of a 5'-wing-core-wing-3', 5'-wing-core-3' or 5'-core-wing-3' structures. In some embodiments, a first block, a second block, a third block, a wing (e.g., a 5'-wing, a 3'-wing) and/or a core of provided oligonucleotides are each independently a block or comprise one or more blocks as described in the present disclosure.

Various blocks, 5'-wings, 3'-wings and cores can be utilized in accordance with the present disclosure, including those described in US 20150211006, US 20150211006, WO 2017015555, WO 2017015575, WO 2017062862, WO 2017160741, blocks, 5'-wings, 3'-wings and cores of each of which are incorporated herein by reference.

In some embodiments, a block is a linkage phosphorus stereochemistry block. For example, in some embodiments, a block comprises only Rp, Sp, or Op linkage phosphorus. In some embodiments, a block is a Rp block comprising only Rp linkage phosphorus. In some embodiments, a block is a Rp/Op block comprising only Rp/Op linkage phosphorus. In some embodiments, a block is a Sp/Op block comprising only Sp/Op linkage phosphorus. In some embodiments, a block is an Op block. In some embodiments, an oligonucleotide, or a region thereof (a first block, a second block, a third block, a wing, a core, etc.) comprises one or more of a Rp block, a Sp block and/or an Op block. In some embodiments, a block comprises one or more, e.g., 1, 2, 3, 4, 5, 6, 7, 8, 9, 10, 11, 12, 13, 14, 15, 16, 17, 18, 19, 20, or more, linkage phosphorus.

In some embodiments, a block is a sugar modification block. In some embodiments, a block is a 2'-modification block wherein each sugar moiety of the block independently comprises the 2'-modification. In some embodiments, a 2'-modification is 2'-OR wherein R is as described in the present disclosure. In some embodiments, a 2'-modification is a 2'-OR wherein R is not hydrogen. In some embodiments, a 2'-modification is 2'-OMe. In some embodiments, a 2'-modification is 2'-MOE. In some embodiments, a modification is a LNA modification. In some embodiments, an oligonucleotide, or a region thereof (a first block, a second block, a third block, a wing, a core, etc.) comprises one or more sugar modification blocks, each independently of its own sugar modification. In some embodiments, a block comprises one or more, e.g., 1, 2, 3, 4, 5, 6, 7, 8, 9, 10, 11, 12, 13, 14, 15, 16, 17, 18, 19, 20, or more, sugar moieties.

As illustrated herein, a block can be of various lengths. In some embodiments, a block is of 1-30, e.g., 1, 2, 3, 4, 5, 6, 7, 8, 9, 10, 11, 12, 13, 14, 15, 16, 17, 18, 19, or 20 nucleobases in length. In some embodiments, a 5'-first block-second-block-third block-3', or a 5'-wing-core-wing-3' is of 5-10-5, 3-10-4, 3-10-6, 4-12-4, etc.

Additional Chemical Moieties

In some embodiments, provided oligonucleotides comprise one or more additional chemical moieties (e.g., other than typical moieties of nucleobases, sugars and/or internucleotidic linkages, etc.), optionally through a linker. In some embodiments, a chemical moiety is a lipid moiety. In some embodiments, a chemical moiety is a carbohydrate moiety. In some embodiments, a chemical moiety is a targeting moiety. In some embodiments, a chemical moiety is a moiety of a ligand. In some embodiments, a chemical moiety can increase delivery of oligonucleotides to certain organelles, cells, tissues, organs, and/or organisms. In some embodiments, a chemical moiety enhances one or more of desired properties and/or activities.

In some embodiments, the present disclosure provides oligonucleotides comprising additional chemistry moieties, optionally connected to the oligonucleotide moiety through a linker. In some embodiments, the present disclosure provides oligonucleotides comprising $(R^D)_b\text{-}L^{M1}\text{-}L^{M2}\text{-}L^{M3}\text{-}$, wherein:

each $R^D$ is independently a chemical moiety;

each of $L^{M1}$, $L^{M2}$, and $L^{M3}$ is independently a covalent bond, or a bivalent or multivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring; and b is 1-1000.

In some embodiments, each of $L^{M1}$, $L^{M2}$, and $L^{M3}$ is independently a covalent bond, or a bivalent or multivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$.

In some embodiments, $L^{M1}$ comprises one or more —N(R')— and one or more —C(O)—. In some embodiments, a linker or $L^{M1}$ is or comprises

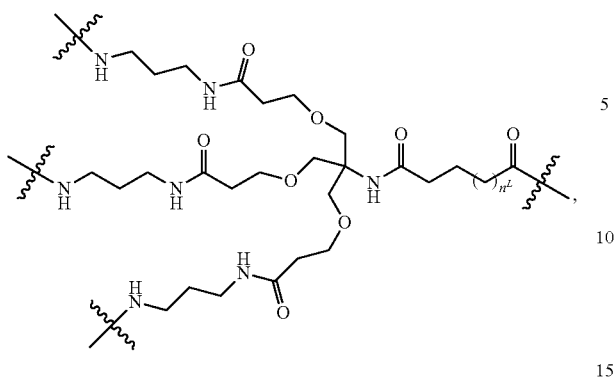

wherein $n^L$ is 1-8. In some embodiments, a linker or -$L^{M1}$-$L^{M2}$-$L^{M3}$- is

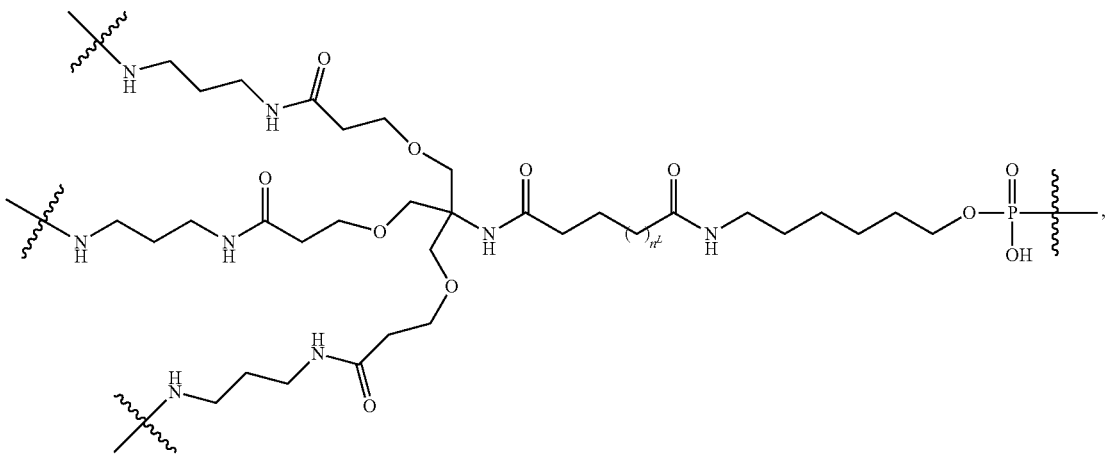

or a salt form thereof, wherein $n^L$ is 1-8. In some embodiments, a linker or -$L^{M1}$-$L^{M2}$-$L^{M3}$- is

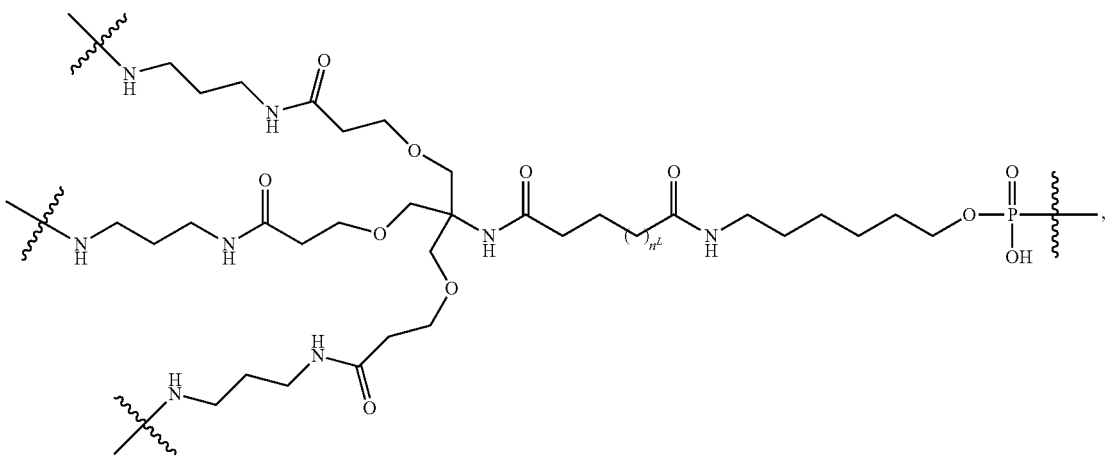

or a salt form thereof, wherein:

$n^L$ is 1-8.

each amino group independently connects to a moiety; and the P atom connects to the 5'-OH of the oligonucleotide.

In some embodiments, the moiety and the linker, or $(R^D)_b$-$L^{M1}$-$L^{M2}$-$L^{M3}$-, is or comprises

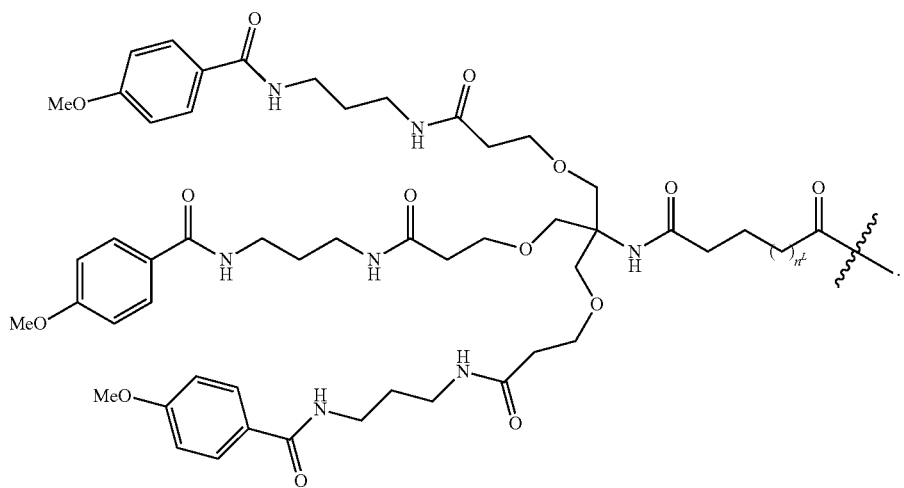
In some embodiments, the moiety and the linker, or $(R^D)_b$-$L^{M1}$-$L^{M2}$-$L^{M3}$-, is or comprises
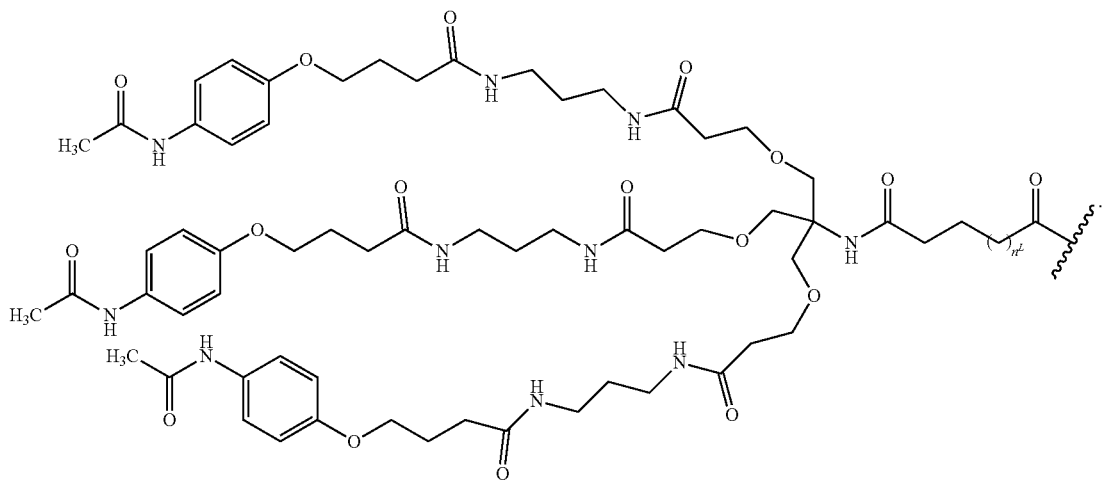
In some embodiments, the moiety and the linker, or $(R^D)_b$-$L^{M1}$-$L^{M2}$-$L^{M3}$-, is or comprises
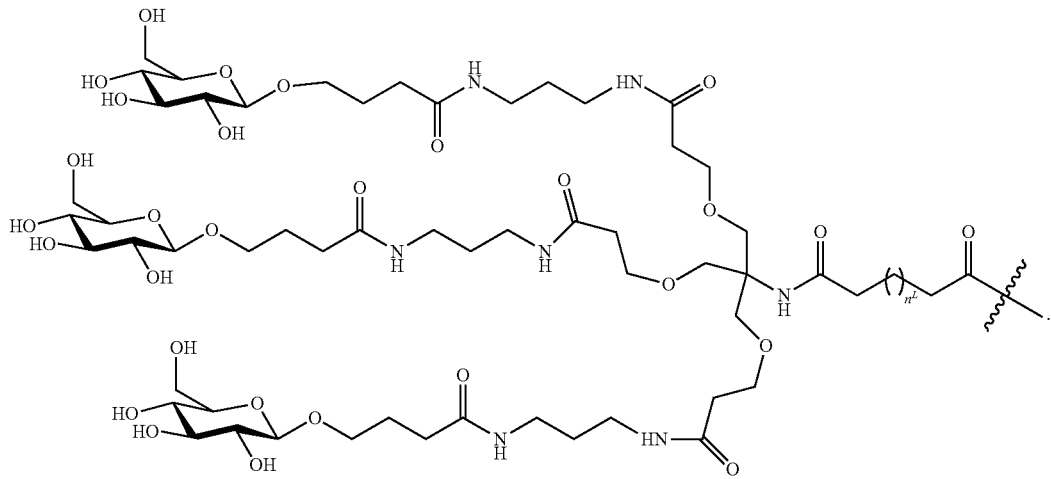

In some embodiments, the moiety and the linker, or $(R^D)_b$-$L^{M1}$-$L^{M2}$-$L^{M3}$-, is or comprises
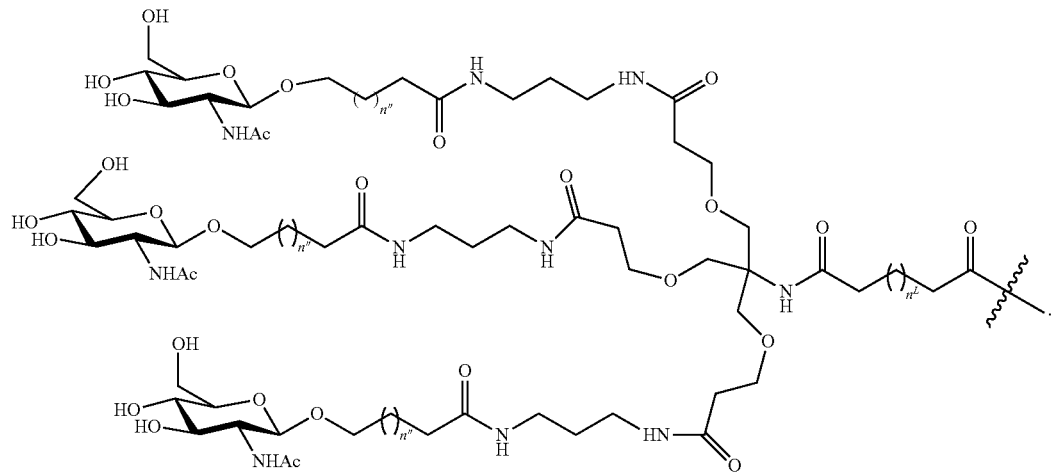
In some embodiments, the moiety and the linker, or $(R^D)_b$-$L^{M1}$-$L^{M2}$-$L^{M3}$-, is or comprises
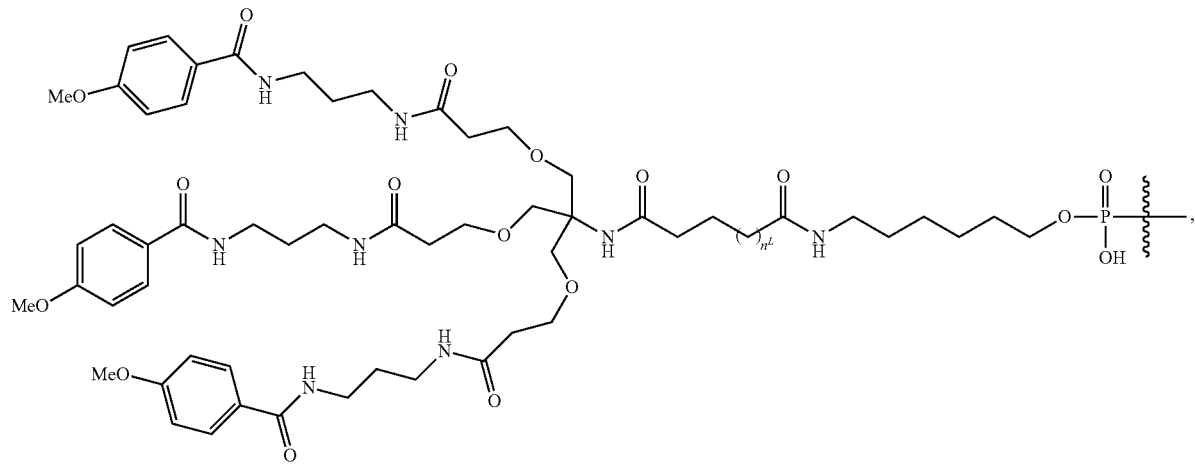
In some embodiments, the moiety and the linker, or $(R^D)_b$-$L^{M1}$-$L^{M2}$-$L^{M3}$-, is or comprises
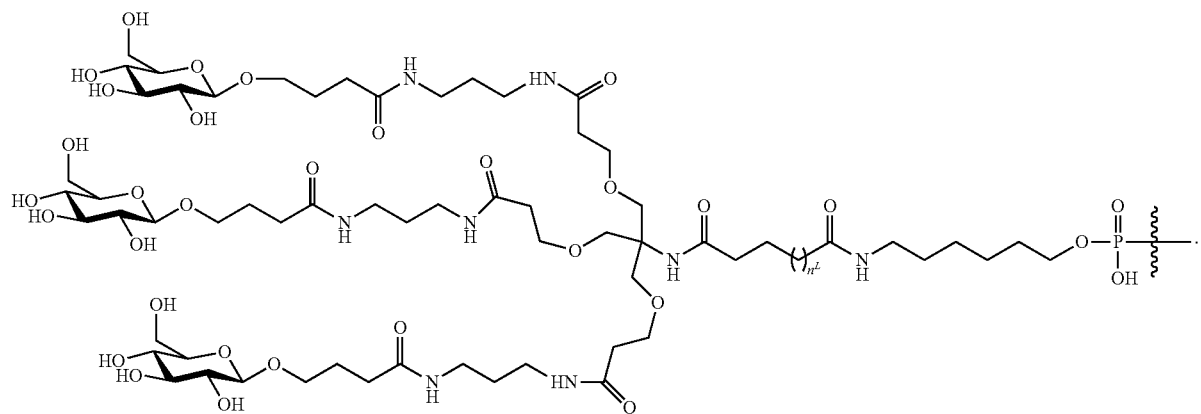

In some embodiments, the moiety and the linker, or $(R^D)_b\text{-}L^{M1}\text{-}L^{M2}\text{-}L^{M3}\text{-}$, is or comprises
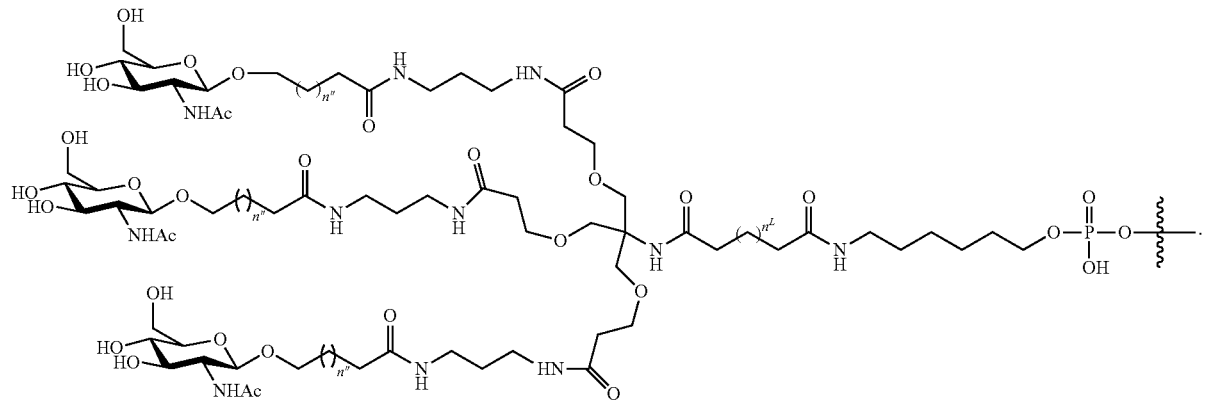
In some embodiments, the linker, or $L^{M1}$, is or comprises
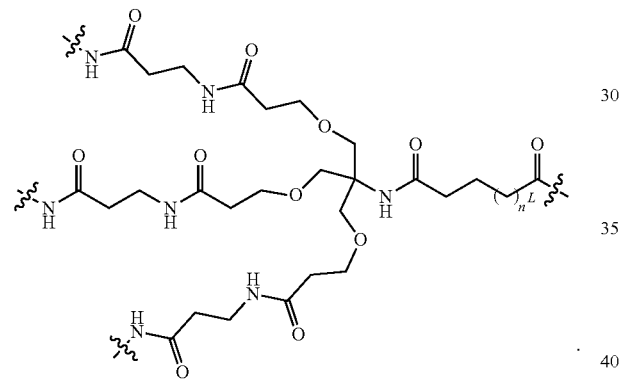
In some embodiments, the moiety and linker, or $(R^D)_b\text{-}L^{M1}\text{-}L^{M2}\text{-}L^{M3}\text{-}$, is or comprises:
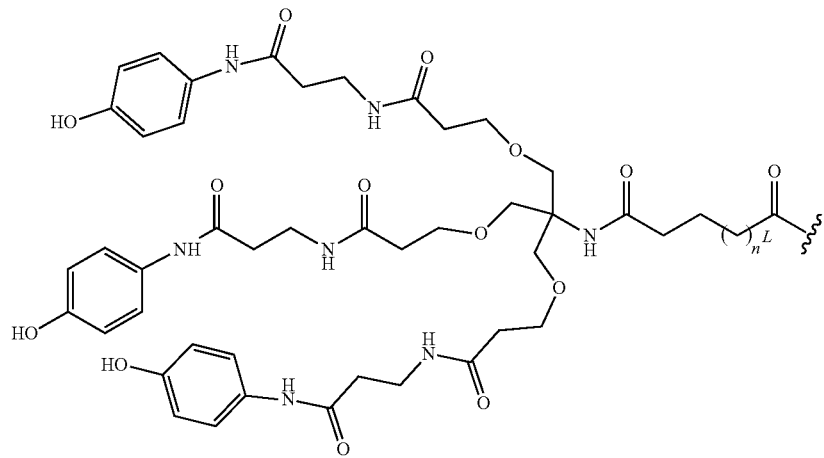

In some embodiments, the moiety and linker, or $(R^D)_b$-$L^{M1}$-$L^{M2}$-$L^{M3}$, is or comprises:

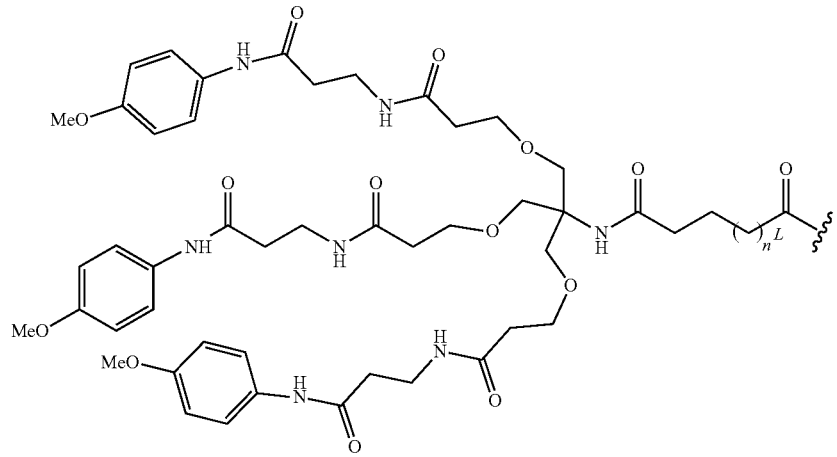

In some embodiments, $n^L$ is 1-8. In some embodiments, $n^L$ is 1, 2, 3, 4, 5, 6, 7, or 8. In some embodiments, $n^L$ is 1. In some embodiments, $n^L$ is 2. In some embodiments, $n^L$ is 3. In some embodiments, $n^L$ is 4. In some embodiments, $n^L$ is 5. In some embodiments, $n^L$ is 6. In some embodiments, $n^L$ is 7. In some embodiments, $n^L$ is 8.

In some embodiments, $L^{M2}$ is a covalent bond, or a bivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]—; and one or more carbon atoms are optionally and independently replaced with $Cy^L$. In some embodiments, $L^{M2}$ is a covalent bond, or a bivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, or —P(O)(R')—. In some embodiments, $L^{M2}$ is a covalent bond, or a bivalent, optionally substituted, linear or branched $C_{1-10}$ aliphatic wherein one or more methylene units are optionally and independently replaced with $C_{1-6}$ alkylene, $C_{1-6}$ alkenylene, —C≡C—, —C(R')$_2$—, —O—, —S—, —N(R')— or —C(O)—. In some embodiments, $L^{M2}$ is —NH—(CH$_2$)$_6$—, wherein —NH— is bonded to $L^{M1}$.

In some embodiments, $L^{M3}$ is —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')—, —OP(O)(SR')—, —OP(O)(R')—, —OP(O)(NR')—, —OP(S)(OR')—, —OP(S)(SR')—, —OP(S)(R')—, —OP(S)(NR')—, —OP(R')—, —OP(OR')—, —OP(SR')—, —OP(NR')—, or —OP(OR')[B(R')$_3$]—. In some embodiments, $L^{M3}$ is —OP(O)(OR')—, or —OP(O)(SR')—, wherein —O— is bonded to $L^{M2}$. In some embodiments, the P atom is connected to a sugar unit, a nucleobase unit, or an internucleotidic linkage. In some embodiments, the P atom is connected to a —OH group through formation of a P—O bond. In some embodiments, the P atom is connected to the 5'-OH group through formation of a P—O bond.

In some embodiments, $L^{M1}$ is a covalent bond. In some embodiments, $L^{M2}$ is a covalent bond. In some embodiments, $L^{M3}$ is a covalent bond. In some embodiments, $L^{M1}$ is $L^{M2}$ as described in the present disclosure. In some embodiments, $L^{M1}$ is $L^{M3}$ as described in the present disclosure. In some embodiments, $L^{M2}$ is $L^{M1}$ as described in the present disclosure. In some embodiments, $L^{M2}$ is $L^{M3}$ as described in the present disclosure. In some embodiments, $L^{M3}$ is $L^{M1}$ as described in the present disclosure. In some embodiments, $L^{M3}$ is $L^{M2}$ as described in the present disclosure. In some embodiments, $L^{M}$ is $L^{M1}$ as described in the present disclosure. In some embodiments, $L^{M}$ is $L^{M2}$ as described in the present disclosure. In some embodiments, $L^{M}$ is $L^{M3}$ as described in the present disclosure. In some embodiments, $L^{M}$ is $L^{M1}$-$L^{M2}$, wherein each of $L^{M1}$ and $L^{M2}$ is independently as described in the present disclosure. In some embodiments, $L^{M}$ is $L^{M1}$-$L^{M3}$, wherein each of $L^{M1}$ and $L^{M3}$ is independently as described in the present disclosure. In some embodiments, $L^{M}$ is $L^{M2}$-$L^{M3}$, wherein each of $L^{M2}$ and $L^{M3}$ is independently as described in the present disclosure. In some embodiments, $L^{M}$ is $L^{M1}$-$L^{M2}$-$L^{M3}$, wherein each of $L^{M1}$, $L^{M2}$ and $L^{M3}$ is independently as described in the present disclosure.

In some embodiments, each $R^D$ is independently a chemical moiety as described in the present disclosure. In some embodiments, $R^D$ is an additional chemical moiety. In some embodiments, $R^D$ is targeting moiety. In some embodiments, $R^D$ is or comprises a carbohydrate moiety. In some embodiments, $R^D$ is or comprises a lipid moiety. In some embodiments, $R^D$ is or comprises a ligand moiety for, e.g., cell receptors such as a sigma receptor, an asialoglycoprotein receptor, etc. In some embodiments, a ligand moiety is or comprises an anisamide moiety, which may be a ligand moiety for a sigma receptor. In some embodiments, a ligand moiety is or comprises a lipid. In some embodiments, a ligand moiety is or comprises a GalNAc moiety, which may be a ligand moiety for an asialoglycoprotein receptor. In some embodiments, $R^D$ is selected from optionally substituted phenyl,

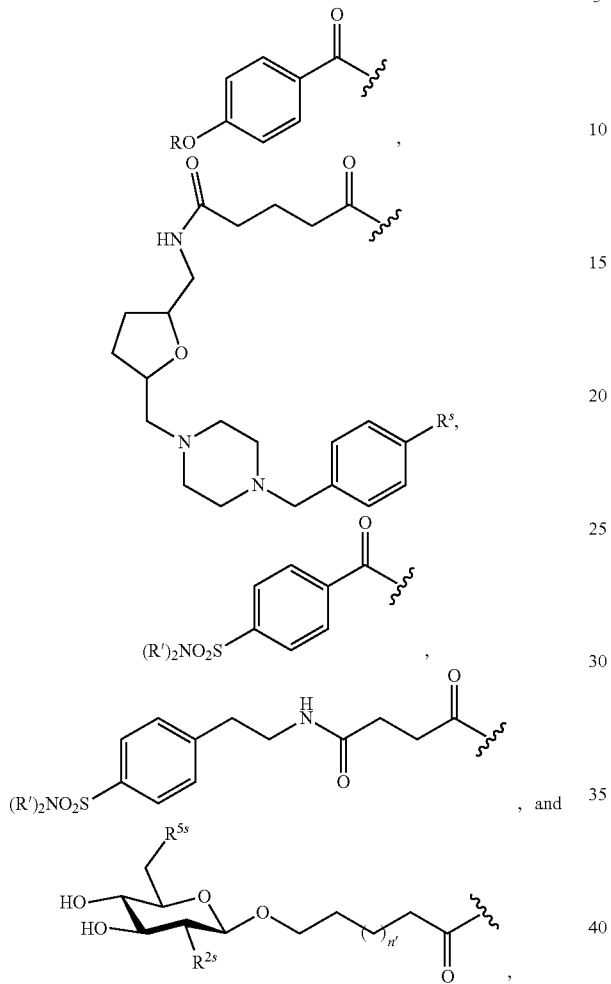

wherein n' is 0 or 1, and each other variable is independently as described in the present disclosure. In some embodiments, $R^s$ is F. In some embodiments, $R^s$ is OMe. In some embodiments, $R^s$ is OH. In some embodiments, $R^s$ is NHAc. In some embodiments, $R^s$ is NHCOCF$_3$. In some embodiments, R' is H. In some embodiments, R is H. In some embodiments, $R^{2s}$ is NHAc, and $R^{5s}$ is OH. In some embodiments, $R^{2s}$ is p-anisoyl, and $R^{5s}$ is OH. In some embodiments, $R^{2s}$ is NHAc and $R^{5s}$ is p-anisoyl. In some embodiments, $R^{2s}$ is OH, and $R^{5s}$ is p-anisoyl. In some embodiments, $R^D$ is selected from

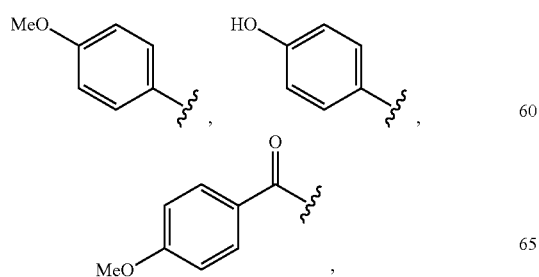

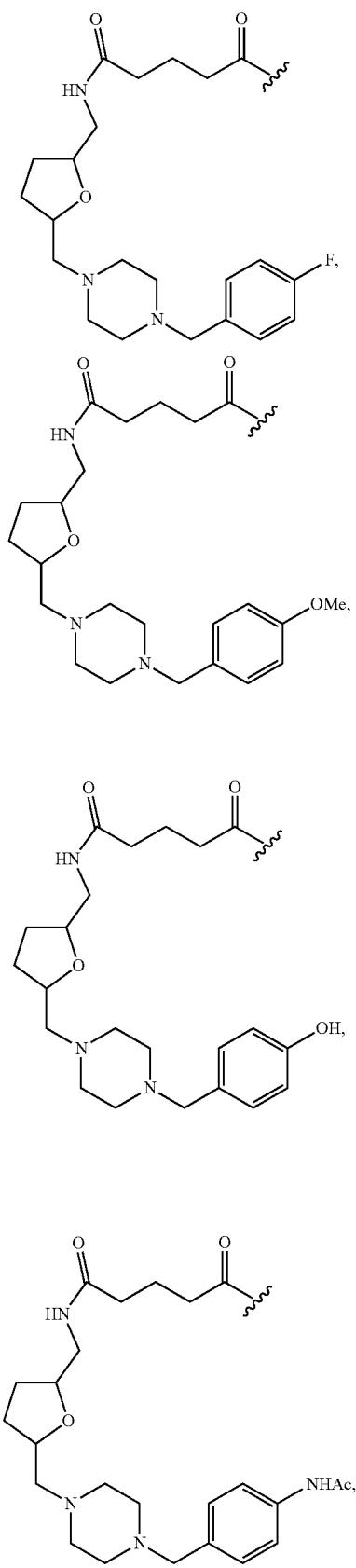

121

-continued

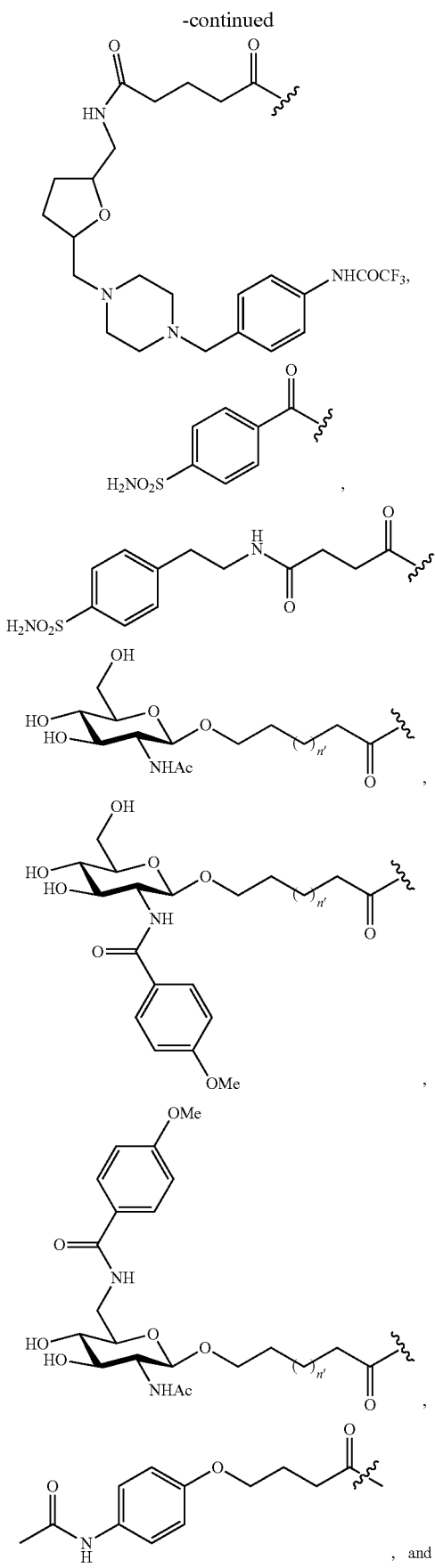

, and

122

-continued

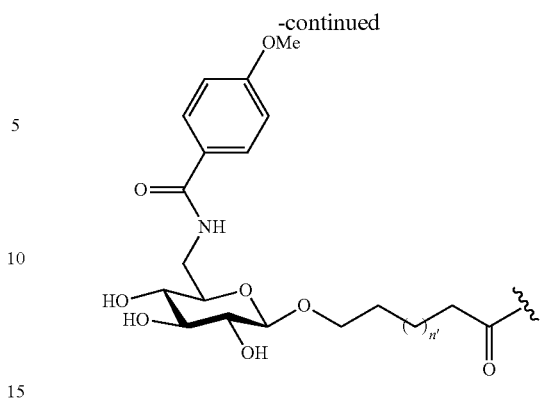

Further embodiments of $R^D$ includes additional chemical moiety embodiments, e.g., those described in the examples.

In some embodiments, n' is 1. In some embodiments, n' is 0.

In some embodiments, n" is 1. In some embodiments, n" is 2.

Lipids

In some embodiments, the present disclosure provides an oligonucleotide composition further comprising an additional chemical moiety, wherein the additional chemical moiety is a lipid. Many lipids can be utilized in provided technologies in accordance with the present disclosure. In some embodiments, a lipid comprises an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein. In some embodiments, a lipid comprises an optionally substituted $C_{10}$-$C_{80}$ saturated or partially unsaturated, aliphatic chain. In some embodiments, a lipid comprises an optionally substituted $C_{10}$-$C_{80}$ linear, saturated or partially unsaturated, aliphatic chain. In some embodiments, a lipid comprises a $C_{10}$-$C_{80}$ linear, saturated or partially unsaturated, aliphatic chain, optionally substituted with one or more $C_{1-4}$ aliphatic group. In some embodiments, a lipid comprises an unsubstituted $C_{10}$-$C_{80}$ linear, saturated or partially unsaturated, aliphatic chain. In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain. In some embodiments, a lipid comprises an optionally substituted $C_{10}$-$C_{80}$ saturated or partially unsaturated, aliphatic chain. In some embodiments, a lipid comprises an optionally substituted $C_{10}$-$C_{80}$ linear, saturated or partially unsaturated, aliphatic chain. In some embodiments, a lipid comprises a $C_{10}$-$C_{80}$ linear, saturated or partially unsaturated, aliphatic chain, optionally substituted with one or more $C_{1-4}$ aliphatic group. In some embodiments, a lipid comprises an unsubstituted $C_{10}$-$C_{80}$ linear, saturated or partially unsaturated, aliphatic chain. In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain. In some embodiments, a lipid comprises an optionally substituted $C_{10}$-$C_{40}$ saturated or partially unsaturated, aliphatic chain. In some embodiments, a lipid comprises an optionally substituted $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, a lipid comprises an unsubstituted $C_{10}$-$C_{40}$ linear, saturated or partially unsaturated, aliphatic chain. In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{40}$ linear, saturated or partially unsaturated, aliphatic chain.

In some embodiments, the additional chemical moiety is a lipid comprising a $C_{10}$-$C_{80}$ linear, saturated or partially unsaturated, aliphatic chain. In some embodiments, the additional chemical moiety is a lipid comprising a $C_{10}$-$C_{80}$ linear, saturated or partially unsaturated, aliphatic chain, optionally substituted with one or more $C_{1-4}$ aliphatic group. In some embodiments, the additional chemical moiety is a lipid comprising a $C_{10}$-$C_{60}$ linear, saturated or partially unsaturated, aliphatic chain. In some embodiments, the additional chemical moiety is a lipid comprising a $C_{10}$-$C_{60}$ linear, saturated or partially unsaturated, aliphatic chain, optionally substituted with one or more $C_{1-4}$ aliphatic group. In some embodiments, the additional chemical moiety is a lipid comprising a $C_{10}$-$C_{40}$ linear, saturated or partially unsaturated, aliphatic chain. In some embodiments, the additional chemical moiety is a lipid comprising a $C_{10}$-$C_{40}$ linear, saturated or partially unsaturated, aliphatic chain, optionally substituted with one or more $C_{1-4}$ aliphatic group.

In some embodiments, the additional chemical moiety is a lipid selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, a lipid has a structure of any of:

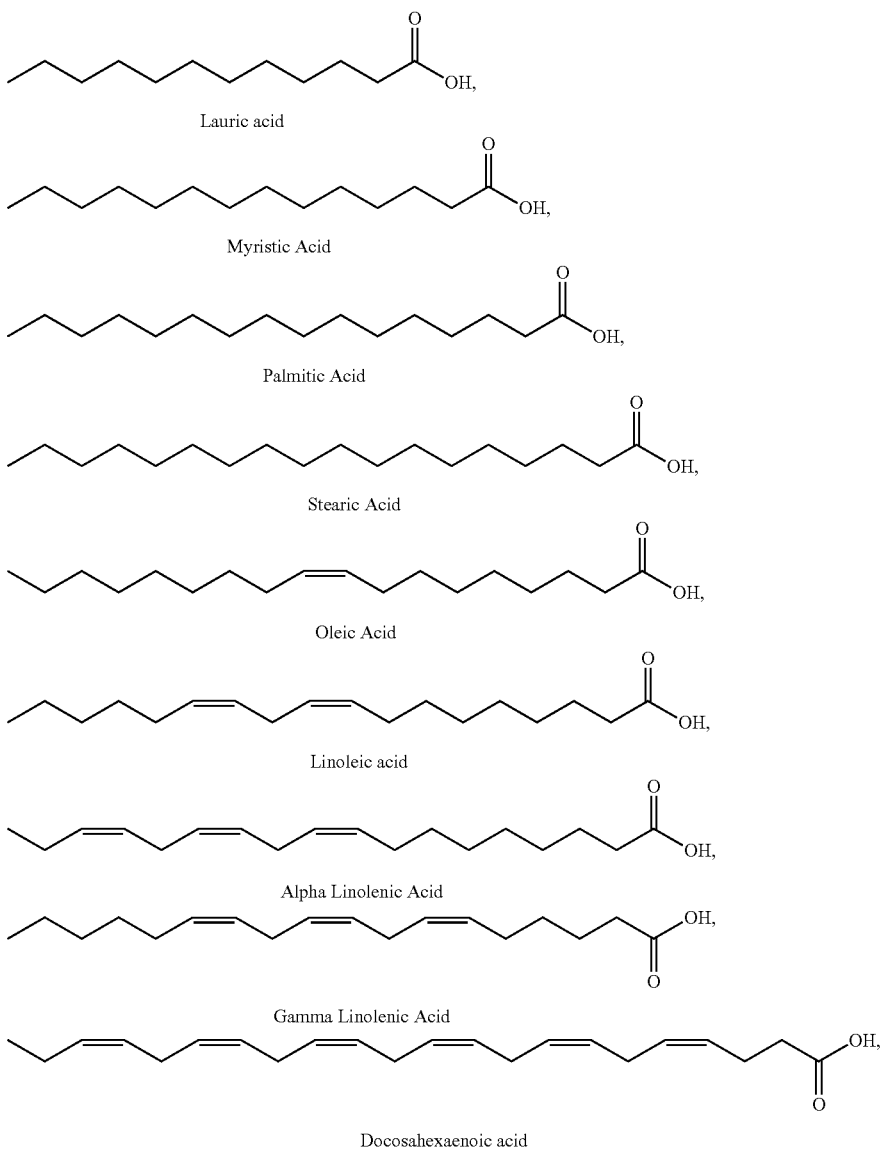

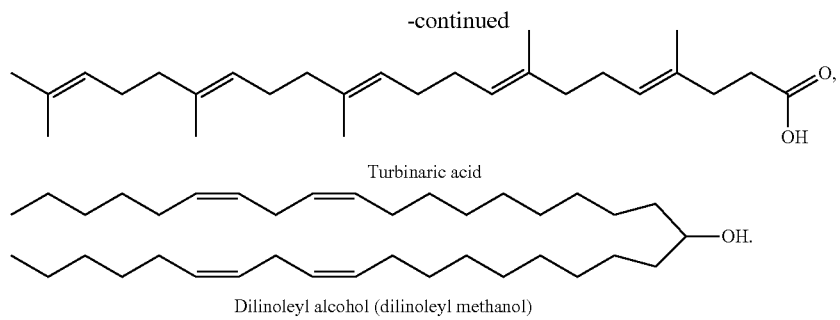

Turbinaric acid

Dilinoleyl alcohol (dilinoleyl methanol)

In some embodiments, a lipid comprises an optionally substituted $C_{10}$-$C_{40}$ saturated or partially unsaturated aliphatic chain. In some embodiments, a lipid comprises an optionally substituted $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, a lipid comprises an unsubstituted $C_{10}$-$C_{40}$ linear, saturated or partially unsaturated, aliphatic chain. In some embodiments, a lipid comprises no more than one optionally substituted $C_{10}$-$C_{40}$ linear, saturated or partially unsaturated, aliphatic chain. In some embodiments, a lipid comprises two or more optionally substituted $C_{10}$-$C_{40}$ linear, saturated or partially unsaturated, aliphatic chain. In some embodiments, a lipid comprises no tricyclic or polycyclic moiety. In some embodiments, a lipid has the structure of $R^1$—COOH, wherein $R^1$ is an optionally substituted $C_{10}$-$C_{40}$ saturated or partially unsaturated aliphatic chain. In some embodiments, a lipid is conjugated through its carboxyl group. In some embodiments, the additional chemical moiety is a lipid. Many lipids can be utilized in provided technologies in accordance with the present disclosure. In some embodiments, a lipid comprises an $R^{LD}$ group, wherein $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein:

each R' is independently —R, —C(O)R, —CO$_2$R, or —SO$_2$R, or:
  two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, a lipid comprises an $R^{LD}$ group, wherein $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein:

each R' is independently —R, —C(O)R, —CO$_2$R, or —SO$_2$R, or:
  two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and —. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and —. In some embodiments, R$^{LD}$ is a hydrocarbon group consisting carbon and hydrogen atoms.

In some embodiments, R$^{LD}$ is an optionally substituted, C$_{10}$-C$_{60}$ saturated or partially unsaturated aliphatic group, wherein one or more methylene units are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R')$_2$—, and —. In some embodiments, R$^{LD}$ is an optionally substituted, C$_{10}$-C$_{60}$ saturated or partially unsaturated aliphatic group, wherein one or more methylene units are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R')$_2$—, and —. In some embodiments, R$^{LD}$ is a hydrocarbon group consisting carbon and hydrogen atoms.

In some embodiments, R$^{LD}$ is an optionally substituted, C$_{10}$-C$_{40}$ saturated or partially unsaturated aliphatic group, wherein one or more methylene units are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R)$_2$—, and —. In some embodiments, R$^{LD}$ is an optionally substituted, C$_{10}$-C$_{60}$ saturated or partially unsaturated aliphatic group, wherein one or more methylene units are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R)$_2$—, and -Cy-. In some embodiments, R$^{LD}$ is a hydrocarbon group consisting carbon and hydrogen atoms.

The aliphatic group of R$^{LD}$ can be a variety of suitable length. In some embodiments, it is C$_{10}$-C$_{80}$. In some embodiments, it is C$_{10}$-C$_{75}$. In some embodiments, it is C$_{10}$-C$_{70}$. In some embodiments, it is C$_{10}$-C$_{65}$. In some embodiments, it is C$_{10}$-C$_{00}$. In some embodiments, it is C$_{10}$-C$_{50}$. In some embodiments, it is C$_{10}$-C$_{40}$. In some embodiments, it is C$_{10}$-C$_{35}$. In some embodiments, it is C$_{10}$-C$_{30}$. In some embodiments, it is C$_{10}$-C$_{25}$. In some embodiments, it is C$_{10}$-C$_{24}$. In some embodiments, it is C$_{10}$-C$_{23}$. In some embodiments, it is C$_{15}$-C$_{22}$. In some embodiments, it is C$_{10}$-C$_{21}$. In some embodiments, it is C$_{12}$-C$_{22}$. In some embodiments, it is C$_{13}$-C$_{22}$. In some embodiments, it is C$_{14}$-C$_{22}$. In some embodiments, it is C$_{15}$-C$_{22}$. In some embodiments, it is C$_{16}$-C$_{22}$. In some embodiments, it is C$_{17}$-C$_{22}$. In some embodiments, it is C$_{18}$-C$_{22}$. In some embodiments, it is C$_{10}$-C$_{20}$. In some embodiments, the lower end of the range is C$_{10}$, C$_{11}$, C$_{12}$, C$_{13}$, C$_{14}$, C$_{15}$, C$_{16}$, C$_{17}$, or Cis. In some embodiments, the higher end of the range is C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, C$_{35}$, C$_{40}$, C$_{45}$, C$_{50}$, C$_{55}$, or C$_{60}$. In some embodiments, it is C$_{10}$. In some embodiments, it is C$_{11}$. In some embodiments, it is C$_{12}$. In some embodiments, it is C$_{13}$. In some embodiments, it is C$_{14}$. In some embodiments, it is C$_{15}$. In some embodiments, it is C$_{16}$. In some embodiments, it is C$_{17}$. In some embodiments, it is C$_{18}$. In some embodiments, it is C$_{19}$. In some embodiments, it is C$_{20}$. In some embodiments, it is C$_{21}$. In some embodiments, it is C$_{22}$. In some embodiments, it is C$_{23}$. In some embodiments, it is C$_{24}$. In some embodiments, it is C$_{25}$. In some embodiments, it is C$_{30}$. In some embodiments, it is C$_{35}$. In some embodiments, it is C$_{40}$. In some embodiments, it is C$_{45}$. In some embodiments, it is C$_{50}$. In some embodiments, it is C$_{55}$. In some embodiments, it is C$_{60}$.

In some embodiments, a lipid comprises no more than one R$^{LD}$ group. In some embodiments, a lipid comprises two or more R$^{LD}$ groups.

In some embodiments, a lipid is conjugated to an oligonucleotide, optionally through a linker, as a moiety comprising an R$^{LD}$ group. In some embodiments, a lipid is conjugated to an oligonucleotide, optionally through a linker, as a moiety comprising no more than one R$^{LD}$ group. In some embodiments, a lipid is conjugated to an oligonucleotide, optionally through a linker, as an R$^{LD}$ group. In some embodiments, a lipid is conjugated to an oligonucleotide, optionally through a linker, as a moiety comprising two or more R$^{LD}$ groups.

In some embodiments, R$^{LD}$ is an optionally substituted, C$_{10}$-C$_{40}$ saturated or partially unsaturated, aliphatic chain. In some embodiments, a lipid comprises an optionally substituted C$_{10}$-C$_{40}$ saturated or partially unsaturated, aliphatic chain.

In some embodiments, R$^{LD}$ is an optionally substituted C$_{10}$-C$_{40}$ linear, saturated or partially unsaturated, aliphatic chain. In some embodiments, a lipid comprises an optionally substituted C$_{10}$-C$_{40}$ linear, saturated or partially unsaturated, aliphatic chain.

In some embodiments, R$^{LD}$ is a C$_{10}$-C$_{40}$ linear, saturated or partially unsaturated, aliphatic chain, optionally substituted with one or more C$_{1-4}$ aliphatic groups. In some embodiments, a lipid comprises a C$_{10}$-C$_{40}$ linear, saturated or partially unsaturated, aliphatic chain, optionally substituted with one or more C$_{1-4}$ aliphatic groups. In some embodiments, R$^{LD}$ is a C$_{10}$-C$_{40}$ linear, saturated or partially unsaturated, aliphatic chain, optionally substituted with one or more C$_{1-2}$ aliphatic groups. In some embodiments, a lipid comprises a C$_{10}$-C$_{40}$ linear, saturated or partially unsaturated, aliphatic chain, optionally substituted with one or more C$_{1-2}$ aliphatic groups. In some embodiments, R$^{LD}$ is a C$_{10}$-C$_{40}$ linear, saturated or partially unsaturated, aliphatic chain, optionally substituted with one or more methyl groups. In some embodiments, a lipid comprises a C$_{10}$-C$_{40}$ linear, saturated or partially unsaturated, aliphatic chain, optionally substituted with one or more methyl groups.

In some embodiments, R$^{LD}$ is an unsubstituted C$_{10}$-C$_{40}$ linear, saturated or partially unsaturated, aliphatic chain. In some embodiments, a lipid comprises an unsubstituted C$_{10}$-C$_{40}$ linear, saturated or partially unsaturated, aliphatic chain.

In some embodiments, a lipid comprises no more than one optionally substituted C$_{10}$-C$_{40}$ linear, saturated or partially unsaturated, aliphatic chain. In some embodiments, a lipid comprises two or more optionally substituted C$_{10}$-C$_{40}$ linear, saturated or partially unsaturated, aliphatic chain.

In some embodiments, R$^{LD}$ is an optionally substituted, C$_{10}$-C$_{60}$ saturated or partially unsaturated, aliphatic chain. In some embodiments, a lipid comprises an optionally substituted C$_{10}$-C$_{60}$ saturated or partially unsaturated, aliphatic chain.

In some embodiments, R$^{LD}$ is an optionally substituted C$_{10}$-C$_{60}$ linear, saturated or partially unsaturated, aliphatic chain. In some embodiments, a lipid comprises an optionally substituted C$_{10}$-C$_{60}$ linear, saturated or partially unsaturated, aliphatic chain.

In some embodiments, R$^{LD}$ is a C$_{10}$-C$_{60}$ linear, saturated or partially unsaturated, aliphatic chain, optionally substituted with one or more C$_{1-4}$ aliphatic groups. In some embodiments, a lipid comprises a C$_{10}$-C$_{60}$ linear, saturated or partially unsaturated, aliphatic chain, optionally substituted with one or more C$_{1-4}$ aliphatic groups. In some embodiments, R$^{LD}$ is a C$_{10}$-C$_{60}$ linear, saturated or partially unsaturated, aliphatic chain, optionally substituted with one or more C$_{1-2}$ aliphatic groups. In some embodiments, a lipid comprises a C$_{10}$-C$_{60}$ linear, saturated or partially unsaturated, aliphatic chain, optionally substituted with one or more $C_{1-2}$ aliphatic groups. In some embodiments, $R^{LD}$ is a $C_{10}$-$C_{60}$ linear, saturated or partially unsaturated, aliphatic chain, optionally substituted with one or more methyl groups. In some embodiments, a lipid comprises a $C_{10}$-$C_{60}$ linear, saturated or partially unsaturated, aliphatic chain, optionally substituted with one or more methyl groups.

In some embodiments, $R^{LD}$ is an unsubstituted $C_{10}$-$C_{60}$ linear, saturated or partially unsaturated, aliphatic chain. In some embodiments, a lipid comprises an unsubstituted $C_{10}$-$C_{60}$ linear, saturated or partially unsaturated, aliphatic chain.

In some embodiments, a lipid comprises no more than one optionally substituted $C_{10}$-$C_{60}$ linear, saturated or partially unsaturated, aliphatic chain. In some embodiments, a lipid comprises two or more optionally substituted $C_{10}$-$C_{60}$ linear, saturated or partially unsaturated, aliphatic chain.

In some embodiments, $R^{LD}$ is an optionally substituted, $C_{10}$-$C_{80}$ saturated or partially unsaturated, aliphatic chain. In some embodiments, a lipid comprises an optionally substituted $C_{10}$-$C_{80}$ saturated or partially unsaturated, aliphatic chain.

In some embodiments, $R^{LD}$ is an optionally substituted $C_{10}$-$C_{80}$ linear, saturated or partially unsaturated, aliphatic chain. In some embodiments, a lipid comprises an optionally substituted $C_{10}$-$C_{80}$ linear, saturated or partially unsaturated, aliphatic chain.

In some embodiments, $R^{LD}$ is a $C_{10}$-$C_{80}$ linear, saturated or partially unsaturated, aliphatic chain, optionally substituted with one or more $C_{1-4}$ aliphatic groups. In some embodiments, a lipid comprises a $C_{10}$-$C_{80}$ linear, saturated or partially unsaturated, aliphatic chain, optionally substituted with one or more $C_{1-4}$ aliphatic groups. In some embodiments, $R^{LD}$ is a $C_{10}$-$C_{80}$ linear, saturated or partially unsaturated, aliphatic chain, optionally substituted with one or more $C_{1-2}$ aliphatic groups. In some embodiments, a lipid comprises a $C_{10}$-$C_{80}$ linear, saturated or partially unsaturated, aliphatic chain, optionally substituted with one or more $C_{1-2}$ aliphatic groups. In some embodiments, $R^{LD}$ is a $C_{10}$-$C_{80}$ linear, saturated or partially unsaturated, aliphatic chain, optionally substituted with one or more methyl groups. In some embodiments, a lipid comprises a $C_{10}$-$C_{80}$ linear, saturated or partially unsaturated, aliphatic chain, optionally substituted with one or more methyl groups.

In some embodiments, $R^{LD}$ is an unsubstituted $C_{10}$-$C_{80}$ linear, saturated or partially unsaturated, aliphatic chain. In some embodiments, a lipid comprises an unsubstituted $C_{10}$-$C_{80}$ linear, saturated or partially unsaturated, aliphatic chain.

In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain.

In some embodiments, $R^{LD}$ is or comprises a $C_{10}$ saturated linear aliphatic chain. In some embodiments, $R^{LD}$ is or comprises a $C_{10}$ partially unsaturated linear aliphatic chain. In some embodiments, $R^{LD}$ is or comprises a $C_{11}$ saturated linear aliphatic chain. In some embodiments, $R^{LD}$ is or comprises a $C_{11}$ partially unsaturated linear aliphatic chain. In some embodiments, $R^{LD}$ is or comprises a $C_{12}$ saturated linear aliphatic chain. In some embodiments, $R^{LD}$ is or comprises a $C_{12}$ partially unsaturated linear aliphatic chain. In some embodiments, $R^{LD}$ is or comprises a $C_{13}$ saturated linear aliphatic chain. In some embodiments, $R^{LD}$ is or comprises a $C_{13}$ partially unsaturated linear aliphatic chain. In some embodiments, $R^{LD}$ is or comprises a $C_{14}$ saturated linear aliphatic chain. In some embodiments, $R^{LD}$ is or comprises a $C_{14}$ partially unsaturated linear aliphatic chain. In some embodiments, $R^{LD}$ is or comprises a $C_{15}$ saturated linear aliphatic chain. In some embodiments, $R^{LD}$ is or comprises a $C_{15}$ partially unsaturated linear aliphatic chain. In some embodiments, $R^{LD}$ is or comprises a $C_{16}$ saturated linear aliphatic chain. In some embodiments, $R^{LD}$ is or comprises a $C_{16}$ partially unsaturated linear aliphatic chain. In some embodiments, $R^{LD}$ is or comprises a $C_{17}$ saturated linear aliphatic chain. In some embodiments, $R^{LD}$ is or comprises a $C_{17}$ partially unsaturated linear aliphatic chain. In some embodiments, $R^{LD}$ is or comprises a $C_{18}$ saturated linear aliphatic chain. In some embodiments, $R^{LD}$ is or comprises a $C_{18}$ partially unsaturated linear aliphatic chain. In some embodiments, $R^{LD}$ is or comprises a $C_{19}$ saturated linear aliphatic chain. In some embodiments, $R^{LD}$ is or comprises a $C_{19}$ partially unsaturated linear aliphatic chain. In some embodiments, $R^{LD}$ is or comprises a $C_{20}$ saturated linear aliphatic chain. In some embodiments, $R^{LD}$ is or comprises a $C_{20}$ partially unsaturated linear aliphatic chain. In some embodiments, $R^{LD}$ is or comprises a $C_{21}$ saturated linear aliphatic chain. In some embodiments, $R^{LD}$ is or comprises a $C_{21}$ partially unsaturated linear aliphatic chain. In some embodiments, $R^{LD}$ is or comprises a $C_{22}$ saturated linear aliphatic chain. In some embodiments, $R^{LD}$ is or comprises a $C_{22}$ partially unsaturated linear aliphatic chain. In some embodiments, $R^{LD}$ is or comprises a $C_{23}$ saturated linear aliphatic chain. In some embodiments, $R^{LD}$ is or comprises a $C_{23}$ partially unsaturated linear aliphatic chain. In some embodiments, $R^{LD}$ is or comprises a $C_{24}$ saturated linear aliphatic chain. In some embodiments, $R^{LD}$ is or comprises a $C_{24}$ partially unsaturated linear aliphatic chain. In some embodiments, $R^{LD}$ is or comprises a $C_{25}$ saturated linear aliphatic chain. In some embodiments, $R^{LD}$ is or comprises a $C_{25}$ partially unsaturated linear aliphatic chain. In some embodiments, $R^{LD}$ is or comprises a $C_{26}$ saturated linear aliphatic chain. In some embodiments, $R^{LD}$ is or comprises a $C_{26}$ partially unsaturated linear aliphatic chain. In some embodiments, $R^{LD}$ is or comprises a $C_{27}$ saturated linear aliphatic chain. In some embodiments, $R^{LD}$ is or comprises a $C_{27}$ partially unsaturated linear aliphatic chain. In some embodiments, $R^{LD}$ is or comprises a $C_{28}$ saturated linear aliphatic chain. In some embodiments, $R^{LD}$ is or comprises a $C_{28}$ partially unsaturated linear aliphatic chain. In some embodiments, $R^{LD}$ is or comprises a $C_{29}$ saturated linear aliphatic chain. In some embodiments, $R^{LD}$ is or comprises a $C_{29}$ partially unsaturated linear aliphatic chain. In some embodiments, $R^{LD}$ is or comprises a $C_{30}$ saturated linear aliphatic chain. In some embodiments, $R^{LD}$ is or comprises a $C_{30}$ partially unsaturated linear aliphatic chain.

In some embodiments, a lipid has the structure of $R^{LD}$—OH. In some embodiments, a lipid has the structure of $R^{LD}$—C(O)OH. In some embodiments, $R^{LD}$ is

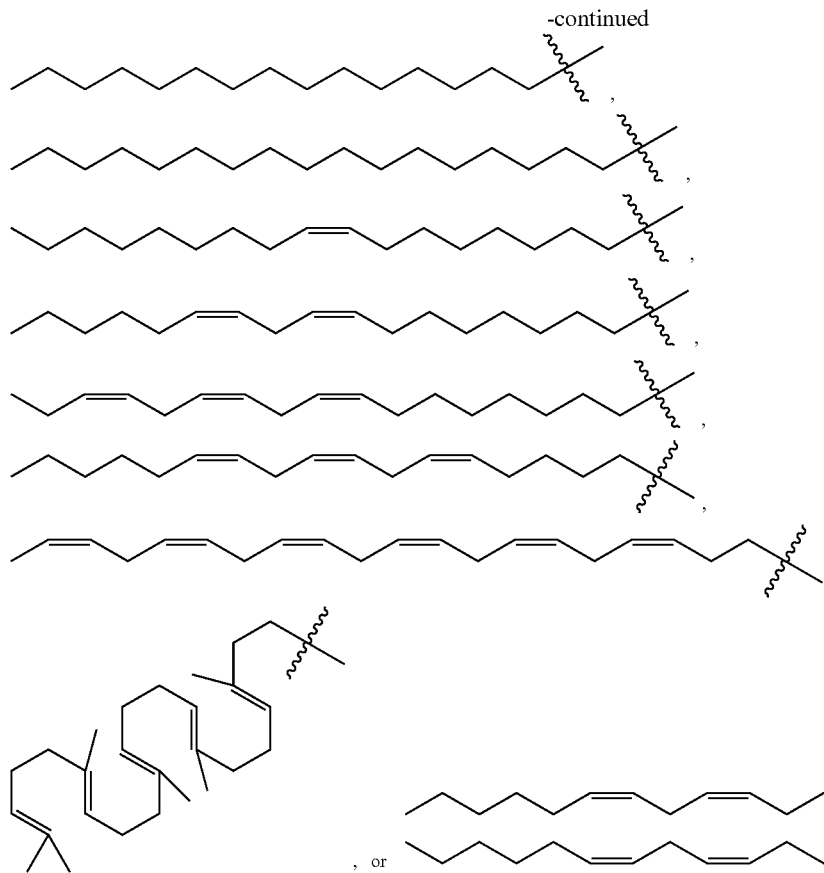

In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, arachidonic acid, and dilinoleyl.

In some embodiments, a lipid is, comprises or consists of any of: an at least partially hydrophobic or amphiphilic molecule, a phospholipid, a triglyceride, a diglyceride, a monoglyceride, a fat-soluble vitamin, a sterol, a fat and a wax. In some embodiments, a lipid is any of: a fatty acid, glycerolipid, glycerophospholipid, sphingolipid, sterol lipid, prenol lipid, saccharolipid, polyketide, and other molecule.

In some embodiments, a lipid is conjugated to an oligonucleotide optionally through a linker moiety. A person having ordinary skill in the art appreciates that various technologies can be utilized to conjugate lipids to an oligonucleotide in accordance with the present disclosure. For example, for lipids comprising carboxyl groups, such lipids can be conjugated through the carboxyl groups.

Lipids can be conjugated to oligonucleotides optionally through linkers. Various types of linkers in the art can be utilized in accordance of the present disclosure. In some embodiments, a linker comprise a phosphate group, which can, for example, be used for conjugating lipids through chemistry similar to those employed in oligonucleotide synthesis. In some embodiments, a linker comprises an amide, ester, or ether group.

In some embodiments, a linker has the structure of -$L^{LD}$-. In some embodiments, $L^{LD}$ is $T^{LD}$ having the structure of

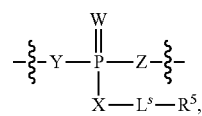

wherein each variable is independently as defined and described. In some embodiments, $T^{LD}$ has the structure of formula I. In some embodiments, $T^{LD}$ with the 5'-O— of an oligonucleotide chain form a phosphorothioate linkage (—OP(O)(S⁻)O—). In some embodiments, $T^{LD}$ with the 5'-O— of an oligonucleotide chain form an Sp phosphorothioate linkage. In some embodiments, $T^{LD}$ with the 5'-O— of an oligonucleotide chain form an Rp phosphorothioate linkage. In some embodiments, $T^{LD}$ with the 5'-O— of an oligonucleotide chain form a phosphate linkage (—OP(O)(O⁻)O—). In some embodiments, $T^{LD}$ with the 5'-O— of an oligonucleotide chain form a phosphorodithioate linkage. In some embodiments, $L^{LD}$ is -L-$T^{LD}$-. In some embodiments, Y connects to -L- and —Z— is a covalent bond, so that P directly connects to a hydroxyl group of the oligonucleotide chain. In some embodiments, P connects to the 5'-end hydroxyl (5'-O—) to form a phosphate group (natural phosphate linkage) or phosphorothioate group (phosphorothioate linkage). In some embodiments, the phosphorothioate linkage is chirally controlled and can be either Rp or Sp. Unless otherwise specified, chiral centers in the linkers (e.g., P in $T^{LD}$) can be either stereorandom or chirally controlled, and they are not considered as part of the backbone chiral centers, e.g., for determining whether a composition is chirally controlled. In some embodiments, $L^{LD}$ is —NH—$(CH_2)_6$-$T^{LD}$-. In some embodiments, $L^{LD}$ is —C(O)—NH—$(CH_2)_6$-$T^{LD}$-.

In some embodiments, a linker has the structure of -L-. In some embodiments, after conjugation to oligonucleotides, a lipid forms a moiety having the structure of -L-$R^{LD}$, wherein each of L and $R^{LD}$ is independently as defined and described herein.

In some embodiments, -L- comprises a bivalent aliphatic chain. In some embodiments, -L- comprises a phosphate group. In some embodiments, -L- comprises a phosphorothioate group. In some embodiments, -L- has the structure of —C(O)NH—$(CH_2)_6$—OP(=O)(S$^-$)—. In some embodiments, -L- has the structure of —C(O)NH—$(CH_2)_6$—OP(=O)(O$^-$)—.

Lipids, optionally through linkers, can be conjugated to oligonucleotides at various suitable locations. In some embodiments, lipids are conjugated through the 5'-OH group. In some embodiments, lipids are conjugated through the 3'-OH group. In some embodiments, lipids are conjugated through one or more sugar moieties. In some embodiments, lipids are conjugated through one or more bases. In some embodiments, lipids are incorporated through one or more internucleotidic linkages. In some embodiments, an oligonucleotide may contain multiple conjugated lipids which are independently conjugated through its 5'-OH, 3'-OH, sugar moieties, base moieties and/or internucleotidic linkages.

In some embodiments, a linker is a moiety that connects two parts of a composition; as a non-limiting example, a linker physically connects an active compound, a provided oligonucleotide (e.g., a SMN2 oligonucleotide), etc., to a lipid. Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group.

In some embodiments, a lipid is conjugated to an active compound, a provided oligonucleotide (e.g., a SMN2 oligonucleotide), etc., optionally through a linker moiety. A person having ordinary skill in the art appreciates that various technologies can be utilized to conjugate lipids to an active compound, a provided oligonucleotide (e.g., a SMN2 oligonucleotide), etc., in accordance with the present disclosure. For example, for lipids comprising carboxyl groups, such lipids can be conjugated through the carboxyl groups. In some embodiments, a lipid is conjugated through a linker having the structure of -L-, wherein L is as defined and described in formula I. In some embodiments, L comprises a phosphate diester or modified phosphate diester moiety. In some embodiments, a compound formed by lipid conjugation has the structure of $(R^{LD}$-L-$)_x$-(an active compound or a provided oligonucleotide (e.g., a SMN2 oligonucleotide), etc.,), wherein x is 1 or an integer greater than 1, and each of $R^{LD}$ and L is independently as defined and described herein. In some embodiments, x is 1. In some embodiments, x is greater than 1. In some embodiments, x is 1-50. In some embodiments, an active compound is an oligonucleotide.

For example, in some embodiments, a conjugate has the following structures:

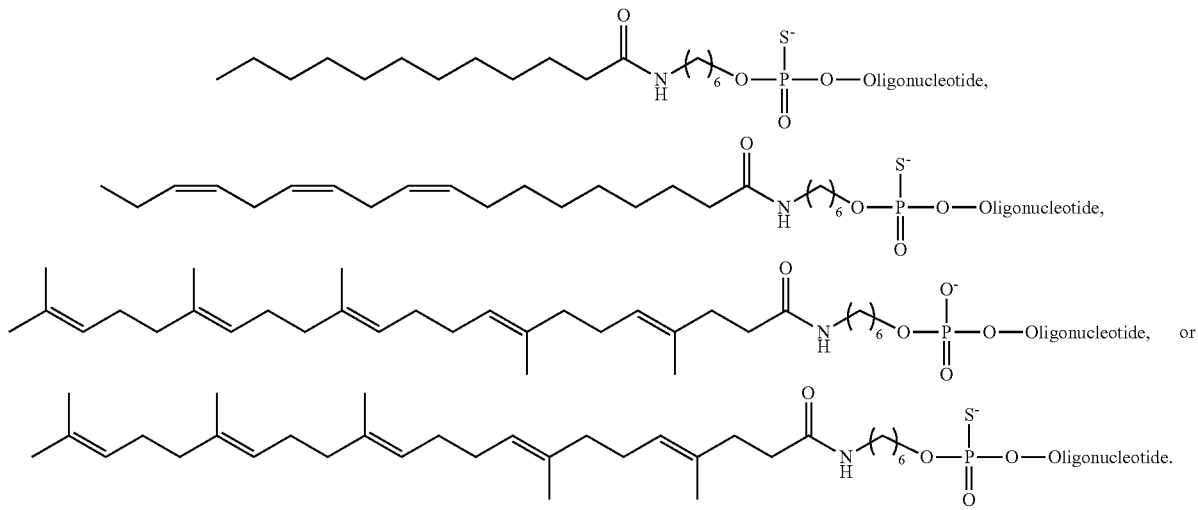

In some embodiments, a linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; and a linker comprising at least one peptide-based cleavage group. In some embodiments, a linker has the structure of -L$^{LD}$-. In some embodiments, a linker has the structure of -L-. In some embodiments, a linker comprises a linkage of formula I. In some embodiments, a linker is —C(O)NH—(CH$_2$)$_6$-L$^I$-, wherein L$^I$ has the structure of formula I as described herein. In some embodiments, a linker is —C(O)NH—(CH$_2$)$_6$—O—P(=O)(SR$^1$)—O—. In some embodiments, R$^1$ is —H, and a linker is —C(O)NH—(CH$_2$)$_6$—O—P(=O)(SH)—O—, in some conditions, e.g., certain pH, —C(O)NH—(CH$_2$)$_6$—O—P(=O)(S$^-$)—O—. In some embodiments, a linker is —C(O)NH—(CH$_2$)$_6$—O—P(=S)(SR$^1$)—O—. In some embodiments, R$^1$ is —H, and a linker is —C(O)NH—(CH$_2$)$_6$—O—P(=S)(SH)—O—, in some conditions, e.g., certain pH, —C(O)NH—(CH$_2$)$_6$—O—P(=S)(S$^-$)—O—. In some embodiments, a linker is —C(O)NH—(CH$_2$)$_6$—O—P(=S)(OR$^1$)—O—, wherein R$^1$ is —CH$_2$CH$_2$CN. In some embodiments, a linker is —C(O)NH—(CH$_2$)$_6$—O—P(=S)(SR$^1$)—O—, wherein R$^1$ is —CH$_2$CH$_2$CN. In some embodiments, a provided oligonucleotide is coupled with a linker and forms a structure of H-linker-oligonucleotide. In some embodiments, a provided oligonucleotide is conjugated to a lipid and forms the structure of lipid-linker-oligonucleotide, e.g., R$^{LD}$-L$^{LD}$-oligonucleotide. In some embodiments, the —O— end of a linker is connected to an oligonucleotide. In some embodiments, the —O— end of a linker is connected to the 5'-end oligonucleotide (—O— being the oxygen in the 5'-OH).

In some embodiments, a linker comprises a PO (phosphodiester linkage), a PS (phosphorothioate linkage) or PS2 (phosphorodithioate linkage). A non-limiting example including a PS linker is shown below. In some embodiments, a linker is —O—P(O)(OH)—O— [phosphodiester], —O—P(O)(SH)—O— [phosphorothioate] or —O—P(S)(SH)—O— [phosphorodithioate]. In some embodiments, a linker comprises a C6 amino moiety (—NH—(CH$_2$)$_6$—), which is illustrated below. In some embodiments, a linker comprises a C6 amino bound to a PO, a PS, or PS2. In some embodiments, a linker is a C6 amino bound to a PO, a PS, or PS2. In some embodiments, a linker, e.g., L$^{LD}$ or L, is —C(O)—NH—(CH$_2$)$_6$—P(O)(OH)—. In some embodiments, a linker, e.g., L$^{LD}$ or L, is —C(O)—NH—(CH$_2$)$_6$—P(O)(OH)—, wherein —C(O)— is connected to a lipid moiety and —P(O)(OH)— is connected to an oligonucleotide chain. In some embodiments, a linker, e.g., L$^{LD}$ or L, is —C(O)—NH—(CH$_2$)$_6$—P(O)(OH)—, wherein —C(O)— is connected to a lipid moiety and —P(O)(OH)— is connected to the 5'-O— of an oligonucleotide chain. In some embodiments, a linker, e.g., L$^{LD}$ or L, is —C(O)—NH—(CH$_2$)$_6$—P(O)(OH)—, wherein —C(O)— is connected to a lipid moiety and —P(O)(OH)— is connected to the 3'-O— of an oligonucleotide chain. In some embodiments, a linker, e.g., L$^{LD}$ or L, is —C(O)—NH—(CH$_2$)$_6$—P(O)(SH)—. In some embodiments, a linker, e.g., L$^{LD}$ or L, is —C(O)—NH—(CH$_2$)$_6$—P(O)(SH)—, wherein —C(O)— is connected to a lipid moiety and —P(O)(SH)— is connected to an oligonucleotide chain. In some embodiments, a linker, e.g., L$^{LD}$ or L, is —C(O)—NH—(CH$_2$)$_6$—P(O)(SH)—, wherein —C(O)— is connected to a lipid moiety and —P(O)(SH)— is connected to the 5'-O— of an oligonucleotide chain. In some embodiments, a linker, e.g., L$^{LD}$ or L, is —C(O)—NH—(CH$_2$)$_6$—P(O)(SH)—, wherein —C(O)— is connected to a lipid moiety and —P(O)(SH)— is connected to the 3'-O— of an oligonucleotide chain. In some embodiments, a linker, e.g., L$^{LD}$ or L, is —C(O)—NH—(CH$_2$)$_6$—P(S)(SH)—. In some embodiments, a linker, e.g., L$^{LD}$ or L, is —C(O)—NH—(CH$_2$)$_6$—P(S)(SH)—, wherein —C(O)— is connected to a lipid moiety and —P(S)(SH)— is connected to an oligonucleotide chain. In some embodiments, a linker, e.g., L$^{LD}$ or L, is —C(O)—NH—(CH$_2$)$_6$—P(S)(SH)—, wherein —C(O)— is connected to a lipid moiety and —P(S)(SH)— is connected to the 5'-O— of an oligonucleotide chain. In some embodiments, a linker, e.g., L$^{LD}$ or L, is —C(O)—NH—(CH$_2$)$_6$—P(S)(SH)—, wherein —C(O)— is connected to a lipid moiety and —P(S)(SH)— is connected to the 3'-O— of an oligonucleotide chain. As appreciated by a person having ordinary skill in the art, at certain pH —P(O)(OH)—, —P(O)(SH)—, —P(S)(SH)— may exist as —P(O)(O$^-$)—, —P(O)(S$^-$)—, —P(S)(S$^-$)—, respectively. In some embodiments, a lipid moiety is R$^{LD}$.

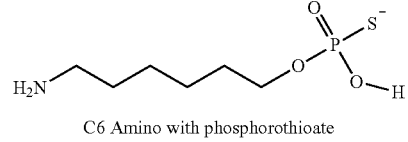

C6 Amino with phosphorothioate

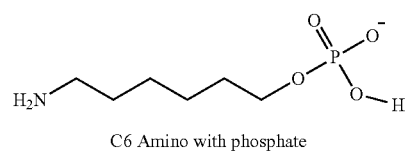

C6 Amino with phosphate

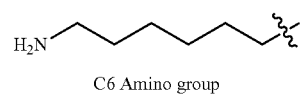

C6 Amino group

Various chemistry and linkers can be used for conjugation in accordance with the present disclosure. For example, lipids, targeting components, etc. can be conjugated to oligonucleotides through linkers using chemistry as described below either on solid phase or in solution phase to prepare certain provided oligonucleotides, for example, as follows:

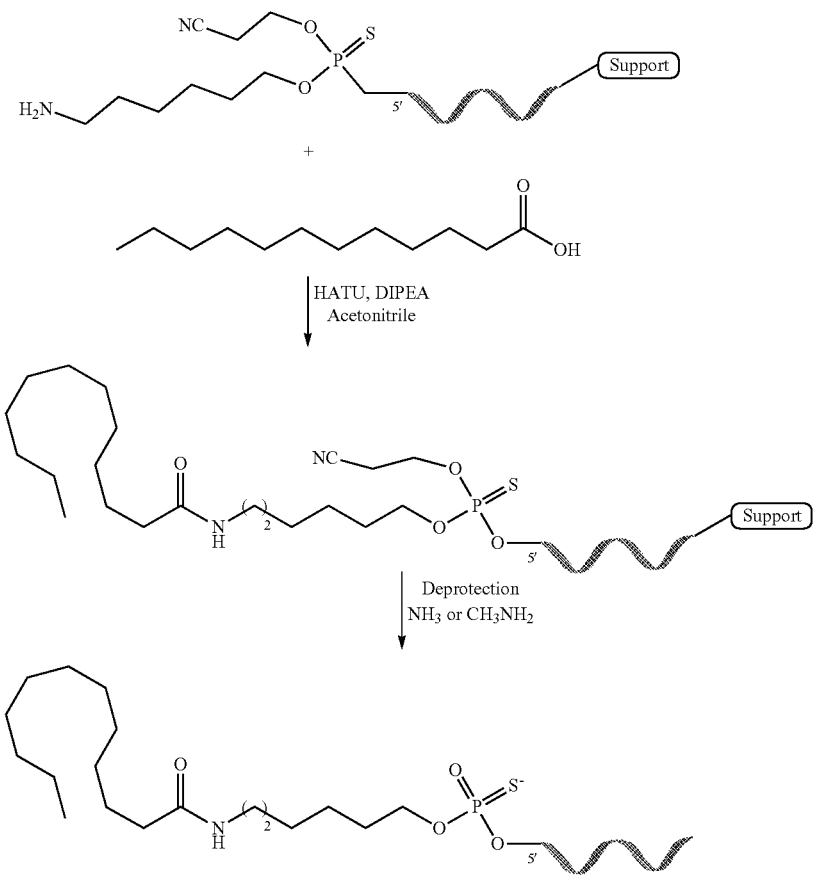

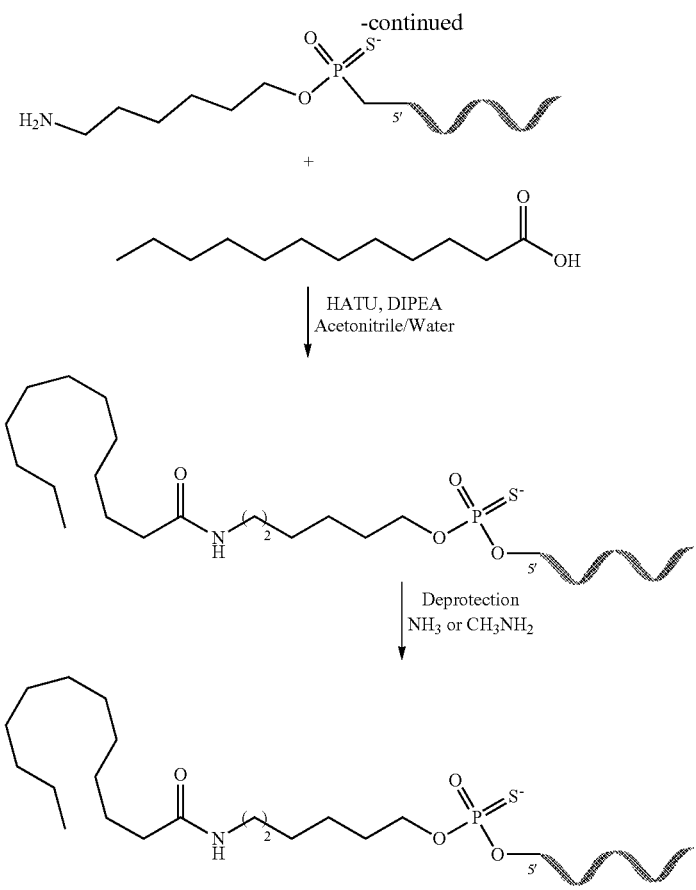

In some embodiments, a provided composition further comprises a targeting component. A targeting component can be either conjugated or not conjugated to a lipid or an oligonucleotide. In some embodiments, a targeting component is conjugated to an oligonucleotide. In some embodiments, an oligonucleotide is conjugated to both a lipid and a targeting component. As described in here, in some embodiments, an oligonucleotide is a provided oligonucleotide. Thus, in some embodiments, a provided oligonucleotide composition further comprises, besides a lipid and oligonucleotides, a target elements. Various targeting components can be used in accordance with the present disclosure, e.g., lipids, antibodies, peptides, carbohydrates, etc. In some embodiments, provided oligonucleotides have the structure of $A^c$-$[L^{LD}$-$(R^{LD})_a]_b$. In some embodiments, provided oligonucleotides have he structure of $[(A^c)_a$-$L^{LD}]_b$-$R^{LD}$. In some embodiments, $L^{LD}$, $R^{LD}$, combinations of $L^{LD}$ and $R^{LD}$, or -$[$-$L^{LD}$-$(R^{LD}))_a]_b$ comprises one or more targeting components.

Targeting moieties can be incorporated into provided technologies through many types of methods in accordance with the present disclosure, for example, those described for lipids and carbohydrates. In some embodiments, targeting moieties are physically mixed with provided oligonucleotide compositions, e.g., chirally controlled oligonucleotide compositions, SMN2 oligonucleotide compositions, etc., to form provided compositions. In some embodiments, a targeting moiety is conjugated to an oligonucleotide. In some embodiments, a targeting moiety is not conjugated to an oligonucleotide.

In some embodiments, provided compositions comprise two or more targeting moieties. In some embodiments, provided oligonucleotide compositions, e.g., chirally controlled oligonucleotide compositions, SMN2 oligonucleotide compositions, etc., comprise two or more conjugated targeting moieties. In some embodiments, the two or more conjugated targeting moieties are the same. In some embodiments, the two or more conjugated targeting moieties are different. In some embodiments, provided oligonucleotide compositions, e.g., chirally controlled oligonucleotide compositions, SMN2 oligonucleotide compositions, etc., comprise no more than one targeting moiety. In some embodiments, oligonucleotides of a provided composition comprise different types of conjugated targeting moieties. In some embodiments, oligonucleotides of a provided composition comprise the same type of targeting moieties.

Targeting moieties can be conjugated to oligonucleotides optionally through linkers, for example, as described for lipids and carbohydrates. Various types of linkers in the art can be utilized in accordance of the present disclosure. In some embodiments, a linker comprises a phosphate group, which can, for example, be used for conjugating targeting moieties through chemistry similar to those employed in oligonucleotide synthesis. In some embodiments, a linker comprises an amide, ester, or ether group. In some embodiments, a linker has the structure of -L-. Targeting moieties can be conjugated through either the same or different linkers compared to lipids.

Targeting moieties, optionally through linkers, can be conjugated to oligonucleotides at various suitable locations. In some embodiments, targeting moieties are conjugated through the 5'-OH group. In some embodiments, targeting moieties are conjugated through the 3'-OH group. In some embodiments, targeting moieties are conjugated through one or more sugar moieties. In some embodiments, targeting moieties are conjugated through one or more bases. In some embodiments, targeting moieties are incorporated through one or more internucleotidic linkages. In some embodiments, an oligonucleotide may contain multiple conjugated targeting moieties which are independently conjugated through its 5'-OH, 3'-OH, sugar moieties, base moieties and/or internucleotidic linkages. Targeting moieties and lipids can be conjugated either at the same, neighboring and/or separated locations. In some embodiments, a targeting moiety is conjugated at one end of an oligonucleotide, and a lipid is conjugated at the other end.

In some embodiments, a targeting moiety interacts with a protein on the surface of targeted cells. In some embodiments, such interaction facilitates internalization into targeted cells. In some embodiments, a targeting moiety comprises a sugar moiety. In some embodiments, a targeting moiety comprises a polypeptide moiety. In some embodiments, a targeting moiety comprises an antibody. In some embodiments, a targeting moiety is an antibody. In some embodiments, a targeting moiety comprises an inhibitor. In some embodiments, a targeting moiety is a moiety from a small molecule inhibitor. In some embodiments, an inhibitor is an inhibitor of a protein on the surface of targeted cells. In some embodiments, an inhibitor is a carbonic anhydrase inhibitor. In some embodiments, an inhibitor is a carbonic anhydrase inhibitor expressed on the surface of target cells. In some embodiments, a carbonic anhydrase is I, II, III, IV, V, VI, VII, VIII, IX, X, XI, XII, XIII, XIV, XV or XVI. In some embodiments, a carbonic anhydrase is membrane bound. In some embodiments, a carbonic anhydrase is IV, IX, XII or XIV. In some embodiments, an inhibitor is for IV, IX, XII and/or XIV. In some embodiments, an inhibitor is a carbonic anhydrase III inhibitor. In some embodiments, an inhibitor is a carbonic anhydrase IV inhibitor. In some embodiments, an inhibitor is a carbonic anhydrase IX inhibitor. In some embodiments, an inhibitor is a carbonic anhydrase XII inhibitor. In some embodiments, an inhibitor is a carbonic anhydrase XIV inhibitor. In some embodiments, an inhibitor comprises or is a sulfonamide (e.g., those described in Supuran, C T. *Nature Rev Drug Discover* 2008, 7, 168-181, which sulfonamides are incorporated herein by reference). In some embodiments, an inhibitor is a sulfonamide. In some embodiments, targeted cells are muscle cells.

In some embodiments, a targeting moiety is $R^{TD}$ wherein $R^{TD}$ is $R^{LD}$ or $R^{CD}$ as described in the present disclosure.

In some embodiments, a targeting component is $R^{LD}$ as defined and described in the present disclosure. In some embodiments, the present disclosure provides oligonucleotides comprising $R^{LD}$. In some embodiments, the present disclosure provides oligonucleotide compositions comprising oligonucleotides comprising $R^{LD}$. In some embodiments, the present disclosure provides oligonucleotide compositions comprising a first plurality of oligonucleotides comprising $R^{LD}$. In some embodiments, the present disclosure provides oligonucleotide compositions, e.g., chirally controlled oligonucleotide compositions, SMN2 oligonucleotide compositions, etc., of oligonucleotides comprising $R^{LD}$. In some embodiments, $R^{LD}$ comprises or is

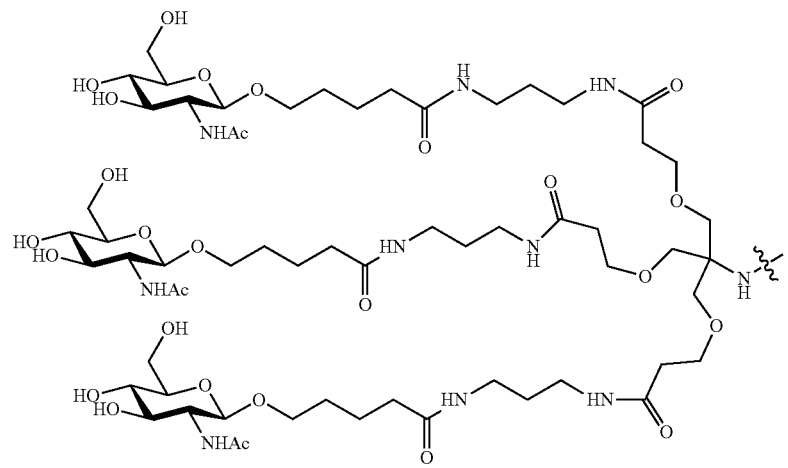

In some embodiments, $R^{LD}$ comprises or is

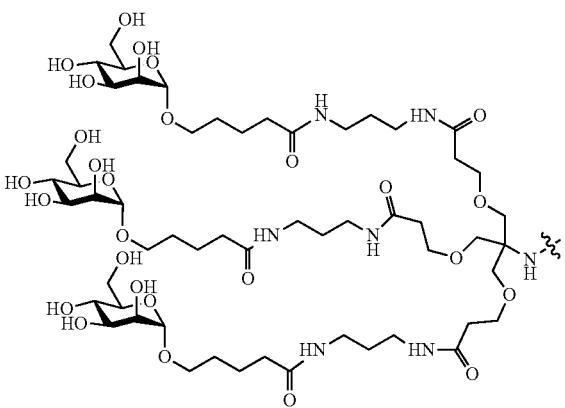

In some embodiments, $R^{LD}$ comprises or is
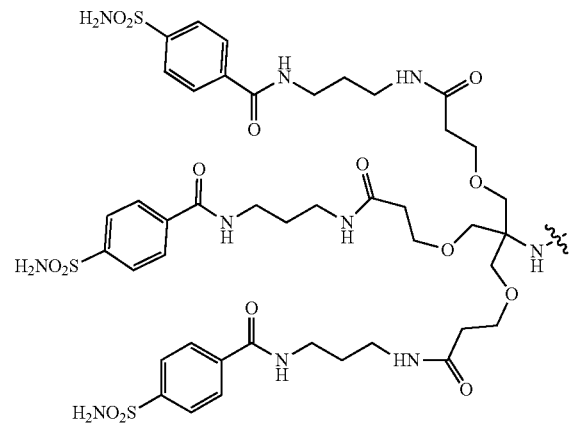
In some embodiments, $R^{LD}$ comprises or is
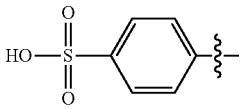
In some embodiments, $R^{LD}$ comprises or is
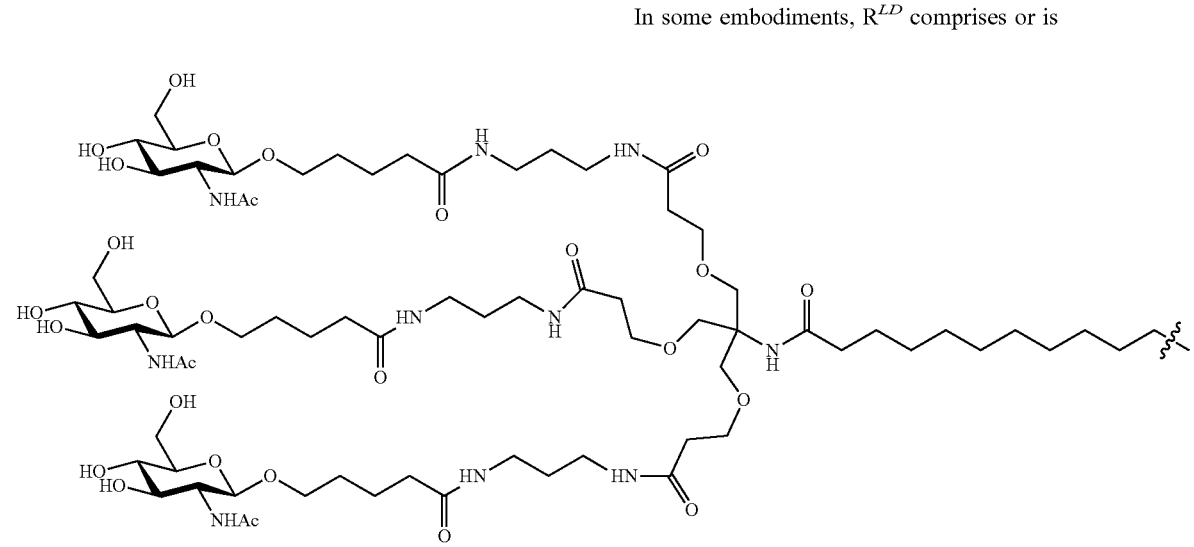
In some embodiments, $R^{LD}$ comprises or is
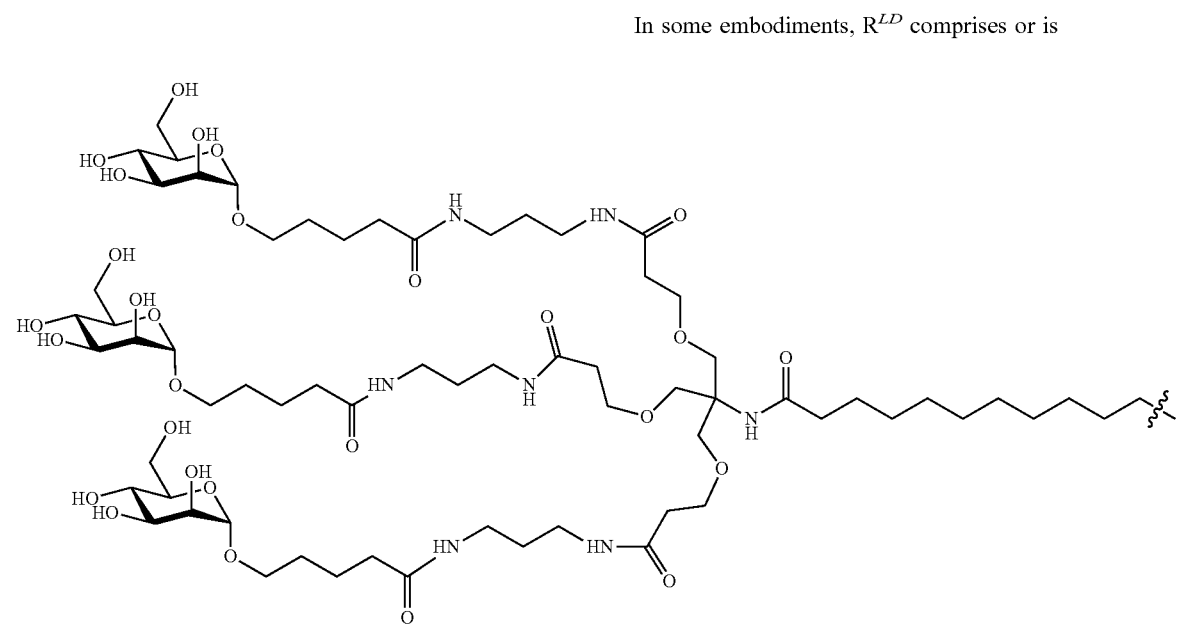

In some embodiments, $R^{LD}$ comprises or is
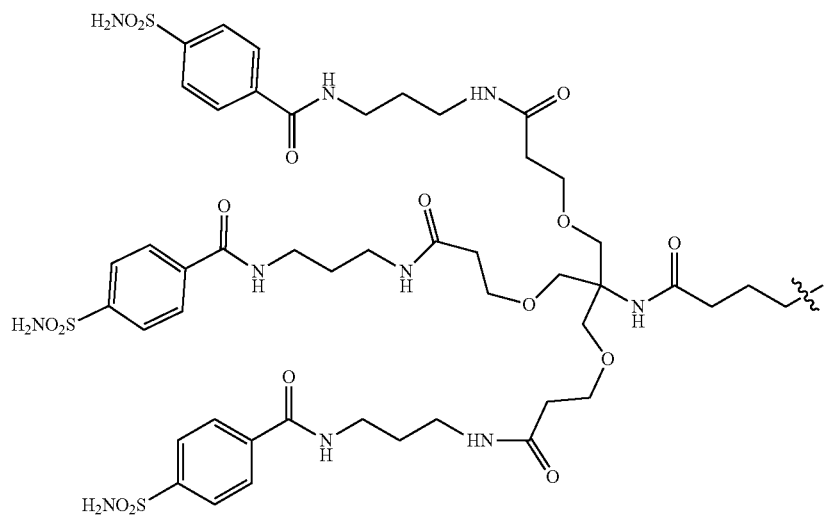
In some embodiments, $R^{LD}$ comprises or is
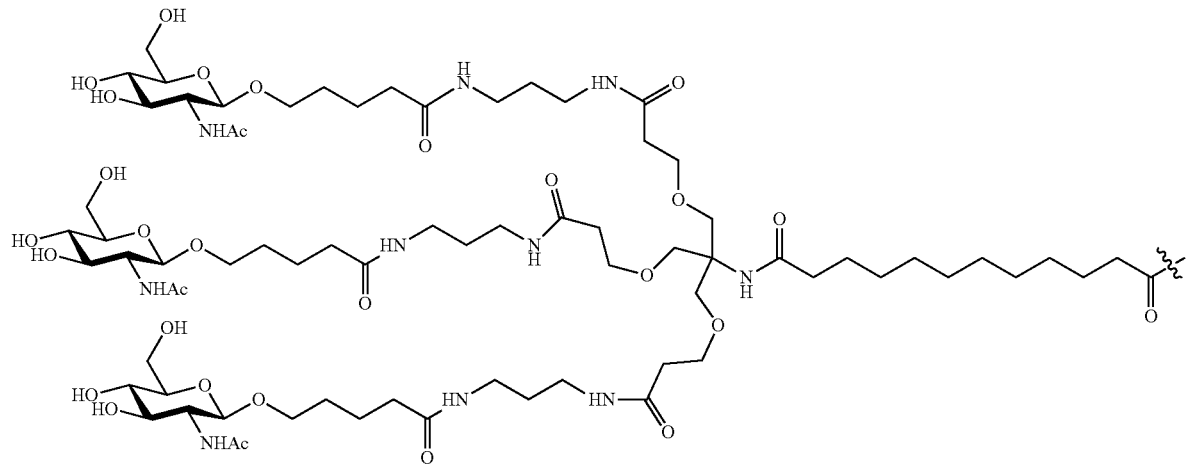
In some embodiments, $R^{LD}$ comprises or is
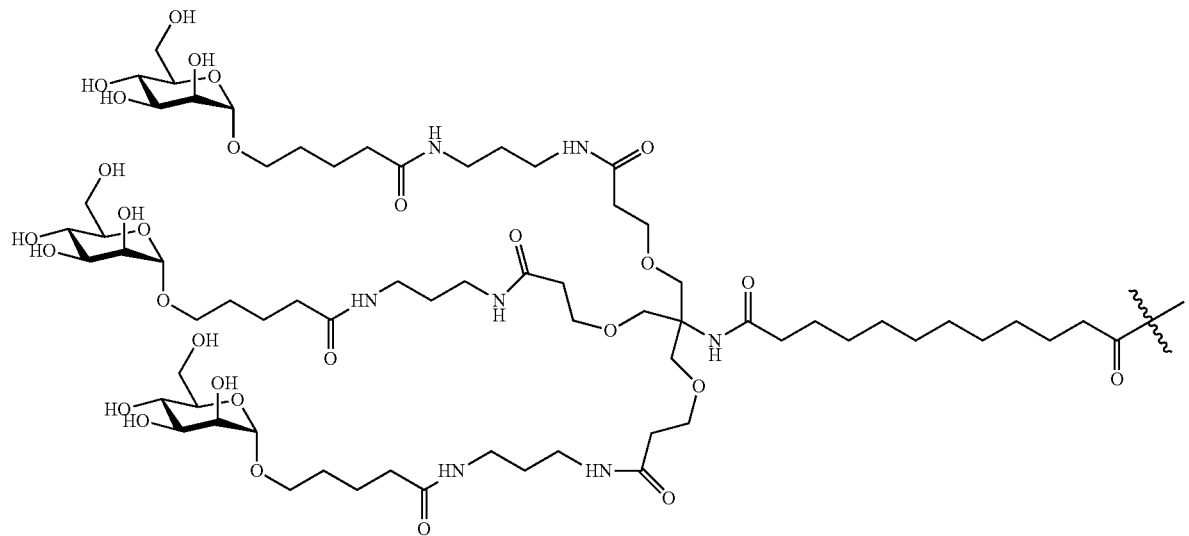

In some embodiments, $R^{LD}$ comprises or is
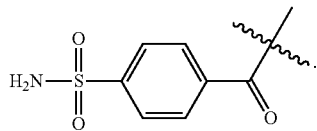 [SMILES: *C(=O)c1ccc(S(N)(=O)=O)cc1]
In some embodiments, $R^{LD}$ comprises or is
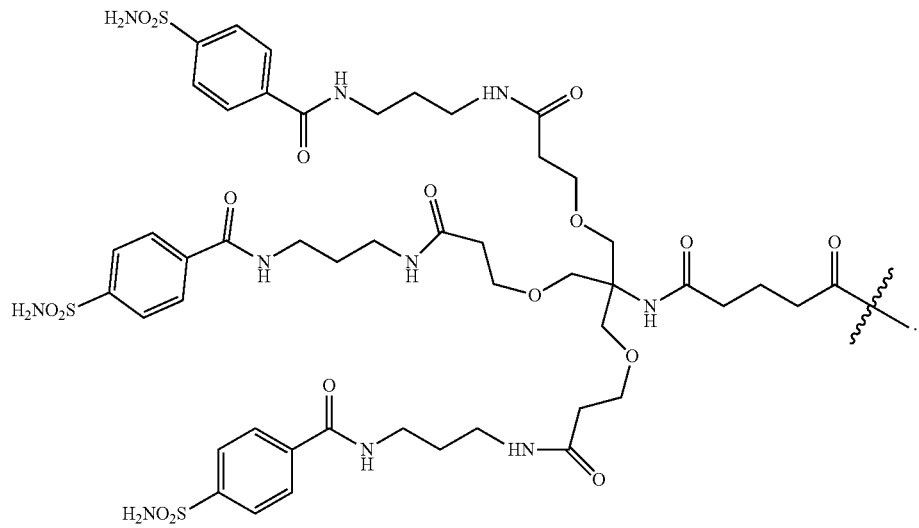 [SMILES: *C(=O)CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
In some embodiments, $R^{LD}$ comprises or is
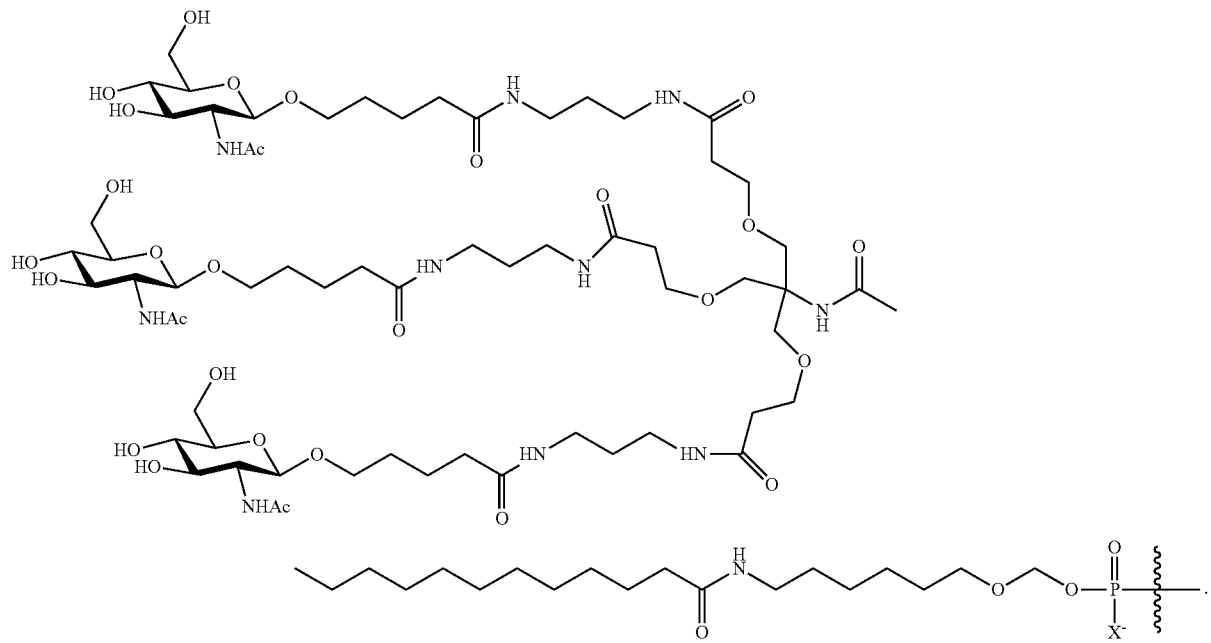
X = O or S In some embodiments, $R^{LD}$ comprises or is
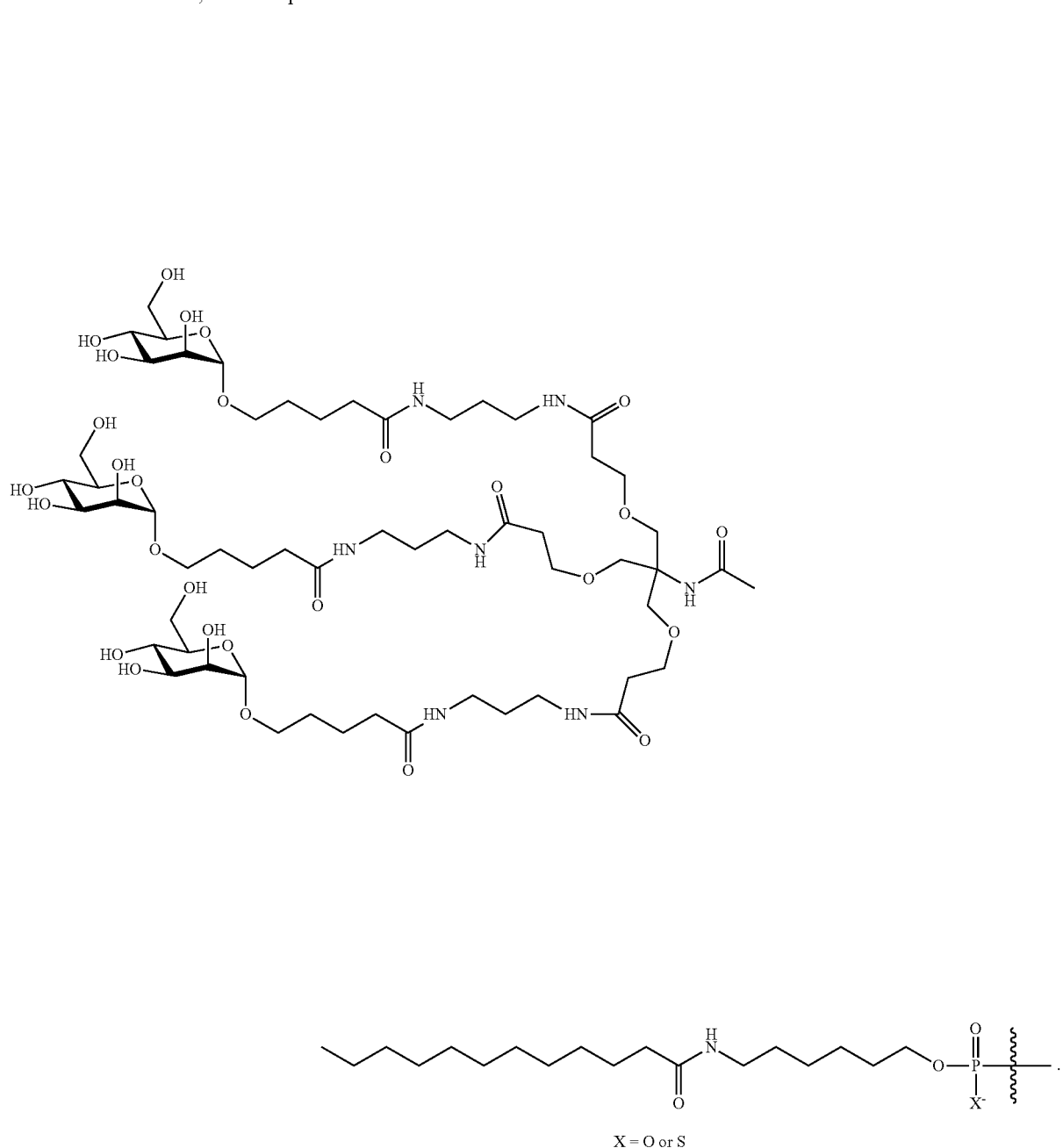
X = O or S
In some embodiments, $R^{LD}$ comprises or is
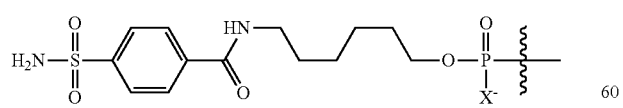
X = O or S.

In some embodiments, $R^{LD}$ comprises or is

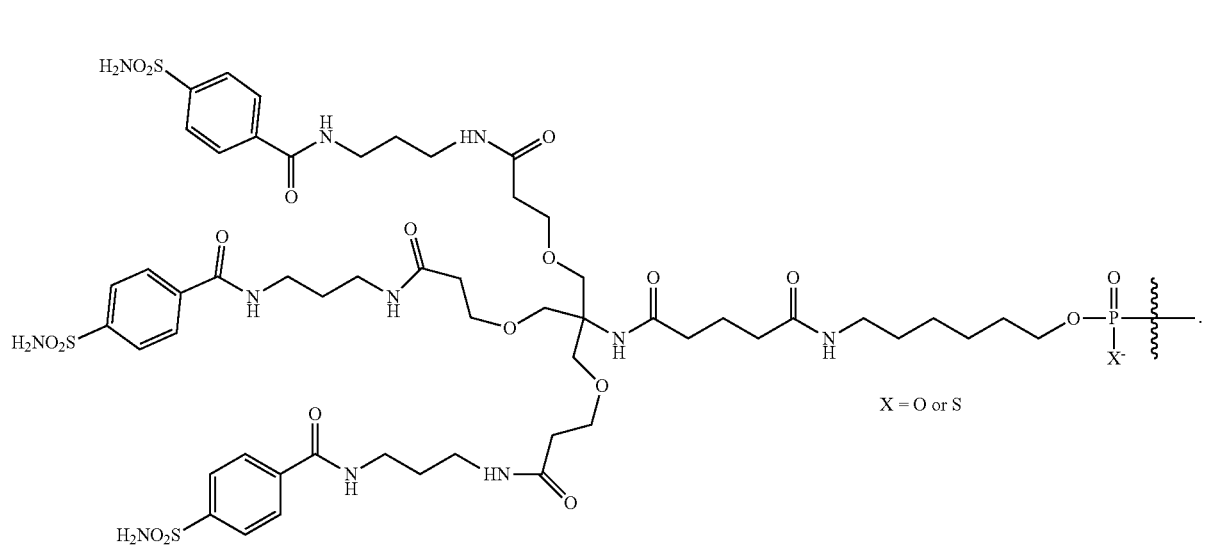

In some embodiments, X is O. In some embodiments, X is S.

In some embodiments, the present disclosure provides technologies (e.g., reagents, methods, etc.) for conjugating various moieties to oligonucleotide chains. In some embodiments, the present disclosure provides technologies for conjugating targeting component to oligonucleotide chains. In some embodiments, the present disclosure provides acids comprising targeting components for conjugation, e.g., $R^{LD}$—COOH. In some embodiments, the present disclosure provides linkers for conjugation, e.g., $L^{LD}$. A person having ordinary skill in the art understands that many known and widely practiced technologies can be utilized for conjugation with oligonucleotide chains in accordance with the present disclosure. In some embodiments, a provided acid is

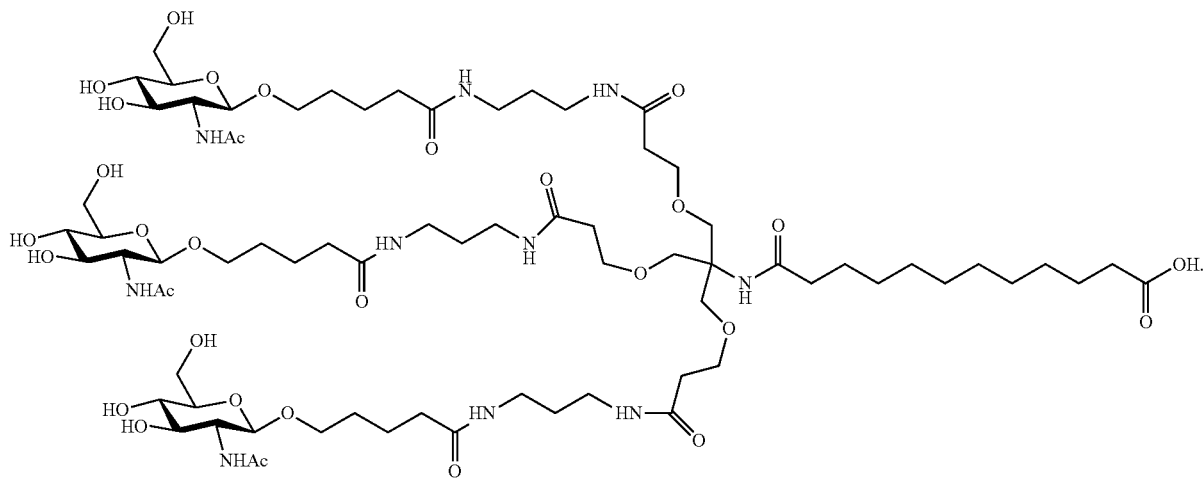

In some embodiments, a provided acid is

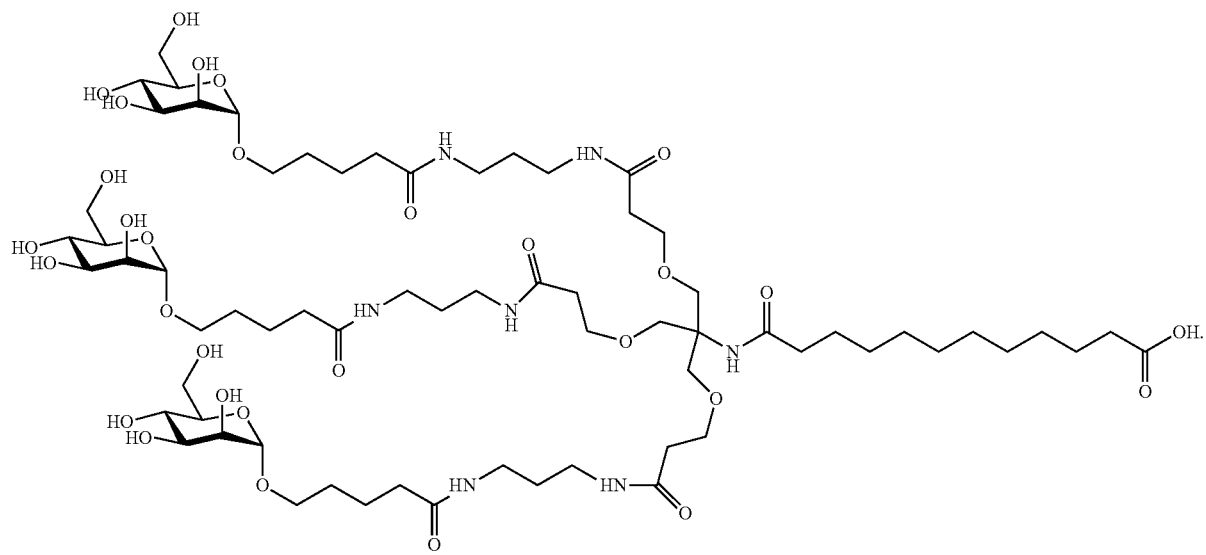

In some embodiments, a provided acid is

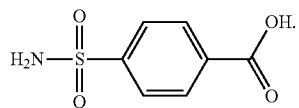

In some embodiments, a provided acid is

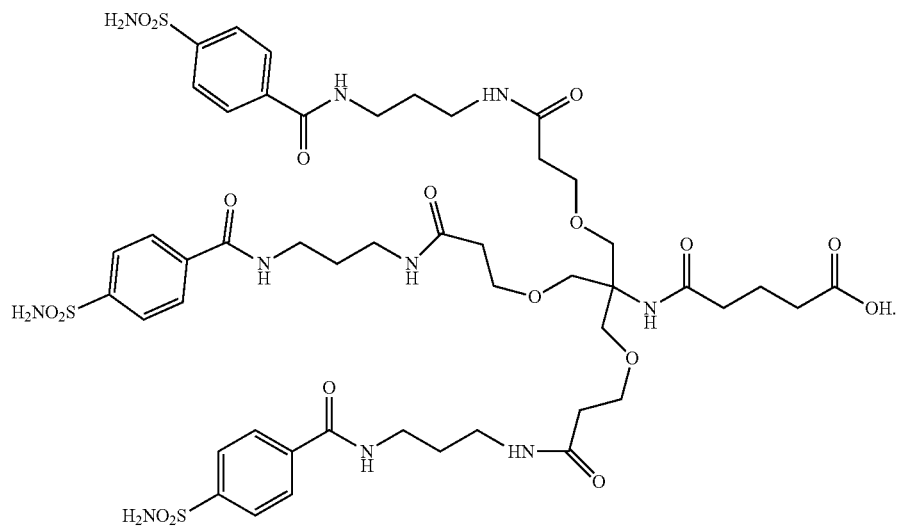 [SMILES: NS(=O)(=O)c1ccc(C(=O)NCCCNC(=O)CCOCC(COCCC(=O)NCCCNC(=O)c2ccc(S(N)(=O)=O)cc2)(COCCC(=O)NCCCNC(=O)c2ccc(S(N)(=O)=O)cc2)NC(=O)CCCC(=O)O)cc1]

In some embodiments, the present disclosure provides methods and reagents for preparing such acids.

In some embodiments, a targeting moiety is $R^{CD}$ as defined and described in the present disclosure. In some embodiments, the present disclosure provides oligonucleotides comprising $R^{CD}$. In some embodiments, the present disclosure provides oligonucleotide compositions comprising oligonucleotides comprising $R^{CD}$. In some embodiments, the present disclosure provides oligonucleotide compositions comprising a first plurality of oligonucleotides comprising $R^{CD}$. In some embodiments, the present disclosure provides oligonucleotide compositions, e.g., chirally controlled oligonucleotide compositions, SMN2 oligonucleotide compositions, etc., of oligonucleotides comprising $R^{CD}$. In some embodiments, oligonucleotides comprising $R^{CD}$ are SMN2 oligonucleotides.

In some embodiments, $R^{TD}$ comprises or is
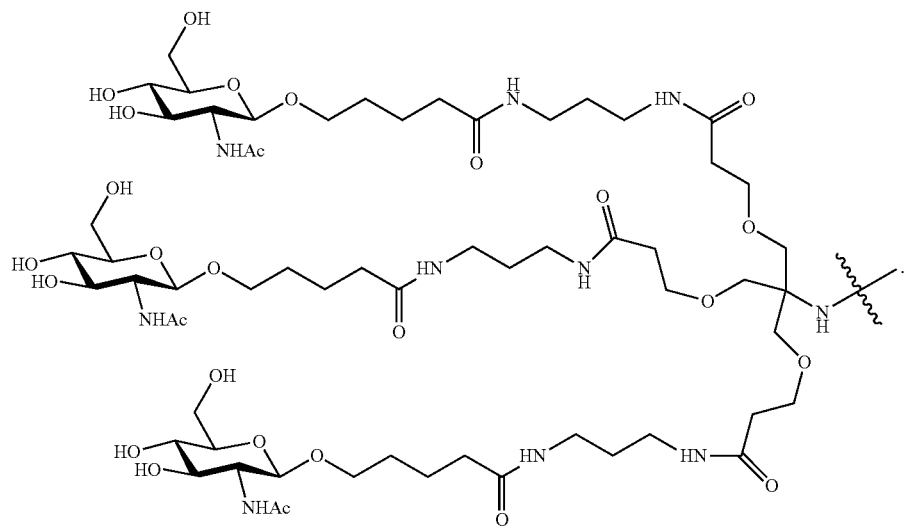
In some embodiments, $R^{TD}$ comprises or is
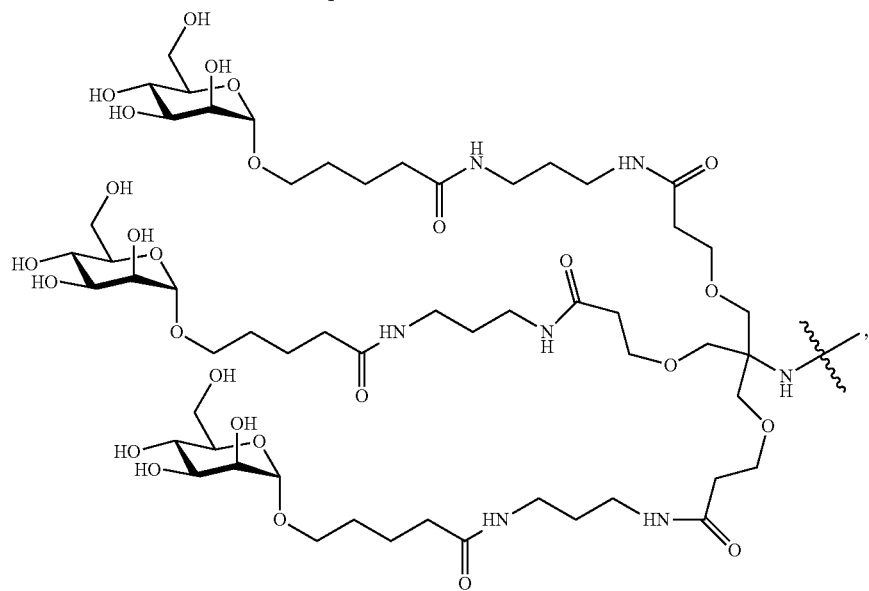
In some embodiments, $R^{TD}$ comprises or is
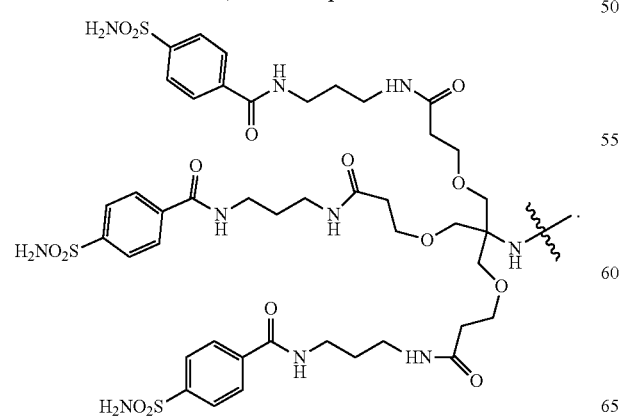

In some embodiments, $R^{TD}$ comprises or is
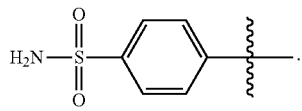 [SMILES: *c1ccc(S(N)(=O)=O)cc1]
In some embodiments, $R^{TD}$ comprises or is
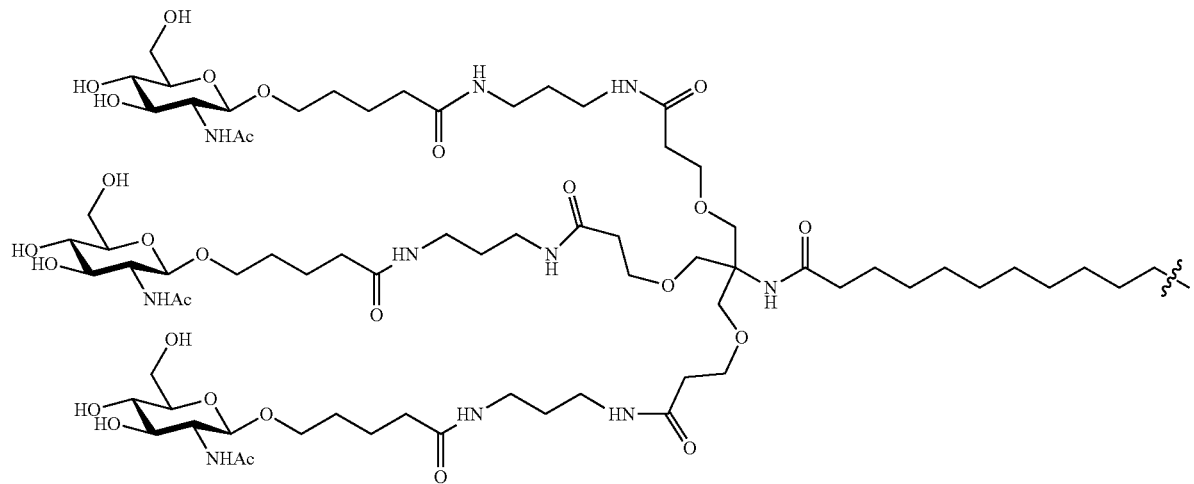
In some embodiments, $R^{TD}$ comprises or is
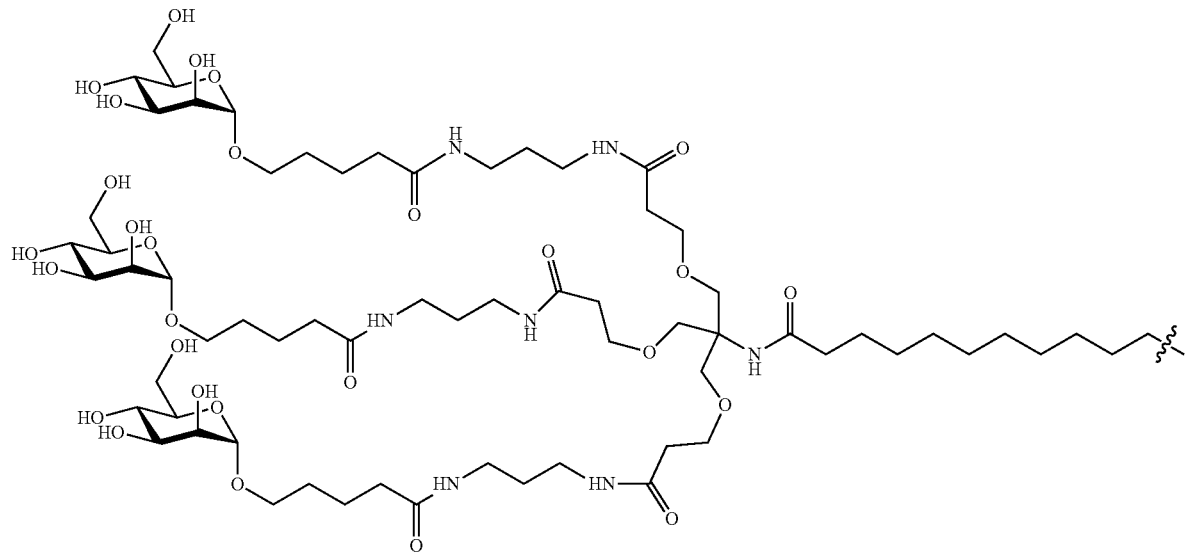

In some embodiments, $R^{TD}$ comprises or is
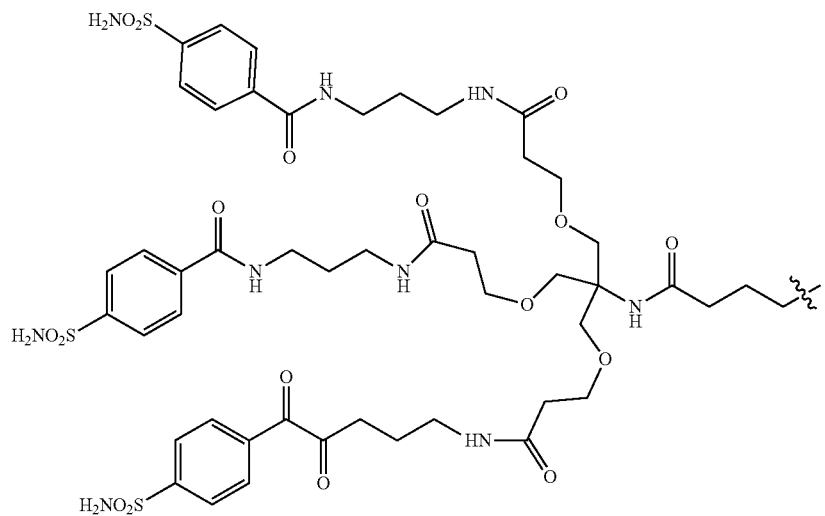
In some embodiments, $R^{TD}$ comprises or is
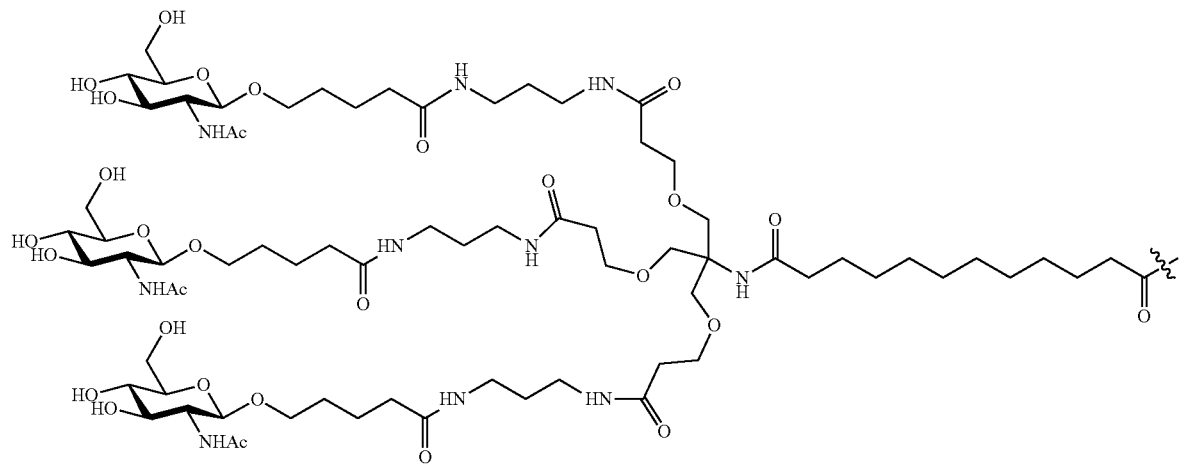
In some embodiments, $R^{TD}$ comprises or is
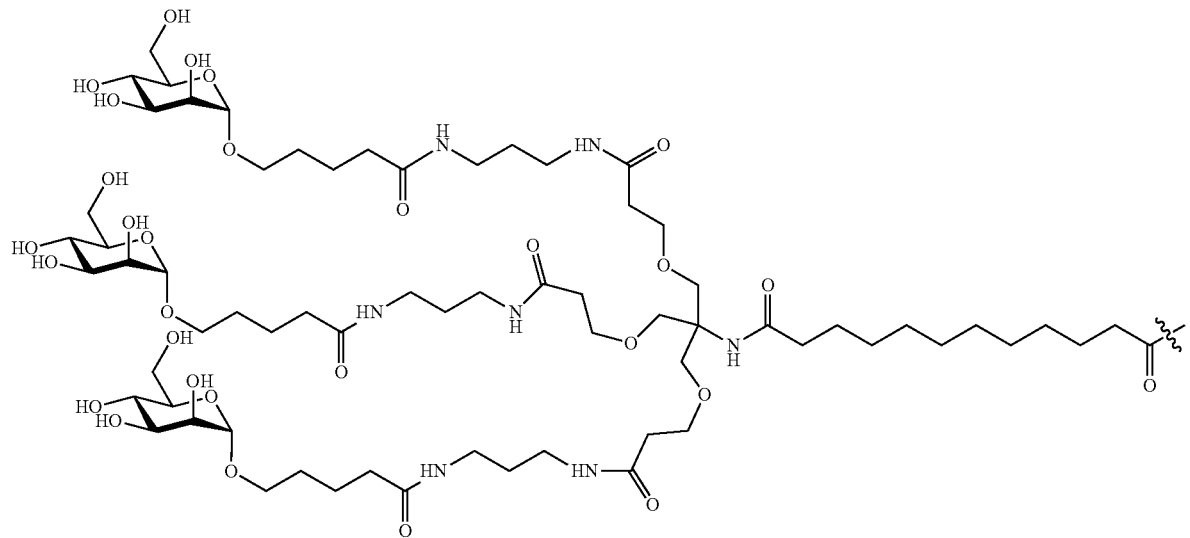

In some embodiments, $R^{TD}$ comprises or is
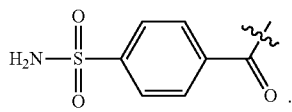     5
.
In some embodiments, $R^{TD}$ comprises or is
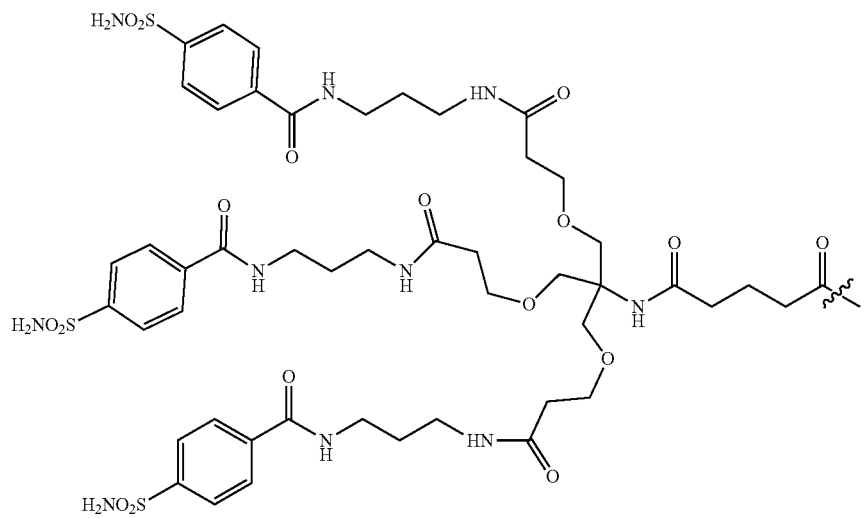
.
In some embodiments, $R^{TD}$ comprises or is
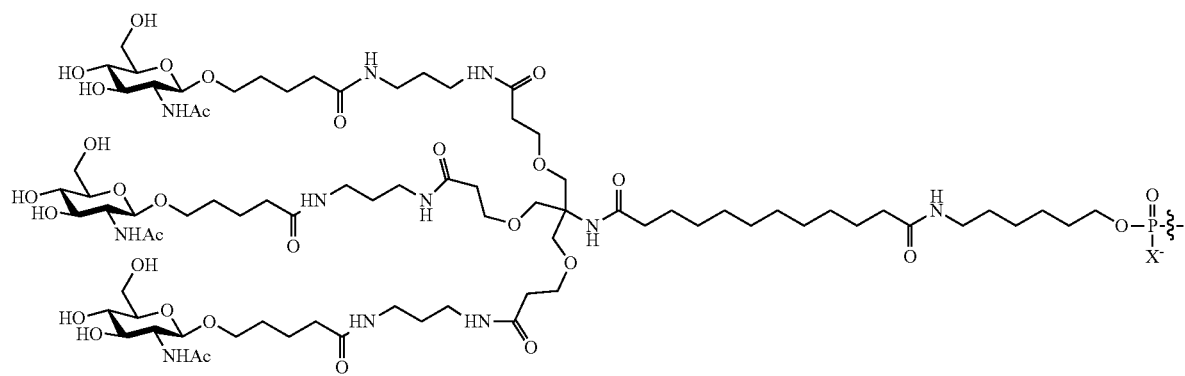
X = O or S
.

In some embodiments, $R^{TD}$ comprises or is

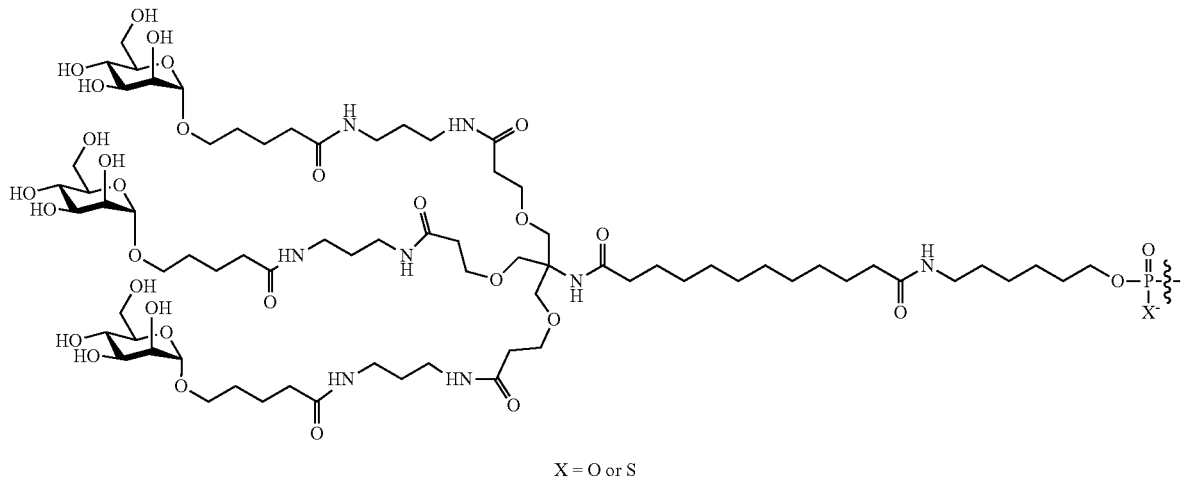

X = O or S

In some embodiments, $R^{TD}$ comprises or is

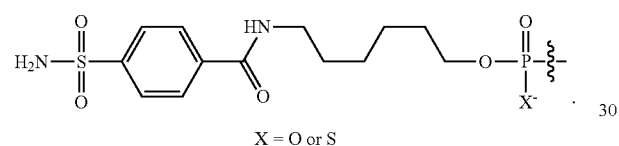

X = O or S

In some embodiments, $R^{TD}$ comprises or is

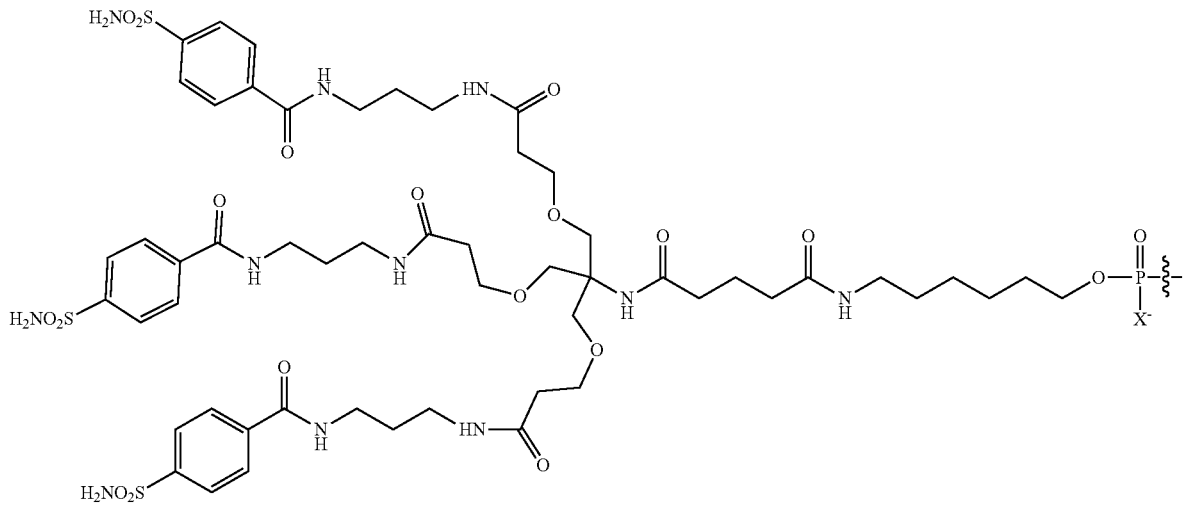

X = O or S

In some embodiments, $R^{TD}$ is a targeting moiety that comprises or is a lipid moiety. In some embodiments, X is O. In some embodiments, X is S.

In some embodiments, the present disclosure provides technologies (e.g., reagents, methods, etc.) for conjugating various moieties to oligonucleotide moieties. In some embodiments, the present disclosure provides technologies for conjugating targeting moiety to oligonucleotide moieties. In some embodiments, the present disclosure provides acids comprising targeting moieties for conjugation, e.g., $R^{LD}$—COOH. In some embodiments, the present disclosure provides linkers for conjugation, e.g., $L^M$. A person having ordinary skill in the art understands that many known and widely practiced technologies can be utilized for conjugation with oligonucleotide moieties in accordance with the present disclosure. In some embodiments, a provided acid is

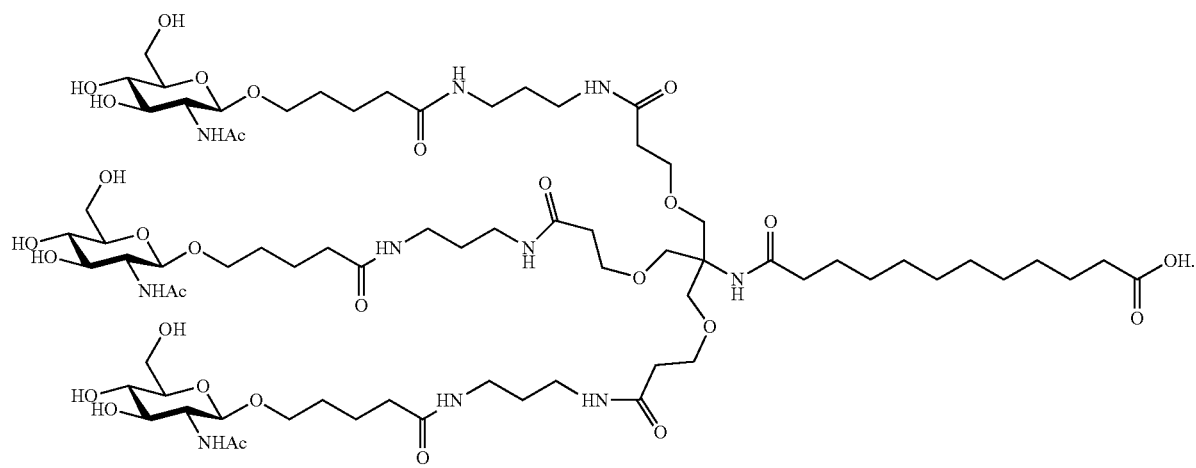
In some embodiments, a provided acid is
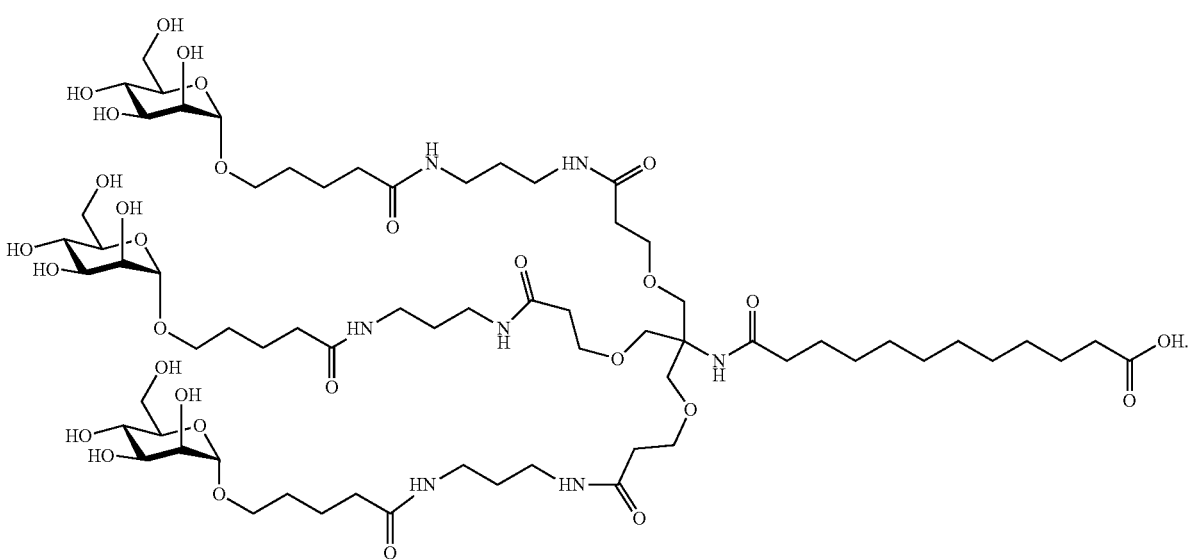
In some embodiments, a provided acid is
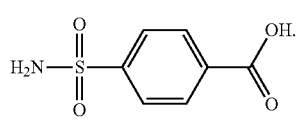 [SMILES: NS(=O)(=O)c1ccc(C(=O)O)cc1]

In some embodiments, a provided acid is

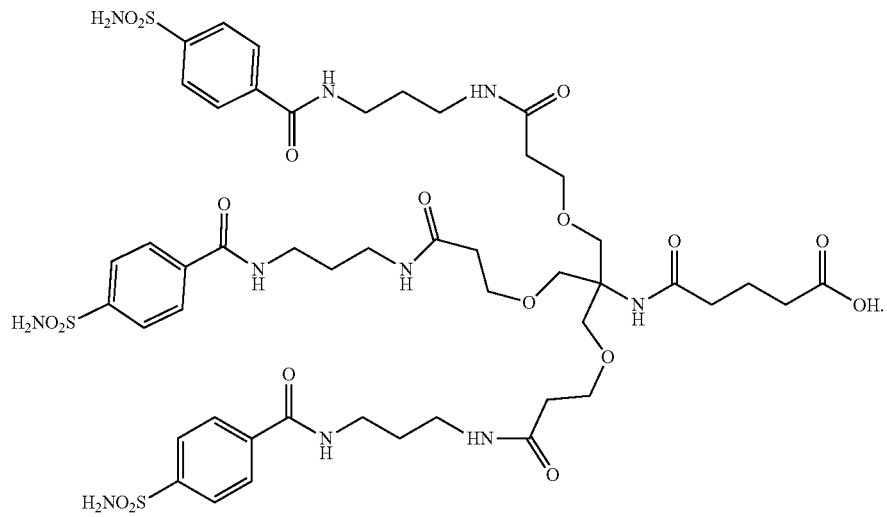

In some embodiments, a provided acid is a fatty acid, which can provide a lipid moiety as a targeting moiety. In some embodiments, the present disclosure provides methods and reagents for preparing such acids.

In some embodiments, provided oligonucleotide compositions, e.g., chirally controlled oligonucleotide compositions, SMN2 oligonucleotide compositions, etc., comprise one or more carbohydrates or carbohydrate moieties. In some embodiments, a carbohydrate moiety is a carbohydrate. In some embodiments, a carbohydrate moiety is or comprises a carbohydrate which is conjugated directly or indirectly to an oligonucleotide. In some embodiments, carbohydrate moieties facilitate targeted delivery of oligonucleotides to desired locations, e.g., cells, tissues, organs, etc. In some embodiments, provided carbohydrate moieties facilitate delivery to liver. As appreciated by a personal having ordinary skill in the art, various carbohydrate moieties are described in the literature and can be utilized in accordance with the present disclosure.

Carbohydrate moieties can be incorporated into oligonucleotides at various locations, for example, sugar units, internucleotidic linkage units, nucleobase units, etc., optionally through one or more bivalent or multivalent (which can be used to connect two or more carbohydrate moieties to oligonucleotides) linkers. In some embodiments, the present disclosure provides technologies for carbohydrate incorporation into oligonucleotides. In some embodiments, the present disclosure provides technologies for incorporating carbohydrate moieties, optionally through one or more linkers, at nucleobase units, as alternative and/or addition to incorporation at internucleotidic linkages and/or sugar units, thereby providing enormous flexibility and/or improved properties and/or activities. In some embodiments, a provided oligonucleotide composition, e.g., a chirally controlled composition, a SMN2 oligonucleotide composition, etc., comprises at least one carbohydrate moiety, optionally through a linker, incorporated into the oligonucleotide at a nucleobase unit.

In some embodiments, an additional chemical moiety is a short peptide, a cell-penetrating peptide, a charged amino acid, or a cationic peptide. In some embodiments, an additional chemical moiety is capable of increasing solubility and/or improving tissue distribution.

In some embodiments, the present disclosure provides oligonucleotide compositions comprising additional chemistry moieties, optionally connected to the oligonucleotide composition moiety through a linker. In some embodiments, the present disclosure provides oligonucleotide compositions comprising $(R^D)_b$-$L^{M1}$-$L^{M2}$-$L^{M3}$-, wherein $(R^D)_b$, $L^{M1}$, $L^{M2}$, and $L^{M3}$ are each as described herein.

In some embodiments, a linker is $L^M$, wherein $L^M$ is a covalent bond, or a bivalent or multivalent, optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy. In some embodiments, $L^M$ is bivalent. In some embodiments, $L^M$ is multivalent. In some embodiments, $L^M$ is

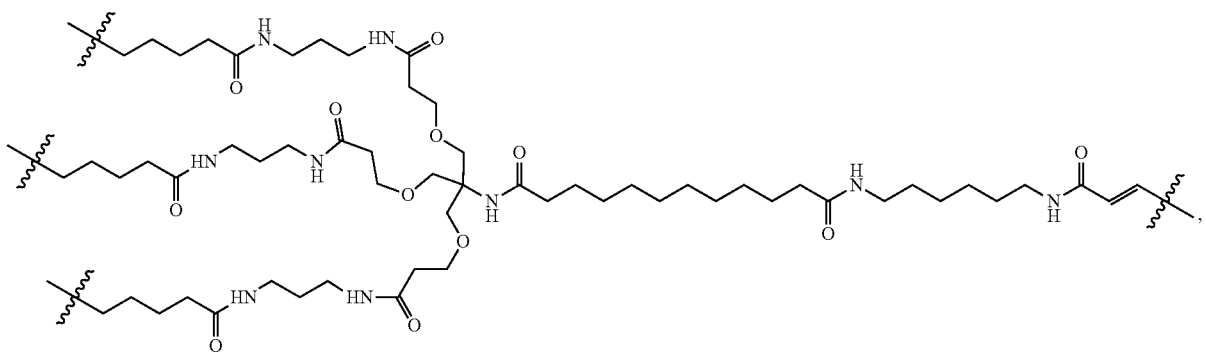
wherein $L^M$ is optionally substituted directly bond to a nucleobase. In some embodiments, $L^M$ is
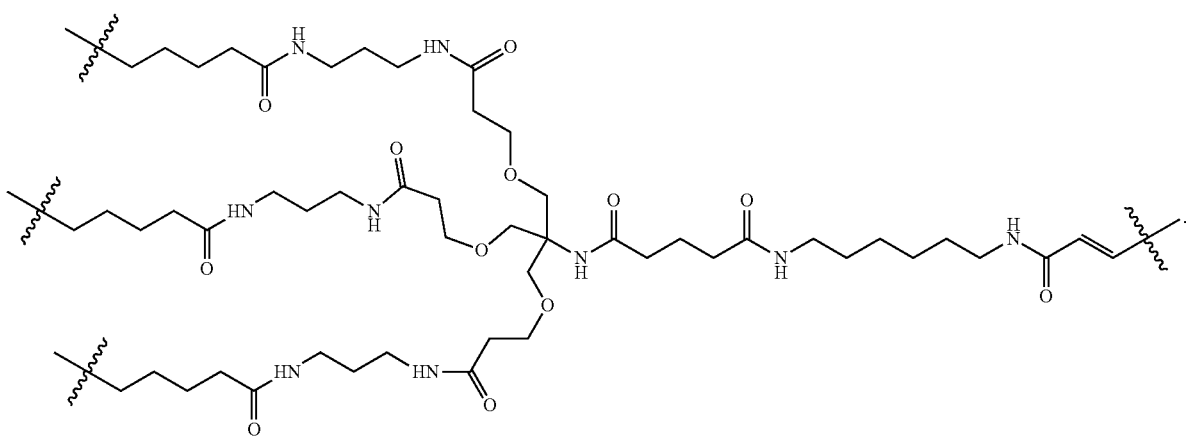 [SMILES: */C=C/C(=O)NCCCCCCNC(=O)CCCC(=O)NC(COCCC(=O)NCCCNC(=O)CCCC*)(COCCC(=O)NCCCNC(=O)CCCC*)COCCC(=O)NCCCNC(=O)CCCC*]
In some embodiments, $L^M$ is
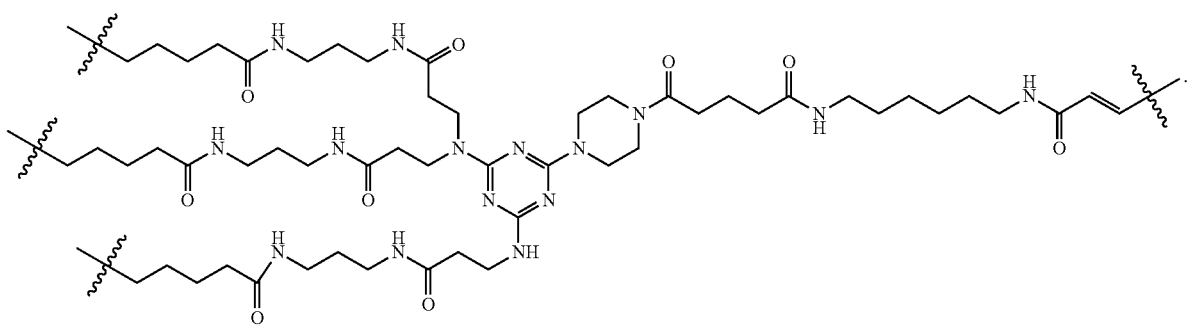 [SMILES: */C=C/C(=O)NCCCCCCNC(=O)CCCC(=O)N1CCN(c2nc(NCCC(=O)NCCCNC(=O)CCCC*)nc(N(CCC(=O)NCCCNC(=O)CCCC*)CCC(=O)NCCCNC(=O)CCCC*)n2)CC1]

In some embodiments, $L^M$ is

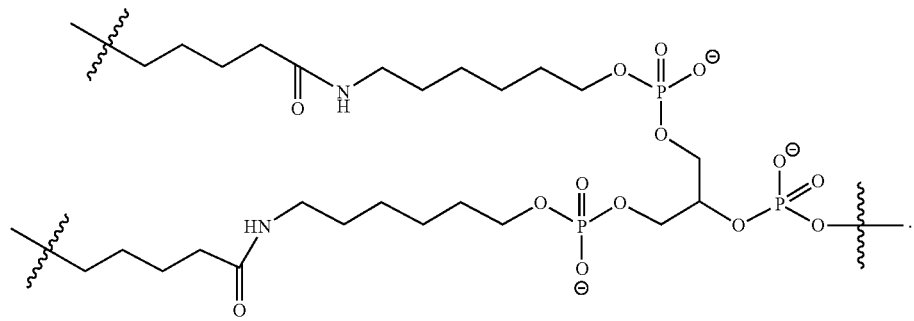

In some embodiments, $L^M$ is

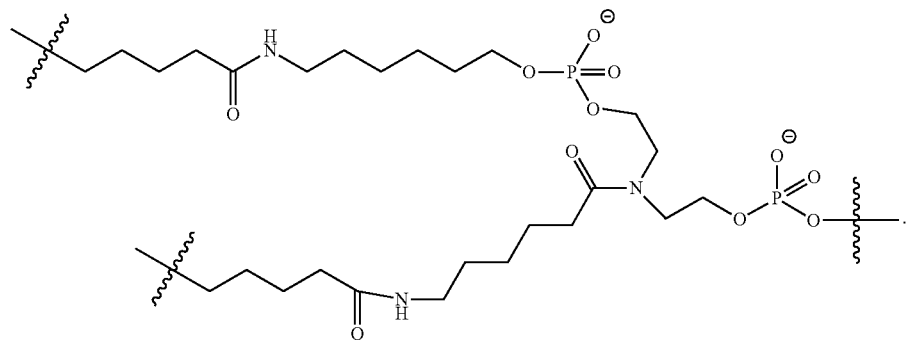

In some embodiments, a carbohydrate moiety is $R^{CD}$, wherein $R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$. In some embodiments, $R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are independently replaced with a tetravalent monosaccharide, disaccharide or polysaccharide moiety. In some embodiments, $R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are independently replaced with a tetravalent GalNac moiety, or a tetravalent moiety of a GalNac derivative.

In some embodiments, $R^{CD}$ is optionally substituted

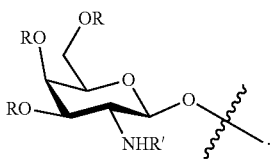

In some embodiments, R' is —C(O)R. In some embodiments, $R^{CD}$ is a monosaccharide moiety. In some embodiments, $R^{CD}$ is a monovalent GalNac moiety. In some embodiments, $R^{CD}$ is

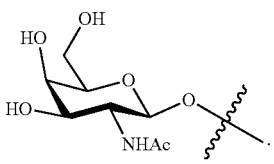

In some embodiments, $R^{CD}$ is optionally substituted

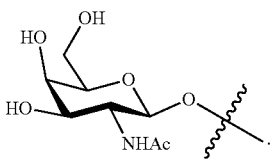

In some embodiments, $R^{CD}$ is optionally substituted

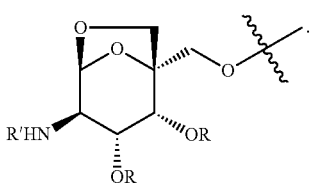

In some embodiments, R' is —C(O)R. In some embodiments, $R^{CD}$ is optionally substituted

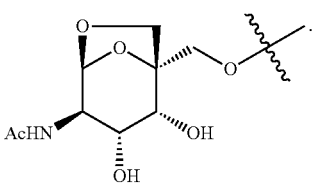

In some embodiments, $R^{CD}$ is a disaccharide moiety. In some embodiments, $R^{CD}$ is a polysaccharide moiety.

In some embodiments, $R^{CD}$ has the structure of $R^G$-L-, wherein $R^G$ is —H, or an optionally substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon. In some embodiments, $R^{CD}$ has the structure of $R^G$-L-, wherein $R^G$ is an optionally substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon. In some embodiments, $R^{CD}$ has the structure of $R^G$-L-, wherein $R^G$ is an optionally substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein at least one heteroatom is oxygen. In some embodiments, $R^G$ is substituted, and at least one substitute of each $R^G$ is bonded to $R^G$ through an oxygen atom. In some embodiments, $R^G$ is substituted, and at least one substitute of each $R^G$ is bonded to $R^G$ through a nitrogen atom. In some embodiments, $R^G$ is independently substituted, and each carbon atom of each $R^G$ is independently bonded to a substituent through an oxygen or nitrogen atom. In some embodiments, $R^G$ is independently substituted, and each carbon atom of each $R^G$ is independently bonded to a substituent through an oxygen or nitrogen atom. In some embodiments, $R^G$ is optionally substituted 3-20 membered heterocyclyl having 1-10 oxygen atoms. In some embodiments, $R^G$ is optionally substituted 3-6 membered heterocyclyl having one oxygen atom. In some embodiments, each $R^G$ is independently optionally substituted 3-20 membered heterocyclyl having 1-10 oxygen atoms. In some embodiments, $R^G$ is independently optionally substituted 3-6 membered heterocyclyl having one oxygen atom. In some embodiments, each carbon of the heterocyclyl ring of $R^G$ is independently boned to an oxygen or nitrogen atom. In some embodiments, two or more carbon atoms of the heterocyclyl ring of $R^G$ are independently boned to an oxygen or nitrogen atom. In some embodiments, two or more carbon atoms of the heterocyclyl ring of $R^G$ are independently boned to an oxygen or nitrogen atom. In some embodiments, three or more carbon atoms of the heterocyclyl ring of $R^G$ are independently boned to an oxygen or nitrogen atom. In some embodiments, four or more carbon atoms of the heterocyclyl ring of $R^G$ are independently boned to an oxygen or nitrogen atom. In some embodiments, five or more carbon atoms of the heterocyclyl ring of $R^G$ are independently boned to an oxygen or nitrogen atom. In some embodiments, two or more carbon atoms of the heterocyclyl ring of $R^G$ are independently boned to an oxygen atom. In some embodiments, three or more carbon atoms of the heterocyclyl ring of $R^G$ are independently boned to an oxygen atom. In some embodiments, four or more carbon atoms of the heterocyclyl ring of $R^G$ are independently boned to an oxygen atom. In some embodiments, five or more carbon atoms of the heterocyclyl ring of $R^G$ are independently boned to an oxygen atom. In some embodiments, $R^G$—H is $C_{3-20}$ polyol comprising a —CHO or —C(O)— group.

In some embodiments, $R^{CD}$ has the structure of $R^G$-L-, wherein $R^G$ is —H, or a substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are R groups. In some embodiments, $R^{CD}$ has the structure of $R^G$-L-, wherein $R^G$ is —H, or a substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are —OR or —N(R)$_2$ groups. In some embodiments, $R^{CD}$ has the structure of $R^G$-L-, wherein $R^G$ is —H, or a substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are —OH and —N(R)$_2$. In some embodiments, R$^{CD}$ has the structure of R$^G$-L-, wherein R$^G$ is —H, or a substituted group selected from C$_3$-C$_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are —OH and —NHR. In some embodiments, R$^{CD}$ has the structure of R$^G$-L-, wherein R$^G$ is —H, or a substituted group selected from C$_3$-C$_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are —OH and —NHC(O)R.

In some embodiments, R$^G$ is substituted 3-20 membered heterocyclyl having 1-10 heteroatoms independently selected from oxygen, nitrogen, sulfur, phosphorus, boron and silicon. In some embodiments, R$^G$ is substituted 3-20 membered heterocyclyl having 1-10 heteroatoms independently selected from oxygen and nitrogen. In some embodiments, R$^G$ is substituted 3-20 membered heterocyclyl having 1-10 oxygen. In some embodiments, R$^G$ is substituted

, or

.

In some embodiments, R$^G$ is substituted

.

In some embodiments, R$^G$ is substituted

.

In some embodiments, R$^G$ is

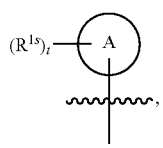

, wherein each variable is independently as described in the present disclosure. In some embodiments, t is 1, 2, 3, 4, 5, 6, 7, 8, 9, or 10. In some embodiments, t is at least 1, 2, 3, 4, 5, 6, 7, 8, 9, or 10. In some embodiments, t is at least 1. In some embodiments, t is at least 2. In some embodiments, t is at least 3. In some embodiments, t is at least 4. In some embodiments, t is at least 5. In some embodiments, t is at least 6. In some embodiments, each R$^{1s}$ is independently —OR' or —N(R')$_2$. In some embodiments, each R' is independently —C(O)R. In some embodiments, each R$^{1s}$ is independently —OR' or —NHR'. In some embodiments, each R$^{1s}$ is independently —OH or —NHR'. In some embodiments, each R$^{1s}$ is independently —OH or —NHC(O)R. In some embodiments, Ring A is optionally substituted

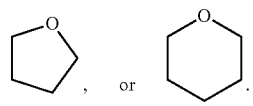

In some embodiments, Ring A is optionally substituted

.

In some embodiments, Ring A is optionally substituted

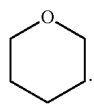

.

In some embodiments, R$^G$ is

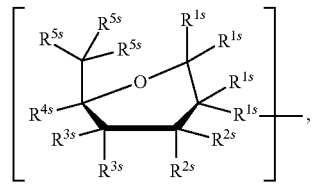

, wherein each variable is independently as described in the present disclosure (i.e., R$^G$—H is

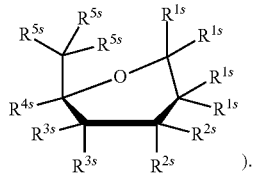

).

In some embodiments, at least 1, 2, 3, 4, 5, or 6 of R$^{1s}$, R$^{2s}$, R$^{3s}$, R$^{4s}$ and R$^{5S}$ are independently —OR' or —N(R')$_2$. In some embodiments, at least 1, 2, 3, 4, 5, or 6 of R$^{1s}$, R$^{2s}$, R$^{3s}$, R$^{4s}$ and R$^{5s}$ are independently —OR' or —NHR'. In some embodiments, at least 1, 2, 3, 4, 5, or 6 of R$^{1s}$, R$^{2s}$, R$^{3s}$, R$^{4s}$ and R$^{5S}$ are independently —OH or —NHR'. In some embodiments, at least 1, 2, 3, 4, 5, or 6 of R$^{1s}$, R$^{2s}$, R$^{3s}$, R$^{4s}$ and R$^{5s}$ are independently —OH or —NHC(O)R. In some embodiments, at least 1, 2, 3, 4, 5, or 6 of R$^{1s}$, R$^{2s}$, R$^{3s}$, R$^{4s}$ and R$^{5s}$ are —OH.

In some embodiments, each ring carbon atom of the cycloaliphatic or heterocyclic ring of R$^G$ is independently substituted. In some embodiments, no more than 1, 2, 3, 4, 5, 6, 7, 8, 9, or 10 ring carbon atoms of the cycloaliphatic or heterocyclic ring of $R^G$ are not substituted. In some embodiments, no more than 1 ring carbon atom is not substituted. In some embodiments, no more than 2 ring carbon atoms are not substituted. In some embodiments, no more than 3 ring carbon atoms are not substituted. In some embodiments, no more than 4 ring carbon atoms are not substituted. In some embodiments, no more than 5 ring carbon atoms are not substituted. In some embodiments, no more than 6 ring carbon atoms are not substituted. In some embodiments, no more than 7 ring carbon atoms are not substituted. In some embodiments, no more than 8 ring carbon atoms are not substituted. In some embodiments, no more than 9 ring carbon atoms are not substituted. In some embodiments, no more than 10 ring carbon atoms are not substituted. In some embodiments, no more than 1, 2, 3, 4, 5, 6, 7, 8, 9, or 10 ring carbon atoms of the cycloaliphatic or heterocyclic ring of $R^G$ are not substituted with —OH or —N(R')$_2$. In some embodiments, no more than 1 ring carbon atom is not substituted with —OH or —N(R')$_2$. In some embodiments, no more than 2 ring carbon atoms are not substituted with —OH or —N(R')$_2$. In some embodiments, no more than 3 ring carbon atoms are not substituted with —OH or —N(R')$_2$. In some embodiments, no more than 4 ring carbon atoms are not substituted with —OH or —N(R')$_2$. In some embodiments, no more than 5 ring carbon atoms are not substituted with —OH or —N(R')$_2$. In some embodiments, no more than 6 ring carbon atoms are not substituted with —OH or —N(R')$_2$. In some embodiments, no more than 7 ring carbon atoms are not substituted with —OH or —N(R')$_2$. In some embodiments, no more than 8 ring carbon atoms are not substituted with —OH or —N(R')$_2$. In some embodiments, no more than 9 ring carbon atoms are not substituted with —OH or —N(R')$_2$. In some embodiments, no more than 10 ring carbon atoms are not substituted with —OH or —N(R')$_2$. In some embodiments, no more than 1, 2, 3, 4, 5, 6, 7, 8, 9, or 10 ring carbon atoms of the cycloaliphatic or heterocyclic ring of $R^G$ are not substituted with —OH. In some embodiments, no more than 1 ring carbon atom is not substituted with —OH. In some embodiments, no more than 2 ring carbon atoms are not substituted with —OH. In some embodiments, no more than 3 ring carbon atoms are not substituted with —OH. In some embodiments, no more than 4 ring carbon atoms are not substituted with —OH. In some embodiments, no more than 5 ring carbon atoms are not substituted with —OH. In some embodiments, no more than 6 ring carbon atoms are not substituted with —OH. In some embodiments, no more than 7 ring carbon atoms are not substituted with —OH. In some embodiments, no more than 8 ring carbon atoms are not substituted with —OH. In some embodiments, no more than 9 ring carbon atoms are not substituted with —OH. In some embodiments, no more than 10 ring carbon atoms are not substituted with —OH. In some embodiments, at least 10%, 20%, 30%, 40%, 50%, 60%, 70%, 80%, 90%, or 95% percent of the ring carbon atoms of the cycloaliphatic or heterocyclic ring of $R^G$ are substituted with —OH or —N(R')$_2$. In some embodiments, no more than 10% the ring carbon atoms are not substituted with —OH or —N(R')$_2$. In some embodiments, no more than 20% the ring carbon atoms are not substituted with —OH or —N(R')$_2$. In some embodiments, no more than 30% of the ring carbon atoms are not substituted with —OH or —N(R')$_2$. In some embodiments, no more than 40% of the ring carbon atoms are not substituted with —OH or —N(R')$_2$. In some embodiments, no more than 50% of the ring carbon atoms are not substituted with —OH or —N(R')$_2$. In some embodiments, no more than 60% of the ring carbon atoms are not substituted with —OH or —N(R')$_2$. In some embodiments, no more than 70% of the ring carbon atoms are not substituted with —OH or —N(R')$_2$. In some embodiments, no more than 80% of the ring carbon atoms are not substituted with —OH or —N(R')$_2$. In some embodiments, no more than 90% of the ring carbon atoms are not substituted with —OH or —N(R')$_2$. In some embodiments, no more than 95% of the ring carbon atoms are not substituted with —OH or —N(R')$_2$. In some embodiments, no more than 10%, 20%, 30%, 40%, 50%, 60%, 70%, 80%, 90%, or 95% of the ring carbon atoms of the cycloaliphatic or heterocyclic ring of $R^G$ are not substituted with —OH. In some embodiments, no more than 10% of the ring carbon atoms are not substituted with —OH. In some embodiments, no more than 20% of the ring carbon atoms are not substituted with —OH. In some embodiments, no more than 30% of the ring carbon atoms are not substituted with —OH. In some embodiments, no more than 40% of the ring carbon atoms are not substituted with —OH. In some embodiments, no more than 50% of the ring carbon atoms are not substituted with —OH. In some embodiments, no more than 60% of the ring carbon atoms are not substituted with —OH. In some embodiments, no more than 70% of the ring carbon atoms are not substituted with —OH. In some embodiments, no more than 80% of the ring carbon atoms are not substituted with —OH. In some embodiments, no more than 90% of the ring carbon atoms are not substituted with —OH. In some embodiments, no more than 95% of the ring carbon atoms are not substituted with —OH. In some embodiments, each ring carbon atom of the cycloaliphatic or heterocyclic ring of $R^G$ is independently substituted. In some embodiments, at least 1, 2, 3, 4, 5, 6, 7, 8, 9, or 10 ring carbon atoms of the cycloaliphatic or heterocyclic ring of $R^G$ are substituted. In some embodiments, at least 1 ring carbon atom is substituted. In some embodiments, at least 2 ring carbon atoms are substituted. In some embodiments, at least 3 ring carbon atoms are substituted. In some embodiments, at least 4 ring carbon atoms are substituted. In some embodiments, at least 5 ring carbon atoms are substituted. In some embodiments, at least 6 ring carbon atoms are substituted. In some embodiments, at least 7 ring carbon atoms are substituted. In some embodiments, at least 8 ring carbon atoms are substituted. In some embodiments, at least 9 ring carbon atoms are substituted. In some embodiments, at least 10 ring carbon atoms are substituted. In some embodiments, at least 1, 2, 3, 4, 5, 6, 7, 8, 9, or 10 ring carbon atoms of the cycloaliphatic or heterocyclic ring of $R^G$ are substituted with —OH or —N(R')$_2$. In some embodiments, at least 1 ring carbon atom is substituted with —OH or —N(R')$_2$. In some embodiments, at least 2 ring carbon atoms are substituted with —OH or —N(R')$_2$. In some embodiments, at least 3 ring carbon atoms are substituted with —OH or —N(R')$_2$. In some embodiments, at least 4 ring carbon atoms are substituted with —OH or —N(R')$_2$. In some embodiments, at least 5 ring carbon atoms are substituted with —OH or —N(R')$_2$. In some embodiments, at least 6 ring carbon atoms are substituted with —OH or —N(R')$_2$. In some embodiments, at least 7 ring carbon atoms are substituted with —OH or —N(R')$_2$. In some embodiments, at least 8 ring carbon atoms are substituted with —OH or —N(R')$_2$. In some embodiments, at least 9 ring carbon atoms are substituted with —OH or —N(R')$_2$. In some embodiments, at least 10 ring carbon atoms are substituted with —OH or —N(R')$_2$. In some embodiments, at least 1, 2, 3, 4, 5, 6, 7, 8, 9, or 10 ring carbon atoms of the cycloaliphatic or heterocyclic ring of $R^G$ are substituted with —OH. In some embodiments, at least 1 ring carbon atom is substituted with —OH. In some embodiments, at least 2 ring carbon atoms are substituted with —OH. In some embodiments, at least 3 ring carbon atoms are substituted with —OH. In some embodiments, at least 4 ring carbon atoms are substituted with —OH. In some embodiments, at least 5 ring carbon atoms are substituted with —OH. In some embodiments, at least 6 ring carbon atoms are substituted with —OH. In some embodiments, at least 7 ring carbon atoms are substituted with —OH. In some embodiments, at least 8 ring carbon atoms are substituted with —OH. In some embodiments, at least 9 ring carbon atoms are substituted with —OH. In some embodiments, at least 10 ring carbon atoms are substituted with —OH. In some embodiments, at least 10%, 20%, 30%, 40%, 50%, 60%, 70%, 80%, 90%, or 95% percent of the ring carbon atoms of the cycloaliphatic or heterocyclic ring of $R^G$ are substituted with —OH or —N(R')$_2$. In some embodiments, at least 10% the ring carbon atoms are substituted with —OH or —N(R')$_2$. In some embodiments, at least 20% the ring carbon atoms are substituted with —OH or —N(R')$_2$. In some embodiments, at least 30% of the ring carbon atoms are substituted with —OH or —N(R')$_2$. In some embodiments, at least 40% of the ring carbon atoms are substituted with —OH or —N(R')$_2$. In some embodiments, at least 50% of the ring carbon atoms are substituted with —OH or —N(R')$_2$. In some embodiments, at least 60% of the ring carbon atoms are substituted with —OH or —N(R')$_2$. In some embodiments, at least 70% of the ring carbon atoms are substituted with —OH or —N(R')$_2$. In some embodiments, at least 80% of the ring carbon atoms are substituted with —OH or —N(R')$_2$. In some embodiments, at least 90% of the ring carbon atoms are substituted with —OH or —N(R')$_2$. In some embodiments, at least 95% of the ring carbon atoms are substituted with —OH or —N(R')$_2$. In some embodiments, at least 10%, 20%, 30%, 40%, 50%, 60%, 70%, 80%, 90%, or 95% of the ring carbon atoms of the cycloaliphatic or heterocyclic ring of $R^G$ are substituted with —OH. In some embodiments, at least 10% of the ring carbon atoms are substituted with —OH. In some embodiments, at least 20% of the ring carbon atoms are substituted with —OH. In some embodiments, at least 30% of the ring carbon atoms are substituted with —OH. In some embodiments, at least 40% of the ring carbon atoms are substituted with —OH. In some embodiments, at least 50% of the ring carbon atoms are substituted with —OH. In some embodiments, at least 60% of the ring carbon atoms are substituted with —OH. In some embodiments, at least 70% of the ring carbon atoms are substituted with —OH. In some embodiments, at least 80% of the ring carbon atoms are substituted with —OH. In some embodiments, at least 90% of the ring carbon atoms are substituted with —OH. In some embodiments, at least 95% of the ring carbon atoms are substituted with —OH. In some embodiments, at least one ring carbon atom is substituted with —N(R')$_2$. In some embodiments, at least one ring carbon atom is substituted with —NHC(O)R. In some embodiments, at least one ring carbon atom is substituted with —NHC(O)R, wherein R is optionally substituted C$_{1-6}$ aliphatic. In some embodiments, at least one ring carbon atom is substituted with —NHAc.

In some embodiments, $R^G$ is optionally substituted

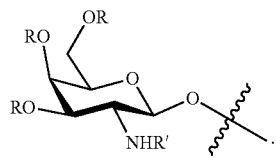

In some embodiments, R' is —C(O)R. In some embodiments, $R^G$ is

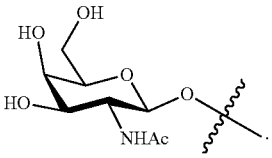

In some embodiments, $R^G$ is optionally substituted

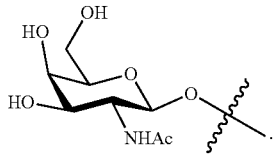

In some embodiments, $R^G$ is optionally substituted

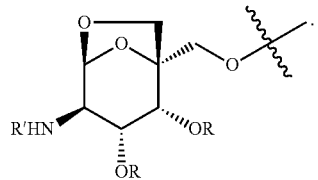

In some embodiments, R' is —C(O)R. In some embodiments, $R^G$ is optionally substituted

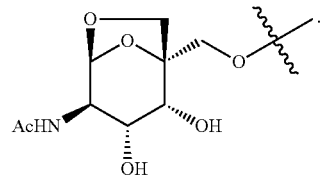 [SMILES: *OC[C@@]12CO[C@@H](O1)[C@H](NC(C)=O)[C@@H](O)[C@H]2O]

In some embodiments, $R^{CD}$, or $R^G$, is of such a structure that $R^{CD}$—H, or $R^G$—H, is

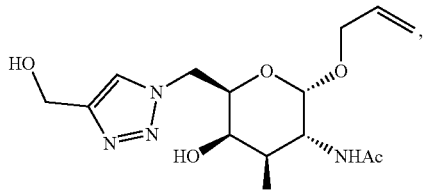

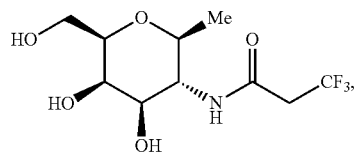

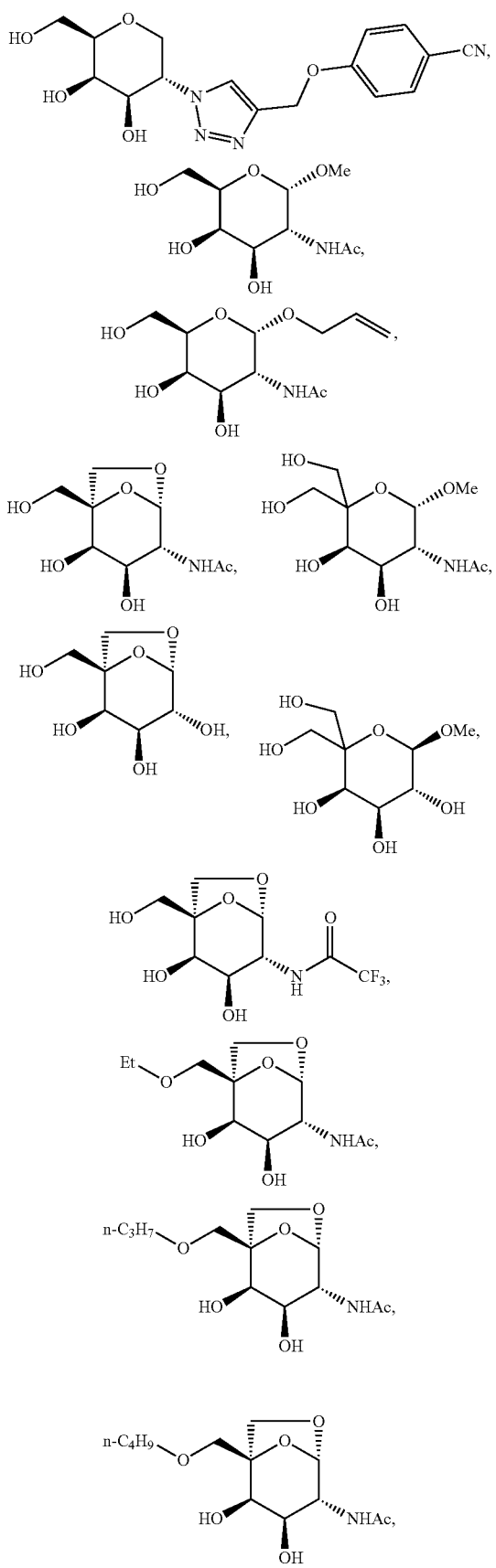

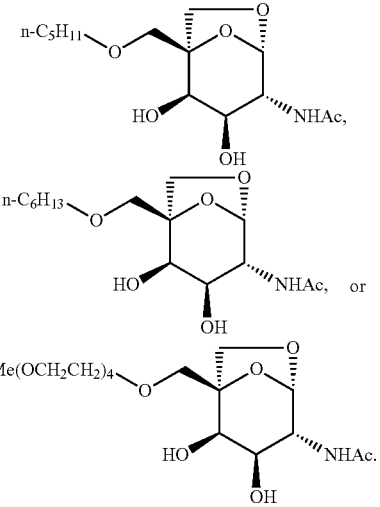

In some embodiments, $R^{CD}$, or $R^G$, is of such a structure that $R^{CD}$—H, or $R^G$—H, is a ligand for the asialoglycoprotein receptor (ASGPR). Various other ASGPR ligands are known in the art and can be utilized in accordance with the present disclose. In some embodiments, carbohydrate moieties described in are useful for targeted delivery of provided oligonucleotide compositions, e.g., chirally controlled oligonucleotide compositions, SMN2 oligonucleotide compositions, etc., to liver.

In some embodiments, L is a covalent bond. In some embodiments, L is bivalent optionally substituted $C_{1-6}$ aliphatic wherein one or more methylene units are independently and optionally replaced with —O—. In some embodiments, L is —O—$CH_2$—.

In some embodiments, $R^{CD}$ is an oligomeric or polymeric moiety of $R^G$—H, wherein each $R^G$ is independently as described in the present disclosure.

In some embodiments, a targeting moiety is capable of binding to the asialoglycoprotein receptor (ASGPR). In some embodiments, a targeting moiety is a ligand for the asialoglycoprotein receptor (ASGPR). In some embodiments, a targeting moiety is a ligand for the asialoglycoprotein receptor (ASGPR) disclosed in: Sanhueza et al. J. Am. Chem. Soc., 2017, 139 (9), pp 3528-3536. In some embodiments, a targeting moiety is a ligand for the asialoglycoprotein receptor (ASGPR) disclosed in: Mamidyala et al. J. Am. Chem. Soc., 2012, 134, pp 1978-1981. In some embodiments, a targeting moiety is a ligand for the asialoglycoprotein receptor (ASGPR) disclosed in Liras et al. US 20160207953. In some embodiments, a targeting moiety is a substituted-6,8-dioxabicyclo[3.2.1]octane-2,3-diol derivative disclosed in Liras et al. US 20160207953. In some embodiments, a targeting moiety is a ligand for the asialoglycoprotein receptor (ASGPR) disclosed in Liras et al. US 20150329555. In some embodiments, a targeting moiety is a substituted-6,8-dioxabicyclo[3.2.1]octane-2,3-diol derivative disclosed in Liras et al. US 20150329555. In some embodiments, a targeting moiety is a ligand for the asialoglycoprotein receptor (ASGPR) disclosed in U.S. Pat. No. 8,877,917, US 20160376585, U.S. Ser. No. 10/086,081, and U.S. Pat. No. 8,106,022. ASGPR ligands described in these documents are incorporated herein by reference. Those skilled in the art will appreciate that various technologies are known in the art, including those described in these documents, for assessing binding of a chemical moiety to ASGPR and can be utilized in accordance with the present disclosure.

In some embodiments, a targeting moiety that is a ligand for the asialoglycoprotein receptor (ASGPR) is $R^G$. In some embodiments, a targeting moiety that is a ligand for the asialoglycoprotein receptor (ASGPR) is $R^{CD}$. In some embodiments, a targeting moiety, carbohydrate moiety, ligand for the asialoglycoprotein receptor, or an additional chemical moiety (e.g., one capable of binding to ASGR), $R^G$, or $R^{CD}$ is $R^x$, wherein $R^x$—H is

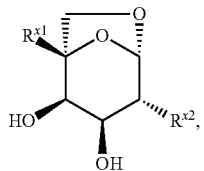

wherein each of $R^{x1}$ and $R^{x2}$ is independently $R^s$ as described in the present disclosure. In some embodiments, $R^x$ is

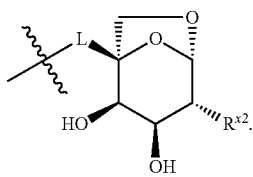

In some embodiments, a targeting moiety, carbohydrate moiety, ligand for the asialoglycoprotein receptor, or an additional chemical moiety (e.g., one capable of binding to ASGR), $R^G$, or $R^{CD}$ is $R^x$, wherein $R^x$—H is

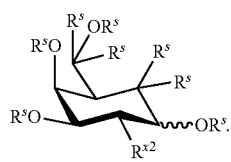

wherein each variable is independently as described in the present disclosure. In some embodiments, $R^x$—H is

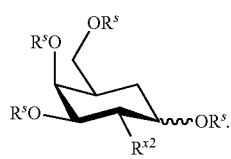

In some embodiments, $R^x$ is

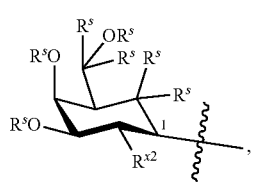

wherein $R^x$ is connected through C1. In some embodiments, $R^x$ is

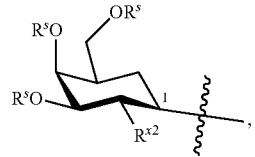

wherein $R^x$ is connected through C1 (stereorandom or stereospecific, if stereospecific may be either configuration). In some embodiments, $R^x$—H is

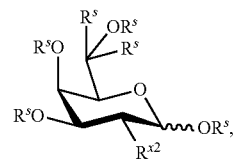

wherein each variable is independently as described in the present disclosure. In some embodiments, $R^x$—H is

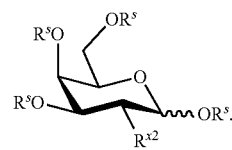

In some embodiments, $R^x$ is

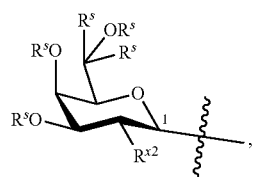

wherein $R^x$ is connected through C1. In some embodiments, $R^x$ is

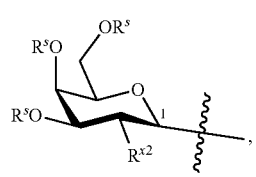

wherein $R^x$ is connected through C1. In some embodiments, $R^x$—H is

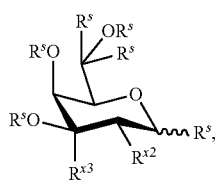

wherein each of $R^{x2}$, $R^{x3}$, and $R^{x6}$ is independently $R^s$ as described in the present disclosure. In some embodiments, $R^x$—H is

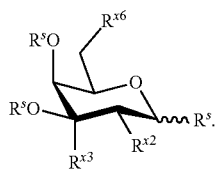

In some embodiments, $R^x$ is

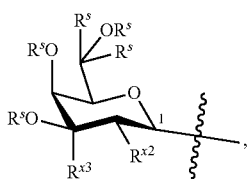

wherein $R^x$ is connected through C1. In some embodiments, $R^x$ is

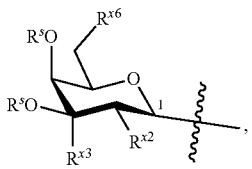

wherein $R^x$ is connected through C1. In some embodiments, $R^x$ is

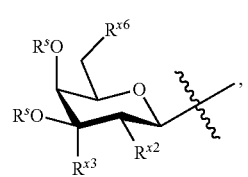

In some embodiments, $R^x$ is

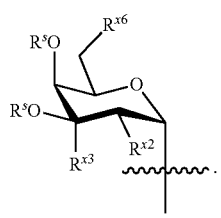

In some embodiments, $R^x$ is

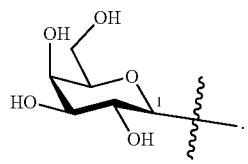

In some embodiments, $R^x$ is

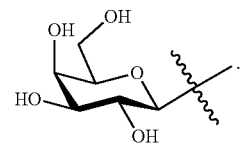

In some embodiments, $R^x$ is

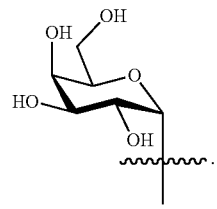

In some embodiments, $R^x$ is optionally substituted galactosyl.

In some embodiments, $R^{x2}$ is —NHR'. In some embodiments, $R^{x2}$ is —NHC(O)R. In some embodiments, $R^{x2}$ is —NHC(O)CH$_3$. In some embodiments, $R^{x2}$ is —NHC(O)CF$_3$. In some embodiments, $R^{x2}$ is —OH. In some embodiments, $R^s$ is —H. In some embodiments, —OR$^s$ is —OC(O)CH$_3$. In some embodiments, —OR$^s$ is —OH. In some embodiments, $R^{x3}$ is —H. In some embodiments, $R^{x3}$ is optionally substituted C$_{1-4}$ alkyl. In some embodiments, $R^{x6}$ is -L-R'. In some embodiments, $R^{x6}$ is —N(R')—R'. In some embodiments, $R^{x6}$ is —NHC(O)C(R')$_2$(NHR'). In some embodiments, $R^{x6}$ is —R'. In some embodiments, $R^{x6}$ is —OR'. In some embodiments, $R^{x6}$ is —OR.

In some embodiments, a SMN2 oligonucleotide can comprise any optional additional chemical moiety, including but not limited to, a carbohydrate moiety, a targeting moiety, a lipid moiety, a GalNAc moiety, etc., described herein or known in the art. In some embodiments, a stereorandom SMN2 oligonucleotide composition can comprise any optional additional chemical moiety, including but not limited to, a carbohydrate moiety, a targeting moiety, a lipid moiety, a GalNAc moiety, etc., described herein or known in the art. In some embodiments, a carbohydrate is any carbohydrate, or variant, derivative or modification thereof, as described herein or known in the art. In some embodiments, a lipid is any lipid, or variant, derivative or modification thereof, as described herein or known in the art. In some embodiments, a GalNAc moiety is any GalNAc, or variant, derivative or modification thereof, as described herein or known in the art. In some embodiments, an oligonucleotide, an oligonucleotide that directs RNA interference, an oligonucleotide that directs RNase H-mediated knockdown, or an oligonucleotide that directs both RNA interference and RNase H-mediated knockdown can comprise any optional additional chemical moiety, including but not limited to, a carbohydrate moiety, a targeting moiety, a lipid moiety, a GalNAc moiety, etc., described herein or known in the art in combination with any other structural element or modification described herein, including but not limited to, base sequence or portion thereof, sugar, base; internucleotidic linkage; stereochemistry or pattern thereof; pattern of modifications of sugars, bases or internucleotidic linkages; format or any structural element thereof, and/or any other structural element or modification described herein; and in some embodiments, the present disclosure pertains to multimers of any such oligonucleotides.

In some embodiments, an additional chemical moiety conjugated to an oligonucleotide is a GalNAc moiety. In some embodiments, an additional chemical moiety conjugated to a stereorandom SMN2 oligonucleotide composition is a GalNAc moiety. In some embodiments, an additional chemical moiety conjugated to a chirally controlled SMN2 oligonucleotide composition is a GalNAc moiety. In some embodiments, an additional chemical moiety is connected to an nucleoside moiety or an internucleotidic linkage through a linker. In some embodiments, a linker attaching a GalNAc moiety is a biocleavable linker. Such a linker allows the intracellular removal of the GalNAc moiety.

In some embodiments, an oligonucleotide is conjugated to Tri-antennary GalNAc Acid (e.g., via a C10, C3 or triazine linker):

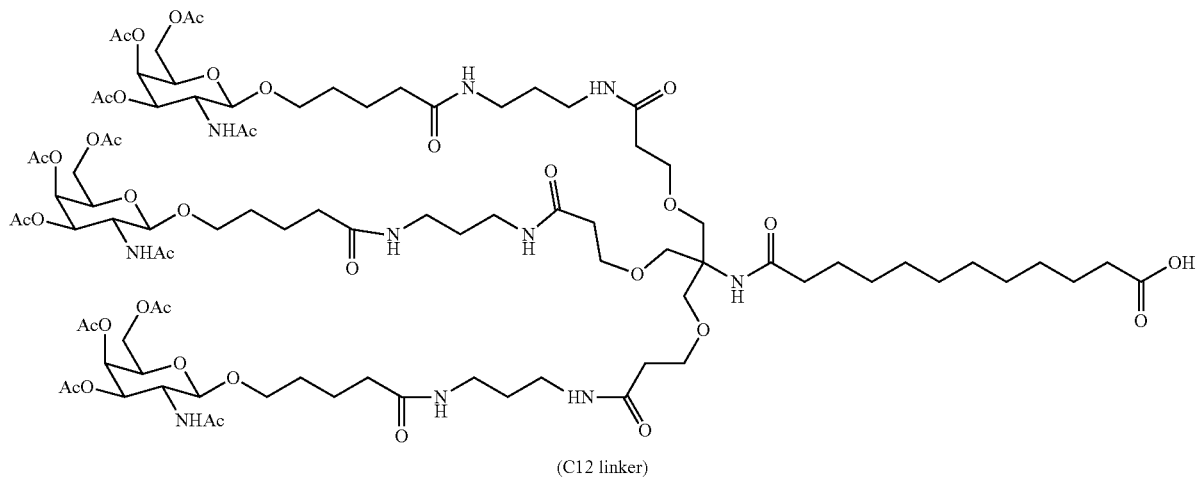

(C12 linker)

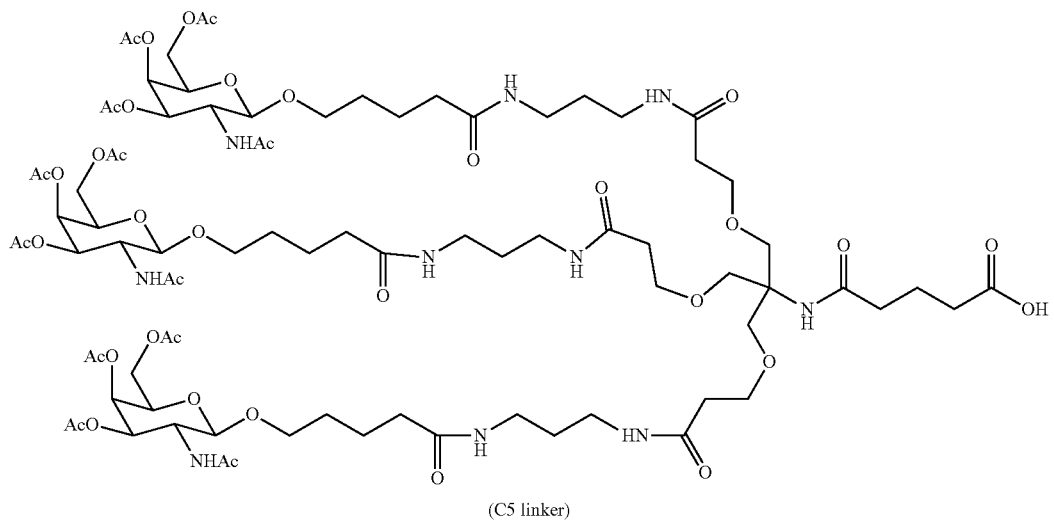

(C5 linker)

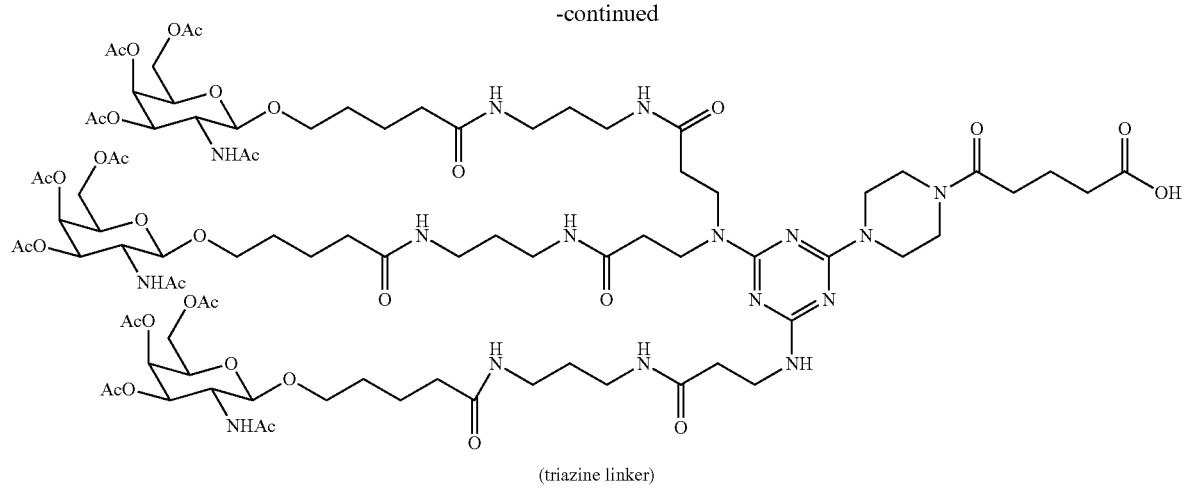
(triazine linker)

In some embodiments, tri-antennary GalNAc acids, e.g., those illustrated above, are conjugated directly to an oligonucleotide chain. In some embodiments, tri-antennary GalNAc acids, e.g., those illustrated above, are conjugated to an oligonucleotide chain through a linker moiety (e.g., L001). As appreciated by those skilled in the art, tri-antennary GalNAc acids may be utilized to incorporate additional chemical moieties into oligonucleotides as Mods, e.g., as those described in Table 1A. In some embodiments, a linker moiety, e.g., L001 (—NH—(CH$_2$)$_6$—, also known as a C6 linker, C6 amine linker or C6 amino linker), is connected to an acid through —NH— (forming an amide group —C(O)—NH—), and the 5'-end of the oligonucleotide chain through a phosphate linkage or phosphorothioate linkage.

In some embodiments, a oligonucleotide is conjugated to an additional chemical moiety suitable for use in delivery to the central nervous system, selected from: glucose, GluNAc (N-acetyl amine glucosamine), lipid, and anisamide, and a molecule of any of the structures of:

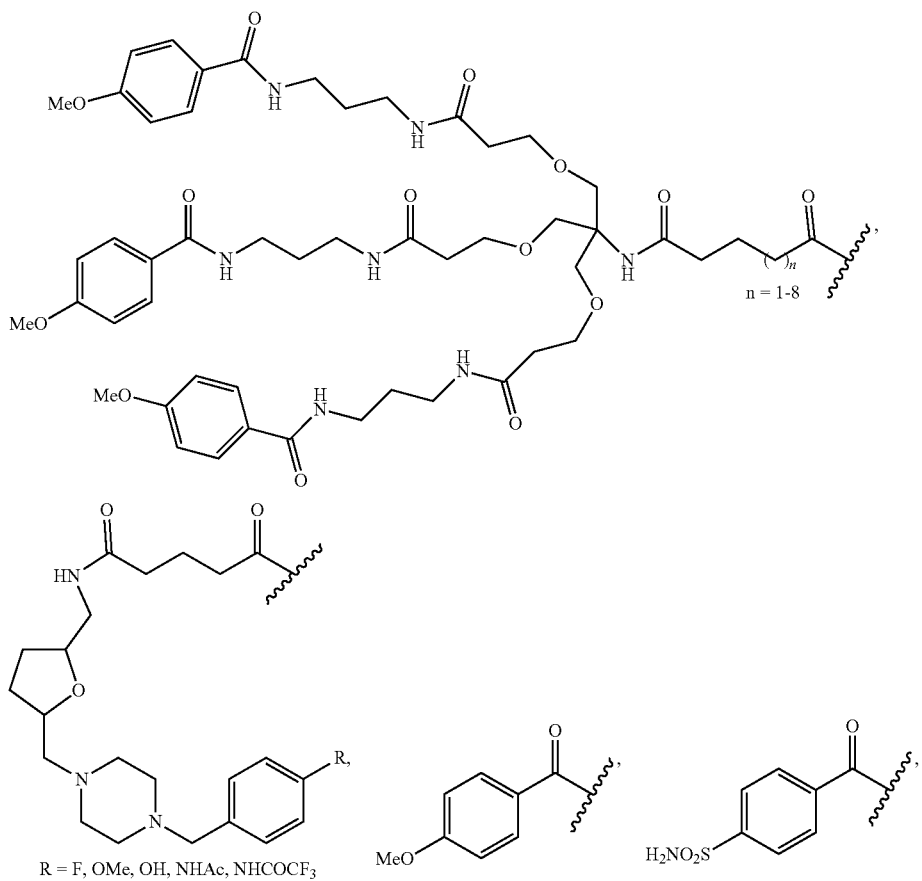

191 192
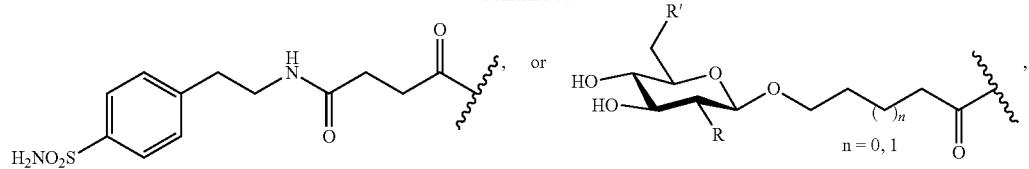
R=NHAc, R'=OH; R=NHCOC6H4OMe(p-anisoyl), R'=OH
R=NHAc, R'=NHCOC6H4OMe(p-anisoyl); R=OH, R'=NHCOC6H4OMe(p-anisoyl),
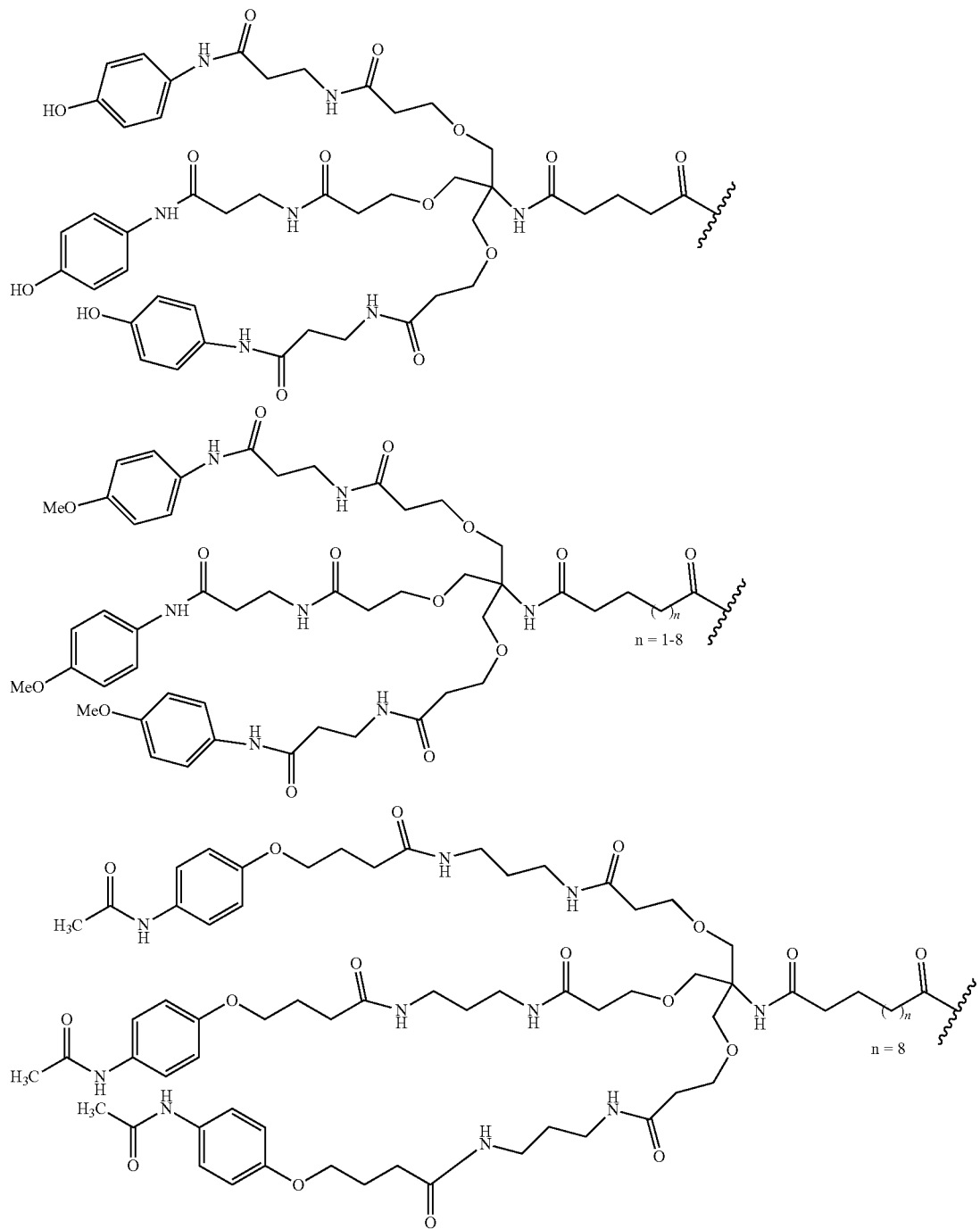

which are described in more detail in Examples 1 and 2.

In some embodiments, an additional chemical moiety conjugated to an oligonucleotide is capable of targeting the oligonucleotide to a cell in the nervous system.

In some embodiments, an additional chemical moiety conjugated to a provided oligonucleotide comprises anisamide or a derivative or analog thereof and is capable of targeting an oligonucleotide to a cell expressing a particular receptor, such as the sigma 1 receptor.

In some embodiments, a provided oligonucleotide composition is formulated for administration to a body cell and/or tissue expressing its target.

In some embodiments, an additional chemical moiety conjugated to an oligonucleotide is capable of targeting the oligonucleotide to a cell in the nervous system.

In some embodiments, an additional chemical moiety conjugated to an oligonucleotide comprises anisamide or a derivative or analog thereof and is capable of targeting the oligonucleotide to a cell expressing a particular receptor, such as the sigma 1 receptor.

In some embodiments, the present disclosure provides a provided compound, e.g., a chirally controlled oligonucleotide of a provided composition, a SMN2 oligonucleotide, having the structure of formula O-I:

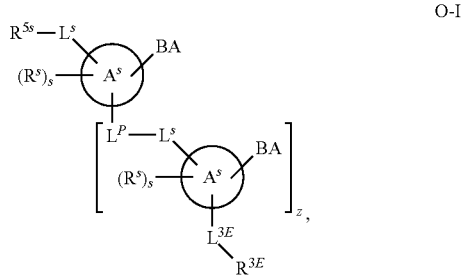

O-I or a salt thereof, wherein:

$R^{5s}$ is independently R' or —OR';

each BA is independently an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus, boron and silicon, a natural nucleobase moiety, and a modified nucleobase moiety;

each $R^s$ is independently —F, —Cl, —Br, —I, —CN, —$N_3$, —NO, —$NO_2$, -L-R', -L-OR', -L-SR', -L-N(R')$_2$, —O-L-OR', —O-L-SR', or —O-L-N(R')$_2$;

each s is independently 0-20;

$L^s$ is —C($R^{5s}$)$_2$—, or L;

each L is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon;

each Ring $A^s$ is independently an optionally substituted 3-20 membered monocyclic, bicyclic or polycyclic ring having 0-10 heteroatoms independently selected from oxygen, nitrogen, sulfur, phosphorus and silicon;

each $L^P$ is independently an internucleotidic linkage;

z is 1-1000;

$L^{3E}$ is L or -L-L-;

$R^{3E}$ is —R', -L-R', —OR', or a solid support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms independently selected from oxygen, nitrogen, sulfur, phosphorus and silicon.

In some embodiments, each $L^P$ independently has the structure of formula I:

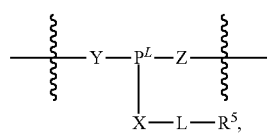

I or a salt form thereof, wherein each variable is independently as described in the present disclosure. In some embodiments, each $L^P$ independently has the structure of formula I, I-a-1, I-a-2, I-b, I-c, I-d, I-e, I-n-1, I-n-2, I-n-3, II, II-a-1, II-a-2, II-b-1, II-b-2, II-c-1, II-c-2, II-d-1, or II-d-2, or a salt form thereof.

In some embodiments, each $L^P$ independently has the structure of formula I, wherein each variable is independently as described in the present disclosure. In some embodiments, each $L^P$ comprising a chiral linkage phosphorus is independently a chirally controlled internucleotidic linkage.

In some embodiments, each BA is independently an optionally substituted group selected from $C_{5-30}$ heteroaryl having 1-10 heteroatoms independently selected from oxygen, nitrogen, sulfur, phosphorus and silicon, and $C_{3-30}$ heterocyclyl having 1-10 heteroatoms independently selected from oxygen, nitrogen, sulfur, phosphorus, boron and silicon;

each Ring $A^s$ is independently an optionally substituted 3-20 membered monocyclic, bicyclic or polycyclic ring having 0-10 heteroatoms independently selected from oxygen, nitrogen, sulfur, phosphorus and silicon; and each $L^P$ independently has the structure of formula I, wherein each variable is independently as described in the present disclosure.

In some embodiments, each BA is independently an optionally substituted $C_{5-30}$ heteroaryl having 1-10 heteroatoms independently selected from oxygen, nitrogen, sulfur, phosphorus and silicon, wherein the heteroaryl comprises one or more heteroatoms selected from oxygen and nitrogen;

each Ring $A^s$ is independently an optionally substituted 5-10 membered monocyclic or bicyclic saturated ring having 0-5 heteroatoms independently selected from oxygen, nitrogen, sulfur, phosphorus and silicon, wherein the ring comprises at least one oxygen atom; and each $L^P$ independently has the structure of formula I, wherein each variable is independently as described in the present disclosure.

In some embodiments, each BA is independently an optionally substituted A, T, C, G, or U, or an optionally substituted tautomer of A, T, C, G, or U;

each Ring $A^s$ is independently an optionally substituted 5-7 membered monocyclic or bicyclic saturated ring having one or more oxygen atoms; and each $L^P$ independently has the structure of formula I, wherein each variable is independently as described in the present disclosure.

In some embodiments, each BA is independently an optionally substituted or protected nucleobase selected from adenine, cytosine, guanosine, thymine, and uracil;

each Ring $A^s$ is independently an optionally substituted 5-7 membered monocyclic or bicyclic saturated ring having one or more oxygen atoms; and each $L^P$ independently has the structure of formula I, wherein each variable is independently as described in the present disclosure.

In some embodiments, one or more $L^P$ is a neutral internucleotidic linkage as described in the present disclosure. In some embodiments, one or more $L^P$ independently have the structure of formula I-n-1, I-n-2, I-n-3, II, II-a-1, II-a-2, II-b-1, II-b-2, II-c-1, II-c-2, II-d-1, or II-d-2 as described in the present disclosure.

In some embodiments, $R^{5s}$-$L^s$- is —$CH_2OH$. In some embodiments, $R^{5s}$-$L^s$- is —$CH(R^{5s})$—OH, wherein $R^{5s}$ is as described in the present disclosure.

In some embodiments, BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, a natural nucleobase moiety, and a modified nucleobase moiety. In some embodiments, BA is optionally substituted $C_{5-30}$ heteroaryl having 1-10 heteroatoms independently selected from oxygen, nitrogen, and sulfur. In some embodiments, BA is optionally substituted natural nucleobases and tautomers thereof. In some embodiments, BA is protected natural nucleobases and tautomers thereof. Various nucleobase protecting groups for oligonucleotide synthesis are known and can be utilized in accordance with the present disclosure. In some embodiments, BA is an optionally substituted nucleobase selected from adenine, cytosine, guanosine, thymine, and uracil, and tautomers thereof. In some embodiments, BA is an optionally protected nucleobase selected from adenine, cytosine, guanosine, thymine, and uracil, and tautomers thereof.

In some embodiments, BA is optionally substituted $C_{3-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{3-30}$ cycloaliphatic, $C_{6-30}$ aryl, $C_{3-30}$ heterocyclyl, and $C_{5-30}$ heteroaryl. In some embodiments, BA is an optionally substituted group selected from $C_{3-30}$ cycloaliphatic, $C_{6-30}$ aryl, $C_{3-30}$ heterocyclyl, $C_{5-30}$ heteroaryl, and a natural nucleobase moiety.

In some embodiments, BA is connected through an aromatic ring. In some embodiments, BA is connected through a heteroatom. In some embodiments, BA is connected through a ring heteroatom of an aromatic ring. In some embodiments, BA is connected through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety. In some embodiments, BA is optionally substituted, or an optionally substituted tautomer of, A, T, C, U, or G. In some embodiments, BA is natural nucleobase A, T, C, U, or G. In some embodiments, BA is an optionally substituted group selected from natural nucleobases A, T, C, U, and G.

In some embodiments, BA is an optionally substituted purine base residue. In some embodiments, BA is a protected purine base residue. In some embodiments, BA is an optionally substituted adenine residue. In some embodiments, BA is a protected adenine residue. In some embodiments, BA is an optionally substituted guanine residue. In some embodiments, BA is a protected guanine residue. In some embodiments, BA is an optionally substituted cytosine residue. In some embodiments, BA is a protected cytosine residue. In some embodiments, BA is an optionally substituted thymine residue. In some embodiments, BA is a protected thymine residue. In some embodiments, BA is an optionally substituted uracil residue. In some embodiments, BA is a protected uracil residue. In some embodiments, BA is an optionally substituted 5-methylcytosine residue. In some embodiments, BA is a protected 5-methylcytosine residue.

In some embodiments, BA is a protected base residue as used in oligonucleotide preparation. In some embodiments, BA is a base residue illustrated in US 2011/0294124, US 2015/0211006, US 2015/0197540, and WO 2015/107425, each of which is incorporated herein by reference.

In some embodiments, each $R^s$ is independently —H, halogen, —CN, —$N_3$, —NO, —$NO_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$ as described in the present disclosure.

In some embodiments, $R^s$ is R', wherein R is as described in the present disclosure. In some embodiments, $R^s$ is R, wherein R is as described in the present disclosure. In some embodiments, $R^s$ is optionally substituted $C_{1-30}$ heteroaliphatic. In some embodiments, $R^s$ comprises one or more silicon atoms. In some embodiments, $R^s$ is —$CH_2$Si(Ph)$_2CH_3$.

In some embodiments, $R^s$ is -$L^s$-R'. In some embodiments, $R^s$ is -$L^s$-R' wherein -$L^s$- is a bivalent, optionally substituted $C_{1-30}$ heteroaliphatic group. In some embodiments, $R^s$ is —$CH_2$Si(Ph)$_2CH_3$.

In some embodiments, $R^s$ is —F. In some embodiments, $R^s$ is —Cl. In some embodiments, $R^s$ is —Br. In some embodiments, $R^s$ is —I. In some embodiments, $R^s$ is —CN. In some embodiments, $R^s$ is —$N_3$. In some embodiments, $R^s$ is —NO. In some embodiments, $R^s$ is —$NO_2$. In some embodiments, $R^s$ is -$L^s$-Si(R)$_3$. In some embodiments, $R^s$ is —Si(R)$_3$. In some embodiments, $R^s$ is -$L^s$-R'. In some embodiments, $R^s$ is —R'. In some embodiments, $R^s$ is -$L^s$-OR'. In some embodiments, $R^s$ is —OR'. In some embodiments, $R^s$ is -$L^s$-SR'. In some embodiments, $R^s$ is —SR'. In some embodiments, $R^s$ is -$L^s$-N(R')$_2$. In some embodiments, $R^s$ is —N(R')$_2$. In some embodiments, $R^s$ is —O-$L^s$-R'. In some embodiments, $R^s$ is —O-$L^s$-Si(R)$_3$. In some embodiments, $R^s$ is —O-$L^s$-OR'. In some embodiments, $R^s$ is —O-$L^s$-SR'. In some embodiments, $R^s$ is —O-$L^s$-N(R')$_2$. In some embodiments, $R^s$ is a 2'-modification as described in the present disclosure. In some embodiments, $R^s$ is —OR, wherein R is as described in the present disclosure. In some embodiments, $R^s$ is —OR, wherein R is optionally substituted $C_{1-6}$ aliphatic. In some embodiments, $R^s$ is —OMe. In some embodiments, $R^s$ is —$OCH_2CH_2OMe$.

In some embodiments, s is 0-20. In some embodiments, s is 1-20. In some embodiments, s is 1-5. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, $L^s$ is L, wherein L is as described in the present disclosure. In some embodiments, L is a bivalent optionally substituted methylene group. In some embodiments, $L^s$ is —$CH_2$—. In some embodiments, each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$.

In some embodiments, $L^s$ is a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched $C_{1-30}$ aliphatic group, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L$^s$ is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, and one or more carbon atoms are optionally and independently replaced with Cy$^L$. In some embodiments, L$^s$ is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—, and one or more carbon atoms are optionally and independently replaced with Cy$^L$. In some embodiments, L$^s$ is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—.

In some embodiments, L$^s$ is a covalent bond. In some embodiments, L$^s$ is optionally substituted bivalent C$_{1-30}$ aliphatic. In some embodiments, L$^s$ is optionally substituted bivalent C$_{1-30}$ heteroaliphatic having 1-10 heteroatoms independently selected from boron, oxygen, nitrogen, sulfur, phosphorus and silicon.

In some embodiments, aliphatic moieties, e.g. those of L$^s$, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc. In some embodiments, heteroaliphatic moieties, e.g. those of L$^s$, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc.

In some embodiments, a methylene unit is replaced with -Cy-, wherein -Cy- is as described in the present disclosure. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —O—. In some embodiments, a methylene unit is replaced with —S—. In some embodiments, a methylene unit is replaced with —N(R')—. In some embodiments, a methylene unit is replaced with —C(O)—. In some embodiments, a methylene unit is replaced with —S(O)—. In some embodiments, a methylene unit is replaced with —S(O)$_2$—. In some embodiments, a methylene unit is replaced with —P(O)(OR')—. In some embodiments, a methylene unit is replaced with —P(O)(SR')—. In some embodiments, a methylene unit is replaced with —P(O)(R')—. In some embodiments, a methylene unit is replaced with —P(O)(NR')—. In some embodiments, a methylene unit is replaced with —P(S)(OR')—. In some embodiments, a methylene unit is replaced with —P(S)(SR')—. In some embodiments, a methylene unit is replaced with —P(S)(R')—. In some embodiments, a methylene unit is replaced with —P(S)(NR')—. In some embodiments, a methylene unit is replaced with —P(R')—. In some embodiments, a methylene unit is replaced with —P(OR')—. In some embodiments, a methylene unit is replaced with —P(SR')—. In some embodiments, a methylene unit is replaced with —P(NR')—. In some embodiments, a methylene unit is replaced with —P(OR')[B(R')$_3$]—. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, each of which may independently be an internucleotidic linkage.

In some embodiments, L$^s$, e.g., when connected to R$^s$, is —CH$_2$—. In some embodiments, L$^s$ is —C(R)$_2$—, wherein at least one R is not hydrogen. In some embodiments, L$^s$ is —CHR—. In some embodiments, R is hydrogen. In some embodiments, L$^s$ is —CHR—, wherein R is not hydrogen. In some embodiments, C of —CHR— is chiral. In some embodiments, L$^s$ is —(R)—CHR—, wherein C of —CHR— is chiral. In some embodiments, L$^s$ is —(S)—CHR—, wherein C of —CHR— is chiral. In some embodiments, R is optionally substituted C$_{1-6}$ aliphatic. In some embodiments, R is optionally substituted C$_{1-6}$ alkyl. In some embodiments, R is optionally substituted C$_{1-5}$ aliphatic. In some embodiments, R is optionally substituted C$_{1-5}$ alkyl. In some embodiments, R is optionally substituted C$_{1-4}$ aliphatic. In some embodiments, R is optionally substituted C$_{1-4}$ alkyl. In some embodiments, R is optionally substituted C$_{1-3}$ aliphatic. In some embodiments, R is optionally substituted C$_{1-3}$ alkyl. In some embodiments, R is optionally substituted C$_2$ aliphatic. In some embodiments, R is optionally substituted methyl. In some embodiments, R is C$_{1-6}$ aliphatic. In some embodiments, R is C$_{1-6}$ alkyl. In some embodiments, R is C$_{1-5}$ aliphatic. In some embodiments, R is C$_{1-5}$ alkyl. In some embodiments, R is C$_{1-4}$ aliphatic. In some embodiments, R is C$_{1-4}$ alkyl. In some embodiments, R is C$_{1-3}$ aliphatic. In some embodiments, R is C$_{1-3}$ alkyl. In some embodiments, R is C$_2$ aliphatic. In some embodiments, R is methyl. In some embodiments, R is C$_{1-6}$ haloaliphatic. In some embodiments, R is C$_{1-6}$ haloalkyl. In some embodiments, R is C$_{1-5}$ haloaliphatic. In some embodiments, R is C$_{1-5}$ haloalkyl. In some embodiments, R is C$_{1-4}$ haloaliphatic. In some embodiments, R is C$_{1-4}$ haloalkyl. In some embodiments, R is C$_{1-3}$ haloaliphatic. In some embodiments, R is C$_{1-3}$ haloalkyl. In some embodiments, R is C$_2$ haloaliphatic. In some embodiments, R is methyl substituted with one or more halogen. In some embodiments, R is —CF$_3$. In some embodiments, L$^s$ is optionally substituted —CH═CH—. In some embodiments, L$^s$ is optionally substituted (E)-CH═CH—. In some embodiments, L$^s$ is optionally substituted (Z)—CH═CH—. In some embodiments, L$^s$ is —C≡C—.

In some embodiments, L$^s$ comprises at least one phosphorus atom. In some embodiments, at least one methylene unit of L$^s$ is replaced with —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—.

In some embodiments, L$^s$ is -Cy-. In some embodiments, -Cy- is optionally substituted monocyclic or bicyclic 3-20 membered heterocyclyl ring having 1-5 heteroatoms. In some embodiments, -Cy- is optionally substituted monocyclic or bicyclic 5-20 membered heterocyclyl ring having 1-5 heteroatoms, wherein at least one heteroatom is oxygen. In some embodiments, -Cy- is optionally substituted bivalent tetrahydrofuran ring. In some embodiments, -Cy- is an optionally substituted furanose moiety.

As described herein, each L is independently a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus, boron and silicon, wherein one or more methylene units are optionally and independently replaced with C$_{1-6}$ alkylene, C$_{1-6}$ alkenylene, —C≡C—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, or —OP(OR')[B(R')$_3$]O—; and one or more carbon atoms are optionally and independently replaced with Cy$^L$.

In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L is a covalent bond, or a bivalent, optionally substituted, linear or branched C$_{1-30}$ aliphatic group, wherein one or more methylene units are optionally and independently replaced by an optionally substituted group selected from C$_{1-6}$ alkylene, C$_{1-6}$ alkenylene, —C≡C—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L is a covalent bond, or a bivalent, optionally substituted, linear or branched C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, and one or more carbon atoms are optionally and independently replaced with Cy$^L$. In some embodiments, L is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—, and one or more carbon atoms are optionally and independently replaced with Cy$^L$. In some embodiments, L is a covalent bond, or a bivalent, optionally substituted, linear or branched group selected from a $C_{1-10}$ aliphatic group and a $C_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—.

In some embodiments, L is a covalent bond. In some embodiments, L is optionally substituted bivalent $C_{1-30}$ aliphatic. In some embodiments, L is optionally substituted bivalent $C_{1-30}$ heteroaliphatic having 1-10 heteroatoms independently selected from boron, oxygen, nitrogen, sulfur, phosphorus and silicon.

In some embodiments, aliphatic moieties, e.g. those of L, R, etc., either monovalent or bivalent or multivalent, and can contain any number of carbon atoms (before any optional substitution) within its range, e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, etc. In some embodiments, heteroaliphatic moieties, e.g. those of L, R, etc., either monovalent or bivalent or multivalent, and can contain any number of carbon atoms (before any optional substitution) within its range, e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, etc.

In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —O—. In some embodiments, a methylene unit is replaced with —S—. In some embodiments, a methylene unit is replaced with —N(R')—. In some embodiments, a methylene unit is replaced with —C(O)—. In some embodiments, a methylene unit is replaced with —S(O)—. In some embodiments, a methylene unit is replaced with —S(O)$_2$—. In some embodiments, a methylene unit is replaced with —P(O)(OR')—. In some embodiments, a methylene unit is replaced with —P(O)(SR')—. In some embodiments, a methylene unit is replaced with —P(O)(R')—. In some embodiments, a methylene unit is replaced with —P(O)(NR')—. In some embodiments, a methylene unit is replaced with —P(S)(OR')—. In some embodiments, a methylene unit is replaced with —P(S)(SR')—. In some embodiments, a methylene unit is replaced with —P(S)(R')—. In some embodiments, a methylene unit is replaced with —P(S)(NR')—. In some embodiments, a methylene unit is replaced with —P(R')—. In some embodiments, a methylene unit is replaced with —P(OR')—. In some embodiments, a methylene unit is replaced with —P(SR')—. In some embodiments, a methylene unit is replaced with —P(NR')—. In some embodiments, a methylene unit is replaced with —P(OR')[B(R')$_3$]—. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, each of which may independently be an internucleotidic linkage.

In some embodiments, L, e.g., when connected to R, is —CH$_2$—. In some embodiments, L is —C(R)$_2$—, wherein at least one R is not hydrogen. In some embodiments, L is —CHR—. In some embodiments, R is hydrogen. In some embodiments, L is —CHR—, wherein R is not hydrogen. In some embodiments, C of —CHR— is chiral. In some embodiments, L is —(R)—CHR—, wherein C of —CHR— is chiral. In some embodiments, L is —(S)—CHR—, wherein C of —CHR— is chiral. In some embodiments, R is optionally substituted $C_{1-6}$ aliphatic. In some embodiments, R is optionally substituted $C_{1-6}$ alkyl. In some embodiments, R is optionally substituted $C_{1-5}$ aliphatic. In some embodiments, R is optionally substituted $C_{1-5}$ alkyl. In some embodiments, R is optionally substituted $C_{1-4}$ aliphatic. In some embodiments, R is optionally substituted $C_{1-4}$ alkyl. In some embodiments, R is optionally substituted $C_{1-3}$ aliphatic. In some embodiments, R is optionally substituted $C_{1-3}$ alkyl. In some embodiments, R is optionally substituted $C_2$ aliphatic. In some embodiments, R is optionally substituted methyl. In some embodiments, R is $C_{1-6}$ aliphatic. In some embodiments, R is $C_{1-6}$ alkyl. In some embodiments, R is $C_{1-5}$ aliphatic. In some embodiments, R is $C_{1-5}$ alkyl. In some embodiments, R is $C_{1-4}$ aliphatic. In some embodiments, R is $C_{1-4}$ alkyl. In some embodiments, R is $C_{1-3}$ aliphatic. In some embodiments, R is $C_{1-3}$ alkyl. In some embodiments, R is $C_2$ aliphatic. In some embodiments, R is methyl. In some embodiments, R is $C_{1-6}$ haloaliphatic. In some embodiments, R is $C_{1-6}$ haloalkyl. In some embodiments, R is $C_{1-5}$ haloaliphatic. In some embodiments, R is $C_{1-5}$ haloalkyl. In some embodiments, R is $C_{1-4}$ haloaliphatic. In some embodiments, R is $C_{1-4}$ haloalkyl. In some embodiments, R is $C_{1-3}$ haloaliphatic. In some embodiments, R is $C_{1-3}$ haloalkyl. In some embodiments, R is $C_2$ haloaliphatic. In some embodiments, R is methyl substituted with one or more halogen. In some embodiments, R is —CF$_3$. In some embodiments, L is optionally substituted —CH═CH—. In some embodiments, L is optionally substituted (E)-CH═CH—. In some embodiments, L is optionally substituted (Z)—CH═CH—. In some embodiments, L is —C≡C—.

In some embodiments, L comprises at least one phosphorus atom. In some embodiments, at least one methylene unit of L is replaced with —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—.

In some embodiments, $Cy^L$ is an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon.

In some embodiments, $Cy^L$ is monocyclic. In some embodiments, $Cy^L$ is bicyclic. In some embodiments, $Cy^L$ is polycyclic.

In some embodiments, $Cy^L$ is saturated. In some embodiments, $Cy^L$ is partially unsaturated. In some embodiments, $Cy^L$ is aromatic. In some embodiments, $Cy^L$ is or comprises a saturated ring moiety. In some embodiments, $Cy^L$ is or comprises a partially unsaturated ring moiety. In some embodiments, $Cy^L$ is or comprises an aromatic ring moiety.

In some embodiments, $Cy^L$ is an optionally substituted $C_{3-20}$ cycloaliphatic ring as described in the present disclosure (for example, those described for R but tetravalent). In some embodiments, a ring is an optionally substituted saturated $C_{3-20}$ cycloaliphatic ring. In some embodiments, a ring is an optionally substituted partially unsaturated $C_{3-20}$ cycloaliphatic ring. A cycloaliphatic ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is an optionally substituted cyclopropyl moiety. In some embodiments, a ring is an optionally substituted cyclobutyl moiety. In some embodiments, a ring is an optionally substituted cyclopentyl moiety. In some embodiments, a ring is an optionally substituted cyclohexyl moiety. In some embodiments, a ring is an optionally substituted cycloheptyl moiety. In some embodiments, a ring is an optionally substituted cyclooctanyl moiety. In some embodiments, a cycloaliphatic ring is a cycloalkyl ring. In some embodiments, a cycloaliphatic ring is monocyclic. In some embodiments, a cycloaliphatic ring is bicyclic. In some embodiments, a cycloaliphatic ring is polycyclic. In some embodiments, a ring is a cycloaliphatic moiety as described in the present disclosure for R with more valences.

In some embodiments, $Cy^L$ is an optionally substituted 6-20 membered aryl ring. In some embodiments, a ring is an optionally substituted tetravalent phenyl moiety. In some embodiments, a ring is a tetravalent phenyl moiety. In some embodiments, a ring is an optionally substituted naphthalene moiety. A ring can be of different size as described in the present disclosure. In some embodiments, an aryl ring is 6-membered. In some embodiments, an aryl ring is 10-membered. In some embodiments, an aryl ring is 14-membered. In some embodiments, an aryl ring is monocyclic. In some embodiments, an aryl ring is bicyclic. In some embodiments, an aryl ring is polycyclic. In some embodiments, a ring is an aryl moiety as described in the present disclosure for R with more valences.

In some embodiments, $Cy^L$ is an optionally substituted 5-20 membered heteroaryl ring having 1-10 heteroatoms independently selected from oxygen, nitrogen, sulfur, phosphorus and silicon. In some embodiments, $Cy^L$ is an optionally substituted 5-20 membered heteroaryl ring having 1-10 heteroatoms independently selected from oxygen, nitrogen, and sulfur. In some embodiments, as described in the present disclosure, heteroaryl rings can be of various sizes and contain various numbers and/or types of heteroatoms. In some embodiments, a heteroaryl ring contains no more than one heteroatom. In some embodiments, a heteroaryl ring contains more than one heteroatom. In some embodiments, a heteroaryl ring contains no more than one type of heteroatom. In some embodiments, a heteroaryl ring contains more than one type of heteroatoms. In some embodiments, a heteroaryl ring is 5-membered. In some embodiments, a heteroaryl ring is 6-membered. In some embodiments, a heteroaryl ring is 8-membered. In some embodiments, a heteroaryl ring is 9-membered. In some embodiments, a heteroaryl ring is 10-membered. In some embodiments, a heteroaryl ring is monocyclic. In some embodiments, a heteroaryl ring is bicyclic. In some embodiments, a heteroaryl ring is polycyclic. In some embodiments, a heteroaryl ring is a nucleobase moiety, e.g., A, T, C, G, U, etc. In some embodiments, a ring is a heteroaryl moiety as described in the present disclosure for R with more valences.

In some embodiments, $Cy^L$ is a 3-20 membered heterocyclyl ring having 1-10 heteroatoms independently selected from oxygen, nitrogen, sulfur, phosphorus and silicon. In some embodiments, $Cy^L$ is a 3-20 membered heterocyclyl ring having 1-10 heteroatoms independently selected from oxygen, nitrogen, and sulfur. In some embodiments, a heterocyclyl ring is saturated. In some embodiments, a heterocyclyl ring is partially unsaturated. A heterocyclyl ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. Heterocyclyl rings can contain various numbers and/or types of heteroatoms. In some embodiments, a heterocyclyl ring contains no more than one heteroatom. In some embodiments, a heterocyclyl ring contains more than one heteroatom. In some embodiments, a heterocyclyl ring contains no more than one type of heteroatom. In some embodiments, a heterocyclyl ring contains more than one type of heteroatoms. In some embodiments, a heterocyclyl ring is monocyclic. In some embodiments, a heterocyclyl ring is bicyclic. In some embodiments, a heterocyclyl ring is polycyclic. In some embodiments, a ring is a heterocyclyl moiety as described in the present disclosure for R with more valences.

As readily appreciated by a person having ordinary skill in the art, many suitable ring moieties are extensively described in and can be used in accordance with the present disclosure, for example, those described for R (which may have more valences for $Cy^L$).

In some embodiments, $Cy^L$ is a sugar moiety in a nucleic acid. In some embodiments, $Cy^L$ is an optionally substituted furanose moiety. In some embodiments, $Cy^L$ is a pyranose moiety. In some embodiments, $Cy^L$ is an optionally substituted furanose moiety found in DNA. In some embodiments, $Cy^L$ is an optionally substituted furanose moiety found in RNA. In some embodiments, $Cy^L$ is an optionally substituted 2'-deoxyribofuranose moiety. In some embodiments, $Cy^L$ is an optionally substituted ribofuranose moiety. In some embodiments, substitutions provide sugar modifications as described in the present disclosure. In some embodiments, an optionally substituted 2'-deoxyribofuranose moiety and/or an optionally substituted ribofuranose moiety comprise substitution at a 2'-position. In some embodiments, a 2'-position is a 2'-modification as described in the present disclosure. In some embodiments, a 2'-modification is —F. In some embodiments, a 2'-modification is —OR, wherein R is as described in the present disclosure. In some embodiments, R is not hydrogen. In some embodiments, $Cy^L$ is a modified sugar moiety, such as a sugar moiety in LNA, alpha-L-LNA or GNA. In some embodiments, $Cy^L$ is a modified sugar moiety, such as a sugar moiety in ENA. In some embodiments, $Cy^L$ is a terminal sugar moiety of an oligonucleotide, connecting an internucleotidic linkage and a nucleobase. In some embodiments, $Cy^L$ is a terminal sugar moiety of an oligonucleotide, for example, when that terminus is connected to a solid support optionally through a linker. In some embodiments, $Cy^L$ is a sugar moiety connecting two internucleotidic linkages and a nucleobase.

Example sugars and sugar moieties are extensively described in the present disclosure.

In some embodiments, $Cy^L$ is a nucleobase moiety. In some embodiments, a nucleobase is a natural nucleobase, such as A, T, C, G, U, etc. In some embodiments, a nucleobase is a modified nucleobase. In some embodiments, $Cy^L$ is optionally substituted nucleobase moiety selected from A, T, C, G, U, and 5 mC. Example nucleobases and nucleobase moieties are extensively described in the present disclosure.

In some embodiments, two $Cy^L$ moieties are bonded to each other, wherein one $Cy^L$ is a sugar moiety and the other is a nucleobase moiety. In some embodiments, such a sugar moiety and nucleobase moiety forms a nucleoside moiety. In some embodiments, a nucleoside moiety is natural. In some embodiments, a nucleoside moiety is modified. In some embodiments, $Cy^L$ is an optionally substituted natural nucleoside moiety selected from adenosine, 5-methyluridine, cytidine, guanosine, uridine, 5-methylcytidine, 2'-deoxyadenosine, thymidine, 2'-deoxycytidine, 2'-deoxyguanosine, 2'-deoxyuridine, and 5-methyl-2'-deoxycytidine. Example nucleosides and nucleosides moieties are extensive described in the present disclosure.

In some embodiments, for example in $L^s$, $Cy^L$ is an optionally substituted nucleoside moiety bonded to an internucleotidic linkage, for example, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, —OP(OR')[B(R')$_3$]O—, etc., which may form an optionally substituted nucleotidic unit. Example nucleotides and nucleosides moieties are extensive described in the present disclosure. In some embodiments, -Cy- is an optionally substituted bivalent 3-30 membered carbocyclylene. In some embodiments, -Cy- is an optionally substituted bivalent 6-30 membered arylene. In some embodiments, -Cy- is an optionally substituted bivalent 5-30 membered heteroarylene having 1-10 heteroatoms independently selected from oxygen, nitrogen and sulfur. In some embodiments, -Cy- is an optionally substituted bivalent 3-30 membered heterocyclylene having 1-10 heteroatoms independently selected from oxygen, nitrogen, sulfur, phosphorus and silicon. In some embodiments, -Cy- is an optionally substituted bivalent 5-30 membered heteroarylene having 1-5 heteroatoms independently selected from oxygen, nitrogen and sulfur. In some embodiments, -Cy- is an optionally substituted bivalent 3-30 membered heterocyclylene having 1-5 heteroatoms independently selected from oxygen, nitrogen, sulfur, phosphorus and silicon.

In some embodiments, each Ring A is independently an optionally substituted 3-20 membered monocyclic, bicyclic or polycyclic ring having 0-10 heteroatoms independently selected from oxygen, nitrogen, sulfur, phosphorus and silicon. In some embodiments, Ring A is an optionally substituted ring, which ring is as described in the present disclosure. In some embodiments, a ring is

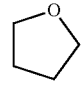

In some embodiments, a ring is

In some embodiments, Ring A is or comprises a ring of a sugar moiety. In some embodiments, Ring A is or comprises a ring of a modified sugar moiety. In some embodiments, each Ring $A^s$ is independently Ring A as described in the present disclosure, for example, in some embodiments, each Ring $A^s$ is independently Ring A, wherein Ring A is optionally substituted

In some embodiments, a sugar unit is of the structure

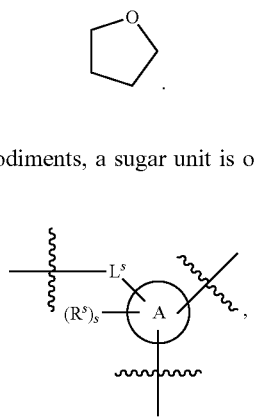

wherein each variable is independently as described in the present disclosure. In some embodiments, a nucleoside unit is of the structure

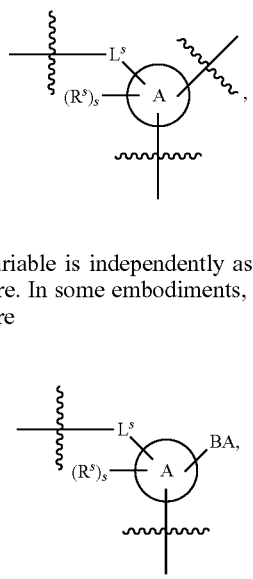

wherein each variable is independently as described in the present disclosure. In some embodiments, a nucleotide unit, e.g., $Nu^M$, $Nu^O$, etc., is of the structure

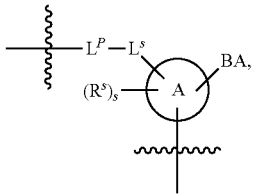

wherein each variable is independently as described in the present disclosure. In some embodiments, for $Nu^O$, $L^P$ is a natural phosphate linkage, and $L^s$ is —C($R^{5s}$)$_2$— as described in the present disclosure.

In some embodiments, $L^s$ is —C($R^{5s}$)$_2$— and

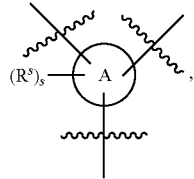

is as described in the present disclosure.

In some embodiments,

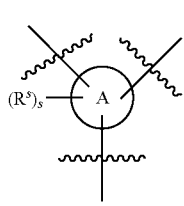 is 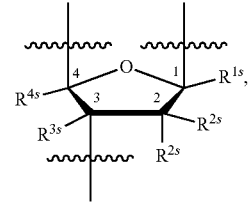,

BA is connected at C1, and each of $R^{1s}$, $R^{2s}$, $R^{3s}$, $R^{4s}$ and $R^{5s}$ is independently as described in the present disclosure. In some embodiments,

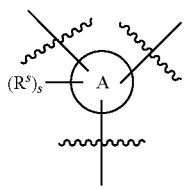 is 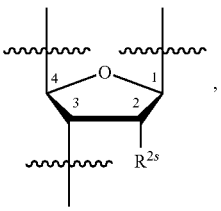, wherein $R^{2s}$ is as described in the present disclosure. In some embodiments,

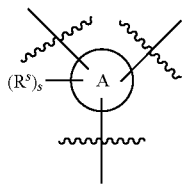 is 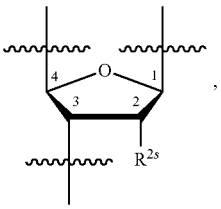, wherein $R^{2s}$ is not —OH. In some embodiments,

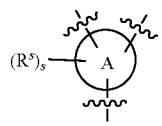 is 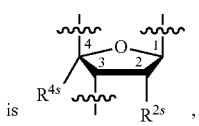, wherein $R^{2s}$ and $R^{4s}$ are R, and the two R groups are taken together with their intervening atoms to form an optionally substituted ring. In some embodiments,

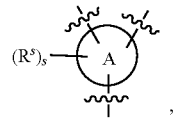

or Ring A, is optionally substituted

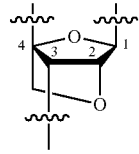

In some embodiments,

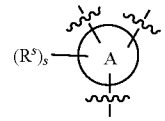

or Ring A, is

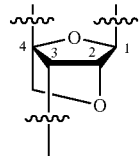

In some embodiments,

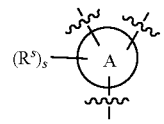

or Ring A, is

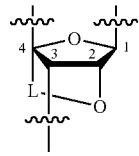

In some embodiments, each of $R^{1s}$, $R^{2s}$, $R^{3s}$, $R^{4s}$, and $R^{5s}$ is independently $R^s$, wherein $R^s$ is as described in the present disclosure.

In some embodiments, $R^{1s}$ is $R^s$ wherein $R^s$ is as described in the present disclosure. In some embodiments, $R^{1s}$ is at 1'-position (BA is at 1'-position). In some embodiments, $R^{1s}$ is —H. In some embodiments, $R^{1s}$ is —F. In some embodiments, $R^{1s}$ is —Cl. In some embodiments, $R^{1s}$ is —Br. In some embodiments, $R^{1s}$ is —I. In some embodiments, $R^{1s}$ is —CN. In some embodiments, $R^{1s}$ is —N$_3$. In some embodiments, $R^{1s}$ is —NO. In some embodiments, $R^{1s}$ is —NO$_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1s}$ is L-L-N(R')$_2$. In some embodiments, $R^{1s}$ is —N(R')$_2$. In some embodiments, $R^{1s}$ is —OR', wherein R' is optionally substituted $C_{1-6}$ aliphatic. In some embodiments, $R^{1s}$ is —OR', wherein R' is optionally substituted $C_{1-6}$ alkyl. In some embodiments, $R^{1s}$ is —OMe. In some embodiments, $R^{1s}$ is -MOE. In some embodiments, $R^{1s}$ is hydrogen. In some embodiments, $R^s$ at one 1'-position is hydrogen, and $R^s$ at the other 1'-position is not hydrogen as described herein. In some embodiments, $R^s$ at both 1'-positions are hydrogen. In some embodiments, $R^s$ at one 1'-position is hydrogen, and the other 1'-position is connected to an internucleotidic linkage. In some embodiments, $R^{1s}$ is —F. In some embodiments, $R^{1s}$ is —Cl. In some embodiments, $R^{1s}$ is —Br. In some embodiments, $R^{1s}$ is —I. In some embodiments, $R^{1s}$ is —CN. In some embodiments, $R^{1s}$ is —N$_3$. In some embodiments, $R^{1s}$ is —NO. In some embodiments, $R^{1s}$ is —NO$_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1s}$ is -L-N(R')$_2$. In some embodiments, $R^{1s}$ is —N(R')$_2$. In some embodiments, $R^{1s}$ is —OR', wherein R' is optionally substituted $C_{1-6}$ aliphatic. In some embodiments, $R^{1s}$ is —OR', wherein R' is optionally substituted $C_{1-6}$ alkyl. In some embodiments, $R^{1s}$ is —OH. In some embodiments, $R^{1s}$ is —OMe. In some embodiments, $R^{1s}$ is -MOE. In some embodiments, $R^{1s}$ is hydrogen. In some embodiments, one $R^{1s}$ at a 1'-position is hydrogen, and the other $R^{1s}$ at the other 1'-position is not hydrogen as described herein. In some embodiments, $R^{1s}$ at both 1'-positions are hydrogen. In some embodiments, $R^{1s}$ is —O-L$^s$-OR'. In some embodiments, $R^{1s}$ is —O-L$^s$-OR', wherein L$^s$ is optionally substituted $C_{1-6}$ alkylene, and R' is optionally substituted $C_{1-6}$ aliphatic. In some embodiments, $R^{1s}$ is —O—(optionally substituted $C_{1-6}$ alkylene)-OR'. In some embodiments, $R^{1s}$ is —O—(optionally substituted $C_{1-6}$ alkylene)-OR', wherein R' is optionally substituted $C_{1-6}$ alkyl. In some embodiments, $R^{1s}$ is —OCH$_2$CH$_2$OMe.

In some embodiments, $R^{2s}$ is $R^s$ wherein $R^s$ is as described in the present disclosure. In some embodiments, if there are two $R^{2s}$ at the 2'-position, one $R^{2s}$ is —H and the other is not. In some embodiments, $R^{2s}$ is at 2'-position (BA is at 1'-position). In some embodiments, $R^{2s}$ is —H. In some embodiments, $R^{2s}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2'}$ is —SR'. In some embodiments, $R^{2s}$ is L-L-N(R')$_2$. In some embodiments, $R^{2s}$ is —N(R')$_2$. In some embodiments, $R^{2s}$ is —OR', wherein R' is optionally substituted $C_{1-6}$ aliphatic. In some embodiments, $R^{2'}$ is —OR', wherein R' is optionally substituted $C_{1-6}$ alkyl. In some embodiments, $R^{2s}$ is —OMe. In some embodiments, $R^{2s}$ is -MOE. In some embodiments, $R^{2s}$ is hydrogen. In some embodiments, $R^s$ at one 2'-position is hydrogen, and $R^s$ at the other 2'-position is not hydrogen as described herein. In some embodiments, $R^s$ at both 2'-positions are hydrogen. In some embodiments, $R^s$ at one 2'-position is hydrogen, and the other 2'-position is connected to an internucleotidic linkage. In some embodiments, $R^{2'}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2s}$ is —SR'. In some embodiments, $R^{2s}$ is -L-N(R')$_2$. In some embodiments, $R^{2s}$ is —N(R')$_2$. In some embodiments, $R^{2s}$ is —OR', wherein R' is optionally substituted $C_{1-6}$ aliphatic. In some embodiments, $R^{2'}$ is —OR', wherein R' is optionally substituted $C_{1-6}$ alkyl. In some embodiments, $R^{2'}$ is —OH. In some embodiments, $R^{2s}$ is —OMe. In some embodiments, $R^{2'}$ is -MOE. In some embodiments, $R^{2s}$ is hydrogen. In some embodiments, one $R^{2s}$ at a 2'-position is hydrogen, and the other $R^{2s}$ at the other 2'-position is not hydrogen as described herein. In some embodiments, $R^{2s}$ at both 2'-positions are hydrogen. In some embodiments, $R^{2s}$ is —O-L$^s$-OR'. In some embodiments, $R^{2s}$ is —O-L$^s$-OR', wherein L$^s$ is optionally substituted $C_{1-6}$ alkylene, and R' is optionally substituted $C_{1-6}$ aliphatic. In some embodiments, $R^{2s}$ is —O—(optionally substituted $C_{1-6}$ alkylene)-OR'. In some embodiments, $R^{2s}$ is —O—(optionally substituted $C_{1-6}$ alkylene)-OR', wherein R' is optionally substituted $C_{1-6}$ alkyl. In some embodiments, $R^{2s}$ is —OCH$_2$CH$_2$OMe.

In some embodiments, $R^{3s}$ is $R^s$ wherein $R^s$ is as described in the present disclosure. In some embodiments, $R^{3s}$ is at 3'-position (BA is at 1'-position). In some embodiments, $R^{3s}$ is —H. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —N$_3$. In some embodiments, $R^{3s}$ is —NO. In some embodiments, $R^{3s}$ is —NO$_2$. In some embodiments, $R^{3s}$ is -L-R'. In some embodiments, $R^{3s}$ is —R'. In some embodiments, $R^{3s}$ is -L-OR'. In some embodiments, $R^{3s}$ is —OR'. In some embodiments, $R^{3s}$ is -L-SR'. In some embodiments, $R^{3s}$ is —SR'. In some embodiments, $R^{3s}$ is -L-N(R')$_2$. In some embodiments, $R^{3s}$ is —N(R')$_2$. In some embodiments, $R^{3s}$ is —OR', wherein R' is optionally substituted $C_{1-6}$ aliphatic. In some embodiments, $R^{3s}$ is —OR', wherein R' is optionally substituted $C_{1-6}$ alkyl. In some embodiments, $R^{3s}$ is —OMe. In some embodiments, $R^{3s}$ is -MOE. In some embodiments, $R^{3s}$ is hydrogen. In some embodiments, $R^s$ at one 3'-position is hydrogen, and $R^s$ at the other 3'-position is not hydrogen as described herein. In some embodiments, $R^s$ at both 3'-positions are hydrogen. In some embodiments, $R^s$ at one 3'-position is hydrogen, and the other 3'-position is connected to an internucleotidic linkage. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —N$_3$. In some embodiments, $R^{3s}$ is —NO. In some embodiments, $R^{3s}$ is —NO$_2$. In some embodiments, $R^{3s}$ is -L-R'. In some embodiments, $R^{3s}$ is —R'. In some embodiments, $R^{3s}$ is -L-OR'. In some embodiments, $R^{3s}$ is —OR'. In some embodiments, $R^{3s}$ is -L-SR'. In some embodiments, $R^{3s}$ is —SR'. In some embodiments, $R^{3s}$ is L-L-N(R')$_2$. In some embodiments, $R^{3s}$ is —N(R')$_2$. In some embodiments, $R^{3s}$ is —OR', wherein R' is optionally substituted $C_{1-6}$ aliphatic. In some embodiments, $R^{3s}$ is —OR', wherein R' is optionally substituted $C_{1-6}$ alkyl. In some embodiments, $R^{3s}$ is —OH. In some embodiments, R3S is —OMe. In some embodiments, $R^{3s}$ is -MOE. In some embodiments, $R^{3s}$ is hydrogen.

In some embodiments, $R^{4s}$ is $R^s$ wherein $R^s$ is as described in the present disclosure. In some embodiments, $R^{4s}$ is at 4'-position (BA is at 1'-position). In some embodiments, $R^{4s}$ is —H. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —N$_3$. In some embodiments, $R^{4s}$ is —NO. In some embodiments, $R^{4s}$ is —NO$_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is -L-N(R')$_2$. In some embodiments, $R^{4s}$ is —N(R')$_2$. In some embodiments, $R^{4s}$ is —OR', wherein R' is optionally substituted $C_{1-6}$ aliphatic. In some embodiments, $R^{4s}$ is —OR', wherein R' is optionally substituted $C_{1-6}$ alkyl. In some embodiments, $R^{4s}$ is —OMe. In some embodiments, $R^{4s}$ is -MOE. In some embodiments, $R^{4s}$ is hydrogen. In some embodiments, $R^s$ at one 4'-position is hydrogen, and $R^s$ at the other 4'-position is not hydrogen as described herein. In some embodiments, $R^s$ at both 4'-positions are hydrogen. In some embodiments, $R^s$ at one 4'-position is hydrogen, and the other 4'-position is connected to an internucleotidic linkage. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —N$_3$. In some embodiments, $R^{4s}$ is —NO. In some embodiments, $R^{4s}$ is —NO$_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is L-L-N(R')$_2$. In some embodiments, $R^{4s}$ is —N(R')$_2$. In some embodiments, $R^{4s}$ is —OR', wherein R' is optionally substituted $C_{1-6}$ aliphatic. In some embodiments, $R^{4s}$ is —OR', wherein R' is optionally substituted $C_{1-6}$ alkyl. In some embodiments, $R^{4s}$ is —OH. In some embodiments, $R^{4s}$ is —OMe. In some embodiments, $R^{4s}$ is -MOE. In some embodiments, $R^{4s}$ is hydrogen.

In some embodiments, $R^{5s}$ is $R^s$ wherein $R^s$ is as described in the present disclosure. In some embodiments, $R^{5s}$ is R' wherein R' is as described in the present disclosure. In some embodiments, $R^{5s}$ is —H. In some embodiments, two or more $R^{5s}$ are connected to the same carbon atom, and at least one is not —H. In some embodiments, $R^{5s}$ is not —H. In some embodiments, R5S is —F. In some embodiments, $R^{5s}$ is —Cl. In some embodiments, $R^{5s}$ is —Br. In some embodiments, R5S is —I. In some embodiments, $R^{5s}$ is —CN. In some embodiments, $R^{5s}$ is —N$_3$. In some embodiments, $R^{5s}$ is —NO. In some embodiments, $R^{5s}$ is —NO$_2$. In some embodiments, $R^{5s}$ is -L-R'. In some embodiments, $R^{5s}$ is —R'. In some embodiments, $R^{5s}$ is -L-OR'. In some embodiments, $R^{5s}$ is —OR'. In some embodiments, $R^{5s}$ is -L-SR'. In some embodiments, $R^{5s}$ is —SR'. In some embodiments, $R^{5s}$ is L-L-N(R')$_2$. In some embodiments, $R^{5s}$ is —N(R')$_2$. In some embodiments, $R^{5s}$ is —OR', wherein R' is optionally substituted $C_{1-6}$ aliphatic. In some embodiments, $R^{5s}$ is —OR', wherein R' is optionally substituted $C_{1-6}$ alkyl. In some embodiments, $R^{5s}$ is —OH. In some embodiments, $R^{5s}$ is —OMe. In some embodiments, $R^{5s}$ is -MOE. In some embodiments, $R^{5s}$ is hydrogen.

In some embodiments, $R^{5s}$ is optionally substituted $C_{1-6}$ aliphatic as described in the present disclosure, e.g., $C_{1-6}$ aliphatic embodiments described for R or other variables. In some embodiments, $R^{5s}$ is optionally substituted $C_{1-6}$ alkyl. In some embodiments, $R^{5s}$ is methyl. In some embodiments, $R^{5s}$ is ethyl.

In some embodiments, $R^{5s}$ is a protected hydroxyl group suitable for oligonucleotide synthesis. In some embodiments, $R^{5s}$ is —OR', wherein R' is optionally substituted $C_{1-6}$ aliphatic. In some embodiments, $R^{5s}$ is DMTrO—. Example protecting groups are widely known for use in accordance with the present disclosure. For additional examples, see Greene, T. W.; Wuts, P. G. M. Protective Groups in Organic Synthesis, 2nd ed.; Wiley: New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, protecting groups of each of which are hereby incorporated by reference.

In some embodiments, two or more of $R^{1s}$, $R^{2s}$, $R^{3s}$, $R^{4s}$, and $R^{5s}$ are R and can be taken together with intervening atom(s) to form a ring as described in the present disclosure. In some embodiments, $R^{2s}$ and $R^{4s}$ are R taken together to form a ring, and a sugar moiety can be a bicyclic sugar moiety, e.g., a LNA sugar moiety.

In some embodiments, $L^s$ is —C($R^{5s}$)$_2$—, wherein each $R^{5s}$ is independently as described in the present disclosure. In some embodiments, one of $R^{5s}$ is H and the other is not H. In some embodiments, none of $R^{5s}$ is H. In some embodiments, $L^s$ is —CHR$^{5s}$—, wherein each $R^{5s}$ is independently as described in the present disclosure. In some embodiments, —C($R^{5s}$)$_2$— is 5'-C, optionally substituted, of a sugar moiety. In some embodiments, the C of —C($R^{5s}$)$_2$— is of R configuration. In some embodiments, the C of —C($R^{5s}$)$_2$— is of S configuration. As described in the present disclosure, in some embodiments, $R^{5s}$ is optionally substituted $C_{1-6}$ aliphatic; in some embodiments, $R^{5s}$ is methyl.

In some embodiments, provided compounds comprise one or more bivalent or multivalent optionally substituted rings, e.g., Ring A, Cy$^L$, those formed by two or more R groups (R and (combinations of) variables that can be R) taken together, etc. In some embodiments, a ring is a cycloaliphatic, aryl, heteroaryl, or heterocyclyl group as described for R but bivalent or multivalent. As appreciated by those skilled in the art, ring moieties described for one variable, e.g., Ring A, can also be applicable to other variables, e.g., Cy$^L$, if requirements of the other variables, e.g., number of heteroatoms, valence, etc., are satisfied. Example rings are extensively described in the present disclosure.

In some embodiments, a ring, e.g., in Ring A, R, etc. which is optionally substituted, is a 3-20 membered monocyclic, bicyclic or polycyclic ring having 0-10 heteroatoms independently selected from oxygen, nitrogen, sulfur, phosphorus and silicon.

In some embodiments, a ring can be of any size within its range, e.g., 3, 4, 5, 6, 7, 8, 9, 10, 11, 12, 13, 14, 15, 16, 17, 18, 19, or 20-membered.

In some embodiments, a ring is monocyclic. In some embodiments, a ring is saturated and monocyclic. In some embodiments, a ring is monocyclic and partially saturated. In some embodiments, a ring is monocyclic and aromatic.

In some embodiments, a ring is bicyclic. In some embodiments, a ring is polycyclic. In some embodiments, a bicyclic or polycyclic ring comprises two or more monocyclic ring moieties, each of which can be saturated, partially saturated, or aromatic, and each which can contain no or 1-10 heteroatoms. In some embodiments, a bicyclic or polycyclic ring comprises a saturated monocyclic ring. In some embodiments, a bicyclic or polycyclic ring comprises a saturated monocyclic ring containing no heteroatoms. In some embodiments, a bicyclic or polycyclic ring comprises a saturated monocyclic ring comprising one or more heteroatoms. In some embodiments, a bicyclic or polycyclic ring comprises a partially saturated monocyclic ring. In some embodiments, a bicyclic or polycyclic ring comprises a partially saturated monocyclic ring containing no heteroatoms. In some embodiments, a bicyclic or polycyclic ring comprises a partially saturated monocyclic ring comprising one or more heteroatoms. In some embodiments, a bicyclic or polycyclic ring comprises an aromatic monocyclic ring. In some embodiments, a bicyclic or polycyclic ring comprises an aromatic monocyclic ring containing no heteroatoms. In some embodiments, a bicyclic or polycyclic ring comprises an aromatic monocyclic ring comprising one or more heteroatoms. In some embodiments, a bicyclic or polycyclic ring comprises a saturated ring and a partially saturated ring, each of which independently contains one or more heteroatoms. In some embodiments, a bicyclic ring comprises a saturated ring and a partially saturated ring, each of which independently comprises no, or one or more heteroatoms. In some embodiments, a bicyclic ring comprises an aromatic ring and a partially saturated ring, each of which independently comprises no, or one or more heteroatoms. In some embodiments, a polycyclic ring comprises a saturated ring and a partially saturated ring, each of which independently comprises no, or one or more heteroatoms. In some embodiments, a polycyclic ring comprises an aromatic ring and a partially saturated ring, each of which independently comprises no, or one or more heteroatoms. In some embodiments, a polycyclic ring comprises an aromatic ring and a saturated ring, each of which independently comprises no, or one or more heteroatoms. In some embodiments, a polycyclic ring comprises an aromatic ring, a saturated ring, and a partially saturated ring, each of which independently comprises no, or one or more heteroatoms. In some embodiments, a ring comprises at least one heteroatom. In some embodiments, a ring comprises at least one nitrogen atom. In some embodiments, a ring comprises at least one oxygen atom. In some embodiments, a ring comprises at least one sulfur atom.

As appreciated by those skilled in the art in accordance with the present disclosure, a ring is typically optionally substituted. In some embodiments, a ring is unsubstituted. In some embodiments, a ring is substituted. In some embodiments, a ring is substituted on one or more of its carbon atoms. In some embodiments, a ring is substituted on one or more of its heteroatoms. In some embodiments, a ring is substituted on one or more of its carbon atoms, and one or more of its heteroatoms. In some embodiments, two or more substituents can be located on the same ring atom. In some embodiments, all available ring atoms are substituted. In some embodiments, not all available ring atoms are substituted. In some embodiments, in provided structures where rings are indicated to be connected to other structures (e.g., Ring A in),

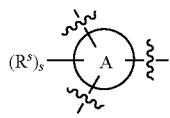

"optionally substituted" is to mean that, besides those structures already connected, remaining substitutable ring positions, if any, are optionally substituted.

In some embodiments, a ring is a bivalent or multivalent $C_{3-30}$ cycloaliphatic ring. In some embodiments, a ring is a bivalent or multivalent $C_{3-20}$ cycloaliphatic ring. In some embodiments, a ring is a bivalent or multivalent $C_{3-10}$ cycloaliphatic ring. In some embodiments, a ring is a bivalent or multivalent 3-30 membered saturated or partially unsaturated carbocyclic ring. In some embodiments, a ring is a bivalent or multivalent 3-7 membered saturated or partially unsaturated carbocyclic ring. In some embodiments, a ring is a bivalent or multivalent 3-membered saturated or partially unsaturated carbocyclic ring. In some embodiments, a ring is a bivalent or multivalent 4-membered saturated or partially unsaturated carbocyclic ring. In some embodiments, a ring is a bivalent or multivalent 5-membered saturated or partially unsaturated carbocyclic ring. In some embodiments, a ring is a bivalent or multivalent 6-membered saturated or partially unsaturated carbocyclic ring. In some embodiments, a ring is a bivalent or multivalent 7-membered saturated or partially unsaturated carbocyclic ring. In some embodiments, a ring is a bivalent or multivalent cyclohexyl ring. In some embodiments, a ring is a bivalent or multivalent cyclopentyl ring. In some embodiments, a ring is a bivalent or multivalent cyclobutyl ring. In some embodiments, a ring is a bivalent or multivalent cyclopropyl ring.

In some embodiments, a ring is a bivalent or multivalent $C_{6-30}$ aryl ring. In some embodiments, a ring is a bivalent or multivalent phenyl ring.

In some embodiments, a ring is a bivalent or multivalent 8-10 membered bicyclic saturated, partially unsaturated or aryl ring. In some embodiments, a ring is a bivalent or multivalent 8-10 membered bicyclic saturated ring. In some embodiments, a ring is a bivalent or multivalent 8-10 membered bicyclic partially unsaturated ring. In some embodiments, a ring is a bivalent or multivalent 8-10 membered bicyclic aryl ring. In some embodiments, a ring is a bivalent or multivalent naphthyl ring.

In some embodiments, a ring is a bivalent or multivalent 5-30 membered heteroaryl ring having 1-10 heteroatoms independently selected from oxygen, nitrogen, sulfur, phosphorus and silicon. In some embodiments, a ring is a bivalent or multivalent 5-30 membered heteroaryl ring having 1-10 heteroatoms independently selected from oxygen, nitrogen, and sulfur. In some embodiments, a ring is a bivalent or multivalent 5-30 membered heteroaryl ring having 1-5 heteroatoms independently selected from oxygen, nitrogen, sulfur, phosphorus and silicon. In some embodiments, a ring is a bivalent or multivalent 5-30 membered heteroaryl ring having 1-5 heteroatoms independently selected from oxygen, nitrogen, and sulfur.

In some embodiments, a ring is a bivalent or multivalent 5-6 membered monocyclic heteroaryl ring having 1-4 heteroatoms independently selected from nitrogen, oxygen, and sulfur. In some embodiments, a ring is a bivalent or multivalent 5-6 membered monocyclic heteroaryl ring having 1-3 heteroatoms independently selected from nitrogen, sulfur, and oxygen.

In some embodiments, a ring is a bivalent or multivalent 5-membered monocyclic heteroaryl ring having 1-4 heteroatoms independently selected from nitrogen, oxygen or sulfur. In some embodiments, a ring is a bivalent or multivalent 6-membered monocyclic heteroaryl ring having 1-4 heteroatoms independently selected from nitrogen, oxygen, and sulfur.

In certain embodiments, a ring is a bivalent or multivalent 8-10 membered bicyclic heteroaryl ring having 1-4 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-5 heteroatoms independently selected from nitrogen, oxygen, and sulfur. In certain embodiments, a ring is a bivalent or multivalent 6,6-fused heteroaryl ring having 1-4 heteroatoms independently selected from nitrogen, oxygen, and sulfur.

In some embodiments, a ring is a bivalent or multivalent 3-30 membered heterocyclic ring having 1-10 heteroatoms independently selected from oxygen, nitrogen, sulfur, phosphorus and silicon. In some embodiments, a ring is a bivalent or multivalent 3-7 membered saturated or partially unsaturated heterocyclic ring having 1-3 heteroatoms independently selected from nitrogen, oxygen, and sulfur. In certain embodiments, a ring is a bivalent or multivalent 5-7 membered partially unsaturated monocyclic ring having 1-3 heteroatoms independently selected from nitrogen, oxygen, and sulfur. In certain embodiments, a ring is a bivalent or multivalent 5-6 membered partially unsaturated monocyclic ring having 1-3 heteroatoms independently selected from nitrogen, oxygen, and sulfur. In certain embodiments, a ring is a bivalent or multivalent 5-membered partially unsaturated monocyclic ring having 1-3 heteroatoms independently selected from nitrogen, oxygen, and sulfur. In certain embodiments, a ring is a bivalent or multivalent 6-membered partially unsaturated monocyclic ring having 1-3 heteroatoms independently selected from nitrogen, oxygen, and sulfur. In certain embodiments, a ring is a bivalent or multivalent 7-membered partially unsaturated monocyclic ring having 1-3 heteroatoms independently selected from nitrogen, oxygen, and sulfur. In some embodiments, a ring is a bivalent or multivalent 3-membered heterocyclic ring having one heteroatom selected from nitrogen, oxygen or sulfur. In some embodiments, a ring is a bivalent or multivalent 4-membered heterocyclic ring having 1-3 heteroatoms independently selected from nitrogen, oxygen, and sulfur. In some embodiments, a ring is a bivalent or multivalent 5-membered heterocyclic ring having 1-3 heteroatoms independently selected from nitrogen, oxygen, and sulfur. In some embodiments, a ring is a bivalent or multivalent 6-membered heterocyclic ring having 1-3 heteroatoms independently selected from nitrogen, oxygen, and sulfur. In some embodiments, a ring is a bivalent or multivalent 7-membered heterocyclic ring having 1-3 heteroatoms independently selected from nitrogen, oxygen, and sulfur.

In some embodiments, a ring is a bivalent or multivalent 7-10 membered bicyclic saturated or partially unsaturated heterocyclic ring having 1-5 heteroatoms independently selected from nitrogen, oxygen, and sulfur. In some embodiments, a ring is a bivalent or multivalent 8-10 membered bicyclic heteroaryl ring having 1-5 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In certain embodiments, a ring is a bivalent or multivalent 6,6-fused heteroaryl ring having 1-5 heteroatoms independently selected from nitrogen, oxygen, and sulfur.

In some embodiments, a ring formed by two or more groups taken together, which is typically optionally substituted, is a monocyclic saturated 5-7 membered ring having no additional heteroatoms in addition to intervening heteroatoms, if any. In some embodiments, a ring formed by two or more groups taken together is a monocyclic saturated 5-membered ring having no additional heteroatoms in addition to intervening heteroatoms, if any. In some embodiments, a ring formed by two or more groups taken together is a monocyclic saturated 6-membered ring having no additional heteroatoms in addition to intervening heteroatoms, if any. In some embodiments, a ring formed by two or more groups taken together is a monocyclic saturated 7-membered ring having no additional heteroatoms in addition to intervening heteroatoms, if any.

In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, and sulfur. In some embodiments, a ring formed by two or more groups taken together is a bicyclic and saturated 8-10 membered bicyclic ring having no additional heteroatoms in addition to intervening heteroatoms, if any. In some embodiments, a ring formed by two or more groups taken together is a bicyclic and saturated 8-membered bicyclic ring having no additional heteroatoms in addition to intervening heteroatoms, if any. In some embodiments, a ring formed by two or more groups taken together is a bicyclic and saturated 9-membered bicyclic ring having no additional heteroatoms in addition to intervening heteroatoms, if any. In some embodiments, a ring formed by two or more groups taken together is a bicyclic and saturated 10-membered bicyclic ring having no additional heteroatoms in addition to intervening heteroatoms, if any. In some embodiments, a ring formed by two or more groups taken together is bicyclic and comprises a 5-membered ring fused to a 5-membered ring. In some embodiments, a ring formed by two or more groups taken together is bicyclic and comprises a 5-membered ring fused to a 6-membered ring. In some embodiments, the 5-membered ring comprises one or more intervening nitrogen, phosphorus and oxygen atoms as ring atoms. In some embodiments, a ring formed by two or more groups taken together comprises a ring system having the backbone structure of

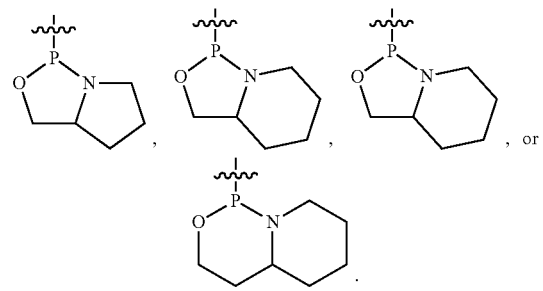

In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, and sulfur.

In some embodiments, a ring formed by two or more groups taken together is monocyclic, bicyclic or polycyclic and comprises a 5-10 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-9 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-8 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-7 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-6 membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 6-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 7-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 8-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 9-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 10-membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 6-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 7-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 8-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 9-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 10-membered ring whose ring atoms consist of carbon atoms and the intervening nitrogen, phosphorus and oxygen atoms.

In some embodiments, rings described herein are unsubstituted. In some embodiments, rings described herein are substituted. In some embodiments, substituents are selected from those described in example compounds provided in the present disclosure.

As described herein, each $L^P$ is independently an internucleotidic linkage as described in the present disclosure, e.g., a natural phosphate linkage, a phosphorothioate diester linkage, a modified internucleotidic linkage, a chiral internucleotidic linkage, a non-negatively charged internucleotidic linkage, etc., In some embodiments, each $L^P$ is independently a linkage having the structure of formula I. In some embodiments, one or more $L^P$ independently have the structure of formula I, I-a-1, I-a-2, I-b, I-c, I-d, I-e, I-n-1, I-n-2, I-n-3, II, II-a-1, II-a-2, II-b-1, II-b-2, II-c-1, II-c-2, II-d-1, or II-d-2, or a salt form thereof. In some embodiments, at least one $L^P$ is a non-negatively charged internucleotidic linkage. In some embodiments, at least one $L^P$ is a neutral internucleotidic linkage. In some embodiments, one or more $L^P$ independently have the structure of formula I-n-1, I-n-2, I-n-3, II, II-a-1, II-a-2, II-b-1, II-b-2, II-c-1, II-c-2, II-d-1, or II-d-2, or a salt form thereof.

In some embodiments, $L^{3E}$ is -$L^s$- or -$L^s$-$L^s$-. In some embodiments, $L^{3E}$ is -$L^s$-. In some embodiments, $L^{3E}$ is -$L^s$-$L^s$-. In some embodiments, $L^{3E}$ is a covalent bond. In some embodiments, $L^{3E}$ is a linker used in oligonucleotide synthesis. In some embodiments, $L^{3E}$ is a linker used in solid phase oligonucleotide synthesis. Various types of linkers are known and can be utilized in accordance with the present disclosure. In some embodiments, a linker is a succinate linker (—O—C(O)—$CH_2$—$CH_2$—C(O)—). In some embodiments, a linker is an oxalyl linker (—O—C(O)—C(O)—). In some embodiments, $L^{3E}$ is a succinyl-piperidine linker (SP) linker. In some embodiments, $L^{3E}$ is a succinyl linker. In some embodiments, $L^{3E}$ is a Q-linker.

In some embodiments, $R^{3E}$ is —R', -$L^s$-R', —OR', or a solid support. In some embodiments, $R^{3E}$ is —R'. In some embodiments, $R^{3E}$ is -$L^s$-R'. In some embodiments, $R^{3E}$ is —OR'. In some embodiments, $R^{3E}$ is a support for oligonucleotide synthesis. In some embodiments, $R^{3E}$ is a solid support. In some embodiments, a solid support is a CPG support. In some embodiments, a solid support is a polystyrene support. In some embodiments, $R^{3E}$ is —H. In some embodiments, -$L^3$-$R^{3E}$ is —H. In some embodiments, $R^{3E}$ is —OH. In some embodiments, -$L^3$-$R^{3E}$ is —OH. In some embodiments, $R^{3E}$ is optionally substituted $C_{1-6}$ aliphatic. In some embodiments, $R^{3E}$ is optionally substituted $C_{1-6}$ alkyl. In some embodiments, $R^{3E}$ is —OR'. In some embodiments, $R^{3E}$ is —OH. In some embodiments, $R^{3E}$ is —OR', wherein R' is not hydrogen. In some embodiments, $R^{3E}$ is —OR', wherein R' is optionally substituted $C_{1-6}$ alkyl. In some embodiments, $R^{3E}$ is a 3'-end cap (e.g., those used in RNAi technologies).

In some embodiments, $R^{3E}$ is a solid support. In some embodiments, $R^{3E}$ is a solid support for oligonucleotide synthesis. Various types of solid support are known and can be utilized in accordance with the present disclosure. In some embodiments, a solid support is HCP. In some embodiments, a solid support is CPG.

In some embodiments, R' is —R, —C(O)R, —C(O)OR, or —S(O)$_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —S(O)$_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is —$(CH_2)_2CN$.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted $C_{1-30}$ heteroaliphatic having 1-10 heteroatoms independently selected from oxygen, nitrogen, sulfur, phosphorus and silicon. In some embodiments, R is optionally substituted $C_{1-20}$ heteroaliphatic having 1-10 heteroatoms. In some embodiments, R is optionally substituted $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted $C_{1-30}$ heteroaliphatic comprising 1-10 groups independently selected from

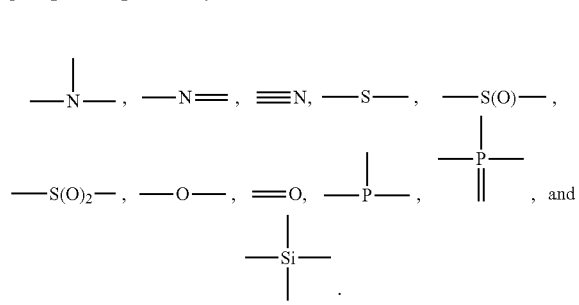

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C=O is formed. In some embodiments, —C=C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, $P^L$ is P(=W). In some embodiments, $P^L$ is P. In some embodiments, $P^L$ is P→B(R')$_3$. In some embodiments, P of $P^L$ is chiral. In some embodiments, P of $P^L$ is Rp. In some embodiments, P of $P^L$ is Sp. In some embodiments, a linkage of formula I is a phosphate linkage or a salt form thereof. In some embodiments, a linkage of formula I is a phosphorothioate linkage or a salt form thereof. In some embodiments, $P^L$ is P*(=W), wherein P* is a chiral linkage phosphorus. In some embodiments, $P^L$ is P*(=O), wherein P* is a chiral linkage phosphorus.

In some embodiments, W is O. In some embodiments, W is S. In some embodiments, W is Se.

In some embodiments, X is —O—. In some embodiments, X is —S—. In some embodiments, Y is —O—. In some embodiments, Z is —O—. In some embodiments, W is —O—, Y is —O—, Z is —O—, and X is —O— or —S—. In some embodiments, W is —S—, Y is —O—, Z is —O—, and X is —O—.

In some embodiments, $R^1$ is R as described in the present disclosure. In some embodiments, $R^1$ is —H.

In some embodiments, $R^5$ is R as described in the present disclosure. In some embodiments, $R^5$ is —H. In some embodiments, —X-$L^s$-$R^5$ comprises or is an optionally substituted moiety of a chiral auxiliary (e.g., H—X-$L^s$-$R^5$ is an optionally substituted (e.g., capped) chiral auxiliary), e.g., as used in chirally controlled oligonucleotide synthesis, such as those described in US 20150211006, US 20150211006, WO 2017015555, WO 2017015575, WO 2017062862, or WO 2017160741, chiral auxiliaries of each of which are incorporated herein by reference.

In some embodiments, a provided oligonucleotide composition, e.g., a chirally controlled oligonucleotide composition, a SMN2 oligonucleotide composition, etc., comprises a plurality of oligonucleotides which have the structure of formula O-I. In some embodiments, an oligonucleotide of formula O-I comprise chemical modifications (e.g., sugar modifications, base modifications, modified internucleotidic linkages, etc., and patterns thereof), stereochemistry (e.g., of chiral linkage phosphorus, etc., and patterns thereof), base sequences, etc., as described in the present disclosure. In some embodiments, a provided chirally controlled SMN2 oligonucleotide composition of formula O-I is a chirally controlled oligonucleotide composition of an oligonucleotide selected from in Table 1A, Table 4, etc., wherein the oligonucleotide comprises at least one chirally controlled internucleotidic linkage.

In some embodiments, the present disclosure provides multimers of oligonucleotides. In some embodiments, at least one of the monomer is a SMN2 oligonucleotide. In some embodiments, a multimer is a multimer of the same oligonucleotides. In some embodiments, a multimer is a multimer of structurally different oligonucleotides. In some embodiments, each oligonucleotide of a multimer performs its functions independently through its own pathways, e.g., RNA interference (RNAi), RNase H dependent, etc. In some embodiments, provided oligonucleotide compositions, e.g., chirally controlled oligonucleotide compositions, SMN2 oligonucleotide compositions, etc., exist in an oligomeric or polymeric form, in which one or more oligonucleotide moieties are linked together by linkers, e.g., L, $L^M$, etc., through nucleobases, sugars, and/or internucleotidic linkages of the oligonucleotide moieties. For example, in some embodiments, a provided multimer compound has the structure of $(A^c)_a$-$L^M$-$(A^c)_b$, wherein each variable is independently as described in the present disclosure.

In some embodiments, a provided compound, e.g., an oligonucleotide of a provided composition, has the structure of:

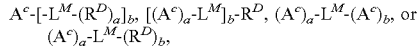

or a salt thereof, wherein:

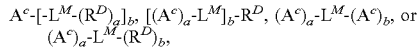

or a salt thereof, wherein:
each $A^c$ is independently an oligonucleotide moiety (e.g., H-$A^c$, $[H]_a$-$A^c$ or $[H]_b$-$A^c$ is an oligonucleotide);
a is 1-1000;
b is 1-1000;
$L^M$ is a multivalent linker; and
each $R^D$ is independently a chemical moiety.

In some embodiments, a provided compound, e.g., an oligonucleotide of a provided composition, have the structure of:

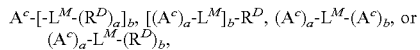

or a salt thereof, wherein:
each $A^c$ is independently an oligonucleotide moiety (e.g., H-$A^c$, $[H]_a$-$A^c$ or $[H]_b$-$A^c$ is an oligonucleotide);
a is 1-1000;
b is 1-1000;
each $R^D$ is independently $R^{LD}$, $R^{CD}$ or $R^{TD}$;
$R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

$R^{LD}$ is an optionally substituted, linear or branched group selected from a $C_{1-100}$ aliphatic group wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

$R^{TD}$ is a targeting moiety;
each $L^M$ is independently a covalent bond, or a bivalent or multivalent, optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon;

each R' is independently —R, —C(O)R, —C(O)OR, or —S(O)$_2$R; and each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms independently selected from oxygen, nitrogen, sulfur, phosphorus and silicon.

In some embodiments, $A^c$-$[-L^M$-$(R^D)_a]_b$, $[(A^c)_a$-$L^M]_b$-$R^D$, or $(A^c)_a$-$L^M$-$(R^D)_b$ is a conjugate of a provided oligonucleotide, e.g., a SMN2 oligonucleotide (optionally chirally controlled), with one or more chemical moieties, e.g., targeting moieties, carbohydrate moieties, lipid moieties, etc., or any other ligand described herein or known in the art.

In some embodiments, $(R^D)_b$-$L^M$- is $(R^D)_b$-$L^{M1}$-$L^{M2}$ as described in the present disclosure.

In some embodiments, H-A$^c$, [H]$_a$-A$^c$ or [H]$_b$-A$^c$ is an oligonucleotide as described in the present disclosure. In some embodiments, H-A$^c$, [H]$_a$-A$^c$ or [H]$_b$-A$^c$ is of formula O-I.

In some embodiments, R$^D$ is an additional chemical moiety as described in the present disclosure. In some embodiments, R$^D$ is a targeting moiety as described in the present disclosure. In some embodiments, R$^D$ is R$^{TD}$, which is a targeting moiety as described in the present disclosure (e.g., targeting moiety described as embodiment for R$^D$ as targeting moiety). In some embodiments, In some embodiments, R$^D$ is R$^{CD}$, wherein R$^{CD}$ is as described in the present disclosure. In some embodiments, R$^{CD}$ comprises one or more carbohydrate moieties. In some embodiments, R$^D$ is R$^{LD}$. In some embodiments, R$^{LD}$ is a lipid moiety as described in the present disclosure.

In some embodiments, a is 1-100. In some embodiments, a is 1-50. In some embodiments, a is 1-40. In some embodiments, a is 1-30. In some embodiments, a is 1-20. In some embodiments, a is 1-15. In some embodiments, a is 1-10. In some embodiments, a is 1-9. In some embodiments, a is 1-8. In some embodiments, a is 1-7. In some embodiments, a is 1-6. In some embodiments, a is 1-5. In some embodiments, a is 1-4. In some embodiments, a is 1-3. In some embodiments, a is 1-2. In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10. In some embodiments, a is more than 10.

In some embodiments, b is 1-100. In some embodiments, b is 1-50. In some embodiments, b is 1-40. In some embodiments, b is 1-30. In some embodiments, b is 1-20. In some embodiments, b is 1-15. In some embodiments, b is 1-10. In some embodiments, b is 1-9. In some embodiments, b is 1-8. In some embodiments, b is 1-7. In some embodiments, b is 1-6. In some embodiments, b is 1-5. In some embodiments, b is 1-4. In some embodiments, b is 1-3. In some embodiments, b is 1-2. In some embodiments, b is 1. In some embodiments, b is 2. In some embodiments, b is 3. In some embodiments, b is 4. In some embodiments, b is 5. In some embodiments, b is 6. In some embodiments, b is 7. In some embodiments, b is 8. In some embodiments, b is 9. In some embodiments, b is 10. In some embodiments, b is 1. In some embodiments, b is 2, 3, 4, 5, 6, 7, 8, 9, 10, 15, 20, or more.

In some embodiments, z is 1-1000. In some embodiments, z+1 is an oligonucleotide length as described in the present disclosure. In some embodiments, z is no less than 4, 5, 6, 7, 8, 9, 10, 11, 12, 13, 14, 15, 16, 17, 18, or 19. In some embodiments, z is no less than 4, 5, 6, 7, 8, 9, 10, 11, 12, 13, or 14. In some embodiments, z is no more than 50, 60, 70, 80, 90, 100, 150, or 200. In some embodiments, z is 5-50, 10-50, 14-50, 14-45, 14-40, 14-35, 14-30, 14-25, 14-100, 14-150, 14-200, 14-250, 14-300, 15-50, 15-45, 15-40, 15-35, 15-30, 15-25, 15-100, 15-150, 15-200, 15-250, 15-300, 16-50, 16-45, 16-40, 16-35, 16-30, 16-25, 16-100, 16-150, 16-200, 16-250, 16-300, 17-50, 17-45, 17-40, 17-35, 17-30, 17-25, 17-100, 17-150, 17-200, 17-250, 17-300, 18-50, 18-45, 18-40, 18-35, 18-30, 18-25, 18-100, 18-150, 18-200, 18-250, 18-300, 19-50, 19-45, 19-40, 19-35, 19-30, 19-25, 19-100, 19-150, 19-200, 19-250, or 19-300. In some embodiments, z is 10. In some embodiments, z is 11. In some embodiments, z is 12. In some embodiments, z is 13. In some embodiments, z is 14. In some embodiments, z is 15. In some embodiments, z is 16. In some embodiments, z is 17. In some embodiments, z is 18. In some embodiments, z is 19. In some embodiments, z is 20. In some embodiments, z is 21. In some embodiments, z is 22. In some embodiments, z is 23. In some embodiments, z is 24. In some embodiments, z is 25. In some embodiments, z is 26. In some embodiments, z is 27. In some embodiments, z is 28. In some embodiments, z is 29. In some embodiments, z is 30. In some embodiments, z is 31. In some embodiments, z is 32. In some embodiments, z is 33. In some embodiments, z is 34.

In some embodiments, L$^M$ is -L$^{M1}$-L$^{M2}$-L$^{M3}$- as described in the present disclosure. In some embodiments, L$^M$ is L$^{M1}$ as described in the present disclosure. In some embodiments, L$^M$ is L$^{M2}$ as described in the present disclosure. In some embodiments, L$^M$ is L$^{M3}$ as described in the present disclosure. In some embodiments, L$^M$ is L as described in the present disclosure.

In some embodiments, at least one L$^M$ is directly bound to a sugar unit of a provided oligonucleotide. In some embodiments, a L$^M$ directly binds to a sugar unit incorporates a lipid moiety into an oligonucleotide. In some embodiments, a L$^M$ directly binds to a sugar unit incorporates a carbohydrate moiety into an oligonucleotide. In some embodiments, a L$^M$ directly binds to a sugar unit incorporates a R$^{LD}$ group into an oligonucleotide. In some embodiments, a L$^M$ directly binds to a sugar unit incorporates a R$^{CD}$ group into an oligonucleotide. In some embodiments, L$^M$ is directed bound through 5'-OH of an oligonucleotide chain. In some embodiments, L$^M$ is directed bound through 3'-OH of an oligonucleotide chain.

In some embodiments, at least one L$^M$ is directly bound to an internucleotidic linkage unit of a provided oligonucleotide. In some embodiments, a L$^M$ directly binds to an internucleotidic linkage unit incorporates a lipid moiety into an oligonucleotide. In some embodiments, a L$^M$ directly binds to an internucleotidic linkage unit incorporates a carbohydrate moiety into an oligonucleotide. In some embodiments, a L$^M$ directly binds to an internucleotidic linkage unit incorporates a R$^{LD}$ group into an oligonucleotide. In some embodiments, a L$^M$ directly binds to an internucleotidic linkage unit incorporates a R$^{CD}$ group into an oligonucleotide.

In some embodiments, at least one L$^M$ is directly bound to a nucleobase unit of a provided oligonucleotide. In some embodiments, a L$^M$ directly binds to a nucleobase unit incorporates a lipid moiety into an oligonucleotide. In some embodiments, a L$^M$ directly binds to a nucleobase unit incorporates a carbohydrate moiety into an oligonucleotide. In some embodiments, a L$^M$ directly binds to a nucleobase unit incorporates a R$^{LD}$ group into an oligonucleotide. In some embodiments, a L$^M$ directly binds to a nucleobase unit incorporates a R$^{CD}$ group into an oligonucleotide.

In some embodiments, L$^M$ is bivalent. In some embodiments, L$^M$ is multivalent. In some embodiments, L$^M$ is

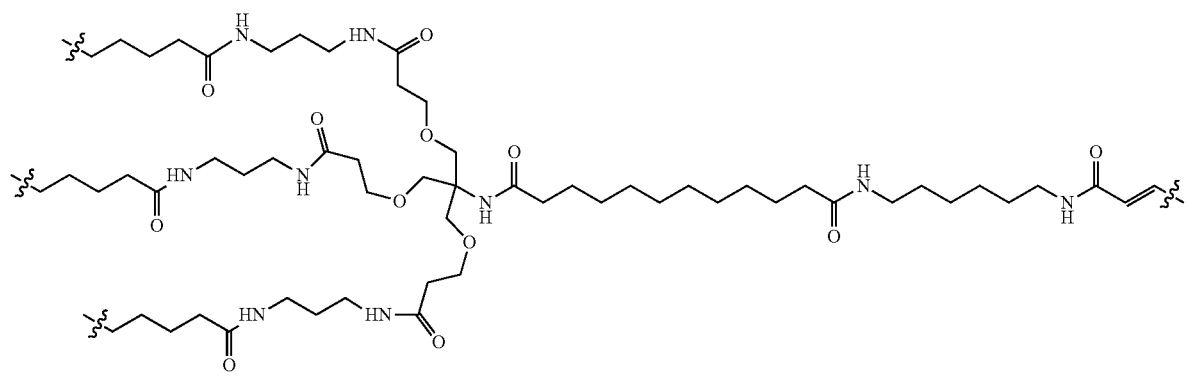
wherein $L^M$ is directly bond to a nucleobase, for example, as in:
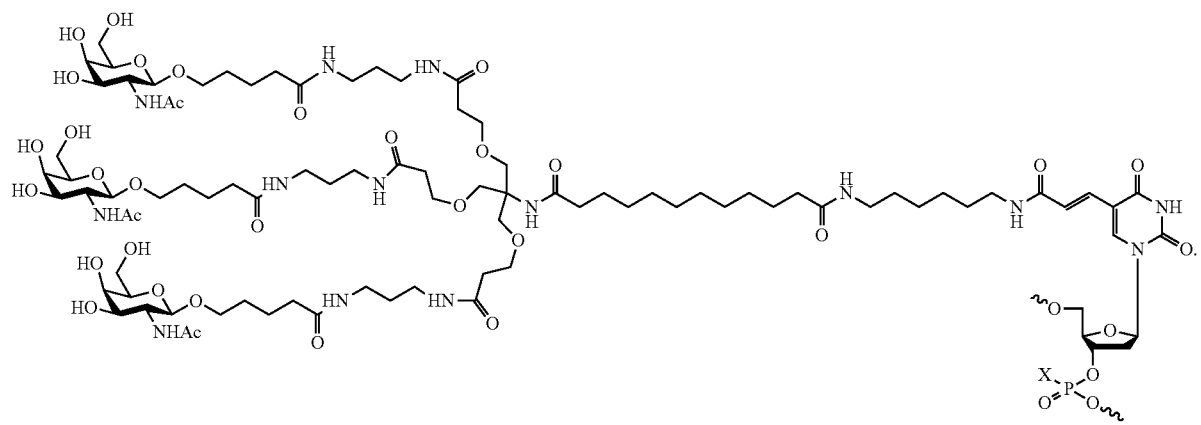
X = S⁻ or O⁻
In some embodiments, $L^M$ is
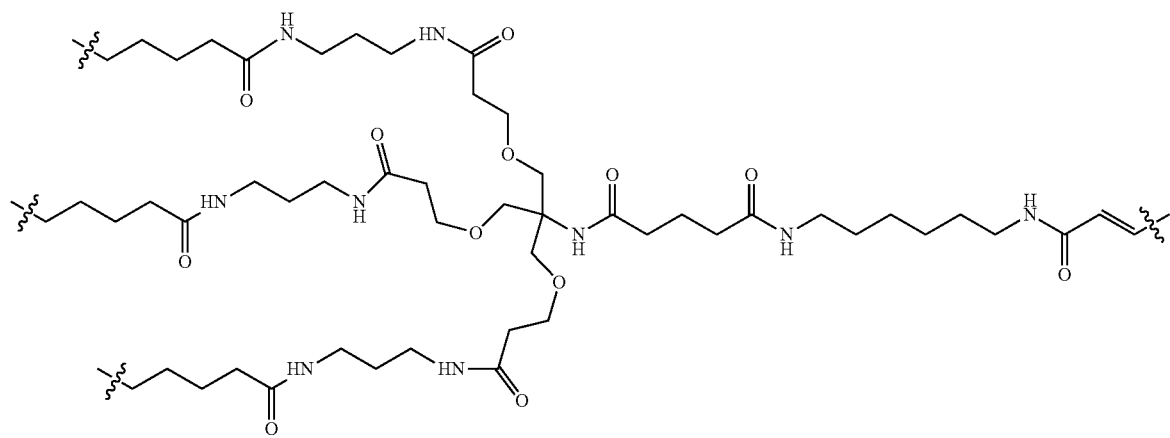

In some embodiments, $L^M$ is

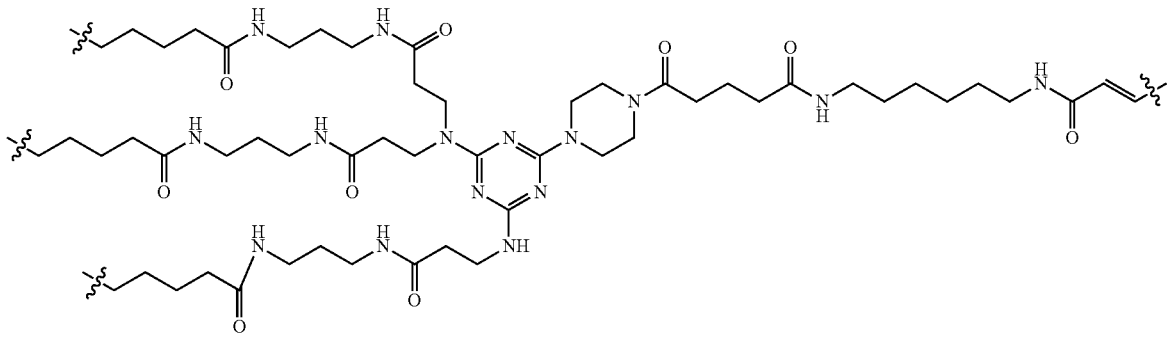

In some embodiments, $L^M$ is

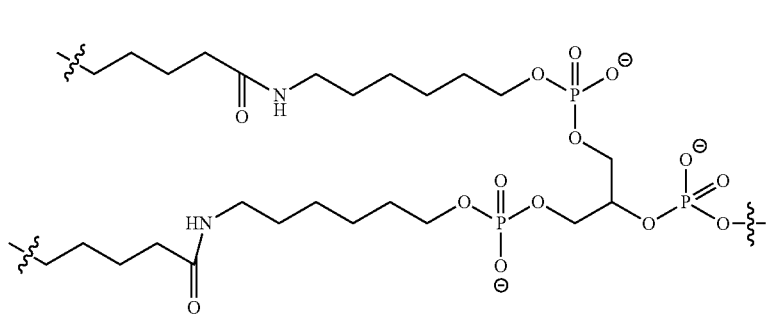

In some embodiments, $L^M$ is

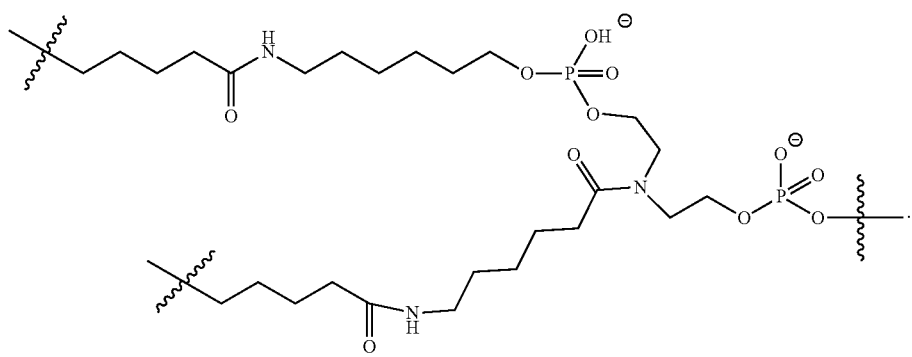 [SMILES: *CCCCC(=O)NCCCCCCOP(=O)([O-])OCCN(CCOP(=O)([O-])O*)C(=O)CCCCCNC(=O)CCCC*]

In some embodiments, $R^{LD}$ is optionally substituted $C_{10}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ to $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{60}$, $C_{70}$, or $C_{80}$ aliphatic. In some embodiments, $R^{LD}$ is optionally substituted $C_{10-80}$ aliphatic. In some embodiments, $R^{LD}$ is optionally substituted $C_{20-80}$ aliphatic. In some embodiments, $R^{LD}$ is optionally substituted $C_{10-70}$ aliphatic. In some embodiments, $R^{LD}$ is optionally substituted $C_{20-70}$ aliphatic. In some embodiments, $R^{LD}$ is optionally substituted $C_{10-60}$ aliphatic. In some embodiments, $R^{LD}$ is optionally substituted $C_{20-60}$ aliphatic. In some embodiments, $R^{LD}$ is optionally substituted $C_{10-50}$ aliphatic. In some embodiments, $R^{LD}$ is optionally substituted $C_{20-50}$ aliphatic. In some embodiments, $R^{LD}$ is optionally substituted $C_{10-40}$ aliphatic. In some embodiments, $R^{LD}$ is optionally substituted $C_{20-40}$ aliphatic. In some embodiments, $R^{LD}$ is optionally substituted $C_{10-30}$ aliphatic. In some embodiments, $R^{LD}$ is optionally substituted $C_{20-30}$ aliphatic. In some embodiments, $R^{LD}$ is unsubstituted $C_{10}$, $C_{15}$, $C_{16}$, $C_{17}$, $C_{18}$, $C_{19}$, $C_{20}$, $C_{21}$, $C_{22}$, $C_{23}$, $C_{24}$, or $C_{25}$ to $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{60}$, $C_{70}$, or $C_{80}$ aliphatic. In some embodiments, $R^{LD}$ is unsubstituted $C_{10-80}$ aliphatic. In some embodiments, $R^{LD}$ is unsubstituted $C_{20-80}$ aliphatic. In some embodiments, $R^{LD}$ is unsubstituted $C_{10-70}$ aliphatic. In some embodiments, $R^{LD}$ is unsubstituted $C_{20-70}$ aliphatic. In some embodiments, $R^{LD}$ is unsubstituted $C_{10-60}$ aliphatic. In some embodiments, $R^{LD}$ is unsubstituted $C_{20-60}$ aliphatic. In some embodiments, $R^{LD}$ is unsubstituted $C_{10-50}$ aliphatic. In some embodiments, $R^{LD}$ is unsubstituted $C_{20-50}$ aliphatic. In some embodiments, $R^{LD}$ is unsubstituted $C_{10-40}$ aliphatic. In some embodiments, $R^{LD}$ is unsubstituted $C_{20-40}$ aliphatic. In some embodiments, $R^{LD}$ is unsubstituted $C_{10-30}$ aliphatic. In some embodiments, $R^{LD}$ is unsubstituted $C_{20-30}$ aliphatic.

In some embodiments, $R^{LD}$ is not hydrogen. In some embodiments, $R^{LD}$ is a lipid moiety. In some embodiments, $R^{LD}$ is a targeting moiety. In some embodiments, $R^{LD}$ is a targeting moiety comprising a carbohydrate moiety. In some embodiments, $R^{LD}$ is a GalNAc moiety.

In some embodiments, $R^{TD}$ is $R^{LD}$, wherein $R^{LD}$ is independently as described in the present disclosure. In some embodiments, $R^{TD}$ is $R^{CD}$, wherein $R^{CD}$ is independently as described in the present disclosure.

In some embodiments, $R^{CD}$ is an optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$. In some embodiments, $R^{CD}$ is an optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are independently replaced with a monosaccharide, disaccharide or polysaccharide moiety. In some embodiments, $R^{CD}$ is an optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(NR')O—, —OP(OR')O—, —OP(SR')O—, —OP(NR')O—, —OP(R')O—, —OP(R')O—, or —OP(OR')[B(R')$_3$]O—; and one or more carbon atoms are independently replaced with a GalNac moiety.

In some embodiments, the present disclosure provides salts of oligonucleotides, e.g., SMN2 oligonucleotides (optionally chirally controlled), and pharmaceutical compositions thereof. In some embodiments, a salt is a pharmaceutically acceptable salt. In some embodiments, each hydrogen ion that may be donated to a base (e.g., under conditions of an aqueous solution, a pharmaceutical composition, etc.) is replaced by a non-H⁺ cation. For example, in some embodiments, a pharmaceutically acceptable salt of an oligonucleotide is an all-metal ion salt, wherein each hydrogen ion (for example, of —OH, —SH, etc.) of each internucleotidic linkage (e.g., a natural phosphate linkage, a phosphorothioate diester linkage, etc.) is replaced by a metal ion. In some embodiments, a provided salt is an all-sodium salt. In some embodiments, a provided pharmaceutically acceptable salt is an all-sodium salt. In some embodiments, a provided salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate diester linkage (acid form —O—P(O)(SH)—O—), if any, exists as its sodium salt form (—O—P(O)(SNa)—O—).

In some embodiments, a percentage, e.g., 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides or segments thereof (e.g., a block, 5'-wing, core, 3'-wing, portions thereof, etc.) are chirally controlled and have a Sp linkage phosphorus. In some embodiments, a percentage, e.g., 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides or segments thereof (e.g., a block, 5'-wing, core, 3'-wing, portions thereof, etc.) are chirally controlled and have a Rp linkage phosphorus. In some embodiments, a percentage, e.g., 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides or segments thereof (e.g., a block, 5'-wing, core, 3'-wing, portions thereof, etc.) are chirally controlled and have a Rp linkage phosphorus. In some embodiments, a percentage, e.g., 1%-100%, e.g., 5%, 10%, 15%, 20%, 25%, 30%, 35%, 40%, 45%, 50%, 55%, 60%, 65%, 70%, 75%, 80%, 85%, 90%, 95%, etc., of internucleotidic linkages in provided oligonucleotides or segments thereof (e.g., a block, 5'-wing, core, 3'-wing, portions thereof, etc.) are natural phosphate linkages. In some embodiments, a percentage is 5%. In some embodiments, a percentage is 10%. In some embodiments, a percentage is 15%. In some embodiments, a percentage is 20%. In some embodiments, a percentage is 25%. In some embodiments, a percentage is 30%. In some embodiments, a percentage is 35%. In some embodiments, a percentage is 40%. In some embodiments, a percentage is 45%. In some embodiments, a percentage is 50%. In some embodiments, a percentage is 55%. In some embodiments, a percentage is 60%. In some embodiments, a percentage is 65%. In some embodiments, a percentage is 66%. In some embodiments, a percentage is 67%. In some embodiments, a percentage is 70%. In some embodiments, a percentage is 75%. In some embodiments, a percentage is 80%. In some embodiments, a percentage is 85%. In some embodiments, a percentage is 90%. In some embodiments, a percentage is 95%. In some embodiments, a percentage is 100%.

In some embodiments, a number, e.g., at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. of internucleotidic linkages in provided oligonucleotides or segments thereof (e.g., a block, 5'-wing, core, 3'-wing, portions thereof, etc.) are chirally controlled and have a Rp linkage phosphorus. In some embodiments, a number, e.g., at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. of internucleotidic linkages in provided oligonucleotides or segments thereof (e.g., a block, 5'-wing, core, 3'-wing, portions thereof, etc.) are chirally controlled and have a Sp linkage phosphorus. In some embodiments, a number, e.g., at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. of internucleotidic linkages in provided oligonucleotides or segments thereof (e.g., a block, 5'-wing, core, 3'-wing, portions thereof, etc.) are natural phosphate linkages. In some embodiments, a number, e.g., at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. of internucleotidic linkages in provided oligonucleotides or segments thereof (e.g., a block, 5'-wing, core, 3'-wing, portions thereof, etc.) are chirally controlled, have a Rp linkage phosphorus, and are consecutive. In some embodiments, a number, e.g., at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. of internucleotidic linkages in provided oligonucleotides or segments thereof (e.g., a block, 5'-wing, core, 3'-wing, portions thereof, etc.) are chirally controlled, have a Sp linkage phosphorus, and are consecutive. In some embodiments, a number, e.g., at least 1-30, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc. of internucleotidic linkages in provided oligonucleotides or segments thereof (e.g., a block, 5'-wing, core, 3'-wing, portions thereof, etc.) are natural phosphate linkages and are consecutive. In some embodiments, a number is 1. In some embodiments, a number is 2. In some embodiments, a number is 3. In some embodiments, a number is 4. In some embodiments, a number is 5. In some embodiments, a number is 6. In some embodiments, a number is 7. In some embodiments, a number is 8. In some embodiments, a number is 9. In some embodiments, a number is 10. In some embodiments, a number is 11. In some embodiments, a number is 12. In some embodiments, a number is 13. In some embodiments, a number is 14. In some embodiments, a number is 15. In some embodiments, a number is 16. In some embodiments, a number is 17. In some embodiments, a number is 18. In some embodiments, a number is 19. In some embodiments, a number is 20. In some embodiments, a number is at least 1. In some embodiments, a number is at least 2. In some embodiments, a number is at least 3. In some embodiments, a number is at least 4. In some embodiments, a number is at least 5. In some embodiments, a number is at least 6. In some embodiments, a number is at least 7. In some embodiments, a number is at least 8. In some embodiments, a number is at least 9. In some embodiments, a number is at least 10. In some embodiments, a number is at least 11. In some embodiments, a number is at least 12. In some embodiments, a number is at least 13. In some embodiments, a number is at least 14. In some embodiments, a number is at least 15. In some embodiments, a number is at least 16. In some embodiments, a number is at least 17. In some embodiments, a number is at least 18. In some embodiments, a number is at least 19. In some embodiments, a number is at least 20.

Purity

In some embodiments, a provided compound, e.g., a provided oligonucleotide, has a purity of 60%-100%. In some embodiments, a provided compound, e.g., a provided oligonucleotide, has a diastereomeric purity of 60%-100%. In some embodiments, a diastereomeric purity is at least 60%, 65%, 70%, 75%, 80%, 85%, 90%, 91%, 92%, 93%, 94%, 95%, 96%, 97%, 98%, or 99%. In some embodiments, a chiral element, e.g., a chiral center (carbon, phosphorus, etc.) of a provided compound, e.g. a provided oligonucleotide, has a diastereomeric purity of 60%-100%. In some embodiments, a chiral element, e.g., a chiral center (carbon, phosphorus, etc.) has a diastereomeric purity of at least 60%, 65%, 70%, 75%, 80%, 85%, 90%, 91%, 92%, 93%, 94%, 95%, 96%, 97%, 98%, or 99%.

In some embodiments, at least 1, 2, 3, 4, 5, 6, 7, 8, 9 or more chiral elements of a provided compound each independently have a diastereomeric purity as described herein. In some embodiments, at least 1, 2, 3, 4, 5, 6, 7, 8, 9 or more chiral carbon centers of a provided compound each independently have a diastereomeric purity as described herein. In some embodiments, at least 1, 2, 3, 4, 5, 6, 7, 8, 9 or more chiral phosphorus centers of a provided compound each independently have a diastereomeric purity as described herein.

In some embodiments, at least 5%-100% of all chiral elements of a provided compound each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral elements of a provided compound each independently have a diastereomeric purity as described herein. In some embodiments, at least 5%-100% of all chiral phosphorus centers of a provided compound each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral phosphorus centers of a provided compound each independently have a diastereomeric purity as described herein.

In some embodiments, each chiral element independently has a diastereomeric purity as described herein. In some embodiments, each chiral center independently has a diastereomeric purity as described herein. In some embodiments, each chiral carbon center independently has a diastereomeric purity as described herein. In some embodiments, each chiral phosphorus center independently has a diastereomeric purity as described herein.

Various linker, carbohydrate moieties and targeting moieties, including many known in the art, can be utilized in accordance with the present disclosure. In some embodiments, a carbohydrate moiety is a targeting moiety. In some embodiments, a targeting moiety is a carbohydrate moiety.

In some embodiments, the present disclosure provides methods for stereoselective formation of chiral elements, e.g., chiral centers. In some embodiments, the present disclosure provides methods with high stereoselectivity. In some embodiments, the present disclosure provides methods with high diastereoselectivity. In some embodiments, the present disclosure provides methods with high enantioselectivity. In some embodiments, the present disclosure provides methods with both high diastereoselectivity and high enantioselectivity. In some embodiments, a selectivity is about 60%-100%. In some embodiments, a selectivity is at least 60%, 65%, 70%, 75%, 80%, 85%, 90%, 91%, 92%, 93%, 94%, 95%, 96%, 97%, 98%, or 99%. In some embodiments, a diastereoselectivity is at least 60%, 65%, 70%, 75%, 80%, 85%, 90%, 91%, 92%, 93%, 94%, 95%, 96%, 97%, 98%, or 99%. In some embodiments, a enantioselectivity is at least 60%, 65%, 70%, 75%, 80%, 85%, 90%, 91%, 92%, 93%, 94%, 95%, 96%, 97%, 98%, or 99%. In some embodiments, both a diastereoselectivity and an enantioselectivity are at least 60%, 65%, 70%, 75%, 80%, 85%, 90%, 91%, 92%, 93%, 94%, 95%, 96%, 97%, 98%, or 99%.

In some embodiments, a percentage, e.g., of purity, diastereomeric purity, selectivity, etc. is at least 60%, 65%, 70%, 75%, 80%, 85%, 90%, 91%, 92%, 93%, 94%, 95%, 96%, 97%, 98%, or 99%. In some embodiments, a percentage is at least 60%. In some embodiments, a percentage is at least 70%. In some embodiments, a percentage is at least 80%. In some embodiments, a percentage is at least 85%. In some embodiments, a percentage is at least 90%. In some embodiments, a percentage is at least 91%. In some embodiments, a percentage is at least 92%. In some embodiments, a percentage is at least 93%. In some embodiments, a percentage is at least 94%. In some embodiments, a percentage is at least 95%. In some embodiments, a percentage is at least 96%. In some embodiments, a percentage is at least 97%. In some embodiments, a percentage is at least 98%. In some embodiments, a percentage is at least 99%. In some embodiments, a percentage is at least 99.5%.

In some embodiments, the present disclosure provides oligonucleotides and oligonucleotide compositions that are chirally controlled. For instance, in some embodiments, a provided composition contains non-random or controlled levels of one or more individual oligonucleotide types, wherein an oligonucleotide type is defined by: 1) base sequence; 2) pattern of backbone linkages; 3) pattern of backbone chiral centers; and 4) pattern of backbone P-modifications. In some embodiments, a particular oligonucleotide type may be defined by 1A) base identity; 1B) pattern of base modification; 1C) pattern of sugar modification; 2) pattern of backbone linkages; 3) pattern of backbone chiral centers; and 4) pattern of backbone P-modifications. In some embodiments, oligonucleotides of the same oligonucleotide type are identical. In some embodiments, the present disclosure provides chirally controlled oligonucleotide compositions, wherein the composition comprises a non-random or controlled level of a plurality of oligonucleotides, wherein oligonucleotides of the plurality share a common base sequence, and comprise the same configuration of linkage phosphorus at at least 1, 2, 3, 4, 5, 6, 7, 8, 9, 10, 11, 12, 13, 14, 15, 16, 17, 18, 19, 20, 21, 22, 23, 24, or 25 chiral internucleotidic linkages (chirally controlled internucleotidic linkages). In some embodiments, oligonucleotides of a predetermined level and/or a provided plurality, e.g., those of formula O-I, $A^c\text{-}[\text{-}L^M\text{-}(R^D)_a]_b$, $[(A^c)_a\text{-}L^M]_b\text{-}R^D$, $(A^c)_a\text{-}L^M\text{-}(A^c)_b$, or $(A^c)_a\text{-}L^M\text{-}(R^D)_b$, comprise 1-30 chirally controlled internucleotidic linkages. In some embodiments, provided oligonucleotides comprise 2-30 chirally controlled internucleotidic linkages. In some embodiments, provided chirally controlled oligonucleotide compositions comprise 5-30 chirally controlled internucleotidic linkages. In some embodiments, provided chirally controlled oligonucleotide compositions comprise 10-30 chirally controlled internucleotidic linkages. In some embodiments, provided chirally controlled oligonucleotide compositions comprise 1 chirally controlled internucleotidic linkage. In some embodiments, provided chirally controlled oligonucleotide compositions comprise 2 chirally controlled internucleotidic linkages. In some embodiments, provided chirally controlled oligonucleotide compositions comprise 3 chirally controlled internucleotidic linkages. In some embodiments, provided chirally controlled oligonucleotide compositions comprise 4 chirally controlled internucleotidic linkages. In some embodiments, provided chirally controlled oligonucleotide compositions comprise 5 chirally controlled internucleotidic linkages. In some embodiments, provided chirally controlled oligonucleotide compositions comprise 6 chirally controlled internucleotidic linkages. In some embodiments, provided chirally controlled oligonucleotide compositions comprise 7 chirally controlled internucleotidic linkages. In some embodiments, provided chirally controlled oligonucleotide compositions comprise 8 chirally controlled internucleotidic linkages. In some embodiments, provided chirally controlled oligonucleotide compositions comprise 9 chirally controlled internucleotidic linkages. In some embodiments, provided chirally controlled oligonucleotide compositions comprise 10 chirally controlled internucleotidic linkages. In some embodiments, provided chirally controlled oligonucleotide compositions comprise 11 chirally controlled internucleotidic linkages. In some embodiments, provided chirally controlled oligonucleotide compositions comprise 12 chirally controlled internucleotidic linkages. In some embodiments, provided chirally controlled oligonucleotide compositions comprise 13 chirally controlled internucleotidic linkages. In some embodiments, provided chirally controlled oligonucleotide compositions comprise 14 chirally controlled internucleotidic linkages. In some embodiments, provided chirally controlled oligonucleotide compositions have 15 chirally controlled internucleotidic linkages. In some embodiments, provided chirally controlled oligonucleotide compositions have 16 chirally controlled internucleotidic linkages. In some embodiments, provided chirally controlled oligonucleotide compositions have 17 chirally controlled internucleotidic linkages. In some embodiments, provided chirally controlled oligonucleotide compositions have 18 chirally controlled internucleotidic linkages. In some embodiments, provided chirally controlled oligonucleotide compositions have 19 chirally controlled internucleotidic linkages. In some embodiments, provided chirally controlled oligonucleotide compositions have 20 chirally controlled internucleotidic linkages. In some embodiments, about 1-100% of all internucleotidic linkages are chirally controlled internucleotidic linkages.

In some embodiments, a provided chirally controlled oligonucleotide composition is a unimer. In some embodiments, a provided chirally controlled oligonucleotide composition is a P-modification unimer. In some embodiments, a provided chirally controlled oligonucleotide composition is a stereounimer. In some embodiments, a provided chirally controlled oligonucleotide composition is a stereounimer of configuration Rp. In some embodiments, a provided chirally controlled oligonucleotide composition is a stereounimer of configuration Sp.

In some embodiments, a provided chirally controlled oligonucleotide composition is an altmer. In some embodiments, a provided chirally controlled oligonucleotide composition is a P-modification altmer. In some embodiments, a provided chirally controlled oligonucleotide composition is a stereoaltmer.

In some embodiments, a provided chirally controlled oligonucleotide composition is a blockmer. In some embodiments, a provided chirally controlled oligonucleotide composition is a P-modification blockmer. In some embodiments, a provided chirally controlled oligonucleotide composition is a stereoblockmer.

In some embodiments, a provided chirally controlled oligonucleotide composition is a gapmer.

In some embodiments, a provided chirally controlled oligonucleotide composition is a skipmer.

In some embodiments, a provided chirally controlled oligonucleotide composition is a hemimer. In some embodiments, a hemimer is an oligonucleotide wherein the 5'-end or the 3'-end region has a sequence that possesses a structure feature that the rest of the oligonucleotide does not have. In some embodiments, the 5'-end or the 3'-end region comprises, or contains no more than, 2 to 20 nucleotides. In some embodiments, a structural feature is a base modification. In some embodiments, a structural feature is a sugar modification. In some embodiments, a structural feature is a P-modification. In some embodiments, a structural feature is stereochemistry of the chiral internucleotidic linkage. In some embodiments, a structural feature is or comprises a base modification, a sugar modification, a P-modification, or stereochemistry of the chiral internucleotidic linkage, or combinations thereof. In some embodiments, a hemimer is an oligonucleotide in which each sugar moiety of the 5'-end region shares a common modification. In some embodiments, a hemimer is an oligonucleotide in which each sugar moiety of the 3'-end region shares a common modification. In some embodiments, a common sugar modification of the 5' or 3'-end region is not shared by any other sugar moieties in the oligonucleotide. In some embodiments, an example hemimer is an oligonucleotide comprising a sequence of substituted or unsubstituted 2'-O-alkyl sugar modified nucleosides, bicyclic sugar modified nucleosides, β-D-ribonucleosides or β-D-deoxyribonucleosides (for example, 2'-MOE modified nucleosides, and LNA or ENA bicyclic sugar modified nucleosides) at one terminus region and a sequence of nucleosides with a different sugar moiety (such as a substituted or unsubstituted 2'-O-alkyl sugar modified nucleosides, bicyclic sugar modified nucleosides or natural ones) at the other terminus region. In some embodiments, an oligonucleotide comprises a tricyclo-DNA (tc-DNA or tcDNA). In some embodiments, the majority of nucleotides in an oligonucleotide are tc-DNA. In some embodiments, all of nucleotides in an oligonucleotide are tc-DNA. In some embodiments, a provided chirally controlled oligonucleotide composition is a combination of one or more of unimer, altmer, blockmer, gapmer, hemimer and skipmer. In some embodiments, a provided chirally controlled oligonucleotide composition is a combination of one or more of unimer, altmer, blockmer, gapmer, and skipmer. For instance, in some embodiments, a provided chirally controlled oligonucleotide composition is both an altmer and a gapmer. In some embodiments, a provided nucleotide is both a gapmer and a skipmer. One of skill in the chemical and synthetic arts will recognize that numerous other combinations of patterns are available and are limited only by the commercial availability and/or synthetic accessibility of constituent parts required to synthesize a provided chirally controlled oligonucleotide composition in accordance with methods of the present disclosure. In some embodiments, a hemimer structure provides advantageous benefits. In some embodiments, provided chirally controlled oligonucleotide compositions are 5'-hemimers that comprises modified sugar moieties in a 5'-end sequence. In some embodiments, provided chirally controlled oligonucleotide compositions are 5'-hemimers that comprises modified 2'-sugar moieties in a 5'-end sequence.

In some embodiments, a provided chirally controlled oligonucleotide composition comprises one or more optionally substituted nucleotides. In some embodiments, a provided chirally controlled oligonucleotide composition comprises one or more modified nucleotides. In some embodiments, a provided chirally controlled oligonucleotide composition comprises one or more optionally substituted nucleosides. In some embodiments, a provided chirally controlled oligonucleotide composition comprises one or more modified nucleosides. In some embodiments, a provided chirally controlled oligonucleotide composition comprises one or more optionally substituted LNAs.

In some embodiments, a provided chirally controlled oligonucleotide composition comprises one or more optionally substituted nucleobases. In some embodiments, a provided chirally controlled oligonucleotide composition comprises one or more optionally substituted natural nucleobases. In some embodiments, a provided chirally controlled oligonucleotide composition comprises one or more optionally substituted modified nucleobases. In some embodiments, a provided chirally controlled oligonucleotide composition comprises one or more 5-methylcytidine; 5-hydroxymethylcytidine, 5-formylcytosine, or 5-carboxylcytosine. In some embodiments, a provided chirally controlled oligonucleotide composition comprises one or more 5-methylcytidine.

In some embodiments, each nucleobase of a provided oligonucleotide, e.g., one of formula O-I, $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, is independently an optionally substituted or protected nucleobase of adenine, cytosine, guanosine, thymine, or uracil. In some embodiments, each BA is independently an optionally substituted or protected nucleobase of adenine, cytosine, guanosine, thymine, or uracil. As appreciated by those skilled in the art, various protected nucleobases, including those widely known in the art, for example, those used in oligonucleotide preparation (e.g., protected nucleobases of WO/2010/064146, WO/2011/005761, WO/2013/012758, WO/2014/010250, US2013/0178612, WO/2014/012081, WO/2015/107425, WO2017/015555, and WO2017/062862, protected nucleobases of each of which are incorporated herein by reference), and can be utilized in accordance with the present disclosure.

In some embodiments, a provided chirally controlled oligonucleotide composition comprises one or more optionally substituted sugars. In some embodiments, a provided chirally controlled oligonucleotide composition comprises one or more optionally substituted sugars found in naturally occurring DNA and RNA. In some embodiments, a provided chirally controlled oligonucleotide composition comprises one or more optionally substituted ribose or deoxyribose. In some embodiments, a provided chirally controlled oligonucleotide composition comprises one or more optionally substituted ribose or deoxyribose, wherein one or more hydroxyl groups of the ribose or deoxyribose moiety is optionally and independently replaced by halogen, R', —N(R')$_2$, —OR', or —SR', wherein each R' is independently described in the present disclosure. In some embodiments, a provided chirally controlled oligonucleotide composition comprises one or more optionally substituted deoxyribose, wherein the 2' position of the deoxyribose is optionally and independently substituted with halogen, R', —N(R')$_2$, —OR', or —SR', wherein each R' is independently described in the present disclosure. In some embodiments, a provided chirally controlled oligonucleotide composition comprises one or more optionally substituted deoxyribose, wherein the 2' position of the deoxyribose is optionally and independently substituted with halogen. In some embodiments, a provided chirally controlled oligonucleotide composition comprises one or more optionally substituted deoxyribose, wherein the 2' position of the deoxyribose is optionally and independently substituted with one or more —F. In some embodiments, a provided chirally controlled oligonucleotide composition comprises one or more optionally substituted deoxyribose, wherein the 2' position of the deoxyribose is optionally and independently substituted with —OR', wherein each R' is independently described in the present disclosure. In some embodiments, a provided chirally controlled oligonucleotide composition comprises one or more optionally substituted deoxyribose, wherein the 2' position of the deoxyribose is optionally and independently substituted with —OR', wherein each R' is independently an optionally substituted $C_1$-$C_6$ aliphatic. In some embodiments, a provided chirally controlled oligonucleotide composition comprises one or more optionally substituted deoxyribose, wherein the 2' position of the deoxyribose is optionally and independently substituted with —OR', wherein each R' is independently an optionally substituted $C_1$-$C_6$ alkyl. In some embodiments, a provided chirally controlled oligonucleotide composition comprises one or more optionally substituted deoxyribose, wherein the 2' position of the deoxyribose is optionally and independently substituted with —OMe. In some embodiments, a provided chirally controlled oligonucleotide composition comprises one or more optionally substituted deoxyribose, wherein the 2' position of the deoxyribose is optionally and independently substituted with —O—methoxyethyl.

In some embodiments, oligonucleotides of a provided chirally controlled oligonucleotide composition are single-stranded oligonucleotides.

In some embodiments, a provided oligonucleotide is chimeric. For example, in some embodiments, a provided chirally controlled oligonucleotide composition (e.g., comprising oligonucleotides which have a base sequence which comprises, consists of, or comprises a portion of, a base sequence of a SMN2 oligonucleotide disclosed herein) is DNA-RNA chimera, DNA-LNA chimera, a chimera comprising any two or more of DNA, RNA, LNA, 2'-modified sugars, etc.

In some embodiments, a provided SMN2 oligonucleotide composition (optionally chirally controlled) comprises a nucleic acid analog, e.g., GNA, LNA, alpha-L-LNA, GNA, PNA, TNA, F-HNA (F-THP or 3'-fluoro tetrahydropyran), MNA (mannitol nucleic acid, e.g., Leumann 2002 Bioorg. Med. Chem. 10: 841-854), ANA (anitol nucleic acid), or Morpholino. In some embodiments, an oligonucleotide comprises a thiomorpholino (TMO), aminoalcohol DNA or other aminoalcohol nucleotide, or a diboranophosphonate, or 3'-5'-triazoylphosphonate.

In some embodiments, oligonucleotides of an oligonucleotide type characterized by 1) a common base sequence and length, 2) a common pattern of base modifications, 3) a common pattern of sugar modifications, 3) a common pattern of backbone linkages, and 4) a common pattern of backbone chiral centers, and 5) a common pattern of additional chemical moieties (if any), have the same chemical structure. For example, they have the same base sequence, the same pattern of nucleoside modifications, the same pattern of backbone linkages (i.e., pattern of internucleotidic linkage types, for example, phosphate, phosphorothioate, etc.), the same pattern of backbone chiral centers (i.e. pattern of linkage phosphorus stereochemistry (Rp/Sp)), and the same pattern of backbone phosphorus modifications.

In some embodiments, inclusion of an exon, e.g., exon 7 of a SMN2 mRNA, or level of an exon-including mRNA, e.g., an exon 7-containing SMN2 mRNA, or its encoded product (e.g., full length SMN protein) is increased by at least about 10%, 15%, 20%, 25%, 30%, 35%, 40%, 45%, 50%, 60%, 70%, or 80% by provided chirally controlled oligonucleotide compositions compared to an appropriate reference composition, e.g., a non-chirally controlled oligonucleotide composition of oligonucleotides of the same constitution as oligonucleotides of the plurality in chirally controlled oligonucleotide compositions at a concentration, e.g., lower than 1 uM, in an appropriate splicing system (e.g., concentrations and/or splicing systems of the Figures). In some embodiments, inclusion of an exon, e.g., exon 7 of a SMN2 mRNA, or level of an exon-including mRNA, e.g., an exon 7-containing SMN2 mRNA, or its encoded product (e.g., full length SMN protein) is increased by at least about 10%, 15%, 20%, 25%, 30%, 35%, 40%, 45%, 50%, 60%, 70%, or 80% by provided oligonucleotide compositions of oligonucleotides comprising additional chemical moieties (e.g., those capable of binding to ASGR) compared to an appropriate reference composition, e.g., an oligonucleotide composition whose oligonucleotides do not contain the additional chemical moieties but are otherwise identical at a concentration, e.g., lower than 1 uM, in an appropriate splicing system (e.g., concentrations and/or splicing systems of the Figures). In some embodiments, a reference composition is a Nusinersen composition. In some embodiments, inclusion of exon 7 of a SMN2 mRNA or level of an exon 7-containing SMN2 mRNA or its gene product is increased by at least about 10%, 15%, 20%, 25%, 30%, 35%, 40%, 45%, 50%, 60%, 70%, or 80% by administration of an oligonucleotide in a cell(s) in vitro. In some embodiments, inclusion of exon 7 of a SMN2 mRNA or level of an exon 7-containing SMN2 mRNA or its gene product is increased by at least about 10%, 15%, 20%, 25%, 30%, 35%, 40%, 45%, 50%, 60%, 70%, or 80% by administration of an oligonucleotide at a concentration of 10 μM or less in a cell(s) in vitro. In some embodiments, inclusion of exon 7 of a SMN2 mRNA or level of an exon 7-containing SMN2 mRNA or its gene product is increased by at least about 10%, 15%, 20%, 25%, 30%, 35%, 40%, 45%, 50%, 60%, 70%, or 80% by administration of an oligonucleotide at a concentration of 5 μM or less in a cell(s) in vitro. In some embodiments, inclusion of exon 7 of a SMN2 mRNA or level of an exon 7-containing SMN2 mRNA or its gene product is increased by at least about 10%, 15%, 20%, 25%, 30%, 35%, 40%, 45%, 50%, 60%, 70%, or 80% by administration of an oligonucleotide at a concentration of 1 μM or less in a cell(s) in vitro. In some embodiments, a cell(s) is a mammalian cell(s). In some embodiments, a cell(s) is a human cell(s).

In some embodiments, each sugar moiety of provided oligonucleotides is modified. In some embodiments, a modified sugar moiety comprises a 2'-modification. In some embodiments, a modified sugar moiety comprises a 2'-modification. In some embodiments, a 2'-modification is 2'-OR, wherein R is as described in the present disclosure. In some embodiments, a 2'-modification is a 2'-OMe. In some embodiments, a 2'-modification is a 2'-MOE. In some embodiments, a 2'-modification is an LNA sugar modification. In some embodiments, a 2'-modification is 2'-F. In some embodiments, each sugar modification is independently a 2'-modification. In some embodiments, each sugar modification is independently 2'-OR or 2'-F. In some embodiments, each sugar modification is independently 2'-OR or 2'-F, wherein R is optionally substituted $C_{1-6}$ alkyl. In some embodiments, each sugar modification is independently 2'-OR or 2'-F, wherein at least one is 2'-F. In some embodiments, each sugar modification is independently 2'-OR or 2'-F, wherein R is optionally substituted $C_{1-6}$ alkyl, and wherein at least one is 2'-OR. In some embodiments, each sugar modification is independently 2'-OR or 2'-F, wherein at least one is 2'-F, and at least one is 2'-OR. In some embodiments, each sugar modification is independently 2'-OR or 2'-F, wherein R is optionally substituted $C_{1-6}$ alkyl, and wherein at least one is 2'-F, and at least one is 2'-OR.

In some embodiments, provided oligonucleotides contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides, e.g., oligonucleotides of a plurality, comprise base modifications, sugar modifications, and/or internucleotidic linkage modifications, wherein the oligonucleotides contain an enriched level of deuterium. In some embodiments, provided oligonucleotides are labeled with deuterium (replacing —$^1$H with —$^2$H) at one or more positions. In some embodiments, one or more $^1$H of an oligonucleotide or any moiety conjugated to the oligonucleotide (e.g., a targeting moiety, etc.) is substituted with $^2$H. Such oligonucleotides can be used in any compositions or methods described herein.

As understood by a person having ordinary skill in the art, a stereorandom or racemic preparation of oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of oligonucleotides, all or most coupling steps are not chirally controlled in that the coupling steps are not specifically conducted to provide enhanced stereoselectivity. An example substantially racemic preparation of oligonucleotides is the preparation of phosphorothioate oligonucleotides through sulfurizing phosphite triesters from commonly used phosphoramidite oligonucleotide synthesis with either tetraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1. In some embodiments, at least two couplings of a nucleotide monomer have a diastereoselectivity lower than about 60:40, 70:30, 80:20, 85:15, 90:10, 91:9, 92:8, 97:3, 98:2, or 99:1. In some embodiments, at least three couplings of a nucleotide monomer have a diastereoselectivity lower than about 60:40, 70:30, 80:20, 85:15, 90:10, 91:9, 92:8, 97:3, 98:2, or 99:1. In some embodiments, at least four couplings of a nucleotide monomer have a diastereoselectivity lower than about 60:40, 70:30, 80:20, 85:15, 90:10, 91:9, 92:8, 97:3, 98:2, or 99:1. In some embodiments, at least five couplings of a nucleotide monomer have a diastereoselectivity lower than about 60:40, 70:30, 80:20, 85:15, 90:10, 91:9, 92:8, 97:3, 98:2, or 99:1. In some embodiments, each coupling of a nucleotide monomer independently has a diastereoselectivity lower than about 60:40, 70:30, 80:20, 85:15, 90:10, 91:9, 92:8, 97:3, 98:2, or 99:1. In some embodiments, in a stereorandom or racemic preparations, at least one internucleotidic linkage has a diastereoselectivity lower than about 60:40, 70:30, 80:20, 85:15, 90:10, 91:9, 92:8, 97:3, 98:2, or 99:1. In some embodiments, at least two internucleotidic linkages have a diastereoselectivity lower than about 60:40, 70:30, 80:20, 85:15, 90:10, 91:9, 92:8, 97:3, 98:2, or 99:1. In some embodiments, at least three internucleotidic linkages have a diastereoselectivity lower than about 60:40, 70:30, 80:20, 85:15, 90:10, 91:9, 92:8, 97:3, 98:2, or 99:1. In some embodiments, at least four internucleotidic linkages have a diastereoselectivity lower than about 60:40, 70:30, 80:20, 85:15, 90:10, 91:9, 92:8, 97:3, 98:2, or 99:1. In some embodiments, at least five internucleotidic linkages have a diastereoselectivity lower than about 60:40, 70:30, 80:20, 85:15, 90:10, 91:9, 92:8, 97:3, 98:2, or 99:1. In some embodiments, each internucleotidic linkage independently has a diastereoselectivity lower than about 60:40, 70:30, 80:20, 85:15, 90:10, 91:9, 92:8, 97:3, 98:2, or 99:1. In some embodiments, a diastereoselectivity is lower than about 60:40. In some embodiments, a diastereoselectivity is lower than about 70:30. In some embodiments, a diastereoselectivity is lower than about 80:20. In some embodiments, a diastereoselectivity is lower than about 90:10. In some embodiments, a diastereoselectivity is lower than about 91:9. In some embodiments, a diastereoselectivity is lower than about 92:8. In some embodiments, a diastereoselectivity is lower than about 93:7. In some embodiments, a diastereoselectivity is lower than about 94:6. In some embodiments, a diastereoselectivity is lower than about 95:5. In some embodiments, a diastereoselectivity is lower than about 96:4. In some embodiments, a diastereoselectivity is lower than about 97:3. In some embodiments, a diastereoselectivity is lower than about 98:2. In some embodiments, a diastereoselectivity is lower than about 99:1. In some embodiments, at least one coupling has a diastereoselectivity lower than about 90:10. In some embodiments, at least two couplings have a diastereoselectivity lower than about 90:10. In some embodiments, at least three couplings have a diastereoselectivity lower than about 90:10. In some embodiments, at least four couplings have a diastereoselectivity lower than about 90:10. In some embodiments, at least five couplings have a diastereoselectivity lower than about 90:10. In some embodiments, each coupling independently has a diastereoselectivity lower than about 90:10. In some embodiments, at least one internucleotidic linkage has a diastereoselectivity lower than about 90:10. In some embodiments, at least two internucleotidic linkages have a diastereoselectivity lower than about 90:10. In some embodiments, at least three internucleotidic linkages have a diastereoselectivity lower than about 90:10. In some embodiments, at least four internucleotidic linkages have a diastereoselectivity lower than about 90:10. In some embodiments, at least five internucleotidic linkages have a diastereoselectivity lower than about 90:10. In some embodiments, each internucleotidic linkage independently has a diastereoselectivity lower than about 90:10.

In some embodiments, a chirally controlled internucleotidic linkage, such as those of oligonucleotides of chirally controlled oligonucleotide compositions, has a diastereoselectivity of 90:10 or more. In some embodiments, each chirally controlled internucleotidic linkage, such as those of oligonucleotides of chirally controlled oligonucleotide compositions, has a diastereoselectivity of 90:10 or more. In some embodiments, the selectivity is 91:9 or more. In some embodiments, the selectivity is 92:8 or more. In some embodiments, the selectivity is 97:3 or more. In some embodiments, the selectivity is 94:6 or more. In some embodiments, the selectivity is 95:5 or more. In some embodiments, the selectivity is 96:4 or more. In some embodiments, the selectivity is 97:3 or more. In some embodiments, the selectivity is 98:2 or more. In some embodiments, the selectivity is 99:1 or more.

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage.

In some embodiments, a particular oligonucleotide type may be defined by
1A) base identity;
1B) pattern of base modification;
1C) pattern of sugar modification;
2) pattern of backbone linkages;
3) pattern of backbone chiral centers;
4) pattern of backbone phosphorus modifications; and
5) pattern of additional chemical moieties (if any).

In some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, provided chirally controlled (and/or stereochemically pure) preparations are of oligonucleotides having a common base sequence of at least 15 bases. In some embodiments, provided chirally controlled (and/or stereochemically pure) preparations are of oligonucleotides having a common base sequence of 15 to 49 bases.

In some embodiments, one or more is one. In some embodiments, one or more is two. In some embodiments, one or more is three. In some embodiments, one or more is four. In some embodiments, one or more is five. In some embodiments, one or more is six. In some embodiments, one or more is seven. In some embodiments, one or more is eight. In some embodiments, one or more is nine. In some embodiments, one or more is ten. In some embodiments, one or more is at least one. In some embodiments, one or more is at least two. In some embodiments, one or more is at least three. In some embodiments, one or more is at least four. In some embodiments, one or more is at least five. In some embodiments, one or more is at least six. In some embodiments, one or more is at least seven. In some embodiments, one or more is at least eight. In some embodiments, one or more is at least nine. In some embodiments, one or more is at least ten.

In some embodiments, provided oligonucleotides or a block thereof comprises a pattern of backbone chiral centers of: S, SS, SSS, SSSS, SSSSS, SSSSSS, SSSSSSS, SSSSSSSS, SSSSSSSSS, SSSSSSSSSS, SSSSSSSSSSS, SSSSSSSSSSSS, SSSSSSSSSSSSS, SSSSSSSSSSSSSS, SSSSSSSSSSSSSSS, SSSSSSSSSSSSSSSS, SSSSSSSSSSSSSSSSS, SSSSSSSSSSSSSSSSSS, SSSSSSSSSSSSSSSSSSS, SSSSSSSSSSSSSSSSSSSS, SSSSSSSSSSSSSSSSSSSSS, SSSSSSSSSSSSSSSSSSSSSS, SSSSSSSSSSSSSSSSSSSSSSS, SSSSSSSSSSSSSSSSSSSSSSSS, R, RR, RRR, RRRR, RRRRR, RRRRRR, RRRRRRR, RRRRRRRR, RRRRRRRRR, RRRRRRRRRR, RRRRRRRRRRR, RRRRRRRRRRRR, RRRRRRRRRRRRR, RRRRRRRRRRRRRR, RRRRRRRRRRRRRRR, RRRRRRRRRRRRRRRR, RRRRRRRRRRRRRRRRR, RRRRRRRRRRRRRRRRRR, RRRRRRRRRRRRRRRRRRR, RRRRRRRRRRRRRRRRRRRR, RRRRRRRRRRRRRRRRRRRRR, RRRRRRRRRRRRRRRRRRRRRR, RRRRRRRRRRRRRRRRRRRRRRR, RRRRRRRRRRRRRRRRRRRRRRRR, OOOS, OOOS, OOOX, OOR, OOS, OOX, OR, ORR, ORRR, ORRRR, ORRRRR, ORRRRRR, ORRRRRRR, ORRRRRRRR, ORRRRRRRRR, ORRRRRRRRRR, ORRRRRRRRRRR, ORRRRRRRRRRRR, ORRRRRRRRRRRRR, ORRRRRRRRRRRRRR, ORRRRRRRRRRRRRRR, ORRRRRRRRRRRRRRRR, ORRRRRRRRRRRRRRRRR, ORRRRRRRRRRRRRRRRRR, OS, OSS, OSSS, OSSSS, OSSSSS, OSSSSSS, OSSSSSSS, OSSSSSSSS, OSSSSSSSSS, OSSSSSSSSSS, OSSSSSSSSSSS, OSSSSSSSSSSSS, OSSSSSSSSSSSSS, OSSSSSSSSSSSSSS, OSSSSSSSSSSSSSSS, OSSSSSSSSSSSSSSSS, OSSSSSSSSSSSSSSSSS, OS, OSO, OSOO, OSOOO, OSOS, OSS, OSSO, OX, OXO, OXOO, OXOOO, RO, ROO, ROOO, ROOOR, ROOOS, ROOR, ROORR, ROR, ROROR, RROOR, RROR, RRRO, RRROR, RS, SR, RSR, RRS, RRSR, SRR, RSRR, RRSRR, RRRS, RRRSR, RRRSRR, RRRSRRR, RSRRR, RRSRRR, SRRR, RRRRS, RRRRSR, RRRRSRR, RRRRSRRR, RRRRSRRRR, SRRRR, RSRRRR, RRSRRRR, RRRSRRRR, RRRRSRRRR, RRRRRS, RRRRRSR, RRRRRSRR, RRRRRSRRR, RRRRRSRRRR, RRRRRSRRRRR, SRRRRR, RSRRRRR, RRSRRRRR, RRRSRRRRR, RRRRSRRRRR, RRRRRSRRRRR, RRRRRRS, RRRRRRSR, RRRRRRSRR, RRRRRRSRRR, RRRRRRSRRRR, RRRRRRSRRRRR, RRRRRRSRRRRRR, SRRRRRR, RSRRRRRR, RRSRRRRRR, RRRSRRRRRR, RRRRSRRRRRR, RRRRRSRRRRRR, RRRRRRSRRRRRR, RRRRRRRS, RRRRRRRSR, RRRRRRRSRR, RRRRRRRSRRR, RRRRRRRSRRRR, RRRRRRRSRRRRR, RRRRRRRSRRRRRR, RRRRRRRSRRRRRRR, SRRRRRRR, RSRRRRRRR, RRSRRRRRRR, RRRSRRRRRRR, RRRRSRRRRRRR, RRRRRSRRRRRRR, RRRRRRSRRRRRRR, RRRRRRRSRRRRRRR, RSSR, RSSRR, RRSSR, RRRSS, RRRSSR, RRRSSRR, RRSSRR, SSRR, RRRSS, RRRSSR, RRRRSSRR, RRRRSSRRR, SSRRR, RSSRRR, RRSSRRR, RRRRSS, RRRRSSR, RRRRSSRR, RRRRSSRRR, RRRRRSSRRR, RRRRRSSRRRR, SSRRRR, RSSRRRR, RRSSRRRR, RRSSRRRR, RRRSSRRRR, RRRRSSRRRR, RRRRRSS, RRRRRSSR, RRRRRSSRR, RRRRRSSRRR, RRRRRSSRRRR, RRRRRSSRRRRR, SSRRRRR, RSSRRRRR, RRSSRRRRR, RRRSSRRRRR, RRRRSSRRRRR, RRRRRSSRRRRR, RRRRRRSSRRRRR, RRRRRRSSRRRRRR, RRRRRRSSRR, RRRRRRSSRRR, RRRRRRSSRRRR, RRRRRRSSRRRRR, SSRRRRRR, RSSRRRRRR, RRSSRRRRRR, RRRSSRRRRRR, RRRRSSRRRRRR, RRRRRSSRRRRRR, RRRRRRSSRRRRRR, RRRRRRRSS, RRRRRRRSSR, RRRRRRRSSRR, RRRRRRRSSRRR, RRRRRRRSSRRRR, RRRRRRRSSRRRRR, RRRRRRRSSRRRRRR, RRRRRRRSSRRRRRRR, SSRRRRRRR, RSSRRRRRRR, RRSSRRRRRRR, RRRSSRRRRRRR, RRRRSSRRRRRRR, RRRRRSSRRRRRRR, RRRRRRSSRRRRRRR, RRRRRRRSSRRRRRRR, RSSS, RRSSS, RRRSSS, RRRSSSR, RSSSR, RRSSSR, SSSR, RRRRSSS, RRRRSSSR, RRRRSSSRR, SSSRR, RSSSRR, RRSSSRR, RRRSSSRR, RRRRSSSRR, RRRRRSSS, RRRRRSSSR, RRRRRSSSRR, RRRRRSSSRRR, SSSRRR, RSSSRRR, RRSSSRRR, RRRSSSRRR, RRRRSSSRRR, RRRRRSSSRRR, RRRRRRSSS, RRRRRRSSSR, RRRRRRSSSRR, RRRRRRSSSRRR, RRRRRRSSSRRRR, SSSRRRR, RSSSRRRR, RRSSSRRRR, RRRSSSRRRR, RRRRSSSRRRR, RRRRRSSSRRRR, RRRRRRSSSRRRR, RRRRRRRSSS, RRRRRRRSSSR, RRRRRRRSSSRR, RRRRRRRSSSRRR, RRRRRRRSSSRRRR, RRRRRRRSSSRRRRR, SSSRRRRR, RSSSRRRRR, RRSSSRRRRR, RRRSSSRRRRR, RRRRSSSRRRRR, RRRRRSSSRRRRR, RRRRRRSSSRRRRR, RRRRRRRRSSS, RRRRRRRRSSSR, RRRRRRRRSSSRR, RRRRRRRRSSSRRR, RRRRRRRRSSSRRRR, RRRRRRRRSSSRRRRR, RRRRRRRRSSSRRRRRR, SSSRRRRRR, RSSSRRRRRR, RRSSSRRRRRR, RRRSSSRRRRRR, RRRRSSSRRRRRR, RRRRRSSSRRRRRR, RRRRRRSSSRRRRRR, RRRRRRRSSSRRRRRR, RSSSS, RRSSSS, RRSSSSR, SSSSR, RSSSSR, RRRSSSS, RRRSSSSR, RRRSSSSRR, SSSSRR, RSSSSRR, RRSSSSRR, RRRSSSSRR, RRRRSSSS, RRRRSSSSR, RRRRSSSSRR, RRRRSSSSRRR, SSSSRRR, RSSSSRRR, RRSSSSRRR, RRRSSSSRRR, RRRRSSSSRRR, RRRRRSSSS, RRRRRSSSSR, RRRRRSSSSRR, RRRRRSSSSRRR, RRRRRSSSSRRRR, SSSSRRRR, RSSSSRRRR, RRSSSSRRRR, RRRSSSSRRRR, RRRRSSSSRRRR, RRRRRSSSSRRRR, RRRRRRSSSS, RRRRRRSSSSR, RRRRRRSSSSRR, RRRRRRSSSSRRR, RRRRRRSSSSRRRR, RRRRRRSSSSRRRRR, SSSSRRRRR, RSSSSRRRRR, RRSSSSRRRRR, RRRSSSSRRRRR, RRRRSSSSRRRRR, RRRRRSSSSRRRRR, RRRRRRRSSSS, RRRRRRRSSSSR, RRRRRRRSSSSRR, RRRRRRRSSSSRRR, RRRRRRRSSSSRRRR, RRRRRRRSSSSRRRRR, RRRRRRRSSSSRRRRRR, SSSSRRRRRR, RSSSSRRRRRR, RRSSSSRRRRRR, RRRSSSSRRRRRR, RRRRSSSSRRRRRR, RRRRRSSSSRRRRRR, RRRRRRSSSSRRRRRR, SSSSS, RSSSSS, RSSSSSR, SSSSSR, RRSSSSS, RRSSSSSR, RRSSSSSRR, SSSSSRR, RSSSSSRR, RRSSSSSRR, RRRSSSSS, RRRSSSSSR, RRRSSSSSRR, RRRSSSSSRRR, SSSSSRRR, RSSSSSRRR, RRSSSSSRRR, RRRSSSSSRRR, RRRRSSSSS, RRRRSSSSSR, RRRRSSSSSRR, RRRRSSSSSRRR, RRRRSSSSSRRRR, SSSSSRRRR, RSSSSSRRRR, RRSSSSSRRRR, RRRSSSSSRRRR, RRRRSSSSSRRRR, RRRRRSSSSS, RRRRRSSSSSR, RRRRRSSSSSRR, RRRRRSSSSSRRR, RRRRRSSSSSRRRR, RRRRRSSSSSRRRRR, SSSSSRRRRR, RSSSSSRRRRR, RRSSSSSRRRRR, RRRSSSSSRRRRR, RRRRSSSSSRRRRR, RRRRRRSSSSS, RRRRRRSSSSSR, RRRRRRSSSSSRR, RRRRRRSSSSSRRR, RRRRRRSSSSSRRRR, RRRRRRSSSSSRRRRR, RRRRRRSSSSSRRRRRR, SSSSSRRRRRR, RSSSSSRRRRRR, RRSSSSSRRRRRR, RRRSSSSSRRRRRR, RRRRSSSSSRRRRRR, RRRRRSSSSSRRRRRR, RSSSSSS, SSSSSS, RRSSSSSS, RRSSSSSSR, SSSSSSR, RSSSSSSR, RRSSSSSSR, RRRSSSSSS, RRRSSSSSSR, RRRSSSSSSRR, SSSSSSRR, RSSSSSSRR, RRSSSSSSRR, RRRSSSSSSRR, RRRRSSSSSS, RRRRSSSSSSR, RRRRSSSSSSRR, RRRRSSSSSSRRR, SSSSSSRRR, RSSSSSSRRR, RRSSSSSSRRR, RRRSSSSSSRRR, RRRRSSSSSSRRR, RRRRRSSSSSS, RRRRRSSSSSSR, RRRRRSSSSSSRR, RRRRRSSSSSSRRR, RRRRRSSSSSSRRRR, SSSSSSRRRR, RSSSSSSRRRR, RRSSSSSSRRRR, RRRSSSSSSRRRR, RRRRSSSSSSRRRR, RRRRRRSSSSSS, RRRRRRSSSSSSR, RRRRRRSSSSSSRR, RRRRRRSSSSSSRRR, RRRRRRSSSSSSRRRR, RRRRRRSSSSSSRRRRR, SSSSSSRRRRR, RSSSSSSRRRRR, RRSSSSSSRRRRR, RRRSSSSSSRRRRR, RRRRSSSSSSRRRRR, RRRRRSSSSSSRRRRR, SSSSSSS, RSSSSSSS, RSSSSSSSR, SSSSSSSR, RSSSSSSSR, RRSSSSSSS, RRSSSSSSSR, RRSSSSSSSRR, SSSSSSSRR, RSSSSSSSRR, RRSSSSSSSRR, RRRSSSSSSS, RRRSSSSSSSR, RRRSSSSSSSRR, RRRSSSSSSSRRR, SSSSSSSRRR, RSSSSSSSRRR, RRSSSSSSSRRR, RRRSSSSSSSRRR, RRRRSSSSSSS, RRRRSSSSSSSR, RRRRSSSSSSSRR, RRRRSSSSSSSRRR, RRRRSSSSSSSRRRR, SSSSSSSRRRR, RSSSSSSSRRRR, RRSSSSSSSRRRR, RRRSSSSSSSRRRR, RRRRRSSSSSSS, RRRRRSSSSSSSR, RRRRRSSSSSSSRR, RRRRRSSSSSSSRRR, RRRRRSSSSSSSRRRR, RRRRRSSSSSSSRRRRR, SSSSSSSRRRRR, RSSSSSSSRRRRR, RRSSSSSSSRRRRR, RRRSSSSSSSRRRRR, RRRRSSSSSSSRRRRR, RSSSSSSSS, RRSSSSSSSS, RRSSSSSSSSR, SSSSSSSSR, RSSSSSSSSR, RRRSSSSSSSS, RRRSSSSSSSSR, RRRSSSSSSSSRR, SSSSSSSSRR, RSSSSSSSSRR, RRSSSSSSSSRR, RRRSSSSSSSSRR, RRRRSSSSSSSS, RRRRSSSSSSSSR, RRRRSSSSSSSSRR, RRRRSSSSSSSSRRR, SSSSSSSSRRR, RSSSSSSSSRRR, RRSSSSSSSSRRR, RRRSSSSSSSSRRR, RRRRRSSSSSSSS, RRRRRSSSSSSSSR, RRRRRSSSSSSSSRR, RRRRRSSSSSSSSRRR, RRRRRSSSSSSSSRRRR, SSSSSSSSRRRR, RSSSSSSSSRRRR, RRSSSSSSSSRRRR, RRRSSSSSSSSRRRR, RRRRSSSSSSSSRRRR, RSSSSSSSSS, RSSSSSSSSSR, SSSSSSSSSR, RSSSSSSSSSR, RRSSSSSSSSS, RRSSSSSSSSSR, RRSSSSSSSSSRR, SSSSSSSSSRR, RSSSSSSSSSRR, RRSSSSSSSSSRR, RRRSSSSSSSSS, RRRSSSSSSSSSR, RRRSSSSSSSSSRR, RRRSSSSSSSSSRRR, SSSSSSSSSRRR, RSSSSSSSSSRRR, RRSSSSSSSSSRRR, RRRRSSSSSSSSS, RRRRSSSSSSSSSR, RRRRSSSSSSSSSRR, RRRRSSSSSSSSSRRR, RRRRSSSSSSSSSRRRR, SSSSSSSSSRRRR, RSSSSSSSSSRRRR, RRSSSSSSSSSRRRR, RRRSSSSSSSSSRRRR, RSSSSSSSSSS, RSSSSSSSSSS, RRSSSSSSSSSS, RRSSSSSSSSSSR, SSSSSSSSSSR, RSSSSSSSSSSR, RRSSSSSSSSSSR, RRRSSSSSSSSSS, RRRSSSSSSSSSSR, RRRSSSSSSSSSSRR, SSSSSSSSSSRR, RSSSSSSSSSSRR, RRSSSSSSSSSSRR, RRRRSSSSSSSSSS, RRRRSSSSSSSSSSR, RRRRSSSSSSSSSSRR, RRRRSSSSSSSSSSRRR, SSSSSSSSSSRRR, RSSSSSSSSSSRRR, RRSSSSSSSSSSRRR, RRRSSSSSSSSSSRRR, RSSSSSSSSSSS, RSSSSSSSSSSSR, SSSSSSSSSSSR, RSSSSSSSSSSSR, RRSSSSSSSSSSS, RRSSSSSSSSSSSR, RRSSSSSSSSSSSRR, SSSSSSSSSSSRR, RSSSSSSSSSSSRR, RRRSSSSSSSSSSS, RRRSSSSSSSSSSSR, RRRSSSSSSSSSSSRR, RRRSSSSSSSSSSSRRR, SSSSSSSSSSSRRR, RSSSSSSSSSSSRRR, RRSSSSSSSSSSSRRR, SSSSSSSSSSSSR, SSSSSSSSSSSSR, RSSSSSSSSSSSS, RSSSSSSSSSSSSR, RSSSSSSSSSSSSRR, SSSSSSSSSSSSRR, RRSSSSSSSSSSSS, RRSSSSSSSSSSSSR, RRSSSSSSSSSSSSRR, RRSSSSSSSSSSSRRR, SSSSSSSSSSSSRRR, RSSSSSSSSSSSSRRR, RSSSSSSSSSSSSS, RSSSSSSSSSSSSSR, SSSSSSSSSSSSR, RRSSSSSSSSSSSSR, RRSSSSSSSSSSSSSR, RRSSSSSSSSSSSSSRR, SSSSSSSSSSSSSRR, RSSSSSSSSSSSSSRR, SSSSSSSSSSSSSR, RSSSSSSSSSSSSSS, RSSSSSSSSSSSSSSR, RSSSSSSSSSSSSSSR, SSSSSSSSSSSSSRR, RSSSSSSSSSSSSSS, RSSSSSSSSSSSSSSR, SSSSSSSSSSSSSSSR, RSSSSSSSSSSSSSSS, SSSSSSSSSSSSSSSR, RRRRRRRRSRRRRRRRR, RRRRRRRSSSRRRRRRR, RRRRRRSSSSSRRRRRR, RRRRRSSSSSSSRRRRR, RRRRSSSSSSSSSRRRR, RRRSSSSSSSSSSSRRR, RRSSSSSSSSSSSSSRR, RSSSSSSSSSSSSSSSR, RSRSRSRSRSRSRSRSR, RSRSRSRSRSRSRSRS, RSRSRSRSRSRSRSR, RSRSRSRSRSRSRS, RSRSRSRSRSRSR, RSRSRSRSRSRS, RSRSRSRSRSR, RSRSRSRSRS XXOXOXXXXXOXOOOOOXXX,
XXOXOXXXXXOXOXOOOOOXX,
XXOXOXXXXXOXOOOOXX,
XXOXOXXXXXOXOXXXXXX,
XXOXOXXXXXOXOXXXXXO,
XXOXOXXXXXOXOXXXXXX,
XXOXOXXXXXOXOXXXXXXXXXO,
XXOXOXXXXXOXOXXXXXXXXXX,
XXOXXXOXOOOXOOXXXXXO,
XXOXXXOXOXOXOOOOOOOXX,
XXOXXXOXOXOXOOOOOOXX,
XXOXXXOXOXOXOOOOOXXX,
XXOXXXOXOXOXOXOOOOOXX,
XXOXXXOXOXOXOXOOOOXX,
XXOXXXOXOXOXOXXXXXX,
XXOXXXOXOXOXOXXXXXO,
XXOXXXOXOXOXOXXXXXX,
XXOXXXOXOXOXOXXXXXXXXXO,
XXOXXXOXOXOXOXXXXXXXXXX,
XXOXXXOXOXXOOOOOOOOXX,
XXOXXXOXOXXOOOOOOOXX,
XXOXXXOXOXXOOOOOXXX,
XXOXXXOXOXXOXOOOOOOXX,
XXOXXXOXOXXOXOOOOXX,
XXOXXXOXOXXOXXXXXX,
XXOXXXOXOXXOXXXXXO,
XXOXXXOXOXXOXXXXXX,
XXOXXXOXOXXOXXXXXXXXXO,
XXOXXXOXOXXOXXXXXXXXXX,
XXOXXXOXXOOXOOXXXXXO,
XXOXXXOXXXOOOOOOOOXX,
XXOXXXOXXXOOOOOOOXX,
XXOXXXOXXXOOOOOXXX,
XXOXXXOXXXOXOOOOOOXX,
XXOXXXOXXXOXOOOOXX,
XXOXXXOXXXOXXXXXX,
XXOXXXOXXXOXXXXXXO,
XXOXXXOXXXOXXXXXXX,
XXOXXXOXXXOXXXXXXXXXO,
XXOXXXOXXXOXXXXXXXXXX,
XXOXXXXXOOOXOOXXXXXO,
XXOXXXXXOXOXOOOOOOOXX,
XXOXXXXXOXOXOOOOOOXX,
XXOXXXXXOXOXOOOOOXXX,
XXOXXXXXOXOXOXOOOOOXX,
XXOXXXXXOXOXOXOOOOXX,
XXOXXXXXOXOXOXXXXXX,
XXOXXXXXOXOXOXXXXXO,
XXOXXXXXOXOXOXXXXXX,
XXOXXXXXOXOXOXXXXXXXXXO,
XXOXXXXXOXOXOXXXXXXXXXX,
XXXOXOXOXOOOXOOXXXXXO,
XXXOXOXOXOXOXOOOOOOOXX,
XXXOXOXOXOXOXOOOOOOXX,
XXXOXOXOXOXOXOOOOOXXX,
XXXOXOXOXOXOXOXOOOOOXX,
XXXOXOXOXOXOXOXOOOOXX,
XXXOXOXOXOXOXOXXXXXX, XXXXXXOXOXOXOXXXXX,
XXXXXXOXOXOXOXXXXXO,
XXXXXXOXOXOXOXXXXXX,
XXXXXXOXOXOXOXXXXXXXXO,
XXXXXXOXOXOXOXXXXXXXXX,
XXXXXXOXOXXXOOOOOOOXX,
XXXXXXOXOXXXOOOOOOXX,
XXXXXXOXOXXXOOOOOXX,
XXXXXXOXOXXXOXOOOOOOXX,
XXXXXXOXOXXXOXOOOOXX,
XXXXXXOXOXXXOXXXXXX,
XXXXXXOXOXXXOXXXXXXO,
XXXXXXOXOXXXOXXXXXXX,
XXXXXXOXOXXXOXXXXXXXXO,
XXXXXXOXOXXXOXXXXXXXXX,
XXXXXXXXXXXXXXXXXX,
XXXXXXXXXXXXXXXXXXX,
XXXXXXXXXXXXXXXXXXXX,
XXXXXXXXXXXXXXXXXXXXX,
XXXXXXXXXXXXXXXXXXXXXX,
XXXXXXXXXXXXXXXXXXXXXXX,
XXXXXXXXXXXXXXXXXXXXXXXX,
XXXXXXXXXXXXXXXXXXXXXXXXX,
XXXXXXXXXXXXXXXXXXXXXXXXXX, or
XXXXXXXXXXXXXXXXXXXXXXXXXXX, or any span of at least 5 consecutive internucleotidic linkages thereof, wherein O indicates a phosphodiester, and X indicates an internucleotidic linkage or modified internucleotidic linkage which is not phosphodiester; in some embodiments, a modified internucleotidic linkage is a phosphorothioate; in some embodiments, a modified internucleotidic linkage is chirally controlled; in some embodiments, a modified internucleotidic linkage is a chirally controlled phosphorothioate.

In some embodiments, the present disclosure provides a chirally controlled SMN2 oligonucleotide having the sequence of any oligonucleotide disclosed herein, wherein at least one linkage phosphorus is Rp. It is understood by a person of ordinary skill in the art that in certain embodiments wherein the chirally controlled SMN2 oligonucleotide comprises a base sequence, each T is independently and optionally replaced with U. In some embodiments, the present disclosure provides a chirally controlled SMN2 oligonucleotide having the sequence of any oligonucleotide disclosed herein, wherein each linkage phosphorus is Rp. In some embodiments, the present disclosure provides a chirally controlled SMN2 oligonucleotide having the sequence of any oligonucleotide disclosed herein, wherein at least one linkage phosphorus is Sp. In some embodiments, the present disclosure provides a chirally controlled SMN2 oligonucleotide having the sequence of any oligonucleotide disclosed herein, wherein each linkage phosphorus is Sp. In some embodiments, the present disclosure provides a chirally controlled SMN2 oligonucleotide having the sequence of any oligonucleotide disclosed herein, wherein the oligonucleotide is a blockmer. In some embodiments, the present disclosure provides a chirally controlled SMN2 oligonucleotide having the sequence of any oligonucleotide disclosed herein, wherein the oligonucleotide is a stereoblockmer. In some embodiments, the present disclosure provides a chirally controlled SMN2 oligonucleotide having the sequence of any oligonucleotide disclosed herein, wherein the oligonucleotide is a P-modification blockmer. In some embodiments, the present disclosure provides a chirally controlled SMN2 oligonucleotide having the sequence of any oligonucleotide disclosed herein, wherein the oligonucleotide is a linkage blockmer. In some embodiments, the present disclosure provides a chirally controlled SMN2 oligonucleotide having the sequence of any oligonucleotide disclosed herein, wherein the oligonucleotide is an altmer. In some embodiments, the present disclosure provides a chirally controlled SMN2 oligonucleotide having the sequence of any oligonucleotide disclosed herein, wherein the oligonucleotide is a stereoaltmer. In some embodiments, the present disclosure provides a chirally controlled SMN2 oligonucleotide having the sequence of any oligonucleotide disclosed herein, wherein the oligonucleotide is a P-modification altmer. In some embodiments, the present disclosure provides a chirally controlled SMN2 oligonucleotide having the sequence of any oligonucleotide disclosed herein, wherein the oligonucleotide is a linkage altmer. In some embodiments, the present disclosure provides a chirally controlled SMN2 oligonucleotide having the sequence of any oligonucleotide disclosed herein, wherein the oligonucleotide is a unimer. In some embodiments, the present disclosure provides a chirally controlled SMN2 oligonucleotide having the sequence of any oligonucleotide disclosed herein, wherein the oligonucleotide is a stereounimer. In some embodiments, the present disclosure provides a chirally controlled SMN2 oligonucleotide having the sequence of any oligonucleotide disclosed herein, wherein the oligonucleotide is a P-modification unimer. In some embodiments, the present disclosure provides a chirally controlled SMN2 oligonucleotide having the sequence of any oligonucleotide disclosed herein, wherein the oligonucleotide is a linkage unimer. In some embodiments, the present disclosure provides a chirally controlled SMN2 oligonucleotide having the sequence of any oligonucleotide disclosed herein, wherein the oligonucleotide is a gapmer. In some embodiments, the present disclosure provides a chirally controlled SMN2 oligonucleotide having the sequence of any oligonucleotide disclosed herein, wherein the oligonucleotide is a skipmer.

In some embodiments, provided oligonucleotides can comprise any base sequence described herein, or portion thereof, wherein a portion is a span of at least 15 contiguous bases, or a span of at least 15 contiguous bases with 1-5 mismatches.

In some embodiments, the base sequence of a SMN2 oligonucleotide has a sufficient length and identity to a SMN2 transcript target to mediate increased level of exon 7-containing SMN2 mRNA relative to exon 7-deleted SMN2 mRNA, or increased inclusion of exon 7 of a SMN2 mRNA, in a cell extract, cell, tissue, organ and/or organism.

In some embodiments, the base sequence of a SMN2 oligonucleotide is complementary to that of a SMN2 target transcript. In some embodiments, the base sequence of a SMN2 oligonucleotide is complementary to that of a SMN2 target sequence when each base of the oligonucleotide is capable of base-pairing with a sequential base on the target strand, when maximally aligned. As a non-limiting example, if a target sequence has, for example, a base sequence of 5'-GCAUAGCGAGCGAGGGAAAAC-3' (SEQ ID NO: 17), an oligonucleotide with a base sequence of 5'GUUUUCCCUCGCUCGCUAUGC-3' (SEQ ID NO: 18) is complementary (fully complementary) to such a target sequence. Unless otherwise specified, substitution of T for U, or vice versa, does not alter the amount of complementarity. In some embodiments, an oligonucleotide that is "substantially complementary" to a SMN2 target sequence is largely or mostly complementary but not 100% complementary. In some embodiments, a sequence (e.g., a SMN2 oligonucleotide) which is substantially complementary has 1, 2, 3, 4 or 5 mismatches from a sequence which is 100% complementary to the target sequence.

In some embodiments, the base sequence of a provided oligonucleotide (e.g., of a SMN2 oligonucleotide) is or comprises any of: UCAUAAUGCUGGCAGACUUA (e.g., WV-2837) (SEQ ID NO: 19); UUCAUAAUGCUGGCA-GACUU (WV-2838) (SEQ ID NO: 20);

UUUCAUAAUGCUGGCAGACU (WV-2839); (SEQ ID NO: 21)

CUUUCAUAAUGCUGGCAGAC (WV-2840); (SEQ ID NO: 22)

ACUUUCAUAAUGCUGGCAGA (WV-2841); (SEQ ID NO: 23)

CACUUUCAUAAUGCUGGCAG (WV-2842); (SEQ ID NO: 24)

UCACUUUCAUAAUGCUGGCA (WV-2843); (SEQ ID NO: 25)

UUCACUUUCAUAAUGCUGGC (WV-2844); (SEQ ID NO: 26)

AUUCACUUUCAUAAUGCUGG (WV-2845); (SEQ ID NO: 27)

GAUUCACUUUCAUAAUGCUG (WV-2846); (SEQ ID NO: 28)

AGAUUCACUUUCAUAAUGCU (WV-2847); (SEQ ID NO: 29)

AAGAUUCACUUUCAUAAUGC (WV-2848); (SEQ ID NO: 30)

UAAGAUUCACUUUCAUAAUG (WV-2849); (SEQ ID NO: 31)

GUAAGAUUCACUUUCAUAAU (WV-2850); (SEQ ID NO: 32)

CUUUCUAACAUCUGAACUUU (WV-2851); (SEQ ID NO: 33)

AACUUUCUAACAUCUGAACU (WV-2852); (SEQ ID NO: 34)

UCAACUUUCUAACAUCUGAA (WV-2853); (SEQ ID NO: 35)

UUUCAACUUUCUAACAUCUG (WV-2854); (SEQ ID NO: 36)

CCUUUCAACUUUCUAACAUC (WV-2855); (SEQ ID NO: 37)

AACCUUUCAACUUUCUAACA (WV-2856); (SEQ ID NO: 38)

CUGCCUACUAGUGAUAUAAA (WV-2857); (SEQ ID NO: 39)

GUCUGCCUACUAGUGAUAUA (WV-2858); (SEQ ID NO: 40)

UGGUCUGCCUACUAGUGAUA (WV-2859); (SEQ ID NO: 41)

GCUGGUCUGCCUACUAGUGA (WV-2860); (SEQ ID NO: 42)

CUGCUGGUCUGCCUACUAGU (WV-2861); (SEQ ID NO: 43)

GUCUGCUGGUCUGCCUACUA (WV-2862); (SEQ ID NO: 44)

AAGUCUGCUGGUCUGCCUAC (WV-2863); (SEQ ID NO: 45)

AAAAGUCUGCUGGUCUGCCU (WV-2864); (SEQ ID NO: 46)

GAAAUUAGAACCAGAGGCUU (WV-2865); (SEQ ID NO: 47)

GAGAAAUUAGAACCAGAGGC (WV-2866); (SEQ ID NO: 48)

AUGAGAAAUUAGAACCAGAG (WV-2867); (SEQ ID NO: 49)

AAAUGAGAAAUUAGAACCAG (WV-2868); (SEQ ID NO: 50)

GCAAAUGAGAAAUUAGAACC (WV-2869); (SEQ ID NO: 51)

CUGCAAAUGAGAAAUUAGAA (WV-2870); (SEQ ID NO: 52)

UCCUGCAAAUGAGAAAUUAG (WV-2871); (SEQ ID NO: 53)

UUUCCUGCAAAUGAGAAAUU (WV-2872); (SEQ ID NO: 54)

CAUUUCCUGCAAAUGAGAAA (WV-2873); (SEQ ID NO: 55)

AGCAUUUCCUGCAAAUGAGA (WV-2874); (SEQ ID NO: 56)

CCAGCAUUUCCUGCAAAUGA (WV-2875); (SEQ ID NO: 57)

UGCCAGCAUUUCCUGCAAAU (WV-2876); (SEQ ID NO: 58)

UAUGCCAGCAUUUCCUGCAA (WV-2877); (SEQ ID NO: 59)

UCUAUGCCAGCAUUUCCUGC (WV-2878); (SEQ ID NO: 60)

GCUCUAUGCCAGCAUUUCCU (WV-2879); (SEQ ID NO: 61)

CUGCUCUAUGCCAGCAUUUC (WV-2880); (SEQ ID NO: 62)

UGCUGCUCUAUGCCAGCAUU (WV-2881); (SEQ ID NO: 63)

AGUGCUGCUCUAUGCCAGCA (WV-2882); (SEQ ID NO: 64)

UUAGUGCUGCUCUAUGCCAG (WV-2883); (SEQ ID NO: 65)

UCCACAAACCAUAAAGUUUU (WV-2884); (SEQ ID NO: 66)

UUUCCACAAACCAUAAAGUU (WV-2885); (SEQ ID NO: 67)

GUUUUCCACAAACCAUAAAG (WV-2886); (SEQ ID NO: 68)

UUGUUUUCCACAAACCAUAA (WV-2887); (SEQ ID NO: 69)

AUUCUAGUAGGGAUGUAGAU (WV-2888); (SEQ ID NO: 70)

GAAUUCUAGUAGGGAUGUAG (WV-2889); (SEQ ID NO: 71)

GAGAAUUCUAGUAGGGAUGU (WV-2890); (SEQ ID NO: 72)

```
                                    (SEQ ID NO: 73)
AUGAGAAUUCUAGUAGGGAU (WV-2891);

(SEQ ID NO: 74)
UUAUUUUAUUCAACAAAAUA (WV-2892);

(SEQ ID NO: 75)
UACUUAUUUUAUUCAACAAA (WV-2893);

(SEQ ID NO: 76)
UUUUACUUAUUUUAUUCAAC (WV-2894);

(SEQ ID NO: 77)
ACAUUUUACUUAUUUUAUUC (WV-2895);

(SEQ ID NO: 78)
AAGACAUUUUACUUAUUUUA (WV-2896);

(SEQ ID NO: 79)
CACAAGACAUUUUACUUAUU (WV-2897);

(SEQ ID NO: 80)
UUUCACAAGACAUUUUACUU (WV-2898);

(SEQ ID NO: 81)
UUGUUUCACAAGACAUUUUA (WV-2899);

(SEQ ID NO: 82)
AUUUUGUUUCACAAGACAUU (WV-2900);

(SEQ ID NO: 83)
AGCAUUUUGUUUCACAAGAC (WV-2901);

(SEQ ID NO: 84)
AAAAGCAUUUUGUUUCACAA (WV-2902);

(SEQ ID NO: 85)
UUAAAAAGCAUUUUGUUUCA (WV-2903);

(SEQ ID NO: 86)
AUGUUAAAAGCAUUUUGUU (WV-2904);

(SEQ ID NO: 87)
UGGAUGUUAAAAGCAUUUU (WV-2905);

(SEQ ID NO: 88)
AUAUGGAUGUUAAAAGCAU (WV-2906);

(SEQ ID NO: 89)
UUUAUAUGGAUGUUAAAAG (WV-2907);

(SEQ ID NO: 90)
AGCUUUAUAUGGAUGUUAAA (WV-2908);

(SEQ ID NO: 91)
GAUAGCUUUAUAUGGAUGUU (WV-2909);

(SEQ ID NO: 92)
AUAGAUAGCUUUAUAUGGAU (WV-2910);

(SEQ ID NO: 93)
UAUAUAGAUAGCUUUAUAUG (WV-2911);

(SEQ ID NO: 94)
CCCUGUAAGGAAAAUAAAGG (WV-2912);

(SEQ ID NO: 95)
AACCCUGUAAGGAAAAUAAA (WV-2913);

(SEQ ID NO: 96)
AAAACCCUGUAAGGAAAAUA (WV-2914);

(SEQ ID NO: 97)
CUAAAACCCUGUAAGGAAAA (WV-2915);

(SEQ ID NO: 98)
GUCUAAAACCCUGUAAGGAA (WV-2916);

(SEQ ID NO: 99)
GAGCACCUUCCUUCUUUUG (WV-2917);

(SEQ ID NO: 100)
GUGAGCACCUUCCUUCUUUU (WV-2918);

(SEQ ID NO: 101)
AUGUGAGCACCUUCCUUCUU (WV-2919);

(SEQ ID NO: 102)
GAAUGUGAGCACCUUCCUUC (WV-2920);

(SEQ ID NO: 103)
AGGAAUGUGAGCACCUUCCU (WV-2921);

(SEQ ID NO: 104)
UAAGGAAUGUGAGCACCUUC (WV-2922);

(SEQ ID NO: 105)
UUUAAGGAAUGUGAGCACCU (WV-2923);

(SEQ ID NO: 106)
AAUUUAAGGAAUGUGAGCAC (WV-2924);

(SEQ ID NO: 107)
UUAAUUUAAGGAAUGUGAGC (WV-2925);

(SEQ ID NO: 108)
CCUUAAUUUAAGGAAUGUGA (WV-2926);

(SEQ ID NO: 109)
CUCCUUAAUUUAAGGAAUGU (WV-2927);

(SEQ ID NO: 110)
ACUUUCAUAAUGCUGGCAGACUUAC (WV-2928);

(SEQ ID NO: 111)
CACUUUCAUAAUGCUGGCAGACUUA (WV-2929);

(SEQ ID NO: 112)
UCACUUUCAUAAUGCUGGCAGACUU (WV-2930);

(SEQ ID NO: 113)
UUCACUUUCAUAAUGCUGGCAGACU (WV-2931);

(SEQ ID NO: 114)
AUUCACUUUCAUAAUGCUGGCAGAC (WV-2932);

(SEQ ID NO: 115)
GAUUCACUUUCAUAAUGCUGGCAGA (WV-2933);

(SEQ ID NO: 116)
AGAUUCACUUUCAUAAUGCUGGCAG (WV-2934);

(SEQ ID NO: 117)
AAGAUUCACUUUCAUAAUGCUGGCA (WV-2935);

(SEQ ID NO: 118)
UAAGAUUCACUUUCAUAAUGCUGGC (WV-2936);

(SEQ ID NO: 119)
GUAAGAUUCACUUUCAUAAUGCUGG (WV-2937);

(SEQ ID NO: 120)
AACUUUCUAACAUCUGAACUUUUA (WV-2938);

(SEQ ID NO: 121)
UCAACUUUCUAACAUCUGAACUUUU (WV-2939);

(SEQ ID NO: 122)
UUUCAACUUUCUAACAUCUGAACUU (WV-2940);

(SEQ ID NO: 123)
CCUUUCAACUUUCUAACAUCUGAAC (WV-2941);

(SEQ ID NO: 124)
AACCUUUCAACUUUCUAACAUCUGA (WV-2942);

(SEQ ID NO: 125)
UUAACCUUUCAACUUUCUAACAUCU (WV-2943);

(SEQ ID NO: 126)
CAUUAACCUUUCAACUUUCUAACAU (WV-2944);
```

UGGUCUGCCUACUAGUGAUAUAAAA (WV-2945); (SEQ ID NO: 127)

GCUGGUCUGCCUACUAGUGAUAUAA (WV-2946); (SEQ ID NO: 128)

CUGCUGGUCUGCCUACUAGUGAUAU (WV-2947); (SEQ ID NO: 129)

GUCUGCUGGUCUGCCUACUAGUGAU (WV-2948); (SEQ ID NO: 130)

AAGUCUGCUGGUCUGCCUACUAGUG (WV-2949); (SEQ ID NO: 131)

AAAAGUCUGCUGGUCUGCCUACUAG (WV-2950); (SEQ ID NO: 132)

AAAAAAGUCUGCUGGUCUGCCUACU (WV-2951); (SEQ ID NO: 133)

AAAAAAAAGUCUGCUGGUCUGCCUA (WV-2952); (SEQ ID NO: 134)

AUAAAAAAAAGUCUGCUGGUCUGCC (WV-2953); (SEQ ID NO: 135)

CAAUAAAAAAAAGUCUGCUGGUCUG (WV-2954); (SEQ ID NO: 136)

AAUGAGAAAUUAGAACCAGAGGCUU (WV-2955); (SEQ ID NO: 137)

CAAAUGAGAAAUUAGAACCAGAGGC (WV-2956); (SEQ ID NO: 138)

UGCAAAUGAGAAAUUAGAACCAGAG (WV-2957); (SEQ ID NO: 139)

CCUGCAAAUGAGAAAUUAGAACCAG (WV-2958); (SEQ ID NO: 140)

UUCCUGCAAAUGAGAAAUUAGAACC (WV-2959); (SEQ ID NO: 141)

AUUUCCUGCAAAUGAGAAAUUAGAA (WV-2960); (SEQ ID NO: 142)

GCAUUUCCUGCAAAUGAGAAAUUAG (WV-2961); (SEQ ID NO: 143)

CAGCAUUUCCUGCAAAUGAGAAAUU (WV-2962); (SEQ ID NO: 144)

GCCAGCAUUUCCUGCAAAUGAGAAA (WV-2963); (SEQ ID NO: 145)

AUGCCAGCAUUUCCUGCAAAUGAGA (WV-2964); (SEQ ID NO: 146)

CUAUGCCAGCAUUUCCUGCAAAUGA (WV-2965); (SEQ ID NO: 147)

CUCUAUGCCAGCAUUUCCUGCAAAU (WV-2966); (SEQ ID NO: 148)

UGCUCUAUGCCAGCAUUUCCUGCAA (WV-2967); (SEQ ID NO: 149)

GCUGCUCUAUGCCAGCAUUUCCUGC (WV-2968); (SEQ ID NO: 150)

GUGCUGCUCUAUGCCAGCAUUUCCU (WV-2969); (SEQ ID NO: 151)

UAGUGCUGCUCUAUGCCAGCAUUUC (WV-2970); (SEQ ID NO: 152)

GUUUUCCACAAACCAUAAAGUUUUA (WV-2971); (SEQ ID NO: 153)

UGUUUUCCACAAACCAUAAAGUUUU (WV-2972); (SEQ ID NO: 154)

UUGUUUUCCACAAACCAUAAAGUUU (WV-2973); (SEQ ID NO: 155)

GAGAAUUCUAGUAGGGAUGUAGAUU (WV-2974); (SEQ ID NO: 156)

UGAGAAUUCUAGUAGGGAUGUAGAU (WV-2975); (SEQ ID NO: 157)

AUGAGAAUUCUAGUAGGGAUGUAGA (WV-2976); (SEQ ID NO: 158)

UAUGAGAAUUCUAGUAGGGAUGUAG (WV-2977); (SEQ ID NO: 159)

UUUACUUAUUUUAUUCAACAAAAUA (WV-2978); (SEQ ID NO: 160)

AUUUUACUUAUUUUAUUCAACAAAA (WV-2979); (SEQ ID NO: 161)

UUCACAAGACAUUUUACUUAUUUUA (WV-2980); (SEQ ID NO: 162)

GUUUCACAAGACAUUUUACUUAUUU (WV-2981); (SEQ ID NO: 163)

UUGUUUCACAAGACAUUUUACUUAU (WV-2982); (SEQ ID NO: 164)

UUUUGUUUCACAAGACAUUUUACUU (WV-2983); (SEQ ID NO: 165)

CAUUUUGUUUCACAAGACAUUUUAC (WV-2984); (SEQ ID NO: 166)

AGCAUUUUGUUUCACAAGACAUUUU (WV-2985); (SEQ ID NO: 167)

AAAGCAUUUUGUUUCACAAGACAUU (WV-2986); (SEQ ID NO: 168)

AAAAAGCAUUUUGUUUCACAAGACA (WV-2987); (SEQ ID NO: 169)

UUAAAAAGCAUUUUGUUUCACAAGA (WV-2988); (SEQ ID NO: 170)

UGUUAAAAAGCAUUUUGUUUCACAA (WV-2989); (SEQ ID NO: 171)

GAUGUUAAAAAGCAUUUUGUUUCAC (WV-2990); (SEQ ID NO: 172)

UGGAUGUUAAAAAGCAUUUUGUUUC (WV-2991); (SEQ ID NO: 173)

UAUGGAUGUUAAAAAGCAUUUUGUU (WV-2992); (SEQ ID NO: 174)

UAUAUGGAUGUUAAAAAGCAUUUUG (WV-2993); (SEQ ID NO: 175)

UUUAUAUGGAUGUUAAAAAGCAUUU (WV-2994); (SEQ ID NO: 176)

GCUUUAUAUGGAUGUUAAAAAGCAU (WV-2995); (SEQ ID NO: 177)

UAGCUUUAUAUGGAUGUUAAAAAGC (WV-2996); (SEQ ID NO: 178)

GAUAGCUUUAUAUGGAUGUUAAAAA (WV-2997); (SEQ ID NO: 179)

UAGAUAGCUUUAUAUGGAUGUUAAA (WV-2998); (SEQ ID NO: 180)

-continued

UAUAGAUAGCUUUAUAUGGAUGUUA (WV-2999); (SEQ ID NO: 181)

UAUAUAGAUAGCUUUAUAUGGAUGU (WV-3000); (SEQ ID NO: 182)

CCUGUAAGGAAAAUAAAGGAAGUUA (WV-3001); (SEQ ID NO: 183)

ACCCUGUAAGGAAAAUAAAGGAAGU (WV-3002); (SEQ ID NO: 184)

AAACCCUGUAAGGAAAAUAAAGGAA (WV-3003); (SEQ ID NO: 185)

UAAAACCCUGUAAGGAAAAUAAAGG (WV-3004); (SEQ ID NO: 186)

UCUAAAACCCUGUAAGGAAAAUAAA (WV-3005); (SEQ ID NO: 187)

UGUCUAAAACCCUGUAAGGAAAAUA (WV-3006); (SEQ ID NO: 188)

AAUGUGAGCACCUUCCUUCUUUUUG (WV-3007); (SEQ ID NO: 189)

GGAAUGUGAGCACCUUCCUUCUUUU (WV-3008); (SEQ ID NO: 190)

AAGGAAUGUGAGCACCUUCCUUCUU (WV-3009); (SEQ ID NO: 191)

UUAAGGAAUGUGAGCACCUUCCUUC (WV-3010); (SEQ ID NO: 192)

AUUUAAGGAAUGUGAGCACCUUCCU (WV-3011); (SEQ ID NO: 193)

UAAUUUAAGGAAUGUGAGCACCUUC (WV-3012); (SEQ ID NO: 194)

CUUAAUUUAAGGAAUGUGAGCACCU (WV-3013); (SEQ ID NO: 195)

UCCUUAAUUUAAGGAAUGUGAGCAC (WV-3014); (SEQ ID NO: 196)

ACUCCUUAAUUUAAGGAAUGUGAGC (WV-3015); (SEQ ID NO: 197)

UUACUCCUUAAUUUAAGGAAUGUGA (WV-3016). (SEQ ID NO: 198)

In some embodiments, the SMN2 oligonucleotide composition is chirally controlled and/or further comprises an additional chemical moiety capable of binding to the asialoglycoprotein receptor (including but not limited to GalNAc or a variant or derivative thereof). For each of the oligonucleotides listed herein from WV-2837 to WV-3016, each sugar comprises 2'-OMe, each internucleotidic linkage was a stereorandom phosphorothioate, and there are no additional chemical moieties. In some embodiments, the base sequence of a SMN2 oligonucleotide is or comprises a SMN2 base sequence listed herein or a portion thereof comprising 15 contiguous bases with 0-3 mismatches, wherein each T can be independently substituted with U. In some embodiments, the base sequence of a provided oligonucleotide, e.g., a SMN2 oligonucleotide, is TCACTTT-CATAATGCTGG (SEQ ID NO: 479) or a portion thereof comprising 15 contiguous bases with 0-3 mismatches, wherein each T can be independently substituted with U. In some embodiments, the base sequence of a provided oligonucleotide, e.g., a SMN2 oligonucleotide composition, is TCACTTTCATAATGCTGG (SEQ ID NO: 1). In some embodiments, a SMN2 oligonucleotide is chirally controlled. Examples of chirally controlled SMN2 oligonucleotides having the base sequence of TCACTTTCATAATGCTGG (SEQ ID NO: 1) include: WV-6767, WV-6768, WV-6769, WV-6770, WV-6771, WV-6772, WV-6773, WV-6774, WV-6775, WV-6776, WV-6777, WV-6778, WV-6779, WV-6780, WV-6781, WV-6782, WV-6783, WV-6784, WV-6785, WV-6786, WV-6787, WV-6788, WV-6789, WV-6790, WV-6791, WV-6792, WV-6793, WV-6794, WV-6795, WV-6796, WV-6797, WV-6798, WV-6799, WV-6800, WV-6801, WV-6802, WV-6803, WV-6804, WV-6805, WV-6806, WV-6807, WV-6808, WV-6809, WV-6810, WV-6811, WV-6812, WV-6813, WV-6815, WV-6817, WV-9064, and WV-9065.

Among other things, the present disclosure provides, in Table 1A and elsewhere, various oligonucleotides, each of which has a defined base sequence. In some embodiments, the disclosure encompasses any oligonucleotide having a base sequence which is, comprises, or comprises a portion of the base sequence of any oligonucleotide disclosed herein, which has any chemical modification, stereochemistry, format, structural feature (e.g., any structure or pattern of modification or portion thereof), and/or any other modification described herein (e.g., conjugation with another moiety, such as a targeting moiety, carbohydrate moiety, etc.; and/or multimerization). In some embodiments, a "portion" (e.g., of a base sequence or a pattern of modifications), is at least 5, 6, 7, 8, 9, 10, 11, 12, 13, 14, 15, 16, 17, 18, 19, or 20 long. In some embodiments, a "portion" of a base sequence is at least 5 nt long. In some embodiments, a "portion" of a base sequence is at least 10 nt long. In some embodiments, a "portion" of a base sequence is at least 15 nt long. In some embodiments, a "portion" of a base sequence is at least 20 nt long.

In some embodiments, the present disclosure provides a SMN2 oligonucleotide having the sequence of any oligonucleotide disclosed herein, wherein each cytosine is optionally and independently replaced by 5-methylcytosine. In some embodiments, the present disclosure provides a SMN2 oligonucleotide having the sequence of any oligonucleotide disclosed herein, wherein at least one cytosine is optionally and independently replaced by 5-methylcytosine. In some embodiments, the present disclosure provides a SMN2 oligonucleotide having the sequence of any oligonucleotide disclosed herein, wherein each cytosine is optionally and independently replaced by 5-methylcytosine. In some embodiments, such SMN2 oligonucleotides are chirally controlled.

In some embodiments, a portion of a base sequence is a span of 10, 11, 12, 13, 14, 15, 16, 17, 18, 19 or more contiguous (consecutive) bases.

In some embodiments, the present disclosure describes a SMN2 oligonucleotide of a sequence recited herein. In some embodiments, the present disclosure describes a SMN2 oligonucleotide of a sequence recited herein, wherein the oligonucleotide is capable of enhancing the level, expression and/or activity of exon 7-containing SMN2 mRNA or its gene product relative to exon 7-deleted SMN2 mRNA, or increasing inclusion of exon 7 of a SMN2 mRNA. In some embodiments, a SMN2 oligonucleotide of a recited sequence comprises any structure described herein. In various sequences, U can be replaced by T or vice versa, or a sequence can comprise a mixture of U and T. In some embodiments, a SMN2 oligonucleotide has a length of no more than about 49, 45, 40, 30, 35, 25, 23 total nucleotides. In some embodiments, a portion is a span of at least 15, 16, 17, 18, 19, 20, 21, 22, 23, 24, or 25 total nucleotides with 0-3 mismatches. In some embodiments, a portion is a span of at least 15, 16, 17, 18, 19, 20, 21, 22, 23, 24, or 25 total nucleotides with 0-3 mismatches, wherein a span with 0 mismatches is complementary and a span with 1 or more mismatches is a non-limiting example of substantial complementarity. In some embodiments, wherein the sequence recited above starts with a U at the 5'-end, the U can be deleted and/or replaced by another base. In some embodiments, the disclosure encompasses any oligonucleotide having a base sequence which is or comprises or comprises a portion of the base sequence of any oligonucleotide disclosed herein, which has a format or a portion of a format disclosed herein.

In some embodiments, a SMN2 oligonucleotide can comprise any base sequence described herein. In some embodiments, a SMN2 oligonucleotide can comprise any base sequence or portion thereof, described herein. In some embodiments, a SMN2 oligonucleotide can comprise any base sequence or portion thereof, described herein, wherein a portion is a span of 15 contiguous bases, or a span of 15 contiguous bases with 1-5 mismatches. In some embodiments, a SMN2 oligonucleotide can comprise any base sequence or portion thereof described herein in combination with any other structural element or modification described herein.

Example oligonucleotides are presented in Table 1A, below.

TABLE 1A

Example oligonucleotides.

| ID | SEQ ID NO: | Description | Base Sequence | Stereo-chemistry |
|---|---|---|---|---|
| WV-2782 | 199 | Teo * m5Ceo * Aeeo * m5Ceo * Teo * Teo* Teo * m5Ceo * Aeo * Teo * Aeo * Aeo * Teo * Geo * m5Ceo * Teo * Geo * Geo | TCACTTTCATAATGCTGG | XXXXXXXXXXXXXXXX |
| WV-6767 | 200 | Teo *S m5Ceo *S Aeo *S m5Ceo *S Teo *S Teo *S Teo *S m5Ceo *S Aeo *S Teo *S Aeo *S Aeo *S Teo *S Geo *S m5Ceo *S Teo *S Geo *S Geo | TCACTTTCATAATGCTGG | SSSSSSSSSSSSSSSS |
| WV-6768 | 201 | Teo *R m5Ceo *R Aeo *R m5Ceo *R Teo *R Teo *R Teo *R m5Ceo *R Aeo *R Teo *R Aeo *R Aeo *R Teo *R Geo *R m5Ceo *R Teo *R Geo *R Geo | TCACTTTCATAATGCTGG | RRRRRRRRRRRRRRRR |
| WV-6769 | 202 | Teo *S m5Ceo *R Aeo *S m5Ceo *R Teo *S Teo *R Teo *S m5Ceo *R Aeo *S Teo *R Aeo *S Aeo *R Teo *S Geo *R m5Ceo *S Teo *R Geo *S Geo | TCACTTTCATAATGCTGG | SRSRSRSRSRSRSRSR |
| WV-6770 | 203 | Teo *R m5Ceo *S Aeo *R m5Ceo *S Teo *R Teo *S Teo *R m5Ceo *S Aeo *R Teo *S Aeo *R Aeo *S Teo *R Geo *S m5Ceo *R Teo *S Geo *R Geo | TCACTTTCATAATGCTGG | RSRSRSRSRSRSRSRS |
| WV-6771 | 204 | Teo *S m5CeoAeo *S m5Ceo Teo *S Teo Teo *S m5CeoAeo *S TeoAeo *S AeoTeo *S Geom5Ceo *S TeoGeo *S Geo | TCACTTTCATAATGCTGG | SOSOSOSOSOSOSOSOS |
| WV-6772 | 205 | Teo *S m5Ceo *S Aeo *S m5Ceo *S Teo *S Teo *S Teo *S m5Ceo *S Aeo *R Teo *S Aeo *S Aeo *S Teo *S Geo *S m5Ceo *S Teo *S Geo *S Geo | TCACTTTCATAATGCTGG | SSSSSSSSSSSSSSSS |
| WV-6773 | 206 | Teo *S m5Ceo *S Aeo *S meCeo *S Teo *S Teo *S Teo *S m5Ceo *R Aeo *R Teo *R Aeo *S Aeo *S Teo *S Geo *S m5Ceo *S Teo *S Geo *S Geo | TCACTTTCATAATGCTGG | SSSSSSSRRRSSSSSS |
| WV-6774 | 207 | Teo *S m5Ceo *S Aeo *S m5Ceo *S Teo *S Teo *S Teo *R m5Ceo *R Aeo *R Teo *R Aeo *R Aeo *S Teo *S Go *S m5Ceo *S Teo *S Geo *S Geo | TCACTTTCATAATGCTGG | SSSSSSRRRRSSSSS |
| WV-6775 | 208 | Teo *S m5Ceo *S Aeo *S m5Ceo *S Teo *S Teo *R Teo *R m5Ceo *R Aeo *R Teo *R Aeo *R Aeo *R Teo *S Geo *S m5Ceo *S Teo *S Geo *S Geo | TCACTTTCATAATGCTGG | SSSSSRRRRRRSSSS |
| WV-6776 | 209 | Teo *S m5Ceo *S Aeo *S m5Ceo *S Teo *R Teo *R Teo *R m5Ceo *R Aeo *R Teo *R Aeo *R Aeo *R Teo *R Geo *S m5Ceo *S Teo *S Geo *S Geo | TCACTTTCATAATGCTGG | SSSSRRRRRRRRSSSS |
| WV-6777 | 210 | Teo *S m5Ceo *S Aeo *S m5Ceo *R Teo *R Teo *R Teo *R m5Ceo *R Aeo *R Teo *R Aeo *R Aeo *R Teo *R Geo *R m5Ceo *S Teo *S Geo *S Geo | TCACTTTCATAATGCTGG | SSSRRRRRRRRRRSSS |
| WV-6778 | 211 | Teo *S m5Ceo *S Aeo *R m5Ceo *R Teo *R Teo *R Teo *R m5Ceo *R Aeo *R Teo *R Aeo *R Aeo *R Teo *R Geo *R m5Ceo *R Teo *S Geo *S Geo | TCACTTTCATAATGCTGG | SSRRRRRRRRRRRRSS |
| WV-6779 | 212 | Teo *S m5Ceo *R Aeo *R m5Ceo *R Teo *R Teo *R Teo *R m5Ceo *R Aeo *R Teo *R Aeo *R Aeo *R Teo *R Geo *R m5Ceo *R Teo *R Geo *S Geo | TCACTTTCATAATGCTGG | SRRRRRRRRRRRRRRS |

TABLE 1A-continued

Example oligonucleotides.

| ID | SEQ ID NO: | Description | Base Sequence | Stereo-chemistry |
|---|---|---|---|---|
| WV-6780 | 213 | Teo *R m5Ceo *R Aeo *R m5Ceo *R Teo *R Teo *R Teo *R m5Ceo *R Aeo *S Teo *R Aeo *R Aeo *R Teo *R Geo *R m5Ceo *R Teo *R Geo *R Geo | TCACTTTCATAATGCTGG | RRRRRRRRSRRRRRRRR |
| WV-6781 | 214 | Teo *R m5Ceo *R Aeo *R m5Ceo *R Teo *R Teo *R Teo *R m5Ceo *S Aeo *S Teo *S Aeo *R Aeo *R Teo *R Geo *R m5Ceo *R Teo *R Geo *R Geo | TCACTTTCATAATGCTGG | RRRRRRRSSSRRRRR |
| WV-6782 | 215 | Teo *R m5Ceo *R Aeo *R m5Ceo *R Teo *R Teo *R Teo *S m5Ceo *S Aeo *S Teo *S Aeo *S Aeo *R Teo *R Geo *R m5Ceo *R Teo *R Geo *R Geo | TCACTTTCATAATGCTGG | RRRRRRSSSSSRRRRR |
| WV-6783 | 216 | Teo *R m5Ceo *R Aeo *R m5Ceo *R Teo *R Teo *S Teo *S m5Ceo *S Aeo *S Teo *S Aeo *S Aeo *S Teo *R Geo *R m5Ceo *R Teo *R Geo *R Geo | TCACTTTCATAATGCTGG | RRRRRSSSSSSSRRRR |
| WV-6784 | 217 | Teo *R m5Ceo *R Aeo *R m5Ceo *R Teo *S Teo *S Teo *S m5Ceo *S Aeo *S Teo *S Aeo *S Aeo *S Teo *S Geo *R m5Ceo *R Teo *R Geo *R Geo | TCACTTTCATAATGCTGG | RRRRSSSSSSSSSRRRR |
| WV-6785 | 218 | Teo *R m5Ceo *R Aeo *R m5Ceo *S Teo *S Teo *S Teo *S m5Ceo *S Aeo *S Teo *S Aeo *S Aeo *S Teo *S Geo *S m5Ceo *R Teo *R Geo *R Geo | TCACTTTCATAATGCTGG | RRRSSSSSSSSSSSSRRR |
| WV-6786 | 219 | Teo *R m5Ceo *R Aeo *S m5Ceo *S Teo *S Teo *S Teo *S m5Ceo *S Aeo *S Teo *S Aeo *S Aeo *S Teo *S Geo *S m5Ceo *S Teo *R Geo *R Geo | TCACTTTCATAATGCTGG | RRSSSSSSSSSSSSSSRR |
| WV-6787 | 220 | Teo *R m5Ceo *S Aeo *S m5Ceo *S Teo *S Teo *S Teo *S m5Ceo *S Aeo *S Teo *S Aeo *S Aeo *S Teo *S Geo *S m5Ceo *S Teo *S Geo *R Geo | TCACTTTCATAATGCTGG | RSSSSSSSSSSSSSSSSR |
| WV-6788 | 221 | Teo *S m5Ceo *S Aeo *S m5Ceo *S Teo *S Teo *S Teo *S m5Ceo *S AeoTeo *S Aeo *S Aeo *S Teo *S Geo *S m5Ceo *S Teo *S Geo *S Geo | TCACTTTCATAATGCTGG | SSSSSSSSOSSSSSS |
| WV-6789 | 222 | Teo *S m5Ceo *S Aeo *S m5Ceo *S Teo *S Teo *S Teo *S m5CeoAeoTeoAeo *S Aeo *S Teo *S Geo *S m5Ceo *S Teo *S Geo *S Geo | TCACTTTCATAATGCTGG | SSSSSSSOOOSSSSSS |
| WV-6790 | 223 | Teo *S m5Ceo *S Aeo *S m5Ceo *S Teo *S Teo *S Teom5CeoAeoTeoAeoAeo *S Teo *S Geo *S m5Ceo *S Teo *S Geo *S Geo | TCACTTTCATAATGCTGG | SSSSSSOOOOOSSSSSS |
| WV-6791 | 224 | Teo *S m5Ceo *S Aeo *S m5Ceo *S Teo *S TeoTeom5CeoAeoTeoAeoAeoTeo *S Geo *S m5Ceo *S Teo *S Geo *S Geo | TCACTTTCATAATGCTGG | SSSSSOOOOOOOSSSSS |
| WV-6792 | 225 | Teo *S m5Ceo *S Aeo *S m5Ceo *S TeoTeom5CeoAeoTeoAeoAeoTeoGeo *S m5Ceo *S Teo *S Geo *S Geo | TCACTTTCATAATGCTGG | SSSSOOOOOOOOSSSSS |
| WV-6793 | 226 | Teo *S m5Ceo *S Aeo *S m5CeoTeoTeoTeom5CeoAeoTeoAeoAeoTeoGeom5Ceo *S Teo *S Geo *S Geo | TCACTTTCATAATGCTGG | SSSOOOOOOOOOOSSS |
| WV-6794 | 227 | Teo *S m5Ceo *S Aeom5CeoTeoTeoTeom5CeoAeoTeoAeoAeoTeoGeom5CeoTeo *S Geo *S Geo | TCACTTTCATAATGCTGG | SSOOOOOOOOOOOOSS |
| WV-6795 | 228 | Teo *S m5CeoAeom5CeoTeoTeoTeom5CeoAeoTeoAeoAeoTeoGeom5CeoTeoGeo *S Geo | TCACTTTCATAATGCTGG | SOOOOOOOOOOOOOS |
| WV-6796 | 229 | Teo *S m5Ceo *S Aeo *S m5Ceo *S Teo *S Teo *S Teo *S m5Ceo *R Aeo *S Teo *R Aeo *S Aeo *S Teo *S Geo *S m5Ceo *S Teo *S Geo *S Geo | TCACTTTCATAATGCTGG | SSSSSSSRSRSSSSSS |
| WV-6797 | 230 | Teo *S m5Ceo *S Aeo *S m5Ceo *S Teo *S Teo *S Teo *S m5CeoAeo *S TeoAeo *S Aeo *S Teo *S Geo *S m5Ceo *S Teo *S Geo *S Geo | TCACTTTCATAATGCTGG | SSSSSSSOSOSSSSSS |

TABLE 1A-continued

Example oligonucleotides.

| ID | SEQ ID NO: | Description | Base Sequence | Stereo-chemistry |
|---|---|---|---|---|
| WV-6798 | 231 | Teo *S m5Ceo *S Aeo *S m5Ceo *S Teo *S Teo *S Teo *R m5Ceo *S Aeo *R Teo *S Aeo *R Aeo *S Teo *S Geo *S m5Ceo *S Teo *S Geo *S Geo | TCACTTTCATAATGCTGG | SSSSSSSRSRSRSSSSSS |
| WV-6799 | 232 | Teo *S m5Ceo *S Aeo *S m5Ceo *S Teo *S Teo *S Teom5Ceo *S AeoTeo *S AeoAeo *S Teo *S Geo *S m5Ceo *S Teo *S Geo *S Geo | TCACTTTCATAATGCTGG | SSSSSSOSOSOSSSSSS |
| WV-6800 | 233 | Teo *S m5Ceo *S Aeo *S m5Ceo *S Teo *S Teo *R Teo *S m5Ceo *R Aeo *S Teo *R Aeo *S Aeo *R Teo *S Geo *S m5Ceo *S Teo *S Geo *S Geo | TCACTTTCATAATGCTGG | SSSSSRSRSRSRSSSSSS |
| WV-6801 | 234 | Teo *S m5Ceo *S Aeo *S m5Ceo *S Teo *S TeoTeo *S m5CeoAeo *S TeoAeo *S AeoTeo *S Geo *S m5Ceo *S Teo *S Geo *S Geo | TCACTTTCATAATGCTGG | SSSSSOSOSOSOSSSSSS |
| WV-6802 | 235 | Teo *S m5Ceo *S Aeo *S m5Ceo *S Teo *R Teo *S Teo *R m5Ceo *S Aeo *R Teo *S Aeo *R Aeo *S Teo *R Geo *S m5Ceo *S Teo *S Geo *S Geo | TCACTTTCATAATGCTGG | SSSSRSRSRSRSRSSSSS |
| WV-6803 | 236 | Teo *S m5Ceo *S Aeo *S m5Ceo *S TeoTeo *S Teom5Co *S AeoTeo *S AeoAeo *S TeoGeo *S m5Ceo *S Teo *S Geo *S Geo | TCACTTTCATAATGCTGG | SSSSOSOSOSOSOSSSSS |
| WV-6804 | 237 | Teo *S m5Ceo *S Aeo *S m5Ceo *R Teo *S Teo *R Teo *S m5Ceo *R Aeo *S Teo *R Aeo *S Aeo *R Teo *S Geo *R m5Ceo *S Teo *S Geo *S Geo | TCACTTTCATAATGCTGG | SSSRSRSRSRSRSRSSSS |
| WV-6805 | 238 | Teo *S m5Ceo *S Aeo *S m5CeoTeo *S TeoTeo *S m5CeoAeo *S TeoAeo *S AeoTeo *S Geom5Ceo *S Teo *S Geo *S Geo | TCACTTTCATAATGCTGG | SSSOSOSOSOSOSOSSSS |
| WV-6806 | 239 | Teo *S m5Ceo *S Aeo *R 5Ceo *S Teo *R Teo *S Teo *R m5Ceo *S Aeo *R Teo *S Aeo *R Aeo *S Teo *R Geo *S m5Ceo *R Teo *S Geo *S Geo | TCACTTTCATAATGCTGG | SSRSRSRSRSRSRSRSS |
| WV-6807 | 240 | Teo *S m5Ceo *S Aeom5Ceo *S TeoTeo *S Teom5Ceo *S AeoTeo *S AeoAeo *S TeoGeo *S m5CeoTeo *S Geo *S Geo | TCACTTTCATAATGCTGG | SSOSOSOSOSOSOSOSS |
| WV-6808 | 241 | Teo *S m5Ceo *S Aeo *S m5Ceo *R Teo *R Teo *S Teo *R m5Ceo *R Aeo *S Teo *R Aeo *R Aeo *S Teo *R Geo *R m5Ceo *S Teo *S Geo *S Geo | TCACTTTCATAATGCTGG | SSSRRSRRSRRSRRSSS |
| WV-6809 | 242 | Teo *S m5Ceo *S Aeo *S m5CeoTeoTeo *S Teom5CeoAeo *S TeoAeoAeo *S TeoGeom5Ceo *S Teo *S Geo *S Geo | TCACTTTCATAATGCTGG | SSSOOSOOSOOSOOSSS |
| WV-6810 | 243 | Teo *S m5Ceo *S Aeo *S m5Ceo *S Teo *S Teo *S Teo *S m5Ceo *S Aeo *R Teo *S Aeo *R Aeo *R Teo *S Geo *R m5Ceo *S Teo *S Geo *S Geo | TCACTTTCATAATGCTGG | SSSSSSSSRSRRSRSSS |
| WV-6811 | 244 | Teo *S m5Ceo *S Aeo *S m5Ceo *S Teo *S Teo *S Teo *S m5Ceo *S AeoTeo *S AeoAeoTeo *S Geo *R m5Ceo *S Teo *S Geo *S Geo | TCACTTTCATAATGCTGG | SSSSSSSSOSOOSRSSS |
| WV-6812 | 245 | Teo *S m5Ceo *S Aeo *R m5Ceo *S Teo *S Teo *S Teo *S m5Ceo *S Aeo *R Teo *S Aeo *R Aeo *R Teo *S Geo *R m5Ceo *S Teo *S Geo *R Geo | TCACTTTCATAATGCTGG | SSRSSSSRSRRSRSSR |
| WV-6813 | 246 | Teo *S m5Ceo *S Aeom5Ceo *S Teo *S Teo *S Teo *S m5Ceo *S AeoTeo *S AeoAeoTeo *S Geom5Ceo *S Teo *S GeoGeo | TCACTTTCATAATGCTGG | SSOSSSSSOSOOSOSSO |
| WV-6814 | 247 | mU * m5mC * mA * m5mC * mU *mU * mU * m5mC * mA * mU * mA * mA * mU * m5mC * mU * mG * mG | UCACUUUCAUAAUGCUGG | XXXXXXXXXXXXXXXX |
| WV-6815 | 248 | mU * S m5mC *S mA *S m5mC *S mU *S mU *S mU *S m5mC *S mA *S mU *S mA *S mA *S mU *S mG *S m5mC *S mU *S mG *S mG | UCACUUUCAUAAUGCUGG | SSSSSSSSSSSSSSSSSS |

TABLE 1A-continued

Example oligonucleotides.

| ID | SEQ ID NO: | Description | Base Sequence | Stereo-chemistry |
|---|---|---|---|---|
| WV-6816 | 249 | mU * mC * mA * mC * mU * mU * mU * mC * mA * mU * mA * mA * mU * mG * mC * mU * mG * mG | UCACUUUCAUAAUGCUGG | XXXXXXXXXXXXXXXXX |
| WV-6817 | 250 | mU *S mC *S mA *S mC *S mU *S mU *S mU *S mC *S mA *S mU *S mA *S mA *S mU *S mG *S mC *S mU *S mG *S mG | UCACUUUCAUAAUGCUGG | SSSSSSSSSSSSSSSSS |
| WV-7306 | 251 | Mod001L001Teo * m5Ceo * Aeo * m5Ceo * Teo * Teo * Teo * m5Ceo * Aeo * Teo * Aeo * Aeo * Teo * Geo * m5Ceo * Teo * Geo * Geo | TCACTTTCATAATGCTGG | OXXXXXXXXXXXXXXXXX |
| WV-7308 | 252 | L001Teo * m5Ceo * Aeo * m5Ceo * Teo * Teo * Teo * m5Ceo * Aeo * Teo * Aeo * Aeo * Teo * Geo * m5Ceo * Teo * Geo * Geo | TCACTTTCATAATGCTGG | OXXXXXXXXXXXXXXXXX |
| WV-9064 | 253 | L001Teo *R m5Ceo *R Aeo *R m5Ceo *R Teo *R Teo *R Teo *R m5Ceo *R Aeo *R Teo *R Aeo *R Aeo *R Teo *R Geo *R m5Ceo *R Teo *R Geo *R Geo | TCACTTTCATAATGCTGG | ORRRRRRRRRRRRRRRRR |
| WV-9065 | 254 | Mod007L001Teo *R m5Ceo *R Aeo *R m5Ceo *R Teo *R Teo *R Teo *R m5Ceo *R Aeo *R Teo *R Aeo *R Aeo *R Teo *R Geo *R m5Ceo *R Teo *R Geo *R Geo | TCACTTTCATAATGCTGG | ORRRRRRRRRRRRRRRRR |
| WV-9066 | 255 | Mod007L001Teo * m5Ceo * Aeo * m5Ceo * Teo * Teo * Teo * m5Ceo * Aeo * Teo * Aeo * Aeo * Teo * Geo * m5Ceo * Teo * Geo * Geo | TCACTTTCATAATGCTGG | OXXXXXXXXXXXXXXXXX |
| WV-9853 | 256 | Mod084L001Teo * Rm5Ceo * RAeo * Rm5Ceo * RTeo * RTeo * RTeo * Rm5Ceo * RAeo * RTeo * RAeo * RAeo * RTeo * RGeo * Rm5Ceo * RTeo * RGeo * RGeo | TCACTTTCATAATGCTGG | ORRRRRRRRRRRRRRRRR |
| WV-15974 | 257 | Geo * Aeo * Teo * Aeo * Geo * m5Ceo * Teo * Teo * Teo * Aeo * Teo * Aeo * Teo * Geo * Geo * Aeo * Teo * Geo * Teo * Teo | GATAGCTTTATATGGATGTT | XXXXXXXXXXXXXXXXXXX |
| WV-15975 | 258 | Teo * Aeo * Geo * m5Ceo * Teo * Teo * Teo * Aeo * Teo * Aeo * Teo * Geo * Geo * Aeo * Teo * Geo * Teo * Teo * Aeo * Aeo | TAGCTTTATATGGATGTTAA | XXXXXXXXXXXXXXXXXXX |
| WV-15976 | 259 | Aeo * Teo * Aeo * Geo * m5Ceo * Teo * Teo * Teo * Aeo * Teo * Aeo * Teo * Geo * Geo * Aeo * Teo * Geo * Teo * Teo * Aeo | ATAGCTTTATATGGATGTTA | XXXXXXXXXXXXXXXXXXX |
| WV-15977 | 260 | Aeo * Teo * Aeo * Geo * Aeo * Teo * Aeo * Geo * m5Ceo * Teo * Teo * Teo * Aeo * Teo * Aeo * Teo * Geo * Geo * Aeo * Teo | ATAGATAGCTTTATATGGAT | XXXXXXXXXXXXXXXXXXX |
| WV-15978 | 261 | Teo * Teo * Aeo * Teo * Aeo * Teo * Geo * Geo * Aeo * Teo * Geo * Teo * Teo * Aeo * Aeo * Aeo * Aeo * Aeo * Geo * m5Ceo | TTATATGGATGTTAAAAGC | XXXXXXXXXXXXXXXXXXX |
| WV-15979 | 262 | Geo * m5Ceo * Teo * Teo * Teo * Aeo * Teo * Aeo * Teo * Geo * Geo * Aeo * Teo * Geo * Teo * Teo * Aeo * Aeo * Aeo * Aeo | GCTTTATATGGATGTTAAAA | XXXXXXXXXXXXXXXXXXX |
| WV-15980 | 263 | Aeo * Geo * m5Ceo * Teo * Teo * Teo * Aeo * Teo * Aeo * Teo * Geo * Geo * Aeo * Teo * Geo * Teo * Teo * Aeo * Aeo * Aeo | AGCTTTATATGGATGTTAAA | XXXXXXXXXXXXXXXXXXX |
| WV-15981 | 264 | Teo * Aeo * Geo * Aeo * Teo * Aeo * Geo * m5Ceo * Teo * Teo * Teo * Aeo * Teo * Aeo * Teo * Geo * Geo * Aeo * Teo * Geo * | TAGATAGCTTTATATGGATG | XXXXXXXXXXXXXXXXXXX |
| WV-15982 | 265 | Aeo * Geo * Aeo * Teo * Aeo * Geo * m5Ceo * Teo * Teo * Teo * Aeo * Teo * Aeo * Teo * Geo * Geo * Aeo * Teo * Geo * Teo | AGATAGCTTTATATGGATGT | XXXXXXXXXXXXXXXXXXX |

TABLE 1A-continued

Example oligonucleotides.

| ID | SEQ ID NO: | Description | Base Sequence | Stereo-chemistry |
|---|---|---|---|---|
| WV-15983 | 266 | Teo * Teo * Teo * Aeo * Teo * Aeo * Teo * Geo * Geo * Aeo * Teo * Geo * Teo * Teo * Aeo * Aeo * Aeo * Aeo * Aeo * Geo | TTTATATGGATGTTAAAAAG | XXXXXXXXXXXXXXXXXX |
| WV-15984 | 267 | Teo * Aeo * Teo * Aeo * Geo * Aeo * Teo * Aeo * Geo * m5Ceo * Teo * Teo * Teo * Aeo * Teo * Aeo * Teo * Geo * Geo * Aeo | TATAGATAGCTTTATATGGA | XXXXXXXXXXXXXXXXXX |
| WV-15985 | 268 | Teo * Geo * Teo * Teo * Aeo * Aeo * Aeo * Aeo * Aeo * Geo * m5Ceo * Aeo * Teo * Teo * Teo * Teo * Geo * Teo * Teo * Teo | TGTTAAAAAGCATTTTGTTT | XXXXXXXXXXXXXXXXXX |
| WV-15986 | 269 | Teo * Geo * Geo * Aeo * Teo * Geo * Teo * Teo * Aeo * Aeo * Aeo * Aeo * Aeo * Geo * m5Ceo * Aeo * Teo * Teo * Teo * Teo | TGGATGTTAAAAAGCATTTT | XXXXXXXXXXXXXXXXXX |
| WV-15987 | 270 | Teo * Aeo * Aeo * Aeo * Aeo * Aeo * Geo * m5Ceo * Aeo * Teo * Teo * Teo * Teo * Geo * Teo * Teo * Teo * m5Ceo * Aeo * m5Ceo | TAAAAAGCATTTGTTTCAC | XXXXXXXXXXXXXXXXXX |
| WV-15988 | 271 | Teo * Teo * Aeo * Aeo * Aeo * Aeo * Aeo * Geo * m5Ceo * Aeo * Teo * Teo * Teo * Teo * Geo * Teo * Teo * Teo * m5Ceo * Aeo | TTAAAAAGCATTTTGTTTCA | XXXXXXXXXXXXXXXXXX |
| WV-15989 | 272 | m5Ceo * Teo * Teo * Teo * Aeo * Teo * Aeo * Teo * Geo * Geo * Aeo * Teo * Geo * Teo * Teo * Aeo * Aeo * Aeo * Aeo * Aeo | CTTTATATGGATGTTAAAAA | XXXXXXXXXXXXXXXXXX |
| WV-15990 | 273 | Aeo * Teo * Geo * Geo * Aeo * Teo * Geo * Teo * Teo * Aeo * Aeo * Aeo * Aeo * Aeo * Geo * m5Ceo * Aeo * Teo * Teo * Teo | ATGGATGTTAAAAAGCATTT | XXXXXXXXXXXXXXXXXX |
| WV-15991 | 274 | Aeo * Teo * Geo * Teo * Teo * Aeo * Aeo * Aeo * Aeo * Aeo * Geo * m5Ceo * Aeo * Teo * Teo * Teo * Teo * Geo * Teo * Teo | ATGTTAAAAAGCATTTTGTT | XXXXXXXXXXXXXXXXXX |
| WV-15991 | 275 | Geo * Aeo * Teo * Geo * Teo * Teo * Aeo * Aeo * Aeo * Aeo * Aeo * Geo * m5Ceo * Aeo * Teo * Teo * Teo * Teo * Geo * Teo | GATGTTAAAAAGCATTTTGT | XXXXXXXXXXXXXXXXXX |
| WV-15993 | 276 | Geo * Geo * Aeo * Teo * Geo * Teo * Teo * Aeo * Aeo * Aeo * Aeo * Aeo * Geo * m5Ceo * Aeo * Teo * Teo * Teo * Teo * Geo | GGATGTTAAAAAGCATTTTG | XXXXXXXXXXXXXXXXXX |
| WV-15994 | 277 | Geo * Teo * Teo * Aeo * Aeo * Aeo * Aeo * Aeo * Geo * m5Ceo * Aeo * Teo * Teo * Teo * Teo * Geo * Teo * Teo * Teo * m5Ceo | GTTAAAAAGCATTTTGTTTC | XXXXXXXXXXXXXXXXXX |
| WV-15995 | 278 | Aeo * Teo * Aeo * Teo * Geo * Geo * Aeo * Teo * Geo * Teo * Teo * Aeo * Aeo * Aeo * Aeo * Aeo * Geo * m5Ceo * Aeo * Teo | ATATGGATGTTAAAAAGCAT | XXXXXXXXXXXXXXXXXX |
| WV-15996 | 279 | Teo * Aeo * Teo * Aeo * Teo * Geo * Geo * Aeo * Teo * Geo * Teo * Teo * Aeo * Aeo * Aeo * Aeo * Aeo * Geo * m5Ceo * Aeo | TATATGGATGTTAAAAAGCA | XXXXXXXXXXXXXXXXXX |
| WV-15997 | 280 | Teo * Aeo * Teo * Geo * Geo * Aeo * Teo * Geo * Teo * Teo * Aeo * Aeo * Aeo * Aeo * Aeo * Geo * m5Ceo * Aeo * Teo * Teo | TATGGATGTTAAAAAGCATT | XXXXXXXXXXXXXXXXXX |
| WV-2837 | 281 | mU * mC * mA * mU * mA * mA * mU * mG * mC * mU * mG * mG * mC * mA * mG * mA * mC * mU * mU * mA | UCAUAAUGCUGGCAGACUUA | XXXXXXXXXXXXXXXXXX |
| WV-2838 | 282 | mU * mU * mC * mA * mU * mA * mA * mU * mG * mC * mU * mG * mG * mC * mA * mG * mA * mC * mU * mU | UUCAUAAUGCUGGCAGACUU | XXXXXXXXXXXXXXXXXX |
| WV-2839 | 283 | mU * mU * mU * mC * mA * mU * mA * mA * mU * mG * mC * mU * mG * mG * mC * mA * mG * mA * mC * mU | UUUCAUAAUGCUGGCAGACU | XXXXXXXXXXXXXXXXXX |

TABLE 1A-continued

Example oligonucleotides.

| ID | SEQ ID NO: | Description | Base Sequence | Stereo-chemistry |
|---|---|---|---|---|
| WV-2840 | 284 | mC * mU * mU * mU * mC * mA * mU * mA * mA * mU * mG * mC * mU * mG * mG * mC * mA * mG * mA * mC | CUUUCAUAAUGCUGGCAGAC | XXXXXXXXXXXXXXXXXXX |
| WV-2841 | 285 | mA * mC * mU * mU * mU * mC * mA * mU * mA * mA * mU * mG * mC * mU * mG * mG * mC * mA * mG * mA | ACUUUCAUAAUGCUGGCAGA | XXXXXXXXXXXXXXXXXXX |
| WV-2842 | 286 | mC * mA * mC * mU * mU * mU * mC * mA * mU * mA * mA * mU * mG * mC * mU * mG * mG * mC * mA * mG | CACUUUCAUAAUGCUGGCAG | XXXXXXXXXXXXXXXXXXX |
| WV-2843 | 287 | mU * mC * mA * mC * mU * mU * mU * mC * mA * mU * mA * mA * mU * mG * mC * mU * mG * mG * mC * mA | UCACUUUCAUAAUGCUGGCA | XXXXXXXXXXXXXXXXXXX |
| WV-2844 | 288 | mU * mU * mC * mA * mC * mU * mU * mU * mC * mA * mU * mA * mA * mU * mG * mC * mU * mG * mG * mC | UUCACUUUCAUAAUGCUGGC | XXXXXXXXXXXXXXXXXXX |
| WV-2845 | 289 | mA * mU * mU * mC * mA * mC * mU * mU * mU * mC * mA * mU * mA * mA * mU * mG * mC * mU * mG * mG | AUUCACUUUCAUAAUGCUGG | XXXXXXXXXXXXXXXXXXX |
| WV-2846 | 290 | mG * mA * mU * mU * mC * mA * mC * mU * mU * mU * mC * mA * mU * mA * mA * mU * mG * mC * mU * mG | GAUUCACUUUCAUAAUGCUG | XXXXXXXXXXXXXXXXXXX |
| WV-2847 | 291 | mA * mG * mA * mU * mU * mC * mA * mC * mU * mU * mU * mC * mA * mU * mA * mA * mU * mG * mC * mU | AGAUUCACUUUCAUAAUGCU | XXXXXXXXXXXXXXXXXXX |
| WV-2848 | 292 | mA * mA * mG * mA * mU * mU * mC * mA * mC * mU * mU * mU * mC * mA * mU * mA * mA * mU * mG * mC | AAGAUUCACUUUCAUAAUGC | XXXXXXXXXXXXXXXXXXX |
| WV-2849 | 293 | mU * mA * mA * mG * mA * mU * mU * mC * mA * mC * mU * mU * mU * mC * mA * mU * mA * mA * mU * mG | UAAGAUUCACUUUCAUAAUG | XXXXXXXXXXXXXXXXXXX |
| WV-2850 | 294 | mG * mU * mA * mA * mG * mA * mU * mU * mC * mA * mC * mU * mU * mU * mC * mA * mU * mA * mA * mU | GUAAGAUUCACUUUCAUAAU | XXXXXXXXXXXXXXXXXXX |
| WV-2851 | 295 | mC * mU * mU * mU * mC * mU * mA * mA * mC * mA * mU * mC * mU * mG * mA * mA * mC * mU * mU * mU | CUUUCUAACAUCUGAACUUU | XXXXXXXXXXXXXXXXXXX |
| WV-2852 | 296 | mA * mA * mC * mU * mU * mU * mC * mU * mA * mA * mC * mA * mU * mC * mU * mG * mA * mA * mC * mU | AACUUUCUAACAUCUGAACU | XXXXXXXXXXXXXXXXXXX |
| WV-2853 | 297 | mU * mC * mA * mA * mC * mU * mU * mU * mC * mU * mA * mA * mC * mA * mU * mC * mU * mG * mA * mA | UCAACUUUCUAACAUCUGAA | XXXXXXXXXXXXXXXXXXX |
| WV-2854 | 298 | mU * mU * mU * mC * mA * mA * mC * mU * mU * mU * mC * mU * mA * mA * mC * mA * mU * mC * mU * mG | UUUCAACUUUCUAACAUCUG | XXXXXXXXXXXXXXXXXXX |
| WV-2855 | 299 | mC * mC * mU * mU * mU * mC * mA * mA * mC * mU * mU * mU * mC * mU * mA * mA * mC * mA * mU * mC | CCUUUCAACUUUCUAACAUC | XXXXXXXXXXXXXXXXXXX |
| WV-2586 | 300 | mA * mA * mC * mC * mU * mU * mU * mC * mA * mA * mC * mU * mU * mU * mC * mU * mA * mA * mC * mA | AACCUUUCAACUUUCUAACA | XXXXXXXXXXXXXXXXXXX |
| WV-2857 | 301 | mC * mU * mG * mC * mC * mU * mA * mC * mU * mA * mG * mU * mG * mA * mU * mA * mU * mA * mA * mA | CUGCCUACUAGUGAUAUAAA | XXXXXXXXXXXXXXXXXXX |

TABLE 1A-continued

Example oligonucleotides.

| ID | SEQ ID NO: | Description | Base Sequence | Stereo-chemistry |
|---|---|---|---|---|
| WV-2858 | 302 | mG * mU * mC * mU * mG * mC * mC * mU * mA * mC * mU * mA * mG * mU * mG * mA * mU * mA * mU * mA | GUCUGCCUACUAGUGAUAUA | XXXXXXXXXX XXXXXXXXX |
| WV-2589 | 303 | mU * mG * mG * mU * mC * mU * mG * mC * mC * mU * mA * mC * mU * mA * mG * mU * mG * mA * mU * mA | UGGUCUGCCUACUAGUGAUA | XXXXXXXXXX XXXXXXXXX |
| WV-2860 | 304 | mG * mC * mU * mG * mG * mU * mC * mU * mG * mC * mC * mU * mA * mC * mU * mA * mG * mU * mG * mA | GCUGGUCUGCCUACUAGUGA | XXXXXXXXXX XXXXXXXXX |
| WV-2861 | 305 | mC * mU * mG * mC * mU * mG * mG * mU * mC * mU * mG * mC * mC * mU * mA * mC * mU * mA * mG * mU | CUGCUGGUCUGCCUACUAGU | XXXXXXXXXX XXXXXXXXX |
| WV-2862 | 306 | mG * mU * mC * mU * mG * mC * mU * mG * mG * mU * mC * mU * mG * mC * mC * mU * mA * mC * mU * mA | GUCUGCUGGUCUGCCUACUA | XXXXXXXXXX XXXXXXXXX |
| WV-2863 | 307 | mA * mA * mG * mU * mC * mU * mG * mC * mU * mG * mG * mU * mC * mU * mG * mC * mC * mU * mA * mC | AAGUCUGCUGGUCUGCCUAC | XXXXXXXXXX XXXXXXXXX |
| WV-2864 | 308 | mA * mA * mA * mA * mG * mU * mC * mU * mG * mC * mU * mG * mG * mU * mC * mU * mG * mC * mC * mU | AAAAGUCUGCUGGUCUGCCU | XXXXXXXXXX XXXXXXXXX |
| WV-2865 | 309 | mG * mA * mA * mA * mU * mU * mA * mG * mA * mA * mC * mC * mA * mG * mA * mG * mG * mC * mU * mU | GAAAUUAGAACCAGAGGCUU | XXXXXXXXXX XXXXXXXXX |
| WV-2866 | 310 | mG * mA * mG * mA * mA * mA * mU * mU * mA * mG * mA * mA * mC * mC * mA * mG * mA * mG * mG * mC | GAGAAAUUAGAACCAGAGGC | XXXXXXXXXX XXXXXXXXX |
| WV-2867 | 311 | mA * mU * mG * mA * mG * mA * mA * mA * mU * mU * mA * mG * mA * mA * mC * mC * mA * mG * mA * mG | AUGAGAAAUUAGAACCAGAG | XXXXXXXXXX XXXXXXXXX |
| WV-2868 | 312 | mA * mA * mA * mU * mG * mA * mG * mA * mA * mA * mU * mU * mA * mG * mA * mA * mC * mC * mA * mG | AAAUGAGAAAUUAGAACCAG | XXXXXXXXXX XXXXXXXXX |
| WV-2869 | 313 | mG * mC * mA * mA * mA * mU * mG * mA * mG * mA * mA * mA * mU * mU * mA * mG * mA * mA * mC * mC | GCAAAUGAGAAAUUAGAACC | XXXXXXXXXX XXXXXXXXX |
| WV-2870 | 314 | mC * mU * mG * mC * mA * mA * mA * mU * mG * mA * mG * mA * mA * mA * mU * mU * mA * mG * mA * mA | CUGCAAAUGAGAAAUUAGAA | XXXXXXXXXX XXXXXXXXX |
| WV-2871 | 315 | mU * mC * mC * mU * mG * mC * mA * mA * mA * mU * mG * mA * mG * mA * mA * mA * mU * mU * mA * mG | UCCUGCAAAUGAGAAAUUAG | XXXXXXXXXX XXXXXXXXX |
| WV-2872 | 316 | mU * mU * mC * mC * mU * mG * mC * mA * mA * mA * mU * mG * mA * mG * mA * mA * mA * mU * mU * mU | UUUCCUGCAAAUGAGAAAUU | XXXXXXXXXX XXXXXXXXX |
| WV-2873 | 317 | mC * mA * mU * mU * mU * mC * mC * mU * mG * mC * mA * mA * mA * mU * mG * mA * mG * mA * mA * mA | CAUUUCCUGCAAAUGAGAAA | XXXXXXXXXX XXXXXXXXX |
| WV-2874 | 318 | mA * mG * mC * mA * mU * mU * mU * mC * mC * mU * mG * mC * mA * mA * mA * mU * mG * mA * mG * mA | AGCAUUUCCUGCAAAUGAGA | XXXXXXXXXX XXXXXXXXX |
| WV-2875 | 319 | mC * mC * mA * mG * mC * mA * mU * mU * mU * mC * mC * mU * mG * mC * mA * mA * mA * mU * mG * mA | CCAGCAUUUCCUGCAAAUGA | XXXXXXXXXX XXXXXXXXX |

TABLE 1A-continued

Example oligonucleotides.

| SEQ ID | SEQ ID NO: | Description | Base Sequence | Stereo-chemistry |
|---|---|---|---|---|
| WV-2876 | 320 | mU * mG * mC * mC * mS * mG * mC * mS * mU * mU * mU * mC * mC * mU * mG * mC * mA * mA * mA * mU | UGCCAGCAUUUCCUGCAAAU | XXXXXXXXXX XXXXXXXXX |
| WV-2877 | 321 | mU * mA * mU * mG * mC * mC * mA * mG * mC * mA * mU * mU * mU * mC * mC * mU * mG * mC * mA * mA | UAUGCCAGCAUUUCCUGCAA | XXXXXXXXXX XXXXXXXXX |
| WV-2878 | 322 | mU * mC * mU * mA * mU * mG * mC * mC * mA * mG * mC * mA * mU * mU * mU * mC * mC * mU * mG * mC | UCUAUGCCAGCAUUUCCUGC | XXXXXXXXXX XXXXXXXXX |
| WV-2879 | 323 | mG * mC * mU * mC * mU * mA * mU * mG * mC * mC * mA * mG * mC * mA * mU * mU * mU * mC * mC * mU | GCUCUAUGCCAGCAUUUCCU | XXXXXXXXXX XXXXXXXXX |
| WV-2880 | 324 | mC * mU * mG * mC * mU * mC * mU * mA * mU * mG * mC * mC * mA * mG * mC * mA * mU * mU * mU * mC | CUGCUCUAUGCCAGCAUUUC | XXXXXXXXXX XXXXXXXXX |
| WV-2881 | 325 | mU * mG * mC * mU * mG * mC * mU * mC * mU * mA * mU * mG * mC * mC * mA * mG * mC * mA * mU * mU | UGCUGCUCUAUGCCAGCAUU | XXXXXXXXXX XXXXXXXXX |
| WV-2882 | 326 | mA * mG * mU * mG * mC * mU * mG * mC * mU * mC * mU * mA * mU * mG * mC * mC * mA * mG * mC * mA | AGUGCUGCUCUAUGCCAGCA | XXXXXXXXXX XXXXXXXXX |
| WV-2883 | 327 | mU * mU * mA * mG * mU * mG * mC * mU * mG * mC * mU * mC * mU * mA * mU * mG * mC * mC * mA * mG | UUAGUGCUGCUCUAUGCCAG | XXXXXXXXXX XXXXXXXXX |
| WV-2884 | 328 | mU * mC * mC * mA * mC * mA * mA * mA * mC * mC * mA * mU * mA * mA * mA * mG * mU * mU * mU * mU | UCCACAAACCAUAAAGUUUU | XXXXXXXXXX XXXXXXXXX |
| WV-2885 | 329 | mU * mU * mU * mC * mC * mA * mC * mA * mA * mA * mC * mC * mA * mU * mA * mA * mA * mG * mU * mU | UUUCCACAAACCAUAAAGUU | XXXXXXXXXX XXXXXXXXX |
| WV-2886 | 330 | mG * mU * mU * mU * mU * mC * mC * mA * mC * mA * mA * mA * mC * mC * mA * mU * mA * mA * mA * mG | GUUUUCCACAAACCAUAAAG | XXXXXXXXXX XXXXXXXXX |
| WV-2887 | 331 | mU * mU * mG * mU * mU * mU * mU * mC * mC * mA * mC * mA * mA * mA * mC * mC * mA * mU * mA * mA | UUGUUUUCCACAAACCAUAA | XXXXXXXXXX XXXXXXXXX |
| WV-2888 | 332 | mA * mU * mU * mC * mU * mA * mG * mU * mA * mG * mG * mG * mA * mU * mG * mU * mA * mG * mA * mU | AUUCUAGUAGGGAUGUAGAU | XXXXXXXXXX XXXXXXXXX |
| WV-2889 | 333 | mG * mA * mA * mU * mU * mC * mU * mA * mG * mU * mA * mG * mG * mG * mA * mU * mG * mU * mA * mG | GAAUUCUAGUAGGGAUGUAG | XXXXXXXXXX XXXXXXXXX |
| WV-2890 | 334 | mG * mA * mG * mA * mA * mU * mU * mC * mU * mA * mG * mU * mA * mG * mG * mG * mA * mU * mG * mU | GAGAAUUCUAGUAGGGAUGU | XXXXXXXXXX XXXXXXXXX |
| WV-2891 | 335 | mA * mU * mG * mA * mG * mA * mA * mU * mU * mC * mU * mA * mG * mU * mA * mG * mG * mG * mA * mU | AUGAGAAUUCUAGUAGGGAU | XXXXXXXXXX XXXXXXXXX |
| WV-2892 | 336 | mU * mU * mA * mU * mU * mU * mU * mA * mU * mU * mC * mA * mA * mC * mA * mA * mA * mA * mU * mA | UUAUUUUAUUCAACAAAAUA | XXXXXXXXXX XXXXXXXXX |
| WV-2893 | 337 | mU * mA * mC * mU * mU * mA * mU * mU * mU * mU * mU * mA * mU * mU * mC * mA * mA * mC * mA * mA * mA | UACUUAUUUUAUUCAACAAA | XXXXXXXXXX XXXXXXXXX |

TABLE 1A-continued

Example oligonucleotides.

| ID | SEQ ID NO: | Description | Base Sequence | Stereo-chemistry |
|---|---|---|---|---|
| WV-2894 | 338 | mU * mU * mU * mU * mA * mC * mU * mU * mA * mU * mU * mU * mU * mA * mU * mU * mC * mA * mA * mC | UUUUACUUAUUUUAUUCAAC | XXXXXXXXXX XXXXXXXXX |
| WV-2895 | 339 | mA * mC * mA * mU * mU * mU * mU * mA * mC * mU * mU * mA * mU * mU * mU * mU * mA * mU * mU * mC | ACAUUUUACUUAUUUUAUUC | XXXXXXXXXX XXXXXXXXX |
| WV-2896 | 340 | mA * mA * mG * mA * mC * mA * mU *mU * mU * mU * mA * mC * mU * mU * mA * mU * mU * mU * mU * mA | AAGACAUUUUACUUAUUUUA | XXXXXXXXXX XXXXXXXXX |
| WV-2897 | 341 | mC * mA * mC * mA * mA * mG * mA * mC * mA * mU * mU * mU * mU * mA * mC * mU * mU * mA * mU * mU | CACAAGACAUUUUACUUAUU | XXXXXXXXXX XXXXXXXXX |
| WV-2898 | 342 | mU * mU * mU * mC * mA * mC * mA * mA * mG * mA * mC * mA * mU * mU * mU * mU * mA * mC * mU * mU | UUUCACAAGACAUUUUACUU | XXXXXXXXXX XXXXXXXXX |
| WV-2899 | 343 | mU * mU * mG * mU * mU * mU * mC * mA * mC * mA * mA * mG * mA * mC * mA * mU * mU * mU * mU * mA | UUGUUUCACAAGACAUUUUA | XXXXXXXXXX XXXXXXXXX |
| WV-2900 | 344 | mA * mU * mU * mU * mU * mG * mU * mU * mU * mC * mA * mC * mA * mA * mG * mA * mC * mA * mU * mU | AUUUUGUUUCACAAGACAUU | XXXXXXXXXX XXXXXXXXX |
| WV-2901 | 345 | mA * mG * mC * mA * mU * mU * mU * mU * mG * mU * mU * mU * mC * mA * mC * mA * mA * mG * mA * mC | AGCAUUUUGUUUCACAAGAC | XXXXXXXXXX XXXXXXXXX |
| WV-2902 | 346 | mA * mA * mA * mA * mG * mC * mA * mU * mU * mU * mU * mG * mU * mU * mU * mC * mA * mC * mA * mA | AAAAGCAUUUUGUUUCACAA | XXXXXXXXXX XXXXXXXXX |
| WV-2903 | 347 | mU * mU * mA * mA * mA * mA * mA * mG * mC * mA * mU * mU * mU * mU * mG * mU * mU * mU * mC * mA | UUAAAAAGCAUUUUGUUUCA | XXXXXXXXXX XXXXXXXXX |
| WV-2904 | 348 | mA * mU * mG * mU * mU * mA * mA * mA * mA * mA * mG * mC * mA * mU * mU * mU * mU * mG * mU * mU | AUGUUAAAAAGCAUUUUGUU | XXXXXXXXXX XXXXXXXXX |
| WV-2905 | 349 | mU * mG * mG * mA * mU * mG * mU * mU * mA * mA * mA * mA * mA * mG * mC * mA * mU * mU * mU * mU | UGGAUGUUAAAAAGCAUUUU | XXXXXXXXXX XXXXXXXXX |
| WV-2906 | 350 | mA * mU * mA * mU * mG * mG * mA * mU * mG * mU * mU * mA * mA * mA * mA * mG * mC * mA * mU | AUAUGGAUGUUAAAAGCAU | XXXXXXXXXX XXXXXXXXX |
| WV-2907 | 351 | mU * mU * mU * mA * mU * mA * mU * mG * mG * mA * mU * mG * mU * mU * mA * mA * mA * mA * mA * mG | UUUAUAUGGAUGUUAAAAAG | XXXXXXXXXX XXXXXXXXX |
| WV-2908 | 352 | mA * mG * mC * mU * mU * mU * mA * mU * mA * mU * mG * mG * mA * mU * mG * mU * mU * mA * mA * mA | AGCUUUAUAUGGAUGUUAAA | XXXXXXXXXX XXXXXXXXX |
| WV-2909 | 353 | mG * mA * mU * mA * mG * mC * mU * mU * mU * mA * mU * mA * mU * mG * mG * mA * mU * mG * mU * mU | GAUAGCUUUAUAUGGAUGUU | XXXXXXXXXX XXXXXXXXX |
| WV-2910 | 354 | mA * mU * mA * mG * mA * mU * mA * mG * mC * mU * mU * mU * mA * mU * mA * mU * mG * mG * mA * mU | AUAGAUAGCUUUAUAUGGAU | XXXXXXXXXX XXXXXXXXX |
| WV-2911 | 355 | mU * mA * mU * mA * mU * mA * mG * mA * mU * mA * mG * mC * mU * mU * mU * mA * mU * mA * mU * mG | UAUAUAGAUAGCUUUAUAUG | XXXXXXXXXX XXXXXXXXX |

TABLE 1A-continued

Example oligonucleotides.

| ID | SEQ ID NO: | Description | Base Sequence | Stereo-chemistry |
|---|---|---|---|---|
| WV-2912 | 356 | mC * mC * mC * mU * mG * mU * mA * mA * mG * mG * mA * mA * mA * mU * mA * mA * mA * mG * mG | CCCUGUAAGGAAAAUAAAGG | XXXXXXXXXX XXXXXXXXX |
| WV-2913 | 357 | mA * mA * mC * mC * mC * mU * mG * mU * mA * mA * mG * mG * mA * mA * mA * mA * mU * mA * mA * mA | AACCCUGUAAGGAAAAUAAA | XXXXXXXXXX XXXXXXXXX |
| WV-2914 | 358 | mA * mA * mA * mC * mC * mC * mU * mG * mU * mA * mA * mG * mG * mA * mA * mA * mA * mU * mA | AAACCCUGUAAGGAAAAUA | XXXXXXXXXX XXXXXXXXX |
| WV-2915 | 359 | mC * mU * mA * mA * mA * mA * mC * mC * mC * mU * mG * mU * mA * mA * mG * mG * mA * mA * mA * mA | CUAAAACCCUGUAAGGAAAA | XXXXXXXXXX XXXXXXXXX |
| WV-2916 | 360 | mG * mU * mC * mU * mA * mA * mA * mA * mC * mC * mC * mU * mG * mU * mA * mA * mG * mG * mA * mA | GUCUAAAACCCUGUAAGGAA | XXXXXXXXXX XXXXXXXXX |
| WV-2917 | 361 | mG * mA * mG * mC * mA * mC * mC * mU * mU * mC * mC * mU * mU * mC * mU * mU * mU * mU * mU * mG | GAGCACCUUCCUUCUUUUG | XXXXXXXXXX XXXXXXXXX |
| WV-2918 | 362 | mG * mU * mG * mA * mG * mC * mA * mC * mC * mU * mU * mC * mC * mU * mU * mC * mU * mU * mU * mU | GUGAGCACCUUCCUUCUUUU | XXXXXXXXXX XXXXXXXXX |
| WV-2919 | 363 | mA * mU * mG * mU * mG * mA * mG * mC * mA * mC * mC * mU * mU * mC * mC * mU * mU * mC * mU * mU | AUGUGAGCACCUUCCUUCUU | XXXXXXXXXX XXXXXXXXX |
| WV-2920 | 364 | mG * mA * mA * mU * mG * mU * mG * mA * mG * mC * mA * mC * mC * mU * mU * mC * mC * mU * mU * mC | GAAUGUGAGCACCUUCCUUC | XXXXXXXXXX XXXXXXXXX |
| WV-2921 | 365 | mA * mG * mG * mA * mA * mU * mG * mU * mG * mA * mG * mC * mA * mC * mC * mU * mU * mC * mC * mU | AGGAAUGUGAGCACCUUCCU | XXXXXXXXXX XXXXXXXXX |
| WV-2922 | 366 | mU * mA * mA * mG * mG * mA * mA * mU * mG * mU * mG * mA * mG * mC * mA * mC * mC * mU * mU * mC | UAAGGAAUGUGAGCACCUUC | XXXXXXXXXX XXXXXXXXX |
| WV-2923 | 367 | mU * mU * mU * mA * mA * mG * mG * mA * mA * mU * mG * mU * mG * mA * mG * mC * mA * mC * mC * mU | UUUAAGGAAUGUGAGCACCU | XXXXXXXXXX XXXXXXXXX |
| WV-2924 | 368 | mA * mA * mU * mU * mU * mA * mA * mG * mG * mA * mA * mU * mG * mU * mG * mA * mG * mC * mA * mC | AAUUUAAGGAAUGUGAGCAC | XXXXXXXXXX XXXXXXXXX |
| WV-2925 | 369 | mU * mU * mA * mA * mU * mU * mU * mA * mA * mG * mG * mA * mA * mU * mG * mU * mG * mA * mG * mC | UUAAUUUAAGGAAUGUGAGC | XXXXXXXXXX XXXXXXXXX |
| WV-2926 | 370 | mC * mC * mU * mU * mA * mA * mU * mU * mU * mA * mA * mG * mG * mA * mA * mU * mG * mU * mG * mA | CCUUAAUUUAAGGAAUGUGA | XXXXXXXXXX XXXXXXXXX |
| WV-2927 | 371 | mC * mU * mC * mC * mU * mU * mA * mA * mU * mU * mU * mA * mA * mA * mG * mG * mA * mA * mU * mG * mU | CUCCUUAAUUUAAGGAAUGU | XXXXXXXXXX XXXXXXXXX |
| WV-2928 | 372 | mA * mC * mU * mU * mU * mC * mA * mU * mA * mA * mU * mG * mC * mU * mG * mG * mC * mA * mG * mA * mC * mU * mU * mA * mC | ACUUUCAUAAUGCUGGCAGACUUAC | XXXXXXXXXX X XXXXXXXXXX XXX |
| WV-2929 | 373 | mC * mA * mC * mU * mU * mU * mC * mA * mU * mA * mA * mU * mG * mC * mU * mG * mG * mC * mA * mG * mA * mC * mU * mU * mA | CACUUUCAUAAUGCUGGCAGACUUA | XXXXXXXXXX XXXXXXXXXX XXXX |

TABLE 1A-continued

Example oligonucleotides.

| ID | SEQ ID NO: | Description | Base Sequence | Stereo-chemistry |
|---|---|---|---|---|
| WV-2930 | 374 | mU * mC * mA * mC * mU * mU * mU * mC * mA * mU * mA * mA * mU * mG * mC * mU * mG * mG * mC * mA * mG * mA * mC * mU * mU | UCACUUUCAUAAUGCUGGCAGACUU | XXXXXXXXXXXXXXXXXXXXXXXX |
| WV-2931 | 375 | mU * mU * mC * mA * mC * mU * mU * mU * mC * mA * mU * mA * mA * mU * mG * mC * mU * mG * mG * mC * mA * mG * mA * mC * mU | UUCACUUUCAUAAUGCUGGCAGACU | XXXXXXXXXXXXXXXXXXXXXXXX |
| WV-2932 | 376 | mA * mU * mU * mC * mA * mC * mU * mU * mU * mC * mA * mU * mA * mA * mU * mG * mC * mU * mG * mG * mC * mA * mG * mA * mC | AUUCACUUUCAUAAUGCUGGCAGAC | XXXXXXXXXXXXXXXXXXXXXXXX |
| WV-2933 | 377 | mG * mA * mU * mU * mC * mA * mC * mU * mU * mU * mC * mA * mU * mA * mA * mU * mG * mC * mU * mG * mG * mC * mA * mG * mA | GAUUCACUUUCAUAAUGCUGGCAGA | XXXXXXXXXXXXXXXXXXXXXXXX |
| WV-2934 | 378 | mA * mG * mA * mU * mU * mC * mA * mC * mU * mU * mU * mC * mA * mU * mA * mA * mU * mG * mC * mU * mG * mG * mC * mA * mG | AGAUUCACUUUCAUAAUGCUGGCAG | XXXXXXXXXXXXXXXXXXXXXXXX |
| WV-2935 | 379 | mA * mA * mG * mA * mU * mU * mC * mA * mC * mU * mU * mU * mC * mA * mU * mA * mA * mU * mG * mC * mU * mG * mG * mC * mA | AAGAUUCACUUUCAUAAUGCUGGCA | XXXXXXXXXXXXXXXXXXXXXXXX |
| WV-2936 | 380 | mU * mA * mA * mG * mA * mU * mU * mC * mA * mC * mU * mU * mU * mC * mA * mU * mA * mA * mU * mG * mC * mU * mG * mG * mC | UAAGAUUCACUUUCAUAAUGCUGGC | XXXXXXXXXXXXXXXXXXXXXXXX |
| WV-2937 | 381 | mG * mU * mA * mA * mG * mA * mU * mU * mC * mA * mC * mU * mU * mU * mC * mA * mU * mA * mA * mU * mG * mC * mU * mG * mG | GUAAGAUUCACUUUCAUAAUGCUGG | XXXXXXXXXXXXXXXXXXXXXXXX |
| WV-2938 | 382 | mA * mA * mC * mU * mU * mU * mC * mU * mA * mA * mC * mA * mU * mC * mU * mG * mA * mA * mC * mU * mU * mU * mU * mU * mA | AACUUUCUAACAUCUGAACUUUUUA | XXXXXXXXXXXXXXXXXXXXXXXX |
| WV-2939 | 383 | mU * mC * mA * mA * mC * mU * mU * mU * mC * mU * mA * mA * mC * mA * mU * mC * mU * mG * mA * mA * mC * mU * mU * mU * mU | UCAACUUUCUAACAUCUGAACUUUU | XXXXXXXXXXXXXXXXXXXXXXXX |
| WV-2940 | 384 | mU * mU * mU * mC * mA * mA * mC * mU * mU * mU * mC * mU * mA * mA * mC * mA * mU * mC * mU * mG * mA * mA * mC * mU * mU | UUUCAACUUUCUAACAUCUGAACUU | XXXXXXXXXXXXXXXXXXXXXXXX |
| WV-2941 | 385 | mC * mC * mU * mU * mU * mC * mA * mA * mC * mU * mU * mU * mC * mU * mA * mA * mC * mA * mU * mC * mU * mG * mA * mA * mC | CCUUUCAACUUUCUAACAUCUGAAC | XXXXXXXXXXXXXXXXXXXXXXXX |
| WV-2942 | 386 | mA * mA * mC * mC * mU * mU * mU * mC * mA * mA * mC * mU * mU * mU * mC * mU * mA * mA * mC * mA * mU * mC * mU * mG * mA | AACCUUUCAACUUUCUAACAUCUGA | XXXXXXXXXXXXXXXXXXXXXXXX |
| WV-2943 | 387 | mU * mU * mA * mA * mC * mC * mU * mU * mU * mC * mA * mA * mC * mU * mU * mU * mC * mU * mA * mA * mC * mA * mU * mC * mU | UUAACCUUUCAACUUUCUAACAUCU | XXXXXXXXXXXXXXXXXXXXXXXX |
| WV-2944 | 388 | mC * mA * mU * mU * mA * mA * mC * mC * mU * mU * mU * mC * mA * mA * | CAUUAACCUUUCAACUUUCUAACAU | XXXXXXXXXX XXXXXXXXXX |

TABLE 1A-continued

Example oligonucleotides.

| ID | SEQ ID NO: | Description | Base Sequence | Stereo-chemistry |
|---|---|---|---|---|
| | | mA * mC * mU * mU * mU * mC * mU * mA * mA * mC * mA * mU | | XXXX |
| WV-2945 | 389 | mU * mG * mG * mU * mC * mU * mG * mC * mC * mU * mA * mC * mU * mA * mG * mU * mG * mA * mU * mA * mU * mA * mA * mA * mA | UGGUCUGCCUACUAGUGAUAUAAAA | XXXXXXXXXX XXXXXXXXXX XXXX |
| WV-2946 | 390 | mG * mC * mU * mG * mG * mU * mC * mU * mG * mC * mC * mU * mA * mC * mU * mA * mG * mU * mG * mA * mU * mA * mU * mA * mA | GCUGGUCUGCCUACUAGUGAUAUAA | XXXXXXXXXX XXXXXXXXXX XXXX |
| WV-2947 | 391 | mC * mU * mG * mC * mU * mG * mG * mU * mC * mU * mG * mC * mC * mU * mA * mC * mU * mA * mG * mU * mG * mA * mU * mA * mU | CUGCUGGUCUGCCUACUAGUGAUAU | XXXXXXXXXX XXXXXXXXXX XXXX |
| WV-2948 | 392 | mG * mU * mC * mU * mG * mC * mU * mG * mG * mU * mC * mU * mG * mC * mC * mU * mA * mC * mU * mA * mG * mU * mG * mA * mU | GUCUGCUGGUCUGCCUACUAGUGAU | XXXXXXXXXX XXXXXXXXXX XXXX |
| WV-2949 | 393 | mA * mA * mG * mU * mC * mU * mG * mC * mU * mG * mG * mU * mC * mU * mG * mC * mC * mU * mA * mC * mU * mA * mG * mU * mG | AAGUCUGCUGGUCUGCCUACUAGUG | XXXXXXXXXX XXXXXXXXXX XXXX |
| WV-2950 | 394 | mA * mA * mA * mA * mG * mU * mC * mU * mG * mC * mU * mG * mG * mU * mC * mU * mG * mC * mC * mU * mA * mC * mU * mA * mG | AAAAGUCUGCUGGUCUGCCUACUAG | XXXXXXXXXX XXXXXXXXXX XXXX |
| WV-2951 | 395 | mA * mA * mA * mA * mA * mA * mG * mU * mC * mU * mG * mC * mU * mG * mG * mU * mC * mU * mG * mC * mC * mU * mA * mC * mU | AAAAAAGUCUGCUGGUCUGCCUACU | XXXXXXXXXX XXXXXXXXXX XXXX |
| WV-2952 | 396 | mA * mA * mA * mA * mA * mA * mA * mA * mG * mU * mC * mU * mG * mC * mU * mG * mG * mU * mC * mU * mG * mC * mC * mU * mA | AAAAAAAAGUCUGCUGGUCUGCCUA | XXXXXXXXXX XXXXXXXXXX XXXX |
| WV-2953 | 397 | mA * mU * mA * mA * mA * mA * mA * mA * mA * mA * mG * mU * mC * mU * mG * mC * mU * mG * mG * mU * mC * mU * mG * mC * mC | AUAAAAAAAAGUCUGCUGGUCUGCC | XXXXXXXXXX XXXXXXXXXX XXXX |
| WV-2954 | 398 | mC * mA * mA * mU * mA * mA * mA * mA * mA * mA * mA * mA * mG * mU * mC * mU * mG * mC * mU * mG * mG * mU * mC * mU * mG | CAAUAAAAAAAAGUCUGCUGGUCUG | XXXXXXXXXX XXXXXXXXXX XXXX |
| WV-2955 | 399 | mA * mA * mU * mG * mA * mG * mA * mA * mA * mU * mU * mA * mG * mA * mA * mC * mC * mA * mG * mA * mG * mG * mC * mU * mU | AAUGAGAAAUUAGAACCAGAGGCUU | XXXXXXXXXX XXXXXXXXXX XXXX |
| WV-2956 | 400 | mC * mA * mA * mA * mU * mG * mA * mG * mA * mA * mA * mU * mU * mA * mG * mA * mA * mC * mC * mA * mG * mA * mG * mG * mC | CAAAUGAGAAAUUAGAACCAGAGGC | XXXXXXXXXX XXXXXXXXXX XXXX |
| WV-2957 | 401 | mU * mG * mC * mA * mA * mA * mU * mG * mA * mG * mA * mA * mA * mU * mU * mA * mG * mA * mA * mC * mC * mA * mG * mA * mG | UGCAAAUGAGAAAUUAGAACCAGAG | XXXXXXXXXX XXXXXXXXXX XXXX |
| WV-2958 | 402 | mC * mC * mU * mG * mC * mA * mA * mA * mU * mG * mA * mG * mA * mA * mA * mU * mU * mA * mG * mA * mA * mC * mC * mA * mG | CCUGCAAAUGAGAAAUUAGAACCAG | XXXXXXXXXX XXXXXXXXXX XXXX |
| WV-2959 | 403 | mU * mU * mC * mC * mU * mG * mC * mA * mA * mA * mU * mG * mA * mG * mA * mA * mG | UUCCUGCAAAUGAGAAAUUAGAACC | XXXXXXXXXX XXXXXXXXXX |

TABLE 1A-continued

Example oligonucleotides.

| SEQ ID | SEQ ID NO: | Description | Base Sequence | Stereo-chemistry |
|---|---|---|---|---|
| | | * mA * mA * mA * mU * mU * mA * mG * mA * mA * mC * mC | | XXXX |
| WV-2960 | 404 | mA * mU * mU * mU * mC * mC * mU * mG * mC * mA * mA * mA * mU * mG * mA * mG * mA * mA * mA * mU * mU * mA * mG * mA * mA | AUUUCCUGCAAAUGAGAAAUUAGAA | XXXXXXXXXX XXXXXXXXXX XXXX |
| WV-2961 | 405 | mG * mC * mA * mU * mU * mU * mC * mC * mU * mG * mC * mA * mA * mA * mU * mG * mA * mG * mA * mA * mA * mU * mU * mA * mG | GCAUUUCCUGCAAAUGAGAAAUUAG | XXXXXXXXXX XXXXXXXXXX XXXX |
| WV-2962 | 406 | mC * mA * mG * mC * mA * mU * mU * mU * mC * mC * mU * mG * mC * mA * mA * mA * mU * mG * mA * mG * mA * mA * mA * mU * mU | CAGCAUUUCCUGCAAAUGAGAAAUU | XXXXXXXXXX XXXXXXXXXX XXXX |
| WV-2963 | 407 | mG * mC * mC * mA * mG * mC * mA * mU * mU * mU * mC * mC * mU * mG * mC * mA * mA * mA * mU * mG * mA * mG * mA * mA * mA | GCCAGCAUUUCCUGCAAAUGAGAAA | XXXXXXXXXX XXXXXXXXXX XXXX |
| WV-2964 | 408 | mA * mU * mG * mC * mC * mA * mG * mC * mA * mU * mU * mU * mC * mC * mU * mG * mC * mA * mA * mA * mU * mG * mA * mG * mA | AUGCCAGCAUUUCCUGCAAAUGAGA | XXXXXXXXXX XXXXXXXXXX XXXX |
| WV-2965 | 409 | mC * mU * mA * mU * mG * mC * mC * mA * mG * mC * mA * mU * mU * mU * mC * mC * mU * mG * mC * mA * mA * mA * mU * mG * mA | CUAUGCCAGCAUUUCCUGCAAAUGA | XXXXXXXXXX XXXXXXXXXX XXXX |
| WV-2966 | 410 | mC * mU * mC * mU * mA * mU * mG * mC * mC * mA * mG * mC * mA * mU * mU * mU * mC * mC * mU * mG * mC * mA * mA * mA * mU | CUCUAUGCCAGCAUUUCCUGCAAAU | XXXXXXXXXX XXXXXXXXXX XXXX |
| WV-2967 | 411 | mU * mG * mC * mU * mC * mU * mA * mU * mG * mC * mC * mA * mG * mC * mA * mU * mU * mU * mC * mC * mU * mG * mC * mA * mA | UGCUCUAUGCCAGCAUUUCCUGCAA | XXXXXXXXXX XXXXXXXXXX XXXX |
| WV-2968 | 412 | mG * mC * mU * mG * mC * mU * mC * mU * mA * mU * mG * mC * mC * mA * mG * mC * mA * mU * mU * mU * mC * mC * mU * mG * mC | GCUGCUCUAUGCCAGCAUUUCCUGC | XXXXXXXXXX XXXXXXXXXX XXXX |
| WV-2969 | 413 | mG * mU * mG * mC * mU * mG * mC * mU * mC * mU * mA * mU * mG * mC * mC * mA * mG * mC * mA * mU * mU * mU * mC * mC * mU | GUGCUGCUCUAUGCCAGCAUUUCCU | XXXXXXXXXX XXXXXXXXXX XXXX |
| WV-2970 | 414 | mU * mA * mG * mU * mG * mC * mU * mG * mC * mU * mC * mU * mA * mU * mG * mC * mC * mA * mG * mC * mA * mU * mU * mU * mC | UAGUGCUGCUCUAUGCCAGCAUUUC | XXXXXXXXXX XXXXXXXXXX XXXX |
| WV-2971 | 415 | mG * mU * mU * mU * mU * mC * mC * mA * mC * mA * mA * mA * mC * mC * mA * mU * mA * mA * mA * mG * mU * mU * mU * mU * mA | GUUUUCCACAAACCAUAAAGUUUUA | XXXXXXXXXX XXXXXXXXXX XXXX |
| WV-2972 | 416 | mU * mG * mU * mU * mU * mU * mC * mC * mA * mC * mA * mA * mA * mC * mC * mA * mU * mA * mA * mA * mG * mU * mU * mU * mU | UGUUUUCCACAAACCAUAAAGUUUU | XXXXXXXXXX XXXXXXXXXX XXXX |
| WV-2973 | 417 | mU * mU * mG * mU * mU * mU * mU * mC * mC * mA * mC * mA * mA * mA * mC * mC * mA * mU * mA * mA * mA * mG * mU * mU * mU | UUGUUUUCCACAAACCAUAAAGUUU | XXXXXXXXXX XXXXXXXXXX XXXX |

TABLE 1A-continued

Example oligonucleotides.

| ID | SEQ ID NO: | Description | Base Sequence | Stereo-chemistry |
|---|---|---|---|---|
| WV-2974 | 418 | mG * mA * mG * mA * mA * mU * mU * mC * mU * mA * mG * mU * mA * mG * mG * mG * mA * mU * mG * mU * mA * mG * mA * mU * mU | GAGAAUUCUAGUAGGGAUGUAGAUU | XXXXXXXXXXXXXXXXXXXXXXXXX |
| WV-2975 | 419 | mU * mG * mA * mG * mA * mA * mU * mU * mC * mU * mA * mG * mU * mA * mG * mG * mG * mA * mU * mG * mU * mA * mG * mA * mU | UGAGAAUUCUAGUAGGGAUGUAGAU | XXXXXXXXXXXXXXXXXXXXXXXXX |
| WV-2976 | 420 | mA * mU * mG * mA * mGA * mA * mA * mU * mU * mC * mU * mA * mG * mU * mA * mG * mG * mG * mA * mU * mG * mU * mA * mG * mA | AUGAGAAUUCUAGUAGGGAUGUAGA | XXXXXXXXXXXXXXXXXXXXXXXXX |
| WV-2977 | 421 | mU * mA * mU * mG * mA * mG * mA * mA * mU * mU * mC * mU * mA * mG * mU * mA * mG * mG * mG * mA * mU * mG * mU * mA * mG | UAUGAGAAUUCUAGUAGGGAUGUAG | XXXXXXXXXXXXXXXXXXXXXXXXX |
| WV-2978 | 422 | mU * mU * mU * mA * mC * mU * mU * mA * mU * mU * mU * mU * mA * mU * mU * mC * mA * mA * mC * mA * mA * mA * mU * mA | UUUACUUAUUUUAUUCAACAAAUA | XXXXXXXXXXXXXXXXXXXXXXXXX |
| WV-2979 | 423 | mA * mU * mU * mU * mU * mA * mC * mU * mU * mA * mU * mU * mU * mU * mA * mU * mU * mC * mA * mA * mC * mA * mA * mA * mA | AUUUUACUUAUUUUAUUCAACAAAA | XXXXXXXXXXXXXXXXXXXXXXXXX |
| WV-2980 | 424 | mU * mU * mC * mA * mC * mA * mA * mG * mA * mC * mA * mU * mU * mU * mU * mA * mC * mU * mU * mA * mU * mU * mU * mU * mA | UUCACAAGACAUUUUACUUAUUUUA | XXXXXXXXXXXXXXXXXXXXXXXXX |
| WV-2981 | 425 | mG * mU * mU * mU * mC * mA * mC * mA * mA * mG * mA * mC * mA * mU * mU * mU * mU * mA * mC * mU * mU * mA * mU * mU * mU | GUUUCACAAGACAUUUUACUUAUUU | XXXXXXXXXXXXXXXXXXXXXXXXX |
| WV-2982 | 426 | mU * mU * mG * mU * mU * mU * mC * mA * mC * mA * mA * mG * mA * mC * mA * mU * mU * mU * mU * mA * mC * mU * mU * mA * mU | UUGUUUCACAAGACAUUUUACUUAU | XXXXXXXXXXXXXXXXXXXXXXXXX |
| WV-2983 | 427 | mU * mU * mU * mU * mG * mU * mU * mU * mC * mA * mC * mA * mA * mG * mA * mC * mA * mU * mU * mU * mU * mA * mC * mU * mU | UUUUGUUUCACAAGACAUUUUACUU | XXXXXXXXXXXXXXXXXXXXXXXXX |
| WV-2984 | 428 | mC * mA * mU * mU * mU * mU * mG * mU * mU * mU * mC * mA * mC * mA * mA * mG * mA * mC * mA * mU * mU * mU * mU * mA * mC | CAUUUUGUUUCACAAGACAUUUUAC | XXXXXXXXXXXXXXXXXXXXXXXXX |
| WV-2985 | 429 | mA * mG * mC * mA * mU * mU * mU * mU * mG * mU * mU * mU * mC * mA * mC * mA * mA * mG * mA * mC * mA * mU * mU * mU * mU | AGGAUUUGUUUCACAAGACAUUUU | XXXXXXXXXXXXXXXXXXXXXXXXX |
| WV-2986 | 430 | mA * mA * mA * mG * mC * mA * mU * mU * mU * mU * mG * mU * mU * mU * mC * mA * mC * mA * mA * mG * mA * mC * mA * mU * mU | AAAGCAUUUUGUUUCACAAGACAUU | XXXXXXXXXXXXXXXXXXXXXXXXX |
| WV-2987 | 431 | mA * mA * mA * mA * mA * mG * mC * mA * mU * mU * mU * mU * mG * mU * mU * mU * mC * mA * mC * mA * mA * mG * mA * mC * mA | AAAAAGCAUUUUGUUUCACAAGACA | XXXXXXXXXXXXXXXXXXXXXXXXX |

TABLE 1A-continued

Example oligonucleotides.

| ID | SEQ ID NO: | Description | Base Sequence | Stereo-chemistry |
|---|---|---|---|---|
| WV-2988 | 432 | mU * mU * mA * mA * mA * mA * mA * mG * mC * mA * mU * mU * mU * mU * mG * mU * mU * mU * mC * mA * mC * mA * mA * mG * mA | UUAAAAAGGAUUUUGUUUCACAAGA | XXXXXXXXXXXXXXXXXXXXXXXX |
| WV-2989 | 433 | mU * mG * mU * mU * mA * mA * mA * mA * mA * mG * mC * mA * mU * mU * mU * mU * mG * mU * mU * mU * mC * mA * mC * mA * mA | UGUUAAAAGCAUUUUGUUUCACAA | XXXXXXXXXXXXXXXXXXXXXXXX |
| WV-2990 | 434 | mG * mA * mU * mG * mU * mU * mA * mA * mA * mA * mA * mG * mC * mA * mU * mU * mU * mU * mG * mU * mU * mU * mC * mA * mC | GAUGUUAAAAGCAUUUUGUUUCAC | XXXXXXXXXXXXXXXXXXXXXXXX |
| WV-2991 | 435 | mU * mG * mG * mA * mU * mG * mU * mU * mA * mA * mA * mA * mA * mG * mC * mA * mU * mU * mU * mU * mG * mU * mU * mU * mC | UGGAUGUUAAAAGCAUUUUGUUUC | XXXXXXXXXXXXXXXXXXXXXXXX |
| WV-2992 | 436 | mU * mA * mU * mG * mG * mA * mU * mG * mU * mU * mA * mA * mA * mA * mA * mG * mC * mA * mU * mU * mU * mU * mG * mU * mU | UAUGGAUGUUAAAAGCAUUUUGUU | XXXXXXXXXXXXXXXXXXXXXXXX |
| WV-2993 | 437 | mU * mA * mU * mA * mU * mG * mG * mA * mU * mG * mU * mU * mA * mA * mA * mA * mA * mG * mC * mA * mU * mU * mU * mU * mG | UAUAUGGAUGUUAAAAGCAUUUUG | XXXXXXXXXXXXXXXXXXXXXXXX |
| WV-2994 | 438 | mU * mU * mU * mA * mU * mA * mU * mG * mG * mA * mU * mG * mU * mU * mA * mA * mA * mA * mA * mG * mC * mA * mU * mU * mU | UUUAUAUGGAUGUUAAAAGCAUUU | XXXXXXXXXXXXXXXXXXXXXXXX |
| WV-2995 | 439 | mG * mC * mU * mU * mU * mA * mU * mA * mU * mG * mG * mA * mU * mG * mU * mU * mA * mA * mA * mA * mA * mG * mC * mA * mU | GCUUUAUAUGGAUGUUAAAAGCAU | XXXXXXXXXXXXXXXXXXXXXXXX |
| WV-2996 | 440 | mU * mA * mG * mC * mU * mU * mU * mA * mU * mA * mU * mG * mG * mA * mU * mG * mU * mU * mA * mA * mA * mA * mA * mG * mC | UAGCUUUAUAUGGAUGUUAAAAGC | XXXXXXXXXXXXXXXXXXXXXXXX |
| WV-2997 | 441 | mG * mA * mU * mA * mG * mC * mU * mU * mU * mA * mU * mA * mU * mG * mG * mA * mU * mG * mU * mU * mA * mA * mA * mA * mA | GAUAGCUUUAUAUGGAUGUUAAAA | XXXXXXXXXXXXXXXXXXXXXXXX |
| WV-2998 | 442 | mU * mA * mG * mA * mU * mA * mG * mC * mU * mU * mU * mA * mU * mA * mU * mG * mG * mA * mU * mG * mU * mU * mA * mA * mA | UAGAUAGCUUUAUAUGGAUGUUAAA | XXXXXXXXXXXXXXXXXXXXXXXX |
| WV-2999 | 443 | mU * mA * mU * mA * mG * mA * mU * mA * mG * mC * mU * mU * mU * mA * mU * mA * mU * mG * mG * mA * mU * mG * mU * mU * mA | UAUAGAUAGCUUUAUAUGGAUGUUA | XXXXXXXXXXXXXXXXXXXXXXXX |
| WV-3000 | 444 | mU * mA * mU * mA * mU * mA * mG * mA * mU * mA * mG * mC * mU * mU * mU * mA * mU * mA * mU * mG * mG * mA * mU * mG * mU | UAUAUAGAUAGCUUUAUAUGGAUGU | XXXXXXXXXXXXXXXXXXXXXXXX |
| WV-3001 | 445 | mC * mC * mU * mG * mU * mA * mA * mG * mG * mA * mA * mA * mA * mU * mA * mA * mA * mG * mG * mA * mA * mG * mU * mU * mA | CCUGUAAGGAAAUAAAGGAAGUUA | XXXXXXXXXXXXXXXXXXXXXXXX |

TABLE 1A-continued

Example oligonucleotides.

| ID | SEQ ID NO: | Description | Base Sequence | Stereo-chemistry |
|---|---|---|---|---|
| WV-3002 | 446 | mA * mC * mC * mC * mU * mG * mU * mA * mA * mG * mG * mA * mA * mA * mA * mU * mA * mA * mA * mG * mG * mA * mA * mG * mU | ACCCUGUAAGGAAAAUAAAGGAAGU | XXXXXXXXXX XXXXXXXXXX XXXX |
| WV-3003 | 447 | mA * mA * mA * mC * mC * mC * mU * mG * mU * mA * mA * mG * mG * mA * mA * mA * mA * mU * mA * mA * mA * mG * mG * mA * mA | AAACCCUGUAAGGAAAAUAAAGGAA | XXXXXXXXXX XXXXXXXXXX XXXX |
| WV-3004 | 448 | mU * mA * mA * mA * mA * mC * mC * mC * mU * mG * mU * mA * mA * mG * mG * mA * mA * mA * mA * mU * mA * mA * mA * mG * mG | UAAAACCCUGUAAGGAAAAUAAAGG | XXXXXXXXXX XXXXXXXXXX XXXX |
| WV-3005 | 449 | mU * mC * mU * mA * mA * mA * mA * mC * mC * mC * mU * mG * mU * mA * mA * mG * mG * mA * mA * mA * mA * mU * mA * mA * mA | UCUAAAACCCUGUAAGGAAAAUAAA | XXXXXXXXXX XXXXXXXXXX XXXX |
| WV-3006 | 450 | mU * mG * mU * mC * mU * mA * mA * mA * mA * mC * mC * mC * mU * mG * mU * mA * mA * mG * mG * mA * mA * mA * mA * mU * mA | UGUCUAAAACCCUGUAAGGAAAAUA | XXXXXXXXXX XXXXXXXXXX XXXX |
| WV-3007 | 451 | mA * mA * mU * mG * mU * mG * mA * mG * mC * mA * mC * mC * mU * mU * mC * mC * mU * mU * mC * mU * mU * mU * mU * mU * mG | AAUGUGAGCACCUUCCUUCUUUUG | XXXXXXXXXX XXXXXXXXXX XXXX |
| WV-3008 | 452 | mG * mG * mA * mA * mU * mG * mU * mG * mA * mG * mC * mA * mC * mC * mU * mU * mC * mC * mU * mU * mC * mU * mU * mU * mU | GGAAUGUGAGCACCUUCCUUCUUUU | XXXXXXXXXX XXXXXXXXXX XXXX |
| WV-3009 | 453 | mA * mA * mG * mG * mA * mA * mU * mG * mU * mG * mA * mG * mC * mA * mC * mC * mU * mU * mC * mC * mU * mU * mC * mU * mU | AAGGAAUGUGAGCACCUUCCUUCUU | XXXXXXXXXX XXXXXXXXXX XXXX |
| WV-3010 | 454 | mU * mU * mA * mA * mG * mG * mA * mA * mU * mG * mU * mG * mA * mG * mC * mA * mC * mC * mU * mU * mC * mC * mU * mU * mC | UUAAGGAAUGUGAGCACCUUCCUUC | XXXXXXXXXX XXXXXXXXXX XXXX |
| WV-3011 | 455 | mA * mU * mU * mU * mA * mA * mG * mG * mA * mA * mU * mG * mU * mG * mA * mG * mC * mA * mC * mC * mU * mU * mC * mC * mU | AUUUAAGGAAUGUGAGCACCUUCCU | XXXXXXXXXX XXXXXXXXXX XXXX |
| WV-3012 | 456 | mU * mA * mA * mU * mU * mU * mA * mA * mG * mG * mA * mA * mU * mG * mU * mG * mA * mG * mC * mA * mC * mC * mU * mU * mC | UAAUUUAAGGAAUGUGAGCACCUUC | XXXXXXXXXX XXXXXXXXXX XXXX |
| WV-3013 | 457 | mC * mU * mU * mA * mA * mU * mU * mU * mA * mA * mG * mG * mA * mA * mU * mG * mU * mG * mA * mG * mC * mA * mC * mC * mU | CUUAAUUUAAGGAAUGUGAGCACCU | XXXXXXXXXX XXXXXXXXXX XXXX |
| WV-3014 | 458 | mU * mC * mC * mU * mU * mA * mA * mU * mU * mU * mA * mA * mG * mG * mA * mA * mU * mG * mU * mG * mA * mG * mC * mA * mC | UCCUUAAUUUAAGGAAUGUGAGCAC | XXXXXXXXXX XXXXXXXXXX XXXX |
| WV-3015 | 459 | mA * mC * mU * mC * mC * mU * mU * mA * mA * mU * mU * mU * mA * mA * mG * mG * mA * mA * mU * mG * mU * mG * mA * mG * mC | ACUCCUUAAUUUAAGGAAUGUGAGC | XXXXXXXXXX XXXXXXXXXX XXXX |

TABLE 1A-continued

Example oligonucleotides.

| ID | SEQ ID NO: | Description | Base Sequence | Stereo-chemistry |
|---|---|---|---|---|
| WV-3016 | 460 | mU * mU * mA * mC * mU * mC * mC * mU * mU * mA * mA * mU * mU * mU * mA * mA * mG * mG * mA * mA * mU * mG * mU * mG * mA | UUACUCCUUAAUUUAAGGAAUGUGA | XXXXXXXXXX XXXXXXXXXX XXXX |
| WV-14512 | 461 | Teo * Rm5Ceo * RAeon001m5Ceo * RTeo * RTeon001Teo * Rm5Ceo * RAeon001Teo * RAeo * RAeon001Teo * RGeo * Rm5Ceon001Teo * RGeo * RGeo | TCACTTTCATAATGCTGG | RRnXRRnXRRnXR RnXRRnXRR |
| WV-14513 | 462 | Teo * Rm5Ceo * RAeon001m5Ceo * RTeo * RTeon001Teo * Sm5Ceo * SAeon001Teo * SAeo * SAeon001Teo * RGeo * Rm5Ceon001Teo * RGeo * RGeo | TCACTTTCATAATGCTGG | RRnXRRnXSSnXS SnXRRnXRR |
| WV-14514 | 463 | Teo * Rm5Ceo * RAeo * Rm5Ceo * RTeo * RTeon001Teo * Rm5Ceo * RAeon001Teo * RAeo * RAeon001Teo * RGeo * Rm5Ceo * RTeo * RGeo * RGeo | TCACTTTCATAATCTGG | RRRRRnXRRnXR RnXRRRRR |
| WV-14515 | 464 | Teo * Rm5Ceo * RAeo * Rm5Ceo * RTeo * RTeon001Teo * Sm5Ceo * SAeon001Teo * SAeo * SAeon001Teo * RGeo * Rm5Ceo * RTeo * RGeo * RGeo | TCACTTTCATAATGCTGG | RRRRRnXSSnSX SnXRRRRR |
| WV-14516 | 465 | Teo * Rm5Ceo * RAeo * Rm5Ceo * RTeo * RTeo * RTeo * Rm5Ceo * RAeon001Teo * RAeo * RAeo * RTeo * RGeo * Rm5Ceo * RTeo * RGeo * RGeo | TCACTTTCATAATGCTGG | RRRRRRRRnXR RRRRRRR |
| WV-14517 | 466 | Teo * Rm5Ceo * RAeo * Rm5Ceo * RTeo * RTeo * RTeo * Sm5Ceo * SAeon001Teo * SAeo * SAeo * RTeo * RGeo * Rm5Ceo * RTeo * RGeo * RGeo | TCACTTTCATAATGCTGG | RRRRRRSSnXS SRRRRRR |
| WV-14518 | 467 | Teo * Rm5Ceo * RAeon001m5Ceo * RTeo * RTeon001Teo * Rm5Ceo * RAeo * STeo * RAeo * RAeon001Teo * RGeo * Rm5Ceon001Teo * RGeo * RGeo | TCACTTTCATAATGCTGG | RRnXRRnSRRSR RnXRRnXRR |
| WV-14519 | 468 | Teo * Rm5Ceo * RAeon001m5Ceo * RTeo * RTeon001Teo * Sm5Ceo * SAeo * STeo * SAeo * SAeon001Teo * RGeo * Rm5Ceon001Teo * RGeo * RGeo | TCACTTTCATAATGCTGG | RRnXRRnXSSSS SnXRRnXRR |
| WV-14520 | 469 | Teo * Rm5Ceo * RAeon001m5Ceo * RTeo * RTeo * RTeo * Rm5Ceo * RAeo * STeo * RAeo * RAeo * RTeo * RGeo * Rm5Ceon001Teo * RGeo * RGeo | TCACTTTCATAATGCTGG | RRnXRRRRRSR RRRRnXRR |
| WV-14521 | 470 | Teo * Rm5Ceo * RAeon001m5Ceo * RTeo * RTeo * RTeo * Sm5Ceo * ASeo * STeo * SAeo * SAeo * RTeo * RGeo * Rm5Ceon001Teo * RGeo * RGeo | TCACTTTCATAATGCTGG | RRnXRRRSSS SSRRnXRR |

All oligonucleotides in the Table are single-stranded (unless otherwise noted).

Moieties and/or modifications (or compounds used to construct oligonucleotide compositions comprising these moieties or modifications):

m: 2'-OMe m5: methyl at 5-position of C (nucleobase is 5-methylcytosine)

m5Ceo: 5-methyl 2'-O-methoxyethyl C eo: 2'-MOE (2'-O-(2-methoxyethyl))

nX: non-negative stereorandom internucleotidic linkage (may also be designated n001):

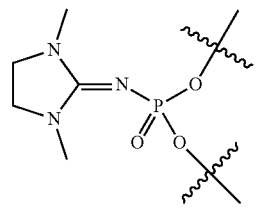 [SMILES: *OP(=O)(N=C1N(C)CCN1C)O*]

O, PO: phosphodiester (phosphate); can be an end group, or a linkage, e.g., a linkage between a linker d an oligonucleotide chain, an internucleotidic linkage, etc. Phosphodiesters indicated in the Stereochemistry/Internucleotidic Linkages column may not be reproduced in the Description column; if no internucleotidic linkage is indicated in the Description column, it is a phosphodiester unless otherwise noted
*, PS: Phosphorothioate; this can be an end group, or a linkage, e.g., a linkage between a linker and an oligonucleotide chain, an internucleotidic linkage, etc.
*R, R: Phosphorothioate in Rp configuration; note that *R indicates a single phosphorothioate in the Rp conformation
*S, S: Phosphorothioate in Sp conformation; note that *S indicates a single phosphorothioate in the Sp conformation
X: Stereorandom phosphorothioate
L001: —NH—(CH$_2$)$_6$— linker (also known as a C6 linker, C6 amine linker or C6 amino linker), connected to Mod, if any, through —NH—, and the 5'-end of the oligonucleotide composition chain through either a phosphate linkage (O or PO) or phosphorothioate linkage (* if phosphorothioate not chirally controlled; can also be Sp if chirally controlled and has an Sp configuration, and Rp if chirally controlled and has an Rp configuration) as illustrated. If no Mod is present, L001 is connected to —H, e.g., in WV-7308. For example, in WV-9065, L001 is connected to Mod007 through —NH— (forming an amide group —C(O)—NH—), and is connected to the oligonucleotide composition chain through a phosphate linkage (indicated by bold underlined in ORRRRRRRRRRRRRRRRRR); in WV-9064, L001 is not connected to any Mod, but to —H, through —NH—, and is connected to the oligonucleotide composition chain through a phosphate linkage (indicated by bold underlined in ORRRRRRRRRRRRRRRRRR).

Mod001:

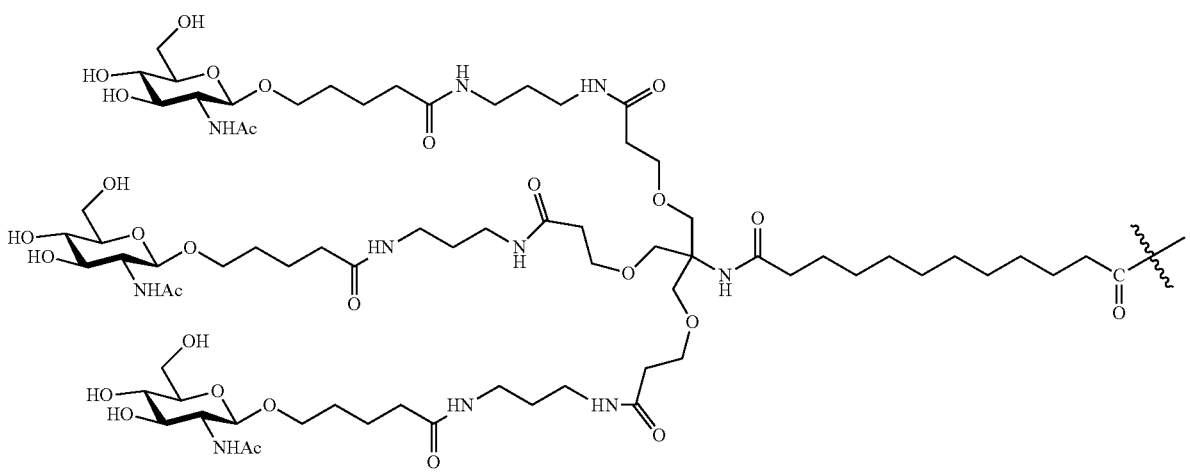

Mod007:

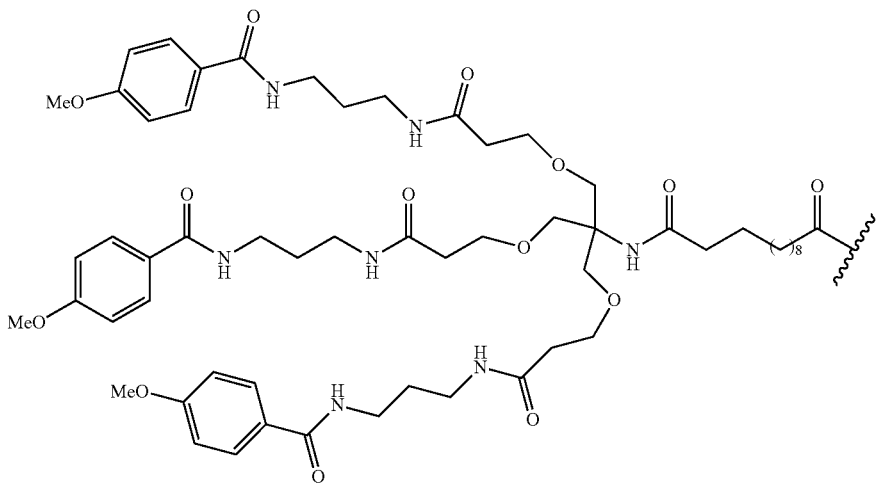

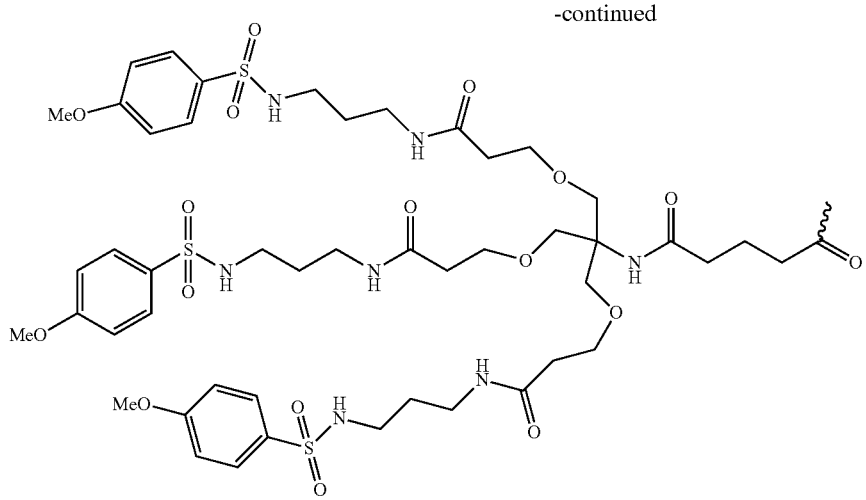

Mod084:

For various oligonucleotide designations, the hyphen is irrelevant; thus, for example, WV-9999 would be the same oligonucleotide as WV9999.

Provided SMN2 oligonucleotide compositions, e.g., chirally controlled SMN2 oligonucleotide compositions, can comprise various number of natural phosphate linkages. In some embodiments, provided SMN2 oligonucleotides comprise one or more natural phosphate linkages and one or more modified internucleotidic linkages. In some embodiments, provided SMN2 oligonucleotides comprise at least two pairs of alternating phosphodiester and phosphorothioate internucleotidic linkages.

In some embodiments, a provided SMN2 oligonucleotide composition is characterized in that, when it is contacted with the transcript in a SMN2 system, inclusion of exon 7 of a SMN2 mRNA or level of exon 7-containing SMN2 relative to exon 7-deleted SMN2 mRNA is improved relative to that observed under reference conditions selected from the group consisting of the absence of the composition, presence of a reference composition, and combinations thereof. In some embodiments, inclusion of exon 7 of a SMN2 mRNA or level of exon 7-containing SMN2 relative to exon 7-deleted SMN2 mRNA is increased 10%, 20%, 30%, 40%, 50%, 60%, 70%, 80%, 90%, 100%, or 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10-fold or more.

In some embodiments, a modification at a linkage phosphorus results in a P-modification moiety characterized in that it can act as a pro-drug, e.g., the P-modification moiety facilitates delivery of a SMN2 oligonucleotide to a desired location prior to removal. For instance, in some embodiments, a P-modification moiety results from PEGylation at the linkage phosphorus. One of skill in the relevant arts will appreciate that various PEG chain lengths are useful and that the selection of chain length will be determined in part by the result that is sought to be achieved by PEGylation. For instance, in some embodiments, PEGylation is effected in order to reduce RES uptake and extend in vivo circulation lifetime of a SMN2 oligonucleotide.

In some embodiments, a PEGylation reagent for use in accordance with the present disclosure is of a molecular weight of about 300 g/mol to about 100,000 g/mol. In some embodiments, a PEGylation reagent is of a molecular weight of about 300 g/mol to about 10,000 g/mol. In some embodiments, a PEGylation reagent is of a molecular weight of about 300 g/mol to about 5,000 g/mol. In some embodiments, a PEGylation reagent is of a molecular weight of about 500 g/mol. In some embodiments, a PEGylation reagent of a molecular weight of about 1000 g/mol. In some embodiments, a PEGylation reagent is of a molecular weight of about 3000 g/mol. In some embodiments, a PEGylation reagent is of a molecular weight of about 5000 g/mol.

In certain embodiments, a PEGylation reagent is PEG500. In certain embodiments, a PEGylation reagent is PEG1000. In certain embodiments, a PEGylation reagent is PEG3000. In certain embodiments, a PEGylation reagent is PEG5000.

In some embodiments, a P-modification moiety is characterized in that it acts as an agent which promotes cell entry and/or endosomal escape, such as a membrane-disruptive lipid or peptide.

In some embodiments, a P-modification moiety is characterized in that it acts as a targeting agent. In some embodiments, a P-modification moiety is or comprises a targeting agent. In some embodiments, a targeting agent is an entity that is associates with a payload of interest (e.g., with a SMN2 oligonucleotide) and also interacts with a target site of interest so that the payload of interest is targeted to the target site of interest when associated with the targeting agent to a materially greater extent than is observed under otherwise comparable conditions when the payload of interest is not associated with the targeting agent. A targeting agent may be, or comprise, any of a variety of chemical moieties, including, for example, small molecule moieties, nucleic acids, polypeptides, carbohydrates, etc. Targeting agents are described further by Adarsh et al., "Organelle Specific Targeted Drug Delivery—A Review," International Journal of Research in Pharmaceutical and Biomedical Sciences, 2011, p. 895.

Examples of such targeting agents include, but are not limited to, proteins (e.g. Transferrin), antibodies (monoclonal and polyclonal antibodies, e.g. IgG, IgA, IgM, IgD, IgE antibodies), sugars/carbohydrates (e.g., monosaccharides and/or oligosaccharides (mannose, mannose-6-phosphate, galactose, and the like)), vitamins (e.g., folate), or other small biomolecules. In some embodiments, a targeting moiety is a steroid molecule (e.g., bile acids including cholic acid, deoxycholic acid, dehydrocholic acid; cortisone; digoxigenin; testosterone; cholesterol; cationic steroids such as cortisone having a trimethylaminomethyl hydrazide group attached via a double bond at the 3-position of the cortisone ring, etc.). In some embodiments, a targeting moiety is a lipophilic molecule (e.g., alicyclic hydrocarbons, saturated and unsaturated fatty acids, waxes, terpenes, and polyalicyclic hydrocarbons such as adamantine and buckminsterfullerenes). In some embodiments, a lipophilic molecule is a terpenoid such as vitamin A, retinoic acid, retinal, or dehydroretinal. In some embodiments, a targeting moiety is a peptide.

In some embodiments, a P-modification moiety is characterized in that it facilitates cell specific delivery.

In some embodiments, a P-modification moiety is characterized in that it falls into one or more of the above-described categories. For instance, in some embodiments, a P-modification moiety acts as a PK enhancer and a targeting ligand. In some embodiments, a P-modification moiety acts as a pro-drug and an endosomal escape agent. One of skill in the relevant arts would recognize that numerous other such combinations are possible and are contemplated by the present disclosure.

In some embodiments, a carbocyclyl, aryl, heteroaryl, or heterocyclyl group, or a bivalent or polyvalent group thereof, is a $C_3$-$C_{30}$ carbocyclyl, aryl, heteroaryl, or heterocyclyl group, or a bivalent and/or polyvalent group thereof.

Assays

Various technologies, including many known in the art, can be utilized for assessing provided oligonucleotides, compositions, methods, etc., in accordance with the present disclosure. For example, various assays, including various phases of clinical trials, were performed for Nusinersen and may be utilized to assess provided oligonucleotides.

In some embodiments, assessment of provided oligonucleotides can be performed by quantifying a change or improvement in the level, activity and/or expression of an exon-inclusion mRNA, e.g., an exon 7-containing SMN2 mRNA (e.g., transcript) or its gene product (e.g., full-length SMN protein). In some embodiments, delivery of provided oligonucleotides can be via a transfection agent or without a transfection agent (e.g., gymnotic).

In some embodiments, the present disclosure provides a method of identifying and/or characterizing an oligonucleotide composition for inclusion of an exon (e.g., exon 7 of SMN2), the method comprising steps of:

providing an oligonucleotide composition comprising a plurality of oligonucleotides;

contacting the oligonucleotide composition with an appropriate splicing system comprising a pre-splicing nucleic acid comprising the exon; and assessing increase of level, activity and/or expression of a splicing product comprising the exon (e.g., an exon 7-containing SMN2 mRNA (e.g., transcript)) or a product encoded by the splicing product (e.g., full-length SMN protein). Among other things, a provided oligonucleotide can be alternatively and/or additionally tested for duration of activity, induction of an immune response or other adverse effects, ease of manufacture, and ability to be delivered to tissues and enter into cells.

In some embodiments, properties of a provided oligonucleotide composition, e.g., a chirally controlled oligonucleotide composition, are compared to a reference oligonucleotide composition (or a negative control oligonucleotide composition). In some embodiments, a reference oligonucleotide composition is a non-chirally controlled oligonucleotide composition of oligonucleotides having the same constitution as a plurality of oligonucleotides in a corresponding chirally controlled oligonucleotide composition. In some embodiments, a reference oligonucleotide composition is a stereorandom oligonucleotide composition. In some embodiments, a reference oligonucleotide composition is a stereorandom oligonucleotide composition such as Nusinersen. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages. In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a chirally un-controlled (or stereorandom) composition of oligonucleotides having the same base sequence and chemical modifications.

In some embodiments, a reference composition is a composition of oligonucleotides having the same base sequence but different chemical modifications, including but not limited to chemical modifications described herein. In some embodiments, a reference composition is a composition of oligonucleotides having the same base sequence but different patterns of internucleotidic linkages and/or stereochemistry of internucleotidic linkages and/or chemical modifications.

Various technologies are known in the art for assessment of level, expression, and/or activity of splicing products that include and/or exclude an exon and products (e.g., proteins) encoded thereby. For example, SMN2 transcripts and the level of exon 7-deleted and exon 7-containing SMN2 mRNA can be quantified with qPCR, SMN2 protein levels can be determined via Western blot, ELISA, or mass spectrometry, etc. In addition, functional assays can be performed on motor neurons (MN) expressing wild-type and/or mutant SMN2 by, e.g., electrophysiology, NMJ formation, etc.

In some embodiments, nucleic acid levels such as RNA levels can be quantitated by a variety of technologies, many of which can be accomplished with kits and materials which are commercially available, and which methods are well known and routine in the art. Such methods include, e.g., Northern blot analysis, competitive polymerase chain reaction (PCR), or quantitative real-time PCR. RNA analysis can be performed on total cellular RNA or poly(A)+ mRNA. Probes and primers can be designed to hybridize to a target, e.g., a SMN2 nucleic acid. In some embodiments, assaying of SMN2 oligonucleotides for increasing the level, activity and/or expression of an exon 7-containing SMN2 transcript or its gene product can be performed using an assay described in, for example, Zhang et al. 2001 Gene Ther. 8: 1532-1538.

In some embodiments, a protein level can be evaluated or quantitated in any method known in the art, including, but not limited to, enzyme-linked immunosorbent assay (ELISA), Western blot analysis (immunoblotting), immunocytochemistry, fluorescence-activated cell sorting (FACS), immunohistochemistry, immunoprecipitation, protein activity assays (for example, caspase activity assays), quantitative protein assays, etc. Antibodies useful for the detection of proteins, e.g., SMN, are known in the art and/or commercially available; additional antibodies, e.g., those to SMN, can be generated if desired.

Evaluation and testing of efficacy of provided oligonucleotides can be performed in vitro or in vivo. For example, in some embodiments, assessment of SMN2 oligonucleotides can be performed in vitro in a cell. In some embodiments, the cell is a cell which expresses SMN2. In some embodiments, a cell (e.g., a SMA patient-derived cell) is capable of expressing SMN2 (e.g., an unspliced SMN2 transcript). Evaluation and testing of efficacy of SMN2 oligonucleotides can be performed in vitro in various cells or cell lines, including but not limited to those described herein. Example SMA patient cell lines include, for example, G03813 cell line (fibroblasts from a SMA patient; see WO 2010/115993). See also: Arnold et al. 2013 Ann. Neurol. 74: 348-362; Rossoll et al. 2003 J. Cell. Biol. 163: 801-812. In some embodiments, assessment of SMN2 oligonucleotides may be accomplished by contacting a cell from a subject with a neurological disease with the SMN2 oligonucleotide and determining whether the level, activity, and/or expression of an exon 7-containing SMN or SMN2 is increased.

Assessment of provided oligonucleotides can be performed in vivo. For example, in some embodiments, SMN2 oligonucleotides can be assessed in animals. In some embodiments, SMN2 oligos can be assessed in humans and/or other animals to mediate a change or improvement in the level, activity, expression, allele-specific expression and/or intracellular distribution of functional SMN2 mRNA and/or protein, and/or to prevent, treat, ameliorate or slow the progress of a SMN2-related condition, disorder, and/or disease, or at least one symptom of a SMN2-related condition, disorder, and/or disease. In some embodiments, such in vivo evaluation and/or testing can determine, after introduction of a SMN2 oligonucleotide, phenotypic changes, such as, improved motor function and respiration. In some embodiments, a motor function can be measured by a determination of changes in any of various tests known in the art including: balance beam, grip strength, hindpaw footprint testing (e.g., in an animal), open field performance, pole climb, rotarod, etc. in accordance with the present disclosure. In some embodiments, respiration can be measured by a determination of changes in any of various tests known in the art including compliance measurements, invasive resistance, whole body plethysmograph, etc.

In some embodiments, assessment of a provided oligonucleotide, e.g., a SMN2 oligonucleotide, can be performed in an animal. In some embodiments, an animal is a Drosophila fly. In some embodiments, an animal is a mouse. For example, SMN2 fly and mouse models and experimental procedures using them are described in, for example, Arnold et al. 2013 Ann. Neurol. 74: 348-362; Lotti et al. 2012 Cell 151: 440-54; Imlach et al. 2012 Cell 151: 427-39; Chan et al. 2003 Hum. Mol. Genet. 12: 1367-76; Edens et al. 2015 Biochim. Biophys. Acta 1852: 685-692; Coady et al. 2010 J. Neurosci. 30: 126-130; Cherry et al. 2014 Assay Drug Dev. Tech. Vol. 12, No. 6; Kobayashi et al. 2011 PLoS One 6: e24269; Kobayashi et al. 2013 PLoS One 8: e60113; Osborne et al. 2012 Hum. Mol. Genet. 21: 4431-4447; Patani 2016 Stem Cells Intl. Article ID 1036974; Russo et al. 2015 World J. Transplant. 5: 209-221; Sahashi et al. 2013 EMBO Mol. Med. 5: 1586-1601; Sleigh et al. 2011 Dis. Mod. Mech. 4: 457-467; Staropoli et al. 2015 Genomics 105: 220-228; Zaworski et al. 2016 PLoS One 0150640; Zhang et al. 2001 Gene Ther. 8: 1532-1538; Zhao et al. 2016 Hum. Mol. Genet. 1-15; and WO 2010/115993. In some embodiments, a SMN2 oligonucleotide administered to a test animal can be tested for its presence within desired tissues (e.g., brain stem and spinal cord).

Certain Biological Applications

As described herein, provided technologies can modulate splicing, particularly, for increasing inclusion of desired exons in splicing products. For example, in some embodiments, provided technologies can increase inclusion of exon 7 of a SMN2 mRNA and/or increase level of exon 7-containing SMN2 mRNA relative to exon 7-deleted SMN2 mRNA compared to a reference condition selected from the group consisting of the absence of the composition, presence of a reference composition, and combinations thereof. In some embodiments, increased inclusion of exon 7 of a SMN2 mRNA or increased level of exon 7-containing SMN2 relative to exon 7-deleted SMN2 mRNA is illustrated, for example, in FIG. 1A to 1C. As demonstrated herein, chirally controlled SMN2 oligonucleotides WV-6775, WV-6777, WV-6779, WV-6768, WV-6780, WV-6781, WV-6782, WV-6783, WV-6784, WV-6785, WV-6786, WV-6787, and WV-6767 were all able to increase inclusion of exon 7 of a SMN2 mRNA or increase level of exon 7-containing SMN2 relative to exon 7-deleted SMN2 mRNA.

In some embodiments, the present disclosure provides methods for treating or preventing a condition, disorder or disease associated with skipping of an exon during splicing, comprising administering to a subject suffering therefrom or susceptible thereto a provided oligonucleotide composition, wherein the provided oligonucleotide composition provides increased level of inclusion of the exon compared to a reference condition selected from the group consisting of the absence of the composition, presence of a reference composition, and combinations thereof. In some embodiments, a provided oligonucleotide composition is a chirally controlled oligonucleotide composition. In some embodiments, a reference condition (or a negative control condition) is a corresponding non-chirally controlled oligonucleotide composition comprising oligonucleotides, e.g., of the same constitution of the plurality of oligonucleotides of the chirally controlled oligonucleotide composition but are not chirally controlled. In some embodiments, oligonucleotides of a provided oligonucleotide composition comprise additional chemical moieties capable of binding to the asialoglycoprotein receptor and oligonucleotides of a reference composition do not contain such additional chemical moieties.

In some embodiments, a condition, disorder or disease is associated with skipping of a SMN2 exon. In some embodiments, a SMN2 exon is exon 7. In some embodiments, a condition, disorder or disease is SMA. In some embodiments, a condition, disorder or disease is ALS.

In some embodiments, the present disclosure provides a method of treating a condition, disorder or disease by administering an oligonucleotide composition comprising a plurality of oligonucleotides sharing a common base sequence, which common base sequence is complementary to a target sequence in a SMN2 transcript, the improvement that comprises using as the oligonucleotide composition a stereocontrolled oligonucleotide composition characterized in that, when it is contacted with the SMN2 transcript in a splicing system, inclusion of exon 7 of a SMN2 mRNA or level of exon 7-containing SMN2 relative to exon 7-deleted SMN2 mRNA is increased relative to that observed under a reference condition selected from the group consisting of absence of the composition, presence of a reference composition, and combinations thereof.

In some embodiments, a SMN2 oligonucleotide comprises a moiety capable of binding to ASGPR (also designated as Asialoglycoprotein Receptor or ASGP receptor).

In some embodiments, a biologically-active agent comprises a moiety capable of binding to ASGPR (also designated as Asialoglycoprotein Receptor or ASGP receptor).

ASGPR is reportedly a highly expressed (approximately 500 000 copies/cell) calcium-ion dependent lectin reported to be primarily found on mammalian hepatocytes. ASGPR is reportedly involved in clearing aged serum glycoproteins via clathrin-mediated endocytosis. The receptor reportedly has high avidity for multivalent GalNAc (N-acetylgalactosamine) and consists of two subunits, a major 48 kDa subunit (ASGPR-1) and a minor 40 kDa subunit (ASGPR-2). These subunits reportedly form oligomers in various configurations with each subunit able to bind a monovalent GalNAc through bivalent calcium-ion chelation to form a tetravalent coordination complex. The low pH of endosomes reportedly causes disruption of the tetravalent calcium-chelation between the ligand and the receptor and release of the ligand into the digestive machinery of hepatocytes. After release of the ligand, the receptor complex reportedly recycles. A single receptor can reportedly cycle up to 200 times with a turnover time of around 15 minutes, allowing large amounts of ligand to be internalized into hepatocytes without saturation effects.

ASGPR1 has also been reported to be expressed in the hippocampus region and/or cerebellum Purkinje cell layer of the mouse. http://mouse.brain-map.org/experiment/show/2048

ASGPR is typically targeted for delivery of agents, e.g., oligonucleotides, to liver, and has been reported to be specific for liver delivery. Among other things, the present disclosure demonstrate that incorporation of chemical moieties capable of binding to ASGPR into agents, e.g., oligonucleotides, can surprisingly improve delivery and/or activities of agents (e.g., SMN2 oligonucleotides) in central nervous system including brain. Among other things, the present disclosure provides technologies (oligonucleotides, compositions, methods, etc.) for improved delivery and/or activities. In some embodiments, the present disclosure pertains to a method of delivering a biologically-active agent to the brain or a portion of the brain of a subject, wherein the biologically-active agent comprises a moiety capable of binding to a ASGP receptor in the brain, and wherein the method comprises the step of administering the biologically-active agent to the subject.

In some embodiments, the present disclosure provides a composition comprising a biologically-active agent conjugated to a moiety capable of binding to an ASGP receptor in the brain.

In some embodiments, the present disclosure pertains to a method of treating a brain-associated or brain-related disorder in a subject, wherein the method comprises the step of administering to the subject a biologically-active agent to the subject, wherein the biologically-active agent comprises a moiety capable of binding to a ASGP receptor in the brain of the subject.

In some embodiments, a brain-associated or brain-related disorder is characterized by biological damage or injury to a portion of the brain which expresses ASGPR.

In some embodiments, a brain-associated or brain-related disorder is characterized by biological damage or injury to a portion of the brain which is or includes the hippocampus region and/or cerebellum Purkinje cell layer.

In some embodiments, a brain-associated or brain-related disorder is Alzheimer's disease, Cushing's Disease, Depression, Epilepsy, head injury, Hypertension, Parkinson's Disease, post-traumatic stress disorder, Schizophrenia, and/or a disorder associated with hippocampal atrophy.

In some embodiments, a biologically-active agent is a nucleic acid, a small molecule, an antibody, a peptide, or a protein.

In some embodiments, a nucleic acid is an oligonucleotide.

In some embodiments, a nucleic acid comprises RNA and/or DNA.

In some embodiments, a nucleic acid is an oligonucleotide, a single-stranded RNAi (RNA interference) agent, a double-stranded RNAi agent, an antisense oligonucleotide, a mRNA or portion thereof.

In some embodiments, a biologically-active agent is a component of a CRISPR system.

In some embodiments, ASGPR is expressed in the hippocampus region and/or cerebellum Purkinje cell layer.

In some embodiments, a moiety capable of binding to a ASGPR is a ASGPR ligand.

In some embodiments, a moiety capable of binding to a ASGPR is lactose, galactose, N-acetylgalactosamine (GalNAc), galactosamine, N-formylgalactosamine, N-propionylgalactosamine, N-n-butanoyl-galactosamine, or N-iso-butanoyl-galactosamine.

In some embodiments, a moiety capable of binding to a ASGP receptor is carbohydrate.

In some embodiments, a moiety capable of binding to a ASGP receptor is GalNAc.

In some embodiments, a moiety capable of binding to a ASGP receptor is GalNAc or a derivative thereof.

In some embodiments, GalNAc is also designated N-acetylgalactosamine, or n-acetyl-α-D-galactosamine, or n-acetyl-α-D-galactosamine, alpha-GalNAc; TN saccharide; alpha-GalpNAc; GalNAc-alpha; n-acetyl-α-D-galactosamine; or N-acetyl-alpha-D-galactosamine.

In some embodiments, a moiety capable of binding to a ASGP receptor is an amino sugar derivative of galactose.

In some embodiments, a GalNAc is a protected or de-protected GalNAc.

In some embodiments, a GalNAc, as the term is used herein, refers to a chemical entity which is structurally similar to a GalNAc and/or which performs at least one function of a GalNAc (e.g., binding to the asialoglycoprotein receptor (ASGR or ASPGR)).

A non-limiting example of a GalNAc moiety at the 5'-end of a provided oligonucleotide, e.g., a SMN2 oligonucleotide (e.g., 5' GalNAc moiety) is shown below, wherein the 5' end structure is represented by:

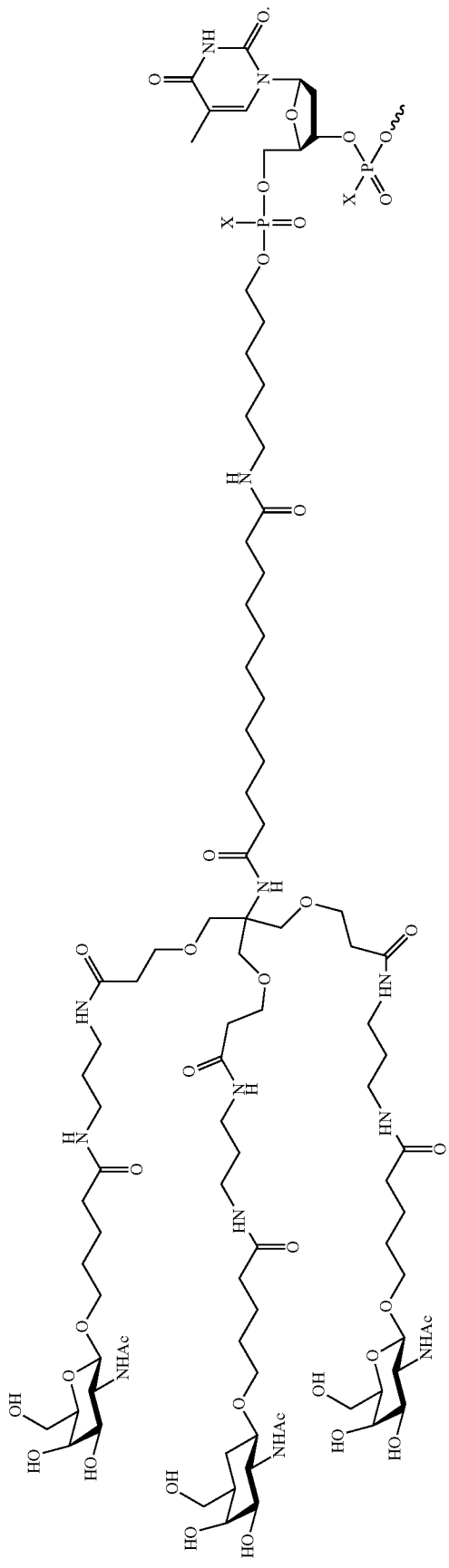

In some embodiments, a GalNAc moiety, e.g., a GalNAc or a variant or derivative thereof, is described in any of: Migawa et al. 2016 Bioorg. Med. Chem. Lett. 26: 2914-7; Ostergaard et al. 2015 Bioconjug. Chem. 26: 1451-1455; Prakash et al. 2014 Nucl. Acids Res. 42: 8796-8807; Prakash et al. 2016 J. Med. Chem. 59: 2718-33; Shemesh et al. 2016 Mol. Ther. Nucl. Acids 5: e319; St-Pierre et al. 2016 Bioorg. Med. Chem. 24: 2397-409; and/or Yu et al. 2016 Mol. Ther. Nucl. Acids 5: e317.

In some embodiments, a chemical moiety (e.g., additional component) conjugated to a provided oligonucleotide, e.g., a SMN2 oligonucleotide binds to asialoglycoprotein receptor (ASGR or ASPGR).

In some embodiments, a chemical moiety (e.g., additional component) conjugated to a provided oligonucleotide, e.g., a SMN2 oligonucleotide binds to ASPGR and comprises any of: Mod031, Mod034, Mod035, Mod036, Mod038, Mod039, Mod040, or Mod041:

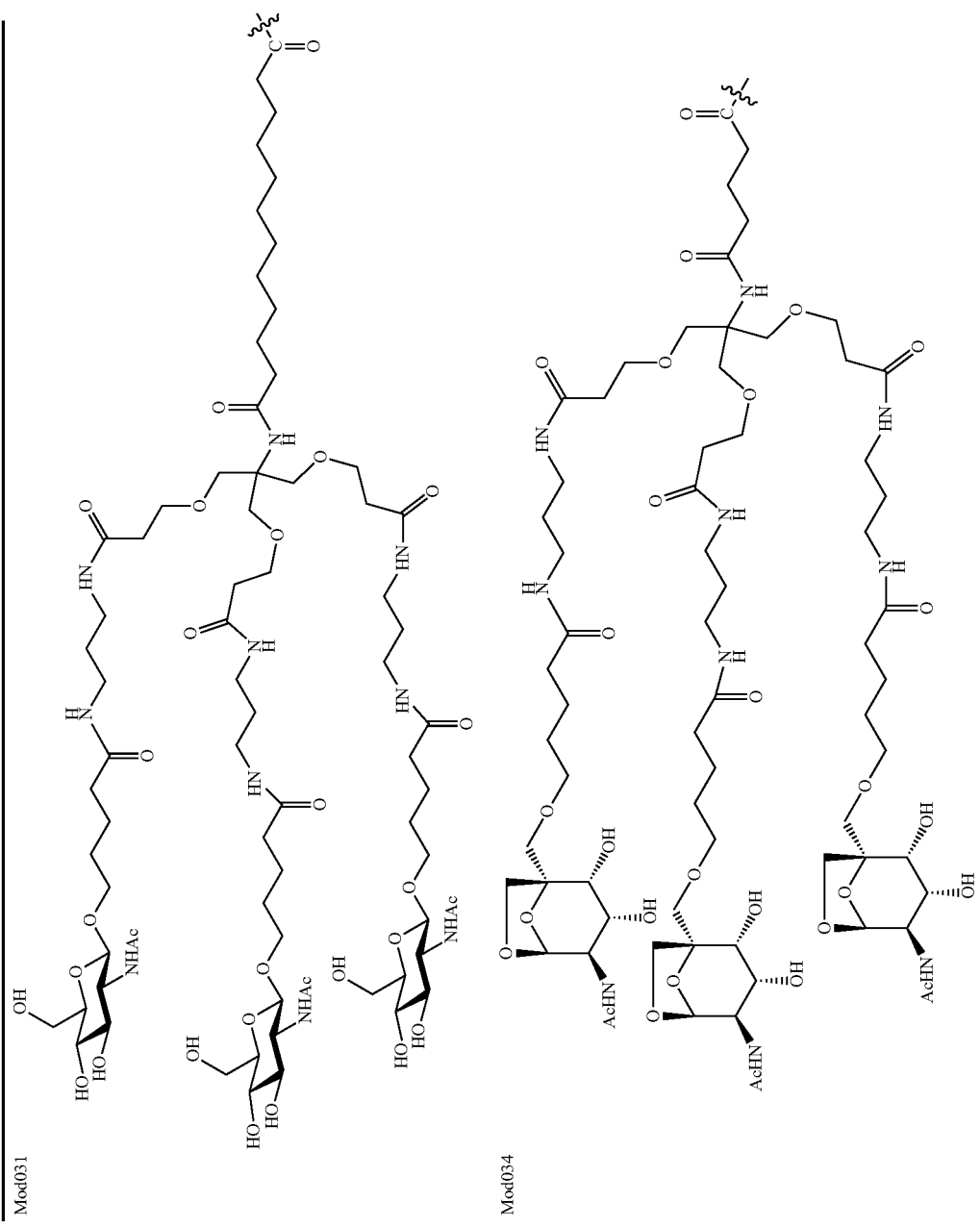

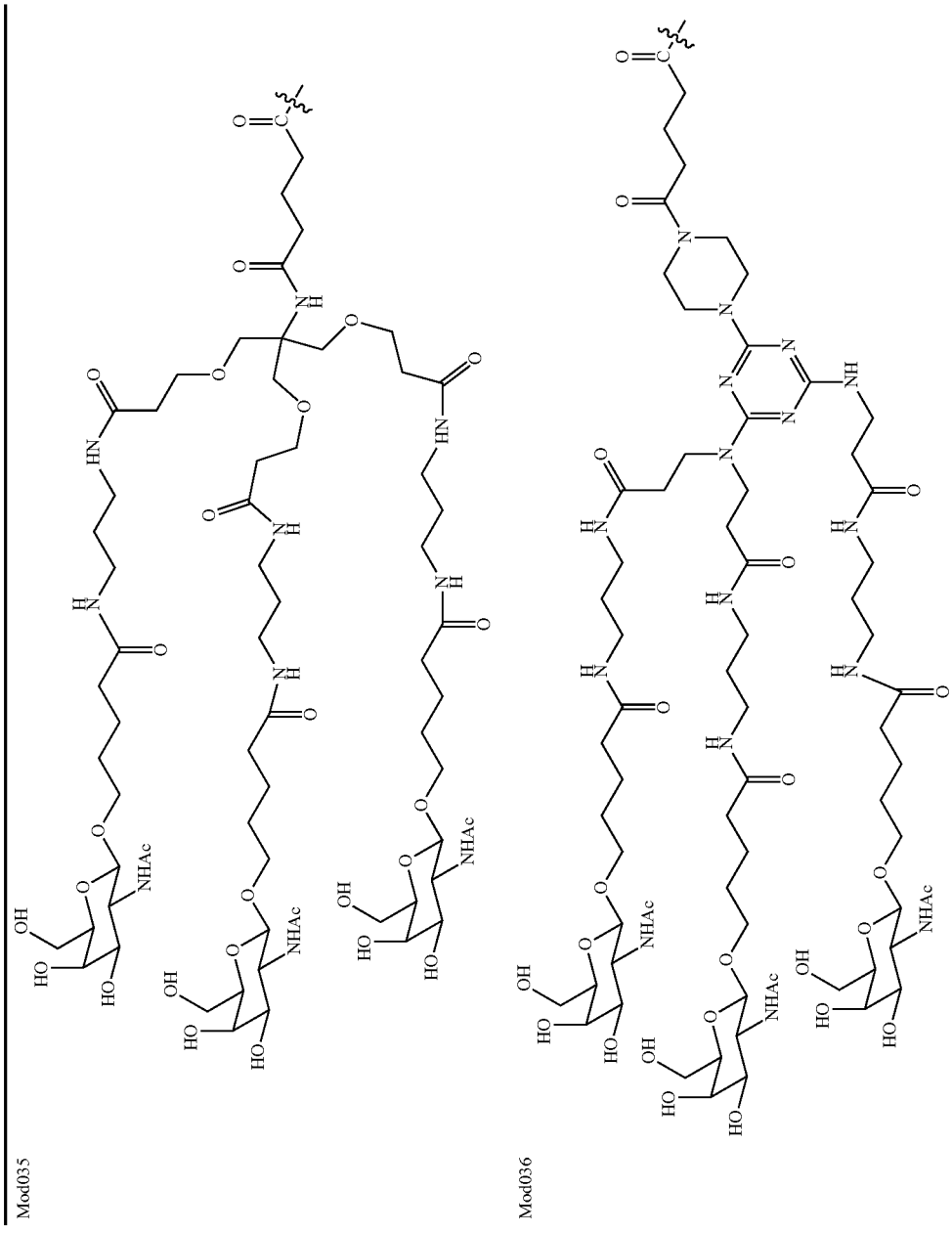

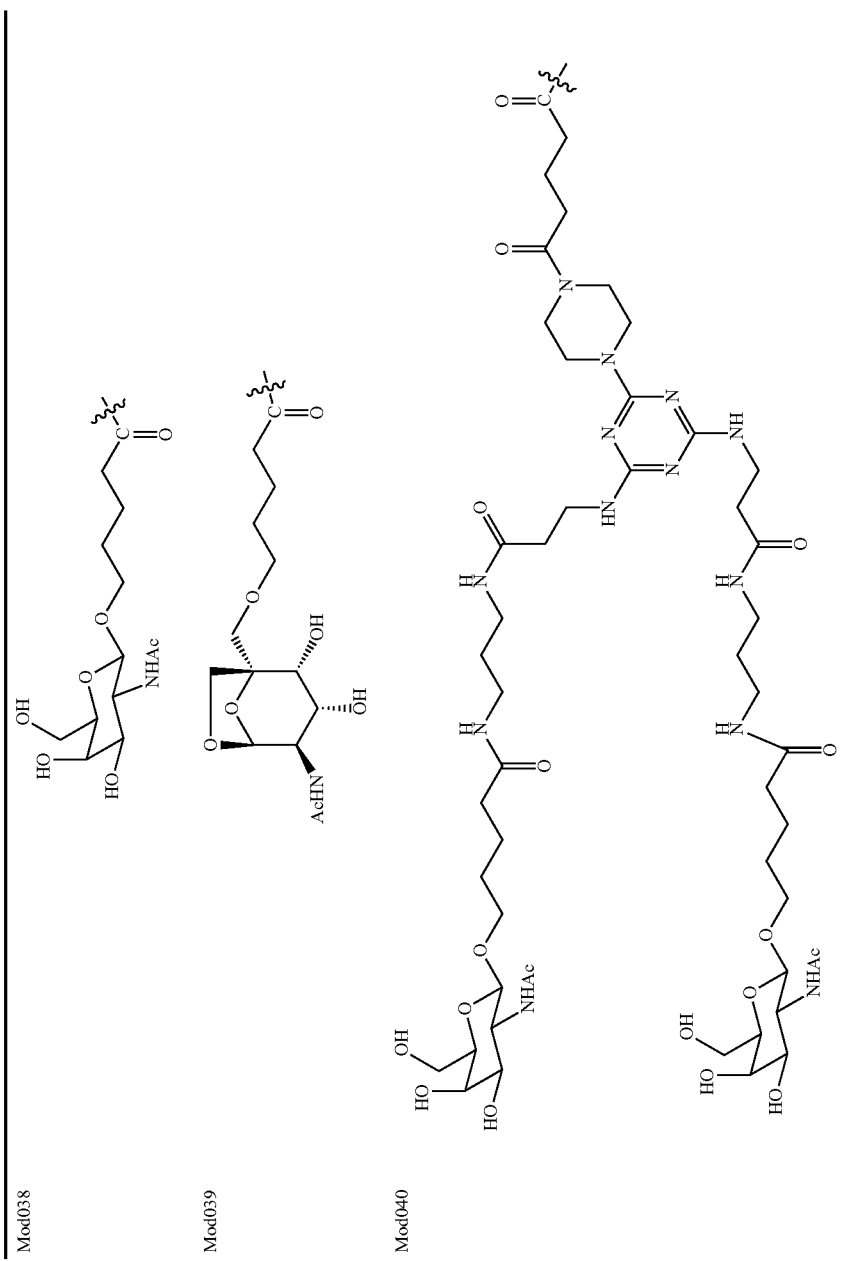

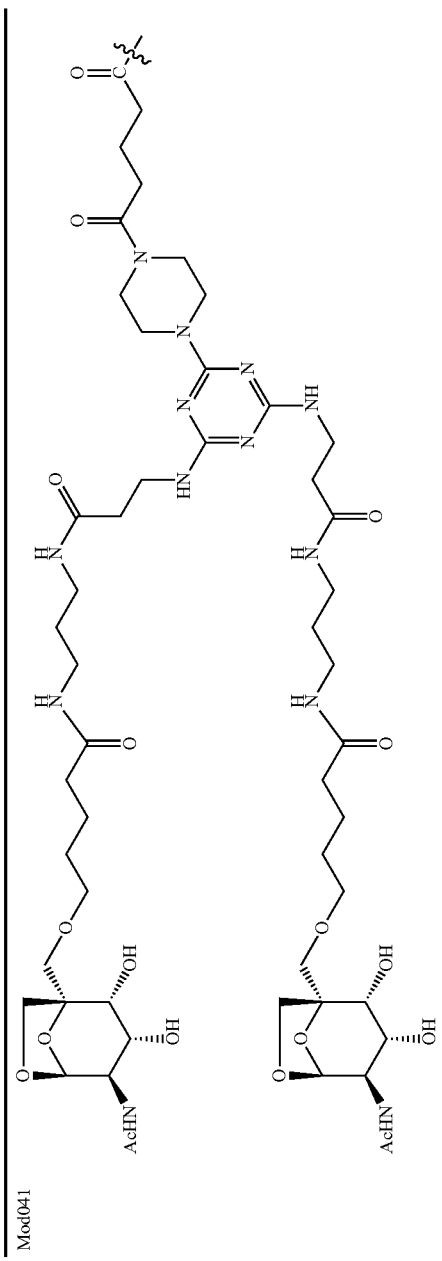
Mod041

In some embodiments, an additional component can be or comprise any of: Mod079, Mod080, Mod081, Mod082 or Mod083. In some embodiments, an additional component can be or comprise any of:
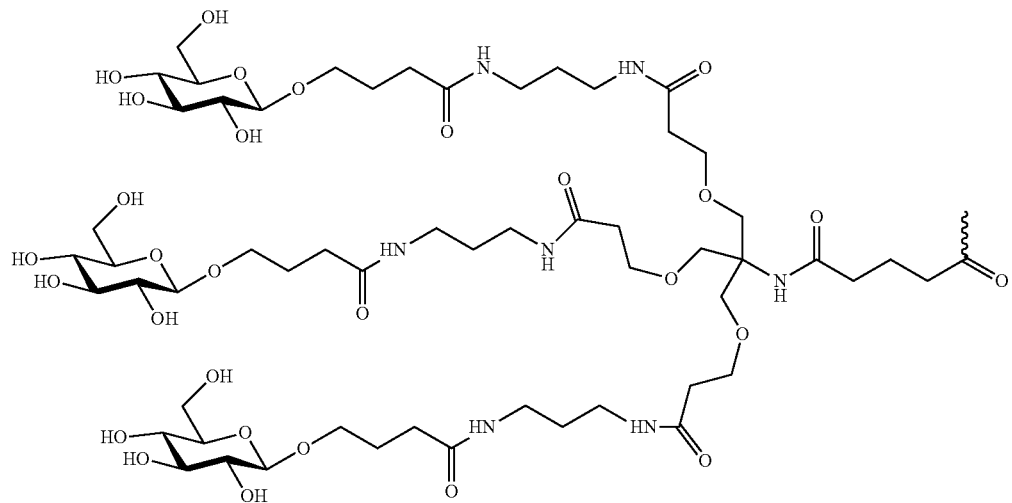
Mod059:
Mod060:
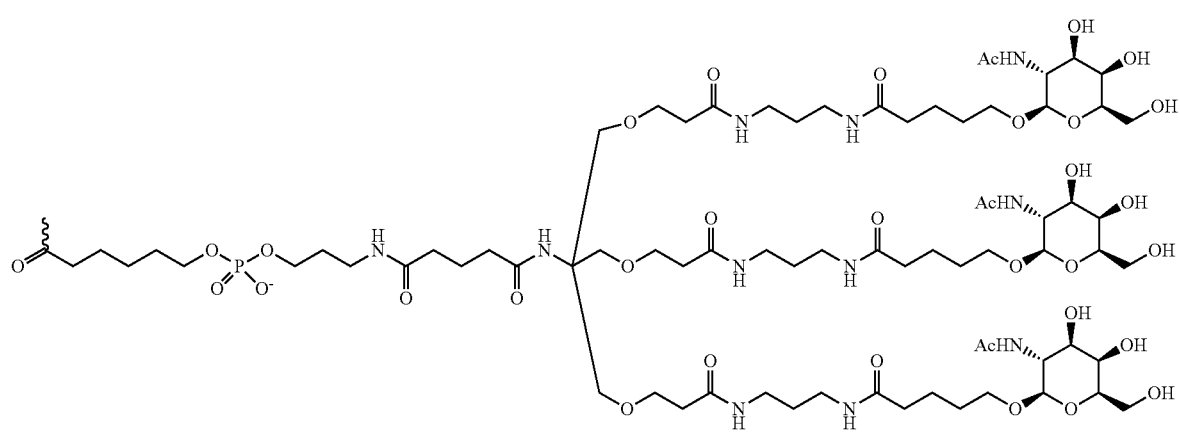

331 332
-continued
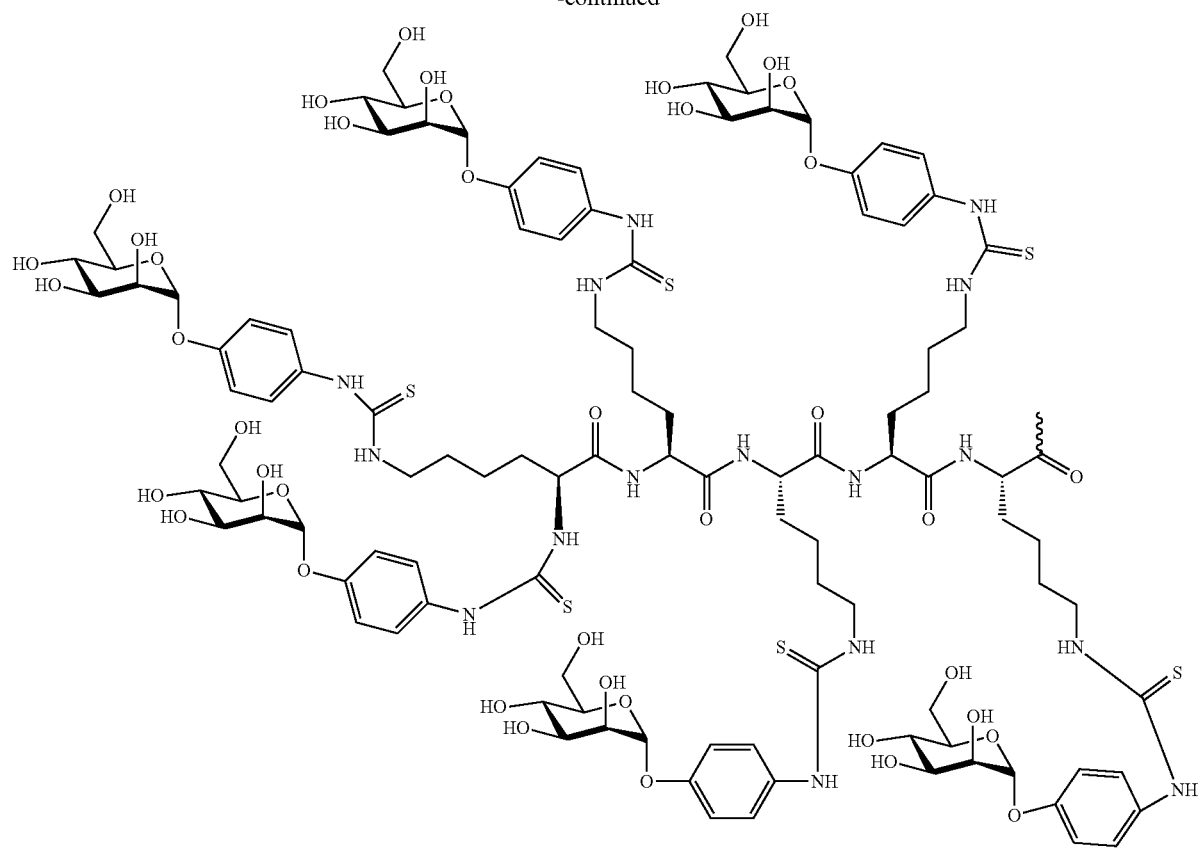
Mod065:
Mod070:
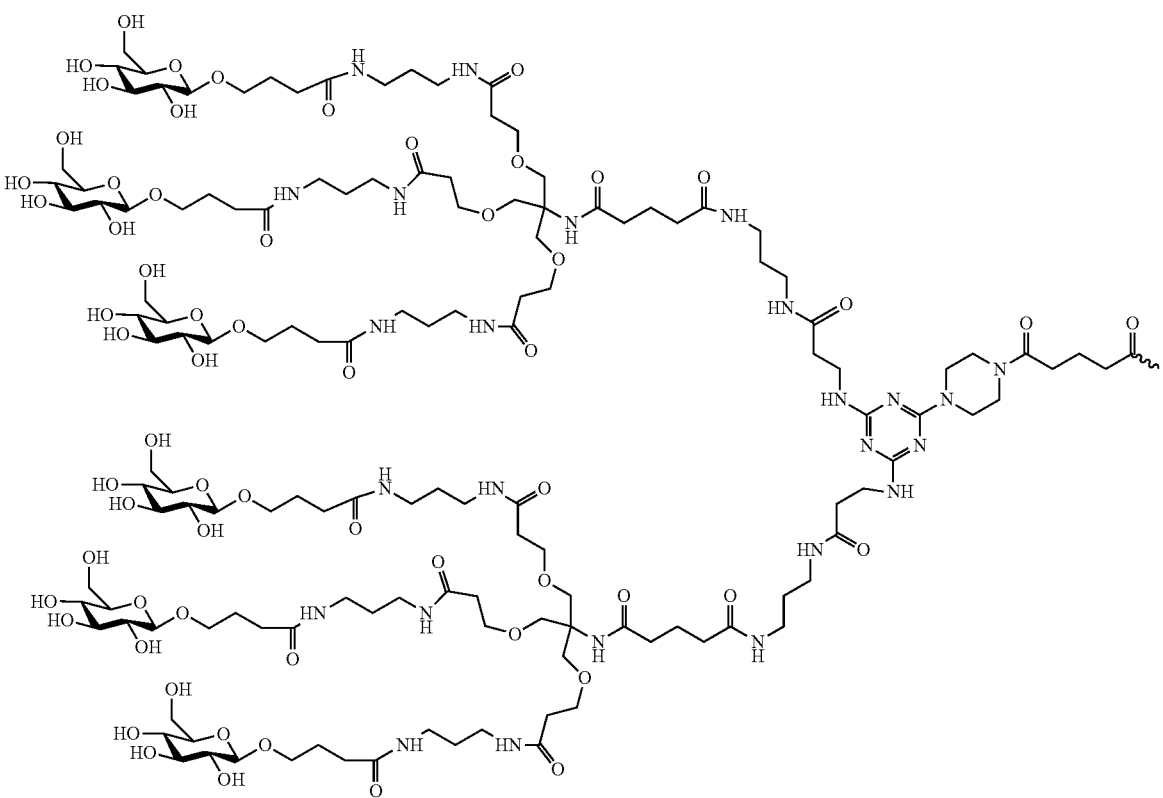

-continued
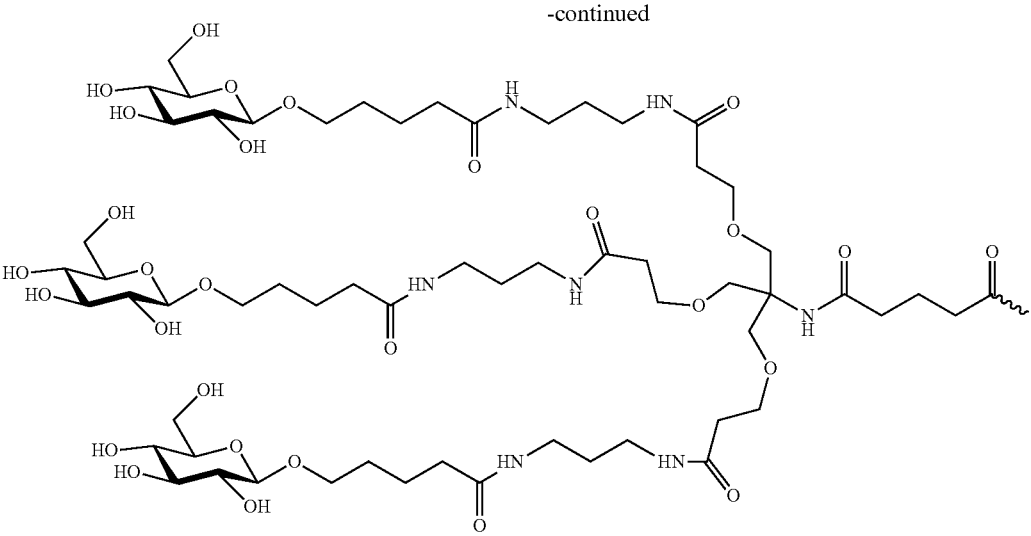
Mod071:
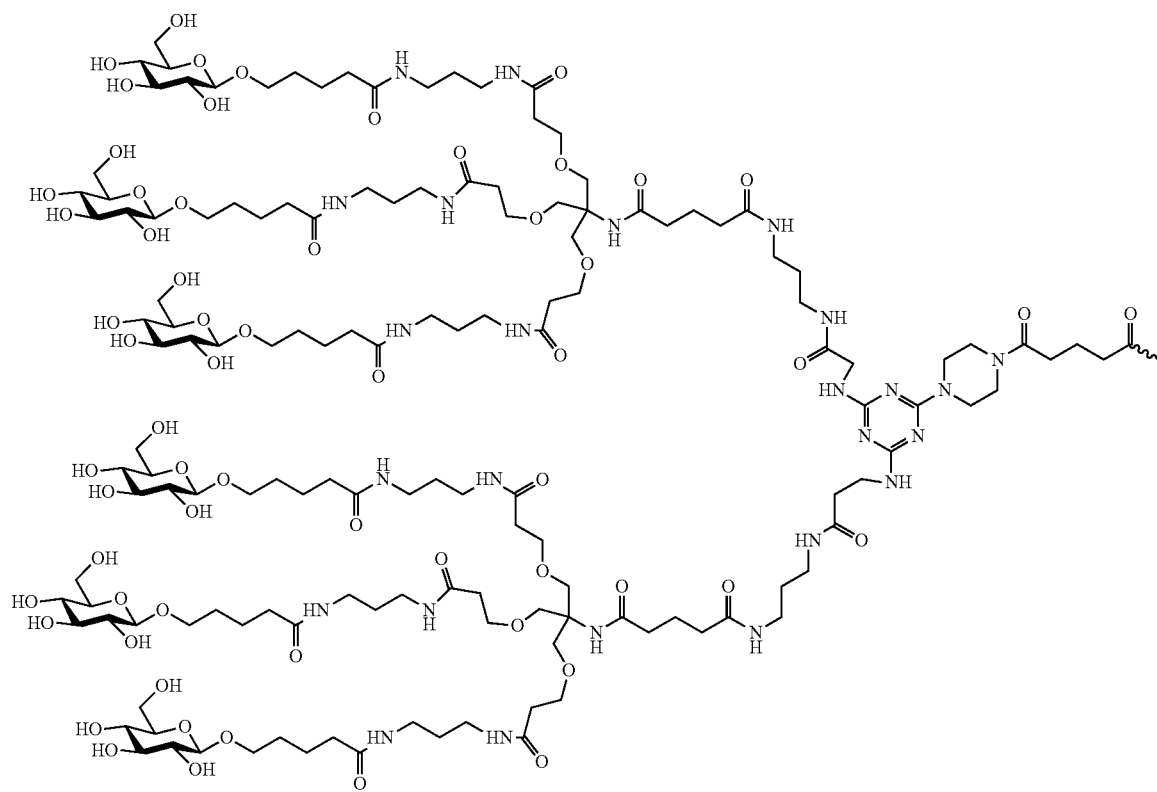

Mod072:
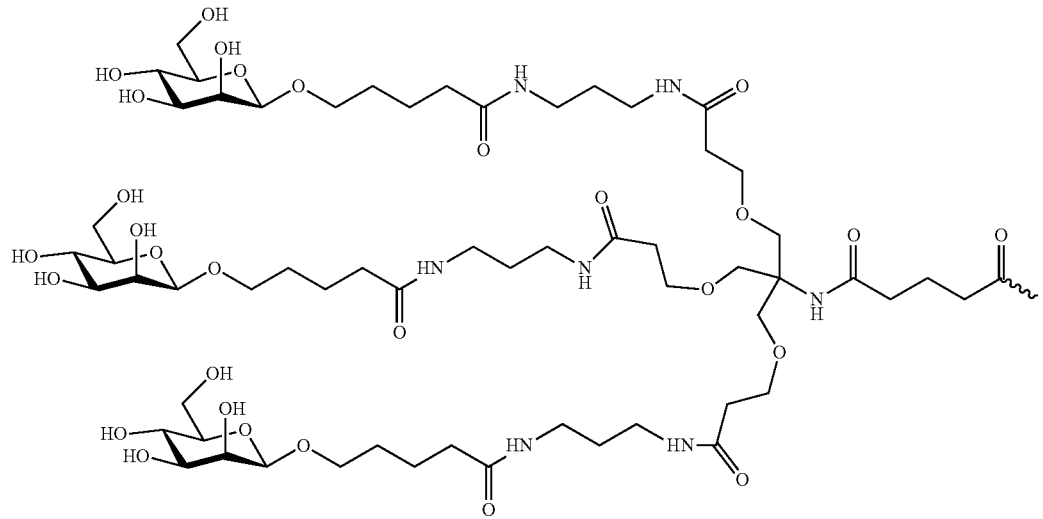
Mod073:
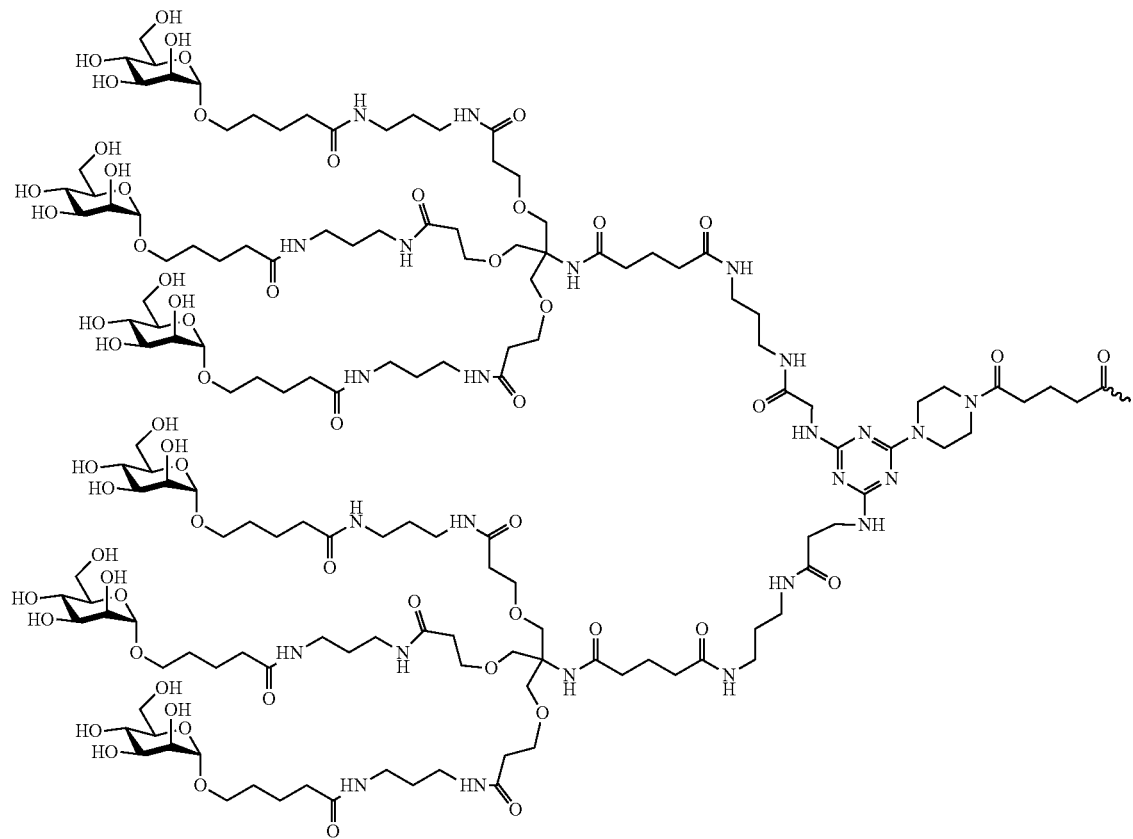

-continued
Mod074:
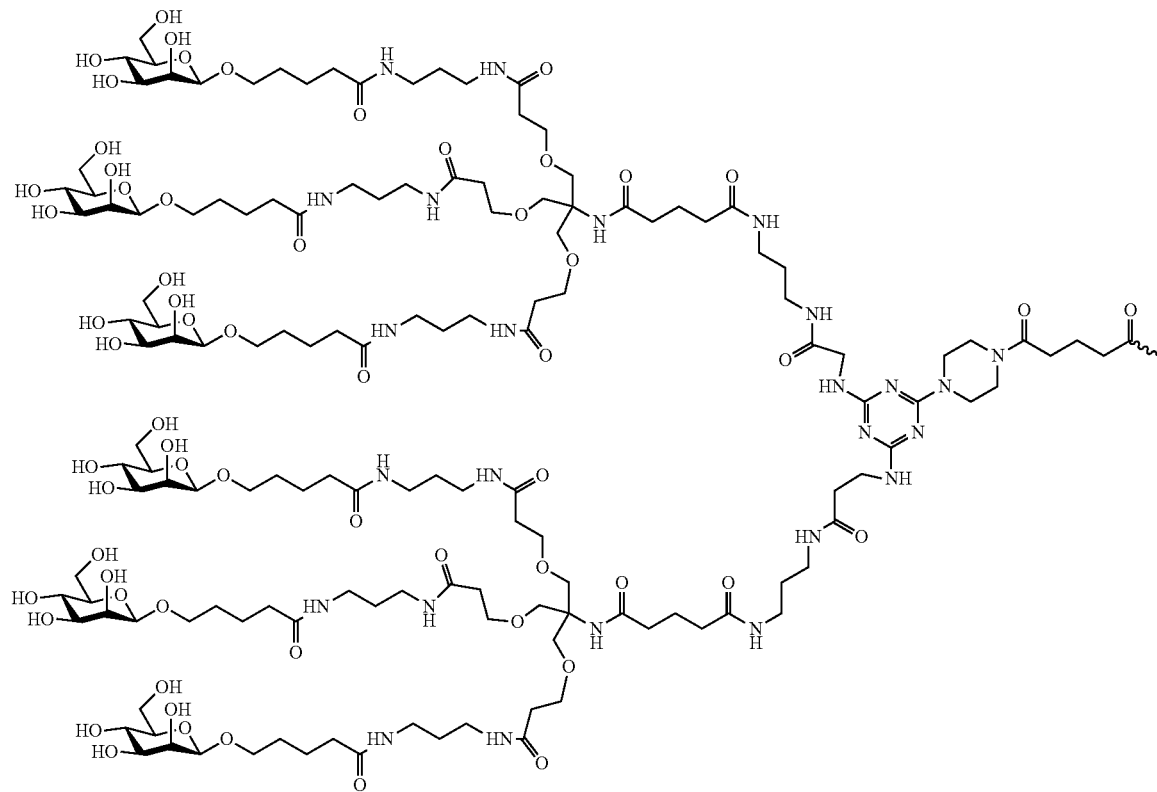
Mod075:
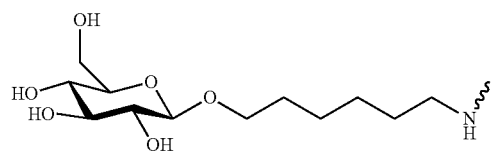
Mod076:
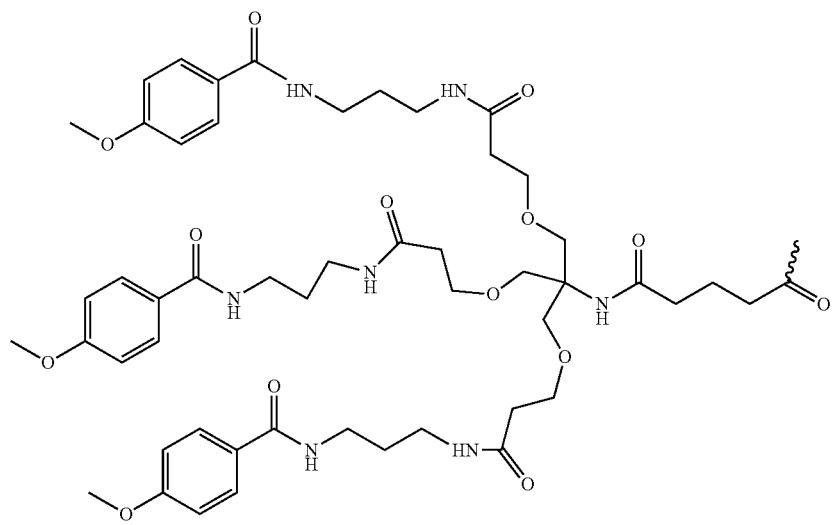

-continued
Mod077:
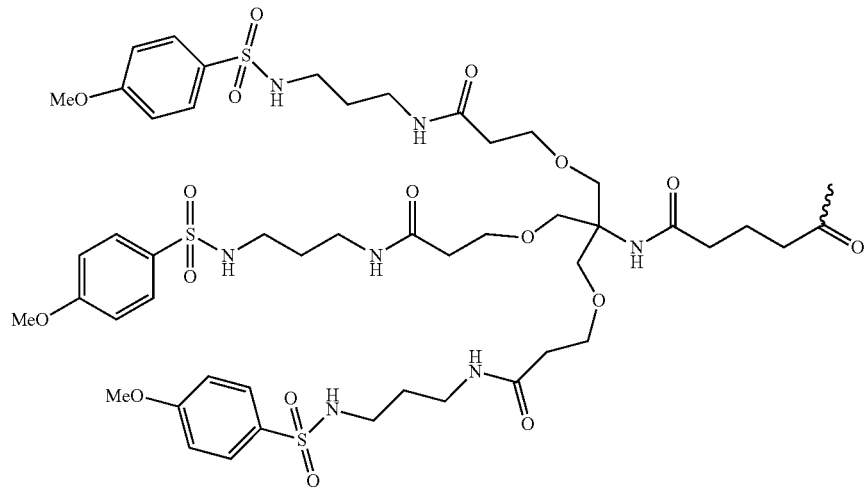
Mod084:
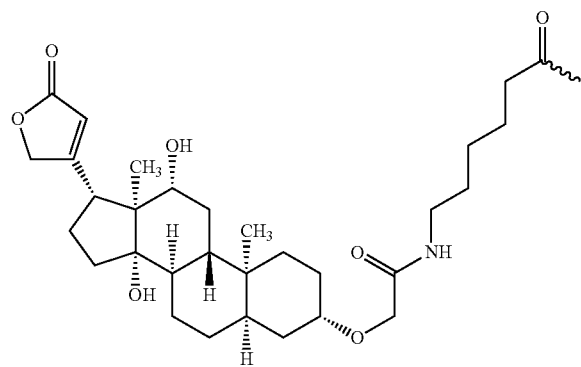
Mod085:
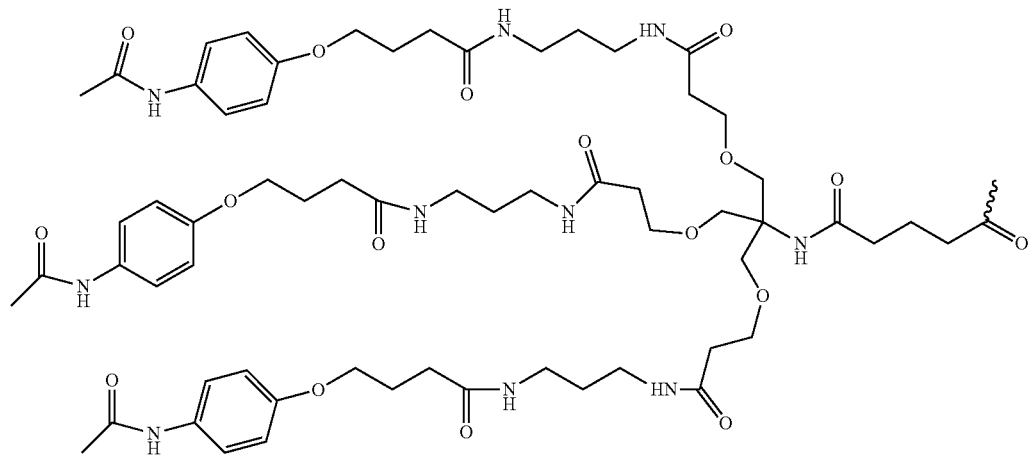

Mod087:

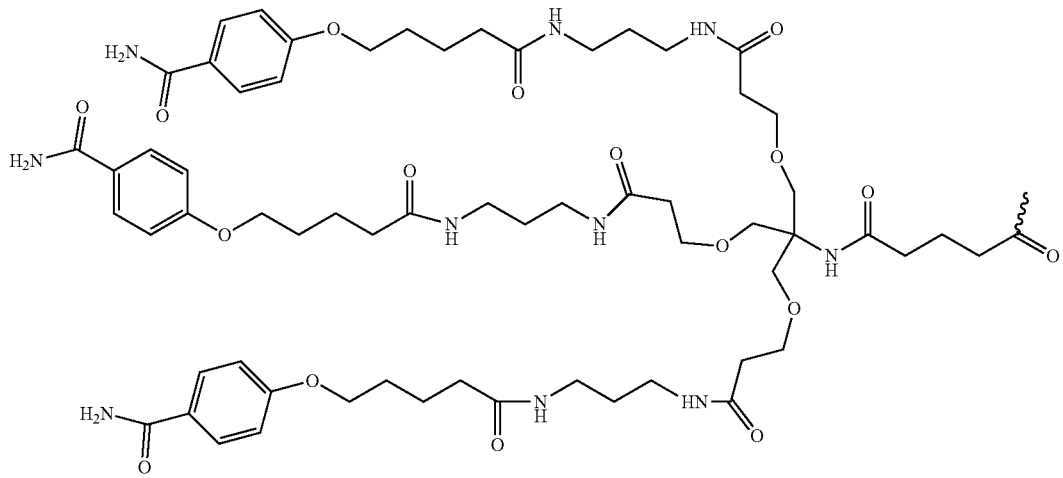

Mod088:

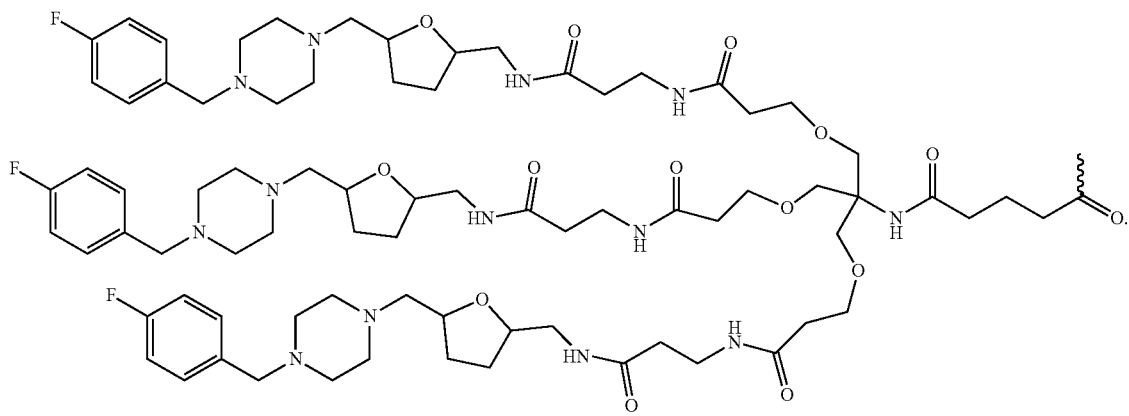

Figure 3:
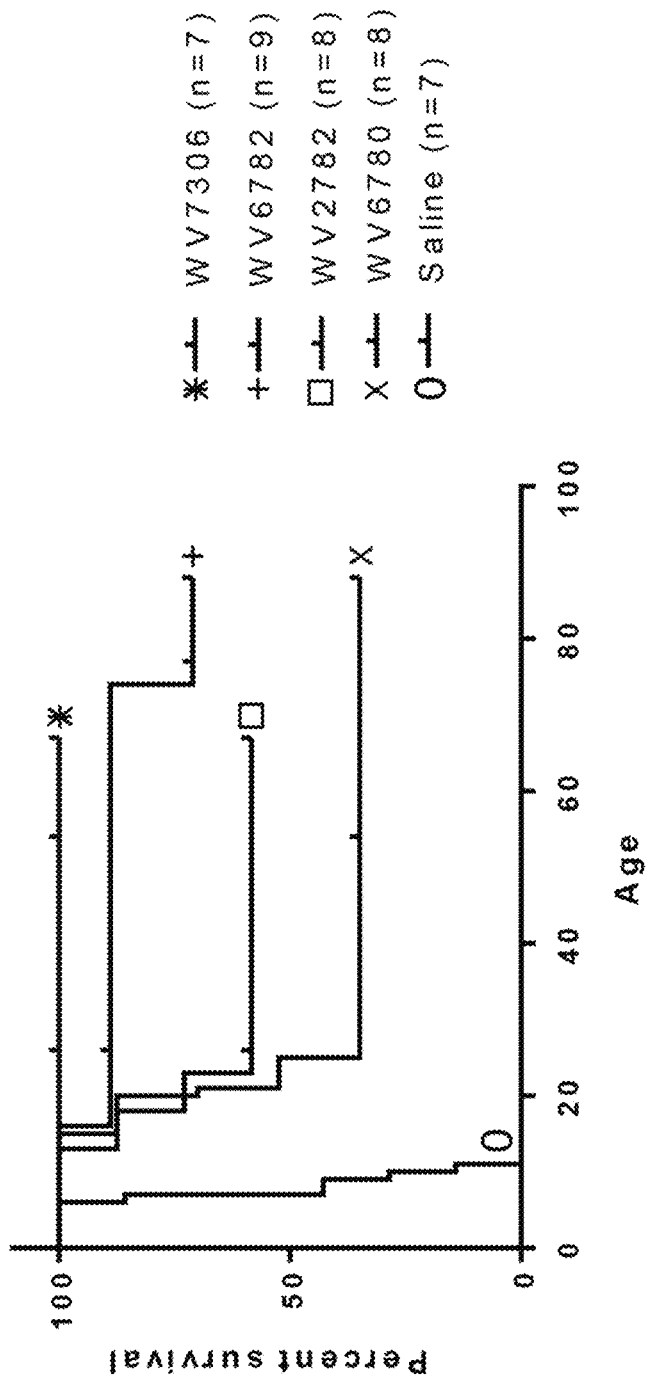
FIG. 3 shows the percentage survival of groups of SMA model mice administered saline (negative control), WV-6782, WV-6780, WV-7306, or WV-2782.

Mod089:

As shown in FIG. 3, and in the data presented below and herein, several oligonucleotides were tested for their activity in SMA model mice.

SMA model mice were administered various oligonucleotides, including WV-2782 (which corresponds to the stereorandomer, Nusinersen); WV-6782 and WV-6780, which are chirally controlled versions of Nusinersen); and WV-7306, which corresponds to Nusinersen (which is stereorandom), further comprising a GalNAc (Mod001L001, shown herein). In this test, the oligonucleotides all comprise the same base sequence and 2' sugar modifications; the oligonucleotide differ in being stereorandom or stereopure (chirally controlled), and in whether they are conjugated to GalNAc or not.

The SMA model mice were evaluated for survival after administration of any one of the various oligonucleotides. Newborn SMA model mice were dosed (Day 0) with 40 mg/kg of oligonucleotide subcutaneously. Mice of that age (Day 0) reportedly have a blood-brain barrier which is incompletely formed, allowing materials administered subcutaneously to reach the brain.

The initial data are shown below in Table 2A and Table 2B and FIG. 3.

TABLE 2A

Activity of SMN2 oligonucleotides in SMA model mice.

| Compound | Number of SMA model mice tested | Youngest currently surviving mouse (Days) | Oldest surviving or currently surviving mouse (Days) |
|---|---|---|---|
| Saline (negative control) | 7 | — | 11 (no animals currently surviving) |
| WV-6782 | 9 | 26* | 88* |
| WV-6780 | 8 | 15* | 88* |
| WV-7306 | 7 | 26* | 67* |
| WV-2782 | 8 | 15* | 67* |

*At least one mouse was alive at the time of data collection.

Currently=At the time of data collection.

At the time of data collection, all the animals that had received saline (negative control) had died, with the oldest surviving to 11 days before dying. At the time of data collection, at least one animal in each group which had received an oligonucleotide was still alive, and the third column provides the age of the oldest surviving animal in each group.

TABLE 2B

Activity of SMN2 oligonucleotides in SMA model mice.

| Compound | Incidence of death | Age at death of various individual mice (Days) |
|---|---|---|
| Saline (negative control) | 7/7 | 6, 7, 7, 7, 9, 10, 11 |
| WV-6782 | 2/9 | 16, 74 |
| WV-6780 | 4/8 | 13, 20, 21, 25 |
| WV-7306 | 0/7 | |
| WV-2782 | 3/8 | 15, 18, 23 |

All of the SMA model mice treated with saline (negative control) died between days 6 and 11. 4 of the 8 SMA model mice treated with WV-6780 (a chirally controlled oligonucleotide) died between days 13 and 25; the remainder remained alive at the time of recordation of these data, with the oldest being 88 days old. 3 of the 8 SMA model mice treated with WV-2782 (stereorandom, corresponding to Nusinersen) died between days 15 and 23; the remainder remained alive at the time of the recordation of these data, with the oldest being 67 days old. 2 of the 9 SMA model mice treated with WV-6782 (chirally controlled oligonucleotide) died, on days 16 and 74; the remainder remain alive, with the oldest being 88 days old. None of the SMA model mice treated with WV-7306 (stereorandom, conjugated to GalNAc) died (data current as of time of last data collection), with the youngest being 26 days old and the oldest being 67 days old.

This test thus showed that, in at least some cases, chirally controlling the internucleotidic linkages of a SMN2 oligonucleotide or conjugating GalNAc to a SMN2 oligonucleotide improved the survival of SMA model mice when the oligonucleotides were administered to the animals.

The experiment described above, whose initial results were shown in Table 2A and Table 2B and FIG. 3, was continued for additional time.

The subsequent results of continuing this experiment (in addition to revisions to earlier data if necessary) are shown in Table 2C, below.

Table 2C. Survival Proportions. 100 would represent 100% of the animals treated with a particular composition surviving on the indicated day; 0 would represent 0% of the animals treated with a particular composition surviving on the indicated day.

| Age (Days) | Saline (n = 7) | VW-6782 (n = 9) | VW-6780 (n = 8) | VW-7306 (n = 7) | VW-2782 (n = 8) |
|---|---|---|---|---|---|
| 0 | 100 | 100 | 100 | 100 | 100 |
| 6 | 85.7 | | | | |
| 7 | 42.9 | | | | |
| 9 | 28.6 | | | | |
| 10 | 14.3 | | | | |
| 11 | 0.0 | | | | |
| 13 | | | 87.5 | | |
| 15 | | | | | 87.5 |
| 16 | | 88.9 | | | |
| 18 | | | | | 75.0 |
| 20 | | | 75.0 | | |
| 21 | | | 62.5 | | |
| 23 | | | | | 62.5 |
| 25 | | | 50.0 | | |
| 39 | | | | 85.7 | |
| 61 | | 77.8 | | | |
| 74 | | 66.7 | | | |
| 82 | | | | 71.4 | |
| 83 | | | | | 62.5 |
| 88 | | | 50.0 | | |
| 94 | | 66.7 | | | 62.5 |
| 102 | | | | | 31.3 |
| 116 | | | 25.0 | | |
| 122 | | | 25.0 | 71.4 | |
| 128 | | 50.0 | | | |
| 134 | | 33.3 | | | |
| 135 | | | | 71.4 | 31.3 |
| 156 | | 33.3 | | | |

The subsequent results of this test supported the earlier results showing that, in at least some cases, chirally controlling the internucleotidic linkages of a SMN2 oligonucleotide or conjugating GalNAc to a SMN2 oligonucleotide improved the survival of SMA model mice when the oligonucleotides were administered to the animals.

A reported adverse effect of Nusinersen administration in human subjects is accumulation in the kidney, even when the oligonucleotide is administered intrathecally. Without wishing to be bound by any particular theory, the present disclosure suggests that conjugation to GalNAc of a SMN2 oligonucleotide may be able to decrease the accumulation of the oligonucleotide in the kidney and increase the accumulation of the oligonucleotide in the liver. Without wishing to be bound by any particular theory, the present disclosure suggests that conjugation to GalNAc of a SMN2 oligonucleotide may be able to improve the efficacy of the oligonucleotide in treating manifestation and symptoms of SMA reported to occur in the liver. In some embodiments, manifestations and symptoms of SMA reported to occur in the liver can be treated by a SMN2 oligonucleotide conjugated with GalNAc.

In some embodiments, the present disclosure pertains to a method of modulation of processing of a selected wild-type cellular mRNA target, the method comprising binding to the target an oligonucleotide having at least one 2'-methoxyethoxy, 2'-dimethylaminooxyethoxy, 2'-dimethylaminoethoxyethoxy, 2'-acetamide, morpholino, or peptide nucleic acid modification which is specifically hybridizable with the mRNA target and which does not elicit cleavage of the mRNA target upon binding, so that processing of the mRNA target is modulated.

In some embodiments of the method, the mRNA target is SMN2.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the modulation of the processing of a selected wild-type cellular mRNA target is modulation of splicing of the mRNA target.

In some embodiments of the method, the oligonucleotide has a 2'-methoxyethoxy, 2'-dimethylaminooxyethoxy, 2'-dimethylaminoethoxyethoxy or 2'-acetamide modification on substantially every sugar.

In some embodiments of the method, the oligonucleotide has at least one phosphorothioate backbone linkage.

In some embodiments of the method, the oligonucleotide is an antisense oligonucleotide.

In some embodiments of the method, the modulation of splicing is a redirection of splicing.

In some embodiments of the method, the modulation of splicing results in an altered ratio of splice products.

In some embodiments of the method, the modulation of splicing results in exclusion of one or more exons from a mature mRNA.

In some embodiments of the method, the oligonucleotide is targeted to at least a portion of an exon to be excluded.

In some embodiments of the method, the oligonucleotide is targeted to an intron-exon junction.

In some embodiments of the method, the oligonucleotide is targeted to at least a portion of a region up to 50 nucleobases upstream from a 5' splice site.

In some embodiments of the method, the redirection of splicing is a decreased frequency of use of the 5' splice site.

In some embodiments of the method, the processing of a selected wild-type cellular mRNA target is polyadenylation of the mRNA target.

In some embodiments of the method, the oligonucleotide is targeted to a polyadenylation signal or polyadenylation site.

In some embodiments of the method, the processing of a selected wild-type cellular mRNA target is regulating stability of the mRNA target, by targeting the oligonucleotide to a sequence which controls the stability of the mRNA target.

In some embodiments of the method, the oligonucleotide which does not elicit cleavage of the mRNA target upon binding contains at least one modification which increases binding affinity for the mRNA target and which increases nuclease resistance of the oligonucleotide.

In some embodiments of the method, the oligonucleotide which does not elicit cleavage of the mRNA target upon binding contains at least one nucleoside having a 2' modification of its sugar moiety.

In some embodiments of the method, every nucleoside of the oligonucleotide has a 2' modification of its sugar moiety.

In some embodiments of the method, the 2' modification is selected from the group consisting of 2'-O-methoxyethyl and 2'-dimethylaminooxyethoxy.

In some embodiments of the method, the oligonucleotide which does not elicit cleavage of the mRNA target upon binding contains at least one modified backbone linkage other than a phosphorothioate backbone linkage.

In some embodiments of the method, the oligonucleotide which does not elicit cleavage of the mRNA target upon binding contains a plurality of modified backbone linkages other than phosphorothioate backbone linkages.

In some embodiments of the method, the oligonucleotide also contains at least one phosphodiester or phosphorothioate backbone linkage.

In some embodiments of the method, the modified backbone linkages alternate with phosphodiester and/or phosphorothioate backbone linkages.

In some embodiments of the method, every backbone linkage is a modified backbone linkage other than a phosphorothioate linkage.

In some embodiments of the method, the modified backbone linkage is a morpholino, peptide nucleic acid or methylene (methylimino) backbone linkage.

In some embodiments of the method, the oligonucleotide which does not elicit cleavage of the mRNA target upon binding contains at least one modified nucleobase.

In some embodiments of the method, the modified nucleobase is a C-5 propyne.

In some embodiments of the method, the altered ratio of splice products results from an increase or a decrease in the amount of a splice product encoding a membrane form of a protein relative to a soluble form of a protein.

In some embodiments of the method, the protein is a receptor.

In some embodiments of the method, the receptor is a hormone or cytokine receptor.

In some embodiments of the method, the oligonucleotide has a morpholino or peptide nucleic acid modification at substantially every backbone linkage.

In some embodiments, the present disclosure pertains to an oligonucleotide of 15 to 40 linked nucleotides or modified nucleotides in length, which oligonucleotide comprises a sequence: at least 80% complementary to intron 7 of the SMN2 gene over the entire length of the oligonucleotide; and at least 85% complementary to the sequence 5'-CCAG-CAUUAUGAAAG-3' (SEQ ID NO: 3); wherein the oligonucleotide comprises at least one modified nucleotide.

In some embodiments, the oligonucleotide is at least 90% complementary to the sequence 5'-CCAG-CAUUAUGAAAG-3' (SEQ ID NO: 3).

In some embodiments, the oligonucleotide further comprises a moiety capable of binding to ASGPR.

In some embodiments, the oligonucleotide further comprises GalNAc.

In some embodiments, the oligonucleotide further comprises GalNAc or a derivative thereof.

In some embodiments, the oligonucleotide comprises a chirally controlled internucleotidic linkage.

In some embodiments, the oligonucleotide comprises a chirally controlled phosphorothioate.

In some embodiments, the oligonucleotide comprises a chirally controlled internucleotidic linkage and a moiety capable of binding to ASGPR.

In some embodiments, the oligonucleotide is 100% complementary to the sequence 5'-CCAG-CAUUAUGAAAG-3' (SEQ ID NO: 3).

In some embodiments, the base sequence of oligonucleotide comprises the sequence 5'-CUUUCAUAAUGCUGG-3' (SEQ ID NO: 471).

In some embodiments, the oligonucleotide comprises at least one modified nucleotide which comprises a modified sugar moiety.

In some embodiments, the oligonucleotide comprises at least one 2'-deoxy ribonucleotide.

In some embodiments of the oligonucleotide, the at least one 2'-deoxy ribonucleotide is 2'-deoxy adenosine or 2'-deoxy guanosine.

In some embodiments of the oligonucleotide, the oligonucleotide comprises at least one modified nucleotide comprising a modified sugar moiety which is modified at the 2'-position.

In some embodiments of the oligonucleotide, the modified sugar moiety comprises a 2'-substituent selected from the group consisting of: H, OR, R, halo, SH, SR, $NH_2$, NHR, $NR_2$, and ON, where R is a $C_1$-$C_6$ alkyl, alkenyl, or alkynyl and halo is F, Cl, Br or I.

In some embodiments of the oligonucleotide, the modified sugar moiety comprises a 2' $OCH_3$.

In some embodiments of the oligonucleotide, the oligonucleotide comprises at least one modified nucleotide selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine.

In some embodiments of the oligonucleotide, the oligonucleotide comprises at least one modified nucleotide selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine.

In some embodiments of the oligonucleotide, the oligonucleotide comprises at least one modified linkage.

In some embodiments of the oligonucleotide, the at least one modified linkage is a phosphorothioate linkage.

In some embodiments of the oligonucleotide, each linkage of the oligonucleotide is a phosphorothioate linkage.

In some embodiments of the oligonucleotide, the modified nucleotide is a locked nucleic acid (LNA) nucleotide.

In some embodiments, the oligonucleotide comprises at least one bicyclic nucleotide.

In some embodiments of the oligonucleotide, each nucleotide of the oligonucleotide is a modified nucleotide.

In some embodiments of the oligonucleotide, each nucleotide of the oligonucleotide comprises a modified sugar moiety.

In some embodiments of the oligonucleotide, each nucleotide of the oligonucleotide is a modified nucleotide and each modified nucleotide comprises the same modification.

In some embodiments of the oligonucleotide, each nucleotide of the oligonucleotide comprises a bicyclic nucleotide.

In some embodiments of the oligonucleotide, each nucleotide of the oligonucleotide comprises a modified sugar moiety which is modified at the 2'-position.

In some embodiments of the oligonucleotide, the modified sugar moiety comprises a 2' substituent selected from the group consisting of: H, OR, R, halo, SH, SR, NH$_2$, NHR, NR$_2$, and ON, where R is a C$_1$-C$_6$ alkyl, alkenyl, or alkynyl and halo is F, Cl, Br or I.

In some embodiments of the oligonucleotide, each modified sugar moiety comprises a 2' OCH$_3$.

In some embodiments, the oligonucleotide is 20 nucleotides or more in length.

A composition comprising an oligonucleotide and a pharmaceutically acceptable carrier.

In some embodiments, the present disclosure pertains to an oligonucleotide of 15 to 40 nucleotides or modified nucleotides in length, wherein the oligonucleotide comprises a sequence: 100% complementary to intron 7 of the SMN2 gene over the entire length of the oligonucleotide; and 100% complementary to the sequence 5'-CCAG-CAUUAUGAAAG-3' (SEQ ID NO: 3) (CCAG-CAUUAUGAAAG (SEQ ID NO: 3)), wherein the oligonucleotide comprises a at least one modified nucleotide comprising a modified sugar moiety.

In some embodiments, the oligonucleotide further comprises a moiety capable of binding to ASGPR.

In some embodiments, the oligonucleotide further comprises GalNAc.

In some embodiments, the oligonucleotide further comprises GalNAc or a derivative thereof.

In some embodiments, the oligonucleotide comprises a chirally controlled internucleotidic linkage.

In some embodiments, the oligonucleotide comprises a chirally controlled phosphorothioate.

In some embodiments, the oligonucleotide comprises a chirally controlled internucleotidic linkage and a moiety capable of binding to ASGPR.

In some embodiments, the oligonucleotide comprises at least one 2'-deoxy ribonucleotide.

In some embodiments, the oligonucleotide comprises at least one 2'-deoxy ribonucleotide is 2'-deoxy adenosine or 2'-deoxy guanosine.

In some embodiments of the oligonucleotide, the oligonucleotide comprises at least one modified nucleotide comprising a modified sugar moiety which is modified at the 2' position.

In some embodiments of the oligonucleotide, the modified sugar moiety comprises a 2'-substituent selected from the group consisting of: H, OR, R, halo, SH, SR, NH$_2$, NHR, NR$_2$, and ON, where R is a C$_1$-C$_6$ alkyl, alkenyl, or alkynyl and halo is F, Cl, Br or I.

In some embodiments of the oligonucleotide, the modified sugar moiety comprises a 2' OCH$_3$.

In some embodiments of the oligonucleotide, the modified nucleotide is selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine.

In some embodiments of the oligonucleotide, the modified nucleotide is selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine.

In some embodiments of the oligonucleotide, the oligonucleotide comprises at least one modified linkage.

In some embodiments of the oligonucleotide, at least one modified linkage is a phosphorothioate linkage.

In some embodiments of the oligonucleotide, each linkage is a phosphorothioate linkage.

In some embodiments, the oligonucleotide comprises a locked nucleic acid (LNA) nucleotide.

In some embodiments, the oligonucleotide comprises at least one bicyclic nucleotide.

In some embodiments of the oligonucleotide, each nucleotide of the oligonucleotide is a modified nucleotide.

In some embodiments of the oligonucleotide, each nucleotide of the oligonucleotide comprises a modified sugar moiety.

In some embodiments of the oligonucleotide, each nucleotide of the oligonucleotide is a modified nucleotide and each modified nucleotide comprises the same modification.

In some embodiments of the oligonucleotide, each nucleotide of the oligonucleotide comprises a bicyclic nucleotide.

In some embodiments of the oligonucleotide, each nucleotide of the oligonucleotide comprises a modified sugar moiety modified at the 2'-position.

In some embodiments of the oligonucleotide, the modified sugar moiety comprises a 2' substituent selected from the group consisting of: H, OR, R, halo, SH, SR, NH$_2$, NHR, NR$_2$, and ON, where R is a C$_1$-C$_6$ alkyl, alkenyl, or alkynyl and halo is F, Cl, Br or I.

In some embodiments of the oligonucleotide, each modified sugar moiety comprises a 2' OCH$_3$.

In some embodiments, the oligonucleotide is 20 nucleotides or more in length.

In some embodiments, a composition comprises the oligonucleotide and a pharmaceutically acceptable carrier.

In some embodiments, the oligonucleotide comprises the complement of the nucleotide sequence CCAG-CAUUAUGAAAGUGAAU (SEQ ID NO: 486), set forth as nucleotides 10-29 of CCAGCAUU03.

In some embodiments, the oligonucleotide consists of the complement of the nucleotide sequence CCAG-CAUUAUGAAAGUGAAU (SEQ ID NO: 486), set forth as nucleotides 10-29 of CCAGCAUU03.

In some embodiments, the present disclosure pertains to a method of increasing the level of exon 7-containing SMN2 mRNA in a cell comprising contacting the cell with an oligonucleotide, which oligonucleotide comprises a sequence: at least 80% complementary to intron 7 of the SMN2 gene over the entire length of the oligonucleotide and at least 85% complementary to the sequence CCAGCAUU or CCAGCAUUAUGAAAG (SEQ ID NO: 3); such that the level of exon 7-containing SMN2 mRNA in the cell is increased.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the oligonucleotide is 15-40 nucleotides in length and is 100% complementary to intron 7 of the SMN2 gene over the full length of the oligonucleotide.

In some embodiments of the method, the oligonucleotide is complementary to the sequence CCAGCAUU.

In some embodiments of the method, the oligonucleotide is complementary to the sequence CCAG-CAUUAUGAAAG (SEQ ID NO: 3).

In some embodiments of the method, the oligonucleotide is 15-40 nucleotides in length.

In some embodiments of the method, the oligonucleotide is about 10-15 nucleotides in length.

In some embodiments of the method, the oligonucleotide is about 15-20 nucleotides in length.

In some embodiments of the method, the oligonucleotide comprises at least one modified nucleotide.

In some embodiments of the method, the oligonucleotide comprises at least one modified sugar moiety.

In some embodiments of the method, the oligonucleotide comprises at least one morpholino moiety.

In some embodiments of the method, the oligonucleotide comprises at least one 2'-deoxy ribonucleotide.

In some embodiments of the method, the 2'-deoxy ribonucleotide is 2'-deoxy adenosine or 2'-deoxy guanosine.

In some embodiments of the method, the oligonucleotide comprises at least one modified nucleotide comprising a modified sugar moiety which is modified at the 2'-position.

In some embodiments of the method, the modified sugar moiety comprises a 2'-substituent selected from the group consisting of: H, OR, R, halo, SH, SR, $NH_2$, NHR, $NR_2$, and ON, where R is a $C_1$-$C_6$ alkyl, alkenyl, or alkynyl and halo is F, Cl, Br or I.

In some embodiments of the method, the oligonucleotide comprises at least one modified nucleotide selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine.

In some embodiments of the method, the oligonucleotide comprises at least one modified nucleotide selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine.

In some embodiments of the method, the oligonucleotide comprises at least one modified linkage.

In some embodiments of the method, the at least one modified linkage is a phosphorothioate linkage.

In some embodiments of the method, the oligonucleotide comprises at least one locked nucleic acid (LNA) nucleotide.

In some embodiments, the present disclosure pertains to a method of increasing the level of exon 7-containing SMN2 mRNA in an organism, comprising administering to the organism an oligonucleotide, which oligonucleotide comprises a sequence: at least 80% complementary to intron 7 of the SMN2 gene over the entire length of the oligonucleotide and at least 85% complementary to the sequence CCAG-CAUU or CCAGCAUUAUGAAAG (SEQ ID NO: 3), such that the level of exon 7-containing SMN2 mRNA in the organism is increased.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the organism is a mammal.

In some embodiments of the method, the organism is a human.

In some embodiments of the method, the human has spinal muscular atrophy (SMA).

In some embodiments, the present disclosure pertains to a method of treating spinal muscular atrophy (SMA) in a patient, comprising administering to the patient an oligonucleotide, which oligonucleotide comprises a sequence: at least 80% complementary to intron 7 of the SMN2 gene over the entire length of the oligonucleotide and at least 85% complementary to the sequence CCAGCAUU or CCAG-CAUUAUGAAAG (SEQ ID NO: 3); in a dose effective to increase the level of exon 7-containing SMN2 mRNA in cells of the patient, such that SMA in the patient is treated.

In some embodiments, the present disclosure pertains to a method for inhibiting an SMN2 pre-mRNA intronic splicing silencer site in a cell or cell extract comprising contacting the cell with an oligonucleotide 100% complementary to the ISSN-N1 sequence CCAGCAUU, such that the SMN2 intronic splicing silencer site is inhibited. In some embodiments of the method, the oligonucleotide further comprises a moiety capable of binding to ASGPR.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the present disclosure pertains to a method for inhibiting an SMN2 pre-mRNA intronic splicing silencer site in an organism comprising administering to the organism an oligonucleotide 100% complementary to the sequence CCAGCAUU, such that the SMN2 intronic splicing silencer site is inhibited.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the present disclosure pertains to a method of administering an oligonucleotide to a subject comprising administering to a subject an oligonucleotide, which oligonucleotide comprises a sequence: at least 80% complementary to intron 7 of the SMN2 gene over the entire length of the oligonucleotide and at least 85% complementary to the sequence CCAGCAUU or CCAGCAUUAUGAAAG (SEQ ID NO: 3); wherein the oligonucleotide is administered at a dose effective to increase the level of exon 7-containing SMN2 mRNA in cells of the subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the subject is suffering from amyotrophic lateral sclerosis (ALS).

In some embodiments of the method, the method is performed in vivo.

In some embodiments of the method, the method is performed in vitro.

In some embodiments of the method, the modified sugar moiety comprises a 2'OCH$_3$.

In some embodiments of the method, each linkage of the oligonucleotide is a phosphorothioate linkage.

In some embodiments of the method, the oligonucleotide comprises at least one bicyclic nucleotide.

In some embodiments of the method, each nucleotide of the oligonucleotide is a modified nucleotide.

In some embodiments of the method, each nucleotide of the oligonucleotide comprises a modified sugar moiety.

In some embodiments of the method, each nucleotide of the oligonucleotide is a modified nucleotide and each modified nucleotide comprises the same modification.

In some embodiments of the method, each nucleotide of the oligonucleotide comprises a bicyclic nucleotide.

In some embodiments of the method, each nucleotide of the oligonucleotide comprises a modified sugar moiety which is modified at the 2'-position.

In some embodiments of the method, the modified sugar moiety comprises a 2'-substituent selected from the group consisting of: H, OR, R, halo, SH, SR, NH$_2$, NHR, NR$_2$, and ON, where R is a C$_1$-C$_6$ alkyl, alkenyl, or alkynyl and halo is F, Cl, Br or I.

In some embodiments of the method, each modified sugar moiety comprises a 2'OCH$_3$.

In some embodiments of the method, the subject is suffering from spinal muscular atrophy (SMA).

In some embodiments of the method, the cell is selected from the group consisting of a spinal muscular atrophy (SMA) patient-derived neuronal cell, a spinal muscular atrophy (SMA) patient-derived muscle cell or a spinal muscular atrophy (SMA) patient-derived fibroblast.

In some embodiments of the method, the cell is selected from the group consisting of an embryonic stem cell, an embryonic stem cell extract, a neuronal stem cell and a neuronal stem cell extract.

In some embodiments, the present disclosure pertains to an oligonucleotide having a nucleotide sequence at least 90% complementary to a target region of TCACTTTCATAATGCTGG (SEQ ID NO: 1) as measured over the entirety of the oligonucleotide, wherein: the 5'-most nucleotide of the target region is nucleotide 121, 122, 123, 124, 125, 126, 127, 128 or 129 of TCACTTTCATAATGCTGG (SEQ ID NO: 1); the oligonucleotide is 12 to 20 nucleotides in length; and each nucleoside of the oligonucleotide comprises a 2'-O-methoxyethyl sugar modification.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the oligonucleotide is 12 nucleotides in length.

In some embodiments, the oligonucleotide is 15 nucleotides in length.

In some embodiments, the oligonucleotide is 18 nucleotides in length.

In some embodiments, the oligonucleotide is 20 nucleotides in length.

In some embodiments, the oligonucleotide comprises at least one phosphorothioate linkage.

In some embodiments, the oligonucleotide is 100% complementary to the target region of TCACTTTCATAATGCTGG (SEQ ID NO: 1).

In some embodiments, the oligonucleotide is 12 nucleotides in length.

In some embodiments, the oligonucleotide is 15 nucleotides in length.

In some embodiments, the oligonucleotide is 18 nucleotides in length.

In some embodiments, the oligonucleotide is 20 nucleotides in length.

In some embodiments, the oligonucleotide comprises at least one phosphorothioate linkage.

In some embodiments, the present disclosure pertains to an oligonucleotide having a nucleotide sequence 100% complementary to a target region of TCACTTTCATAATGCTGG (SEQ ID NO: 1) as measured over the entirety of the oligonucleotide, wherein: the 5'-most nucleotide of the target region is nucleotide 123 of TCACTTTCATAATGCTGG (SEQ ID NO: 1); the oligonucleotide is 12 to 20 nucleotides in length; and each nucleoside of the oligonucleotide comprises a 2'-O-methoxyethyl sugar modification.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the oligonucleotide is 12 nucleotides in length.

In some embodiments, the oligonucleotide is 15 nucleotides in length.

In some embodiments, the oligonucleotide is 18 nucleotides in length.

In some embodiments, the oligonucleotide is 20 nucleotides in length.

In some embodiments, the oligonucleotide comprises at least one phosphorothioate linkage.

In some embodiments, the present disclosure pertains to an oligonucleotide having a nucleotide sequence 100% complementary to a target region of TCACTTTCATAATGCTGG (SEQ ID NO: 1) as measured over the entirety of the oligonucleotide, wherein: the 5'-most nucleotide of the target region is nucleotide 124 of TCACTTTCATAATGCTGG (SEQ ID NO: 1); the oligonucleotide is 12 to 20 nucleotides in length; and each nucleoside of the oligonucleotide comprises a 2'-O-methoxyethyl sugar modification.

In some embodiments, the oligonucleotide is 12 nucleotides in length.

In some embodiments, the oligonucleotide is 15 nucleotides in length.

In some embodiments, the oligonucleotide is 18 nucleotides in length.

In some embodiments, the oligonucleotide is 20 nucleotides in length.

In some embodiments, the oligonucleotide comprises at least one phosphorothioate linkage.

In some embodiments, the oligonucleotide comprises at least one phosphorothioate linkage.

In some embodiments of the oligonucleotide, each internucleoside linkage is a phosphorothioate linkage.

In some embodiments, the present disclosure pertains to an oligonucleotide having a nucleotide sequence 100% complementary to a target region of TCACTTTCATAATGCTGG (SEQ ID NO: 1) as measured over the entirety of the oligonucleotide, wherein: the 5'-most nucleotide of the target region is nucleotide 125 of TCACTTTCATAATGCTGG (SEQ ID NO: 1); the oligonucleotide is 12 to 20 nucleotides in length; and each nucleoside of the oligonucleotide comprises a 2'-O-methoxyethyl sugar modification.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the oligonucleotide is 12 nucleotides in length.

In some embodiments, the oligonucleotide is 15 nucleotides in length.

In some embodiments, the oligonucleotide is 18 nucleotides in length.

In some embodiments, the oligonucleotide is 20 nucleotides in length.

In some embodiments, the oligonucleotide comprises at least one phosphorothioate linkage.

In some embodiments, the present disclosure pertains to an oligonucleotide targeted to intron 7 of a nucleic acid molecule encoding SMN2, wherein: the oligonucleotide comprises TCATAATGCTGG (SEQ ID NO: 483) and is at least 90% complementary to the nucleic acid molecule encoding SMN2 as measured over the entirety of the oligonucleotide; the oligonucleotide is 12 to 20 nucleotides in length; and each nucleoside of the oligonucleotide comprises a 2'-O-methoxyethyl sugar modification.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the oligonucleotide is 12 nucleotides in length.

In some embodiments, the oligonucleotide is 15 nucleotides in length.

In some embodiments, the oligonucleotide is 18 nucleotides in length.

In some embodiments, the oligonucleotide is 20 nucleotides in length.

In some embodiments, the oligonucleotide comprises at least one phosphorothioate linkage.

In some embodiments of the oligonucleotide, each internucleoside linkage is a phosphorothioate linkage.

In some embodiments of the oligonucleotide, the base sequence of the oligonucleotide comprises CTTTCATAAT GCTGG (SEQ ID NO: 484).

In some embodiments, the present disclosure pertains to a pharmaceutical composition comprising an oligonucleotide as described herein.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments, the present disclosure pertains to a method comprising administering by a bolus injection into the intrathecal space of a subject with infantile-onset type I spinal muscular atrophy (SMA) an oligonucleotide comprising or consisting of 18 linked nucleosides, wherein the oligonucleotide has a nucleobase sequence consisting of the nucleobase sequence TCACTTTCATAATGCTGG (SEQ ID NO: 1), wherein each internucleoside linkage of the oligonucleotide is a phosphorothioate linkage, wherein each nucleoside of the oligonucleotide is a 2'-MOE nucleoside, and wherein the administering of the oligonucleotide ameliorates at least one symptom of SMA in the subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the oligonucleotide is administered at a dose from 0.5 to 10 milligrams of oligonucleotide per kilogram of body weight of the subject.

In some embodiments of the method, inclusion of exon 7 of SMN2 mRNA in a motoneuron in the subject is increased.

In some embodiments of the method, a 5 mg to 20 mg dose of an oligonucleotide is administered.

In some embodiments, the present disclosure pertains to a method comprising administering by a bolus injection into the intrathecal space of a human subject having type II spinal muscular atrophy (SMA) an oligonucleotide comprising an oligonucleotide consisting of 18 linked nucleosides, wherein the oligonucleotide has a nucleobase sequence consisting of the nucleobase sequence TCACTTTCATAATGCTGG (SEQ ID NO: 1), wherein each internucleoside linkage of the oligonucleotide is a phosphorothioate linkage, wherein each nucleoside of the oligonucleotide is a 2'-MOE nucleoside, and wherein the administering of the oligonucleotide ameliorates at least one symptom of SMA in the human subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the oligonucleotide is administered at a dose from 0.01 to 10 milligrams of oligonucleotide per kilogram of body weight of the subject.

In some embodiments of the method, inclusion of exon 7 of SMN2 mRNA in a motoneuron in the subject is increased.

In some embodiments of the method, a 5 mg to 20 mg dose of the oligonucleotide is administered.

In some embodiments of the method, a first dose of the oligonucleotide is administered when the subject is from 1 to 2 years of age.

In some embodiments of the method, a first dose of the oligonucleotide is administered when the subject is from 1 to 15 years of age.

In some embodiments of the method, a first dose of the oligonucleotide is administered when the subject is from 1 to 2 years of age.

In some embodiments of the method, a first dose of the oligonucleotide is administered when the subject is from 1 to 15 years of age.

In some embodiments of the method, inclusion of exon 7 amino acids in SMN2 polypeptide in a motoneuron in the subject is increased.

In some embodiments of the method, inclusion of exon 7 amino acids in SMN2 polypeptide in a motoneuron in the subject is increased.

In some embodiments, the present disclosure pertains to a method comprising administering by a bolus injection into the intrathecal space of a human subject having type III spinal muscular atrophy (SMA) an oligonucleotide comprising an oligonucleotide consisting of 18 linked nucleosides, wherein the oligonucleotide has a nucleobase sequence consisting of the nucleobase sequence TCACTTTCATAATGCTGG (SEQ ID NO: 1), wherein each internucleoside linkage of the oligonucleotide is a phosphorothioate linkage, wherein each nucleoside of the oligonucleotide is a 2'-MOE nucleoside, and wherein the administering of the oligonucleotide ameliorates at least one symptom of SMA in the human subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

In some embodiments of the method, the oligonucleotide is administered at a dose from 0.01 to 10 milligrams of oligonucleotide per kilogram of body weight of the subject.

In some embodiments of the method, inclusion of exon 7 of SMN2 mRNA in a motoneuron in the subject is increased.

In some embodiments of the method, a 5 mg to 20 mg dose of the oligonucleotide is administered.

In some embodiments of the method, a first dose of the oligonucleotide is administered when the subject is from 1 to 2 years of age.

In some embodiments of the method, a first dose of the oligonucleotide is administered when the subject is from 1 to 15 years of age.

In some embodiments of the method, a first dose of the oligonucleotide is administered when the subject is from 1 to 2 years of age.

In some embodiments of the method, a first dose of the oligonucleotide is administered when the subject is from 1 to 15 years of age.

In some embodiments of the method, inclusion of exon 7 amino acids in SMN2 polypeptide in a motoneuron in the subject is increased.

In some embodiments of the method, inclusion of exon 7 amino acids in SMN2 polypeptide in a motoneuron in the subject is increased.

In some embodiments, the present disclosure pertains to a method of increasing inclusion of exon 7 in SMN2 messenger ribonucleic acid (mRNA) transcripts in a human subject having loss of both functional copies of the SMN1 gene, the method comprising administering by a bolus injection into the intrathecal space of the human subject an oligonucleotide comprising an oligonucleotide consisting of 18 linked nucleosides, wherein the oligonucleotide has a nucleobase sequence consisting of the nucleobase sequence TCACTTTCATAATGCTGG (SEQ ID NO: 1), wherein each internucleoside linkage of the oligonucleotide is a phosphorothioate linkage, wherein each nucleoside of the oligonucleotide is a 2'-MOE nucleoside, and wherein the administering of the oligonucleotide increases inclusion of exon 7 in SMN2 mRNA transcripts in the human subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide comprises a chirally controlled internucleotidic linkage and a moiety capable of binding to ASGPR.

The method of claim 1, wherein the human subject is identified by a genetic test as having a mutation in the SMN1 gene.

The method of claim 1, wherein the oligonucleotide is administered at a dose from 0.01 to 10 milligrams of oligonucleotide per kilogram of body weight of the subject.

The method of claim 1, wherein a 5 mg to 20 mg dose of the oligonucleotide is administered.

In some embodiments, the present disclosure pertains to a method of increasing exon 7 inclusion in SMN2 messenger ribonucleic acid (mRNA) transcripts in a human subject having mutations in the SMN1 gene that lead to functional SMN protein deficiency, the method comprising administering by a bolus injection into the intrathecal space of the human subject an oligonucleotide comprising an oligonucleotide consisting of 18 linked nucleosides, wherein the oligonucleotide has a nucleobase sequence consisting of the nucleobase sequence TCACTTTCATAATGCTGG (SEQ ID NO: 1), wherein each internucleoside linkage of the oligonucleotide is a phosphorothioate linkage, wherein each nucleoside of the oligonucleotide is a 2'-MOE nucleoside, and wherein the administering of the oligonucleotide increases exon 7 inclusion in SMN2 mRNA transcripts in the human subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide a chirally controlled internucleotidic linkage and a moiety capable of binding to ASGPR.

In some embodiments of the method, the oligonucleotide is administered at a dose from 0.01 to 10 milligrams of oligonucleotide per kilogram of body weight of the subject.

In some embodiments of the method, a 5 mg to 20 mg dose of the oligonucleotide is administered.

In some embodiments of the method, a first dose of the oligonucleotide is administered within one week of birth of the subject.

In some embodiments of the method, a first dose of the oligonucleotide is administered within one month of birth of the subject.

In some embodiments of the method, a first dose of the oligonucleotide is administered within three months of birth of the subject.

In some embodiments of the method, a first dose of the oligonucleotide is administered within six months of birth of the subject.

In some embodiments of the method, a first dose of the oligonucleotide is administered when the subject is from 1 to 2 years of age.

In some embodiments of the method, a first dose of the oligonucleotide is administered when the subject is from 1 to 15 years of age.

In some embodiments, the present disclosure pertains to a method of treating spinal muscular atrophy (SMA) in a human subject having SMA, the method comprising administering by a bolus injection into the intrathecal space of the human subject an oligonucleotide comprising an oligonucleotide consisting of 18 linked nucleosides, wherein the oligonucleotide has a nucleobase sequence consisting of the nucleobase sequence TCACTTTCATAATGCTGG (SEQ ID NO: 1), wherein each internucleoside linkage of the oligonucleotide is a phosphorothioate linkage, wherein each nucleoside of the oligonucleotide is a 2'-MOE nucleoside, and wherein the administering of the oligonucleotide increases inclusion of exon 7 in SMN2 messenger ribonucleic acid (mRNA) transcripts in the human subject.

In some embodiments of the method, the oligonucleotide further comprises a moiety capable of binding to ASGPR.

In some embodiments of the method, the oligonucleotide further comprises GalNAc.

In some embodiments of the method, the oligonucleotide further comprises GalNAc or a derivative thereof.

In some embodiments of the method, the oligonucleotide comprises a chirally controlled internucleotidic linkage.

In some embodiments of the method, the oligonucleotide comprises a chirally controlled phosphorothioate.

In some embodiments of the method, the oligonucleotide a chirally controlled internucleotidic linkage and a moiety capable of binding to ASGPR.

In some embodiments of the method, the oligonucleotide is administered at a dose from 0.01 to 10 milligrams of oligonucleotide per kilogram of body weight of the subject.

In some embodiments of the method, a 5 mg to 20 mg dose of the oligonucleotide is administered.

In some embodiments of the method, a first dose of the oligonucleotide is administered within one week of birth of the subject.

In some embodiments of the method, a first dose of the oligonucleotide is administered within one month of birth of the subject.

In some embodiments of the method, a first dose of the oligonucleotide is administered within three months of birth of the subject.

In some embodiments of the method, a first dose of the oligonucleotide is administered within six months of birth of the subject.

In some embodiments of the method, a first dose of the oligonucleotide is administered when the subject is from 1 to 2 years of age.

In some embodiments of the method, a first dose of the oligonucleotide is administered when the subject is from 1 to 15 years of age.

Pharmaceutical Compositions

In some embodiments, the present disclosure provides pharmaceutical compositions comprising provided oligonucleotides, or a pharmaceutically acceptable salt thereof, and a pharmaceutical carrier. In some embodiments, provided oligonucleotides are a plurality of oligonucleotides of a chirally controlled oligonucleotide composition. In some embodiments, provided oligonucleotides are salts. In some embodiments, provided oligonucleotides are metal salts (lithium, sodium, potassium, magnesium, calcium, etc.) or ammonium salts (e.g., —N(R)$_4$ wherein each R is independently as described in the present disclosure). In some embodiments, provided oligonucleotides are sodium salts. In some embodiments, provided oligonucleotides are all-sodium salts, wherein all natural phosphate linkages and phosphorothioate linkages exist as sodium salt form. In some embodiments, provided pharmaceutical compositions are chirally controlled oligonucleotide compositions.

When used as therapeutics, a provided chirally controlled oligonucleotide composition or oligonucleotide composition described herein is typically administered as a pharmaceutical composition. In some embodiments, the pharmaceutical composition is suitable for administration of an oligonucleotide to an area of the body affected by a condition, disorder, and/or disease, including but not limited to the central nervous system. In some embodiments, a pharmaceutical composition comprises a therapeutically effective amount of a provided oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers.

In some embodiments, provided oligonucleotides are formulated for administration to a body cell and/or tissue. In some embodiments, such a body cell and/or tissue is a neuron or a cell and/or tissue of the central nervous system. In some embodiments, broad distribution of oligonucleotides and compositions within the central nervous system may be achieved with intraparenchymal administration, intrathecal administration, or intracerebroventricular administration.

In some embodiments, a pharmaceutical composition is formulated for intrathecal, intraventricular, intravenous injection, oral administration, buccal administration, inhalation, nasal administration, topical administration, ophthalmic administration or otic administration. In some embodiments, a pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide, or a composition thereof, in admixture with a pharmaceutically acceptable excipient. One of skill in the art will recognize that pharmaceutical compositions may include pharmaceutically acceptable salts of the chirally controlled oligonucleotide, or composition thereof.

In some embodiments, a variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGylated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly(lactic acid), liquid depot, polymer micelles, quantum dots and lipoplexes. In some embodiments, an oligonucleotide is conjugated to another molecular.

In therapeutic and/or diagnostic and/or research applications, provided agents, e.g., oligonucleotides, and compositions thereof can be formulated for a variety of modes of administration, including systemic and topical or localized administration. Techniques and formulations generally may be found in Remington, The Science and Practice of Pharmacy (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. In some embodiments, an exact dosage may depend upon the route of administration, the form in which the compound is administered, the subject to be treated, the body weight of the subject to be treated, and the preference and experience of the attending physician.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraarticullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate provided agents, e.g., oligonucleotides, into dosages suitable for administration, e.g., systemic administration, is widely practiced and can be utilized in accordance with the present disclosure. With proper choice of carrier and suitable manufacturing practice, compositions of the present disclosure, in particular, those formulated as solutions, may be administered parenterally, such as by intravenous injection.

Provided agents, e.g., oligonucleotides, can be formulated readily using pharmaceutically acceptable carriers well known in the art into dosages suitable for oral administration. In some embodiments, such carriers enable provided agents, e.g., oligonucleotides, to be formulated as tablets, pills, capsules, liquids, gels, syrups, slurries, suspensions and the like, for oral ingestion by a subject (e.g., patient) to be treated.

In some embodiments, for nasal or inhalation delivery, provided agents may be formulated by methods known to those of skill in the art, and may include, for example, examples of solubilizing, diluting, or dispersing substances such as saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. In some embodiments, broad distribution of oligonucleotides and compositions within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, a targeted tissue is brain tissue. In certain embodiments, a targeted tissue is striatal tissue. In certain embodiments, decreasing EC50 is desirable because it reduces the dose required to achieve a pharmacological result in a subject in need thereof.

In certain embodiments, an oligonucleotide is delivered by injection or infusion once every month, every two months, every 90 days, every 3 months, every 6 months, twice a year or once a year.

In some embodiments, the present disclosure provides pharmaceutical compositions wherein an active ingredient is contained in an effective amount to achieve its intended purpose. Many technologies for determination of an effective amount can be utilized in accordance with the present disclosure.

In addition to the active ingredients, provided pharmaceutical compositions may contain suitable pharmaceutically acceptable carriers comprising excipients and auxiliaries which facilitate processing of active agents into preparations which can be used pharmaceutically. In some embodiments, preparations formulated for oral administration may be in the form of tablets, dragees, capsules, or solutions.

In some embodiments, pharmaceutical preparations for oral use can be obtained by combining an active compound, e.g., a SMN2 oligonucleotide with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethylcellulose, sodium carboxymethyl-cellulose (CMC), and/or polyvinylpyrrolidone (PVP: povidone). If desired, disintegrating agents may be added, such as cross-linked polyvinylpyrrolidone, agar, or alginic acid or a salt thereof such as sodium alginate.

In some embodiments, dragee cores are provided with suitable coatings. In some embodiments, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active agent doses.

Pharmaceutical preparations that can be used orally include push-fit capsules made of gelatin, as well as soft, sealed capsules made of gelatin, and a plasticizer, such as glycerol or sorbitol. Push-fit capsules can contain one or more active ingredients in admixture with one or more filler such as lactose, binders such as starches, and/or lubricants such as talc or magnesium stearate and, optionally, stabilizers. In soft capsules, an active compound, e.g., a SMN2 oligonucleotide may be dissolved or suspended in suitable liquids, such as fatty oils, liquid paraffin, or liquid polyethylene glycols (PEGs). In addition, stabilizers may be added.

In some embodiments, a composition can be obtained by combining an active agent with a lipid. In some embodiments, a lipid is conjugated to an active compound, e.g., a SMN2 oligonucleotide. In some embodiments, a lipid is not conjugated to an active compound, e.g., a SMN2 oligonucleotide. In some embodiments, a lipid comprises a $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, the lipid is selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, an active agent is an oligonucleotide. In some embodiments, an active compound, e.g., a SMN2 oligonucleotide is an oligonucleotide of a sequence comprising or consisting of a sequence of an oligonucleotide listed in Table 1A. In some embodiments, a composition comprises a lipid and an active agent, and further comprises another component selected from: another lipid, and a targeting compound or moiety. In some embodiments, a lipid is an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; and a targeting lipid; and any other reported in the art. In some embodiments, a composition comprises a lipid and a portion of another lipid capable of mediating at least one function of another lipid. In some embodiments, a targeting compound or moiety is capable of targeting an agent or a composition (e.g., a composition comprising a lipid and an active compound (e.g., a SMN2 oligonucleotide)) to a particular cell or tissue or subset of cells or tissues. In some embodiments, a targeting moiety is designed to take advantage of cell- or tissue-specific expression of particular targets, receptors, proteins, or other subcellular components. In some embodiments, a targeting moiety is a ligand (e.g., a small molecule, antibody, peptide, protein, carbohydrate, aptamer, etc.) that targets an agent or a composition to a cell or tissue, and/or binds to a target, receptor, protein, or other subcellular component. In some embodiments, an oligonucleotide further comprises an additional chemical moiety comprising any of or any derivative of: a fibronectin derivative, a Fibronectin 3 derivative, a centyrin, Adnectin, Pronectin, a conotoxin, an anticalin, lipocalin, an avimer, A domain, a bicyclic peptide, a cysknot, a DARPin, an ankyrin, a fynomer, SH3 domain (fyn kinase), a Kunitz domain, serine protease inhibitor, a thioredoxin, an affilin, a gamma-beta-crystallin, an affibody, Z domain of bacterial protein A, OBody, OB-fold, a short peptide, a long peptide, a cyclic peptide, a bicyclic peptide, wherein the additional chemical moiety is optionally modified to increase binding affinity or specificity to a target (e.g., a target protein or receptor) on the surface of a cell in a target tissue or organ. In some embodiments, an oligonucleotide further comprises an albumin-binding domain or an eGLP1 peptide.

In some embodiments, lipids for use in preparation of pharmaceutical composition for delivery of active agents do not prevent or interfere with functions of active agents. Non-limiting example lipids include lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

As described in the present disclosure, lipid conjugation, such as conjugation with fatty acids, may improve one or more properties of oligonucleotides.

In some embodiments, a provided pharmaceutical composition can direct an active gent to particular organelles, cells, tissues, or organs, as desired. In some embodiments, a provided pharmaceutical composition can target an active agent to a central nervous system cell or tissue. In some embodiments, the present disclosure provides pharmaceutical compositions for delivery of active agents, wherein each of the compositions comprises an active compound, e.g., a SMN2 oligonucleotide, and a lipid. In some embodiments, for delivery to a central nervous system cell or tissue, a lipid is selected from lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl alcohol.

In some embodiments, one or more additional therapeutic agents (or therapies or treatment), e.g., which may be administered to treat or prevent a condition, disorder or disease, e.g., SMA, ALS, etc., may be administered together with provided oligonucleotides. In some embodiments, an additional therapeutic agent is a stereorandom oligonucleotide (e.g., Nusinersen), butyrate, calcium, DcpS inhibitor, gabapentin, histone deacetylase (HDAC) inhibitor, hydroxyurea, LDN-76070, neuroprotective agent, P38 and HuR protein activator, phenylbutyrate, proteasome inhibitor, PTC compound, read-through inducing compound, Rho-kinase inhibitor, riluzole [Rilutek (Trademark), Sanofi Aventis], salbutanol, STATS activator, valproic acid or a vitamin, such as vitamin D. In some embodiments, an additional therapeutic agent is a DcpS inhibitor, including but not limited to: Suberoylanilide hydroxamic acid; LBH589; trichostatin A; trichostatin A in combination with nutrition or nutritional supplements; histone deacetylase (HDAC) inhibitor, including but not limited to: RG3039; and 2,4-diaminoquinazoline; P38 and HuR protein activator, including but not limited to: celecoxib; proteasome inhibitor, including but not limited to: bortezomib; read-through inducing compound, including but not limited to: TC007; Rho-kinase inhibitor, including but not limited to: Y-27632; and Fasudil; or STATS activator, including but not limited to: prolactin. See, for example, Awano et al. 2014 Neurother. 11: 786-795; Bogdanik et al. 2015 Proc. Natl. Acad. Sci. USA E5863-E5872; Coady et al. 2010 J. Neurosci. 30: 126-130; Cherry et al. 2014 Assay Drug Dev. Tech. Vol. 12, No. 6; Chang et al. 2011 Stem Cells 29: 2090-2093; Iascone et al. 2015 F1000 Prime Reports 7:04; Hua et al. Nature 478: 123-126; Hua et al. 2010 Gen. Dev. 24: 1634-1644; Hua et al. 2008 Am. J. Hum. Genet. 82: 834-848; Howell et al. 2014 Future Med. Chem. 6: 1081-1099; Fischbeck 2012 Prog. Neurobiol. 99: 251-261; Hester et al. 2011 Mol. Ther. 19: 1905-1912; d'Ydewalle et al. 2015 Neurother. 12: 303-316; Douglas et al. 2013 Mol. Cell. Neurosci. 56: 169-185; Corti et al. 2012 Sci. Trans. Med. 4: 165ra162; Kell et al. 2014 Mol. Ther. 3 e174; Lorson et al. 2012 Fut. Med. Chem. 4: 2067-2084; Lorson et al. 2010 Human Mol. Genet. 19: R111-R118; Meyer et al. 2015 Mol. Ther. 23: 477-487; Mitrpant et al. 2013 PLoS One 8: e62114; Naryshkin et al. 2014 Science 345: 688-693; Nizzardo et al. 2015 Nature Scientific Reports 5:11746; Singh et al. 2013 Nucl. Acids Res. 41: 8144-8165; Nurputra et al. 2013 Ann. Hum. Genet. 77: 435-463; Osman et al. 2014 Hum. Mol. Genet. 23: 4832-4845; Palacio et al. 2015 Nat. Chem. Biol. 11: 511-517; Pao et al. 2014 Mol. Ther. 22: 854-861; Staropoli et al. 2015 Genomics 105: 220-228; Park et al. 2010 Curr. Neur. Neur. Rep. 10: 108-117; Passini et al. 2010 J. Clin. Invest. 120: 1253; Passini et al. 2011 Sci. trans. Med. 3, issue 72, 72ra18; Porensky et al. 2013 Hum. Gen Ther. 24: 489-498; Porensky et al. 2012 Hum. Mol. Genet. 21: 1623-1638; Rigo et al. 2014 J. Pharm. Exp. Ther. 350: 46-55; Robbins et al. 2014 Hum. Mol. Genet. 23: 4559-4568; Sareen et al. 2012 PLoS One 7: e39113; Sellers et al. 2016 Proc. Natl. Acad. Sci. US 113: 2514-2519; Seo et al. 2013 Biochim. Biophys. Acata 1832: 2180-2190; Singh et al. 2009 RNA Biol. 6: 341-350; Singh et al. 2015 Fut. Med. Chem. 7: 1793-1808; Sivanesan et al. 2013 Transl. Neurosci. 4(1); Skordis et al. 2003 Proc. Natl. Acad. Sci. US 100: 4114-4119; Tanaka et al. 2012 Neural Plasticity, article 369284; Tisdale et al. 2015 J. Neurosci. 35: 8691-8700; Van Meerbeke et al. 2011 Discovery Med. 12: 291-305; Williams et al. 2009 J. Neurosci. 29: 7633-7638; Zanetta et al. 2014 J. Cell. Mol. Med. 18: 187-196; Zhou et al. 2012 Mol. Cell. 33: 223-228; Zhou et al. 2013 Hum. Gene Ther. 24: 331-342; and Arnold et al.

2013 Ann. Neurol. 74: 348-362; and U.S. Pat. Nos. 8,110,560; 8,586,559; 9,476,042; 7,838,657; 8,110,560; 8,361,977; 8,586,559; 8,637,478; 8,802,642; 8,980,853; 9,217,147; 9,222,091; and WO 2007/002390; WO 2010/091308. In some embodiments, an additional therapeutic agent is an agent for replacement SMN2, administered as either a replacement SMN protein or as a nucleic acid (e.g., a mRNA) intended for expression of SMN protein. In some embodiments, a replacement therapy comprises administration of an adeno-associated virus vector capable of expressing SMN protein. See, for example, Arnold et al. 2013 Ann. Neurol. 74: 348-362; Benkhelifa-Ziyyat et al. 2013 Mol. Ther. 21: 282-290. In some embodiments, an additional therapeutic targets GEMINs, which have a key role in snRNP biogenesis; reportedly, targeting GEMINs may at least partially restore the function of SMN without augmenting its level. See, for example, Borg et al. 2014 Front. Neurosci. Vol. 8. In some embodiments, an additional therapeutic agent or therapy is a standard of care for SMA patients, for example, that described in Wang et al. 2007 J. Child Neurol. 22: 1027-49. In some embodiments, an additional therapy can include muscle stretching, swimming, aquatic therapy, or other forms of physical exercise. In some embodiments, a SMA patient can also be assisted by a bracer, walker, manual or power wheelchair and/or other ambulatory or mobility aid. In some embodiments, a SMA patient can receive a tracheostomy and/or mechanical ventilation.

In some embodiments, an additional therapy can include a treatment for any of: fatty acid oxidation abnormality, gastroesophageal reflux, breathing difficulty, swallowing difficulty, delayed gastric emptying, constipation, malnutrition, viral, bacterial and/or fungal infections, especially in the lungs, and/or fatigue, which are all conditions not uncommon among SMA patients, and for which various treatments are known in the art. See Arnold et al. 2015 Muscle Nerve 51: 157-167.

In some embodiments, one or more additional therapeutic agents, therapies or treatments administered together with a provided SMN2 oligonucleotide is a treatment for a symptom or condition associated with SMA, including but not limited to: difficulties in breathing, swallowing, maintaining proper nutrition, movement and back issues. In some embodiments, an additional treatment includes any of: the use of a tracheotomy, ventilation, chest percussion, in-exsufflator, special mask, mouthpiece and/or machine to aid in breathing, the use of aspiration, a tube or other device for assistance in swallowing or sucking food; the use of a crutch, leg brace, walker or wheelchair; the use of a specialized computer, phone, tablet or other device for assistance in writing and/or drawing; the use of a device or surgery to correct back or spine problems; administration of oxygen or oxygen therapy; and/or pain medication.

In some embodiments, a second therapeutic agent administered with a first SMN2 oligonucleotide is a second, different, SMN2 oligonucleotide.

In some embodiments, SMN2 oligonucleotides disclosed herein can be used for a method for the prevention and/or treatment of a SMN2-related condition, disorder or disease, or for the manufacture of medicament for use in such a method. In some embodiments, a SMN2-related condition, disorder or disease is SMA. In some embodiments, a SMN2-related condition, disorder or disease is ALS.

In some embodiments, a subject suffering from a SMN2-related condition, disorder or disease may be amenable to treatment only within a limited therapeutic window. Reportedly, there are phases in SMA (presymptomatic, rapid disease progression, and later plateau/slow progression). Reportedly, preclinical studies have shown the importance of early SMN restoration, and the diminishing returns of late rescue in mouse models. Several mouse studies have also reported that treatment is decreasingly effective if the disorder has increasingly progressed. See, for example, Le et al. 2011 Hum. Mol. Genet. 20: 3578-91; and Lutz et al. 2011 J. Clin. Invest. 121: 3029-41; Robbins Hum. Mol. Genet. Apr. 9, 2014.

In some embodiments, a provided stereocontrolled oligonucleotide composition is administered at a dose and/or frequency lower than that of an otherwise comparable reference oligonucleotide composition (e.g., a stereorandom oligonucleotide otherwise having the same base sequence, and pattern of internucleotidic linkages and base and sugar modifications as the stereocontrolled oligonucleotide) with comparable effect, e.g., in increase level, expression and/or activity of exon 7-containing SMN2 mRNA or its gene product relative to exon 7-deleted SMN2 mRNA, or increasing the inclusion of exon 7 of a SMN2 mRNA. In some embodiments, a stereocontrolled oligonucleotide composition is administered at a dose and/or frequency lower than that of an otherwise comparable stereorandom reference oligonucleotide composition with comparable effect, e.g., in enhancing level, expression and/or activity of exon 7-containing SMN2 mRNA or its gene product relative to exon 7-deleted SMN2 mRNA, or increasing the inclusion of exon 7 of a SMN2 mRNA. In some embodiments, a chirally controlled oligonucleotide composition can be administered at a higher dose (unit dose or total dose over a period of time) and/or higher frequency, without the intention to be limited by theory, low side effects, low toxicities, etc.

The stereorandom SMN2 oligonucleotide Nusinersen is reportedly available as a solution for intrathecal injection in a 12 mg/5 mL single-dose vial. For treatment of Spinal Muscular Atrophy in pediatric and adults patients, Nusinersen is dosed at 12 mg intrathecally per administration. A dosing regimen is reportedly: Initial: 4 loading doses; administer the first 3 doses at 14-day intervals and the fourth dose 30 days after the third dose; Maintenance: One dose every 4 months. In some embodiments, a provided chirally controlled oligonucleotide, e.g., a chirally controlled SMN2 oligonucleotide, is in a single dose vial. In some embodiments, a provided chirally controlled oligonucleotide, e.g., a chirally controlled SMN2 oligonucleotide, is in a single dose vial for intrathecal injection. In some embodiments, a chirally controlled oligonucleotide is in solution in a single dose vial for intrathecal injection. In some embodiments, a chirally controlled oligonucleotide is in solution at no more than 12 mg/5 ml in a single dose vial for intrathecal injection. In some embodiments, a chirally controlled SMN2 oligonucleotide has the dosing regimen of: Initial: 4 loading doses; administer the first 3 doses at 14-day intervals and the fourth dose 30 days after the third dose; Maintenance: One dose every 4 months.

In some embodiments, provided oligonucleotides, compositions and methods, e.g., SMN2 oligonucleotides, compositions, and methods, provide improved delivery. In some embodiments, provided oligonucleotides, compositions and methods provide improved cytoplasmatic delivery. In some embodiments, improved delivery is to a population of cells. In some embodiments, improved delivery is to a tissue. In some embodiments, improved delivery is to an organ. In some embodiments, improved delivery is to the central nervous system or a portion thereof, e.g., CNS. In some embodiments, improved delivery is to an organism. Example structural elements (e.g., chemical modifications, stereochemistry, backbone chemistry and stereochemistry, additional chemical moieties, if any, etc.), oligonucleotides, compositions and methods that provide improved delivery are extensively described in this disclosure.

Various dosing regimens can be utilized to administer provided chirally controlled oligonucleotide compositions. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week f or more than one week. In some embodiments, a dosing regimen comprises administering one dose per week for 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks f or more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month for more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for about 30 weeks. In some embodiments, a dosing regimen comprises administering one dose per week for 26 weeks. In some embodiments, an oligonucleotide is administered according to a dosing regimen that differs from that utilized for a chirally uncontrolled (e.g., stereorandom) oligonucleotide composition of the same sequence, and/or of a different chirally controlled oligonucleotide composition of the same sequence. In some embodiments, an oligonucleotide is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, an oligonucleotide is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, an oligonucleotide has a longer dosing regimen compared to the corresponding chirally uncontrolled oligonucleotide composition. In some embodiments, an oligonucleotide has a shorter time period between at least two doses compared to the corresponding chirally uncontrolled oligonucleotide composition. Without wishing to be limited by theory, Applicant notes that in some embodiments longer dosing regimen, and/or shorter time periods between doses, may be due to the improved safety of a chirally controlled oligonucleotide composition.

In some embodiments, with their improved delivery (and other properties), provided compositions can be administered in lower dosages and/or with lower frequency to achieve biological effects, for example, clinical efficacy.

A single dose can contain various amounts of oligonucleotides. In some embodiments, a single dose can contain various amounts of a type of chirally controlled oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more (e.g., about 350, 400, 450, 500, 550, 600, 650, 700, 750, 800, 850, 900, 950, 1000 or more) mg of a type of chirally controlled oligonucleotide. In some embodiments, a single dose contains about 1 mg of a type of chirally controlled oligonucleotide. In some embodiments, a single dose contains about 5 mg of a type of chirally controlled oligonucleotide. In some embodiments, a single dose contains about 10 mg of a type of chirally controlled oligonucleotide. In some embodiments, a single dose contains about 15 mg of a type of chirally controlled oligonucleotide. In some embodiments, a single dose contains about 20 mg of a type of chirally controlled oligonucleotide. In some embodiments, a single dose contains about 50 mg of a type of chirally controlled oligonucleotide. In some embodiments, a single dose contains about 100 mg of a type of chirally controlled oligonucleotide. In some embodiments, a single dose contains about 150 mg of a type of chirally controlled oligonucleotide. In some embodiments, a single dose contains about 200 mg of a type of chirally controlled oligonucleotide. In some embodiments, a single dose contains about 250 mg of a type of chirally controlled oligonucleotide. In some embodiments, a single dose contains about 300 mg of a type of chirally controlled oligonucleotide. In some embodiments, a chirally controlled oligonucleotide is administered at a lower amount in a single dose, and/or in total dose, than a chirally uncontrolled oligonucleotide. In some embodiments, a chirally controlled oligonucleotide is administered at a lower amount in a single dose, and/or in total dose, than a chirally uncontrolled oligonucleotide due to improved efficacy. In some embodiments, a chirally controlled oligonucleotide is administered at a higher amount in a single dose, and/or in total dose, than a chirally uncontrolled oligonucleotide. In some embodiments, a chirally controlled oligonucleotide is administered at a higher amount in a single dose, and/or in total dose, than a chirally uncontrolled oligonucleotide due to improved safety.

In some embodiments, provided chirally controlled oligonucleotide compositions can increase the level, expression and/or activity of exon 7-containing SMN2 mRNA or its gene product relative to exon 7-deleted SMN2 mRNA, or increasing inclusion of exon 7 of a SMN2 mRNA. In some embodiments, a SMN2-related disorder is SMA or ALS. Symptoms of a SMN2-related disorder include those described herein and known in the art.

In some embodiments, the present disclosure provides methods of using provided oligonucleotides and/or compositions which target SMN2 and are useful for treating and/or for manufacturing a treatment for a SMN2-related condition, disorder or disease. In some embodiments, a base sequence of an oligonucleotide can comprise or consist of a base sequence which has a specified maximum number of mismatches from a specified base sequence.

In some embodiments, the present disclosure pertains to the use of a composition comprising a SMN2 oligonucleotide for the manufacture of a medicament for treating a neurodegenerative disease.

In some embodiments, the present disclosure pertains to a method of treating or ameliorating an SMN2-related condition, disorder or disease in a subject, the method comprising administering to the subject a therapeutically effective amount of an oligonucleotide complementary to SMN2.

In some embodiments, the present disclosure pertains to a method comprising administering to an animal a composition comprising a SMN2 oligonucleotide. In some embodiments, the animal is a subject, e.g., a human.

In some embodiments, a subject suitable for treatment of a SMN2-related condition, disorder or disease, such as administration of a SMN2 oligonucleotide, can be identified or diagnosed by a health care professional. In some embodiments, a SMN2-related condition, disorder or disease is SMA. In some embodiments, a SMN2-related disorder can be diagnosed by one or more reported symptoms. In some embodiments, a symptom is muscle weakness or muscle atrophy. In some embodiments, a symptom is inability to sit, stand, or walk, or to do so for a prolonged time. In some embodiments, a symptom is proximal predominant weakness; reduced or absent reflexes; tongue fasciculations; or limb tremor (polyminimyoclonus). In some embodiments, a symptom is pneumonia or difficulty in breathing or swallowing. In some embodiments, infant SMA patients can be identified due to a condition known as hypotonic or "floppy" baby or infant. In some embodiments, in SMA patients with intermediate forms of the disease the differential includes other disorders of the peripheral nervous system including myopathy (dystrophinopathies, limb girdle muscular dystrophy, metabolic myopathies, or inflammatory myopathies), neuropathy (inflammatory neuropathies), neuromuscular junction disorders (myasthenia gravis or congenital myasthenic syndromes), and other motor neuron disorders (non-5q form of SMA or late onset hexosaminidase A deficiency). In some embodiments, in SMA patients with adult onset disease the differential overlaps with that of the intermediate forms of the disease but also includes later onset disorders such as amyotrophic lateral sclerosis and Kennedy disease (X-linked spinobulbar muscular atrophy).

In some embodiments, a patient can be diagnosed with SMA by any of: electromyography, MM, muscle biopsy, and a genetic test to evaluate the absence of a functional SMN1 gene from both chromosomes (e.g., a homozygous deletion or other mutation). In some embodiments, a patient can be diagnosed for SMA with any of other modalities including NCS/EMG, creatine kinase and/or imaging. In some embodiments, a SMA patient can be identified due to a family history of SMA and genetic screening of relatives and/or parents. In some embodiments, prenatal screening for homozygous deletions or mutations of SMN1 by chorionic villus sampling or amniocentesis to obtain fetal DNA is performed. In some embodiments, pre-implantation embryonic testing during in vitro fertilization is performed.

In some embodiments, a diagnosis of a subject as having a neurological disease can be performed by the assessment of one or more symptoms, e.g., a symptom of motor neuron degeneration. In some embodiments, to diagnose a neurological disease, a physical exam may be followed by a thorough neurological exam. In some embodiments, a neurological exam may assess motor and sensory skills, nerve function, hearing and speech, vision, coordination and balance, mental status, and changes in mood or behavior. Non-limiting symptoms of a disease associated with a neurological disease may be weakness in the arms, legs, feet, or ankles; slurring of speech; difficulty lifting the front part of the foot and toes; hand weakness or clumsiness; muscle paralysis; rigid muscles; involuntary jerking or writing movements (chorea); involuntary, sustained contracture of muscles (dystonia); bradykinesia; loss of automatic movements; impaired posture and balance; lack of flexibility; tingling parts in the body; electric shock sensations that occur with movement of the head; twitching in arm, shoulders, and tongue; difficulty swallowing; difficulty breathing; difficulty chewing; partial or complete loss of vision; double vision; slow or abnormal eye movements; tremor; unsteady gait; fatigue; loss of memory; dizziness; difficulty thinking or concentrating; difficulty reading or writing; misinterpretation of spatial relationships; disorientation; depression; anxiety; difficulty making decisions and judgments; loss of impulse control; difficulty in planning and performing familiar tasks; aggressiveness; irritability; social withdrawal; mood swings; dementia; change in sleeping habits; wandering; change in appetite.

In some embodiments, a provided composition, e.g., a provided chirally controlled oligonucleotide composition, prevents, treats, ameliorates, or slows progression of at least one symptom of a SMN2-related disorder.

Various technologies can be utilized to prepare provided oligonucleotides and compositions in accordance with the present disclosure, for example, technologies described in US 20150211006, US 20150211006, WO 2017015555, WO 2017015575, WO 2017062862, WO 2017160741, oligonucleotide preparation technologies (e.g., cycles, monomers, chiral auxiliaries, conditions, etc.) are incorporated herein by reference.

Among other things, the present disclosure provides the following Example Embodiments:

1. A composition comprising a plurality of oligonucleotides of a particular oligonucleotide type defined by:
   1) base sequence;
   2) pattern of backbone linkages;
   3) pattern of backbone chiral centers; and
   4) pattern of backbone phosphorus modifications, oligonucleotides of the plurality comprise at least 1, 2, 3, 4, 5, 6, 7, 8, 9, 10, 11, 12, 13, 14, 15, 16, 17, 18, 19, or 20 chirally controlled internucleotidic linkages; and the pattern of backbone chiral centers is or comprises:
(Rp/Op)t[(Np/Op)n]y(Rp/Op)m, wherein each of (Rp/Op)t and (Rp/Op)m independently comprises at least 1, 2, 3, 4, 5, 6, 7, 8, 9, or 10 Rp;
(Rp)(Rp/Op)t[(Np/Op)n]y(Rp/Op)m(Rp); or
(Rp)t[(Np/Op)n]y(Rp)m;

wherein:
each Np is independently Rp or Sp,
each of t, n, y, and m is independently 1-50.

2. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
each chiral internucleotidic linkage of the oligonucleotides of the plurality is independently a chirally controlled internucleotidic linkage; and
the pattern of backbone chiral centers is or comprises:
(Rp/Op)t[(Np/Op)n]y(Rp/Op)m, wherein each of (Rp/Op)t and (Rp/Op)m independently comprises at least 1, 2, 3, 4, 5, 6, 7, 8, 9, or 10 Rp;
(Rp)(Rp/Op)t[(Np/Op)n]y(Rp/Op)m(Rp); or
(Rp)t[(Np/Op)n]y(Rp)m;

wherein:
each Np is independently Rp or Sp,
each of t, n, y, and m is independently 1-50.

3. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
oligonucleotides of the plurality comprise at least 1, 2, 3, 4, 5, 6, 7, 8, 9, 10, 11, 12, 13, 14, 15, 16, 17, 18, 19, or 20 chiral modified internucleotidic linkages each independently having a stereopurity of at least 90%, 91%, 92%, 93%, 94%, 95%, 96%, 97%, 98%, or 99% at its chiral linkage phosphorus; and
the pattern of backbone chiral centers is or comprises:
(Rp/Op)t[(Np/Op)n]y(Rp/Op)m, wherein each of (Rp/Op)t and (Rp/Op)m independently comprises at least 1, 2, 3, 4, 5, 6, 7, 8, 9, or 10 Rp;
(Rp)(Rp/Op)t[(Np/Op)n]y(Rp/Op)m(Rp); or
(Rp)t[(Np/Op)n]y(Rp)m;

wherein:
each Np is independently Rp or Sp,
each of t, n, y, and m is independently 1-50.

4. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
each chiral linkage phosphorus center of the oligonucleotides of the plurality independently has a stereopurity of at least 90%, 91%, 92%, 93%, 94%, 95%, 96%, 97%, 98%, or 99%; and
the pattern of backbone chiral centers is or comprises:
(Rp/Op)t[(Np/Op)n]y(Rp/Op)m, wherein each of (Rp/Op)t and (Rp/Op)m independently comprises at least 1, 2, 3, 4, 5, 6, 7, 8, 9, or 10 Rp;
(Rp)(Rp/Op)t[(Np/Op)n]y(Rp/Op)m(Rp); or
(Rp)t[(Np/Op)n]y(Rp)m;

wherein:
each Np is independently Rp or Sp,
each of t, n, y, and m is independently 1-50.

5. The composition of any one of the preceding embodiments, wherein the composition is a chirally controlled oligonucleotide composition characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

6. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
which composition is chirally controlled in that it is enriched, relative to a substantially racemic preparation of oligonucleotides having the same base sequence, for oligonucleotides of the particular oligonucleotide type, wherein:
the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

7. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
oligonucleotides of the plurality comprise at least 1, 2, 3, 4, 5, 6, 7, 8, 9, 10, 11, 12, 13, 14, 15, 16, 17, 18, 19, or 20 chirally controlled internucleotidic linkages; and
the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

8. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
each chiral internucleotidic linkage of the oligonucleotides of the plurality is independently a chirally controlled internucleotidic linkage; and
the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

9. A composition comprising a plurality of oligonucleotides of a particular oligonucleotide type defined by:

1) base sequence;
2) pattern of backbone linkages;
3) pattern of backbone chiral centers; and
4) pattern of backbone phosphorus modifications,
oligonucleotides of the plurality comprise at least 1, 2, 3, 4, 5, 6, 7, 8, 9, 10, 11, 12, 13, 14, 15, 16, 17, 18, 19, or 20 chiral modified internucleotidic linkages each independently having a stereopurity of at least 90%, 91%, 92%, 93%, 94%, 95%, 96%, 97%, 98%, or 99% at its chiral linkage phosphorus; and
the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

10. A composition comprising a plurality of oligonucleotides of a particular oligonucleotide type defined by:
1) base sequence;
2) pattern of backbone linkages;
3) pattern of backbone chiral centers; and
4) pattern of backbone phosphorus modifications,
each chiral linkage phosphorus center of the oligonucleotides of the plurality independently has a stereopurity of at least 90%, 91%, 92%, 93%, 94%, 95%, 96%, 97%, 98%, or 99%; and
the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a negative control reference composition, and combinations thereof.

11. The composition of any one of the preceding embodiments, wherein a transcript is a pre-mRNA.

12. The composition of any one of the preceding embodiments, wherein inclusion of a nucleic acid sequence is or comprises inclusion of an exon.

13. The composition of any one of the preceding embodiments, wherein splicing of the transcript provides mRNA.

14. The composition of any one of the preceding embodiments, wherein level of inclusion of an exon is increased.

15. The composition of any one of the preceding embodiments, wherein inclusion of the exon provides an mRNA that encodes a protein that has higher activity and/or stability compared to a protein encoded by a corresponding mRNA which does not include the exon but otherwise has the same exons.

16. The composition of any one of the preceding embodiments, wherein inclusion of the exon provides an mRNA that encodes a protein that has higher activity and/or stability in that the protein can ameliorate a symptom of a condition, disorder or disease compared to a protein encoded by a corresponding mRNA which does not include the exon but otherwise has the same exons.

17. The composition of any one of the preceding embodiments, wherein inclusion of the exon provides an mRNA that encodes a protein that are less associated with, or not associated with, a condition, disease or disorder, compared to a protein encoded by a corresponding mRNA which does not include the exon but otherwise has the same exons.

18. The composition of any one of the preceding embodiments, wherein the plurality of oligonucleotides are of the same constitution.

19. The composition of any one of the preceding embodiments, wherein the oligonucleotide composition can increase inclusion of an exon by 10%, 20%, 30%, 40%, 50%, 60%, 70%, 80%, 90%, 100% or more, or 1.1, 1.2, 1.3, 1.4, 1.5, 2, 3, 4, 5, 6, 7, 8, 9, 10 fold or more, relative to an appropriate stereorandom oligonucleotide composition comprising a plurality of oligonucleotides of the same constitution as the plurality of oligonucleotides of the oligonucleotide composition under an appropriate condition.

20. An oligonucleotide composition comprising a SMN2 oligonucleotide which comprises one or more ASGR-binding moieties.

21. The composition of embodiment 20, wherein the oligonucleotide composition can increase inclusion of an exon by 10%, 20%, 30%, 40%, 50%, 60%, 70%, 80%, 90%, 100% or more, or 1.1, 1.2, 1.3, 1.4, 1.5, 2, 3, 4, 5, 6, 7, 8, 9, 10 fold or more, relative to a reference oligonucleotide composition which is identical to the oligonucleotide composition except that its SMN2 oligonucleotide does not contain any ASGR-binding moieties.

22. The composition of any one of the preceding embodiments, wherein the oligonucleotide composition can increase inclusion of an exon by 30% or more.

23. The composition of any one of the preceding embodiments, wherein the oligonucleotide composition can increase inclusion of an exon by 40% or more.

24. The composition of any one of the preceding embodiments, wherein the oligonucleotide composition can increase inclusion of an exon by 50% or more.

25. The composition of any one of the preceding embodiments, wherein an appropriate condition comprises an oligonucleotide concentration of 0.1 uM or less.

26. The composition of any one of the preceding embodiments, wherein an appropriate condition is a condition utilized to produce one or more data of the present disclosure.

27. The composition of any one of the preceding embodiments, wherein inclusion of the exon is inclusion of exon 7 of SMN2.

28. The composition of any one of the preceding embodiments, wherein inclusion of the exon provides increased levels of full-length SMN protein.

29. The composition of any one of the preceding embodiments, wherein a condition, disease or disorder is a SMN2-associated condition, disease or disorder.

30. The composition of embodiment 29, wherein the condition, disease or disorder is SMA.

31. The composition of embodiment 29, wherein the condition, disease or disorder is ALS.

32. An oligonucleotide composition, wherein the oligonucleotide comprises at least one modification of a sugar, base or internucleotidic linkage, and the base sequence of the oligonucleotide comprises at least 15 contiguous bases of a base sequence of an oligonucleotide disclosed in the specification, and the oligonucleotide is capable of increasing the level of an exon 7-containing SMN2 transcript when administered to a system comprising unspliced exon 7-containing SMN2 transcript.

33. A composition comprising a plurality of oligonucleotides of a particular oligonucleotide type characterized by:
a) a common base sequence;
b) a common pattern of base modifications;
c) a common pattern of sugar modifications;
d) a common pattern of backbone linkages;
e) a common pattern of backbone chiral centers; and
f) a common pattern of additional chemical moieties, if any;

which composition is chirally controlled in that it is enriched, relative to a substantially racemic preparation of oligonucleotides having the same common base sequence, for oligonucleotides of the particular oligonucleotide type; and wherein the oligonucleotide targets a SMN2 transcript and can mediate an increase in the level, activity and/or expression of an exon 7-containing SMN2 transcript or its gene product.

34. A chirally controlled oligonucleotide composition comprising oligonucleotides which have:
   a) a common base sequence having a region of complementarity to an SMN2 RNA;
   b) a common pattern of backbone linkages, which comprises at least one chiral internucleotidic linkage comprising a chiral linkage phosphorus;
   which composition is chirally controlled in that the composition is enriched, relative to a substantially racemic preparation of oligonucleotides having the same common base sequence and the same common pattern of backbone linkages, for oligonucleotides that have a) the common base sequence, b) the common pattern of backbone linkages; and c) a specific stereochemical configuration selected from Rp and Sp at the chiral linkage phosphorus of the at least one chiral internucleotidic linkage (chirally controlled internucleotidic linkage);
   wherein the oligonucleotides comprise a nucleotidic unit which comprises a 2'-substituent.

35. An composition of an oligonucleotide, wherein the oligonucleotide comprises at least one modification of a sugar, base or internucleotidic linkage, and the base sequence of the oligonucleotide comprises at least 15 contiguous bases of a base sequence of an oligonucleotide disclosed in the specification, and the oligonucleotide is capable of increasing the level of an exon 7-containing SMN2 transcript when administered to a splicing system comprising unspliced exon 7-containing SMN2 transcript.

36. The composition of any of embodiments 32-35, wherein the composition is chirally controlled.

37. The composition of embodiment 36, wherein the oligonucleotide composition can increase the level of an exon 7-containing SMN2 transcript by 10%, 20%, 30%, 40%, 50%, 60%, 70%, 80%, 90%, 100% or more relative to a stereorandom oligonucleotide composition having the same base sequence, pattern of sugar modifications, pattern of internucleotidic linkages, and additional chemical moieties, if any.

38. The composition of any one of the preceding embodiments, wherein a splicing system is an in vitro splicing system.

39. The composition of any one of the preceding embodiments, wherein a splicing system is a cell, tissue or organ.

40. The composition of any one of the preceding embodiments, wherein the oligonucleotides have a length of 15 to 100 nucleobases.

41. The composition of any one of the preceding embodiments, wherein the oligonucleotides have a length of 15 to 50 nucleobases.

42. The composition of any one of the preceding embodiments, wherein the oligonucleotides have a length of 17 to 50 nucleobases.

43. The composition of any one of the preceding embodiments, wherein the oligonucleotides have a length of 17 to 25 nucleobases.

44. The composition of any one of the preceding embodiments, wherein the oligonucleotides have a length of 17 to 23 nucleobases.

45. The composition of any one of the preceding embodiments, wherein the oligonucleotides hybridize to an intron.

46. The composition of any one of the preceding embodiments, wherein the oligonucleotides have a base sequence complementary to an intron sequence of a transcript.

47. The composition of any one of the preceding embodiments, wherein the oligonucleotides have a base sequence 100% complementary to an intron sequence of a transcript.

48. The composition of any one of the preceding embodiments, wherein the oligonucleotides have a base sequence complementary to an intron sequence of a SMN2 pre-mRNA.

49. The composition of any one of the preceding embodiments, wherein the oligonucleotides have a base sequence complementary to an intron 7 sequence of a SMN2 pre-mRNA.

50. The composition of any one of the preceding embodiments, wherein the oligonucleotides hybridize to a SMN2 sequence that is or comprises ISS-N1 or a portion thereof.

51. The composition of any one of the preceding embodiments, wherein the oligonucleotides hybridize to a SMN2 sequence that is or comprises CCAGCAUU.

52. The composition of any one of the preceding embodiments, wherein the oligonucleotides have a base sequence complementary to a SMN2 sequence that is or comprises ISS-N1 or a portion thereof.

53. The composition of any one of the preceding embodiments, wherein the oligonucleotides have a base sequence complementary to a SMN2 sequence that is or comprises CCAGCAUU.

54. The composition of any one of the preceding embodiments, wherein the oligonucleotides have a base sequence that is or comprises a base sequence complementary to 5'-CCAGCAUU-3', wherein each N is independently A, T, C, G or U.

55. The composition of any one of the preceding embodiments, wherein the oligonucleotides have a base sequence that is or comprises a base sequence complementary to 5'-CCAGCNNNNNGAAAG-3' (SEQ ID NO: 4), wherein each N is independently A, T, C, G or U.

56. The composition of any one of the preceding embodiments, wherein the oligonucleotides have a base sequence that is or comprises a base sequence complementary to 5'-CCAGCAUUAUGAAAG-3' (SEQ ID NO: 3), wherein each N is independently A, T, C, G or U.

57. The composition of any one of the preceding embodiments, wherein sequence of the oligonucleotides is or comprises CUUUCNNNNNGCUGG (SEQ ID NO: 480), wherein each N is independently A, T, C, G or U.

58. The composition of any one of the preceding embodiments, wherein sequence of the oligonucleotides is or comprises AATGCTGG, wherein each T may be optionally and independently replaced with U.

59. The composition of any one of the preceding embodiments, wherein sequence of the oligonucleotides is or comprises TCACTTTCATAATGCTGG (SEQ ID NO: 479), wherein each T may be optionally and independently replaced with U.

60. The composition of any one of the preceding embodiments, wherein sequence of the oligonucleotides is TCACTTTCATAATGCTGG (SEQ ID NO: 479), wherein each T may be optionally and independently replaced with U.

61. The composition of any one of the preceding embodiments, wherein sequence of the oligonucleotides is TCACTTTCATAATGCTGG (SEQ ID NO: 1).

62. The composition of any one of the preceding embodiments, wherein the oligonucleotides have a base sequence that is or comprises a base sequence of a SMN2 oligonucleotide disclosed in the specification.

63. The composition of any one of the preceding embodiments, wherein the oligonucleotides have a base sequence that is a base sequence of a SMN2 oligonucleotide disclosed in the specification.

64. The composition of any one of the preceding embodiments, wherein oligonucleotides have a base sequence that is the base sequence of a SMN2 oligonucleotide disclosed the specification, and have the pattern of sugar modifications and/or the pattern of internucleotidic linkages a SMN2 oligonucleotide disclosed in the specification.

65. The composition of any one of the preceding embodiments, wherein the oligonucleotides have a base sequence of a SMN2 oligonucleotide disclosed in the specification, and have the pattern of sugar modifications and the pattern of internucleotidic linkages of a SMN2 oligonucleotide disclosed in the specification.

66. The composition of any one of the preceding embodiments, wherein each nucleobase is independently an optionally substituted A, T, C, G, or U, or an optionally substituted tautomer of A, T, C, G, or U.

67. The composition of any one of the preceding embodiments, wherein each nucleobase is independently an optionally substituted A, T, C, G, or U.

68. The composition of any one of the preceding embodiments, wherein each nucleobase is independently A, T, C, 5 mC, G, or U.

69. The composition of any one of the preceding embodiments, wherein the oligonucleotides comprise one or more modified sugar moieties.

70. The composition of any one of the preceding embodiments, wherein each sugar moiety is independently

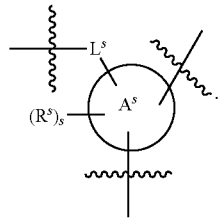

71. The composition of any one of the preceding embodiments, wherein each sugar moiety is independently an optionally substituted beta-D-deoxyribofuranose or beta-D-ribofuranose moiety.

72. The composition of any one of the preceding embodiments, wherein each sugar moiety is independently

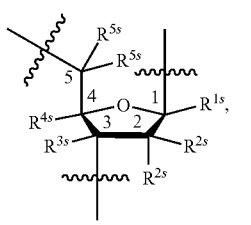 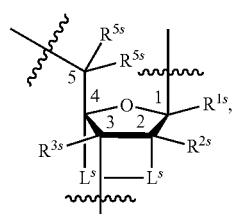

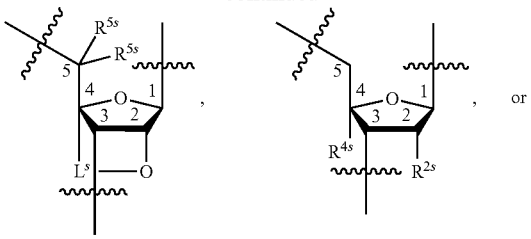

73. The composition of any one of the preceding embodiments, wherein one or more sugar moieties comprise a 2'-modification.

74. The composition of any one of the preceding embodiments, wherein a 2'-modification is —$R^{2s}$, wherein —$R^{2s}$ is —F or —OR, wherein R is optionally substituted $C_{1-6}$ alkyl.

75. The composition of any one of the preceding embodiments, wherein a 2'-modification is 2'-OMe.

76. The composition of any one of the preceding embodiments, wherein a 2'-modification is 2'-MOE.

77. The composition of embodiment 70, wherein each sugar moiety comprises 2'-MOE.

78. The composition of embodiment 70, wherein each sugar moiety is

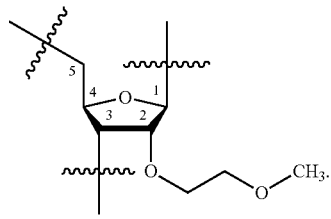

79. The composition of any one of the preceding embodiments, wherein a sugar moiety is

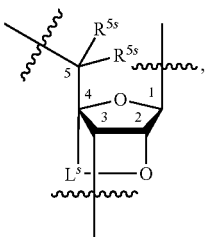

wherein $L^s$ is optionally substituted $C_{1-6}$ alkylene.

80. The composition of embodiment 79, wherein $L^s$ is optionally substituted methylene.

81. The composition of embodiment 79, wherein $L^s$ is —$CH_2$—.

82. The composition of embodiment 79, wherein $L^s$ is —(R)—CH(Me)-.

83. The composition of embodiment 79, wherein $L^s$ is —(S)—CH(Me)-.

84. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, sugar moieties of each of the oligonucleotides are modified.

85. The composition of any one of the preceding embodiments, wherein each sugar modification is the same, if applicable.

86. The composition of any one of the preceding embodiments, wherein the oligonucleotides comprise one or more modified internucleotidic linkages.

87. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, internucleotidic linkages of each of the oligonucleotides are modified.

88. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, internucleotidic linkages of each of the oligonucleotides are modified internucleotidic linkages comprising chiral linkage phosphorus.

89. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, internucleotidic linkages of each of the oligonucleotides are chirally controlled.

90. The composition of any one of the preceding embodiments, wherein each sugar modification is the same, if applicable.

91. The composition of any one of the preceding embodiments, wherein the oligonucleotides comprise one or more modified internucleotidic linkages.

92. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, internucleotidic linkages of each of the oligonucleotides are modified.

93. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, internucleotidic linkages of each of the oligonucleotides are modified internucleotidic linkages comprising chiral linkage phosphorus.

94. The composition of any one of the preceding embodiments, wherein at least 10%, 20%, 30%, 40%, 50%, 60%, 70%, 80%, 90%, or 100%, or at least 1, 2, 3, 4, 5, 6, 7, 8, 9, 10, 11, 12, 13, 14, 15, 16, 17, 18, 19, or 20, internucleotidic linkages of each of the oligonucleotides are chirally controlled.

95. The composition of any one of the preceding embodiments, wherein at least 5 internucleotidic linkages of each of the oligonucleotides are chirally controlled.

96. The composition of any one of the preceding embodiments, wherein at least 10 internucleotidic linkages of each of the oligonucleotides are chirally controlled.

97. The composition of any one of the preceding embodiments, wherein each chiral phosphorus of the oligonucleotides is independently chirally controlled.

98. The composition of any one of the preceding embodiments, wherein each internucleotidic linkage of the oligonucleotides independently has the structure of formula I, I-a, I-b, I-c, I-n-1, I-n-2, I-n-3, II, II-a-1, II-a-2, II-b-1, II-b-2, II-c-1, II-c-2, II-d-1, or II-d-2, or a salt form thereof.

99. The composition of any one of the preceding embodiments, wherein the oligonucleotides each comprise a neutral internucleotidic linkage having the structure of formula I, I-a, I-b, I-c, I-n-1, I-n-2, I-n-3, II, II-a-1, II-a-2, II-b-1, II-b-2, II-c-1, II-c-2, II-d-1, or II-d-2.

100. The composition of any one of the preceding embodiments, wherein each internucleotidic linkage of the oligonucleotides independently has the structure of formula I:

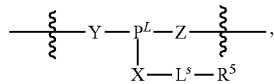

or a salt form thereof, wherein:
$P^L$ is P(=W), P, or P→B(R')$_3$;
W is O, S or Se;
each of $R^1$ and $R^5$ is independently —H, -$L^s$-R, halogen, —CN, —NO$_2$, -$L^s$-Si(R)$_3$, —OR, —SR, or —N(R)$_2$;
each of X, Y and Z is independently —O—, —S—, —N(-$L^s$-$R^1$)—, or $L^s$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;
each R' is independently —R, —C(O)R, —C(O)OR, or —S(O)$_2$R;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

101. The composition of any one of the preceding embodiments, wherein $P^L$ is P(=W), or P.
102. The composition of any one of the preceding embodiments, wherein W is O or S.
103. The composition of any one of the preceding embodiments, wherein W is O.
104. The composition of any one of the preceding embodiments, wherein X is O or S.
105. The composition of any one of the preceding embodiments, wherein at least one X is S.
106. The composition of any one of the preceding embodiments, wherein Y is O.
107. The composition of any one of the preceding embodiments, wherein Z is O.
108. The composition of any one of the preceding embodiments, wherein -$L^s$-$R^5$ is —H.
109. The composition of any one of the preceding embodiments, wherein each internucleotidic linkage of the oligonucleotides is independently natural phosphate linkage or phosphorothioate linkage.
110. The composition of any one of the preceding embodiments, wherein each chiral linkage phosphorus of the oligonucleotides independently has a stereopurity of 90%, 91%, 92%, 93%, 94%, 95%, 96%, 97%, 98%, or 99% or more.
111. The composition of any one of the preceding embodiments, wherein each chiral linkage phosphorus of the oligonucleotides independently has a stereopurity of 95% or more.
112. The composition of any one of the preceding embodiments, wherein each chiral linkage phosphorus of the oligonucleotides independently has a stereopurity of 97% or more.
113. The composition of any one of the preceding embodiments, wherein the oligonucleotides of the plurality has a diastereopurity of no less than (D)$^n$ in the composition, wherein n is the number of chirally controlled internucleotidic linkage in each of the oligonucleotides, wherein D is 90%-100%.
114. The composition of any one of the preceding embodiments, wherein the oligonucleotides of the plurality has a diastereopurity of no less than (D)$^n$ in the composition, wherein n is the number of chirally controlled internucleotidic linkage in each of the oligonucleotides, wherein D is 95%.
115. The composition of any one of the preceding embodiments, wherein the oligonucleotides of the plurality has a diastereopurity of no less than (D)$^n$ in the composition, wherein n is the number of chirally controlled internucleotidic linkage in each of the oligonucleotides, wherein D is 97%.
116. The composition of any one of the preceding embodiments, wherein diastereopurity of an oligonucleotide is product of stereopurity of each chiral linkage phosphorus in the oligonucleotide.
117. The composition of any one of the preceding embodiments, wherein the oligonucleotides each comprises at least 1, 2, 3, 4, 5, 6, 7, 8, 9, 10, 11, 12, 13, 14, 15, 16, 17, 18, 19, or 20, internucleotidic linkages comprising a linkage phosphorus in Rp configuration.
118. The composition of any one of the preceding embodiments, wherein the oligonucleotides each comprises at least 5 internucleotidic linkages comprising a linkage phosphorus in Rp configuration.
119. The composition of any one of the preceding embodiments, wherein the oligonucleotides each comprises at least 10 internucleotidic linkages comprising a linkage phosphorus in Rp configuration.
120. The composition of any one of the preceding embodiments, wherein at least 10%, 20%, 30%, 40%, 50%, 60%, 70%, 80%, or 90%, or 100%, internucleotidic linkages of the oligonucleotides comprises a linkage phosphorus in Rp configuration.
121. The composition of any one of the preceding embodiments, wherein at least 40%, 50%, 60%, 70%, 80%, or 90%, or 100%, internucleotidic linkages of the oligonucleotides comprises a linkage phosphorus in Rp configuration.
122. The composition of any one of the preceding embodiments, wherein at least 50% internucleotidic linkages of the oligonucleotides comprises a linkage phosphorus in Rp configuration.
123. The composition of any one of the preceding embodiments, wherein at least 60% internucleotidic linkages of the oligonucleotides comprises a linkage phosphorus in Rp configuration.
124. The composition of any one of the preceding embodiments, wherein at least 70% internucleotidic linkages of the oligonucleotides comprises a linkage phosphorus in Rp configuration.
125. The composition of any one of the preceding embodiments, wherein the oligonucleotides comprise or are a 5'-first block-second block-third block-3' structure.
126. The composition of any one of the preceding embodiments, wherein the first block is a 5'-wing, the second block is a core, and the third block is a 3'-wing.
127. The composition of any one of the preceding embodiments, wherein the first block comprises at least 1, 2, 3, 4, 5, 6, 7, 8, 9, 10, 11, 12, 13, 14, 15, 16, 17, 18, 19, or 20 nucleobases and/or internucleotidic linkages.
128. The composition of any one of the preceding embodiments, wherein the first block comprises at least 1, 2, 3, 4, 5, 6, 7, 8, 9, 10, 11, 12, 13, 14, 15, 16, 17, 18, 19, or 20 Rp linkage phosphorus.
129. The composition of any one of the preceding embodiments, wherein at least 10%, 20%, 30%, 40%, 50%, 60%, 70%, 80%, 90%, or 100%, linkage phosphorus of the first block is chirally controlled and is Rp.
130. The composition of any one of the preceding embodiments, wherein the second block comprises at least 1, 2, 3, 4, 5, 6, 7, 8, 9, 10, 11, 12, 13, 14, 15, 16, 17, 18, 19, or 20 Rp or Sp linkage phosphorus.
131. The composition of any one of the preceding embodiments, wherein the second block comprises at least 1, 2, 3, 4, 5, 6, 7, 8, 9, 10, 11, 12, 13, 14, 15, 16, 17, 18, 19, or 20 Rp linkage phosphorus.
132. The composition of any one of the preceding embodiments, wherein the second block comprises more Rp than Sp, if any, linkage phosphorus.
133. The composition of any one of the preceding embodiments, wherein the second block comprises at least 1, 2, 3, 4, 5, 6, 7, 8, 9, 10, 11, 12, 13, 14, 15, 16, 17, 18, 19, or 20 natural phosphate linkages.
134. The composition of any one of the preceding embodiments, wherein the third block comprises at least 1, 2, 3, 4, 5, 6, 7, 8, 9, 10, 11, 12, 13, 14, 15, 16, 17, 18, 19, or 20 nucleobases and/or internucleotidic linkages.

135. The composition of any one of the preceding embodiments, wherein the third block comprises at least 1, 2, 3, 4, 5, 6, 7, 8, 9, 10, 11, 12, 13, 14, 15, 16, 17, 18, 19, or 20 Rp linkage phosphorus.

136. The composition of any one of the preceding embodiments, wherein at least 10%, 20%, 30%, 40%, 50%, 60%, 70%, 80%, 90%, or 100%, linkage phosphorus of the third block is chirally controlled and is Rp.

137. The composition of any one of the preceding embodiments, wherein the first block optionally comprises a sugar modification not in the second block.

138. The composition of any one of the preceding embodiments, wherein the first block optionally comprises a sugar modification not in the third block.

139. The composition of any one of the preceding embodiments, wherein the pattern of backbone chiral centers of a first block comprises or is (Sp)t, (Rp)t, (Np/Op)t, (Rp/Op)t, or Rp(Rp/Op)t.

140. The composition of any one of the preceding embodiments, wherein the pattern of backbone chiral centers of a second block comprises or is [(Np/Op)n]y, [(Rp/Op)n]y, or [(Sp/Op)n]y.

141. The composition of any one of the preceding embodiments, wherein the pattern of backbone chiral centers of a third block comprises or is (Sp)m, (Rp)m, (Np/Op)m, (Rp/Op)m, or (Rp/Op)mRp.

142. The composition of any one of the preceding embodiments, wherein the pattern of backbone chiral centers is or comprises (Rp/Op)t[(Np/Op)n]y(Rp/Op)m.

143. The composition of any one of the preceding embodiments, wherein each of (Rp/Op)t and (Rp/Op)m independently comprises at least 1, 2, 3, 4, 5, 6, 7, 8, 9, or 10 Rp.

144. The composition of any one of the preceding embodiments, wherein each of (Rp/Op)t and (Rp/Op)m independently comprises at least 2 Rp.

145. The composition of any one of the preceding embodiments, wherein the pattern of backbone chiral centers is or comprises (Rp)(Rp/Op)t[(Np/Op)n]y(Rp/Op)m(Rp).

146. The composition of any one of the preceding embodiments, wherein the pattern of backbone chiral centers is or comprises (Rp)t[(Np/Op)n]y(Rp)m.

147. The composition of any one of the preceding embodiments, wherein the pattern of backbone chiral centers is or comprises (Rp)t[(Np)n]y(Rp)m.

148. The composition of any one of the preceding embodiments, wherein the pattern of backbone chiral centers is or comprises (Np)t[(Op)n(Sp)m]y.

149. The composition of any one of the preceding embodiments, wherein the pattern of backbone chiral centers is or comprises (Np)t[(Rp)n(Sp)m]y.

150. The composition of any one of the preceding embodiments, wherein at least one Np is Rp.

151. The composition of any one of the preceding embodiments, wherein at least one Np is Sp.

152. The composition of any one of the preceding embodiments, wherein each Np is the same.

153. The composition of any one of the preceding embodiments, wherein the pattern of backbone chiral centers is or comprises (Rp)t[(Sp)n]y(Rp)m.

154. The composition of any one of the preceding embodiments, wherein the pattern of backbone chiral centers is (Rp)t[(Sp)n]y(Rp)m.

155. The composition of any one of the preceding embodiments, wherein y is 1-20.

156. The composition of embodiment 155, wherein y is 1.

157. The composition of embodiment 155, wherein y is 2, 3, 4, 5, 6, 7, 8, 9, 10, 11, 12, 13, 14, or 15.

158. The composition of any one of the preceding embodiments, wherein t is 1-20.

159. The composition of embodiment 158, wherein t is 1.

160. The composition of embodiment 158, wherein t is 2, 3, 4, 5, 6, 7, 8, 9, 10, 11, 12, 13, 14, or 15.

161. The composition of embodiment 158, wherein t is 3 or more.

162. The composition of embodiment 158, wherein t is 4 or more.

163. The composition of embodiment 158, wherein t is 5 or more.

164. The composition of embodiment 158, wherein t is 4.

165. The composition of embodiment 158, wherein t is 5.

166. The composition of embodiment 158, wherein t is 6.

167. The composition of embodiment 158, wherein t is 7.

168. The composition of embodiment 158, wherein t is 8.

169. The composition of embodiment 158, wherein t is 9.

170. The composition of any one of the preceding embodiments, wherein n is 1-20.

171. The composition of embodiment 170, wherein n is 1.

172. The composition of embodiment 170, wherein n is 2, 3, 4, 5, 6, 7, 8, 9, 10, 11, 12, 13, 14, or 15.

173. The composition of embodiment 170, wherein n is 3 or more.

174. The composition of embodiment 170, wherein n is 4 or more.

175. The composition of embodiment 170, wherein n is 5 or more.

176. The composition of embodiment 170, wherein n is 5 or more.

177. The composition of embodiment 170, wherein n is 2.

178. The composition of embodiment 170, wherein n is 3.

179. The composition of embodiment 170, wherein n is 4.

180. The composition of embodiment 170, wherein n is 5.

181. The composition of embodiment 170, wherein n is 6.

182. The composition of any one of the preceding embodiments, wherein m is 1-20.

183. The composition of embodiment 182, wherein m is 1.

184. The composition of embodiment 182, wherein m is 2, 3, 4, 5, 6, 7, 8, 9, 10, 11, 12, 13, 14, or 15.

185. The composition of embodiment 182, wherein m is 3 or more.

186. The composition of embodiment 182, wherein m is 4 or more.

187. The composition of embodiment 182, wherein m is 5 or more.

188. The composition of embodiment 182, wherein m is 4.

189. The composition of embodiment 182, wherein m is 5.

190. The composition of embodiment 182, wherein m is 6.

191. The composition of embodiment 182, wherein m is 7.

192. The composition of embodiment 182, wherein m is 8.

193. The composition of embodiment 182, wherein m is 9.

194. The composition of any one of the preceding embodiments, wherein the oligonucleotides are salts.

195. The composition of any one of the preceding embodiments, wherein the oligonucleotides are a sodium salt.

196. The composition of any one of the preceding embodiments, wherein the oligonucleotides are all-sodium salts, wherein each internucleotidic linkage is a sodium salt form of the internucleotidic linkage.

197. The composition of any one of the preceding embodiments, wherein the oligonucleotides comprise a chemical moiety selected from a targeting moiety, a lipid moiety, and a carbohydrate moiety.

198. The composition of any one of the preceding embodiments, wherein the oligonucleotides comprise a chemical moiety selected from a glucose, GluNAc, lipid and anisamide moiety.
199. The composition of any one of the preceding embodiments, wherein an oligonucleotide is conjugated via a linker to a second oligonucleotide.
200. A compound having the structure of formula O-I:

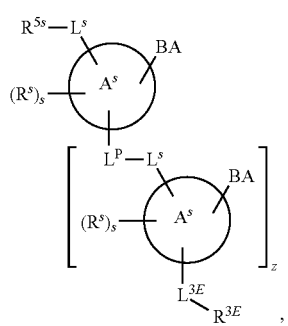

O-I or a salt thereof, wherein:

$R^{5s}$ is independently R' or —OR';

each BA is independently an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each $R^s$ is independently —F, —Cl, —Br, —I, —CN, —$N_3$, —NO, —$NO_2$, -L-R', -L-OR', -L-SR', -L-N(R')$_2$, —O-L-OR', —O-L-SR', or —O-L-N(R')$_2$;

s is 0-20;

$L^s$ is —C($R^{5s}$)$_2$—, or L;

each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N (R')—, —N(R')C(O)O—, —S(O)—, —S(O)$_2$—, —S(O)$_2$N (R')—, —C(O)S—, —C(O)O—, —P(O)(OR')—, —P(O) (SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP (NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring $A^s$ is independently an optionally substituted 3-20 membered monocyclic, bicyclic or polycyclic ring having 0-10 heteroatoms;

each $L^P$ is independently an internucleotidic linkage;

z is 1-1000;

$L^{3E}$ is L or -L-L-;

$R^{3E}$ is —R', -L-R', —OR', or a solid support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

201. The compound of embodiment 200, wherein each $L^P$ independently has the structure of formula I, I-a, I-b, I-c, I-n-1, I-n-2, I-n-3, II, II-a-1, II-a-2, II-b-1, II-b-2, II-c-1, II-c-2, II-d-1, or II-d-2.

202. The compound of embodiment 201, wherein 1, 2, 3, 4, 5, 6, 7, 8, 9, 10 or more $L^P$ each independently have the structure of formula I-n-1, I-n-2, I-n-3, II, II-a-1, II-a-2, II-b-1, II-b-2, II-c-1, II-c-2, II-d-1, or II-d-2.

203. A compound having the structure of formula O-I:

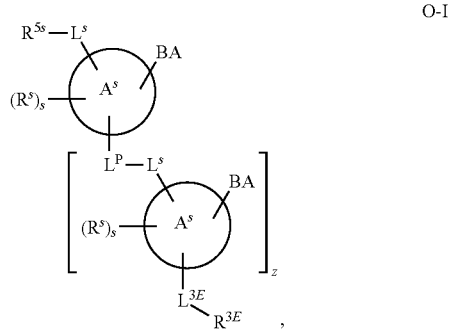

O-I or a salt thereof, wherein:

$R^{5s}$ is independently R' or —OR';

each BA is independently an optionally substituted group selected from $C_{3-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

each $R^s$ is independently —F, —Cl, —Br, —I, —CN, —$N_3$, —NO, —$NO_2$, -L-R', -L-OR', -L-SR', -L-N(R')$_2$, —O-L-OR', —O-L-SR', or —O-L-N(R')$_2$;

s is 0-20;

$L^s$ is —C($R^{5s}$)$_2$—, or L;

each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each Ring $A^s$ is independently an optionally substituted 3-20 membered monocyclic, bicyclic or polycyclic ring having 0-10 heteroatoms;

each $L^P$ independently has the structure of formula I:

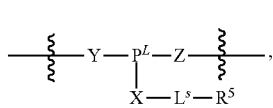

I or a salt form thereof, wherein:
$P^L$ is P(=W), P, or P→B(R')$_3$;
W is O, S or Se;
each of $R^1$ and $R^5$ is independently —H, -$L^s$-R, halogen, —CN, —NO$_2$, -$L^s$-Si(R)$_3$, —OR, —SR, or —N(R)$_2$;
each of X, Y and Z is independently —O—, —S—, —N(-$L^s$-$R^1$)—, or $L^s$;
z is 1-1000;
$L^{3E}$ is L or -L-L-;
$R^{3E}$ is —R', -L-R', —OR', or a solid support;
each R' is independently —R, —C(O)R, —C(O)OR, or —S(O)$_2$R;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

204. The compound of any one of embodiments 200-203, wherein $R^{5s}$-$L^s$- is $R^{5s}$—C($R^{5s}$)$_2$—.

205. The compound of embodiment 204, wherein $R^{5s}$-$L^s$- is HO—C($R^{5s}$)$_2$—.

206. The compound of any one of embodiments 200-205, wherein $L^s$ is —C($R^{5s}$)$_2$—.

207. The compound of any one of embodiments 200-205, wherein $L^s$ is —CH$_2$—.

208. The compound of any one of embodiments 200-207, wherein each BA is independently optionally substituted A, T, C, G or U, or an optionally substituted tautomer of A, T, C, G or U.

209. The compound of any one of embodiments 200-207, wherein each BA is independently A, T, C, 5 mC, G or U.

210. The compound of any one of embodiments 200-209, wherein z is no less than 15.

211. The compound of any one of embodiments 200-210, wherein $L^{3E}$ is a covalent bond.

212. The compound of any one of embodiments 200-211, wherein $R^{3E}$ is —OH.

213. The compound of any one of embodiments 200-212, wherein

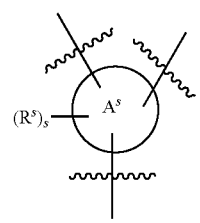

is

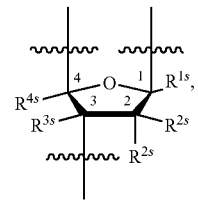

and BA is connected at C1, and $L^s$ is connected to C4, wherein each of $R^{1s}$, $R^{2s}$, $R^{3s}$, and $R^{4s}$ is independently $R^s$.

214. The compound of any one of embodiments 200-213, wherein at least one or each

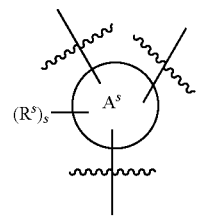

is independently

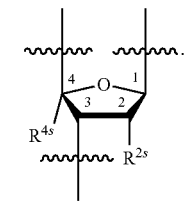

215. The compound of any one of embodiments 200-213, wherein at least one or each is independently

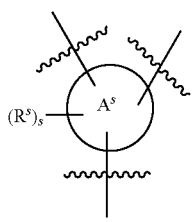

is independently

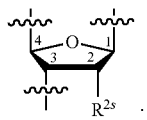

216. The compound of embodiment 215, wherein $R^{2s}$ is —F or —OR, wherein R is not hydrogen.
217. The compound of embodiment 215, wherein $R^{2s}$ is —F or —OR, wherein R is optionally substituted $C_{1-6}$ alkyl.
218. The compound of embodiment 215, wherein $R^{2s}$ is —F, —OMe, or —OCH$_2$CH$_2$OCH$_3$.
219. The compound of embodiment 215, wherein $R^{2s}$ is —OCH$_2$CH$_2$OCH$_3$.
220. The compound of any one of embodiments 200-214, wherein at least one or each

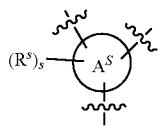

is independently

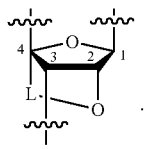

221. The compound of embodiment 220, wherein L is optionally substituted $C_{1-6}$ alkylene.
222. The compound of embodiment 220, wherein L is optionally substituted —CH$_2$—.
223. The compound of embodiment 220, wherein L is —CH$_2$—.
224. The compound of embodiment 220, wherein L is —(R)—CH(CH$_3$)—.
225. The compound of embodiment 220, wherein L is —(S)—CH(CH$_3$)—.
226. The compound of any one of embodiments 200-225, wherein each $L^P$ independently has the structure of formula I:

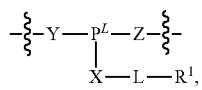

I or a salt form thereof, wherein:
$P^L$ is P(=W), P, or P→B(R')$_3$;
W is O, S or Se;
$R^1$ is -L-R, halogen, —CN, —NO$_2$, —Si(R')$_3$, —OR', —SR', or —N(R')$_2$;
each of X, Y and Z is independently —O—, —S—, —N(-L-R$^1$)—, or L;
each R' is independently —R, —C(O)R, —C(O)OR, or —S(O)$_2$R;
each L is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;
each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or
two R groups are optionally and independently taken together to form a covalent bond, or:
two or more R groups on the same atom are optionally and independently taken together with the atom to form an optionally substituted, 3-30 membered monocyclic, bicyclic or polycyclic ring having, in addition to the atom, 0-10 heteroatoms; or
two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.
227. The compound of any one of embodiments 200-226, wherein $P^L$ is P(=W) or P.
228. The compound of any one of embodiments 200-227, wherein W is O or S.
229. The compound of any one of embodiments 200-228, wherein W is O.
230. The compound of any one of embodiments 200-229, wherein Y is O.
231. The compound of any one of embodiments 200-230, wherein Z is O.
232. The compound of any one of embodiments 200-231, wherein X is O or S.
233. The compound of any one of embodiments 200-231, wherein at least one X is S.
234. The compound of any one of embodiments 200-232, wherein -L$^s$-R$^5$ is —H or -L-R$^1$ is —H.
235. The compound of any one of the preceding embodiments, wherein each sugar unit independently has the structure of 236. The compound of any one of the preceding embodiments, wherein each nucleoside unit independently has the structure of

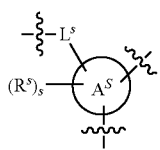

237. The compound of any one of the preceding embodiments, wherein each nucleotide unit independently has the structure of

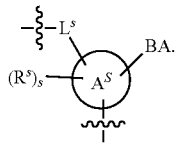

238. The compound of any one of the preceding embodiments, wherein the oligonucleotide is conjugated to a chemical moiety through a linker.
239. The compound of any one of the preceding embodiments, wherein the oligonucleotide is conjugated to a carbohydrate moiety through a linker.
240. The compound of any one of the preceding embodiments, wherein the oligonucleotide is conjugated to a target moiety through a linker.
241. The compound of any of embodiments 200-240, wherein the moiety is or comprises a ligand moiety of a receptor.
242. The compound of embodiment 241, wherein the receptor is a sigma-receptor.
243. The compound of embodiment 241, wherein the receptor is a sigma 1-receptor.
244. The compound of embodiment 242 or 243, wherein the ligand is an anisamide.
245. The compound of embodiment 241, wherein the receptor is asialoglycoprotein receptor.
246. The compound of embodiment 241, wherein the moiety is or comprises GalNAc.
247. The compound of any one of embodiments 200-245, wherein the moiety and the linker has the structure of:

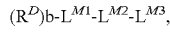

wherein:
each $R^D$ is independently a chemical moiety;
each of $L^{M1}$, $L^{M2}$, and $L^{M3}$ is independently is a covalent bond, or a bivalent or multivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;
each $Cy^L$ is independently an optionally substituted tetravalent group selected from a $C_{3-20}$ cycloaliphatic ring, a $C_{6-20}$ aryl ring, a 5-20 membered heteroaryl ring, and a 3-20 membered heterocyclyl ring; and
b is 1-1000.
248. An oligonucleotide comprising one or more structures of:

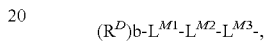

wherein:
each of $L^{M1}$, $L^{M2}$, and $L^{M3}$ is independently is a covalent bond, or a bivalent or multivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;
each $Cy^L$ is independently an optionally substituted tetravalent group selected from a $C_{3-20}$ cycloaliphatic ring, a $C_{6-20}$ aryl ring, a 5-20 membered heteroaryl ring, and a 3-20 membered heterocyclyl ring; and
b is 1-1000.
249. The compound of embodiment 247 or 248, wherein b is 1, and $L^{M1}$ is bivalent.
250. The compound of embodiment 247 or 248, wherein b is 3, and $L^{M1}$ is tetravalent.
251. The compound of any one of embodiments 247-250, wherein $L^{M1}$ comprises one or more —N(R')— and one or more —C(O)—.
252. The compound of any one of embodiments 247-251, wherein $L^{M2}$ is a covalent bond, or a bivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$.

253. The compound of any one of embodiments 247-251, wherein L$^{M2}$ is a covalent bond, or a bivalent, optionally substituted, linear or branched C$_{1-10}$ aliphatic wherein one or more methylene units are optionally and independently replaced with C$_{1-6}$ alkylene, C$_{1-6}$ alkenylene, —C≡C—, —C(R')$_2$—, —O—, —S—, —N(R')—, or —C(O)—.

254. The compound of any one of embodiments 247-253, wherein L$^{M2}$-NH—(CH$_2$)$_6$—, wherein —NH— is bonded to L$^{M1}$.

255. The compound of any one of embodiments 247-254, wherein L$^{M3}$ is —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')—, —OP(O)(SR')—, —OP(O)(R')—, —OP(O)(NR')—, —OP(S)(OR')—, —OP(S)(SR')—, —OP(S)(R')—, —OP(S)(NR')—, —OP(R')—, —OP(OR')—, —OP(SR')—, —OP(NR')—, or —OP(OR')[B(R')$_3$]—.

256. The compound of any one of embodiments 247-254, wherein L$^{M3}$ is —OP(O)(OR')—, or —OP(O)(SR')—, wherein —O— is bonded to L$^{M2}$.

257. The compound of any one of embodiments 255-256, wherein the P atom is connected to a sugar unit, a nucleobase unit, or an internucleotidic linkage.

258. The compound of any one of embodiments 255-257, wherein the P atom is connected to a —OH group through formation of a P—O bond.

259. A compound having the structure:

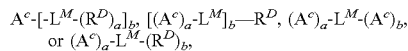

or a salt thereof, wherein:
each A$^c$ is independently an oligonucleotide moiety (e.g., H-A$^c$, [H]$_a$-A$^c$ or [H]$_b$-A$^c$ is an oligonucleotide);
a is 1-1000;
b is 1-1000;
L$^M$ is a multivalent linker; and
each R$^D$ is independently a chemical moiety; and
wherein the compound targets a SMN2 transcript and is capable of mediating an increase in an exon 7-containing SMN2 transcript or a gene product thereof.

260. The compound of embodiment 259, wherein the compound has the structure of A$^c$-[-L$^M$-(R$^D$)$_a$]$_b$ or a salt thereof.

261. The compound of embodiment 259, wherein the compound has the structure of [(A$^c$)$_a$-L$^M$]$_b$—R$^D$ or a salt thereof.

262. The compound of embodiment 259, wherein the compound has the structure of (A$^c$)$_a$-L$^M$-(A$^c$)$_b$ or a salt thereof.

263. The compound of embodiment 259, wherein the compound has the structure of (A$^c$)$_a$-L$^M$-(R$^D$)$_b$ or a salt thereof.

264. The compound of any one of embodiments 259-263, wherein [H]$_a$-A$^c$ or [H]$_b$-A$^c$ is a compound of any one of embodiments 1-237.

265. The compound of any one of embodiments 259-263, wherein the oligonucleotide is an oligonucleotide of any one of embodiments 238-258.

266. The compound of any one of 259-265, wherein each L$^M$ is independently a covalent bond, or a bivalent or multivalent, optionally substituted, linear or branched group selected from a C$_{1-100}$ aliphatic group and a C$_{1-100}$ heteroaliphatic group having 1-30 heteroatoms, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)$_S$—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$.

267. The compound of any one of 259-265, wherein L$^M$ is -L$^{M1}$-L$^{M2}$-L$^{M3}$-.

268. The compound of any one of embodiments 255-258, wherein the P atom is connected to the 5'-OH group through formation of a P—O bond.

269. The compound of any one of the preceding embodiments, wherein the oligonucleotide is conjugated to a lipid moiety through a linker.

270. The compound of any one of embodiments 200-269, wherein the moiety or R$^D$ binds to ASGR.

271. The compound of any one of embodiments 200-270, wherein the moiety or R$^D$ is GalNAc or a derivative thereof.

272. The compound of any one of embodiments 200-269, wherein the moiety or R$^D$ is selected from: optionally substituted phenyl,

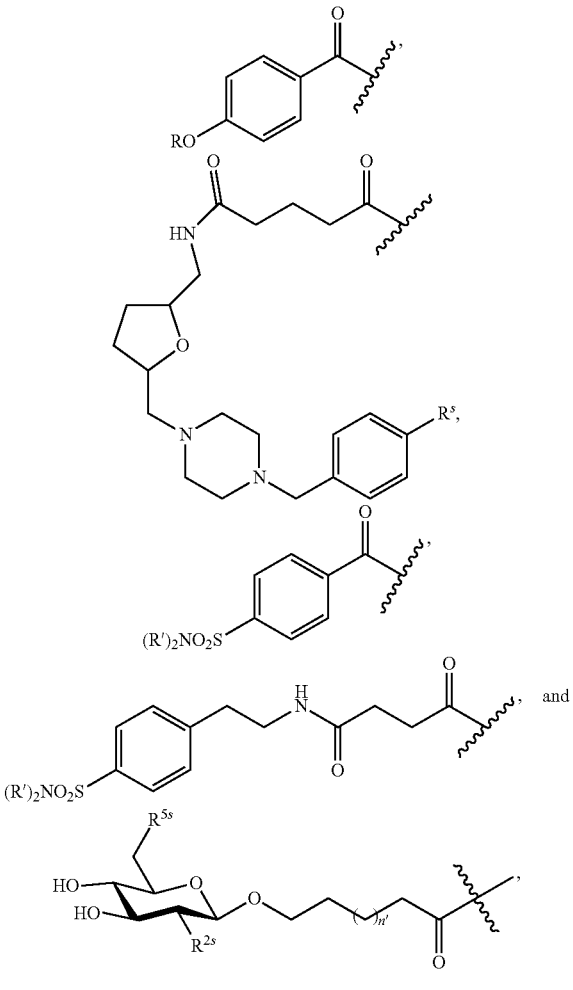

wherein n' is 0 or 1.

273. The compound of any one of embodiments 200-272, wherein the moiety or $R^D$ is selected from:
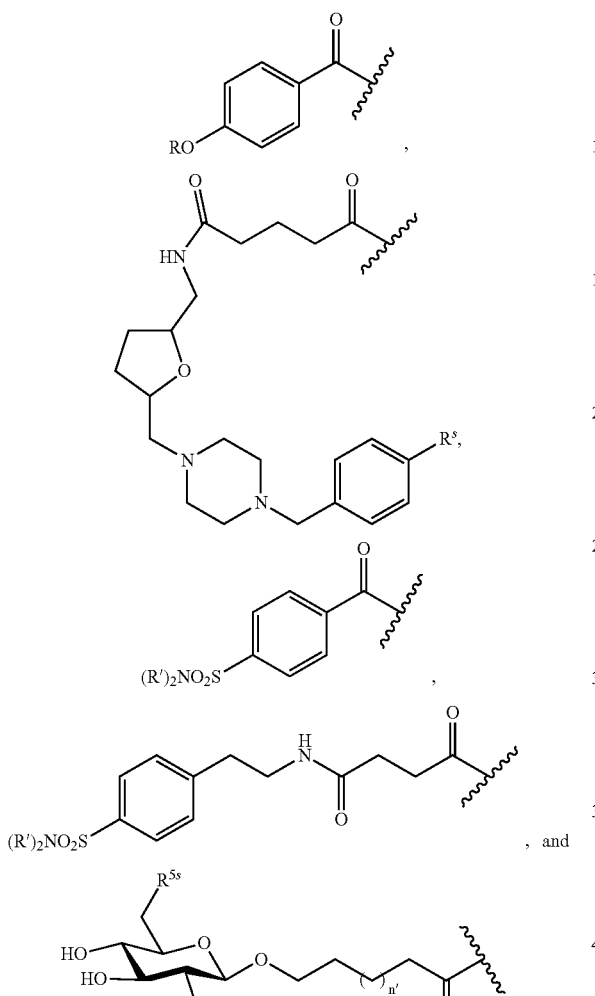
wherein n' is 0 or 1.
274. The compound of any one of embodiments 272-273, wherein n' is 0.
275. The compound of any one of embodiments 272-273, wherein n' is 1.
276. The compound of any one of embodiments 272-275, wherein the moiety or $R^D$ is selected from:
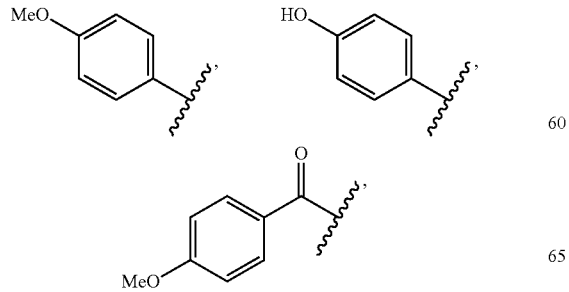
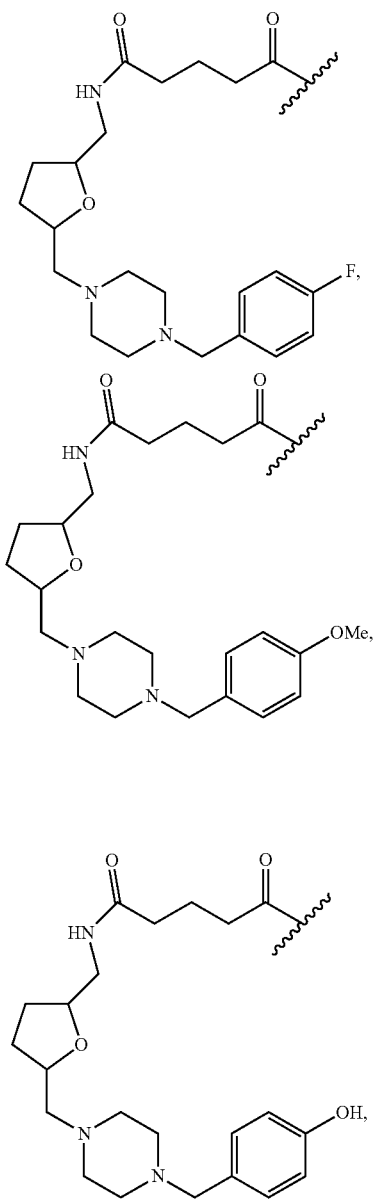
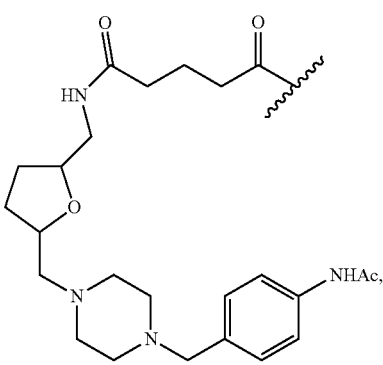

397
-continued
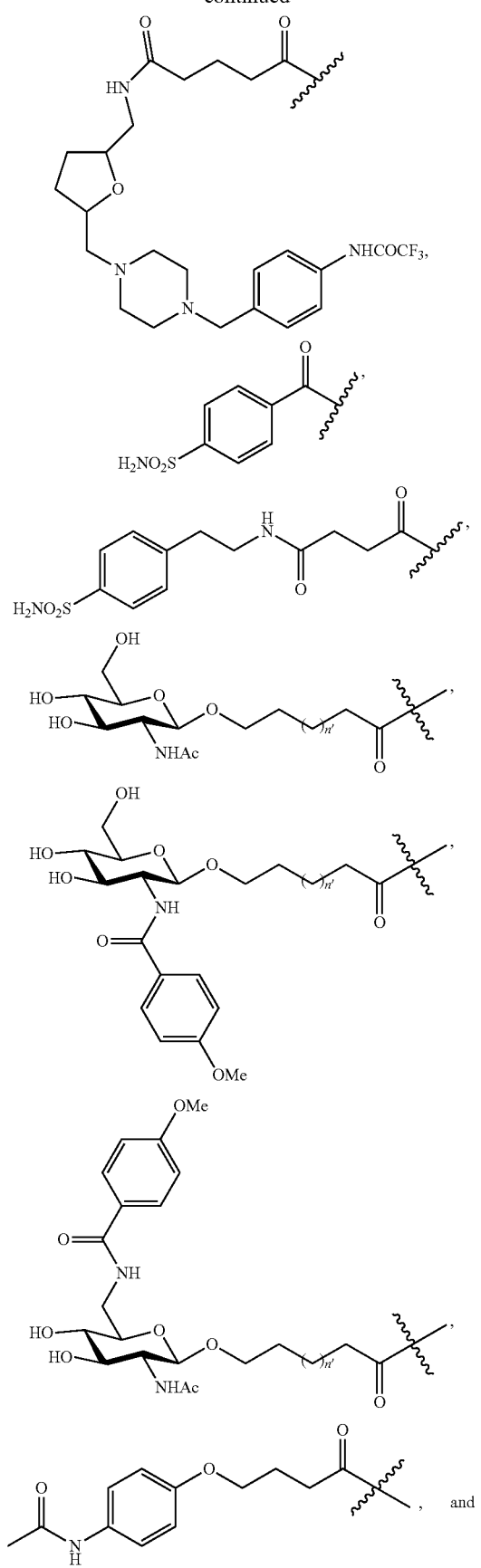
277. The compound of any one of embodiments 272-275, wherein the moiety or $R^D$ is selected from:
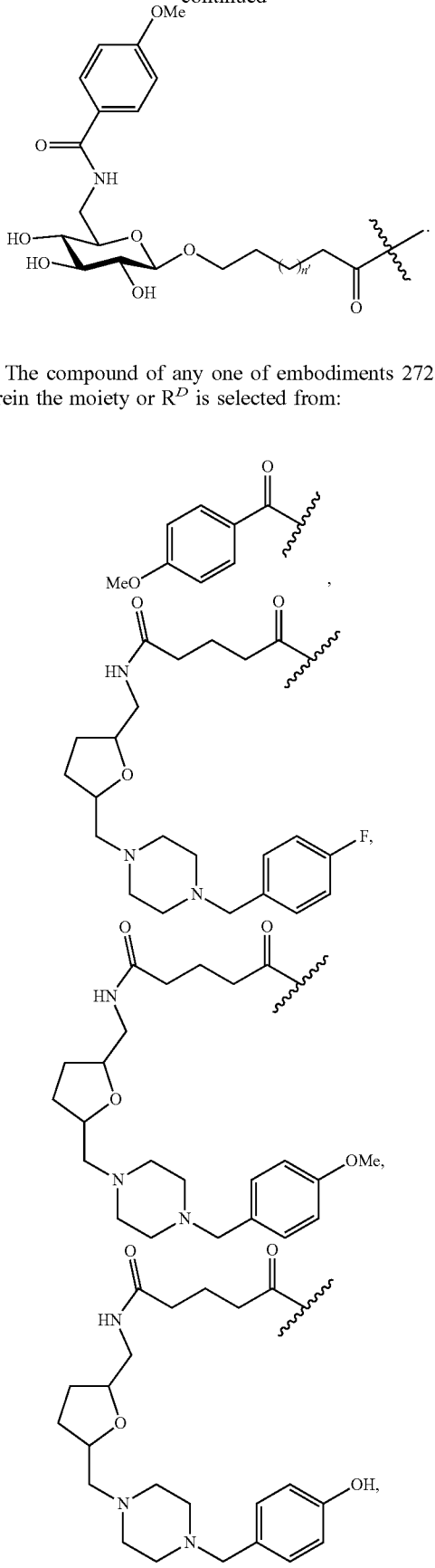

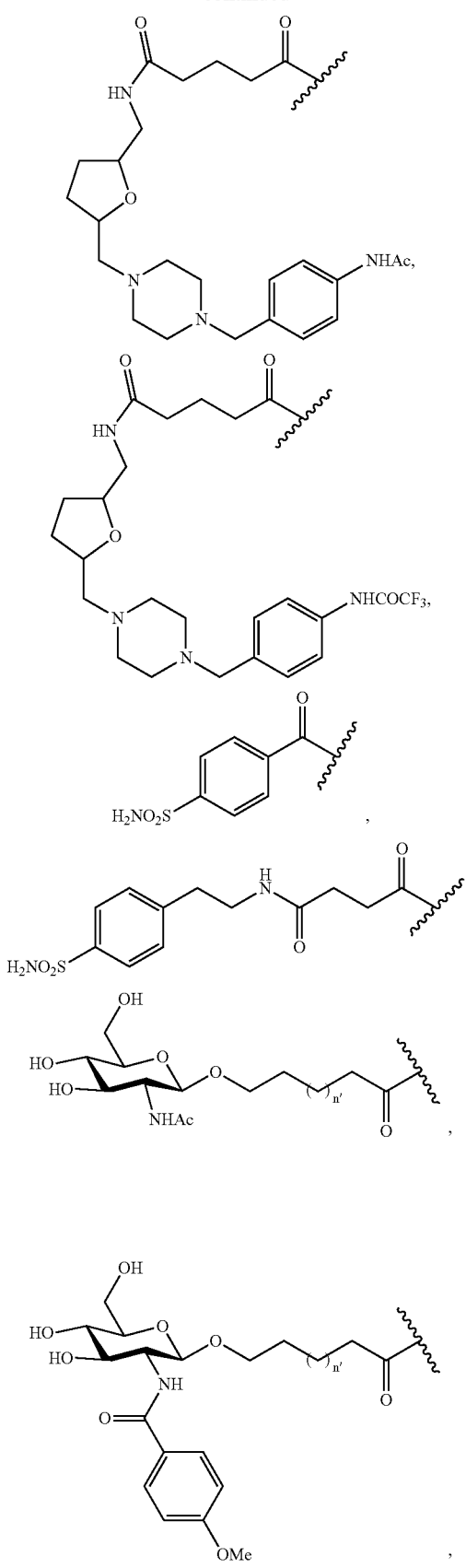

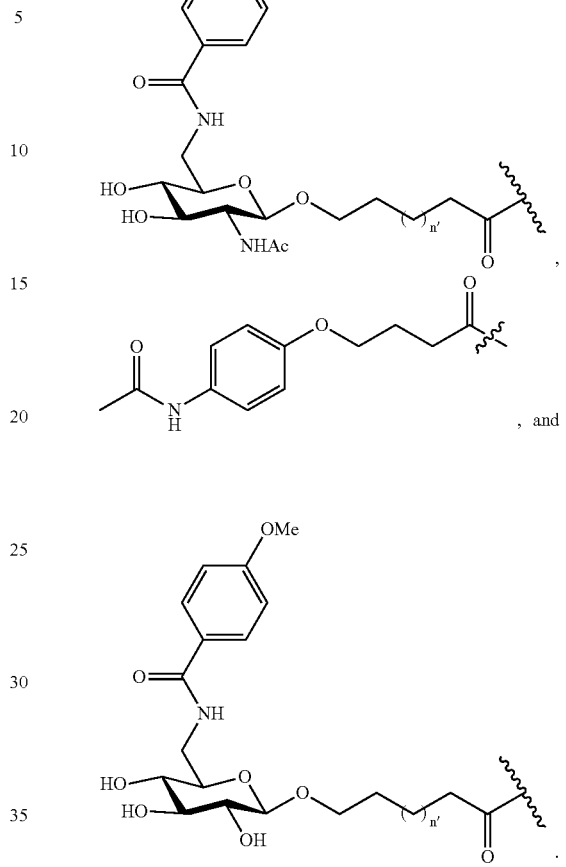

278. The compound of any one of embodiments 200-277, wherein the linker is $L^M$, wherein $L^M$ is a covalent bond, or a bivalent or multivalent, optionally substituted, linear or branched group selected from a $C_{1-100}$ aliphatic group and a $C_{1-100}$ heteroaliphatic group having 1-30 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$.

279. The compound of embodiment 278, wherein $L^M$ is multivalent, and connects two or more moieties to the oligonucleotide.

280. The compound of embodiment 278, wherein $L^M$ is tetravalent, and connects three moieties to the oligonucleotide.

281. The compound of any one of embodiments 200-280, wherein the linker or $L^{M1}$ is or comprises:

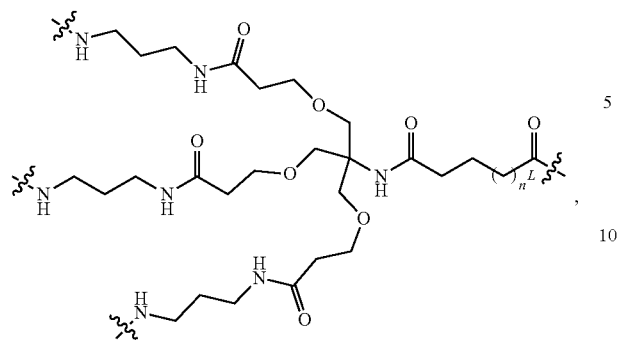

wherein $n^L$ is 1-8.

282. The compound of any one of embodiments 200-281, wherein the linker or -$L^{M1}$-$L^{M2}$-$L^{M3}$- is:

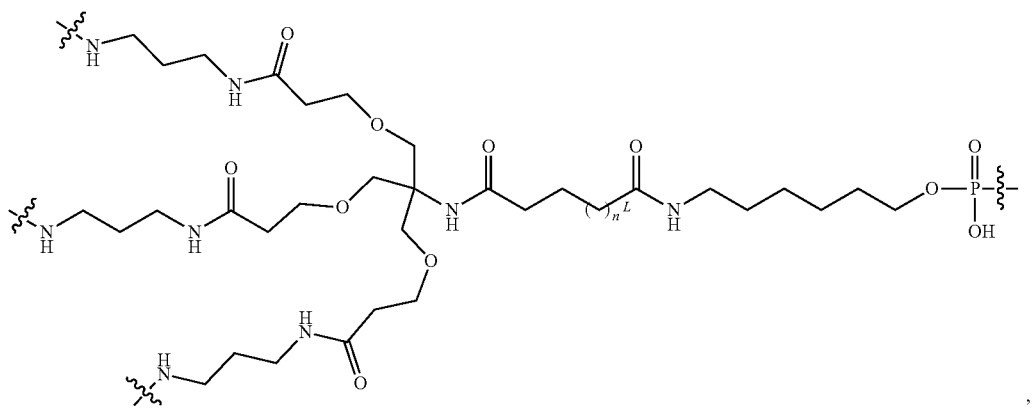

or a salt form thereof, wherein $n^L$ is 1-8.

283. The compound of any one of embodiments 200-282, wherein the linker or $L^{M1}$-$L^{M2}$-$L^{M3}$- is

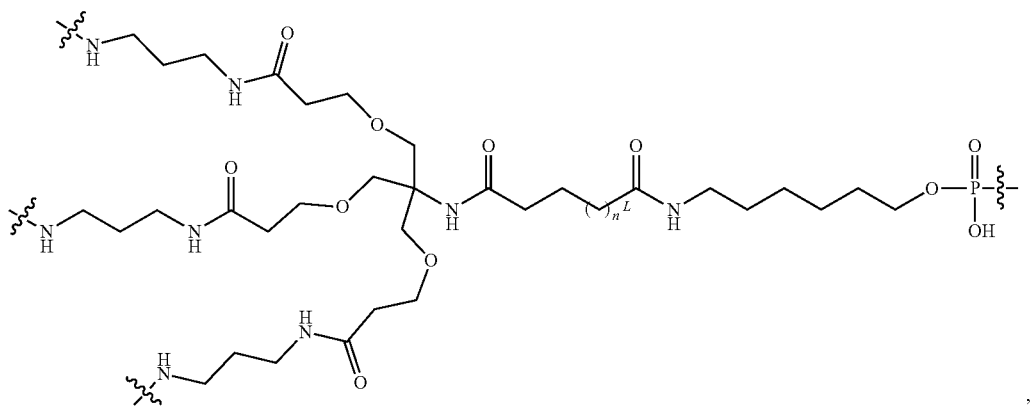

or a salt form thereof, wherein:
$n^L$ is 1-8.
each amino group independently connects to a moiety; and
the P atom connects to the 5'-OH of the oligonucleotide.

284. The compound of any one of embodiments 200-283, wherein the moiety and the linker, or $(R^D)$b-$L^{M1}$-$L^{M2}$-$L^{M3}$-, is or comprises:

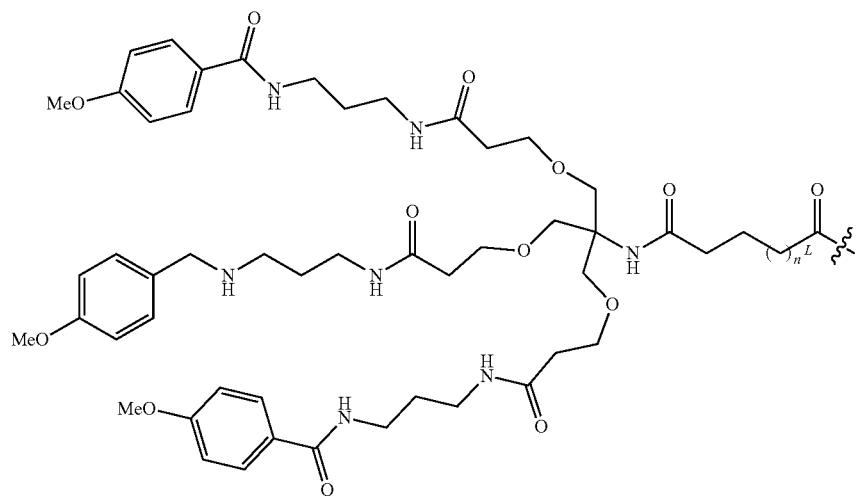
285. The compound of any one of embodiments 200-283, wherein the moiety and the linker, or $(R^D)b\text{-}L^{M1}\text{-}L^{M2}\text{-}L^{M3}\text{-}$, is or comprises:
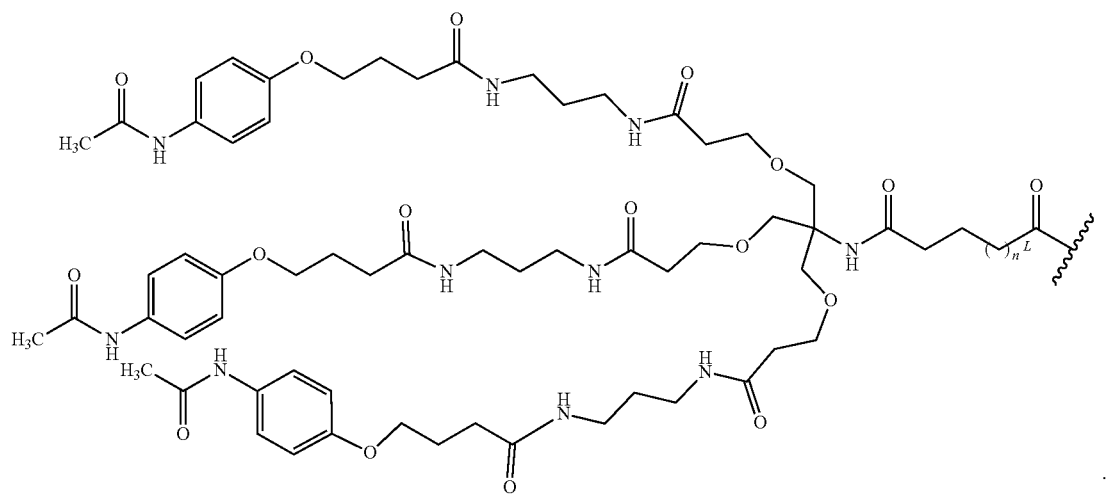
286. The compound of any one of embodiments 200-283, wherein the moiety and the linker, or $(R^D)b\text{-}L^{M1}\text{-}L^{M2}\text{-}L^{M3}\text{-}$, is or comprises:

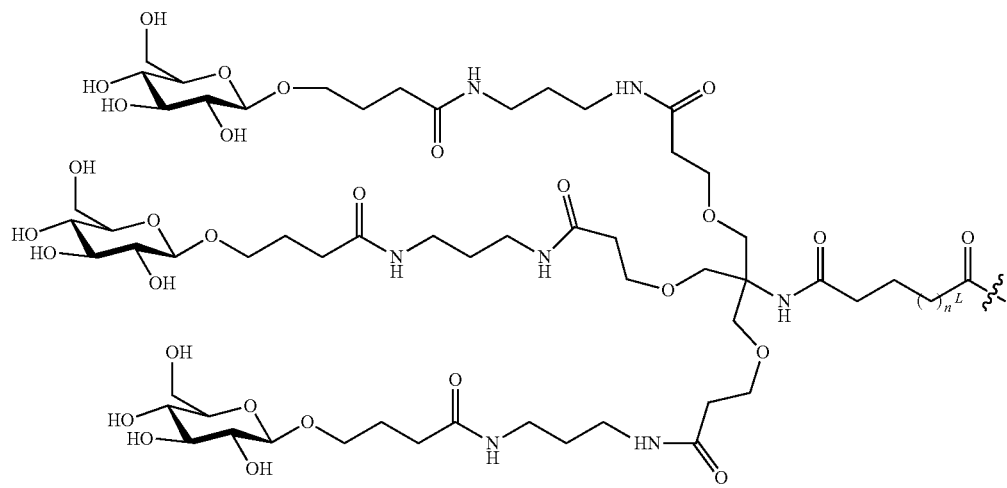
287. The compound of any one of embodiments 200-283, wherein the moiety and the linker, or $(R^D)b\text{-}L^{M1}\text{-}L^{M2}\text{-}L^{M3}\text{-}$, is or comprises:
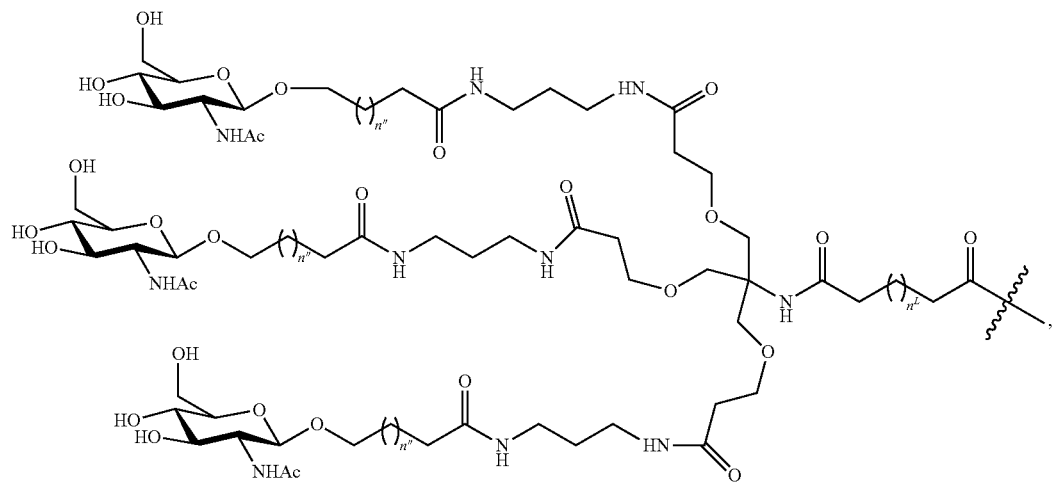
wherein n" is 1 or 2.
288. The compound of embodiment 287, wherein n" is 1.
289. The compound of embodiment 287, wherein n" is 2.
290. The compound of any one of embodiments 200-283, wherein the moiety and the linker, or $(R^D)b\text{-}L^{M1}\text{-}L^{M2}\text{-}L^{M3}\text{-}$, is:

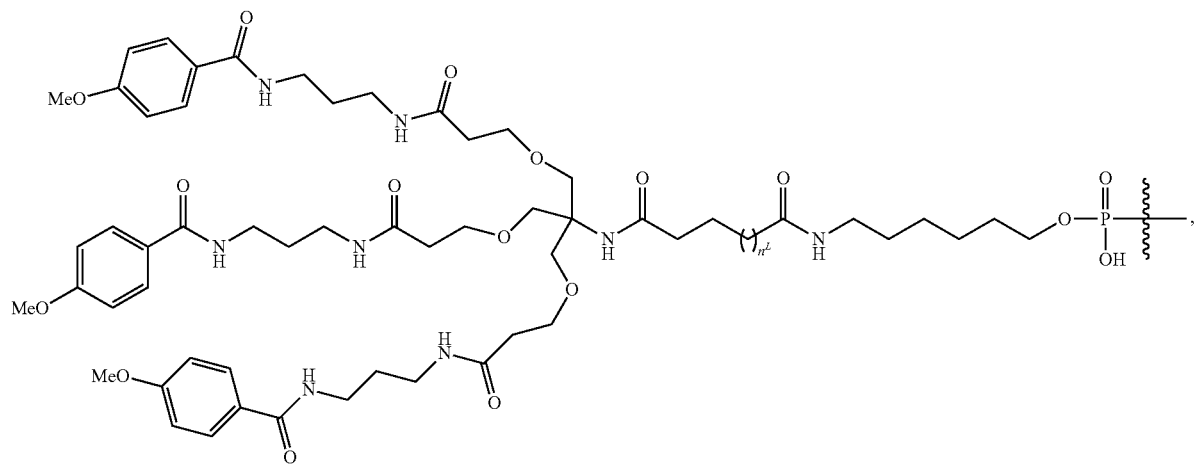
or a salt form thereof.
291. The compound of any one of embodiments 200-283, wherein the moiety and the linker, or $(R^D)b\text{-}L^{M1}\text{-}L^{M2}\text{-}L^{M3}\text{-}$, is:
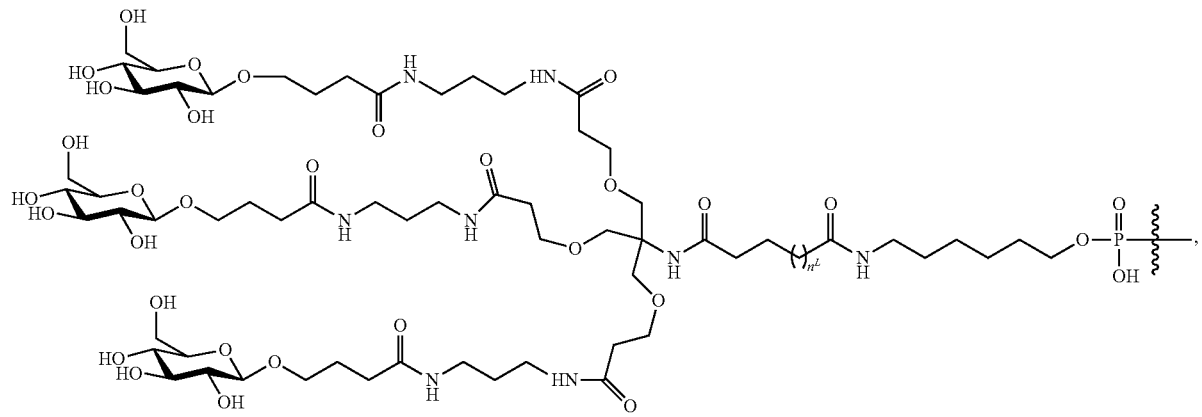
or a salt form thereof.
292. The compound of any one of embodiments 200-283, wherein the moiety and the linker, or $(R^D)b\text{-}L^{M1}\text{-}L^{M2}\text{-}L^{M3}\text{-}$, is:
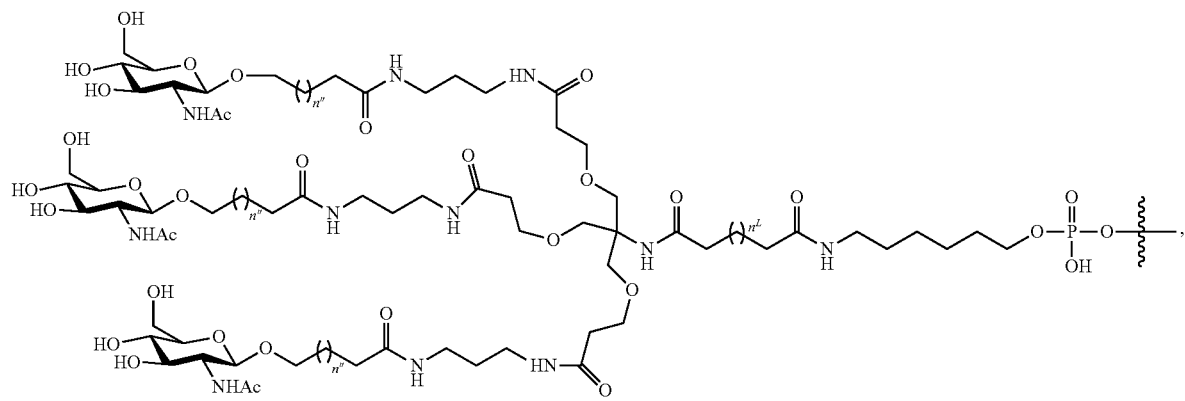
or a salt form thereof, wherein n" is 1 or 2.

293. The compound of embodiment 292, wherein n" is 1.
294. The compound of embodiment 292, wherein n" is 2.
295. The compound of any one of embodiments 200-280, wherein the linker, or $L^{M1}$, is or comprises:

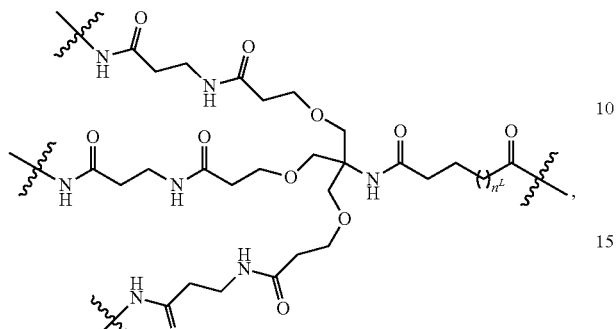

wherein $n^L$ is 1-8.

296. The compound of embodiment 295, wherein the moiety and linker, or $(R^D)b\text{-}L^{M1}\text{-}L^{M2}\text{-}L^{M3}\text{-}$, is or comprises:

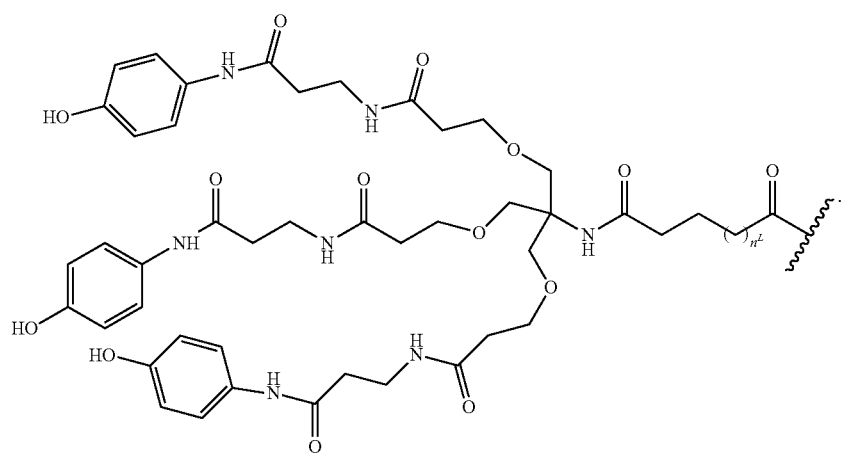

297. The compound of embodiment 295, wherein the moiety and linker, or $(R^D)b\text{-}L^{M1}\text{-}L^{M2}\text{-}L^{M3}\text{-}$, is or comprises:

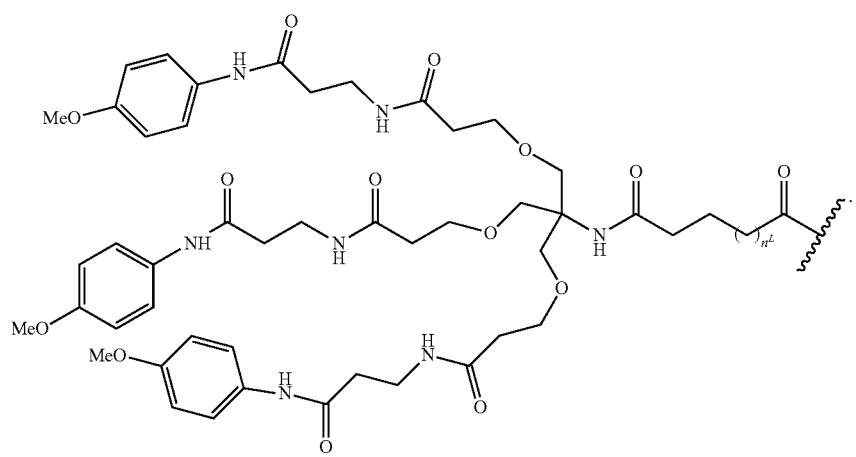

298. The compound of any one of embodiments 278-297, wherein $n^L$ is 1.

299. The compound of any one of embodiments 278-297, wherein $n^L$ is 8.

300. The compound of any one of the preceding embodiments, wherein each heteroatom is independently selected from oxygen, nitrogen, sulfur, boron, silicon, and phosphorus.

301. The compound of any one of the preceding embodiments, wherein each heteroatom is independently selected from oxygen, nitrogen, sulfur, and phosphorus.

302. The compound of any one of the preceding embodiments, wherein each heteroatom is independently selected from oxygen, nitrogen, and sulfur.

303. The compound of any one of the preceding embodiments, having a purity of at least 50%, 60%, 70%, 80%, 85%, 90%, 95%, 96%, 97%, 98%, or 99%.

304. The compound of any one of the preceding embodiments, having a diastereomeric purity of at least 50%, 60%, 70%, 80%, 85%, 90%, 95%, 96%, 97%, 98%, or 99%.

305. The compound of any one of the preceding embodiments, wherein the compound is a sodium salt.

306. The compound of any one of the preceding embodiments, wherein the compound is a sodium salt, in which each natural phosphate linkage is in its sodium salt form —O—P(O)(ONa)—O— and each phosphorothioate linkage is in its sodium salt form —O—P(O)(SNa)—O—.

307. The compound of any one of the preceding embodiments, wherein the compound is an oligonucleotide of the plurality of the composition of any one of embodiments 1-199.

308. The compound of any one of the preceding embodiments, wherein the compound comprises a base sequence targeting a SMN2 intron sequence.

309. The compound of any one of the preceding embodiments, wherein the compound comprises a base sequence targeting a SMN2 intron 7 sequence.

310. The compound of any one of the preceding embodiments, wherein the compound comprises a base sequence selected from Table 1A, or a portion thereof, wherein the portion is of 10, 11, 12, 13, 14, 15, 16, 17, 18, or 19 consecutive nucleobases.

311. The compound of any one of the preceding embodiments, wherein the compound targets a SMN2 transcript and is capable of mediating an increase in the level, activity and/or expression of an exon 7-containing SMN2 transcript or its gene product.

312. The composition of any one of embodiments 1-199, wherein oligonucleotides of the plurality are each independently a compound of any one of embodiments 200-311.

313. An oligonucleotide composition comprising a plurality of oligonucleotides which have:
 a) a common base sequence;
 b) a common pattern of backbone linkages, which comprises at least one chiral internucleotidic linkage comprising a chiral linkage phosphorus;
 which composition is chirally controlled in that the composition is enriched, relative to a substantially racemic preparation of oligonucleotides having the same common base sequence and the same common pattern of backbone linkages, for oligonucleotides that have a) the common base sequence; b) the common pattern of backbone linkages; and c) a specific stereochemical configuration selected from Rp and Sp at the chiral linkage phosphorus of the at least one chiral internucleotidic linkage (chirally controlled internucleotidic linkage),
 wherein each oligonucleotide of the plurality is independently a compound of any one of the preceding embodiments.

314. An oligonucleotide composition comprising a plurality of oligonucleotides which have:
 a) a common base sequence;
 b) a common pattern of backbone linkages;
 c) a common pattern of backbone chiral centers;
 which composition is chirally controlled in that level of the plurality of oligonucleotides in the composition is not random; and
 wherein each oligonucleotide of the plurality is independently a compound of any one of the preceding embodiments.

315. An oligonucleotide composition comprising a plurality of oligonucleotides of a particular oligonucleotide type characterized by:
 a) a common base sequence;
 b) a common pattern of backbone linkages;
 c) a common pattern of backbone chiral centers;
 which composition is chirally controlled in that it is enriched, relative to a substantially racemic preparation of oligonucleotides having the same common base sequence, for oligonucleotides of the particular oligonucleotide type; and
 wherein each oligonucleotide of the plurality is independently a compound of any one of the preceding embodiments.

316. The composition of any one of the preceding embodiments, wherein the composition is a pharmaceutical composition.

317. A pharmaceutical composition comprising a compound of any one of the preceding embodiments or a pharmaceutically acceptable salt thereof, and optionally a pharmaceutically acceptable carrier.

318. A pharmaceutical composition comprising a composition of any one of the preceding embodiments, and optionally a pharmaceutically acceptable carrier.

319. A method for altering splicing of a target transcript, comprising administering an oligonucleotide composition comprising a plurality of oligonucleotides of a particular oligonucleotide type defined by:
 1) base sequence;
 2) pattern of backbone linkages;
 3) pattern of backbone chiral centers; and
 4) pattern of backbone phosphorus modifications,
 which composition is chirally controlled in that it is enriched, relative to a substantially racemic preparation of oligonucleotides having the same common base sequence, for oligonucleotides of the particular oligonucleotide type, wherein:
 the oligonucleotide composition is characterized in that, when it is contacted with a transcript in a transcript splicing system, splicing of the transcript is altered in that level of inclusion of a nucleic acid sequence is increased relative to that observed under a reference condition selected from the group consisting of absence of the composition, presence of a reference composition, and combinations thereof.

320. In a method for altering transcript splicing of a target transcript by contacting the transcript with an oligonucleotide composition comprising oligonucleotides sharing a common base sequence,
 the improvement that comprises using as the oligonucleotide composition a chirally controlled oligonucleotide composition comprising a plurality of oligonucleotides of a particular oligonucleotide type defined by:

1) base sequence;
2) pattern of backbone linkages;
3) pattern of backbone chiral centers; and
4) pattern of backbone phosphorus modifications, which composition is chirally controlled in that it is enriched, relative to a substantially racemic preparation of oligonucleotides having the same common base sequence, for oligonucleotides of the particular oligonucleotide type, wherein:

the chirally controlled oligonucleotide composition is characterized in that, when it is contacted with a transcript in a transcript splicing system, splicing of the transcript is altered in that level of inclusion of a nucleic acid sequence is increased relative to that observed when using an otherwise comparable oligonucleotide composition, comprising oligonucleotides of the same common base sequence, that is not chirally controlled.

321. The method of any one of the preceding embodiments, wherein the oligonucleotide composition comprising a plurality of oligonucleotides of a particular oligonucleotide type is a composition of any one of the preceding embodiments.

322. A method for altering splicing of a target transcript, comprising administering a composition of any one of the preceding embodiments.

323. In a method for altering transcript splicing of a target transcript by contacting the transcript with an oligonucleotide composition comprising oligonucleotides sharing a common base sequence, the improvement that comprises using as the oligonucleotide composition a composition of any one of the preceding embodiments.

324. The method of any one of the preceding embodiments, wherein a transcript is a pre-mRNA.

325. The method of any one of the preceding embodiments, wherein inclusion of a nucleic acid sequence is or comprises inclusion of an exon.

326. The method of any one of the preceding embodiments, wherein splicing of the transcript provides mRNA.

327. The method of any one of the preceding embodiments, wherein level of inclusion of an exon is increased.

328. The method of any one of the preceding embodiments, wherein inclusion of the exon provides an mRNA that encodes a protein that has higher activity and/or stability compared to a protein encoded by a corresponding mRNA which does not include the exon but otherwise has the same exons.

329. The method of any one of the preceding embodiments, wherein inclusion of the exon provides an mRNA that encodes a protein that has higher activity and/or stability in that the protein can ameliorate a symptom of a condition, disorder or disease compared to a protein encoded by a corresponding mRNA which does not include the exon but otherwise has the same exons.

330. The method of any one of the preceding embodiments, wherein inclusion of the exon provides an mRNA that encodes a protein that are less associated with, or not associated with, a condition, disease or disorder, compared to a protein encoded by a corresponding mRNA which does not include the exon but otherwise has the same exons.

331. The method of any one of the preceding embodiments, wherein the plurality of oligonucleotides are of the same constitution.

332. The method of any one of the preceding embodiments, wherein the oligonucleotide composition can increase inclusion of an exon by 10%, 20%, 30%, 40%, 50%, 60%, 70%, 80%, 90%, 100% or more, or 1.1, 1.2, 1.3, 1.4, 1.5, 2, 3, 4, 5, 6, 7, 8, 9, 10 fold or more, relative to an appropriate stereorandom oligonucleotide composition comprising a plurality of oligonucleotides of the same constitution as the plurality of oligonucleotides of the oligonucleotide composition under an appropriate condition.

333. The method of any one of the preceding embodiments, wherein the oligonucleotide composition can increase inclusion of an exon by 30% or more.

334. The method of any one of the preceding embodiments, wherein the oligonucleotide composition can increase inclusion of an exon by 40% or more.

335. The method of any one of the preceding embodiments, wherein the oligonucleotide composition can increase inclusion of an exon by 50% or more.

336. The method of any one of the preceding embodiments, wherein an appropriate condition comprises an oligonucleotide concentration of 0.1 uM or less.

337. The method of any one of the preceding embodiments, wherein an appropriate condition is a condition utilized to produce one or more data of the present disclosure.

338. The method of any one of the preceding embodiments, wherein inclusion of the exon is inclusion of exon 7 of SMN2.

339. The method of any one of the preceding embodiments, wherein inclusion of the exon provides increased levels of full-length SMN protein.

340. The method of any one of the preceding embodiments, wherein a condition, disease or disorder is a SMN2-associated condition, disease or disorder.

341. The method of any one of embodiments 319-340, wherein the condition, disease or disorder is SMA.

342. The method of any one of embodiments 319-340, wherein the condition, disease or disorder is ALS.

343. The method of any one of embodiments 319-342, wherein the system is a cell.

344. The method of any one of embodiments 319-342, wherein the system is a tissue.

345. The method of any one of embodiments 319-342, wherein the system is an organ.

346. The method of any one of embodiments 319-342, wherein the system is an organism.

347. The method of any one of embodiments 319-342, wherein the system is a subject.

348. The method of any one of embodiments 319-342, wherein the method preferentially increases level of a non-disease-associated transcript or protein over disease associated transcript or protein.

349. A method for increasing a level of exon 7-containing SMN2 transcripts or a gene product thereby in a system, comprising administering a compound or a composition of any one of the preceding embodiments.

350. A method of increasing the level of an exon 7-containing SMN2 transcript or its gene product in a cell, comprising contacting the cell with a compound or composition of any one of the preceding embodiments, wherein the compound or oligonucleotides of the composition comprise a base sequence that is complementary to at least 15 contiguous nucleobases of SMN2.

351. A method of increasing the level of an exon 7-containing SMN2 transcript or its gene product in a cell, comprising contacting the cell with a compound or composition of any one of the preceding embodiments, wherein the compound or oligonucleotides of the composition comprise a base sequence that is complementary to at least 15 contiguous nucleobases of SMN2 intron 7.

352. A method of increasing the level of an exon 7-containing SMN2 transcript or its gene product in a cell, comprising contacting the cell with a compound or composition of any one of the preceding embodiments, wherein the compound or oligonucleotides of the composition comprise a base sequence that is, or comprises at least 15 contiguous nucleobases of, of an SMN2 oligonucleotide described in the specification.

353. A method for increasing the level of an exon 7-containing SMN2 transcript in a subject, the method comprising steps of:
   administering to the subject a compound or composition of any one of the preceding embodiments,
   wherein the compound or composition is capable of increasing the level of an exon 7-containing SMN2 transcript or its gene product in the subject.

354. A method of increasing the level of an exon 7-containing SMN2 transcript or its gene product in a subject comprising administering to the subject a therapeutically effective amount of a composition of any one of the preceding embodiments, wherein oligonucleotides of the composition specifically targets a SMN2 transcript.

355. A method for treating a condition, disorder or disease associated with splicing, wherein inclusion of an exon is not associated, or less associated, with the condition, disorder or disease compared to exclusion of the exon, comprising administering to a subject a compound or composition of any one of the preceding embodiments.

356. A method for preventing or treating a SMN2-related condition, disorder or disease, comprising administering to a subject suffering therefrom or susceptible thereto a compound or composition of any one of the preceding embodiments.

357. The method of any one of the preceding embodiments, wherein a SMN2-related condition, disorder or disease is SMA or ALS.

358. A method for preventing or treating SMA, comprising administering to a subject suffering therefrom or susceptible thereto a compound or composition of any one of the preceding embodiments.

359. A method for preventing or treating ALS, comprising administering to a subject suffering therefrom or susceptible thereto a compound or composition of any one of the preceding embodiments.

360. A method for treating a SMN2-related condition, disorder or disease in a subject, comprising administering to the subject a therapeutically effective amount of a compound or composition of any of preceding embodiments, wherein the compound or oligonucleotide of the composition specifically target a SMN2 transcript.

361. The method of embodiment 360, wherein the SMN2-related condition, disorder or disease is selected from SMA (spinal muscular atrophy) and ALS (amyotrophic lateral sclerosis).

362. The method of any one of the preceding embodiments, further comprises administering a second agent.

363. The method of any one of the preceding embodiments, wherein a second agent is administered prior to, concurrently with or subsequent to the compound or composition.

364. The method of any one of the preceding embodiments, wherein a second agent is or comprises an oligonucleotide targeting SMN2.

365. The composition, compound or method of any one of the preceding embodiments, wherein a reference condition is an otherwise identical condition absence of the composition.

366. The composition, compound or method of any one of embodiments 1-365, wherein a reference condition is an otherwise identical condition presence of a negative control reference composition instead of the composition.

367. The composition, compound or method of embodiments 366, wherein a negative control reference composition is a corresponding non-chirally controlled oligonucleotide composition which is otherwise identical or comparable.

368. The composition, compound or method of embodiments 366, wherein a negative control reference composition is a Nusinersen composition.

369. The use of a composition or compound of any one of the preceding embodiments for preparation of a pharmaceutical composition for treating a SMN2-related condition, disorder or disease.

370. The use of a composition or compound of any one of the preceding embodiments for preparation or manufacture of a pharmaceutical composition or medicament for treating a SMN2-related condition, disorder or disease.

371. The use of a composition or a compound of any one of the preceding embodiments for the preparation or manufacture of a pharmaceutical composition or medicament for treating a condition, disorder or disease.

EXEMPLIFICATION

Certain examples of provided technologies (compounds (oligonucleotides, reagents, etc.), compositions, methods (methods of preparation, use, assessment, etc.)) were presented below.

Various technologies for preparing oligonucleotides and oligonucleotide compositions (both stereorandom and chirally controlled) are known and can be utilized in accordance with the present disclosure, including, for example, those in WO/2010/064146, WO/2011/005761, WO/2013/012758, WO/2014/010250, US2013/0178612, WO/2014/012081, WO/2015/107425, WO/2017/015555, and WO/2017/062862, the methods and reagents of each of which are incorporated herein by reference. In some embodiments, certain oligonucleotides and compositions thereof were prepared by methods described in WO/2010/064146, WO/2011/005761, WO/2013/012758, WO/2014/010250, US2013/0178612, WO/2014/012081, WO/2015/107425, WO/2017/015555, and/or WO/2017/062862, optionally with optimization of, e.g., certain reaction conditions, procedures, etc.

Example 1. Conjugation of Oligonucleotides

In some embodiments, the present disclosure provides methods for conjugation of oligonucleotides, for example, for better delivery to CNS. Examples 1 and 2 describe certain example conjugation methods.

In some embodiments, provided chirally controlled oligonucleotide compositions comprise chemical moieties connected to the 5'-end optionally through linker moieties. In some embodiments, provided chirally controlled oligonucleotide compositions comprises chemical moieties connected to the 5'-end —OH optionally through a linker. In some embodiments, an example conjugation strategy is as described below:

417            418

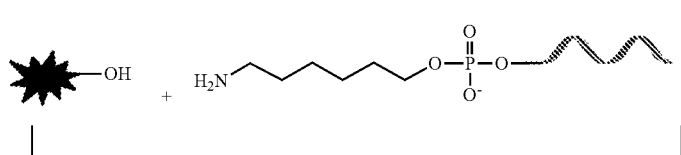            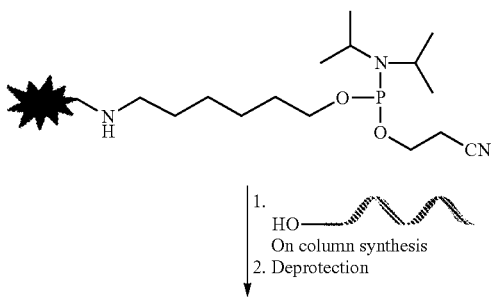

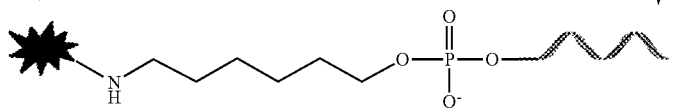

= Chemical moiety, such as targeting moiety (targeting ligand), lipid moiety, carbohydrate moiety, etc.

In some embodiments, provided chirally controlled oligonucleotide compositions comprise chemical moieties connected to the 3'-end optionally through linker moieties. In some embodiments, the present disclosure provides the following 3' conjugation strategies:

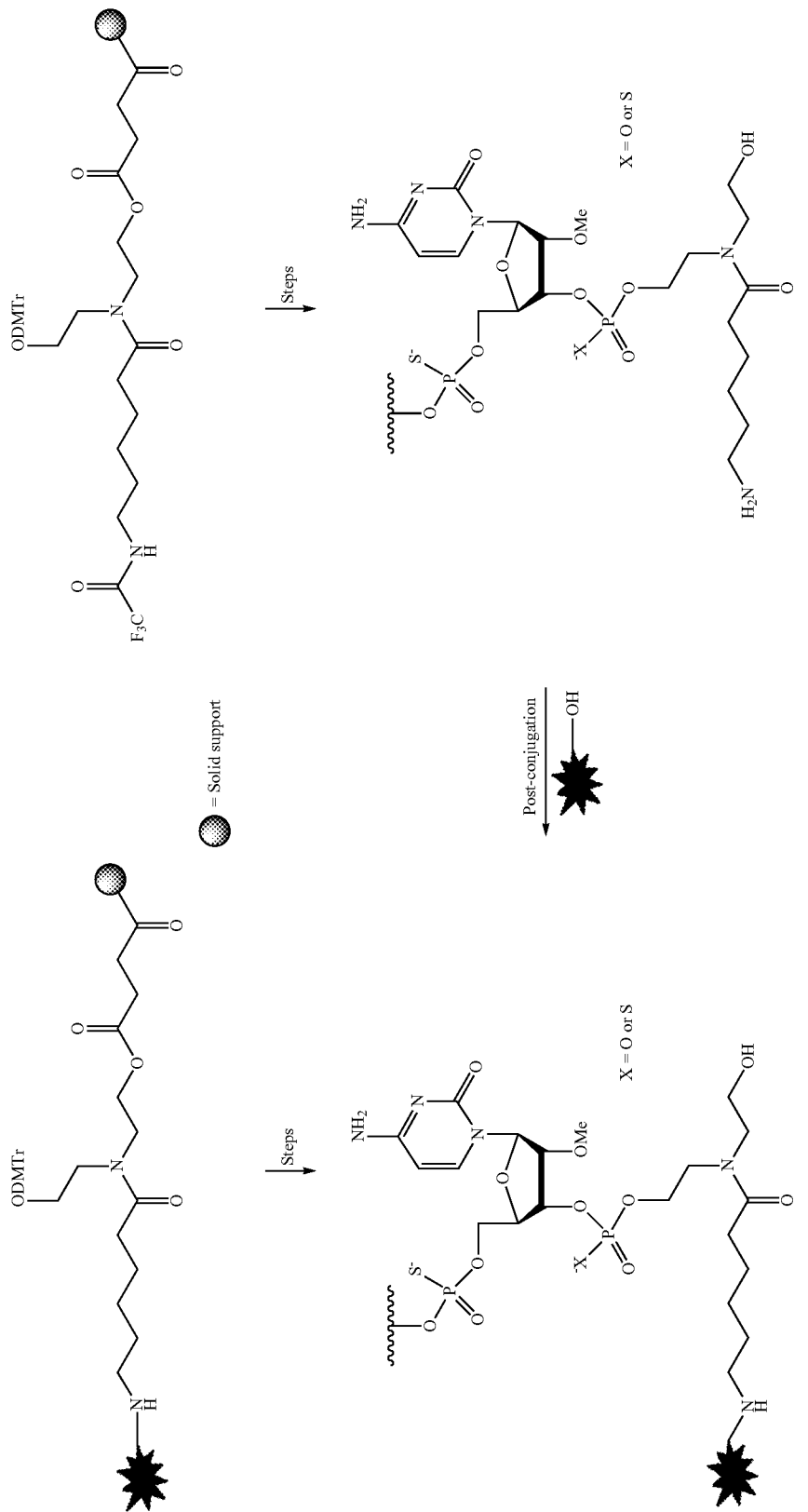

Various chemical moieties, e.g., ligand for cell receptors, can be utilized in accordance with the present disclosure, for example, those described in Juliano et al., J. Am. Chem. Soc. 2010, 132, 8848; Banerjee R et al., Int J Cancer. 2004, 112, 693; J. Med. Chem., 2017, 60 (10), pp 4161-4172; etc. In some embodiments, a chemical moiety is selected from:
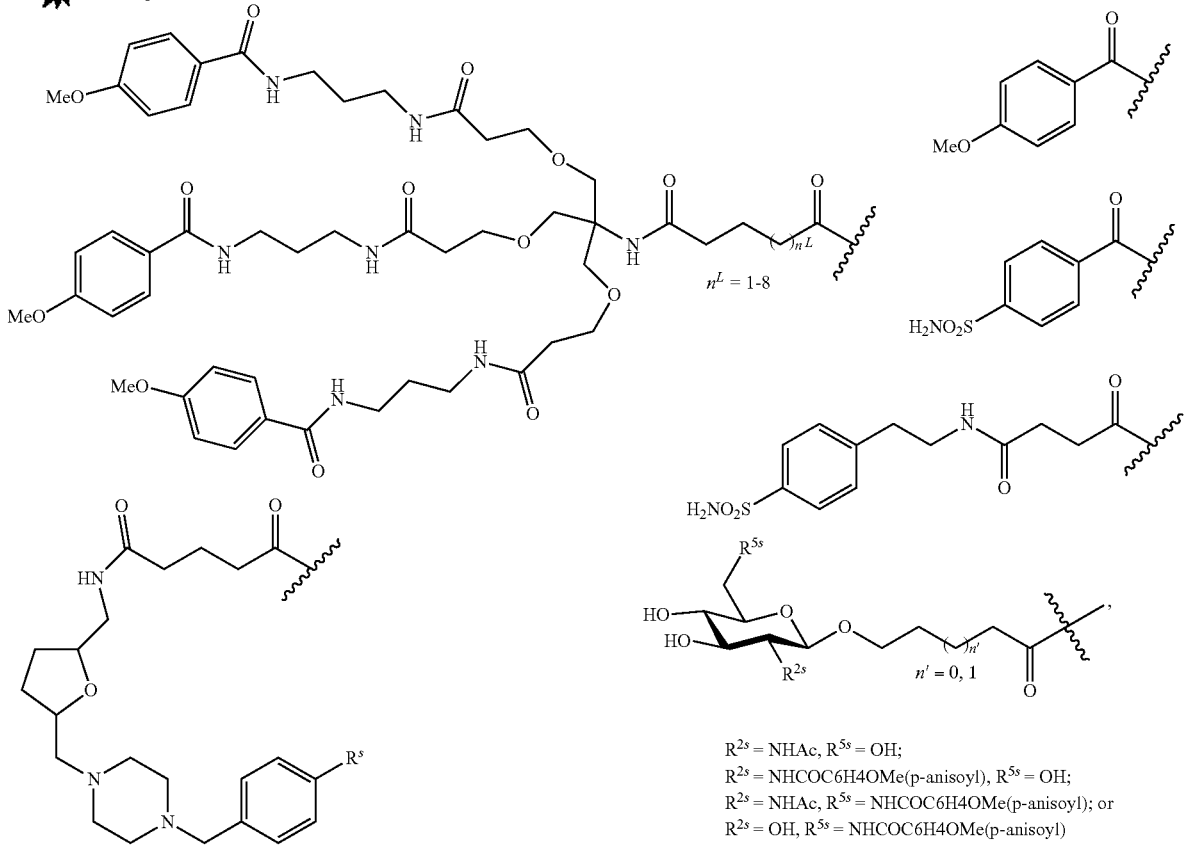
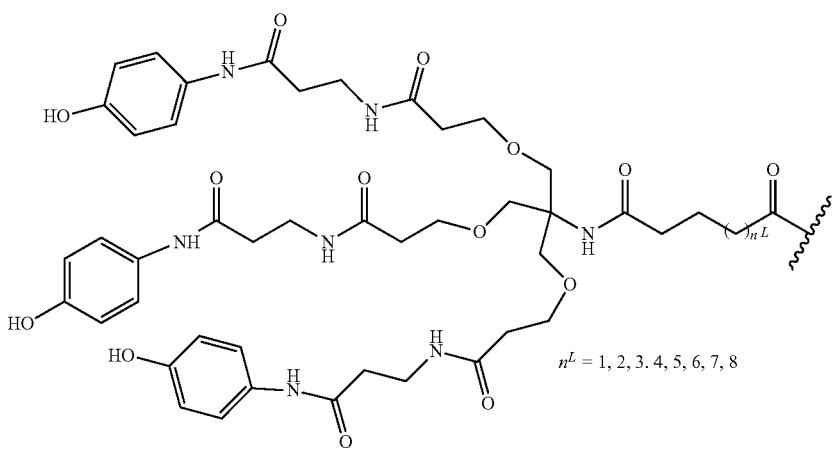

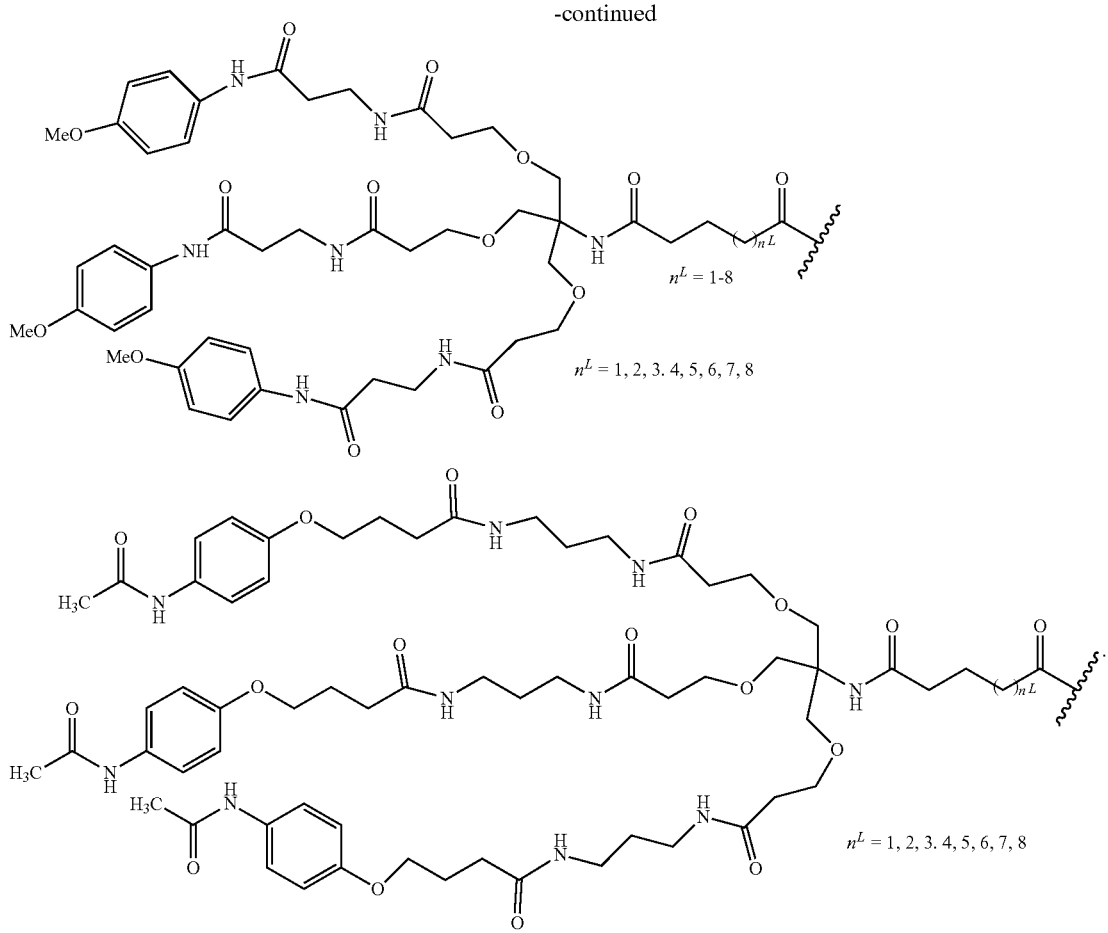
Among other things, a number of conjugated oligonucleotides having the following example structures were prepared:
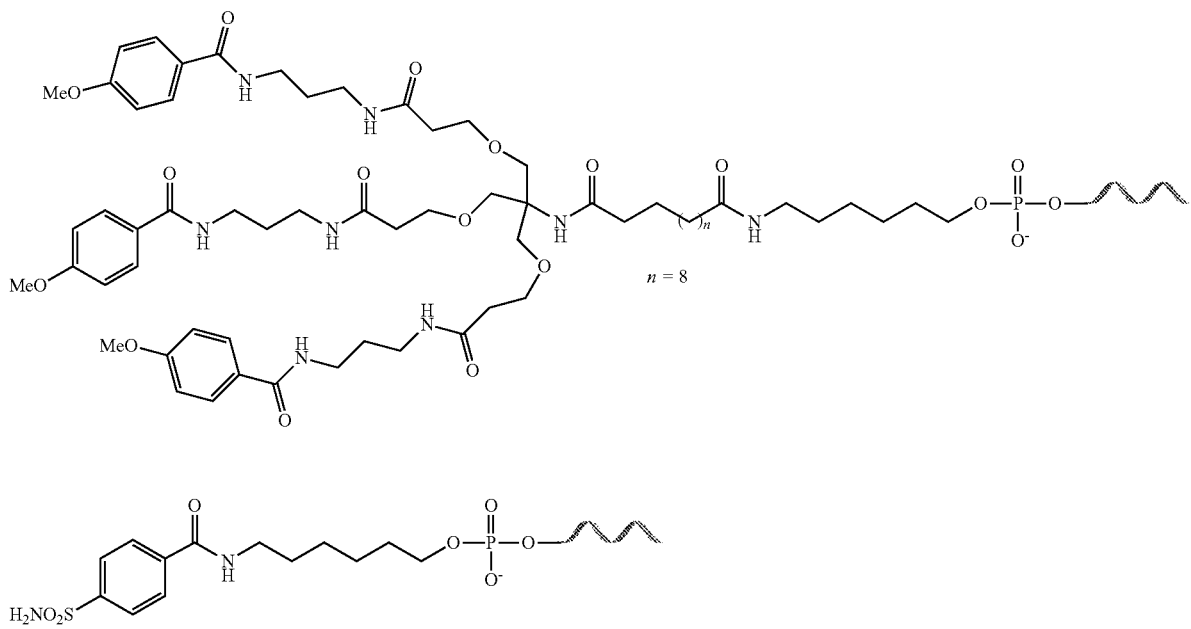

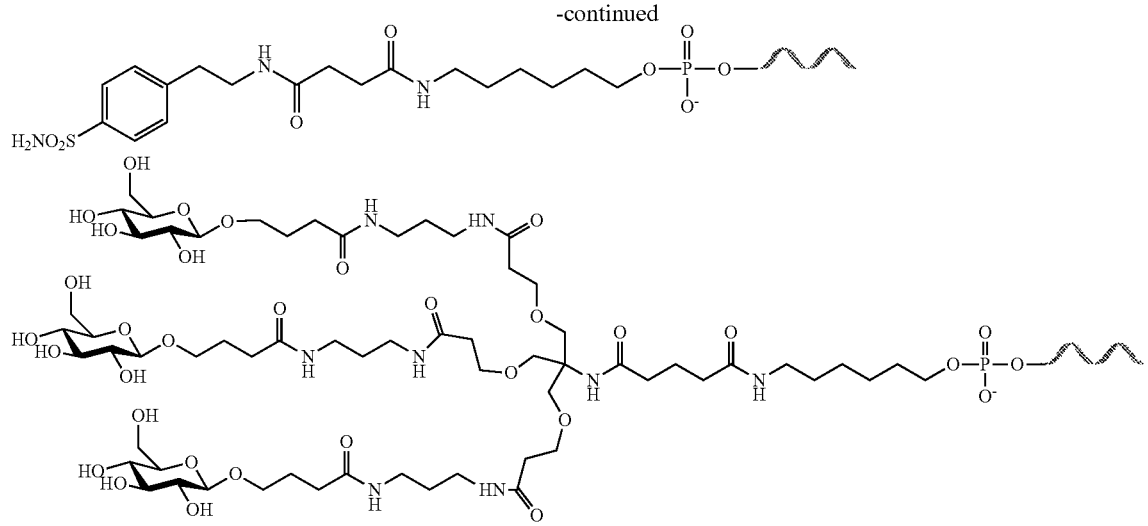
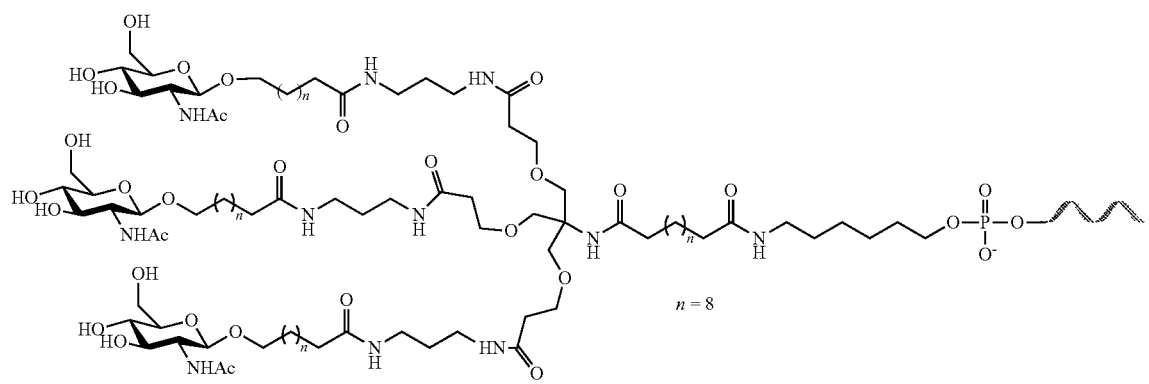
Example 2. Example Compound for Conjugation—Synthesis of 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic Acid
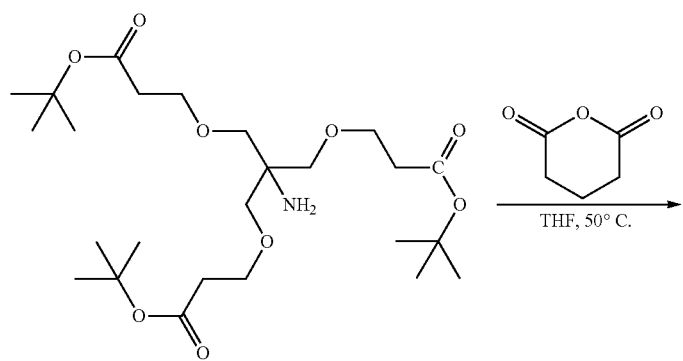

-continued
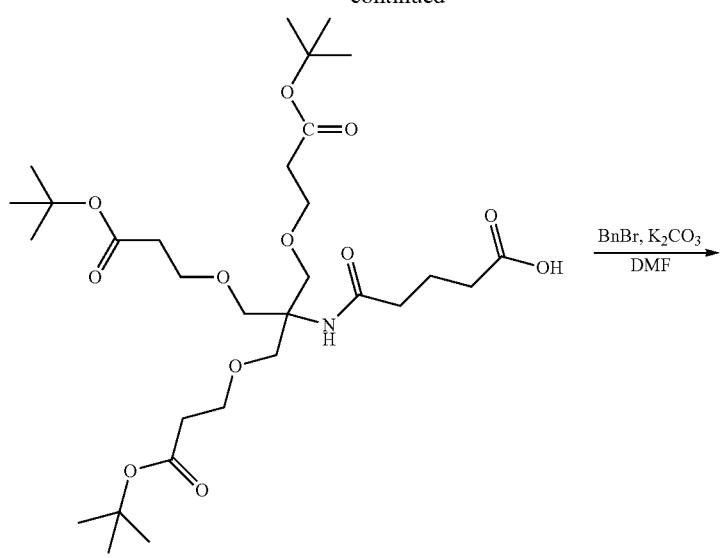
without purification, use directly for next step
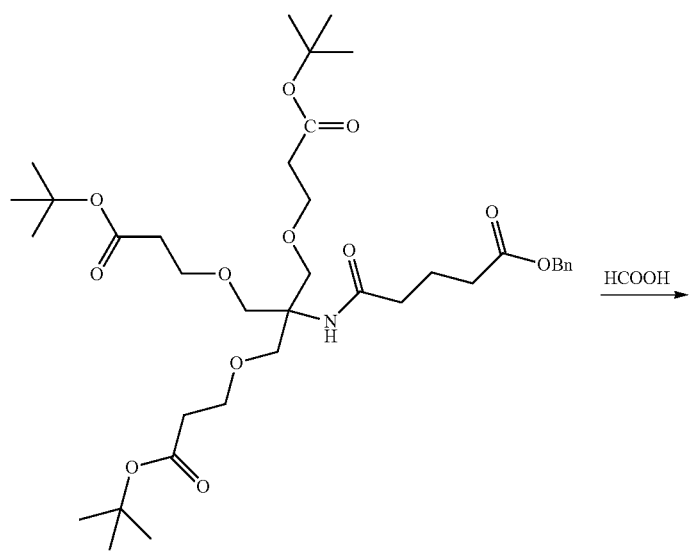
97% over 2 steps
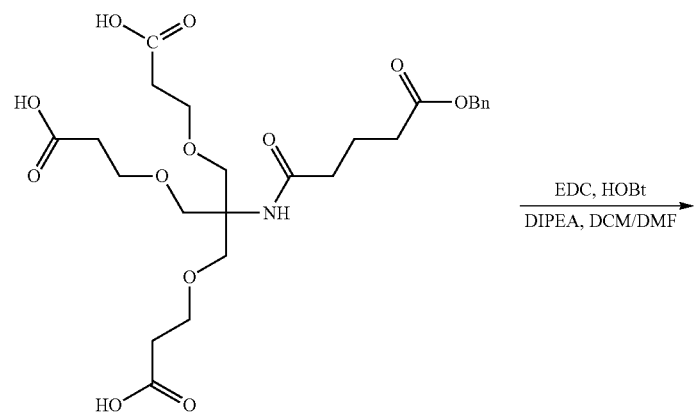

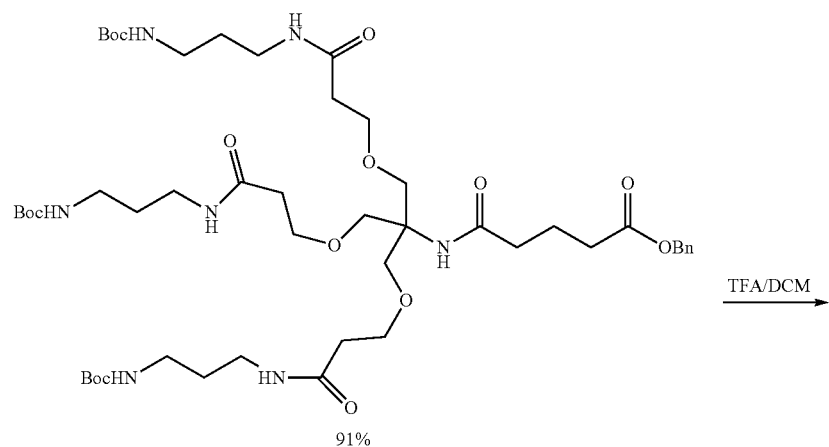
TFA/DCM →
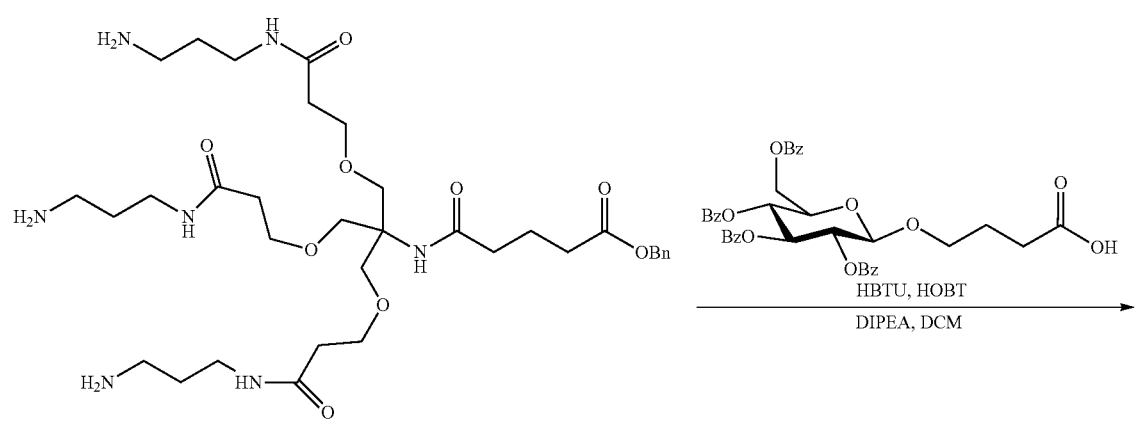
HBTU, HOBT
DIPEA, DCM →
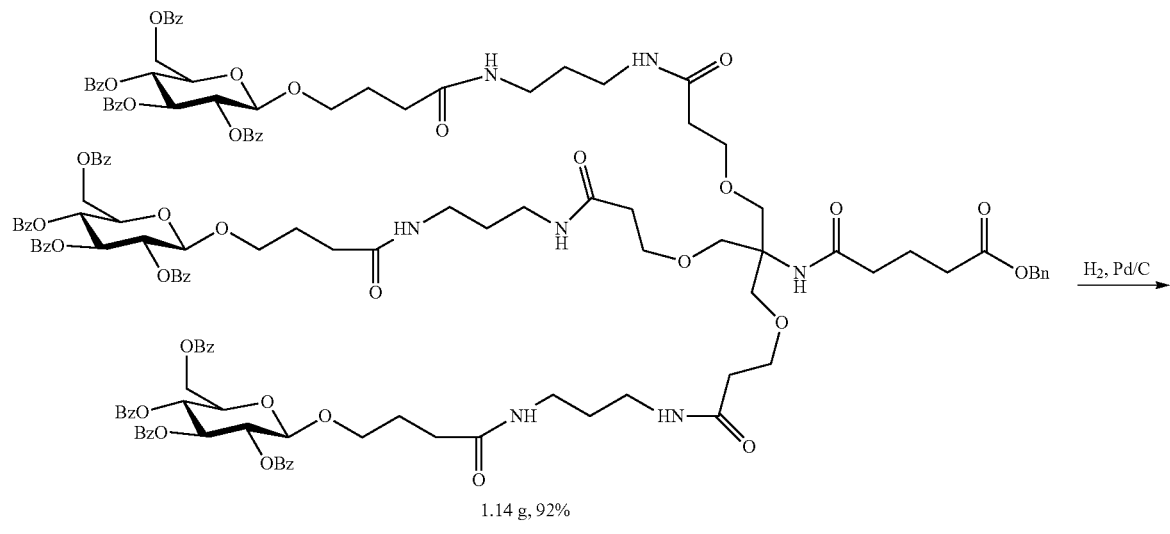
1.14 g, 92%
H₂, Pd/C →

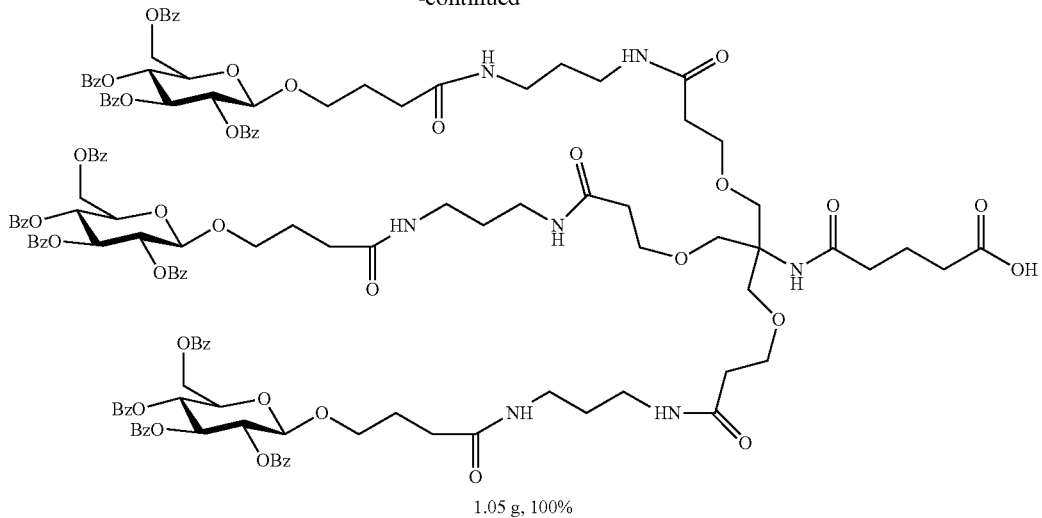

1.05 g, 100%

Step 1: A solution of di-tert-butyl 3,3'-(2-amino-2-((3-(tert-butoxy)-3-oxopropoxy)methyl)propane-1,3-diyl)bis(oxy))dipropanoate 1 (4.0 g, 7.91 mmol) and dihydro-2H-pyran-2,6(3H)-dione (0.903 g, 7.91 mmol) in THF (40 mL) was stirred at 50° C. for 3 hrs and at rt for 3 hrs. LC-MS showed desired product. Solvent was evaporated to give acid 2, which was directly used for next step without purification.

Step 2: To a solution of 5-((9-((3-(tert-butoxy)-3-oxopropoxy)methyl)-2,2,16,16-tetramethyl-4,14-dioxo-3,7,11,15-tetraoxaheptadecan-9-yl)amino)-5-oxopentanoic acid 2 (4.90 g, 7.91 mmol) and (bromomethyl)benzene (1.623 g, 9.49 mmol) in DMF was added anhydrous $K_2CO_3$ (3.27 g, 23.73 mmol). The mixture was stirred at 40° C. for 4 hrs and at room temperature for overnight. Solvent was evaporated under reduced pressure. The reaction mixture was diluted with EtOAc, washed with water, dried over anhydrous sodium sulfate, concentrated under reduced pressure to give a residue, which was purified by ISCO eluting with 10% EtOAc in hexane to 50% EtOAc in hexane to give di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate 3 (5.43 g, 7.65 mmol, 97% yield) as a colorless oil. $^1$H NMR (400 MHz, Chloroform-d) δ 7.36-7.28 (m, 5H), 6.10 (s, 1H), 5.12 (s, 2H), 3.70 (s, 6H), 3.64 (t, J=8.0 Hz, 6H), 2.50-2.38 (m, 8H), 2.22 (t, J=7.3 Hz, 2H), 1.95 (p, J=7.4 Hz, 2H), 1.45 (s, 27H); MS, 710.5 (M+H)+.

Step 3: A solution of di-tert-butyl 3,3'-((2-(5-(benzyloxy)-5-oxopentanamido)-2-((3-(tert-butoxy)-3-oxopropoxy)methyl)propane-1,3-diyl)bi s(oxy))dipropanoate 3 (5.43 g, 7.65 mmol) in formic acid (50 mL) was stirred at room temperature for 48 hrs. LC-MS showed the reaction was not complete. Solvent was evaporated under reduced pressure. The crude product was re-dissolved in formic acid (50 mL) and was stirred at room temperature for 6 hrs. LC-MS showed the reaction was complete. Solvent was evaporated under reduced pressure, co-evaporated with toluene (3×) under reduced pressure, and dried under vacuum to give 3,3'-((2-(5-(benzyloxy)-5-oxopentanamido)-2-((2-carboxyethoxy)methyl)propane-1,3-diyl)bis(oxy))dipropanoic acid 4 (4.22 g, 7.79 mmol, 102% yield) as a white solid. $^1$H NMR (500 MHz, DMSO-$d_6$) δ 12.11 (s, 3H), 7.41-7.27 (m, 5H), 6.97 (s, 1H), 5.07 (s, 2H), 3.55 (t, J=6.4 Hz, 6H), 3.53 (s, 6H), 2.40 (t, J=6.3 Hz, 6H), 2.37-2.26 (m, 2H), 2.08 (t, J=7.3 Hz, 2H), 1.70 (p, J=7.4 Hz, 2H); MS, 542.3 (M+H)+.

Step 4: A solution of 3,3'-((2-(5-(benzyloxy)-5-oxopentanamido)-2-((2-carboxyethoxy)methyl)propane-1,3-diyl)bis(oxy))dipropanoic acid 4 (4.10 g, 7.57 mmol) and HOBt (4.60 g, 34.1 mmol) in DCM (60 mL) and DMF (15 mL) at 0° C. was added tert-butyl (3-aminopropyl)carbamate (5.94 g, 34.1 mmol), EDAC HCl salt (6.53 g, 34.1 mmol) and DIPEA (10.55 ml, 60.6 mmol). The reaction mixture was stirred at 0° C. for 15 minutes and at room temperature for 20 hrs. LC-MS showed the reaction was not complete. EDAC HCl salt (2.0 g) and tert-butyl (3-aminopropyl)carbamate (1.0 g) was added into the reaction mixture. The reaction mixture was stirred at room temperature for 4 hrs. Solvent was evaporated to give a residue, which was dissolved in EtOAc (300 mL), washed with water (1×), saturated sodium bicarbonate (2×), 10% citric acid (2×) and water, dried over sodium sulfate, and concentrated to give a residue which was purified by ISCO (80 g gold cartridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate 5 (6.99 g, 6.92 mmol, 91% yield) as a white solid. $^1$H NMR (500 MHz, Chloroform-d) δ 7.38-7.33 (m, 5H), 6.89 (brs, 3H), 6.44 (s, 1H), 5.23 (brs, 3H), 5.12 (s, 2H), 3.71-3.62 (m, 12H), 3.29 (q, J=6.2 Hz, 6H), 3.14 (q, J=6.5 Hz, 6H), 2.43 (dt, J=27.0, 6.7 Hz, 8H), 2.24 (t, J=7.2 Hz, 2H), 1.96 (p, J=7.5 Hz, 2H), 1.64-1.59 (m, 6H), 1.43 (d, J=5.8 Hz, 27H); MS (ESI): 1011.5 (M+H)+.

Step 5: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (0.326 g, 0.46 mmol) in DCM (5 mL) was added TFA (2 mL). The reaction mixture was stirred at room temperature for 4 hrs. LC-MS showed the reaction was completed. Solvent was evaporated under reduced pressure to give benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate as a colorless oil. Directly use for next step without purification.

Step 6: To a solution of 5-(((2R,3R,4R,5R,6R)-3-acetamido-4,5-diacetoxy-6-(acetoxymethyl)tetrahydro-2H-pyran-2-yl)oxy)pentanoic acid (1.10 g, 1.61 mmol), HBTU (0.558 g, 1.47 mmol), HOBT (0.062 g, 0.46 mmol) and DIPEA (1.2 mL, 6.9 mmol) in DCM (6 mL) followed by benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate in acetonitrile (5 mL). The mixture was stirred at room temperature for 3 hrs. Solvent was evaporated under reduced pressure to give a residue, which was purified by ISCO (40 g gold column) eluting with DCM to 20% MeOH in DCM to give 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic benzyl ester (1.14 g, 92% yield) as a white solid. MS (ESI): 1353.7 (M/2+H)$^+$.

Step 7: To a solution of 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic benzyl ester (1.09 g, 0.400 mmol) in EtOAc (50 mL) was added 10% Pd—C (200 mg) and methanol (2 mL). The reaction mixture was stirred at room temperature for 3 hrs. LC-MS showed the reaction was complete, diluted with EtOAc, and filtered through celite, washed with 20% MeOH in EtOAc, concentrated under reduced pressure to give 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic acid (1.06 g, 100%) as a white solid. MS (ESI): 1308.1 (M+H)$^+$.

Example 3. Example Compounds for Conjugation—Synthesis of 4-oxo-4-((4-sulfamoylphenethyl)amino)butanoic Acid

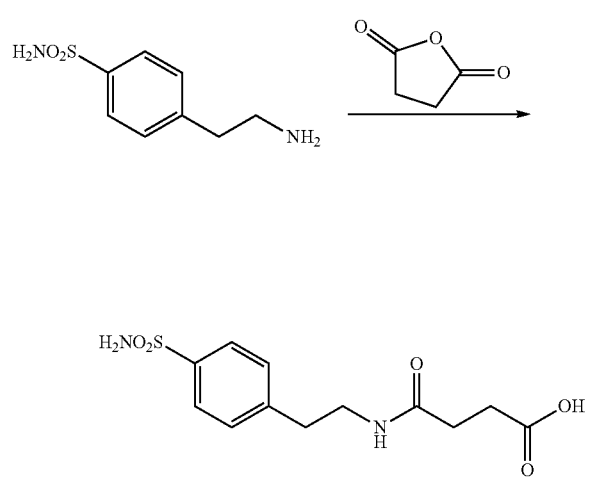

To solid reagents 4-(2-aminoethyl)benzenesulfonamide (2.00 g, 9.99 mmol) and dihydrofuran-2,5-dione (0.999 g, 9.99 mmol) was added THF (30 mL). The reaction mixture was stirred at 60° C. for 7 hrs. Solvent was evaporated under reduced pressure to give 4-oxo-4-((4-sulfamoylphenethyl) amino)butanoic acid (3.00 g, 9.99 mmol, 100% yield) as a white solid. $^1$H NMR (400 MHz, DMSO-d$_6$) δ 12.09 (s, 1H), 7.96 (t, J=5.6 Hz, 1H), 7.72 (d, J=8.1 Hz, 2H), 7.38 (d, J=8.1 Hz, 2H), 7.29 (s, 2H), 3.26 (q, J=6.8 Hz, 2H), 2.76 (t, J=7.2 Hz, 2H), 2.40 (t, J=6.9 Hz, 2H), 2.27 (t, J=6.9 Hz, 2H); MS (ESI), 301.1 (M+H)$^+$.

Example 4. Example Conjugation—Example Conjugation of Sulfonamides with Oligonucleotides General Procedure: To a solution of sulfonamide (5 equivalents), in 2 ml DMF was added HATU (4.5 equivalents) and DIPEA (25 equivalents). This mixture was stirred well for 2 minutes.

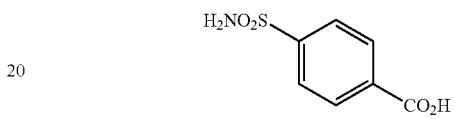

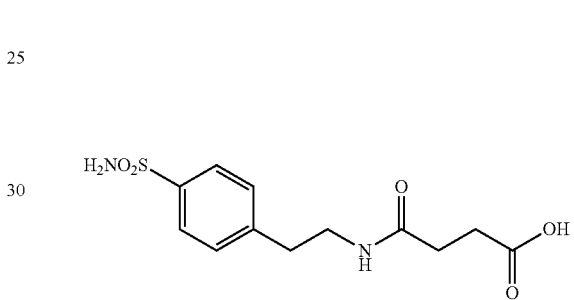

To this solution was added, a solution of an oligonucleotide (1 equivalent) in water and shaken well for 60 minutes. The solvent was removed under vacuum and crude product was purified by RP column (C18) chromatography to obtain the product. The purified product was desalted over a C-18 cartridge using sodium acetate solution.

In an example procedure, following the general procedure outlined above, 4-sulfamoyl benzoic acid (11 mg, 54.5 μmol), HATU (18.6 mg, 49 μmol) and DIPEA (35 mg, 272 μmol) were stirred for 2 minutes in 2 ml DMF (Scheme 1). This activated HATU intermediate was added into a solution of an oligonucleotide (e.g., 75 mg, 10.9 μmol) in 0.75 ml water. The reaction vial was shaken for 60 minutes. Solvent was removed under reduced pressure, purification and desalting was performed as described above. Amount of product obtained was 20 mg. Molecular weight of the product calculated: 7063; Deconvoluted mass obtained: 7065.

In an example procedure, following the general procedure outlined above, 4-sulfamoyl benzoic acid (16.3 mg, 54.5 μmol), HATU (18.6 mg, 49 μmol) and DIPEA (35 mg, 272 μmol) were stirred for 2 minutes in 2 ml DMF (Scheme 2). This activated HATU intermediate was added into a solution of an oligonucleotide (e.g., 75 mg, 10.9 μmol) in 0.75 ml water. The reaction vial was shaken for 60 minutes. Solvent was removed under reduced pressure, purification and desalting was performed as described above. Amount of product obtained was 13 mg. Molecular weight of the product calculated: 7162; Deconvoluted mass obtained: 7165.

Example 5. Example Conjugation—Example Conjugation of Triantennary Anisamide with Oligonucleotides

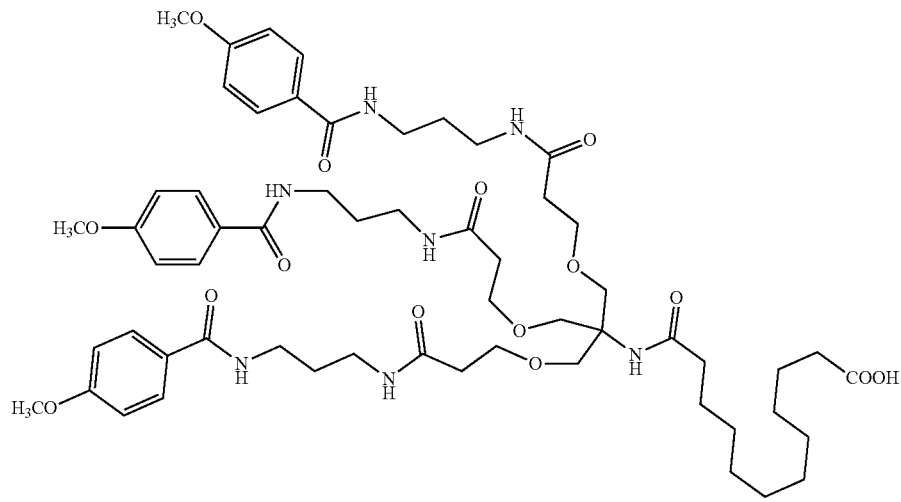 [SMILES: COc1ccc(C(=O)NCCCNC(=O)CCOCC(COCCC(=O)NCCCNC(=O)c2ccc(OC)cc2)(COCCC(=O)NCCCNC(=O)c2ccc(OC)cc2)NC(=O)CCCCCCCCCCC(=O)O)cc1]

General Procedure: To a solution of triantennary anisamide (2 equivalents), in 2 ml DMF was added HATU (1.8 equivalents) and DIPEA (10 equivalents). This mixture was stirred well for 2 minutes. To this solution was added a solution of an oligonucleotide (1 equivalent) in water and shaken well for 60 minutes. The solvent was removed under vacuum and crude product was purified by RP column (C8) chromatography to obtain the product. The purified product was desalted over a C-18 cartridge using sodium acetate solution.

In an example procedure, a solution of triantennary anisamide (11 mg, 9.8 μmol), in 2 ml DMF was added HATU (3.34 mg, 8.82 μmol) and DIPEA (6.3 mg, 9 μl, 49 μmol). This mixture was stirred well for 2 minutes. To this solution was added a solution of an oligonucleotide (e.g., 33.7 mg, 4.9 μmol) in 0.88 ml water and shaken well for 60 minutes. The solvent was removed under vacuum and crude product was purified by RP column (C8) chromatography to obtain the product (25 mg). The purified product was desalted over a C-18 cartridge using sodium acetate solution. Molecular weight of product calculated:7982; De-convoluted mass obtained: 7987.

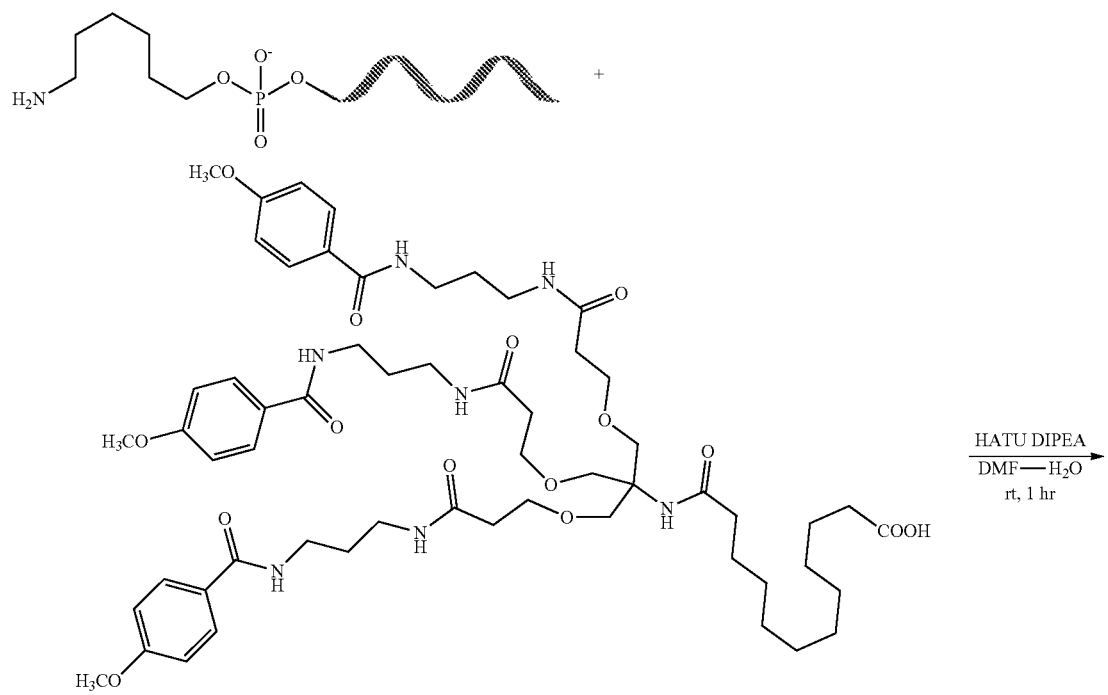

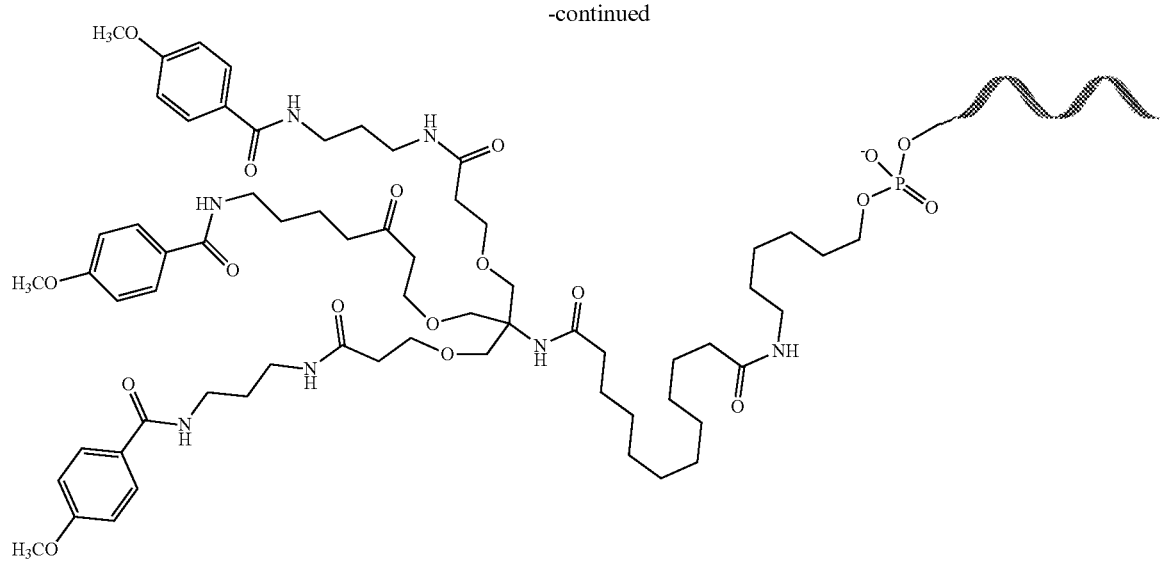

In an example procedure, a solution of triantennary anisamide (13 mg, 11.6 μmol), in 2 ml DMF was added HATU (4 mg, 10.4 μmol) and DIPEA (7.5 mg, 10.3 μl, 58 μmol). This mixture was stirred well for 2 minutes. To this solution was added a solution of an oligonucleotide (e.g., 40 mg, 5.8 μmol) in 1 ml water and shaken well for 60 minutes. The solvent was removed under vacuum and the crude product was purified by RP column (C8) chromatography to obtain the product. The purified product was desalted over a C-18 cartridge using sodium acetate solution. Molecular weight of product calculated:7970; De-convoluted mass obtained: 7975.

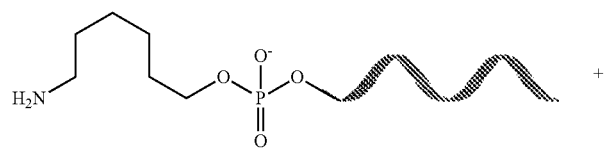

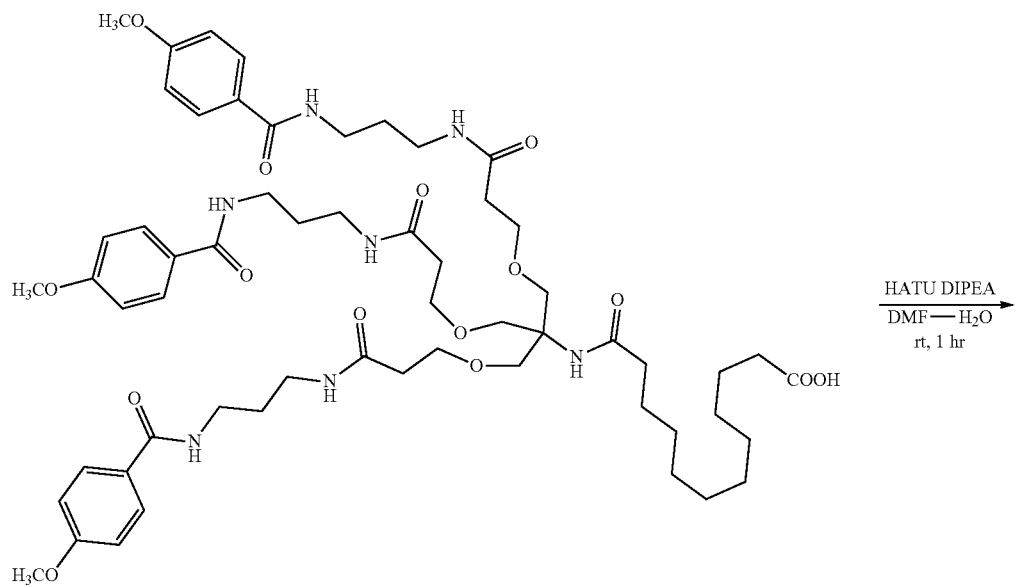

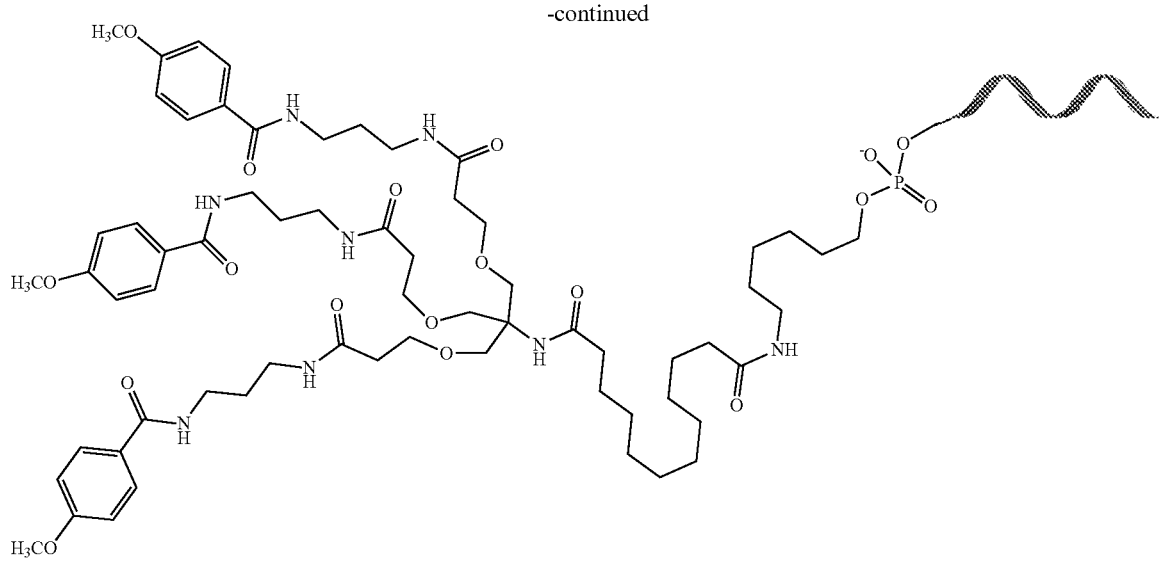

Example 6. Example Conjugation—Example Conjugation of Triantennary Glucosamine/Glucose Derivative with Oligonucleotides To a solution of triantennary glucosamine or glucose derivative (2 equivalents), in 2 ml DMF was added HATU (1.8 equivalents) and DIPEA (10 equivalents). This mixture was stirred well for 2 minutes. To this solution was added a solution of an oligonucleotide (1 equivalent) in water and shaken well for 60 minutes. The solvent was removed under vacuum and crude product was treated with 30% NH$_4$OH solution at room temperature for 24 hours. The solvent was removed under vacuum and the crude product was purified by RP column (C8) chromatography to obtain the product. The purified product was desalted over a C-18 cartridge using sodium acetate solution.

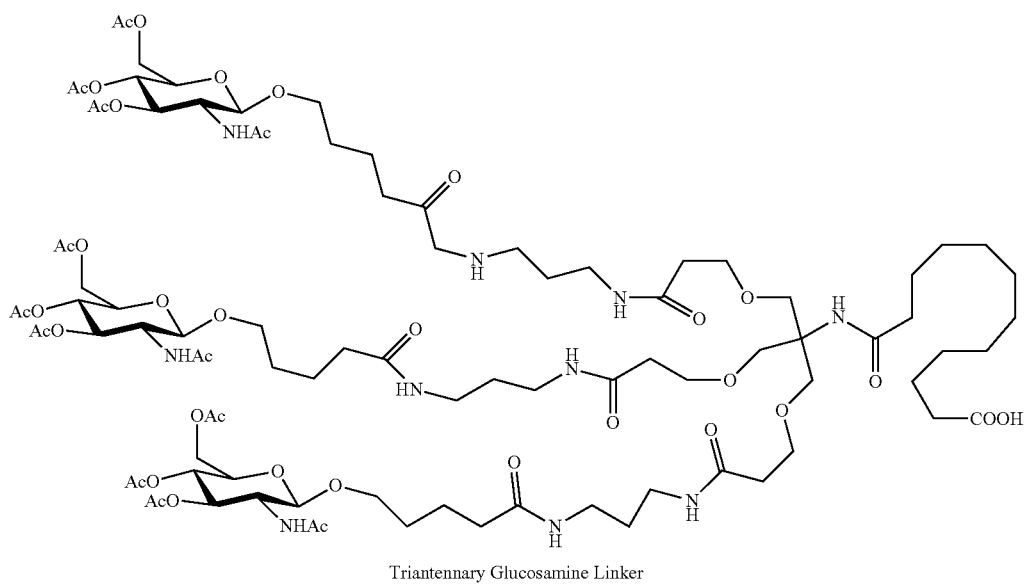

Triantennary Glucosamine Linker

-continued

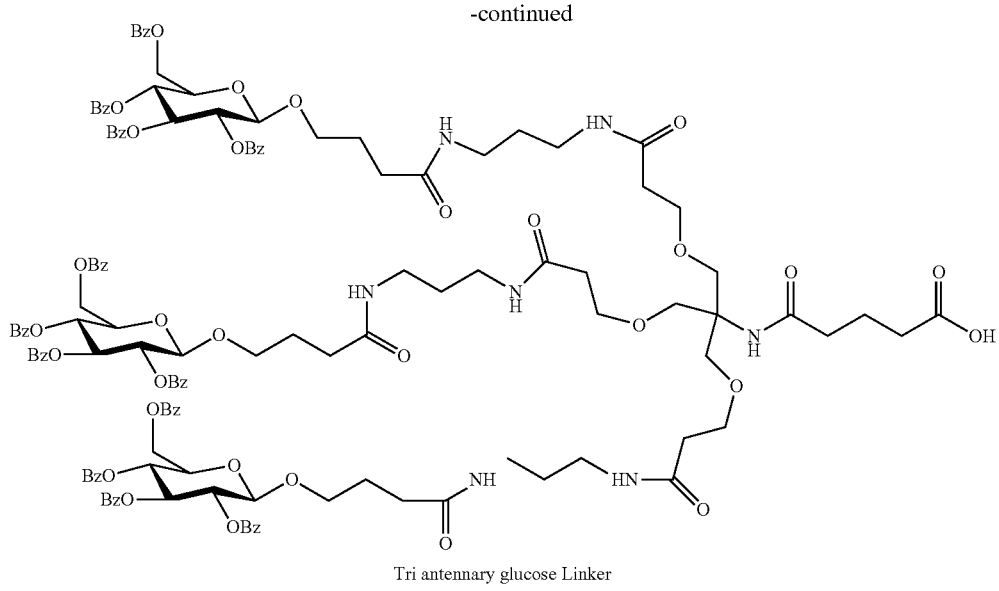

Tri antennary glucose Linker

In an example procedure, following the general procedure shown above, Glucosamine derivative (23.3 mg, 11.6 µmol), HATU (4 mg, 10.44 µmol) and DIPEA (7.5 mg, 58 µmol) was stirred in 2 ml DMF. To this solution was added of an oligonucleotide (e.g., 40 mg (5.8 µmol)) in 1 ml water. The reaction mixture was stirred for 60 minutes to obtain the desired product. This product was treated with $NH_4OH$ as described above. Amount of product obtained was 20 mg. Molecular weight calculated: 8496; Deconvoluted mass obtained: 8494.

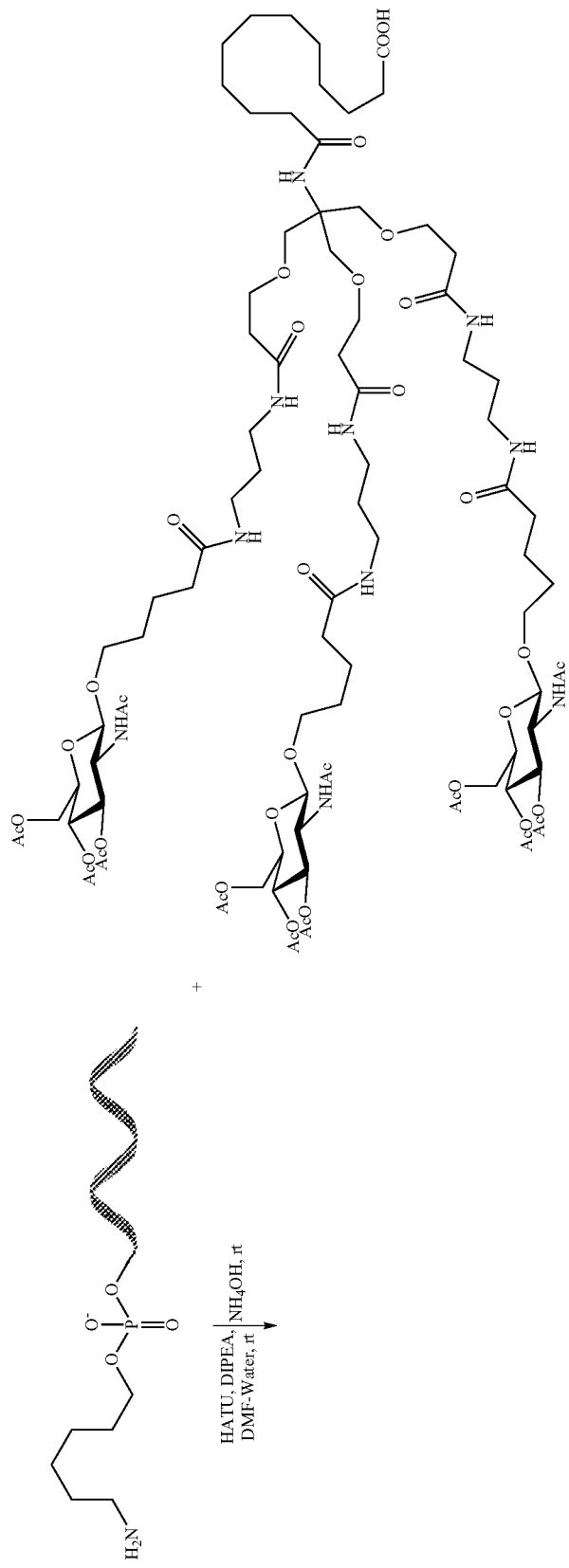

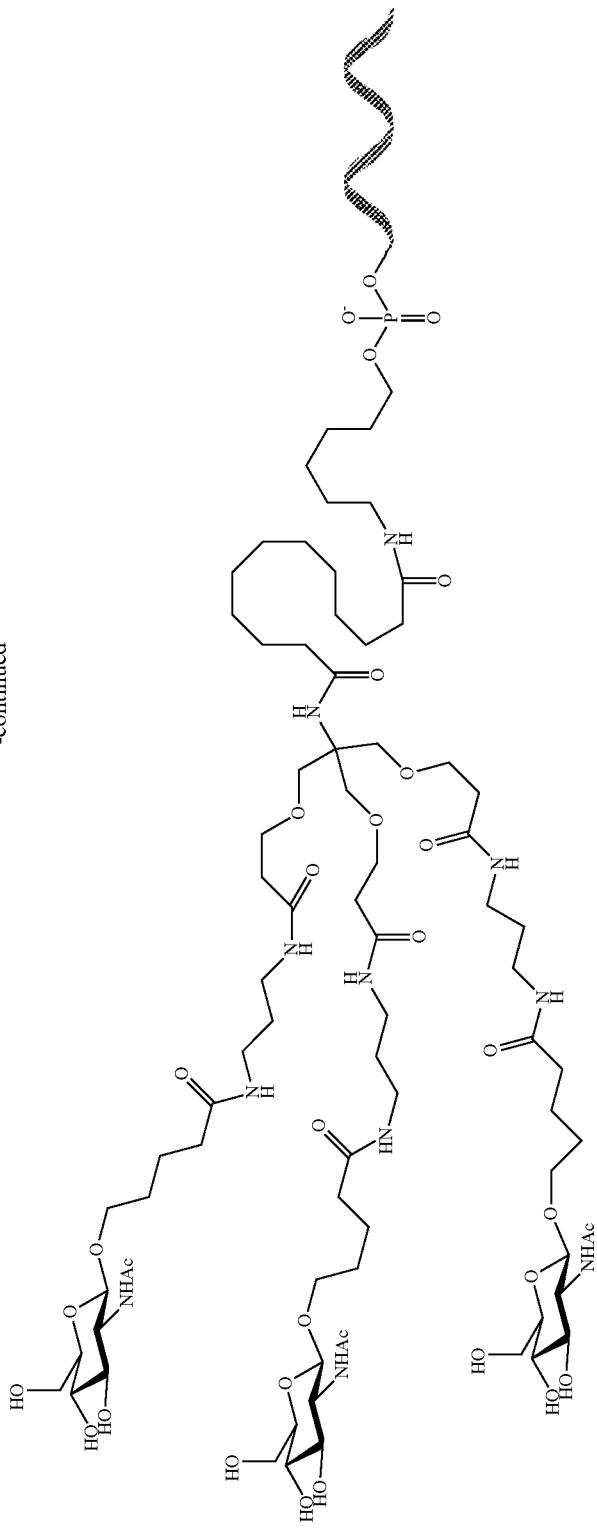

In an example procedure, following the general procedure shown above, glucose derivative (57 mg, 21.8 µmol), HATU (7.5 mg, 19.6 µmol) and DIPEA (14.6 mg, 109 µmol) was stirred in 2 ml DMF. To this solution was added an oligonucleotide (e.g., 75 mg (10.9 µmol)) in 1 ml water. The reaction mixture was stirred for 60 minutes to obtain the desired product. This product was heated at 40° C. with $NH_4OH$ as described above to obtain the final product. Molecular weight calculated: 8227; Deconvoluted mass obtained: 8233.

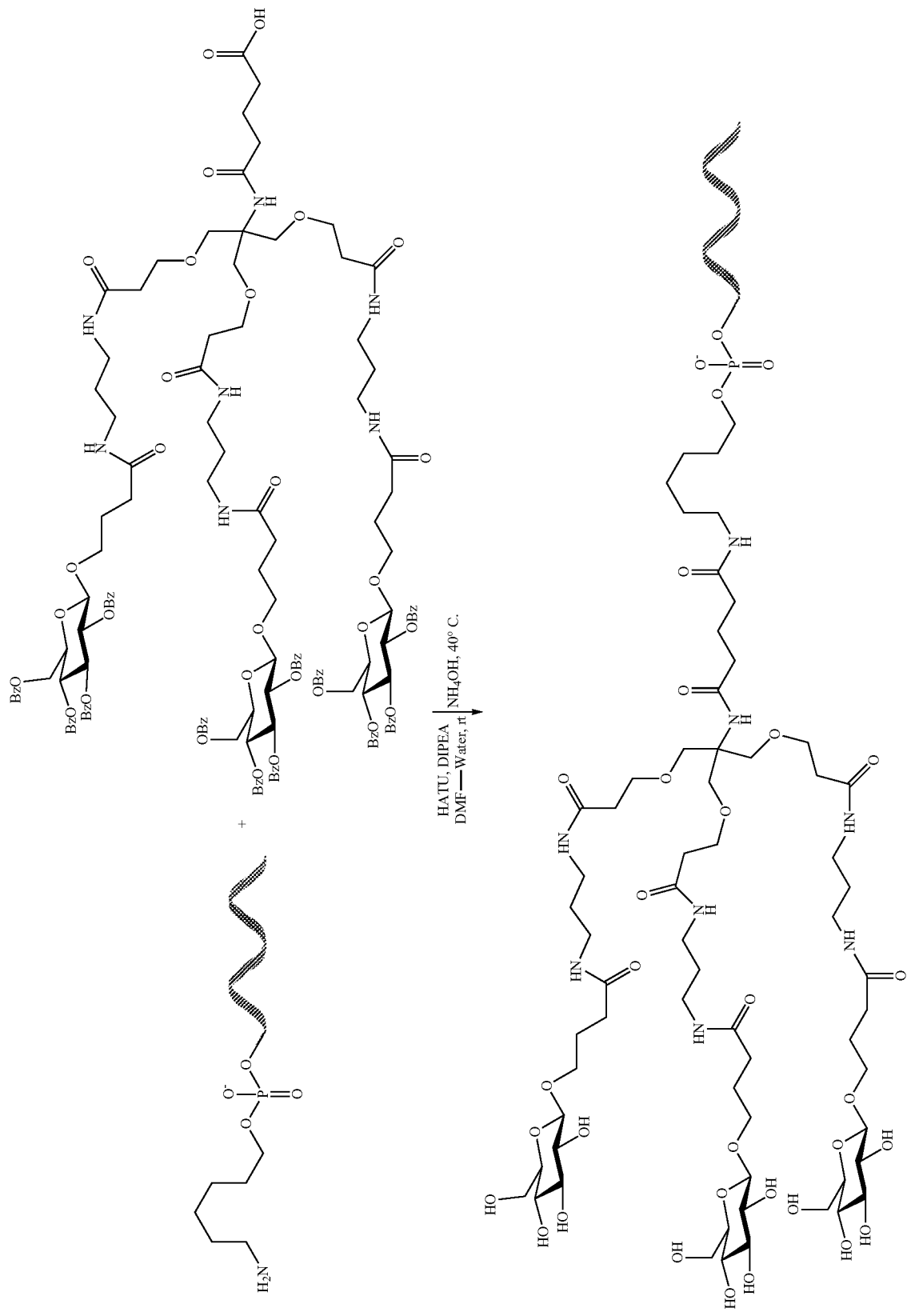

In an example procedure, following the general procedure shown above, Glucose derivative (30 mg, 11.6 µmol), HATU (4 mg, 10.4 µmol) and DIPEA (7.5 mg, 58 µmol) was stirred in 2 ml DMF. To this solution was added an oligonucleotide (e.g., 40 mg (5.8 µmol)) of in 1 ml water. The reaction mixture was stirred for 60 minutes to obtain the desired product. This product was heated at 40° C. with $NH_4OH$ as described above to obtain the product. Molecular weight calculated: 8214; Deconvoluted mass obtained: 8218.

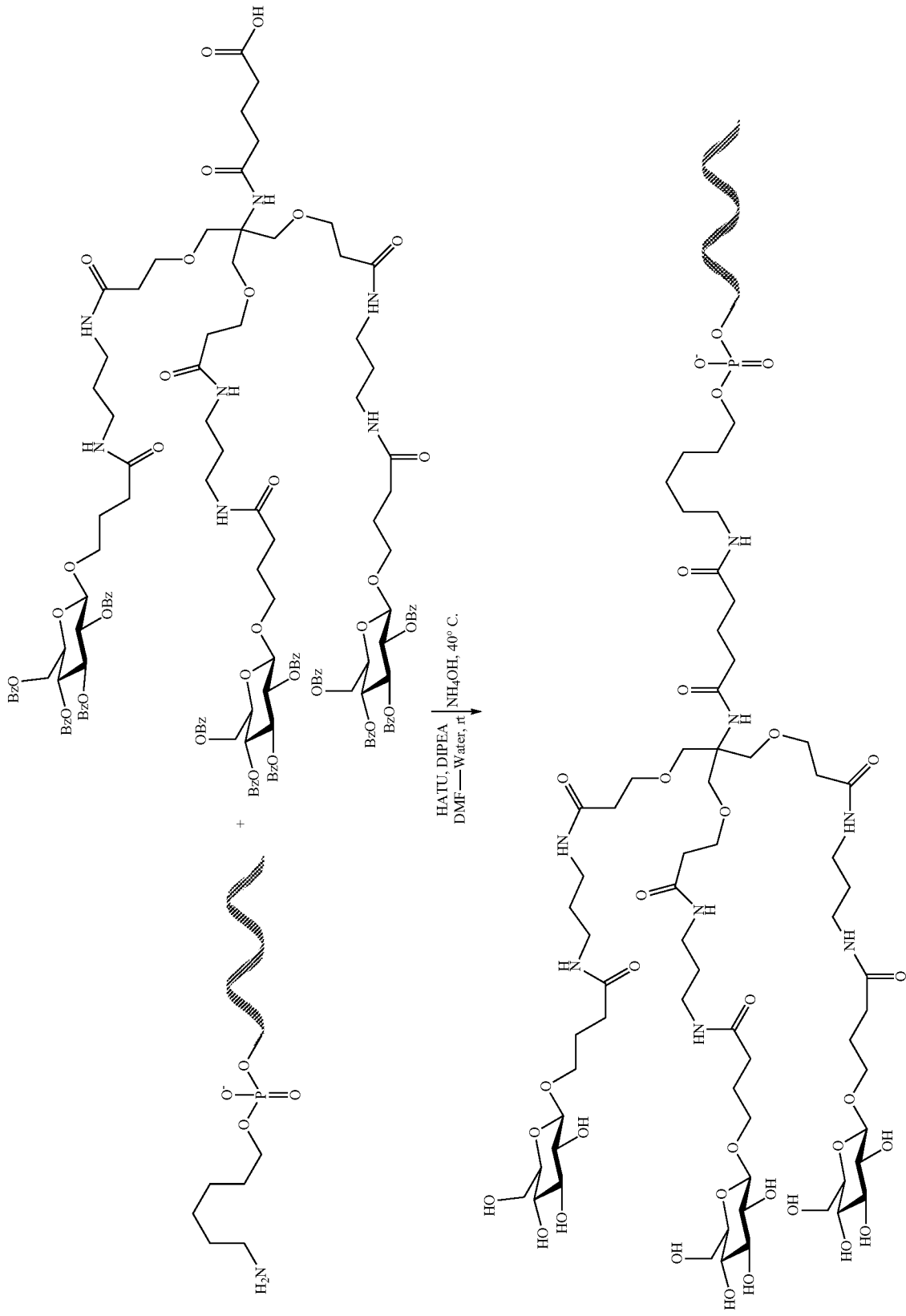

In an example procedure, following the general procedure shown above, Glucosamine derivative (24 mg, 12 µmol), HATU (4 mg, 10.4 µmol) and DIPEA (7.5 mg, 58 µmol) was stirred in 2 ml DMF. To this solution was added an oligonucleotide (e.g., 40 mg (5.8 µmol)) of in 1 ml water. The reaction mixture was stirred for 60 minutes to obtain the desired product. This product was heated at 40° C. with $NH_4OH$ as described above to obtain the product. Molecular weight calculated:8477; Deconvoluted mass obtained: 8484.

457 458
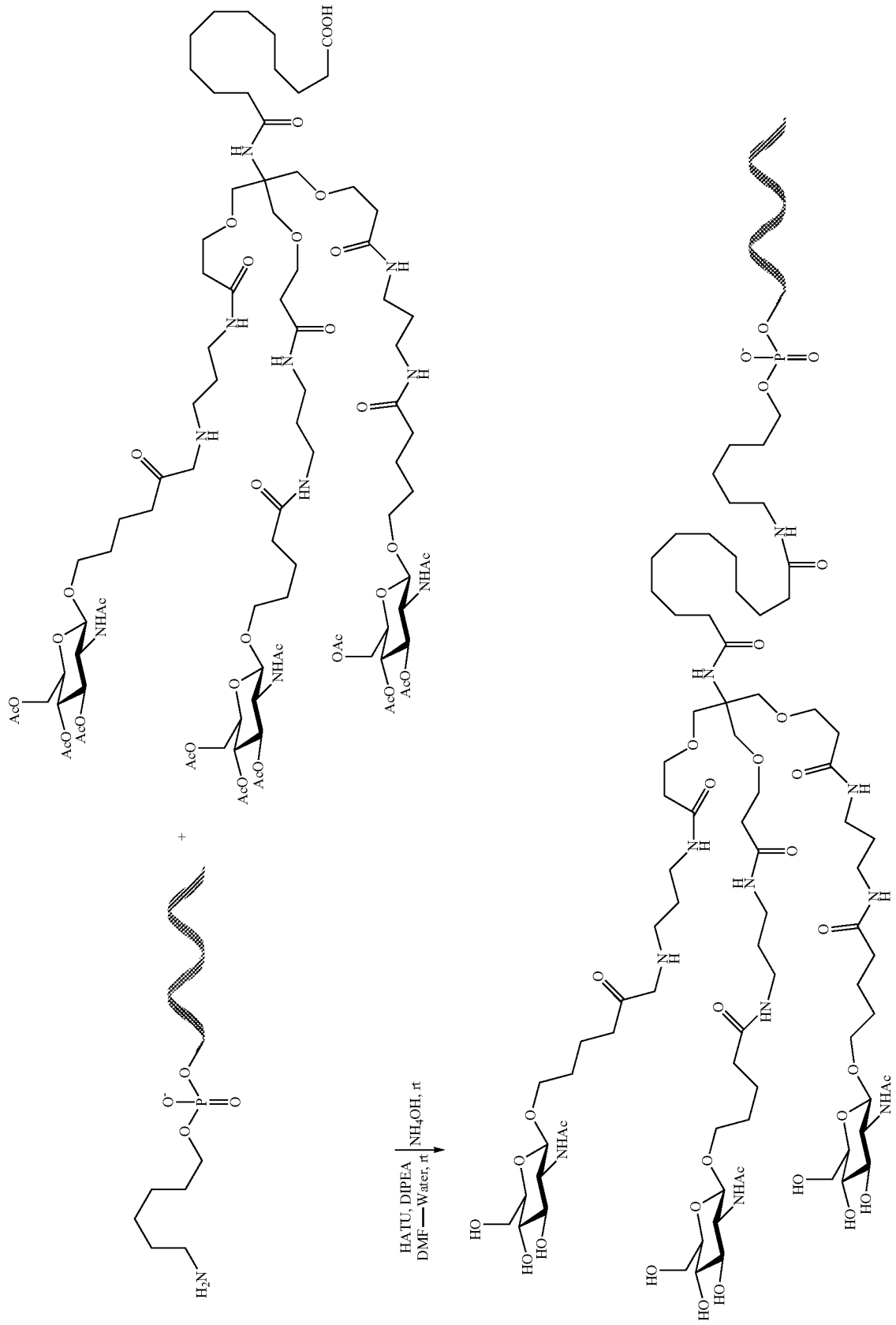

Example 7. Example Additional Chemical Moieties
Synthesis of 1-((((2R,3R,4R,5R,6R)-3-acetamido-4,5-diacetoxy-6-(acetoxymethyl)tetrahydro-2H-pyran-2-yl)oxy)-16,16-bis((3-((3-(5-0(2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic Acid
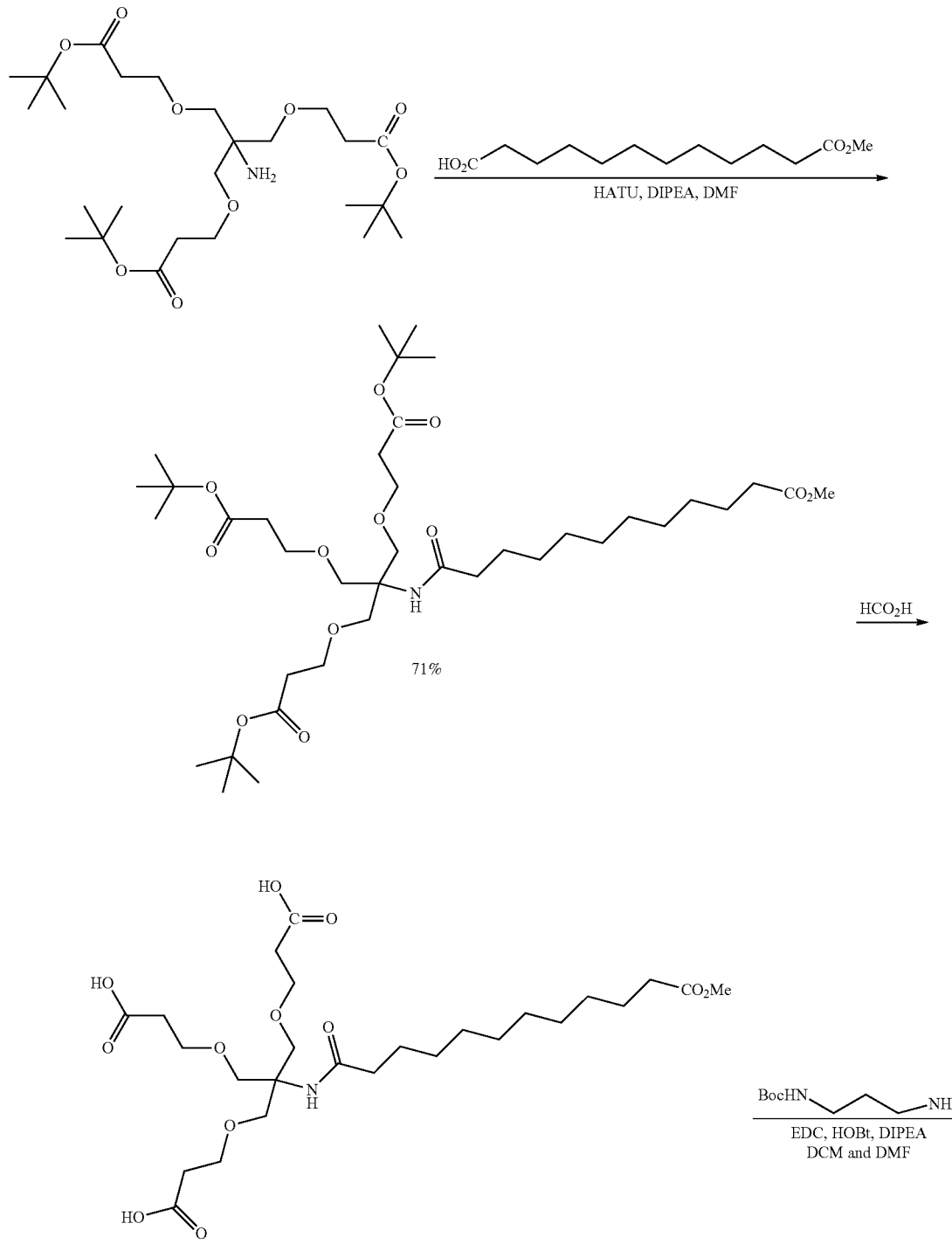

-continued
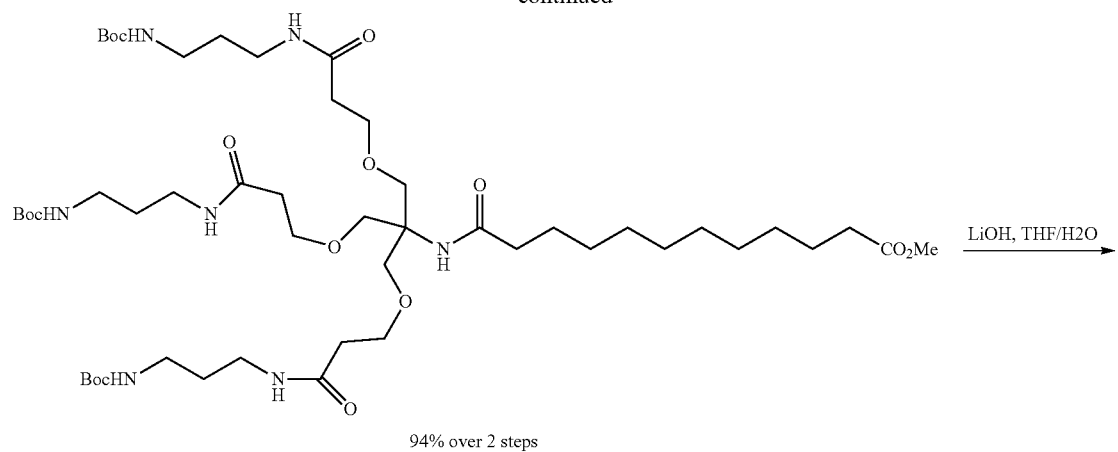
94% over 2 steps
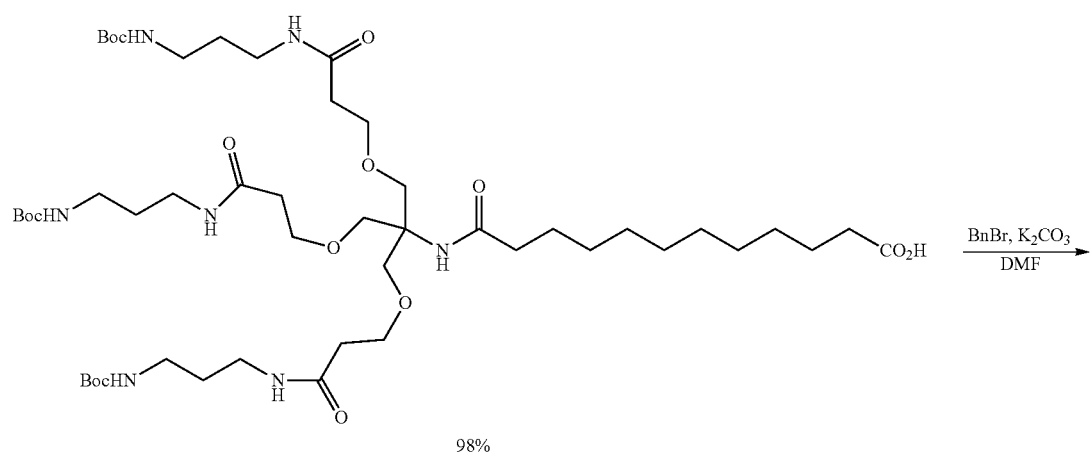
98%
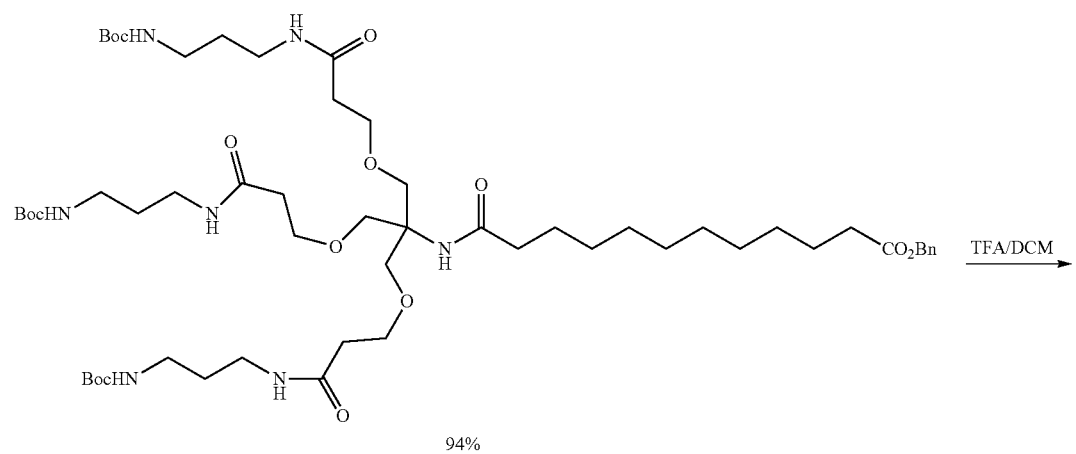
94%
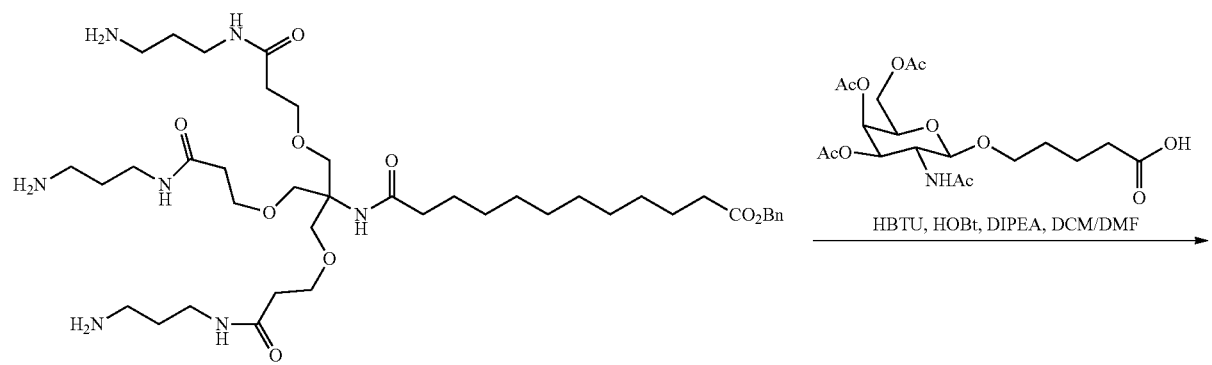

-continued

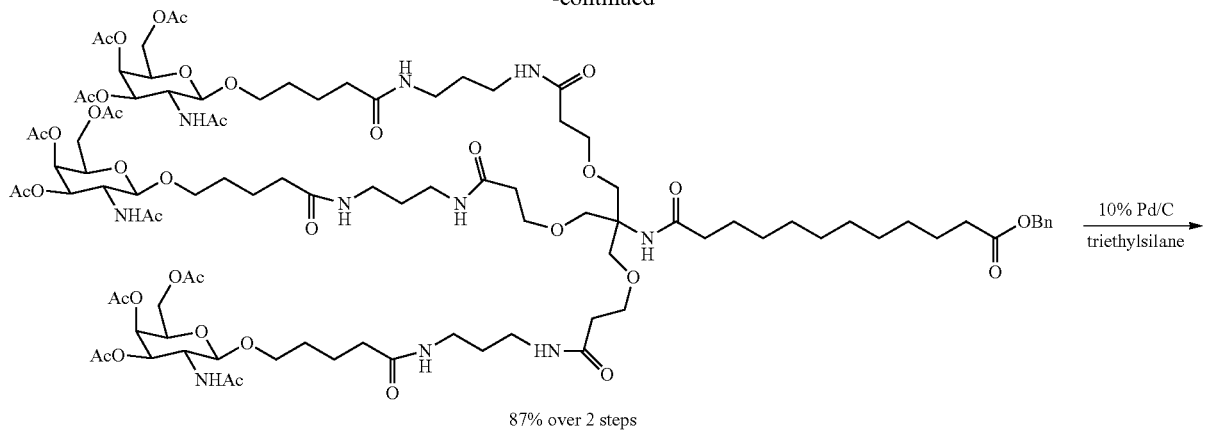

87% over 2 steps

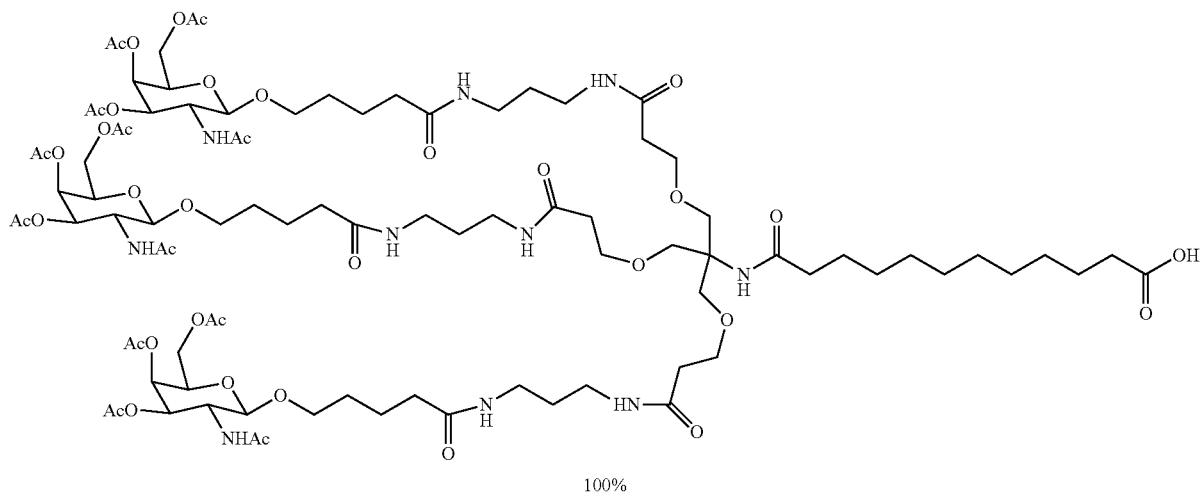

100%

Step 1: To a solution of di-tert-butyl 3,3'-((2-amino-2-((3-(tert-butoxy)-3-oxopropoxy)methyl)propane-1,3-diyl)bis(oxy))dipropanoate (5.0 g, 9.89 mmol) and 12-methoxy-12-oxododecanoic acid (2.416 g, 9.89 mmol) in DMF (45 mL) was added HATU (3.76 g, 9.89 mmol) and DIPEA (2.58 ml, 14.83 mmol). The reaction mixture was stirred at room temperature for 5 hrs. Solvent was concentrated under reduced pressure, and diluted with brine, extracted with EtOAc, dried over anhydrous sodium sulfate, and concentrated to give a residue, which was purified by ISCO (120 g gold silica gel cartridge) eluting with 10% EtOAc in hexane to 40% EtOAc in hexane to give di-tert-butyl 3,3'-((2-((3-(tert-butoxy)-3-oxopropoxy)methyl)-2-(12-methoxy-12-oxododecanamido)propane-1,3-diyl)bis(oxy))dipropanoate (5.13 g, 7.01 mmol, 70.9% yield) as a colorless oil. $^1$H NMR (400 MHz, Chloroform-d) δ 6.03 (s, 1H), 3.74-3.61 (m, 15H), 2.45 (t, J=6.3 Hz, 6H), 2.31 (td, J=7.5, 3.9 Hz, 2H), 2.19-2.10 (m, 2H), 1.64-1.59 (m, 4H), 1.46 (s, 27H), 1.32-1.24 (m, 12H); MS (ESI), 732.6 (M+H)+.

Step 2: A solution of di-tert-butyl 3,3'-((2-((3-(tert-butoxy)-3-oxopropoxy)methyl)-2-(12-methoxy-12-oxododecanamido)propane-1,3-diyl)bis(oxy))dipropanoate (5.0 g, 6.83 mmol) in formic acid (50 mL) was stirred at room temperature for 48 hrs. Solvent was evaporated under reduced pressure, co-evaporated with toluene (3×) to give a white solid, which was dried under high vacuum for 2 days. LC-MS and H NMR showed the reaction is not complete. The crude product was redissolved in formic acid (50 mL). The reaction mixture was stirred at room temperature for 24 hrs. LC-MS showed the reaction was complete. Solvent was evaporated under reduced pressure, co-evaporated with toluene (3×), dried over high vacuum to give 3,3'-((2-((2-carboxyethoxy)methyl)-2-(12-methoxy-12-oxododecanamido)propane-1,3-diyl)bis(oxy))dipropanoic acid (4.00 g) as a white solid. MS (ESI): 562.4 (M−H)⁻.

Step 3: A solution of 3,3'-((2-((2-carboxyethoxy)methyl)-2-(12-methoxy-12-oxododecanamido)propane-1,3-diyl)bis(oxy))dipropanoic acid (3.85 g, 6.83 mmol) and HOBt (3.88 g, 28.7 mmol) in DCM (60 mL) and DMF (15 mL) at 0° C. was added tert-butyl (3-aminopropyl)carbamate (4.76 g, 27.3 mmol), EDAC HCl salt (5.24 g, 27.3 mmol) and DIPEA (8.33 ml, 47.8 mmol). The reaction mixture was stirred at 0° C. for 15 minutes and at room temperature for 20 hrs. LC-MS showed the reaction was not complete. t-Butyl (3-mainopropyl) carbamate (1.59 g, 9.12 mmol) and EDC HCl salt (1.75 g, 9.13 mol) was added into the reaction mixture. The reaction mixture was continually stirred at room temperature for 4 hrs. Solvent was evaporated to give a residue, which was dissolved in EtOAc (300 mL), washed with water (1×), saturated sodium bicarbonate (2×), 10% citric acid (2×) and water, dried over sodium sulfate, and concentrated to give a residue which was purified by ISCO (80 g gold cartridge) eluting with DCM to 30% MeOH in DCM to give methyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.61 g, 6.40 mmol, 94% yield over 2 steps) as a white solid. MS (ESI): 1033.5 (M+H)$^+$.

Step 4: To a solution of methyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.56 g, 6.35 mmol) in THF (75 mL) was added aq. LiOH (0.457 g, 19.06 mmol) in water (25 mL). The mixture was stirred at room temperature for overnight. LC-MS showed the reaction was completed. Solvent was evaporated, acidified using 1 N HCl (45 mL), extracted with DCM (3×), dried over anhydrous sodium sulfate, concentrated to give 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oic acid (6.31 g, 6.20 mmol, 98% yield) as a white solid. MS (ESI): 1019.6 (M+H)$^+$.

Step 5: To a solution of 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oic acid (6.31 g, 6.20 mmol) and (bromomethyl)benzene (1.272 g, 7.44 mmol) in DMF (40 mL) was added K$_2$CO$_3$ (2.57 g, 18.59 mmol). The mixture was stirred at 40° C. for 4 hours and at room temperature for overnight. Solvent was evaporated under reduced pressure. The reaction mixture was diluted with EtOAc, washed with water, dried over anhydrous sodium sulfate, concentrated under reduced pressure to give a residue, which was purified by ISCO (80 g cartridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.41 g, 5.78 mmol, 93% yield) as a colorless oil. $^1$H NMR (400 MHz, DMSO-d$_6$) δ 7.80 (t, J=5.7 Hz, 3H), 7.39-7.30 (m, 5H), 6.95 (s, 1H), 6.74 (t, J=5.8 Hz, 3H), 5.07 (s, 2H), 3.53 (J, J=7.3 Hz, 6H), 3.51 (s, 6H), 3.02 (q, J=6.7 Hz, 6H), 2.94-2.85 (m, 6H), 2.29 (dt, J=26.1, 6.9 Hz, 8H), 2.02 (q, J=9.7, 8.6 Hz, 2H), 1.56-1.39 (m, 10H), 1.35 (s, 27H), 1.20 (brs, 14H); MS (ESI): 1019.6 (M+H)$^+$.

Step 6: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (2.42 g, 2.183 mmol) in DCM (40 mL) was added 2,2,2-trifluoroacetic acid (8 ml, 105 mmol). The reaction mixture was stirred at room temperature for overnight. Solvent was evaporated under reduced pressure, co-evaporated with toluene (2×), triturated with ether, dried under high vacuum for overnight. Directly use TFA salt for next step.

Step 7: To a solution of 5-(((2R,3R,4R,5R,6R)-3-acetamido-4,5-diacetoxy-6-(acetoxymethyl)tetrahydro-2H-pyran-2-yl)oxy)pentanoic acid (3.91 g, 8.73 mmol), HBTU (3.48 g, 9.17 mmol) and HOBT (1.239 g, 9.17 mmol) in DCM (25 mL) was added DIPEA (6.08 ml, 34.9 mmol) followed by benzyl 12-((1,19-diamino-10-((3-((3-aminopropyl)amino)-3-oxopropoxy)methyl)-5,15-dioxo-8,12-dioxa-4,16-diazanonadecan-10-yl)amino)-12-oxododecanoate (1.764 g, 2.183 mmol) in DMF (4.0 mL). The mixture was stirred at room temperature for 5 hrs. Solvent was evaporated under reduced pressure to give a residue, which was purified by ISCO (40 g gold column) eluting with 5% MeOH in DCM for 5 column value to remove HOBt followed by 5% to 30% MeOH in DCM to give 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic benzyl ester (3.98 g, 87% yield) as a white solid. $^1$H NMR (400 MHz, DMSO-d$_6$) δ 7.82-7.74 (m, 6H), 7.69 (t, J=5.6 Hz, 3H), 7.33-7.27 (m, 5H), 6.94 (s, 1H), 5.16 (d, J=3.4 Hz, 3H), 5.03 (s, 2H), 4.92 (dd, J=11.2, 3.4 Hz, 3H), 4.43 (d, J=8.4 Hz, 3H), 4.02-3.95 (m, 9H), 3.82 (dt, J=11.2, 8.8 Hz, 3H), 3.65 (dt, J=10.5, 5.6 Hz, 3H), 3.51-3.44 (m, 12H), 3.36 (dt, J=9.6, 6.0 Hz, 3H), 3.01-2.95 (m, 12H), 2.29 (t, J=7.4 Hz, 2H), 2.23 (t, J=6.3 Hz, 6H), 2.05 (s, 9H), 1.99 (t, J=7.0 Hz, 8H), 1.94 (s, 9H), 1.84 (s, 9H), 1.72 (s, 9H), 1.50-1.14 (m, 34H); MS (ESI): 1049.0 (M/2+H)$^+$.

Step 8: To a round bottom flask flushed with Ar was added 10% Pd/C (165 mg, 0.835 mmol) and EtOAc (15 mL). A solution of benzyl protected tris-GalNAc (1.75 g, 0.835 mmol) in methanol (15 mL) was added followed by triethylsilane (2.67 ml, 16.70 mmol) dropwise. The mixture was stirred at room temperature for 3 hrs. LC-MS showed the reaction was complete, diluted with EtOAc, and filtered through celite, washed with 20% MeOH in EtOAc, concentrated under reduced pressure to give 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic acid (1.67 g, 0.832 mmol, 100% yield) as a white solid. $^1$H NMR (400 MHz, DMSO-d$_6$) δ 11.95 (s, 1H), 7.83-7.74 (m, 6H), 7.69 (t, J=5.7 Hz, 3H), 6.93 (s, 1H), 5.16 (d, J=3.4 Hz, 3H), 4.92 (dd, J=11.2, 3.4 Hz, 3H), 4.43 (d, J=8.4 Hz, 3H), 4.01-3.94 (m, 9H), 3.82 (dt, J=11.3, 8.8 Hz, 3H), 3.66 (dt, J=10.7, 5.6 Hz, 3H), 3.54-3.43 (m, 12H), 3.41-3.33 (m, 3H), 3.03-2.94 (m, 12H), 2.24 (t, J=7.4 Hz, 10H), 2.14 (t, J=7.4 Hz, 2H), 2.06 (s, 9H), 2.00 (t, J=7.2 Hz, 8H), 1.95 (s, 9H), 1.84 (s, 9H), 1.73 (s, 9H), 1.51-1.14 (m, 34H). MS (ESI): 1003.8 (M/2+H)$^+$.

General Procedure for the Anisamide Formation

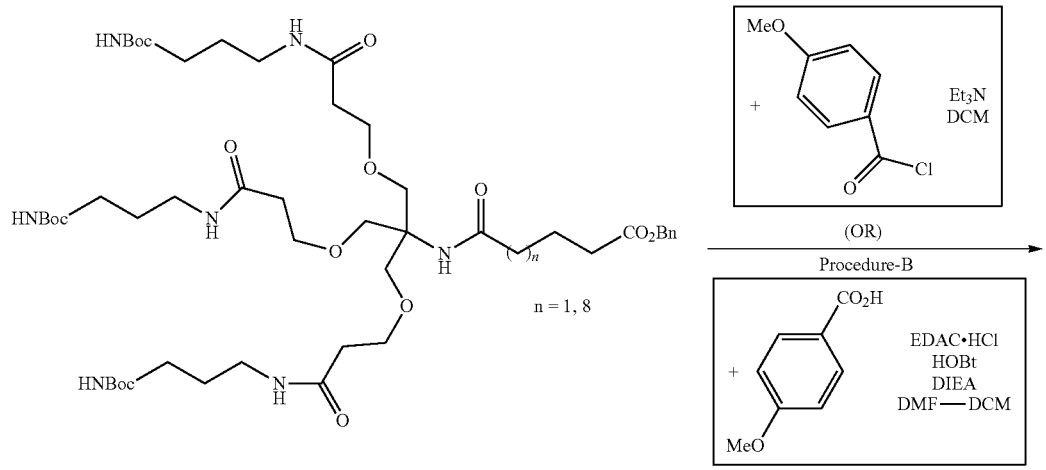

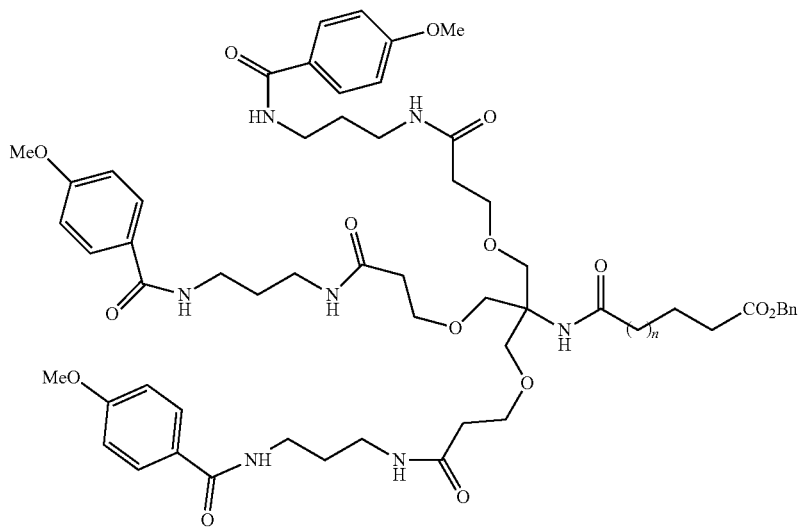

Procedure-A: The crude amine from the previous step was dissolved in a mixture of DCM (100 ml) and Et$_3$N (10 equ.) at RT. During this process, the reaction mixture was cooled with a water bath. Then 4-Methoxybenzoyl chloride (4 equ) was added dropwise to the reaction mixture under argon atmosphere at RT, stirring continued for 3 h. Reaction mixture was diluted with water and extracted with DCM. Organic layer was extracted with aq. NaHCO$_3$, 1N HCl, brine then dried with magnesium sulfate evaporated to dryness. The crude product was purified by silica column chromatography using DCM-MeOH as eluent.

Procedure-B: The crude amine (0.27 equ), acid and HOBt (1 equ) were dissolved in a mixture of DCM and DMF (2:1) in an appropriate sized RBF under argon. EDAC.HCl (1.25 equ) was added portion wise to the reaction mixture under constant stirring. After 15 mins, the reaction mixture was cooled to ~10° C. then DIEA (2.7 equ) was added over a period of 5 mins. Slowly warmed the reaction mixture to ambient temperature and stirred under argon for overnight. TLC indicated completion of the reaction TLC condition, DCM:MeOH (9.5:0.5). Solvents were removed under reduced pressure, then water was added to the residue, and a gummy solid separated out. The clear solution was decanted, and the solid residue was dissolved in EtOAc and washed successively with water, 10% aqueous citric acid, aq. NaHCO$_3$, followed by saturated brine. The organic layer was separated and dried over magnesium sulfate. Solvent was removed under reduced pressure then the crude product was purified with silica column to get the pure product.

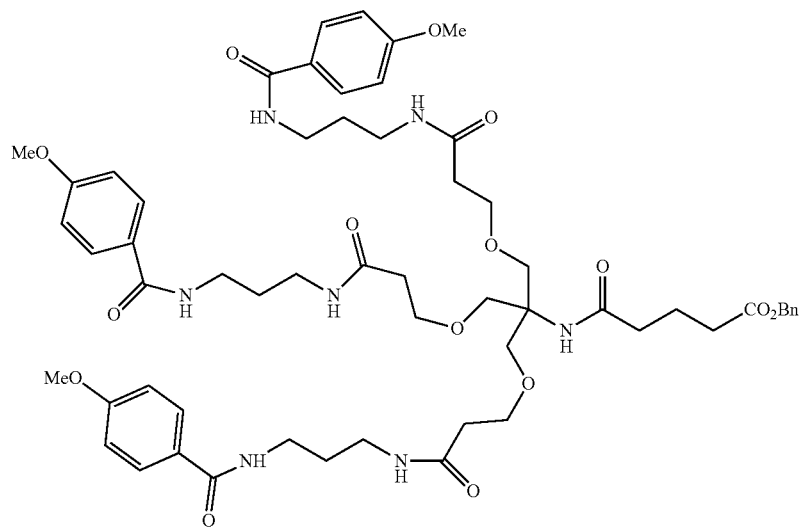 [SMILES: COc1ccc(C(=O)NCCCNC(=O)CCOCC(COCCC(=O)NCCCNC(=O)c2ccc(OC)cc2)(COCCC(=O)NCCCNC(=O)c2ccc(OC)cc2)NC(=O)CCCC(=O)OCc2ccccc2)cc1]
Anizamide was obtained from the amine in 32% yield over 2 steps using the above procedure-B: 1H NMR (CDCl$_3$): δ=7.74 (d, 6H), 7.44 (t, 2H), 7.34 (t, 1H), 7.26 (m, 5H), 7.05 (m, 3H), 6.83 (d, 6H), 6.46 (s, 1H), 5.01 (s, 2H), 3.75 (s, 9H), 3.57 (m, 12H), 3.37 (m, 6H), 3.25 (m, 6H), 2.31 (m, 8H), 2.11 (m, 2H), 1.84 (m, 2H), 1.62 (m, 6H) ppm.
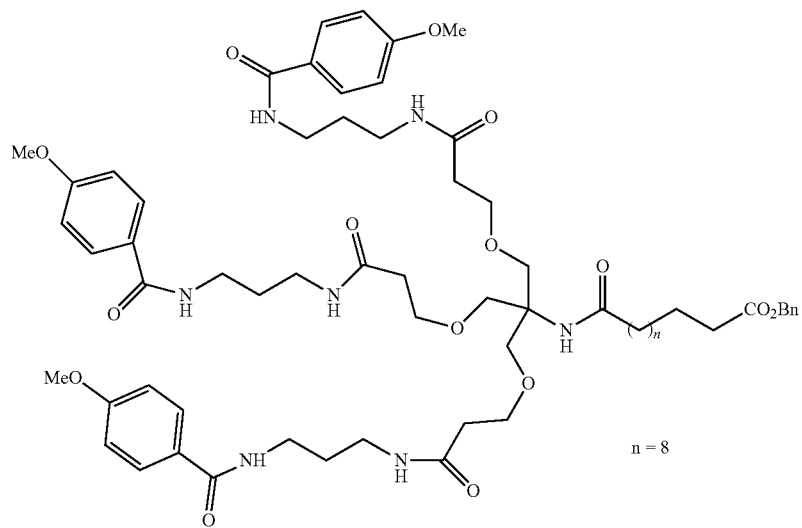
Anizamide was obtained from the amine in 57% yield over 2 steps using the above procedure-A: 1H NMR (CDCl$_3$): δ=7.75 (m, 3H), 7.73 (d, 6H), 7.43 (t, 3H), 7.25 (m, 5H), 6.80 (d, 6H), 6.51 (brs, 1H), 5.01 (s, 2H), 3.72 (s, 9H), 3.58 (m, 6H), 3.21 (m, 12H), 2.33 (t, 3H), 2.25 (t, 2H), 2.02 (t, 2H), 1.64 (q, 6H), 1.52 (p, 2H), 1.41 (q, 2H), 1.12 (m, 12H) ppm.

General Procedure for the Debenzylation

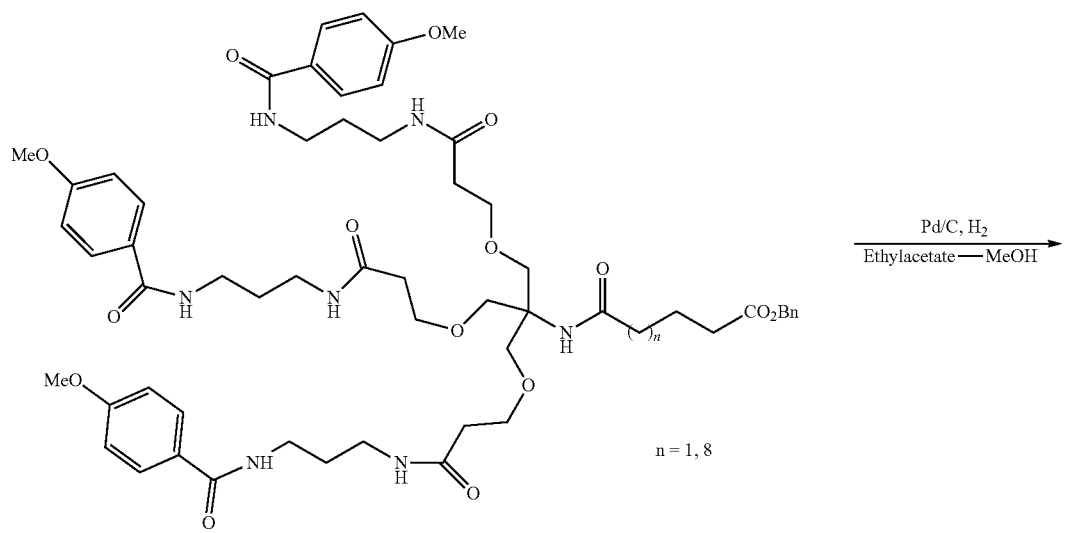

The benzyl ester (10 g) was dissolved in a mixture of ethyl acetate (100 ml) and methanol (25 ml) then Pd/C, 1 g (10% palladium content) was added under argon atmosphere then the reaction mixture was vacuumed and flushed with hydrogen and stirred at RT under H2 atmosphere for 3 h. TLC indicated completion of the reaction, filtered through pad of celite and washed with methanol, evaporated to dryness to yield a foamy white solid.

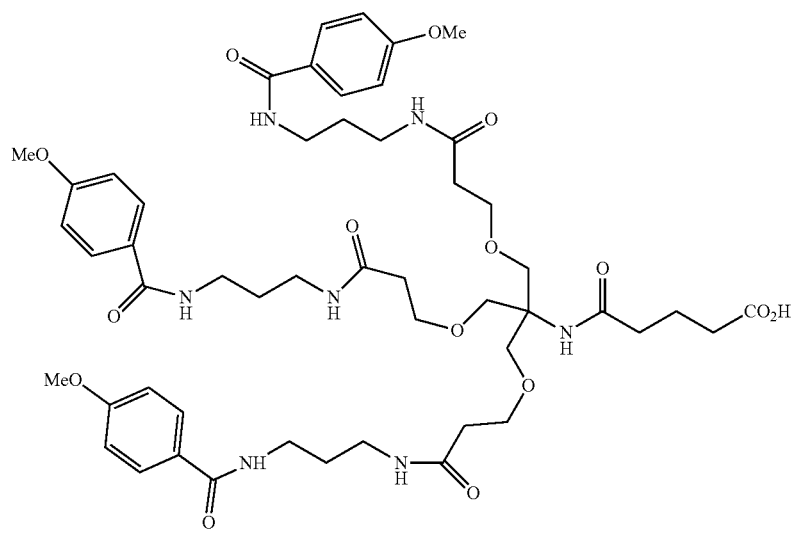 [SMILES: COc1ccc(C(=O)NCCCNC(=O)CCOCC(COCCC(=O)NCCCNC(=O)c2ccc(OC)cc2)(COCCC(=O)NCCCNC(=O)c2ccc(OC)cc2)NC(=O)CCCC(=O)O)cc1]
Yield 98%, 1H NMR (CD$_3$OD): δ=8.35 (t, 1H), 8.01 (t, 1H), 7.82 (d, 6H), 7.27 (d, 1H), 6.99 (d, 6H), 3.85 (s, 9H), 3.68 (m, 12H), 3.41 (m, 6H), 3.29 (m, 6H), 2.42 (m, 6H), 2.31 (q, 2H), 2.21 (td, 2H), 1.80 (m, 8H) ppm.
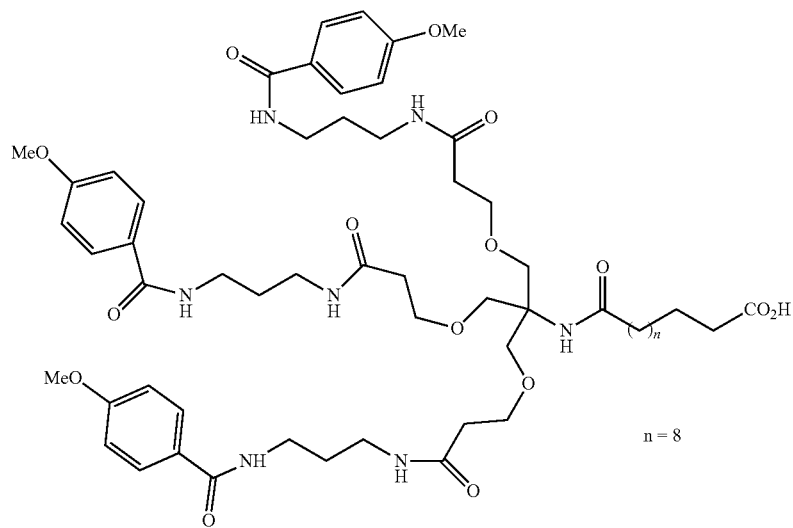
n = 8
Yield 94%, 1H NMR (CD$_3$OD): δ=8.36 (t, 2H), 8.02 (t, 2H), 7.82 (d, 6H), 7.23 (d, 1H), 6.98 (d, 6H), 3.85 (s, 9H), 3.70 (s, 6H), 3.67 (t, 6H), 3.41 (q, 4H), 3.28 (m, 8H), 2.42 (t, 6H), 2.27 (t, 2H), 2.13 (t, 2H), 1.79 (p, 6H), 1.54 (dp, 4H), 1.25 (m, 12H) ppm.

Additional compounds, including oligonucleotides comprising analogues of anisamide, are presented below:
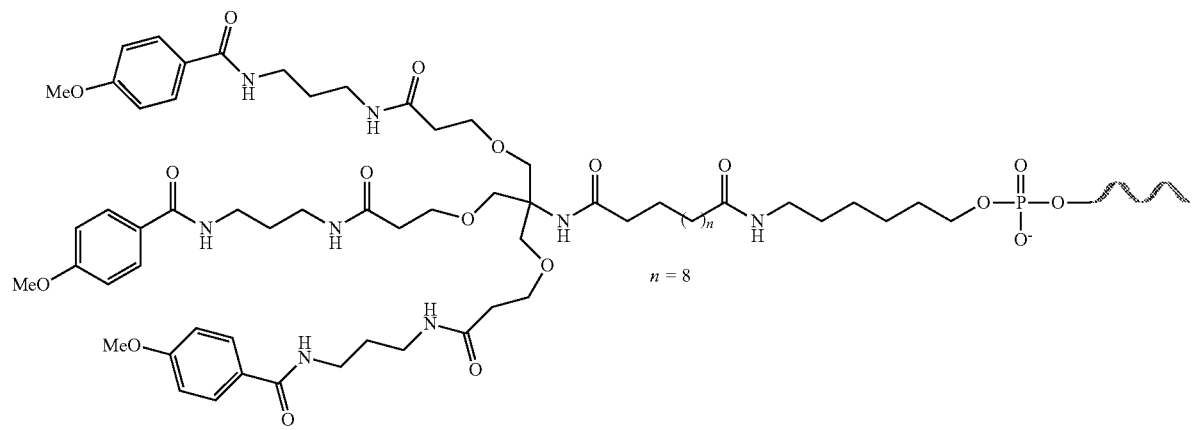
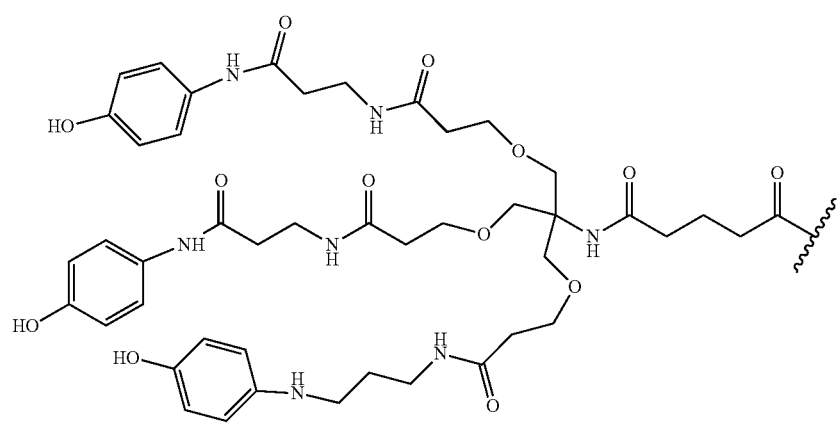
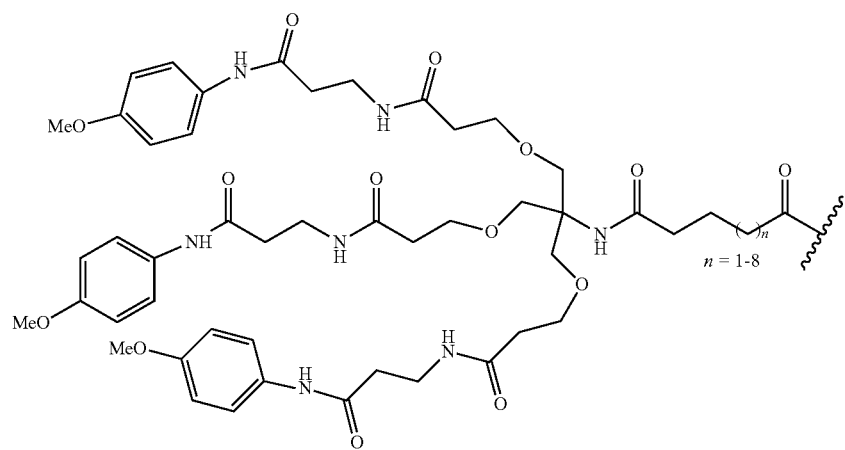

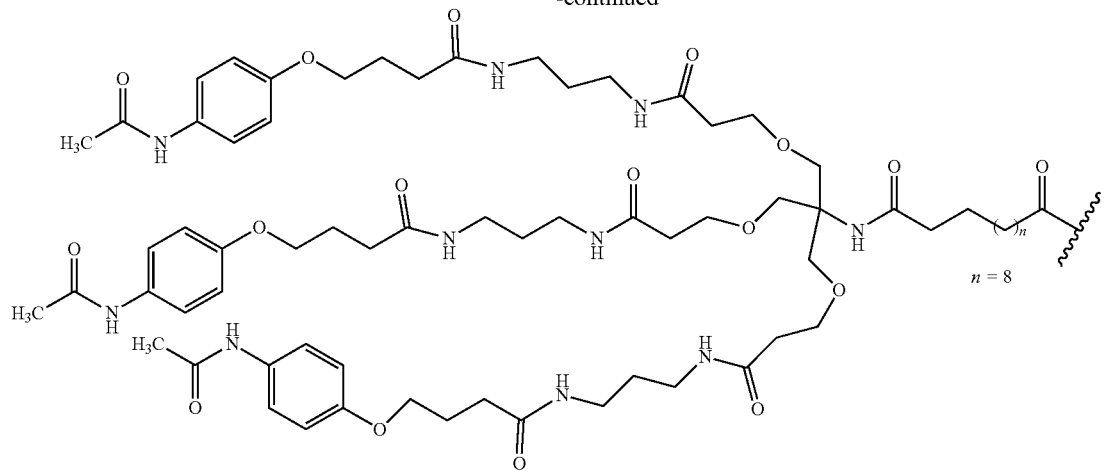

Example 8. Example Preparation of Oligonucleotides Comprising Additional Chemical Moieties Synthesis of WV-7308 was performed on an ÄKTA OP100 synthesizer (GE healthcare) using a 67-mL Fine-LINE column at a 1500 umol scale using CPG (Loading 83 umol/g). During synthesis, chain elongation consisted of four steps namely detritylation, coupling, oxidation/thiolation and capping. Detritylation was performed using 3% DCA in toluene with a UV watch command set at 436 nm. Following detritylation, 4 CV of ACN was used to wash off the detritylation reagent. Coupling was performed using 0.2 M cyanoethyl amidite solutions in ACN and 0.5 M CMIMT. All phosphoramidite and CMIMT solutions were prepared and dried over 3 Å molecular sieves for at least 3 hours prior to synthesis. ChemGenes CLP-1553 C-6 TFA-amino CED phosphoramidite was used to install the amino linker. Coupling was performed by mixing 33% (by volume) of amidite solution with 67% of the activator in-line prior to addition to the column. The coupling mixture was then recirculated for 15 minutes. Following coupling, the column was washed with no less than 2 CV of ACN. Thiolation was then performed with 0.2 M xanthane hydride in pyridine with a contact time of 6 min for 2 CV. After a 2 CV thio wash step using ACN, capping was performed using 0.5 CV of Capping A (20% N-methylimidazole in Acetonitrile (ACN)) and Capping B reagents mixed inline (1:1) followed by a 2 CV ACN wash.

Cleavage and Deprotection of WV-7308: The oligonucleotide bound to the solid support was washed with 6 CV of 20% diethylamine in acetonitrile for 15 min then washed with acetonitrile and dried. The sample was then treated with a 30% ammonium hydroxide solution at 50° C. for 12 hours. The mixture was then cooled on an ice bath and filtered. The cake was washed with water (3×100 mL). The filtrate liquor was obtained and analyzed by UPLC and a purity of 86% FLP found. The mixture was then neutralized with acetic acid to a pH value 6.1 and analyzed by nanodrop to give a crude of 72,757 OD.

Purification of WV-7308: Ion Exchange purification was performed on an ÄKTA 100 Explorer (GE Healthcare) using 20 mM NaOH and 2.5 M NaCl as eluents attaining FLP purity of 94%.

Desalting of WV-7308: The purified WV-7308 sample (72,520 OD) was then desalted on 2K generated cellulose membrane and concentrated in preparation for the conjugation. MW (Calc.): 7306.3; MS (Found): 7306.7.

Preparation of WV-7306: Triantennay GalNAc (2.0 eq), and HATU (1.9 eq.) were dissolved in anhydrous acetonitrile. This was followed by the addition of DIPEA (10 eq) into the tube. The mixture was then stirred for 10 min at room temperature. This mixture was then added to WV-7308 dissolved in water and the mixture was shaken for 60 min at 37° C. The progress of the reaction was monitored by LC-MS and UPLC. It was found that the reaction was complete after 1 h. The resultant GalNAc-conjugated oligo WV-7306 was then treated with conc. ammonium hydroxide for 1 h at 37° C. The formation of the final product was monitored by LC-MS and UPLC. The acetonitrile and ammonia were evaporated under vacuum (by speed vac) overnight. The conjugated sample was dissolved in water and purified by reversed phase HPLC. Following purification, the material was desalted and lyophilized to obtain WV-7306 with a yield of 10,492 OD. MW (Calc.): 8916.2; MS (Found): 8917.4.

Example 9. Example Assays for Assessing Provided Technologies

As appreciated by those having ordinary skill in the art, various technologies can be utilized in accordance with the present disclosure to assess properties and/or activities of provided technologies, e.g., oligonucleotides, oligonucleotide compositions, methods, etc. Among other things, various technologies are available for assessing presence (inclusion) and/or absence (exclusion) of exons in splicing products and protein products encoded thereby, both in vitro and in vivo, and many such technologies can be utilized in accordance with the present disclosure. Described in this example are certain such assays.

Electroporation and cell culture. In an example procedure, patient fibroblasts GM03813 (Coriell Institute) were grown in DMEM+15% FBS medium until confluency, trypsinized with 0.05% Trypsin-EDTA, washed in DMEM+15% FBS and resuspended in BTXpress Electroporation Buffer in concentration 3×10$^6$ cells/mL. In round-bottom 96 well plate 63 uL of cells were mixed with 7 uL of ASO in a well with the following concentrations of ASO in water: 0(vehicle control), 20 uM, 10 uM, 5 uM, 2.5 uM, 1.25 uM, 0.625 uM, and 0.3125 uM to yield 2, 1, 0.5, 0.25, 0.125, 0.0625, and 0.03125 μM ASO concentration upon electroporation. Two ASOs were used in the study: WV6768 or WV2782. Then 60 uL of cell-ASO mixtures (total of 2 wells per condition) were transferred in 96-Well Disposable Electroporation Plate (Harvard Bioscience) and transfected via electroporation under the following conditions: 225V, 1 ms, 3 pulses, 900000 cells per condition. Cells were subsequently moved into 0.5 ml of prewarmed DMEM+15% FBS medium in a 24 well-plate for RNA analysis. RNA was collected 96 hours after electroporation.

RNA isolation and cDNA Synthesis. In an example procedure, total RNA was extracted using Trizol (Fisher scientific) and PureLink RNA Mini Kit (Fisher scientific) using the manufacturers protocol. SuperScript VILO Master Mix (Fisher scientific) was used to make cDNA from total RNA using the manufacturers protocol.

| 5X VILO ™ Reaction Mix | 4.0 µL |
| 10X SuperScript ™ Enzyme Mix | 2.0 µL |
| RNA (up to 2.5 µg) | x µL |
| DEPC-treated water to | 20 µL |

In some embodiments, a tube was gently mixed and incubated at 25° C. for 10 minutes. The tube was then incubated 42° C. for 60 minutes. In some embodiments, the reaction was terminated at 85° C. at 5 minutes. In some embodiments, cDNA was then diluted 1:3 in water to make a working concentration for qPCR.

qPCR step: In an example procedure, qPCR was performed on a BIORAD CFX384 Real-Time PCR detection system using Roche Lightcycler 480 Mastermix (Roche) in 20 ul total reaction volume. For example,

| Roche LightCycler 480 Mastermix | 10.0 µL |
| SMN2 specific probe and primer mix (20X) | 1.0 µL |
| GapDH internal control probe and primer mix (20X) | 1.0 µL |
| Cdna 1:3 diluted | 2.5 µL |
| Water | 5.5 µL |

Example probes and primers used for qPCR can be designed and prepared as needed, or all commercially available. Certain examples were listed below. The probes were FAM-MGB. All probe and primer sets were made by Applied Biosystems.

```
SMN2 exon 7 incorporation probe set
(Full length SMN2)
FWD:                                    (SEQ ID NO: 472)
TAT CAT ACT GGC TAT TAT ATG GGT TTT Probe:                                  (SEQ ID NO: 473)
AAG GAG AAA TGC TGG CAT AGA GCA GC REV:                                    (SEQ ID NO: 474)
TCG TTT CTT TAG TGG TGT CAT TTA G SMN2 exon 7 exclusion probe set (Delta7 SMN2)
FWD:                                    (SEQ ID NO: 475)
TGG CTA TCA TAG TGG CTA TTA TAT GGA A Probe:                                  (SEQ ID NO: 476)
CTG GCA TAG AGC AGC ACT AAA TGA CAC CAC REV:                                    (SEQ ID NO: 477)
TCC AGA TCT GTC TGA TCG TTT CTT
```

In some embodiments, all transcripts were normalized to an internal control, e.g., GAPDH. To calculate the percentage of SMN2 exon7 incorporation, typically the following formula was used:

Oligonucleotide treated[Full Length/(Full length+Delta7)]–no oligonucleotide control[Full Length/(Full length+Delta7)]

Example results were present in the Figures.

Provided oligonucleotides and compositions thereof were assessed in mouse models. Certain data were presented in Tables 1A, 2B, 2C and FIG. 3. As demonstrated herein, chiral control of linkage phosphorus stereochemistry or incorporation of ASGR-binding moieties can significantly improve activates of SMN2 oligonucleotide like nusinersen.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, within the scope of the appended claims and equivalents thereto, claimed technologies may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. A composition comprising a plurality of oligonucleotides of a particular oligonucleotide type defined by:
   1) base sequence, wherein the base sequence comprises 15 contiguous bases of TCACTTTCATAATGCTGG (SEQ ID NO: 479), wherein each T can be independently substituted with U;
   2) Pattern of backbone linkages;
   3) Pattern of backbone chiral centers; and
   4) pattern of backbone phosphorus modifications,
   oligonucleotides of the plurality comprise at least 5 chiral modified internucleotidic linkages each independently having a stereopurity of at least 90% at its chiral linkage phosphorus; and
   the pattern of backbone chiral centers is or comprises:
   (Rp/Op)t[(Np/Op)n]y(Rp/Op)m, wherein each of (Rp/Op)t and (Rp/Op)m independently comprises at least 1, 2, 3, 4, 5, 6, 7, 8, 9, or 10 Rp;
   (Rp)(Rp/Op)t[(Np/Op)n]y(Rp/Op)m(Rp); or
   (Rp)t[(Np/Op)n]y(Rp)m;
   wherein:
   each Np is independently Rp or Sp,
   Sp indicates S configuration of a chiral linkage phosphorus of a chiral modified internucleotidic linkage,
   Rp indicates R configuration of a chiral linkage phosphorus of a chiral modified internucleotidic linkage,
   Op indicates an achiral linkage phosphorus of a natural phosphate linkage,
   each of t, n, y, and m is independently 1-50.

2. The composition of claim 1, wherein the pattern of backbone chiral centers is or comprises (Rp)t[(Sp)n]y(Rp)m, wherein t is 4 or more, n is 1, 2, 3, 4, or 5, y is 1, and m is 4 or more.

3. The composition of claim 2, wherein the composition is a chirally controlled oligonucleotide composition characterized in that, when it is contacted with a transcript in a SMN2 transcript splicing system, inclusion of exon 7 of SMN2 is increased by 2 fold or more relative to that observed under a reference condition which is absence of the composition.

4. The composition of claim 2, wherein the composition is a chirally controlled oligonucleotide composition characterized in that, when it is contacted with a transcript in a SMN2 transcript splicing system, inclusion of exon 7 of SMN2 is increased by 2 fold or more relative to that observed under a reference condition which is presence of composition of nusinersen: Teo*m5Ceo*Aeo*m5Ceo*Teo*Teo*Teo*m5Ceo*Aeo*Teo*Aeo*Aeo*Teo*Geo*m (SEQ ID NO: 199), wherein each * independently represents a phosphorothioate internucleotidic linkage, each m5Ceo independently represents a 5-methyl 2'-O-methoxyethyl C, and each eo independently represents a 2'-O-(2-methoxyethyl) modification.

5. The composition of claim 1, wherein each oligonucleotide of the plurality independently comprises an additional chemical moiety capable of binding to the asialoglycoprotein receptor.

6. The composition of claim 5, wherein the additional chemical moiety is or comprises GalNAc.

7. The composition of claim 1, wherein the base sequence comprises TCACTTTCATAATGCTGG (SEQ ID NO: 479), wherein each T can be independently substituted with U.

8. The composition of claim 1, wherein the base sequence is TCACTTTCATAATGCTGG (SEQ ID NO: 1).

9. The composition of claim 1, wherein the pattern of backbone chiral centers comprises at least 50% Rp.

10. The composition of claim 1, wherein the pattern of backbone chiral centers comprises at least 70% Rp.

11. The composition of claim 1, wherein oligonucleotides of the particular oligonucleotide type comprise at least 12 chiral modified internucleotidic linkages in the Rp configuration.

12. The composition of claim 1, wherein each oligonucleotide of the plurality is independently Teo *R m5Ceo *R Aeo *R m5Ceo *R Teo *R Teo *R Teo *R m5Ceo *R Aeo *S Teo *R Aeo *R Aeo *R Teo *R Geo *R m5Ceo *R Teo *R Geo *R Geo (SEQ ID NO: 213) or a pharmaceutically acceptable salt thereof,
wherein each *R independently represents a phosphorothioate internucleotidic linkage in the Rp configuration, each *S independently represents a phosphorothioate internucleotidic linkage in the Sp configuration, each m5Ceo independently represents a 5-methyl 2'-O-methoxyethyl C, and each eo independently represents a 2'-O-(2-methoxyethyl) modification.

13. The composition of claim 1, wherein each oligonucleotide of the plurality is independently Teo *R m5Ceo *R Aeo *R m5Ceo *R Teo *R Teo *R Teo *R m5Ceo *S Aeo *S Teo *S Aeo *R Aeo *R Teo *R Geo *R m5Ceo *R Teo *R Geo *R Geo (SEQ ID NO: 214) or a pharmaceutically acceptable salt thereof,
wherein each *R independently represents a phosphorothioate internucleotidic linkage in the Rp configuration, each *S independently represents a phosphorothioate internucleotidic linkage in the Sp configuration, each m5Ceo independently represents a 5-methyl 2'-O-methoxyethyl C, and each eo independently represents a 2'-O-(2-methoxyethyl) modification.

14. The composition of claim 1, wherein each oligonucleotide of the plurality is independently Teo *R m5Ceo *R Aeo *R m5Ceo *R Teo *R Teo *R Teo *S m5Ceo *S Aeo *S Teo *S Aeo *S Aeo *R Teo *R Geo *R m5Ceo *R Teo *R Geo *R Geo (SEQ ID NO: 215) or a pharmaceutically acceptable salt thereof,
wherein each *R independently represents a phosphorothioate internucleotidic linkage in the Rp configuration, each *S independently represents a phosphorothioate internucleotidic linkage in the Sp configuration, each m5Ceo independently represents a 5-methyl 2'-O-methoxyethyl C, and each eo independently represents a 2'-O-(2-methoxyethyl) modification.

* * * * *

SEQUENCE LISTING

```
<160> NUMBER OF SEQ ID NOS: 486

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1
tcactttcat aatgctgg                                                  18

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(4)
<223> OTHER INFORMATION: t or u
<220> FEATURE:
<221> NAME/KEY: modified_base
<222> LOCATION: (6)..(10)
<223> OTHER INFORMATION: a, c, u, g, t, unknown or other
<220> FEATURE:
<221> NAME/KEY: modified_base
<222> LOCATION: (13)..(13)
<223> OTHER INFORMATION: t or u

<400> SEQUENCE: 2
cnnncnnnnn gcngg                                                     15

<210> SEQ ID NO 3
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ccagcauuau gaaag                                                     15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(10)
<223> OTHER INFORMATION: a, t, c, g or u

<400> SEQUENCE: 4
ccagcnnnnn gaaag                                                     15

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

```
<221> NAME/KEY: modified_base
<222> LOCATION: (2)..(2)
<223> OTHER INFORMATION: t or u
<220> FEATURE:
<221> NAME/KEY: modified_base
<222> LOCATION: (5)..(5)
<223> OTHER INFORMATION: t or u
<220> FEATURE:
<221> NAME/KEY: modified_base
<222> LOCATION: (8)..(8)
<223> OTHER INFORMATION: t or u

<400> SEQUENCE: 5 anaangcngg                                                              10

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: t or u
<220> FEATURE:
<221> NAME/KEY: modified_base
<222> LOCATION: (6)..(6)
<223> OTHER INFORMATION: t or u
<220> FEATURE:
<221> NAME/KEY: modified_base
<222> LOCATION: (9)..(9)
<223> OTHER INFORMATION: t or u

<400> SEQUENCE: 6
canaangcng g                                                            11

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: t or u
<220> FEATURE:
<221> NAME/KEY: modified_base
<222> LOCATION: (4)..(4)
<223> OTHER INFORMATION: t or u
<220> FEATURE:
<221> NAME/KEY: modified_base
<222> LOCATION: (7)..(7)
<223> OTHER INFORMATION: t or u
<220> FEATURE:
<221> NAME/KEY: modified_base
<222> LOCATION: (10)..(10)
<223> OTHER INFORMATION: t or u

<400> SEQUENCE: 7
ncanaangcn gg                                                           12

<210> SEQ ID NO 8
<211> LENGTH: 13
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: t or u
<220> FEATURE:
<221> NAME/KEY: modified_base
<222> LOCATION: (5)..(5)
<223> OTHER INFORMATION: t or u
<220> FEATURE:
<221> NAME/KEY: modified_base
<222> LOCATION: (8)..(8)
<223> OTHER INFORMATION: t or u
<220> FEATURE:
<221> NAME/KEY: modified_base
<222> LOCATION: (11)..(11)
<223> OTHER INFORMATION: t or u

<400> SEQUENCE: 8
nncanaangc ngg                                                        13

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: t or u
<220> FEATURE:
<221> NAME/KEY: modified_base
<222> LOCATION: (6)..(6)
<223> OTHER INFORMATION: t or u
<220> FEATURE:
<221> NAME/KEY: modified_base
<222> LOCATION: (9)..(9)
<223> OTHER INFORMATION: t or u
<220> FEATURE:
<221> NAME/KEY: modified_base
<222> LOCATION: (12)..(12)
<223> OTHER INFORMATION: t or u

<400> SEQUENCE: 9
nnncanaang cngg                                                       14

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(4)
<223> OTHER INFORMATION: t or u
<220> FEATURE:
<221> NAME/KEY: modified_base
<222> LOCATION: (7)..(7)
```

```
<223> OTHER INFORMATION: t or u
<220> FEATURE:
<221> NAME/KEY: modified_base
<222> LOCATION: (10)..(10)
<223> OTHER INFORMATION: t or u
<220> FEATURE:
<221> NAME/KEY: modified_base
<222> LOCATION: (13)..(13)
<223> OTHER INFORMATION: t or u

<400> SEQUENCE: 10
cnnncanaan gcngg                                                          15

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(5)
<223> OTHER INFORMATION: t or u
<220> FEATURE:
<221> NAME/KEY: modified_base
<222> LOCATION: (8)..(8)
<223> OTHER INFORMATION: t or u
<220> FEATURE:
<221> NAME/KEY: modified_base
<222> LOCATION: (11)..(11)
<223> OTHER INFORMATION: t or u
<220> FEATURE:
<221> NAME/KEY: modified_base
<222> LOCATION: (14)..(14)
<223> OTHER INFORMATION: t or u

<400> SEQUENCE: 11
acnnncanaa ngcngg                                                         16

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(6)
<223> OTHER INFORMATION: t or u
<220> FEATURE:
<221> NAME/KEY: modified_base
<222> LOCATION: (9)..(9)
<223> OTHER INFORMATION: t or u
<220> FEATURE:
<221> NAME/KEY: modified_base
<222> LOCATION: (12)..(12)
<223> OTHER INFORMATION: t or u
<220> FEATURE:
<221> NAME/KEY: modified_base
<222> LOCATION: (15)..(15)
<223> OTHER INFORMATION: t or u

<400> SEQUENCE: 12
cacnnncana angcngg                                                        17
```

-continued

```
<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: t or u
<220> FEATURE:
<221> NAME/KEY: modified_base
<222> LOCATION: (6)..(8)
<223> OTHER INFORMATION: t or u
<220> FEATURE:
<221> NAME/KEY: modified_base
<222> LOCATION: (11)..(11)
<223> OTHER INFORMATION: t or u
<220> FEATURE:
<221> NAME/KEY: modified_base
<222> LOCATION: (14)..(14)
<223> OTHER INFORMATION: t or u
<220> FEATURE:
<221> NAME/KEY: modified_base
<222> LOCATION: (17)..(17)
<223> OTHER INFORMATION: t or u

<400> SEQUENCE: 13
nncacnnnca naangcngg                                                  19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(3)
<223> OTHER INFORMATION: t or u
<220> FEATURE:
<221> NAME/KEY: modified_base
<222> LOCATION: (7)..(9)
<223> OTHER INFORMATION: t or u
<220> FEATURE:
<221> NAME/KEY: modified_base
<222> LOCATION: (12)..(12)
<223> OTHER INFORMATION: t or u
<220> FEATURE:
<221> NAME/KEY: modified_base
<222> LOCATION: (15)..(15)
<223> OTHER INFORMATION: t or u
<220> FEATURE:
<221> NAME/KEY: modified_base
<222> LOCATION: (18)..(18)
<223> OTHER INFORMATION: t or u

<400> SEQUENCE: 14
anncacnnnc anaangcngg                                                 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(8)
<223> OTHER INFORMATION: t or u
<220> FEATURE:
<221> NAME/KEY: modified_base
<222> LOCATION: (10)..(10)
<223> OTHER INFORMATION: t or u
<220> FEATURE:
<221> NAME/KEY: modified_base
<222> LOCATION: (16)..(16)
<223> OTHER INFORMATION: t or u

<400> SEQUENCE: 15
ccagcannan gaaagnga                                                    18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(8)
<223> OTHER INFORMATION: t or u
<220> FEATURE:
<221> NAME/KEY: modified_base
<222> LOCATION: (10)..(10)
<223> OTHER INFORMATION: t or u
<220> FEATURE:
<221> NAME/KEY: modified_base
<222> LOCATION: (16)..(16)
<223> OTHER INFORMATION: t or u
<220> FEATURE:
<221> NAME/KEY: modified_base
<222> LOCATION: (20)..(20)
<223> OTHER INFORMATION: t or u

<400> SEQUENCE: 16
ccagcannan gaaagngaan                                                  20

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gcauagcgag cgagggaaaa c                                                21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18 guuucccuc gcucgcuaug c                                                 21
```

```
<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ucauaaugcu ggcagacuua                                                   20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uucauaaugc uggcagacuu                                                   20

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uuucauaaug cuggcagacu                                                   20

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cuuucauaau gcuggcagac                                                   20

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
acuuucauaa ugcuggcaga                                                   20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cacuuucaua augcuggcag                                                   20

<210> SEQ ID NO 25
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ucacuuucau aaugcuggca                                              20

<210> SEQ ID NO 26
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uucacuuuca uaaugcuggc                                              20

<210> SEQ ID NO 27
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
auucacuuuc auaaugcugg                                              20

<210> SEQ ID NO 28
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gauucacuuu cauaaugcug                                              20

<210> SEQ ID NO 29
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
agauucacuu ucauaaugcu                                              20

<210> SEQ ID NO 30
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aagauucacu uucauaaugc                                              20

<210> SEQ ID NO 31
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uaagauucac uuucauaaug                                                   20

<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
guaagauuca cuuucauaau                                                   20

<210> SEQ ID NO 33
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
cuuucuaaca ucugaacuuu                                                   20

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
aacuuucuaa caucugaacu                                                   20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ucaacuuucu aacaucugaa                                                   20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uuucaacuuu cuaacaucug                                                   20

<210> SEQ ID NO 37
<211> LENGTH: 20
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 37
ccuuucaacu uucuaacauc                                                      20

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
aaccuuucaa cuuucuaaca                                                      20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cugccuacua gugauauaaa                                                      20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gucugccuac uagugauaua                                                      20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uggucugccu acuagugaua                                                      20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gcuggucugc cuacuaguga                                                      20

<210> SEQ ID NO 43
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 43
cugcuggucu gccuacuagu                                                    20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gucugcuggu cugccuacua                                                    20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aagucugcug gucugccuac                                                    20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aaaagucugc uggucugccu                                                    20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gaaauuagaa ccagaggcuu                                                    20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gagaaauuag aaccagaggc                                                    20

<210> SEQ ID NO 49
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 49
augagaaauu agaaccagag                                                    20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aaaugagaaa uuagaaccag                                                    20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gcaaaugaga aauuagaacc                                                    20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cugcaaauga gaaauuagaa                                                    20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uccugcaaau gagaaauuag                                                    20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uuuccugcaa augagaaauu                                                    20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 55
cauuuccugc aaaugagaaa					20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
agcauuuccu gcaaaugaga					20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ccagcauuuc cugcaaauga					20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ugccagcauu uccugcaaau					20

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uaugccagca uuuccugcaa					20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ucuaugccag cauuuccugc					20

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 61
gcucuaugcc agcauuuccu                                              20

<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
cugcucuaug ccagcauuuc                                              20

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ugcugcucua ugccagcauu                                              20

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
agugcugcuc uaugccagca                                              20

<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uuagugcugc ucuaugccag                                              20

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uccacaaacc auaaaguuuu                                              20

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 67
uuuccacaaa ccauaaaguu                                               20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68 guuuccaca aaccauaaag                                                20

<210> SEQ ID NO 69
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uuguuuucca caaaccauaa                                               20

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
auucuaguag ggauguagau                                               20

<210> SEQ ID NO 71
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gaauucuagu agggauguag                                               20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gagaauucua guagggaugu                                               20

<210> SEQ ID NO 73
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
```

```
augagaauuc uaguagggau                                                 20

<210> SEQ ID NO 74
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uuauuuuauu caacaaaaua                                                 20

<210> SEQ ID NO 75
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uacuuauuuu auucaacaaa                                                 20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuuuacuuau uuuauucaac                                                 20

<210> SEQ ID NO 77
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77 acauuuacu uauuuuauuc                                                  20

<210> SEQ ID NO 78
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
aagacauuuu acuuauuuua                                                 20

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
```

-continued

```
cacaagacau uuuacuuauu                                              20

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uuucacaaga cauuuacuu                                               20

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uuguuucaca agacauuuua                                              20

<210> SEQ ID NO 82
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auuuuguuuc acaagacauu                                              20

<210> SEQ ID NO 83
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
agcauuuugu uucacaagac                                              20

<210> SEQ ID NO 84
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
aaaagcauuu uguuucacaa                                              20

<210> SEQ ID NO 85
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uuaaaaagca uuuuguuuca                                              20
```

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
auguuaaaaa gcauuuuguu                                              20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uggauguuaa aaagcauuuu                                              20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
auauggaugu uaaaaagcau                                              20

<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uuuauaugga uguuaaaaag                                              20

<210> SEQ ID NO 90
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
agcuuuauau ggauguuaaa                                              20

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gauagcuuua uauggauguu                                              20

```
<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auagauagcu uuauauggau                                              20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uauauagaua gcuuuauaug                                              20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cccuguaagg aaaauaaagg                                              20

<210> SEQ ID NO 95
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aacccuguaa ggaaaauaaa                                              20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
aaaacccugu aaggaaaaua                                              20

<210> SEQ ID NO 97
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
cuaaaacccu guaaggaaaa                                              20
```

```
<210> SEQ ID NO 98
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gucuaaaacc cuguaaggaa                                                  20

<210> SEQ ID NO 99
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gagcaccuuc cuucuuuuug                                                  20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gugagcaccu uccuucuuuu                                                  20

<210> SEQ ID NO 101
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
augugagcac cuuccuucuu                                                  20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gaaugugagc accuuccuuc                                                  20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
aggaauguga gcaccuuccu                                                  20

<210> SEQ ID NO 104
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uaaggaaugu gagcaccuuc                                              20

<210> SEQ ID NO 105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uuuaaggaau gugagcaccu                                              20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
aauuuaagga augugagcac                                              20

<210> SEQ ID NO 107
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uuaauuuaag gaaugugagc                                              20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
ccuuaauuua aggaauguga                                              20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
cuccuuaauu uaaggaaugu                                              20

<210> SEQ ID NO 110
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
acuuucauaa ugcuggcaga cuuac                                          25

<210> SEQ ID NO 111
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
cacuuucaua augcuggcag acuua                                          25

<210> SEQ ID NO 112
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
ucacuuucau aaugcuggca gacuu                                          25

<210> SEQ ID NO 113
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uucacuuuca uaaugcuggc agacu                                          25

<210> SEQ ID NO 114
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
auucacuuuc auaaugcugg cagac                                          25

<210> SEQ ID NO 115
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gauucacuuu cauaaugcug gcaga                                          25

<210> SEQ ID NO 116
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 116
agauucacuu ucauaaugcu ggcag                                           25

<210> SEQ ID NO 117
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
aagauucacu ucauaaugc uggca                                            25

<210> SEQ ID NO 118
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uaagauucac uuucauaaug cuggc                                           25

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
guaagauuca cuuucauaau gcugg                                           25

<210> SEQ ID NO 120
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aacuuucuaa caucugaacu uuuua                                           25

<210> SEQ ID NO 121
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
ucaacuuucu aacaucugaa cuuuu                                           25

<210> SEQ ID NO 122
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 122
uuucaacuuu cuaacaucug aacuu                                          25

<210> SEQ ID NO 123
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123 ccuucaacu uucuaacauc ugaac                                           25

<210> SEQ ID NO 124
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
aaccuuucaa cuuucuaaca ucuga                                          25

<210> SEQ ID NO 125
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uuaaccuuuc aacuuucuaa caucu                                          25

<210> SEQ ID NO 126
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
cauuaaccuu ucaacuuucu aacau                                          25

<210> SEQ ID NO 127
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uggucugccu acuagugaua uaaaa                                          25

<210> SEQ ID NO 128
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 128
gcuggucugc cuacuaguga uauaa                                            25

<210> SEQ ID NO 129
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
cugcuggucu gccuacuagu gauau                                            25

<210> SEQ ID NO 130
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gucugcuggu cugccuacua gugau                                            25

<210> SEQ ID NO 131
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
aagucugcug gucugccuac uagug                                            25

<210> SEQ ID NO 132
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
aaaagucugc uggucugccu acuag                                            25

<210> SEQ ID NO 133
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
aaaaaagucu gcuggucugc cuacu                                            25

<210> SEQ ID NO 134
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 134
aaaaaaaagu cugcuggucu gccua                                              25

<210> SEQ ID NO 135
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
auaaaaaaaa gucugcuggu cugcc                                              25

<210> SEQ ID NO 136
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
caauaaaaaa aagucugcug gucug                                              25

<210> SEQ ID NO 137
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
aaugagaaau uagaaccaga ggcuu                                              25

<210> SEQ ID NO 138
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
caaaugagaa auuagaacca gaggc                                              25

<210> SEQ ID NO 139
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugcaaaugag aaauuagaac cagag                                              25

<210> SEQ ID NO 140
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ccugcaaaug agaaauuaga accag                                              25

<210> SEQ ID NO 141
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uuccugcaaa ugagaaauua gaacc                                              25

<210> SEQ ID NO 142
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
auuuccugca aaugagaaau uagaa                                              25

<210> SEQ ID NO 143
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143 gcauuccug caaaugagaa auuag                                               25

<210> SEQ ID NO 144
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cagcauuucc ugcaaaugag aaauu                                              25

<210> SEQ ID NO 145
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gccagcauuu ccugcaaaug agaaa                                              25

<210> SEQ ID NO 146
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 146
augccagcau uccugcaaa ugaga                                          25

<210> SEQ ID NO 147
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
cuaugccagc auuccugca aauga                                          25

<210> SEQ ID NO 148
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
cucuaugcca gcauuccug caaau                                          25

<210> SEQ ID NO 149
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ugcucuaugc cagcauuucc ugcaa                                         25

<210> SEQ ID NO 150
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gcugcucuau gccagcauuu ccugc                                         25

<210> SEQ ID NO 151
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gugcugcucu augccagcau uccu                                          25

<210> SEQ ID NO 152
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
```
uagugcugcu cuaugccagc auuuc                                              25

<210> SEQ ID NO 153
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153 guuuccaca aaccauaaag uuuua                                               25

<210> SEQ ID NO 154
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154 uguuuccac aaaccauaaa guuu                                                25

<210> SEQ ID NO 155
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuguuuucca caaaccauaa aguuu                                              25

<210> SEQ ID NO 156
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gagaauucua guagggaugu agauu                                              25

<210> SEQ ID NO 157
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ugagaauucu aguagggaug uagau                                              25

<210> SEQ ID NO 158
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
augagaauuc uaguagggau guaga                                        25

<210> SEQ ID NO 159
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uaugagaauu cuaguaggga uguag                                        25

<210> SEQ ID NO 160
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
uuuacuuauu uuauucaaca aaaua                                        25

<210> SEQ ID NO 161
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
auuuuacuua uuuuauucaa caaaa                                        25

<210> SEQ ID NO 162
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uucacaagac auuuuacuua uuuua                                        25

<210> SEQ ID NO 163
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
guuucacaag acauuuuacu uauuu                                        25

<210> SEQ ID NO 164
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
uuguuucaca agacauuuua cuuau                                        25

<210> SEQ ID NO 165
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uuuuguuuca caagacauuu uacuu                                           25

<210> SEQ ID NO 166
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
cauuuuguuu cacaagacau uuuac                                           25

<210> SEQ ID NO 167
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
agcauuuugu uucacaagac auuuu                                           25

<210> SEQ ID NO 168
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aaagcauuuu guuucacaag acauu                                           25

<210> SEQ ID NO 169
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
aaaaagcauu uuguuucaca agaca                                           25

<210> SEQ ID NO 170
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uuaaaaagca uuuuguuuca caaga                                           25

<210> SEQ ID NO 171
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uguuaaaaag cauuuuguuu cacaa                                              25

<210> SEQ ID NO 172
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gauguuaaaa agcauuuugu uucac                                              25

<210> SEQ ID NO 173
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uggauguuaa aaagcauuuu guuuc                                              25

<210> SEQ ID NO 174
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uauggauguu aaaaagcauu uuguu                                              25

<210> SEQ ID NO 175
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uauauggaug uuaaaaagca uuuug                                              25

<210> SEQ ID NO 176
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
uuuauaugga uguuaaaaag cauuu                                              25

```
<210> SEQ ID NO 177
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
gcuuuauaug gauguuaaaa agcau                                          25

<210> SEQ ID NO 178
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uagcuuuaua uggauguuaa aaagc                                          25

<210> SEQ ID NO 179
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
gauagcuuua uauggauguu aaaaa                                          25

<210> SEQ ID NO 180
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uagauagcuu uauauggaug uuaaa                                          25

<210> SEQ ID NO 181
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uauagauagc uuuauaugga uguua                                          25

<210> SEQ ID NO 182
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
uauauagaua gcuuuauaug gaugu                                          25

<210> SEQ ID NO 183
```

-continued

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
ccuguaagga aaauaaagga aguua                                               25

<210> SEQ ID NO 184
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
acccuguaag gaaauaaag gaagu                                                25

<210> SEQ ID NO 185
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
aaacccugua aggaaaauaa aggaa                                               25

<210> SEQ ID NO 186
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uaaaacccug uaggaaaau aaagg                                                25

<210> SEQ ID NO 187
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
ucuaaaaccc uguaggaaa auaaa                                                25

<210> SEQ ID NO 188
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ugucuaaaac ccuguaagga aaaua                                               25

<210> SEQ ID NO 189
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
aaugugagca ccuuccuucu uuuug                                          25

<210> SEQ ID NO 190
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
ggaaugugag caccuuccuu cuuuu                                          25

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
aaggaaugug agcaccuucc uucuu                                          25

<210> SEQ ID NO 192
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
uuaaggaaug ugagcaccuu ccuuc                                          25

<210> SEQ ID NO 193
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
auuuaaggaa ugugagcacc uuccu                                          25

<210> SEQ ID NO 194
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
uaauuuaagg aaugugagca ccuuc                                          25

<210> SEQ ID NO 195
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 195
cuuaauuuaa ggaaugugag caccu                                          25

<210> SEQ ID NO 196
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uccuuaauuu aaggaaugug agcac                                          25

<210> SEQ ID NO 197
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
acuccuuaau uuaaggaaug ugagc                                          25

<210> SEQ ID NO 198
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uuacuccuua auuuaaggaa uguga                                          25

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tcactttcat aatgctgg                                                  18

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tcactttcat aatgctgg                                                  18

<210> SEQ ID NO 201
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 201
tcactttcat aatgctgg                                                 18

<210> SEQ ID NO 202
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
tcactttcat aatgctgg                                                 18

<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tcactttcat aatgctgg                                                 18

<210> SEQ ID NO 204
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tcactttcat aatgctgg                                                 18

<210> SEQ ID NO 205
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tcactttcat aatgctgg                                                 18

<210> SEQ ID NO 206
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tcactttcat aatgctgg                                                 18

<210> SEQ ID NO 207
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 207
tcactttcat aatgctgg                                                   18

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tcactttcat aatgctgg                                                   18

<210> SEQ ID NO 209
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tcactttcat aatgctgg                                                   18

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tcactttcat aatgctgg                                                   18

<210> SEQ ID NO 211
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tcactttcat aatgctgg                                                   18

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tcactttcat aatgctgg                                                   18

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 213
tcactttcat aatgctgg                                                 18

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tcactttcat aatgctgg                                                 18

<210> SEQ ID NO 215
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tcactttcat aatgctgg                                                 18

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tcactttcat aatgctgg                                                 18

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tcactttcat aatgctgg                                                 18

<210> SEQ ID NO 218
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tcactttcat aatgctgg                                                 18

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tcactttcat aatgctgg                                                18

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tcactttcat aatgctgg                                                18

<210> SEQ ID NO 221
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tcactttcat aatgctgg                                                18

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tcactttcat aatgctgg                                                18

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tcactttcat aatgctgg                                                18

<210> SEQ ID NO 224
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tcactttcat aatgctgg                                                18

<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 225
tcactttcat aatgctgg                                                 18

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tcactttcat aatgctgg                                                 18

<210> SEQ ID NO 227
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tcactttcat aatgctgg                                                 18

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tcactttcat aatgctgg                                                 18

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tcactttcat aatgctgg                                                 18

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tcactttcat aatgctgg                                                 18

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
```
tcactttcat aatgctgg                                                   18

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tcactttcat aatgctgg                                                   18

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tcactttcat aatgctgg                                                   18

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tcactttcat aatgctgg                                                   18

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tcactttcat aatgctgg                                                   18

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tcactttcat aatgctgg                                                   18

<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tcactttcat aatgctgg        18

<210> SEQ ID NO 238
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tcactttcat aatgctgg        18

<210> SEQ ID NO 239
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
tcactttcat aatgctgg        18

<210> SEQ ID NO 240
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tcactttcat aatgctgg        18

<210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tcactttcat aatgctgg        18

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tcactttcat aatgctgg        18

<210> SEQ ID NO 243
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tcactttcat aatgctgg        18

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tcactttcat aatgctgg                                                 18

<210> SEQ ID NO 245
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tcactttcat aatgctgg                                                 18

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tcactttcat aatgctgg                                                 18

<210> SEQ ID NO 247
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ucacuuucau aaugcugg                                                 18

<210> SEQ ID NO 248
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
ucacuuucau aaugcugg                                                 18

<210> SEQ ID NO 249
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ucacuuucau aaugcugg                                                 18

<210> SEQ ID NO 250
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
ucacuuucau aaugcugg                                                       18

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tcactttcat aatgctgg                                                       18

<210> SEQ ID NO 252
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
tcactttcat aatgctgg                                                       18

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
tcactttcat aatgctgg                                                       18

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tcactttcat aatgctgg                                                       18

<210> SEQ ID NO 255
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tcactttcat aatgctgg                                                       18

```
<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tcactttcat aatgctgg                                                 18

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gatagcttta tatggatgtt                                               20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
tagctttata tggatgttaa                                               20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
atagctttat atggatgtta                                               20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
atagatagct ttatatggat                                               20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ttatatggat gttaaaaagc                                               20

<210> SEQ ID NO 262
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gctttatatg gatgttaaaa                                                  20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
agctttatat ggatgttaaa                                                  20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
tagatagctt tatatggatg                                                  20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
agatagcttt atatggatgt                                                  20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tttatatgga tgttaaaaag                                                  20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tatagatagc tttatatgga                                                  20

<210> SEQ ID NO 268
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
tgttaaaaag cattttgttt                                              20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tggatgttaa aaagcatttt                                              20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
taaaaagcat tttgtttcac                                              20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ttaaaaagca ttttgtttca                                              20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctttatatgg atgttaaaaa                                              20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
atggatgtta aaagcattt                                               20

<210> SEQ ID NO 274
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 274
atgttaaaaa gcattttgtt                                                 20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gatgttaaaa agcattttgt                                                 20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ggatgttaaa aagcattttg                                                 20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gttaaaaagc attttgtttc                                                 20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
atatggatgt taaaaagcat                                                 20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tatatggatg ttaaaaagca                                                 20

<210> SEQ ID NO 280
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 280
tatggatgtt aaaaagcatt                                              20

<210> SEQ ID NO 281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ucauaaugcu ggcagacuua                                              20

<210> SEQ ID NO 282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
uucauaaugc uggcagacuu                                              20

<210> SEQ ID NO 283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
uuucauaaug cuggcagacu                                              20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
cuuucauaau gcuggcagac                                              20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
acuuucauaa ugcuggcaga                                              20

<210> SEQ ID NO 286
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 286
cacuuucaua augcuggcag                                                   20

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ucacuuucau aaugcuggca                                                   20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uucacuuuca uaaugcuggc                                                   20

<210> SEQ ID NO 289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
auucacuuuc auaaugcugg                                                   20

<210> SEQ ID NO 290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
gauucacuuu cauaaugcug                                                   20

<210> SEQ ID NO 291
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
agauucacuu ucauaaugcu                                                   20

<210> SEQ ID NO 292
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 292
aagauucacu uucauaaugc                                               20

<210> SEQ ID NO 293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uaagauucac uuucauaaug                                               20

<210> SEQ ID NO 294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
guaagauuca cuuucauaau                                               20

<210> SEQ ID NO 295
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
cuuucuaaca ucugaacuuu                                               20

<210> SEQ ID NO 296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aacuuucuaa caucugaacu                                               20

<210> SEQ ID NO 297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ucaacuuucu aacaucugaa                                               20

<210> SEQ ID NO 298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uuucaacuuu cuaacaucug        20

<210> SEQ ID NO 299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ccuuucaacu uucuaacauc        20

<210> SEQ ID NO 300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
aaccuuucaa cuuucuaaca        20

<210> SEQ ID NO 301
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
cugccuacua gugauauaaa        20

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
gucugccuac uagugauaua        20

<210> SEQ ID NO 303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
uggucugccu acuagugaua        20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 304
gcuggucugc cuacuaguga                                              20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
cugcuggucu gccuacuagu                                              20

<210> SEQ ID NO 306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gucugcuggu cugccuacua                                              20

<210> SEQ ID NO 307
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
aagucugcug gucugccuac                                              20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
aaaagucugc uggucugccu                                              20

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gaaauuagaa ccagaggcuu                                              20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
```

```
gagaaauuag aaccagaggc                                          20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
augagaaauu agaaccagag                                          20

<210> SEQ ID NO 312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
aaaugagaaa uuagaaccag                                          20

<210> SEQ ID NO 313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gcaaaugaga aauuagaacc                                          20

<210> SEQ ID NO 314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
cugcaaauga gaaauuagaa                                          20

<210> SEQ ID NO 315
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
uccugcaaau gagaaauuag                                          20

<210> SEQ ID NO 316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
```

-continued uuuccugcaa augagaaauu                                              20

<210> SEQ ID NO 317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
cauuuccugc aaaugagaaa                                              20

<210> SEQ ID NO 318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
agcauuuccu gcaaaugaga                                              20

<210> SEQ ID NO 319
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
ccagcauuuc cugcaaauga                                              20

<210> SEQ ID NO 320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ugccagcauu uccugcaaau                                              20

<210> SEQ ID NO 321
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
uaugccagca uuuccugcaa                                              20

<210> SEQ ID NO 322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
ucuaugccag cauuuccugc                                              20

<210> SEQ ID NO 323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
gcucuaugcc agcauuccu                                                    20

<210> SEQ ID NO 324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
cugcucuaug ccagcauuuc                                                   20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
ugcugcucua ugccagcauu                                                   20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
agugcugcuc uaugccagca                                                   20

<210> SEQ ID NO 327
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
uuagugcugc ucuaugccag                                                   20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
uccacaaacc auaaaguuuu                                                   20

<210> SEQ ID NO 329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uuuccacaaa ccauaaaguu                                              20

<210> SEQ ID NO 330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330 guuuccaca aaccauaaag                                               20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
uuguuuucca caaaccauaa                                              20

<210> SEQ ID NO 332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
auucuaguag ggauguagau                                              20

<210> SEQ ID NO 333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
gaauucuagu agggauguag                                              20

<210> SEQ ID NO 334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
gagaauucua guagggaugu                                              20

```
<210> SEQ ID NO 335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
augagaauuc uaguagggau                                                   20

<210> SEQ ID NO 336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
uuauuuuauu caacaaaaua                                                   20

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uacuuauuuu auucaacaaa                                                   20

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
uuuuacuuau uuuauucaac                                                   20

<210> SEQ ID NO 339
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
acauuuuacu uauuuuauuc                                                   20

<210> SEQ ID NO 340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
aagacauuuu acuuauuuua                                                   20

<210> SEQ ID NO 341
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
cacaagacau uuuacuuauu                                                 20

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uuucacaaga cauuuuacuu                                                 20

<210> SEQ ID NO 343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uuguuucaca agacauuuua                                                 20

<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
auuuuguuuc acaagacauu                                                 20

<210> SEQ ID NO 345
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
agcauuuugu uucacaagac                                                 20

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
aaaagcauuu uguuucacaa                                                 20

<210> SEQ ID NO 347
<211> LENGTH: 20
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
uuaaaaagca uuuuguuuca                                                  20

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
auguuaaaaa gcauuuuguu                                                  20

<210> SEQ ID NO 349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
uggauguuaa aaagcauuuu                                                  20

<210> SEQ ID NO 350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
auauggaugu uaaaaagcau                                                  20

<210> SEQ ID NO 351
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uuuauaugga uguuaaaaag                                                  20

<210> SEQ ID NO 352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
agcuuuauau ggauguuaaa                                                  20

<210> SEQ ID NO 353
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 353
gauagcuuua uauggauguu                                              20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
auagauagcu uuauauggau                                              20

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
uauauagaua gcuuuauaug                                              20

<210> SEQ ID NO 356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
cccuguaagg aaaauaaagg                                              20

<210> SEQ ID NO 357
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
aacccuguaa ggaaaauaaa                                              20

<210> SEQ ID NO 358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aaaacccugu aaggaaaaua                                              20

<210> SEQ ID NO 359
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 359
cuaaaacccu guaaggaaaa                                                   20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
gucuaaaacc cuguaaggaa                                                   20

<210> SEQ ID NO 361
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
gagcaccuuc cuucuuuuug                                                   20

<210> SEQ ID NO 362
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
gugagcaccu uccuucuuuu                                                   20

<210> SEQ ID NO 363
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
augugagcac cuuccuucuu                                                   20

<210> SEQ ID NO 364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
gaaugugagc accuuccuuc                                                   20

<210> SEQ ID NO 365
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 365
aggaauguga gcaccuuccu                                                   20

<210> SEQ ID NO 366
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
uaaggaaugu gagcaccuuc                                                   20

<210> SEQ ID NO 367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
uuuaaggaau gugagcaccu                                                   20

<210> SEQ ID NO 368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
aauuuaagga augugagcac                                                   20

<210> SEQ ID NO 369
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
uuaauuuaag gaaugugagc                                                   20

<210> SEQ ID NO 370
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
ccuuaauuua aggaauguga                                                   20

<210> SEQ ID NO 371
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 371
cuccuuaauu uaaggaaugu                                               20

<210> SEQ ID NO 372
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
acuuucauaa ugcuggcaga cuuac                                         25

<210> SEQ ID NO 373
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
cacuuucaua augcuggcag acuua                                         25

<210> SEQ ID NO 374
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ucacuuucau aaugcuggca gacuu                                         25

<210> SEQ ID NO 375
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
uucacuuuca uaaugcuggc agacu                                         25

<210> SEQ ID NO 376
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
auucacuuuc auaaugcugg cagac                                         25

<210> SEQ ID NO 377
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
gauucacuuu cauaaugcug gcaga                                    25

<210> SEQ ID NO 378
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
agauucacuu ucauaaugcu ggcag                                    25

<210> SEQ ID NO 379
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
aagauucacu uucauaaugc uggca                                    25

<210> SEQ ID NO 380
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
uaagauucac uuucauaaug cuggc                                    25

<210> SEQ ID NO 381
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
guaagauuca cuuucauaau gcugg                                    25

<210> SEQ ID NO 382
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
aacuuucuaa caucugaacu uuuua                                    25

<210> SEQ ID NO 383
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ucaacuuucu aacaucugaa cuuuu                                             25

<210> SEQ ID NO 384
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
uuucaacuuu cuaacaucug aacuu                                             25

<210> SEQ ID NO 385
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
ccuuucaacu uucuaacauc ugaac                                             25

<210> SEQ ID NO 386
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aaccuuucaa cuuucuaaca ucuga                                             25

<210> SEQ ID NO 387
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
uuaaccuuuc aacuuucuaa caucu                                             25

<210> SEQ ID NO 388
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
cauuaaccuu ucaacuuucu aacau                                             25

<210> SEQ ID NO 389
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
uggucugccu acuagugaua uaaaa                    25

<210> SEQ ID NO 390
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
gcuggucugc cuacuaguga uauaa                    25

<210> SEQ ID NO 391
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
cugcuggucu gccuacuagu gauau                    25

<210> SEQ ID NO 392
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
gucugcuggu cugccuacua gugau                    25

<210> SEQ ID NO 393
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aagucugcug gucugccuac uagug                    25

<210> SEQ ID NO 394
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
aaaagucugc uggucugccu acuag                    25

<210> SEQ ID NO 395
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
aaaaaagucu gcuggucugc cuacu                                    25

<210> SEQ ID NO 396
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
aaaaaaaagu cugcuggucu gccua                                    25

<210> SEQ ID NO 397
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
auaaaaaaaa gucugcuggu cugcc                                    25

<210> SEQ ID NO 398
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
caauaaaaaa aagucugcug gucug                                    25

<210> SEQ ID NO 399
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
aaugagaaau uagaaccaga ggcuu                                    25

<210> SEQ ID NO 400
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
caaaugagaa auuagaacca gaggc                                    25

<210> SEQ ID NO 401
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ugcaaaugag aaauuagaac cagag                                    25

<210> SEQ ID NO 402
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 402
ccugcaaaug agaaauuaga accag                                            25

<210> SEQ ID NO 403
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 403
uuccugcaaa ugagaaauua gaacc                                            25

<210> SEQ ID NO 404
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 404 auuccugca aaugagaaau uagaa                                             25

<210> SEQ ID NO 405
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 405 gcauuccug caaaugagaa auuag                                             25

<210> SEQ ID NO 406
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 406
cagcauuucc ugcaaaugag aaauu                                            25

<210> SEQ ID NO 407
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 407
gccagcauuu ccugcaaaug agaaa                                            25

<210> SEQ ID NO 408
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 408
augccagcau uuccugcaaa ugaga                                    25

<210> SEQ ID NO 409
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 409
cuaugccagc auuccugca aauga                                     25

<210> SEQ ID NO 410
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 410
cucuaugcca gcauuccug caaau                                     25

<210> SEQ ID NO 411
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 411
ugcucuaugc cagcauuucc ugcaa                                    25

<210> SEQ ID NO 412
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 412
gcugcucuau gccagcauuu ccugc                                    25

<210> SEQ ID NO 413
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 413
gugcugcucu augccagcau uuccu                                    25

```
<210> SEQ ID NO 414
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uagugcugcu cuaugccagc auuuc                                          25

<210> SEQ ID NO 415
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415 guuuccaca aaccauaaag uuuua                                           25

<210> SEQ ID NO 416
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416 uguuuccac aaaccauaaa guuuu                                           25

<210> SEQ ID NO 417
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uuguuuucca caaaccauaa aguuu                                          25

<210> SEQ ID NO 418
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
gagaauucua guagggaugu agauu                                          25

<210> SEQ ID NO 419
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
ugagaauucu aguagggaug uagau                                          25

<210> SEQ ID NO 420
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
augagaauuc uaguagggau guaga                                          25

<210> SEQ ID NO 421
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uaugagaauu cuaguaggga uguag                                          25

<210> SEQ ID NO 422
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uuuacuuauu uuauucaaca aaaua                                          25

<210> SEQ ID NO 423
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
auuuuacuua uuuuauucaa caaaa                                          25

<210> SEQ ID NO 424
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uucacaagac auuuuacuua uuuua                                          25

<210> SEQ ID NO 425
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
guuucacaag acauuuuacu uauuu                                          25

<210> SEQ ID NO 426
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uuguuucaca agacauuuua cuuau                                             25

<210> SEQ ID NO 427
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
uuuuguuuca caagacauuu uacuu                                             25

<210> SEQ ID NO 428
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
cauuuuguuu cacaagacau uuuac                                             25

<210> SEQ ID NO 429
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
agcauuuugu uucacaagac auuuu                                             25

<210> SEQ ID NO 430
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
aaagcauuuu guuucacaag acauu                                             25

<210> SEQ ID NO 431
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
aaaaagcauu uuguuucaca agaca                                             25

<210> SEQ ID NO 432
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 432
uuaaaaagca uuuguuuca caaga                                          25

<210> SEQ ID NO 433
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uguuaaaaag cauuuguuu cacaa                                          25

<210> SEQ ID NO 434
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
gauguuaaaa agcauuuugu uucac                                         25

<210> SEQ ID NO 435
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
uggauguuaa aaagcauuuu guuuc                                         25

<210> SEQ ID NO 436
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
uauggauguu aaaaagcauu uuguu                                         25

<210> SEQ ID NO 437
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
uauauggaug uuaaaaagca uuuug                                         25

<210> SEQ ID NO 438
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 438
uuuauaugga uguuaaaaag cauuu                                          25

<210> SEQ ID NO 439
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
gcuuuauaug gauguuaaaa agcau                                          25

<210> SEQ ID NO 440
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
uagcuuuaua uggauguuaa aaagc                                          25

<210> SEQ ID NO 441
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
gauagcuuua uauggauguu aaaaa                                          25

<210> SEQ ID NO 442
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
uagauagcuu uauauggaug uuaaa                                          25

<210> SEQ ID NO 443
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uauagauagc uuuauaugga uguua                                          25

<210> SEQ ID NO 444
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 444
uauauagaua gcuuuauaug gaugu                                            25

<210> SEQ ID NO 445
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ccuguaagga aaauaaagga aguua                                            25

<210> SEQ ID NO 446
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
acccuguaag gaaaauaaag gaagu                                            25

<210> SEQ ID NO 447
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
aaacccugua aggaaaauaa aggaa                                            25

<210> SEQ ID NO 448
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uaaaacccug uaaggaaaau aaagg                                            25

<210> SEQ ID NO 449
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ucuaaaaccc uguaaggaaa auaaa                                            25

<210> SEQ ID NO 450
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 450
ugucuaaaac ccuguaagga aaaua                                              25

<210> SEQ ID NO 451
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
aaugugagca ccuuccuucu uuuug                                              25

<210> SEQ ID NO 452
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
ggaaugugag caccuuccuu cuuuu                                              25

<210> SEQ ID NO 453
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
aaggaaugug agcaccuucc uucuu                                              25

<210> SEQ ID NO 454
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uuaaggaaug ugagcaccuu ccuuc                                              25

<210> SEQ ID NO 455
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
auuuaaggaa ugugagcacc uuccu                                              25

<210> SEQ ID NO 456
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 456
uaauuuaagg aaugugagca ccuuc                                        25

<210> SEQ ID NO 457
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
cuuaauuuaa ggaaugugag caccu                                        25

<210> SEQ ID NO 458
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uccuuaauuu aaggaaugug agcac                                        25

<210> SEQ ID NO 459
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
acuccuuaau uuaaggaaug ugagc                                        25

<210> SEQ ID NO 460
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
uuacuccuua auuuaaggaa uguga                                        25

<210> SEQ ID NO 461
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
tcactttcat aatgctgg                                                18

<210> SEQ ID NO 462
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
tcactttcat aatgctgg                                                    18

<210> SEQ ID NO 463
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
tcactttcat aatgctgg                                                    18

<210> SEQ ID NO 464
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
tcactttcat aatgctgg                                                    18

<210> SEQ ID NO 465
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
tcactttcat aatgctgg                                                    18

<210> SEQ ID NO 466
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
tcactttcat aatgctgg                                                    18

<210> SEQ ID NO 467
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tcactttcat aatgctgg                                                    18

<210> SEQ ID NO 468
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
tcactttcat aatgctgg							18

<210> SEQ ID NO 469
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
tcactttcat aatgctgg							18

<210> SEQ ID NO 470
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
tcactttcat aatgctgg							18

<210> SEQ ID NO 471
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
cuuucauaau gcugg							15

<210> SEQ ID NO 472
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 472
tatcatactg gctattatat gggtttt						27

<210> SEQ ID NO 473
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 473
aaggagaaat gctggcatag agcagc						26

<210> SEQ ID NO 474
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 474 tcgtttctttt agtggtgtca tttag                                              25

<210> SEQ ID NO 475
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 475
tggctatcat actggctatt atatggaa                                             28

<210> SEQ ID NO 476
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 476
ctggcataga gcagcactaa atgacaccac                                           30

<210> SEQ ID NO 477
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 477
tccagatctg tctgatcgtt tctt                                                 24

<210> SEQ ID NO 478
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
tcactttcat aatgctgg                                                        18

<210> SEQ ID NO 479
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: t or u
<220> FEATURE:
<221> NAME/KEY: modified_base
<222> LOCATION: (5)..(7)
<223> OTHER INFORMATION: t or u
<220> FEATURE:
<221> NAME/KEY: modified_base
<222> LOCATION: (10)..(10)
<223> OTHER INFORMATION: t or u
<220> FEATURE:
<221> NAME/KEY: modified_base

```
<222> LOCATION: (13)..(13)
<223> OTHER INFORMATION: t or u
<220> FEATURE:
<221> NAME/KEY: modified_base
<222> LOCATION: (16)..(16)
<223> OTHER INFORMATION: t or u

<400> SEQUENCE: 479
ncacnnncan aangcngg                                                 18

<210> SEQ ID NO 480
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(10)
<223> OTHER INFORMATION: a, t, c, g or u

<400> SEQUENCE: 480
cuuucnnnnn gcugg                                                    15

<210> SEQ ID NO 481
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(8)
<223> OTHER INFORMATION: t or u
<220> FEATURE:
<221> NAME/KEY: modified_base
<222> LOCATION: (10)..(10)
<223> OTHER INFORMATION: t or u

<400> SEQUENCE: 481
ccagcannan gaaag                                                    15

<210> SEQ ID NO 482
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(10)
<223> OTHER INFORMATION: a, c, u, g, t, unknown or other

<400> SEQUENCE: 482
ccagcnnnnn gaaag                                                    15

<210> SEQ ID NO 483
<211> LENGTH: 12
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 483
tcataatgct gg                                                         12

<210> SEQ ID NO 484
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 484
ctttcataat gctgg                                                      15

<210> SEQ ID NO 485
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 485
ccagcauuau gaaaguga                                                   18

<210> SEQ ID NO 486
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 486
ccagcauuau gaaagugaau                                                 20